US009517127B2

(12) United States Patent
Wortz et al.

(10) Patent No.: US 9,517,127 B2
(45) Date of Patent: *Dec. 13, 2016

(54) PROSTHETIC CAPSULAR DEVICES, SYSTEMS, AND METHODS

(71) Applicant: Omega Ophthalmics LLC, Lexington, KY (US)

(72) Inventors: Gary N. Wortz, Nicholasville, KY (US); Rick William Ifland, Versailles, KY (US)

(73) Assignee: Omega Ophthalmics LLC, Lexington, KY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/138,679

(22) Filed: Apr. 26, 2016

(65) Prior Publication Data

US 2016/0235524 A1 Aug. 18, 2016

Related U.S. Application Data

(63) Continuation of application No. 14/968,427, filed on Dec. 14, 2015, now Pat. No. 9,358,103.

(Continued)

(51) Int. Cl.
*A61F 2/16* (2006.01)

(52) U.S. Cl.
CPC ............. *A61F 2/1694* (2013.01); *A61F 2/16* (2013.01); *A61F 2/1648* (2013.01);
(Continued)

(58) Field of Classification Search
CPC .... A61F 2/1624; A61F 2/1629; A61F 2/1694; A61F 2002/1681; A61F 2002/169; A61F 2002/16901; A61F 2002/16902
(Continued)

(56) References Cited

U.S. PATENT DOCUMENTS 4,073,014 A 2/1978 Poler
4,435,856 A 3/1984 L'Esperance
(Continued)

FOREIGN PATENT DOCUMENTS

EP 0 337 390 10/1989
EP 0 294 039 7/1993
(Continued)

OTHER PUBLICATIONS

Becker et al., "Accuracy of lens power calculation and centration of an aspheric intraocular lens", Ophthalmologel, Oct. 2006, vol. 103, Issue 10, pp. 873-876.
(Continued)

*Primary Examiner* — David H. Willse
*Assistant Examiner* — Javier Blanco
(74) *Attorney, Agent, or Firm* — Knobbe Martens Olson & Bear, LLP

(57) ABSTRACT

A prosthetic capsular device configured to be inserted in an eye includes a housing structure and a ring structure. The housing structure includes a first side, a second side opposite the first side, a third side, a fourth side opposite the third side, a posterior side including a refractive surface, an anterior side opposite the posterior side, and a longitudinal axis. The first side, the second side, the third side, the fourth side, the posterior side, and the anterior side at least partially define a cavity configured to contain an intraocular device (e.g., an IOL). The anterior side includes an opening. The ring structure includes a ring structure portion extending radially outward from proximate one of an end of the first side and an end of the second side.

17 Claims, 158 Drawing Sheets

Related U.S. Application Data

(60) Provisional application No. 62/114,231, filed on Feb. 10, 2015, provisional application No. 62/168,493, filed on May 29, 2015, provisional application No. 62/216,591, filed on Sep. 10, 2015.

(52) U.S. Cl.
CPC ...... *A61F 2/1691* (2013.01); *A61F 2002/169* (2015.04); *A61F 2002/1681* (2013.01); *A61F 2002/1689* (2013.01); *A61F 2002/16901* (2015.04); *A61F 2002/16902* (2015.04)

(58) Field of Classification Search
USPC ... 623/6.37, 6.38, 6.46, 6.39, 6.4, 6.41, 6.43
See application file for complete search history.

(56) References Cited

U.S. PATENT DOCUMENTS

| | | | |
|---|---|---|---|
| 4,629,461 A | 12/1986 | Clayman et al. | |
| 4,685,921 A | 8/1987 | Peyman | |
| 4,731,078 A | 3/1988 | Stoy et al. | |
| 4,888,012 A | 12/1989 | Horn et al. | |
| 4,892,543 A | 1/1990 | Turley | |
| 4,932,966 A | 6/1990 | Christie et al. | |
| 5,171,266 A | 12/1992 | Wiley et al. | |
| 5,222,981 A | 6/1993 | Werblin | |
| 5,275,623 A | 1/1994 | Sarfarazi | |
| 5,326,347 A | 7/1994 | Cumming | |
| 5,522,891 A | 6/1996 | Klaas | |
| 5,562,731 A | 10/1996 | Cumming | |
| 5,628,795 A | 5/1997 | Langerman | |
| 5,628,798 A | 5/1997 | Eggleston et al. | |
| 5,674,282 A | 10/1997 | Cumming | |
| 5,702,402 A | 12/1997 | Brady | |
| 5,800,533 A | 9/1998 | Eggleston et al. | |
| 5,964,802 A | 10/1999 | Anello et al. | |
| 5,968,094 A | 10/1999 | Werblin et al. | |
| 6,015,435 A | 1/2000 | Valunin et al. | |
| 6,027,531 A | 2/2000 | Tassignon | |
| 6,113,633 A | 9/2000 | Portney | |
| 6,117,171 A | 9/2000 | Skottun | |
| 6,136,026 A | 10/2000 | Israel | |
| 6,217,612 B1 | 4/2001 | Woods | |
| 6,235,055 B1 | 5/2001 | Chu | |
| 6,299,641 B1 | 10/2001 | Woods | |
| 6,322,589 B1 | 11/2001 | Cumming | |
| 6,413,276 B1 | 7/2002 | Werblin | |
| 6,428,574 B1 | 8/2002 | Valunin et al. | |
| 6,443,985 B1 | 9/2002 | Woods | |
| 6,454,801 B1 | 9/2002 | Portney | |
| 6,464,725 B2 | 10/2002 | Skotton | |
| 6,488,708 B2 | 12/2002 | Sarfarazi | |
| 6,503,276 B2 | 1/2003 | Lang et al. | |
| 6,524,340 B2 | 2/2003 | Israel | |
| 6,533,813 B1 | 3/2003 | Lin et al. | |
| 6,537,281 B1 | 3/2003 | Portney | |
| 6,537,317 B1 | 3/2003 | Steinert et al. | |
| 6,576,012 B2 | 6/2003 | Lang | |
| 6,596,026 B1 | 7/2003 | Gross et al. | |
| 6,645,246 B1 | 11/2003 | Weinschenk, III et al. | |
| 6,695,881 B2 | 2/2004 | Peng et al. | |
| 6,749,634 B2 | 6/2004 | Hanna | |
| 6,761,737 B2 | 7/2004 | Zadno-Azizi et al. | |
| 6,764,511 B2 | 7/2004 | Zadno-Azizi et al. | |
| 6,786,934 B2 | 9/2004 | Zadno-Azizi et al. | |
| 6,818,158 B2 | 11/2004 | Pham et al. | |
| 6,827,738 B2 | 12/2004 | Willis et al. | |
| 6,846,326 B2 | 1/2005 | Zadno-Azizi et al. | |
| 6,858,040 B2 | 2/2005 | Nguyen et al. | |
| 6,881,225 B2 | 4/2005 | Okada | |
| 6,884,261 B2 | 4/2005 | Zadno-Azizi et al. | |
| 6,899,732 B2 | 5/2005 | Zadno-Azizi et al. | |
| 6,921,416 B2 | 7/2005 | Khoury | |
| 6,926,736 B2 | 8/2005 | Peng et al. | |
| 6,960,230 B2 | 11/2005 | Haefliger | |
| 6,972,033 B2 | 12/2005 | McNicholas | |
| 7,001,374 B2 | 2/2006 | Peyman | |
| 7,025,783 B2 | 4/2006 | Brady et al. | |
| 7,029,497 B2 | 4/2006 | Zhang et al. | |
| 7,041,134 B2 | 5/2006 | Nguyen et al. | |
| 7,087,080 B2 | 8/2006 | Zadno-Azizi et al. | |
| 7,118,596 B2 | 10/2006 | Zadno-Azizi et al. | |
| 7,122,053 B2 | 10/2006 | Esch | |
| 7,125,422 B2 | 10/2006 | Woods et al. | |
| 7,144,423 B2 | 12/2006 | McDonald | |
| 7,150,760 B2 | 12/2006 | Zhang | |
| 7,198,640 B2 | 4/2007 | Nguyen | |
| 7,223,288 B2 | 5/2007 | Zhang et al. | |
| 7,226,478 B2 | 6/2007 | Ting et al. | |
| 7,452,362 B2 | 11/2008 | Zadno-Azizi et al. | |
| 7,452,378 B2 | 11/2008 | Zadno-Azizi et al. | |
| 7,662,179 B2 | 2/2010 | Sarfarazi | |
| 7,744,603 B2 | 6/2010 | Zadno-Azizi et al. | |
| 7,744,646 B2 | 6/2010 | Zadno-Azizi et al. | |
| 7,771,471 B2 | 8/2010 | Dell | |
| 7,780,729 B2 | 8/2010 | Nguyen et al. | |
| 7,806,929 B2 | 10/2010 | Brown | |
| 7,811,320 B2 | 10/2010 | Werblin | |
| 7,988,291 B2 | 8/2011 | Ianchulev | |
| 8,025,823 B2 | 9/2011 | Pham et al. | |
| 8,034,107 B2 | 10/2011 | Stenger | |
| 8,048,155 B2 | 11/2011 | Shadduck | |
| 8,052,752 B2 | 11/2011 | Woods et al. | |
| 8,062,361 B2 | 11/2011 | Nguyen et al. | |
| 8,088,161 B2 | 1/2012 | Aharoni et al. | |
| 8,100,965 B2 | 1/2012 | Cumming et al. | |
| 8,162,927 B2 | 4/2012 | Peyman | |
| 8,187,325 B2 | 5/2012 | Zadno-Azizi et al. | |
| 8,246,679 B2 | 8/2012 | Nguyen et al. | |
| 8,343,216 B2 | 1/2013 | Brady et al. | |
| 8,398,709 B2 | 3/2013 | Ben Nun | |
| 8,506,074 B2 | 8/2013 | Gerbaud | |
| 8,545,556 B2 | 10/2013 | Woods et al. | |
| 8,556,967 B2 | 10/2013 | Sarfarazi | |
| 8,574,295 B2 | 11/2013 | Roholt | |
| 8,579,971 B2 | 11/2013 | Webb | |
| 8,585,758 B2 | 11/2013 | Woods | |
| 8,663,235 B2 | 3/2014 | Tassignon | |
| 8,728,158 B2 | 5/2014 | Whitsett | |
| 8,778,022 B2 | 7/2014 | Blum et al. | |
| 8,821,166 B2 | 9/2014 | Akura et al. | |
| 8,834,565 B2 | 9/2014 | Ben Nun | |
| 8,900,300 B1 | 12/2014 | Wortz | |
| 8,915,588 B2 | 12/2014 | Blum et al. | |
| 8,931,896 B2 | 1/2015 | Blum et al. | |
| 9,005,283 B2 | 4/2015 | Nguyen et al. | |
| 9,039,760 B2 | 5/2015 | Brady et al. | |
| 9,072,600 B2 | 7/2015 | Tran | |
| 9,095,424 B2 | 8/2015 | Kahook et al. | |
| 9,124,796 B2 | 9/2015 | Blum et al. | |
| 9,125,736 B2 | 9/2015 | Kahook et al. | |
| 9,149,356 B2 | 10/2015 | Sarfarazi | |
| 9,186,243 B2 | 11/2015 | Van Noy | |
| 9,198,752 B2 | 12/2015 | Woods | |
| 9,289,287 B2 | 3/2016 | Kahook et al. | |
| 9,339,375 B2 | 5/2016 | Lee et al. | |
| 9,358,103 B1 | 6/2016 | Wortz et al. | |
| 9,414,907 B2 | 8/2016 | Wortz et al. | |
| 9,439,754 B2 | 9/2016 | Wortz | |
| 2001/0047204 A1 | 11/2001 | Zhou et al. | |
| 2001/0051825 A1 | 12/2001 | Peterson | |
| 2002/0128710 A1 | 9/2002 | Eggleston | |
| 2002/0143395 A1 | 10/2002 | Skottun | |
| 2002/0173846 A1 | 11/2002 | Blake et al. | |
| 2003/0004569 A1 | 1/2003 | Haefliger | |
| 2003/0050695 A1 | 3/2003 | Lin et al. | |
| 2003/0187505 A1 | 10/2003 | Liao | |
| 2004/0082993 A1 | 4/2004 | Woods | |
| 2004/0082995 A1 | 4/2004 | Woods | |
| 2004/0167622 A1 | 8/2004 | Sunalp et al. | |
| 2005/0021138 A1 | 1/2005 | Woods | |
| 2005/0085907 A1 | 4/2005 | Hanna | |
| 2005/0107875 A1 | 5/2005 | Cumming | |

(56) References Cited

U.S. PATENT DOCUMENTS

| | | |
|---|---|---|
| 2005/0113911 A1 | 5/2005 | Peyman |
| 2005/0113913 A1 | 5/2005 | Duvert |
| 2005/0222577 A1 | 10/2005 | Vaquero |
| 2005/0234285 A1 | 10/2005 | Khoury |
| 2006/0047339 A1 | 3/2006 | Brown |
| 2006/0095128 A1 | 5/2006 | Blum et al. |
| 2006/0212116 A1 | 9/2006 | Woods |
| 2006/0259139 A1 | 11/2006 | Zadno-Azizi et al. |
| 2007/0027538 A1 | 2/2007 | Aharoni et al. |
| 2007/0027541 A1 | 2/2007 | Aharoni et al. |
| 2007/0032868 A1 | 2/2007 | Woods |
| 2007/0083261 A1 | 4/2007 | Colvard |
| 2007/0093892 A1 | 4/2007 | Mackool |
| 2007/0118216 A1 | 5/2007 | Pynson |
| 2007/0123981 A1 | 5/2007 | Tassignon |
| 2007/0162118 A1 | 7/2007 | Rozakis et al. |
| 2007/0213816 A1 | 9/2007 | Sarfarazi |
| 2008/0221676 A1 | 9/2008 | Coleman et al. |
| 2009/0005864 A1 | 1/2009 | Eggleston |
| 2009/0182423 A1 | 7/2009 | Zheng |
| 2010/0030225 A1 | 2/2010 | Ianchulev |
| 2010/0211171 A1 | 8/2010 | Sarfarazi |
| 2010/0228344 A1 | 9/2010 | Shadduck |
| 2010/0280609 A1 | 11/2010 | Simonov et al. |
| 2011/0015541 A1 | 1/2011 | Padrick et al. |
| 2011/0153014 A1 | 6/2011 | Zhang et al. |
| 2011/0181834 A1 | 7/2011 | Gerbaud |
| 2011/0288638 A1 | 11/2011 | Smiley et al. |
| 2012/0179249 A1 | 7/2012 | Coleman |
| 2012/0226351 A1 | 9/2012 | Peyman |
| 2013/0116781 A1 | 5/2013 | Ben Nun |
| 2013/0190868 A1 | 7/2013 | Kahook et al. |
| 2013/0310931 A1 | 11/2013 | Kahook et al. |
| 2014/0052246 A1 | 2/2014 | Kahook et al. |
| 2014/0067059 A1 | 3/2014 | Webb |
| 2014/0172089 A1 | 6/2014 | Lee et al. |
| 2014/0228949 A1 | 8/2014 | Argento et al. |
| 2014/0371852 A1 | 12/2014 | Aharoni et al. |
| 2015/0127102 A1 | 5/2015 | Wortz |
| 2015/0142106 A1 | 5/2015 | Wortz |
| 2015/0289970 A1 | 10/2015 | Akura |
| 2015/0335420 A1 | 11/2015 | Blum et al. |
| 2015/0366656 A1 | 12/2015 | Wortz et al. |
| 2015/0366659 A1 | 12/2015 | Wortz et al. |
| 2016/0008126 A1 | 1/2016 | Salahieh et al. |
| 2016/0058553 A1 | 3/2016 | Salahieh et al. |
| 2016/0113760 A1 | 4/2016 | Conrad |

FOREIGN PATENT DOCUMENTS

| | | |
|---|---|---|
| EP | 0 528 325 | 12/1996 |
| EP | 0 732 090 | 6/2002 |
| EP | 1 499 264 | 8/2006 |
| EP | 1 100 411 | 11/2006 |
| EP | 1 653 886 | 1/2008 |
| EP | 1 852 090 | 1/2009 |
| EP | 1 475 055 | 4/2010 |
| EP | 1 438 930 | 9/2011 |
| EP | 2 315 559 | 1/2012 |
| EP | 2 412 337 | 2/2012 |
| EP | 1 296 616 | 5/2012 |
| EP | 1 906 881 | 8/2012 |
| EP | 1 694 253 | 8/2013 |
| EP | 2 851 038 | 3/2015 |
| EP | 2 512 374 | 11/2015 |
| FR | 2 966 340 | 4/2012 |
| JP | 02-011134 | 1/1990 |
| JP | 2005-143886 | 6/2005 |
| WO | WO 98/17205 | 4/1998 |
| WO | WO 99/62433 | 12/1999 |
| WO | WO 02/071983 | 9/2002 |
| WO | WO 2006/124016 | 11/2006 |
| WO | WO 2010/002215 | 1/2010 |
| WO | WO 2013/126380 | 8/2013 |
| WO | WO 2015/044235 | 4/2015 |
| WO | WO 2015/195825 | 12/2015 |

OTHER PUBLICATIONS

Postive Phase I/II Interim Data of Bimatoprost Sustained-Release Implant for IOP Therapy in Glaucoma, Nov. 16, 2015, http://www.allergan.com/NEWS/NEWS/Thomson-Reuters/Positive-Phase-I-II-Interim-Data-of-Bimatoprost-Su.

International Preliminary Report on Patentability, dated Aug. 26, 2014, in PCT App. No. PCT/US2013/026820.

International Search Report and Written Opinion issued in PCT Application No. PCT/US2013/026820, dated May 31, 2013.

International Search Report and Written Opinion issued in PCT Application No. PCT/US2015/036263, dated Oct. 7, 2015.

International Search Report and Written Opinion issued in PCT Application No. PCT/US2015/065887, dated Apr. 6, 2016.

Kleinmann, "Open-Capsule Device for PCO Prevention", Oct. 17, 2013.

Kleiman et al., "Post-operative Results With Implantation of the Acrysof SA-60 Intraocular Lens into the Ciliary Sulcus", ARVO Annual Meeting Abstract Search and Program Planner, May 2002, vol. 2002, Abstract No. 380.

Koeppl, C. et al., "Change in IOL position and capsular bag size with an angulated intraocular lens early after cataract surgery", Journal of Cataract and Refractive Surgery, Feb. 2005, vol. 31, Issue 2, pp. 348-353.

Krader, "Small-aperture optic Iol broadens range of vision", Dec. 1, 2014.

Lim et al., "Surgical management of late dislocated lens capsular bag with intraocular lens and endocapsular tension ring", Journal of Cataract and Refractive Surgery, Mar. 2006, vol. 31, Issue 3, pp. 533-535.

Notice of Allowance issued in Japanese Patent Application No. 2014-558790, dated Jun. 25, 2015, in 3 pages.

Notice of Allowance issued in U.S. Appl. No. 14/968,427, dated Apr. 26, 2016.

Office Action issued in Japanese Patent Application No. 2014-558790, dated Feb. 3, 2015, in 9 pages.

Office Action issued in European Application No. 13710641.5, dated Oct. 1, 2015, in 5 pages.

Restriction Requirement issued in U.S. Appl. No. 14/968,427, dated Mar. 24, 2016.

"Tracking IOP With an IOL," Sep. 15, 2014.

Wirtitsch et al., "Effect of haptic design on change in axial lens position after cataract surgery", Journal of Cataract and Refractive Surgery, Jan. 2004, vol. 30, Issue 1, pp. 45-51.

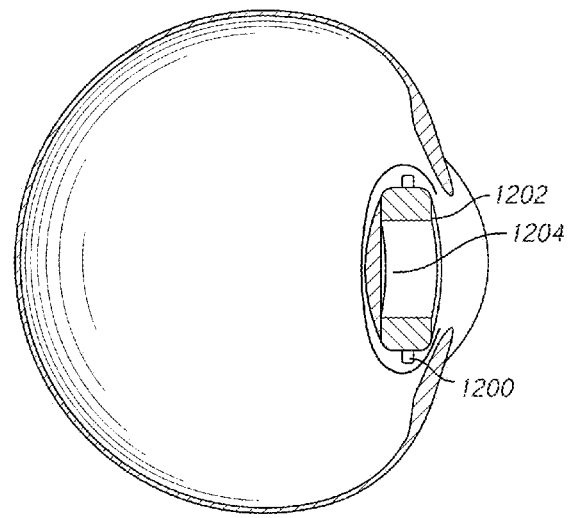
FIG. 12A
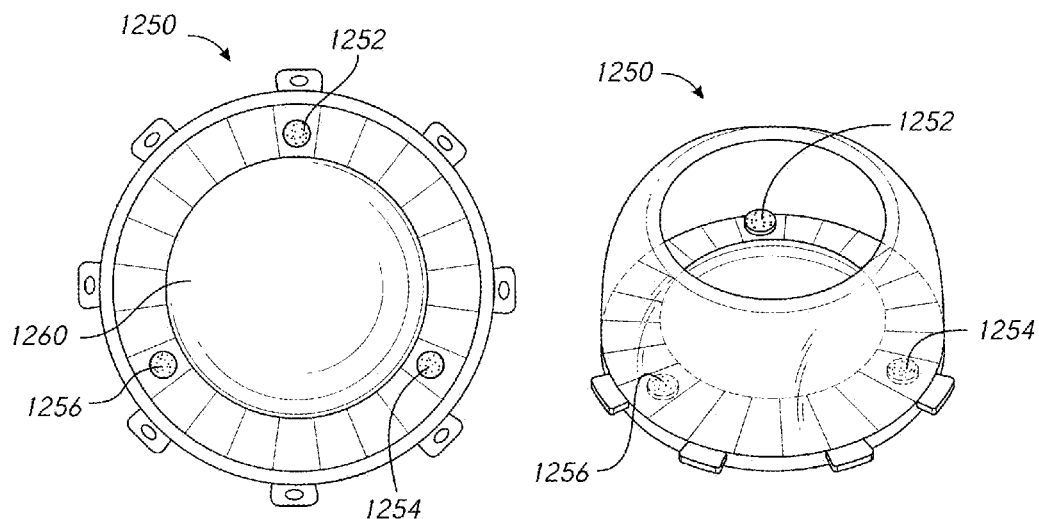
FIG. 12B
FIG. 12C

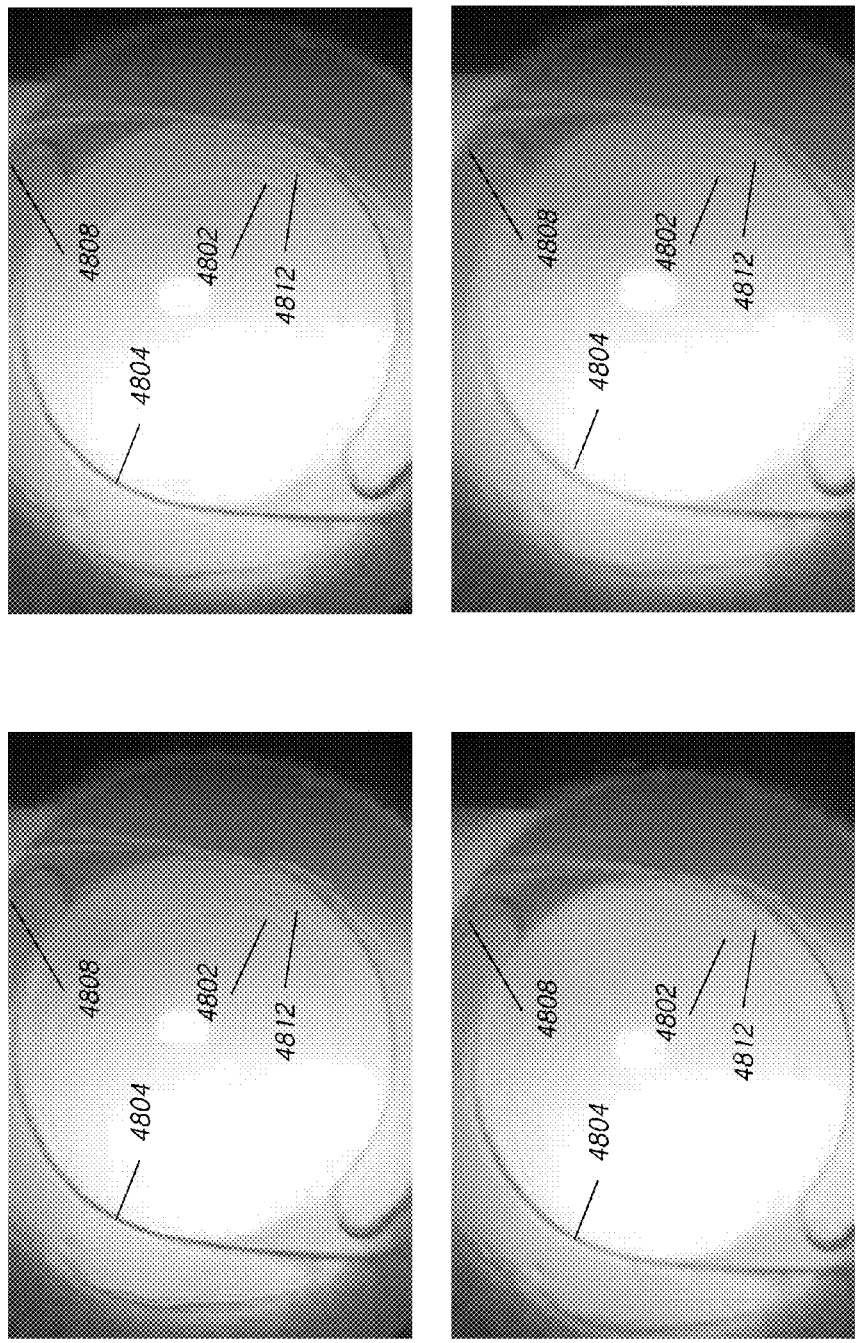

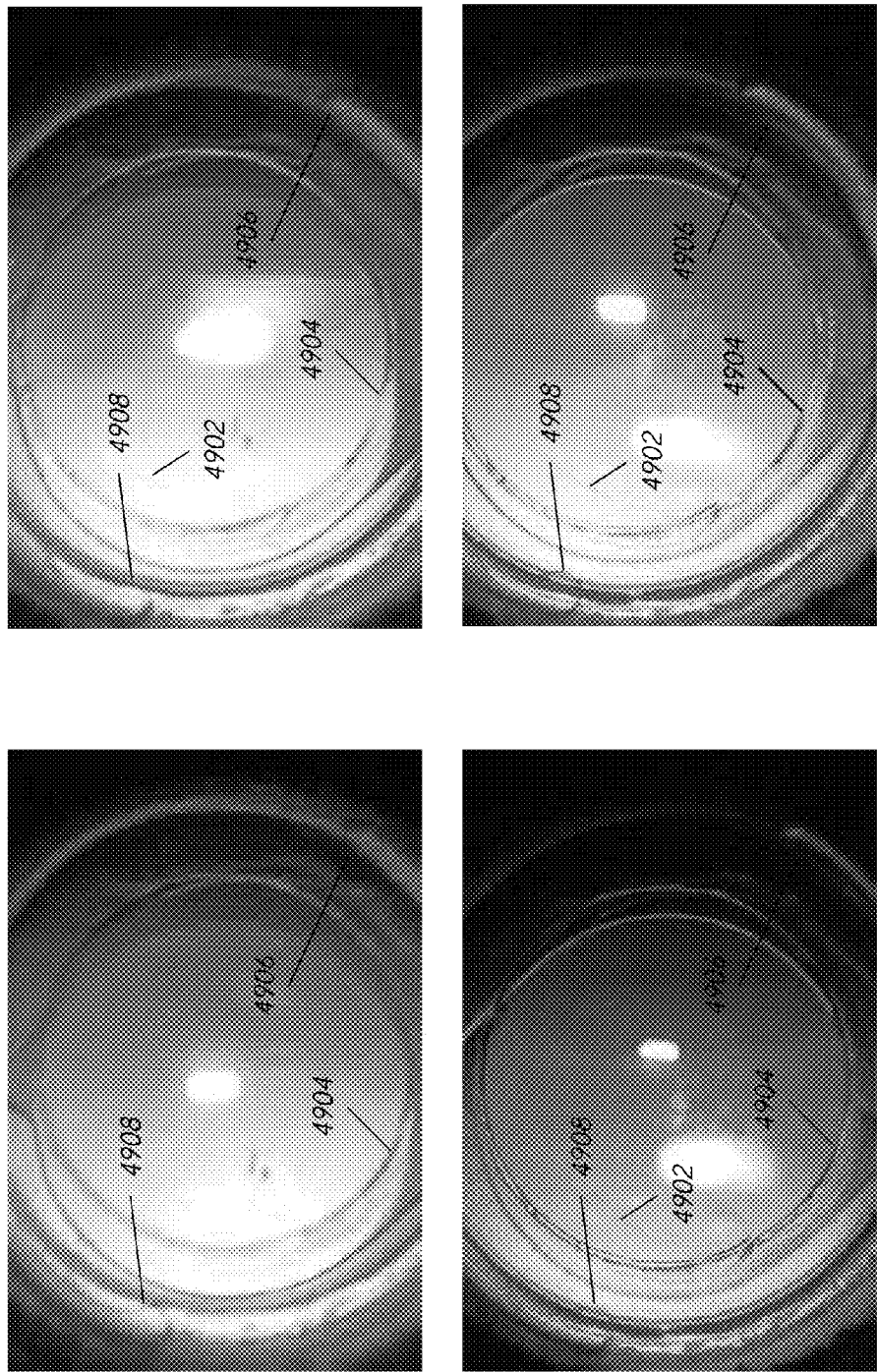

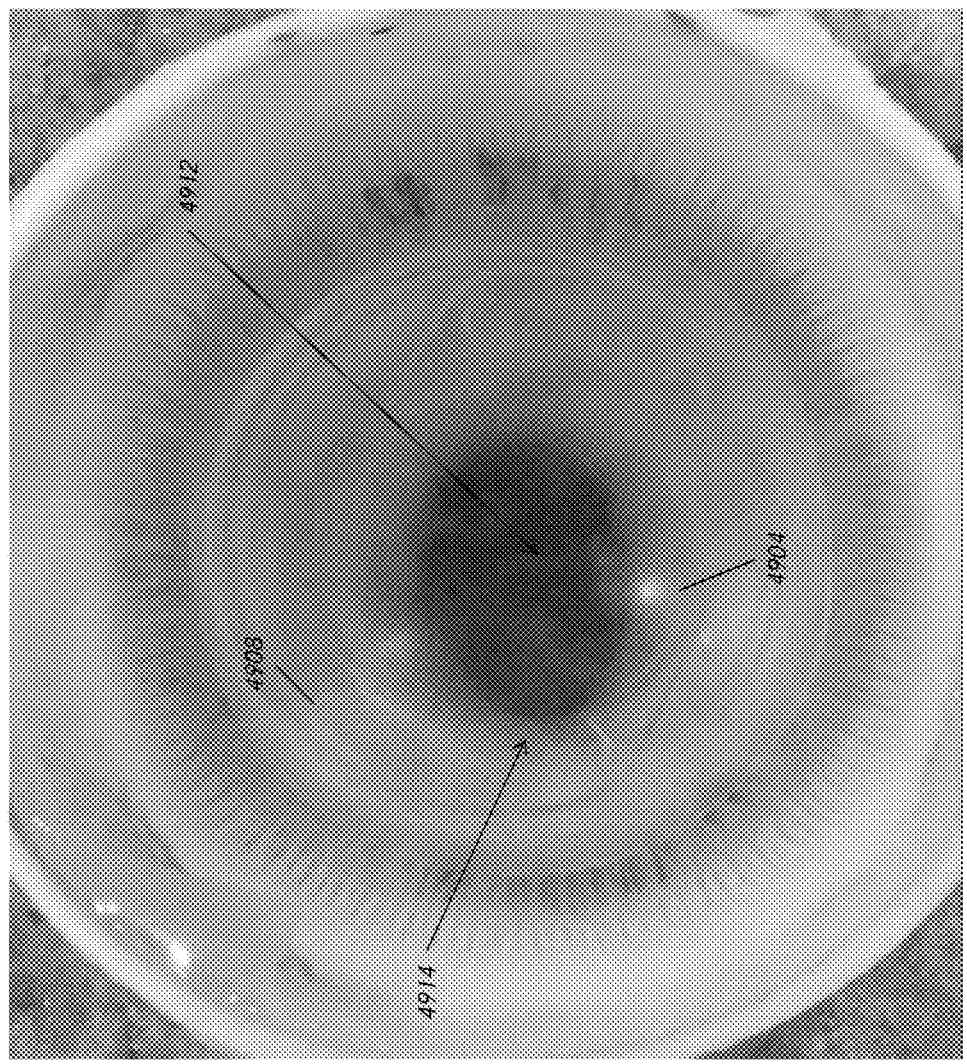

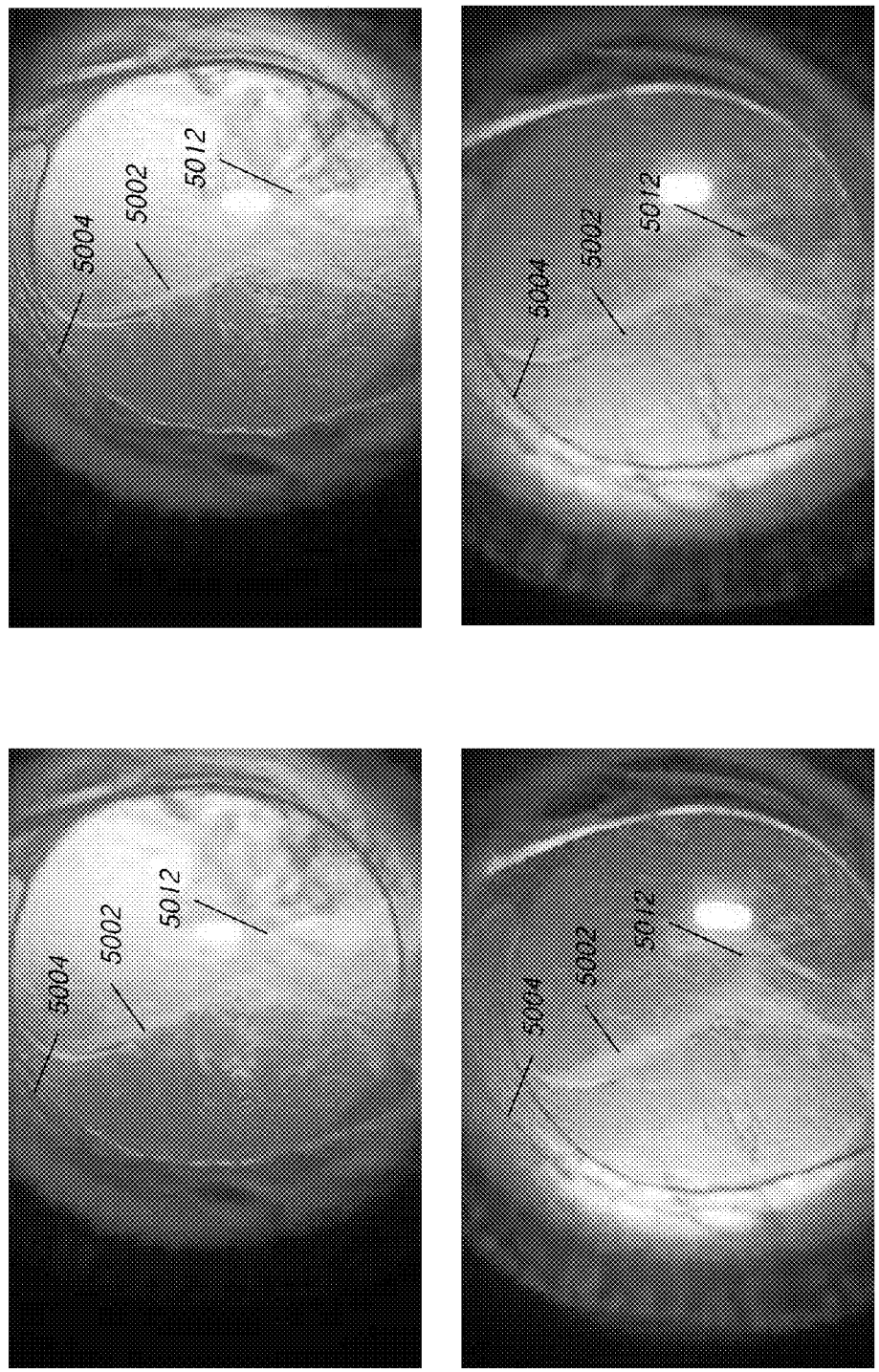

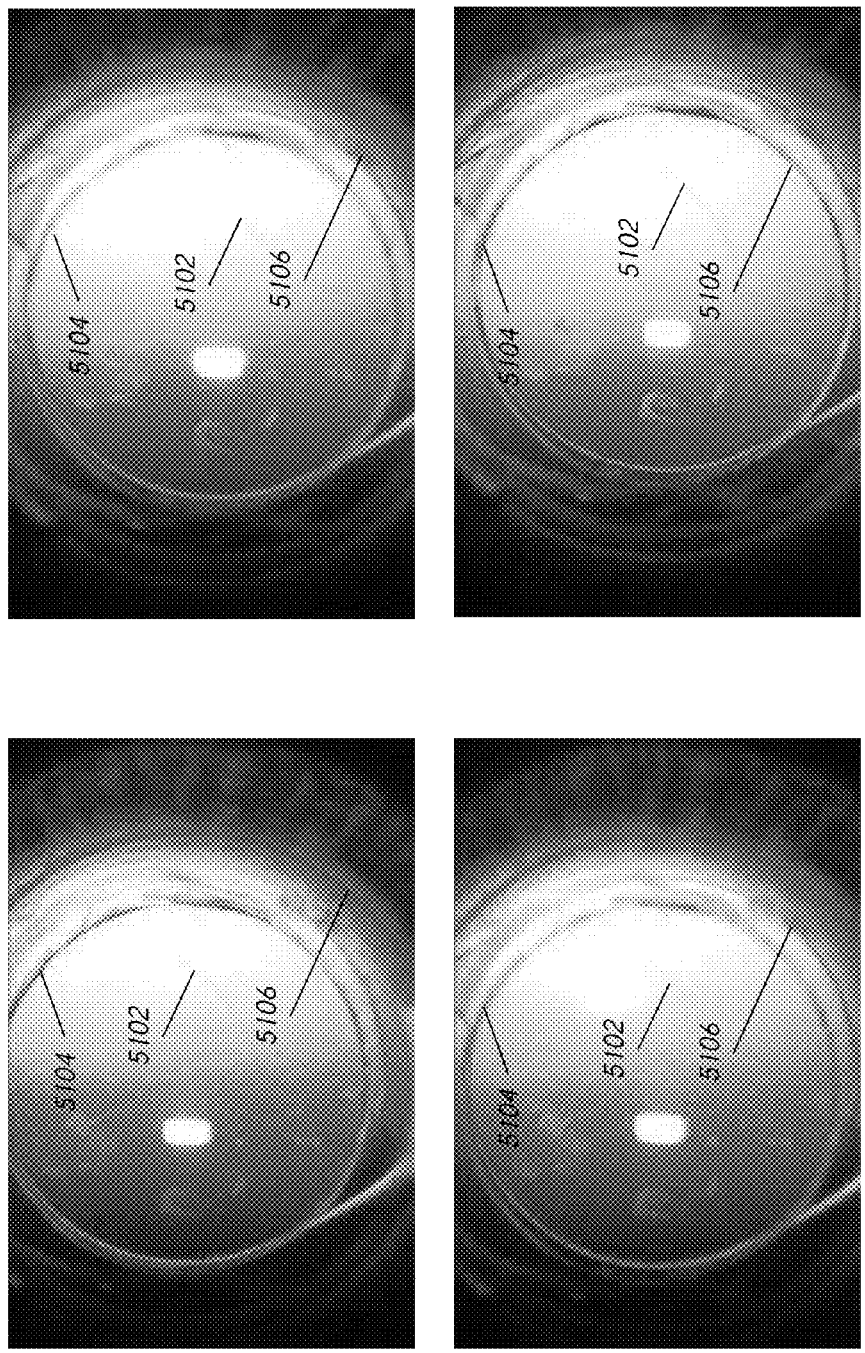

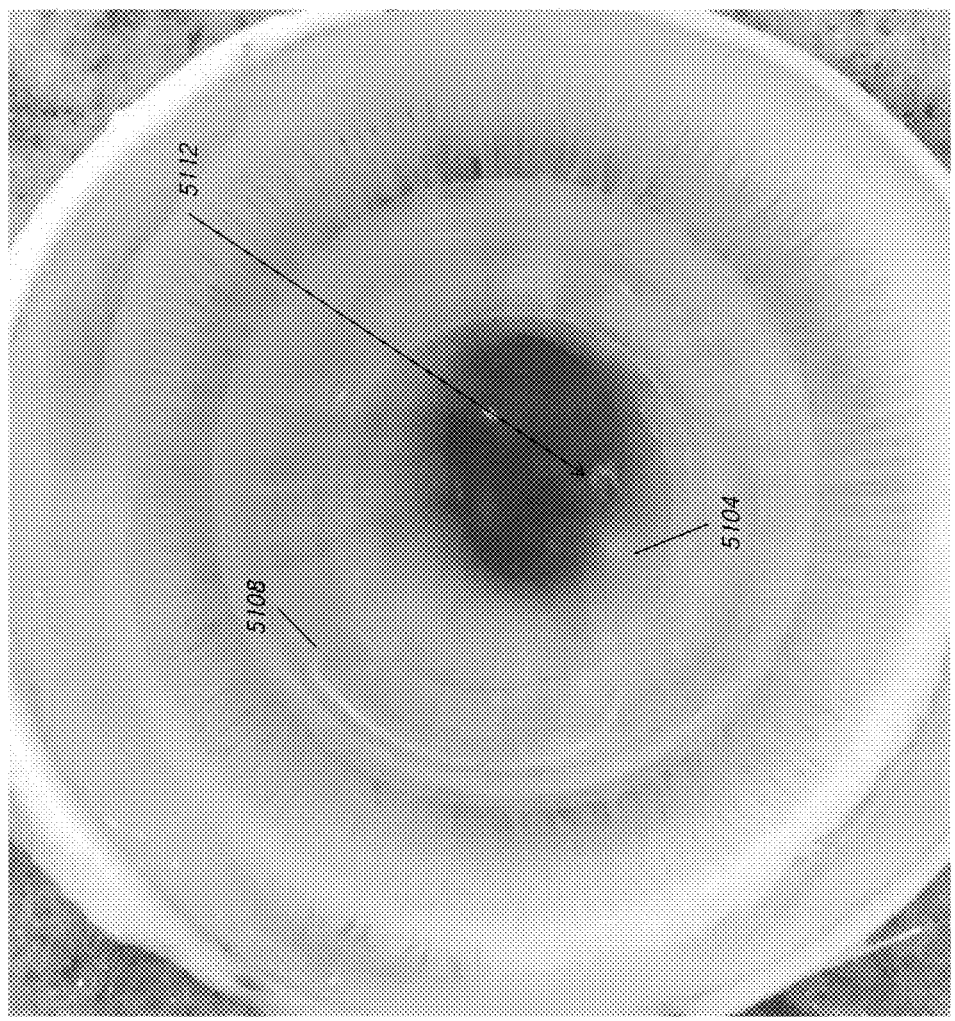

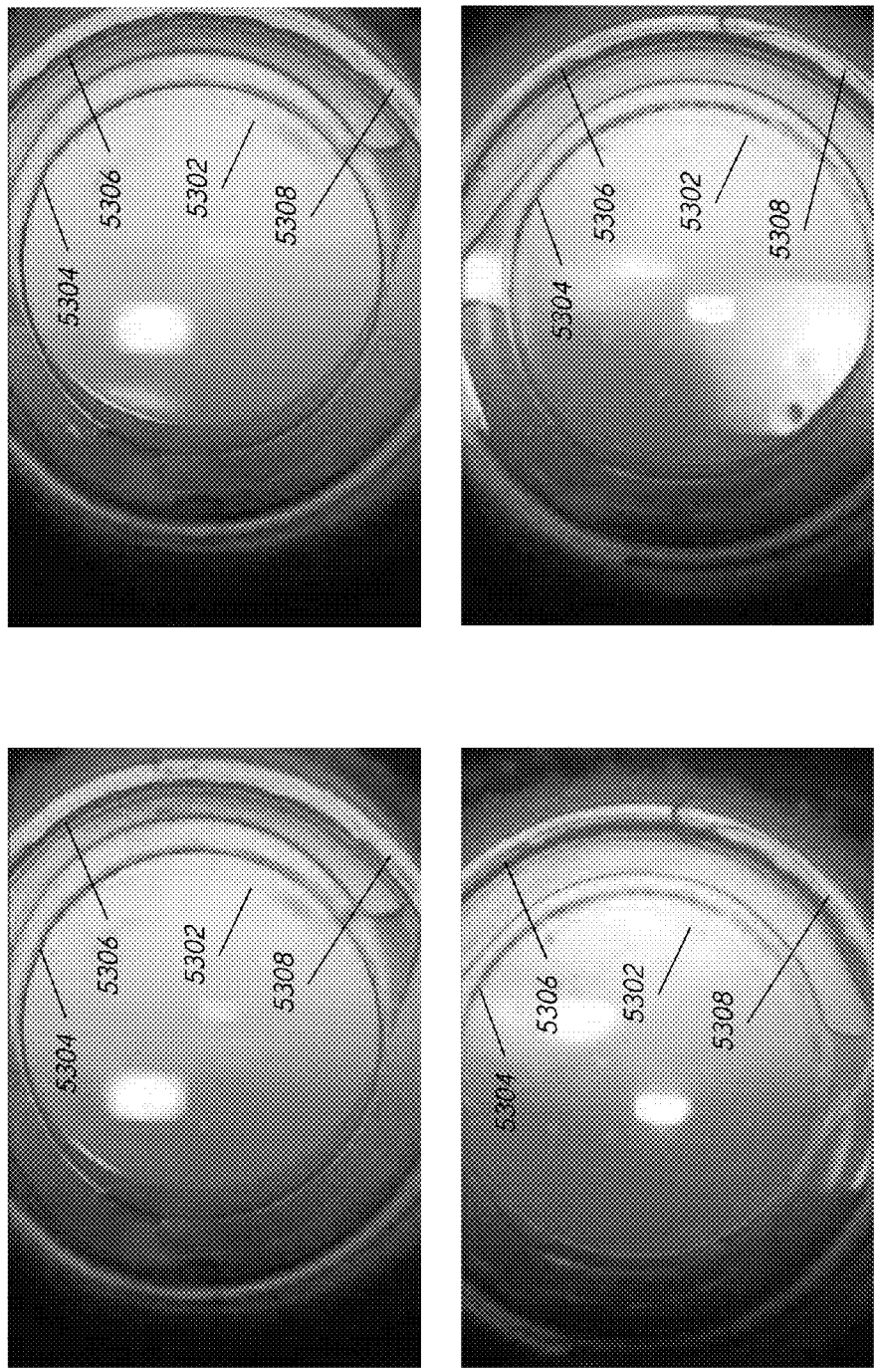

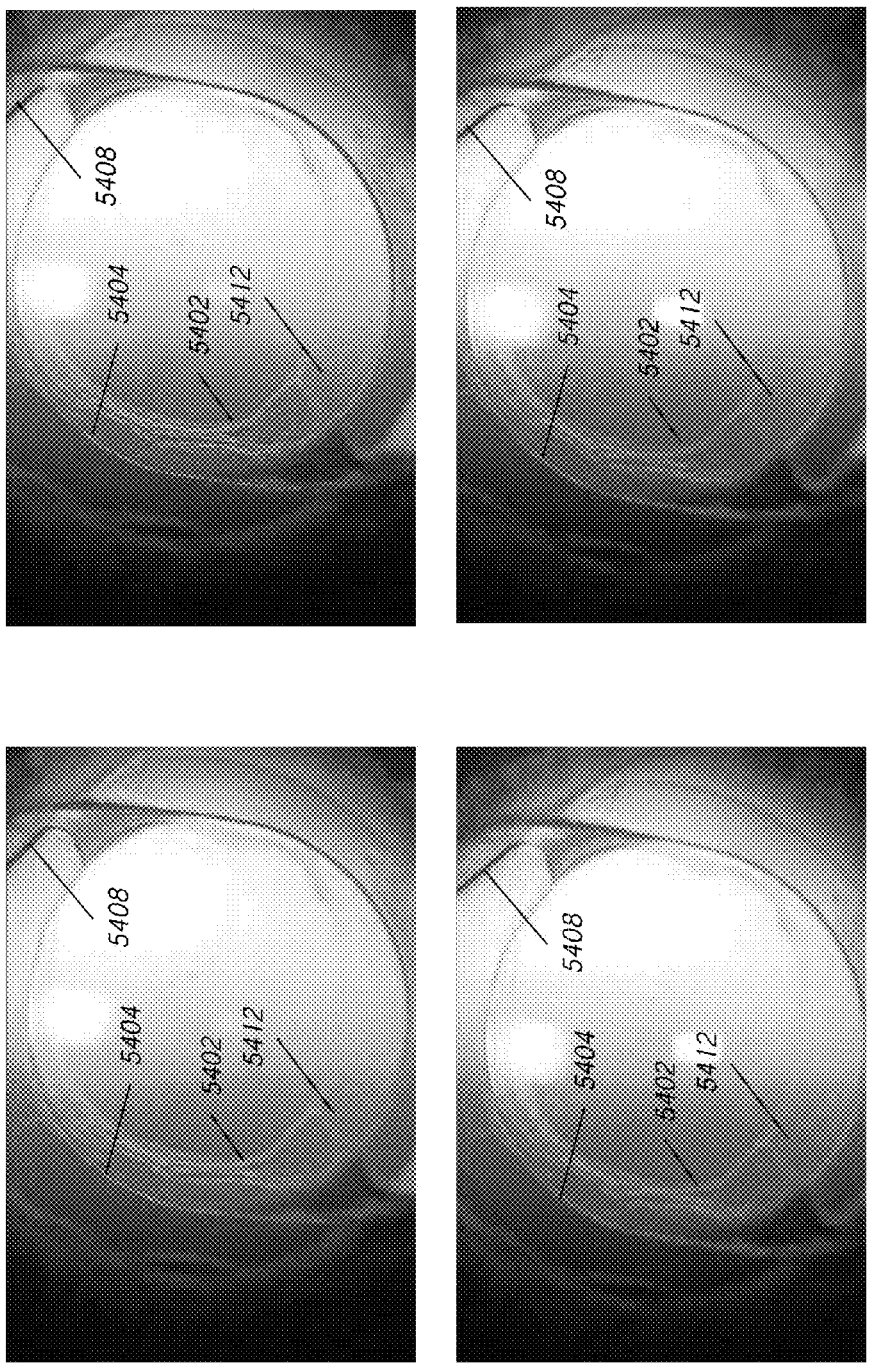

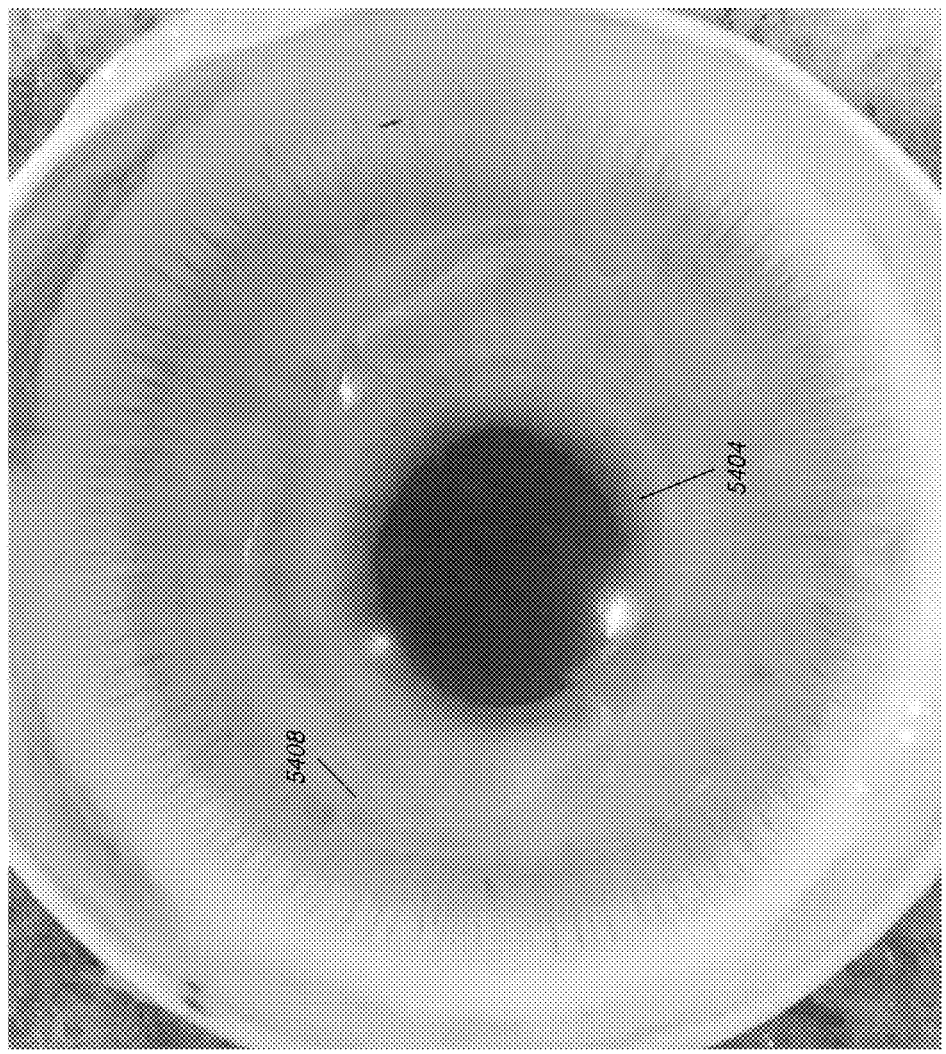

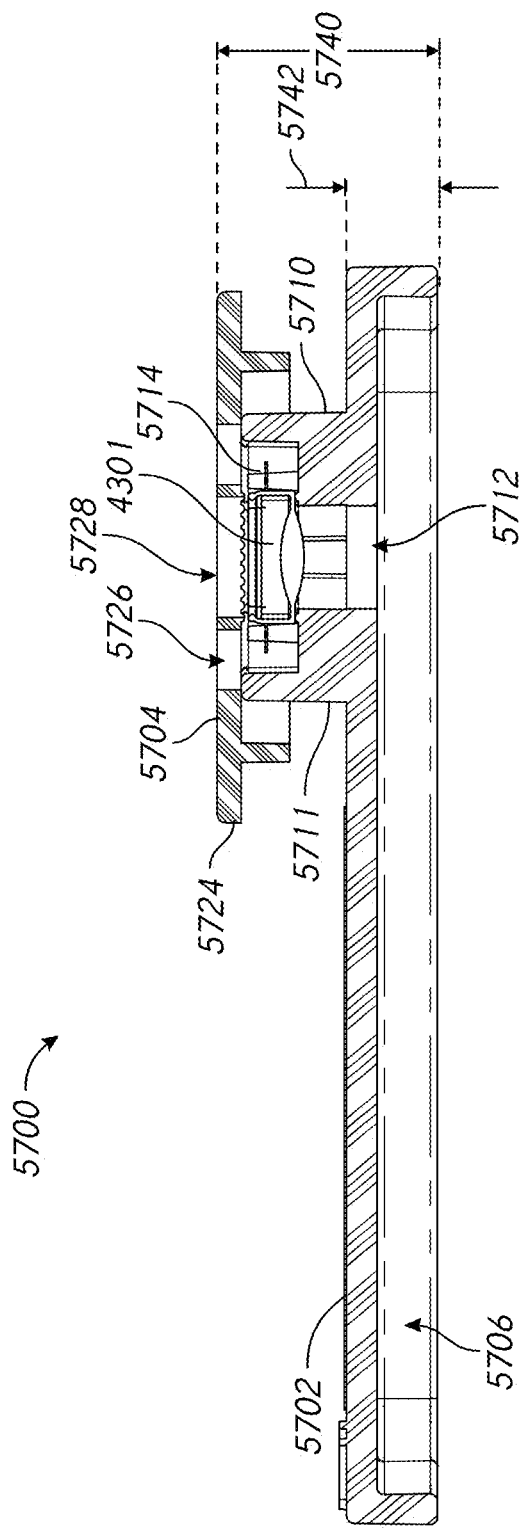

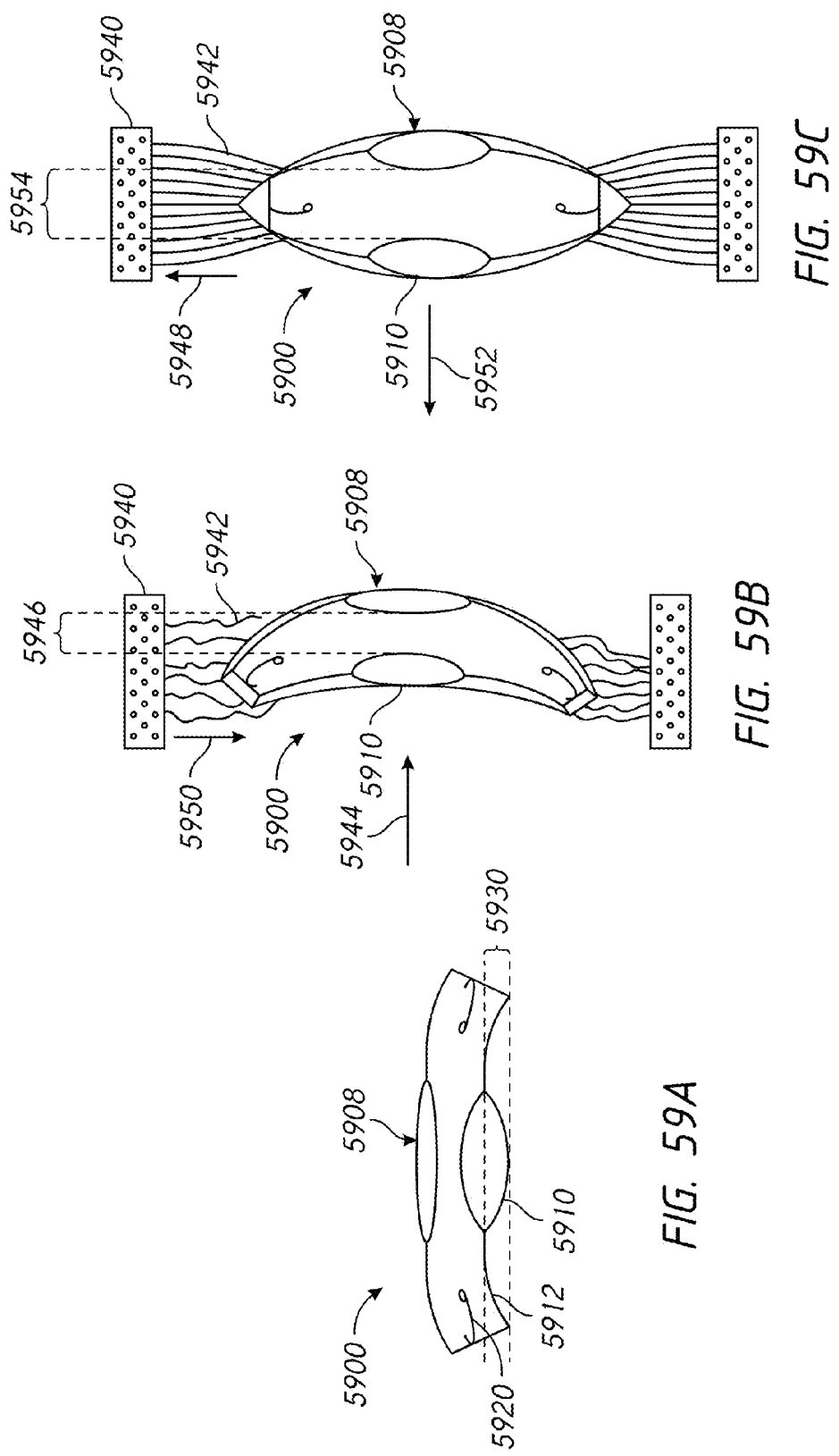

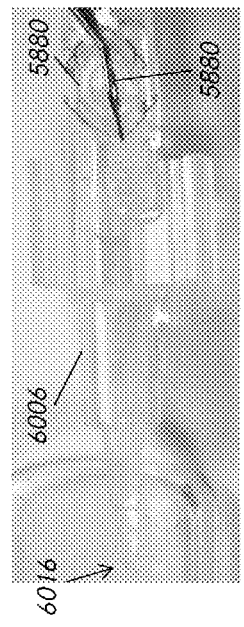
FIG. 60D
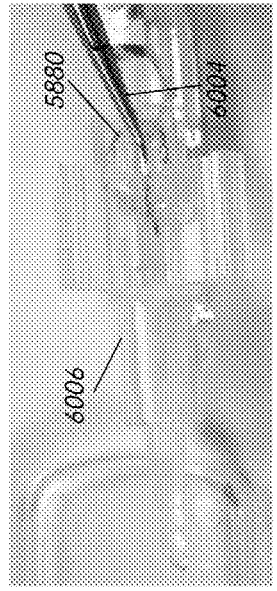
FIG. 60E
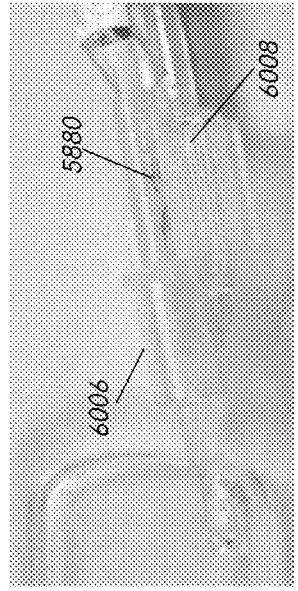
FIG. 60F
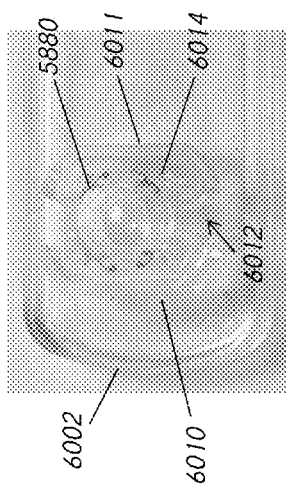
FIG. 60A
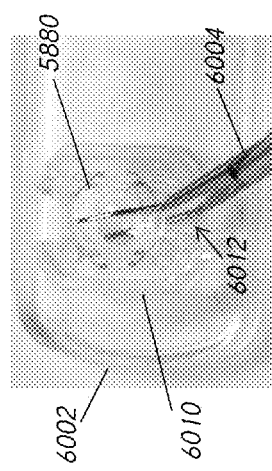
FIG. 60B
FIG. 60C

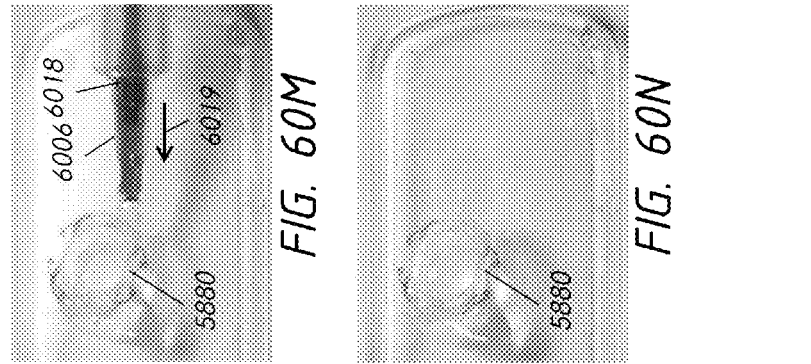

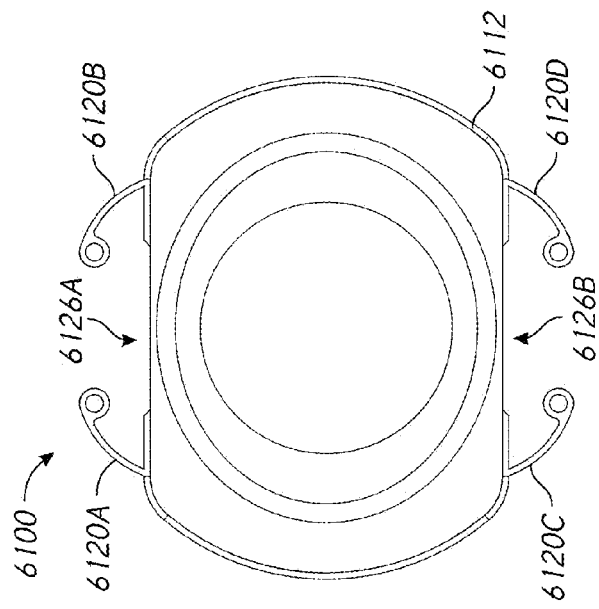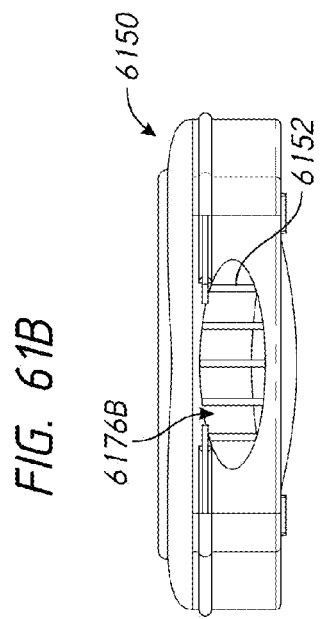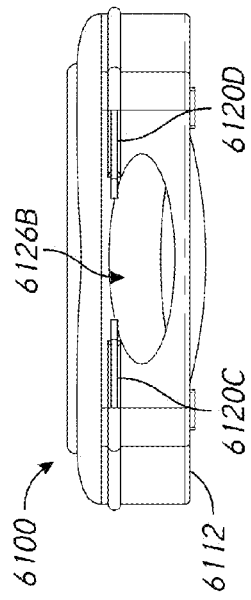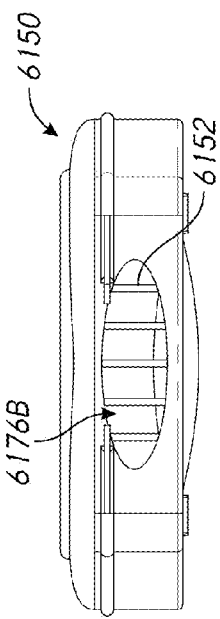
FIG. 61A
FIG. 61B
FIG. 61C
FIG. 61D

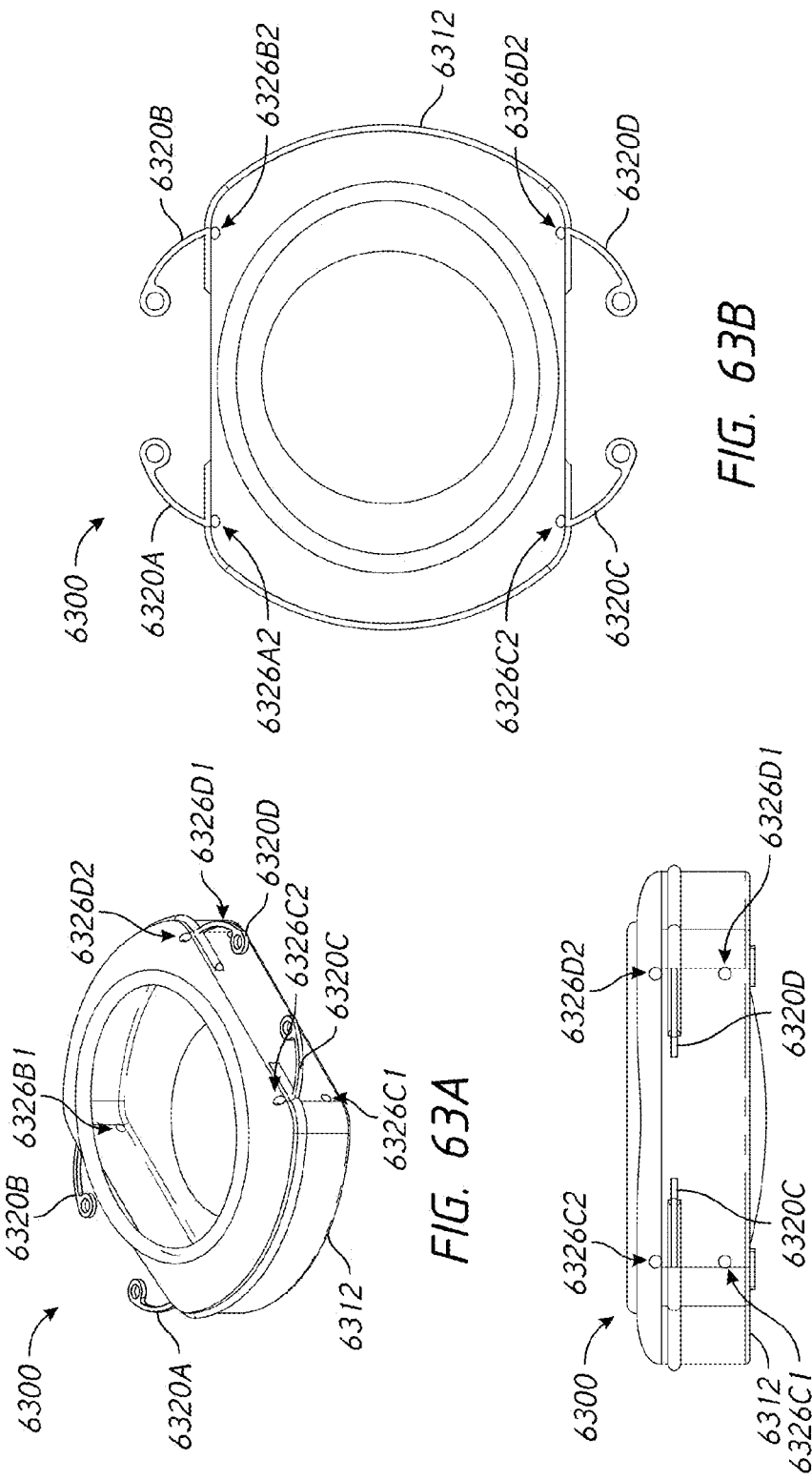

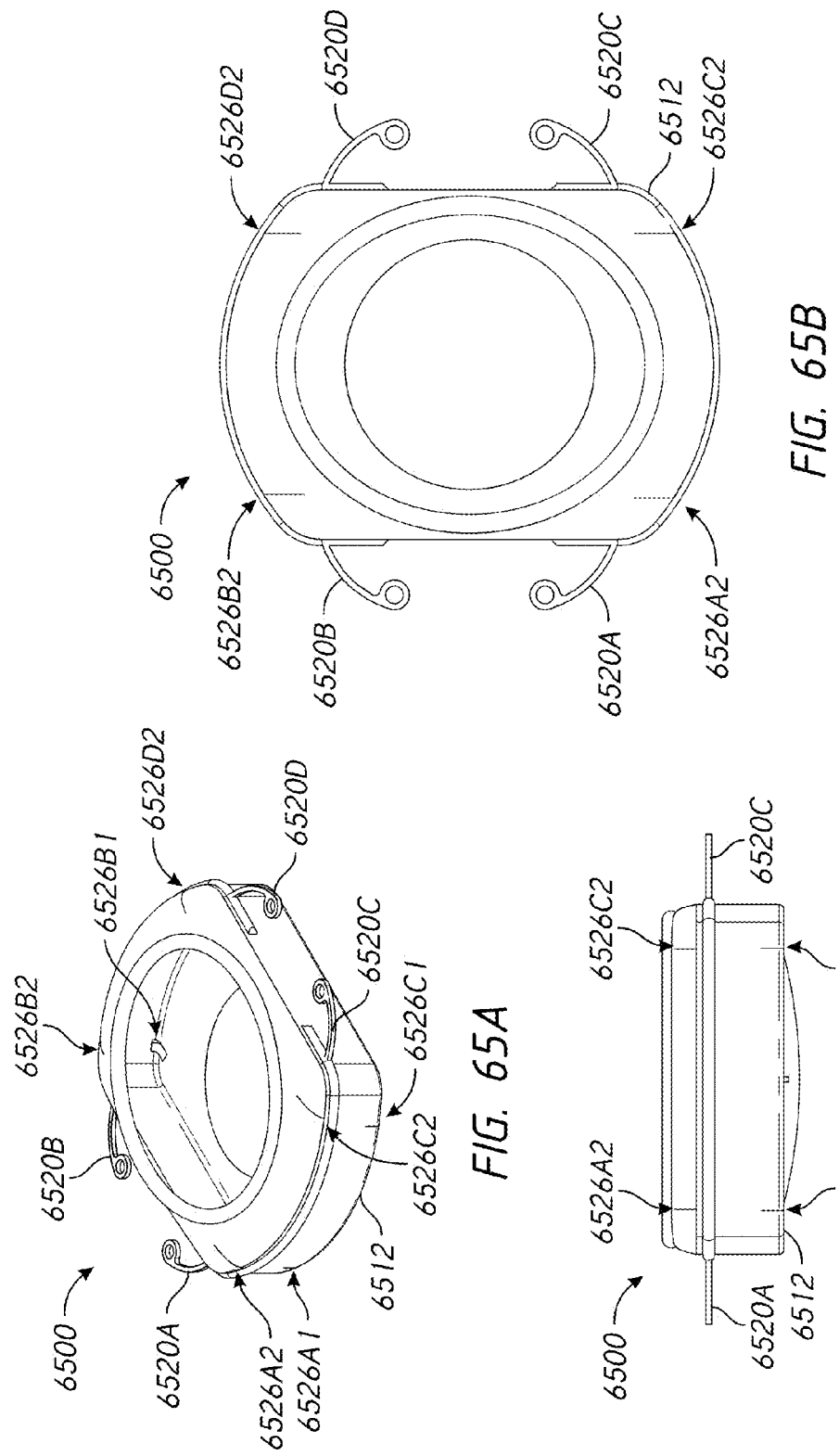

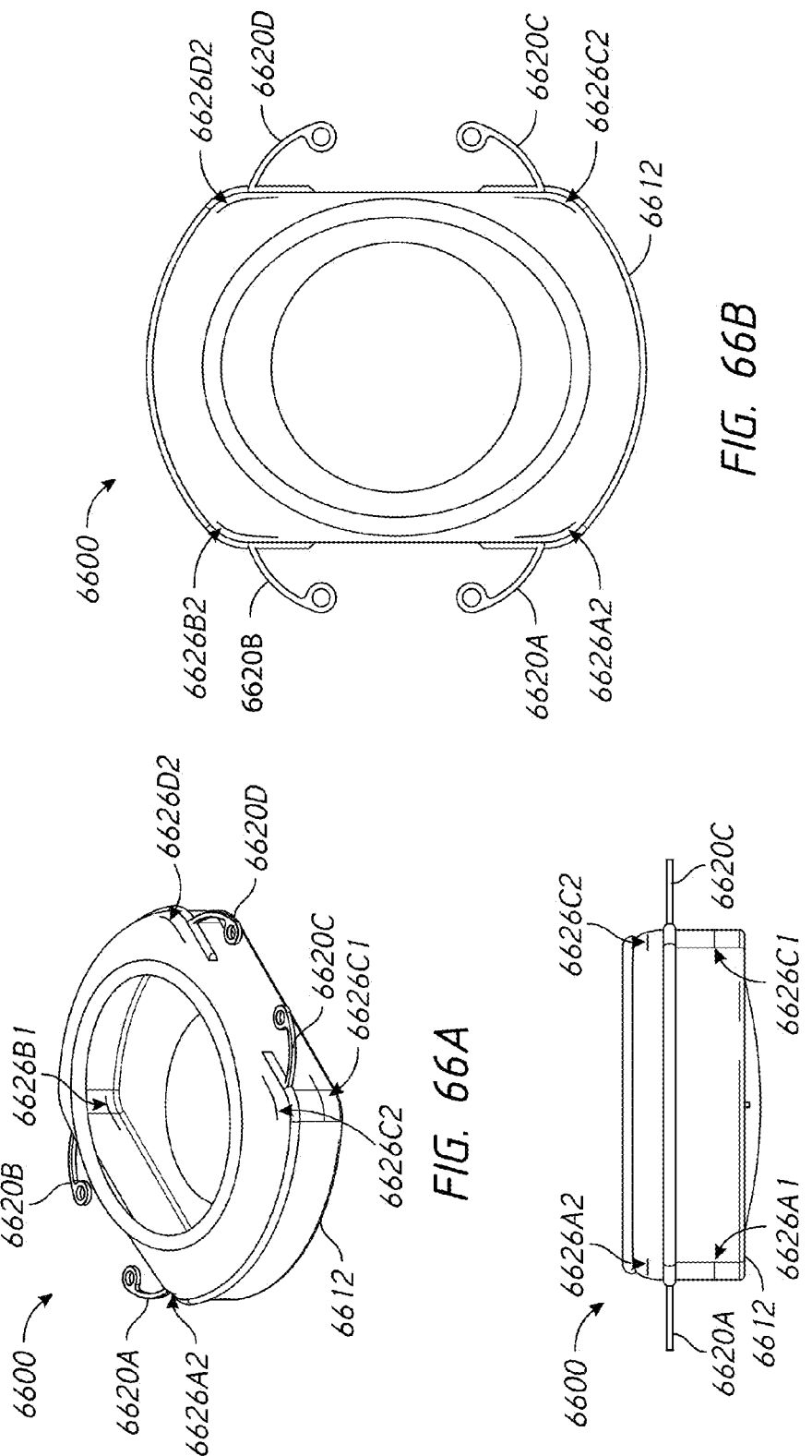

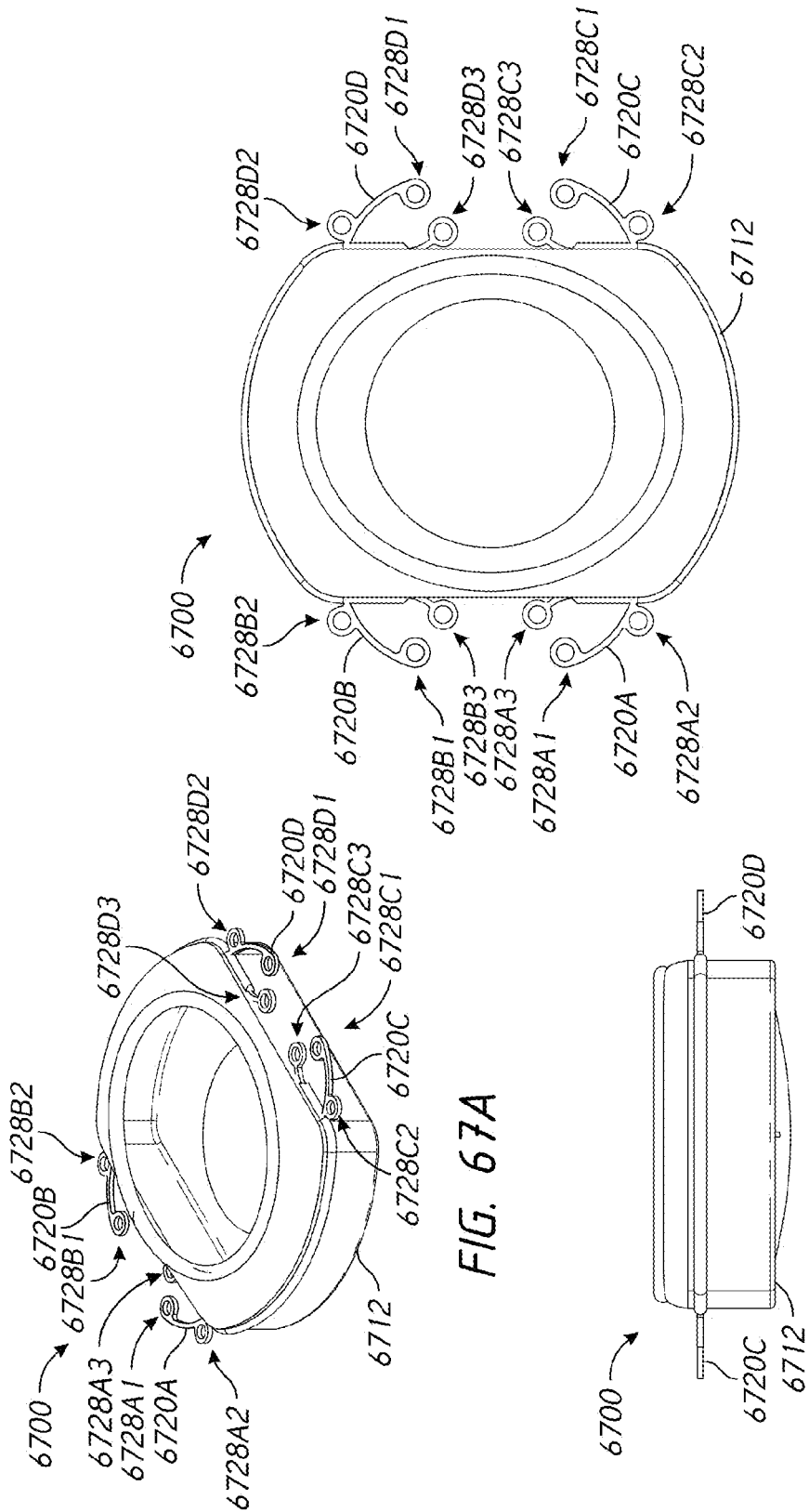

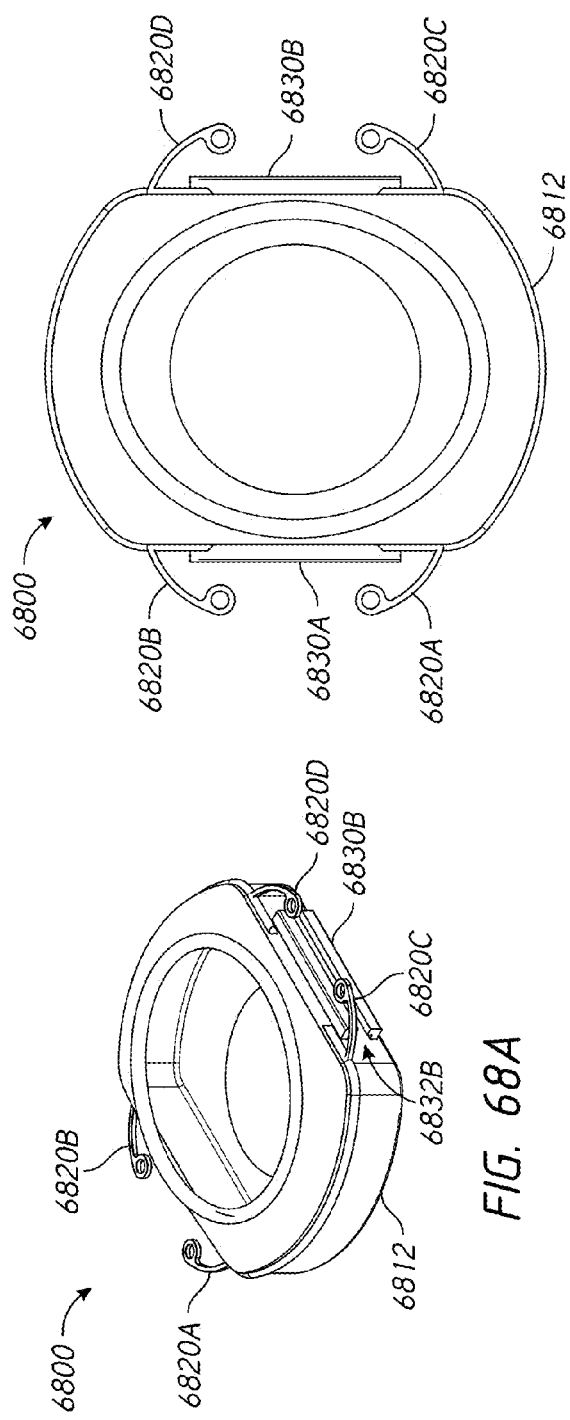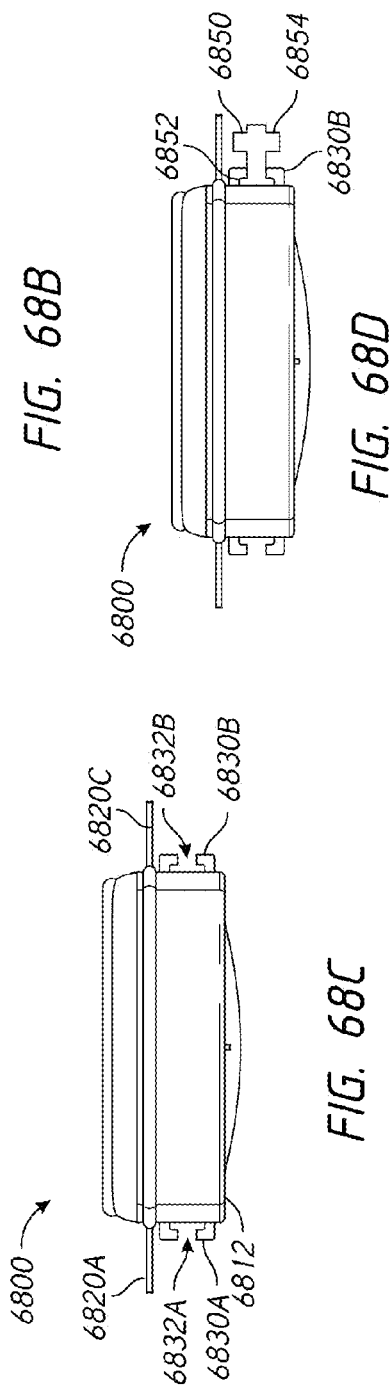

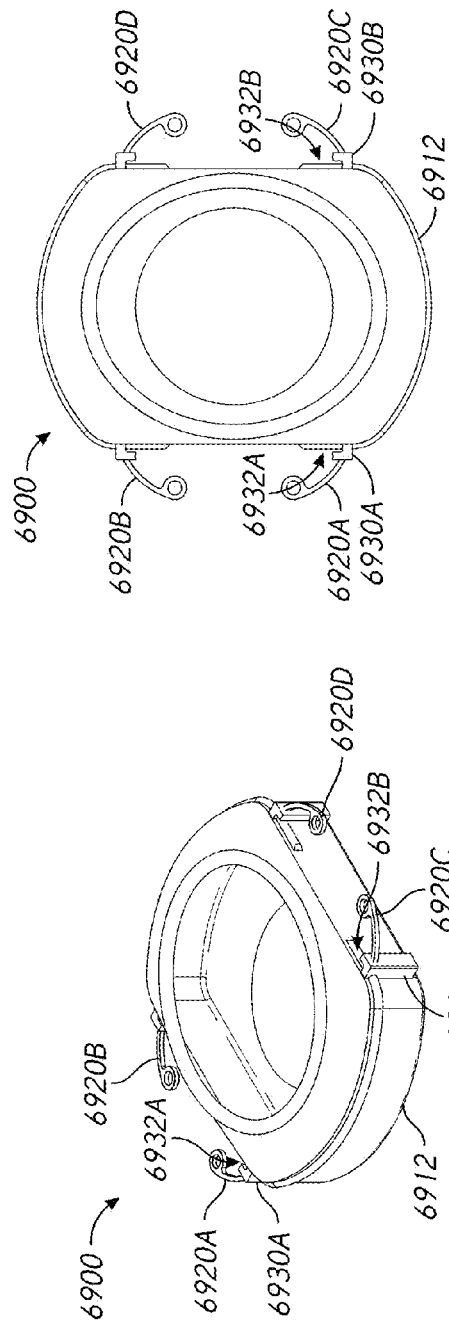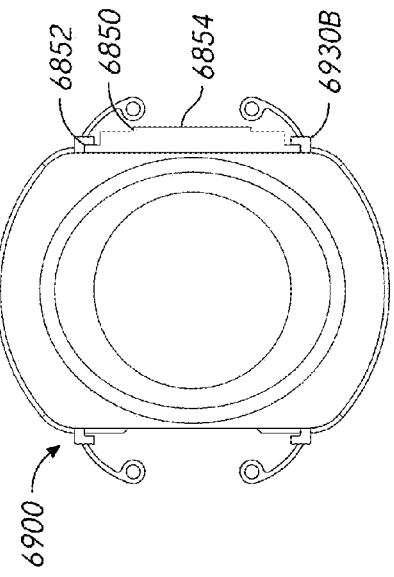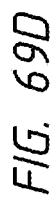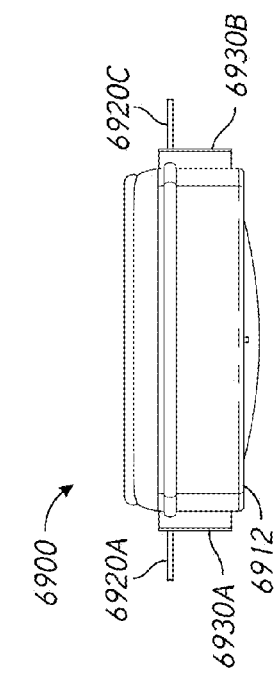

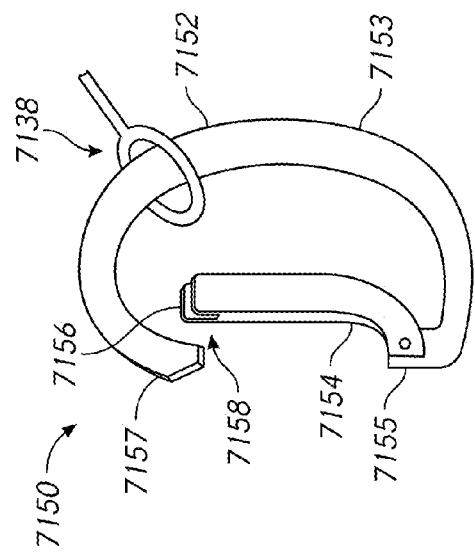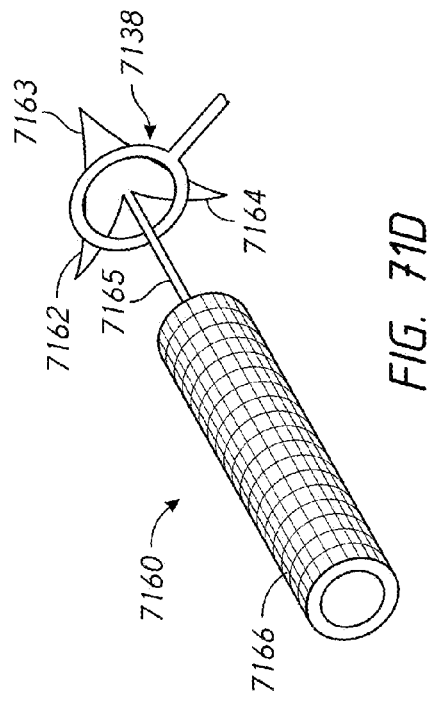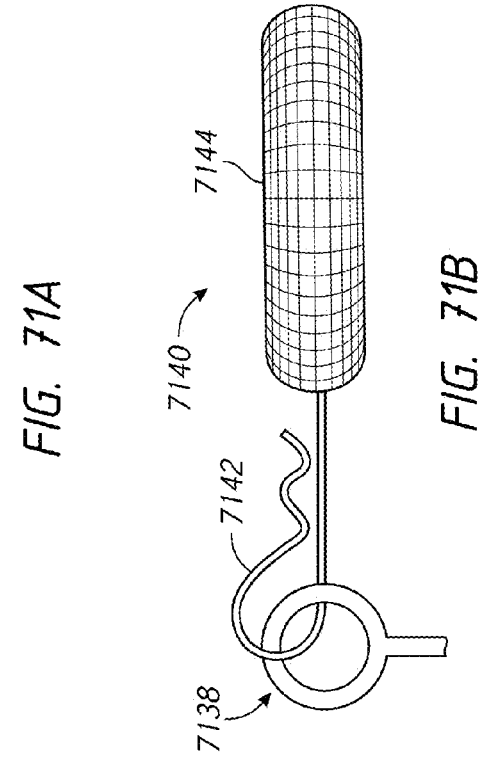

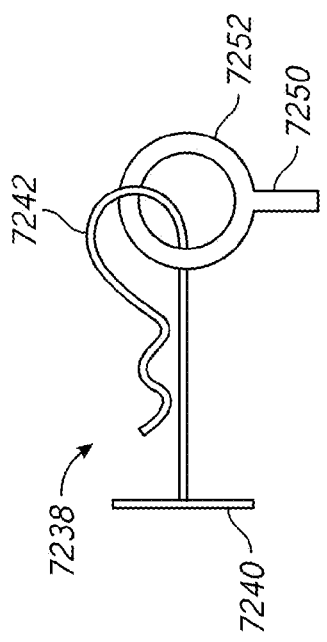
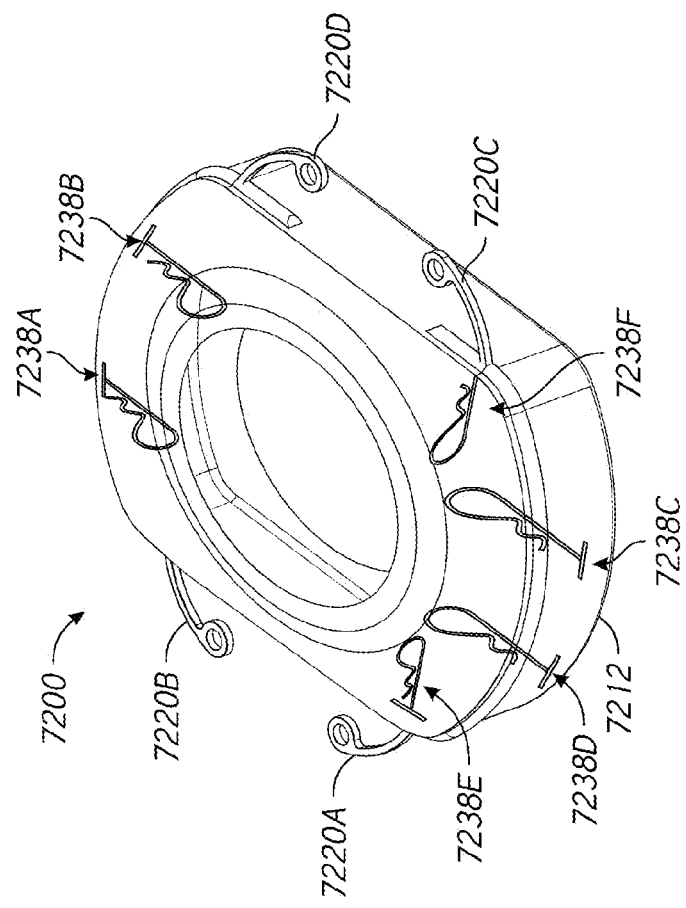
FIG. 72B
FIG. 72A

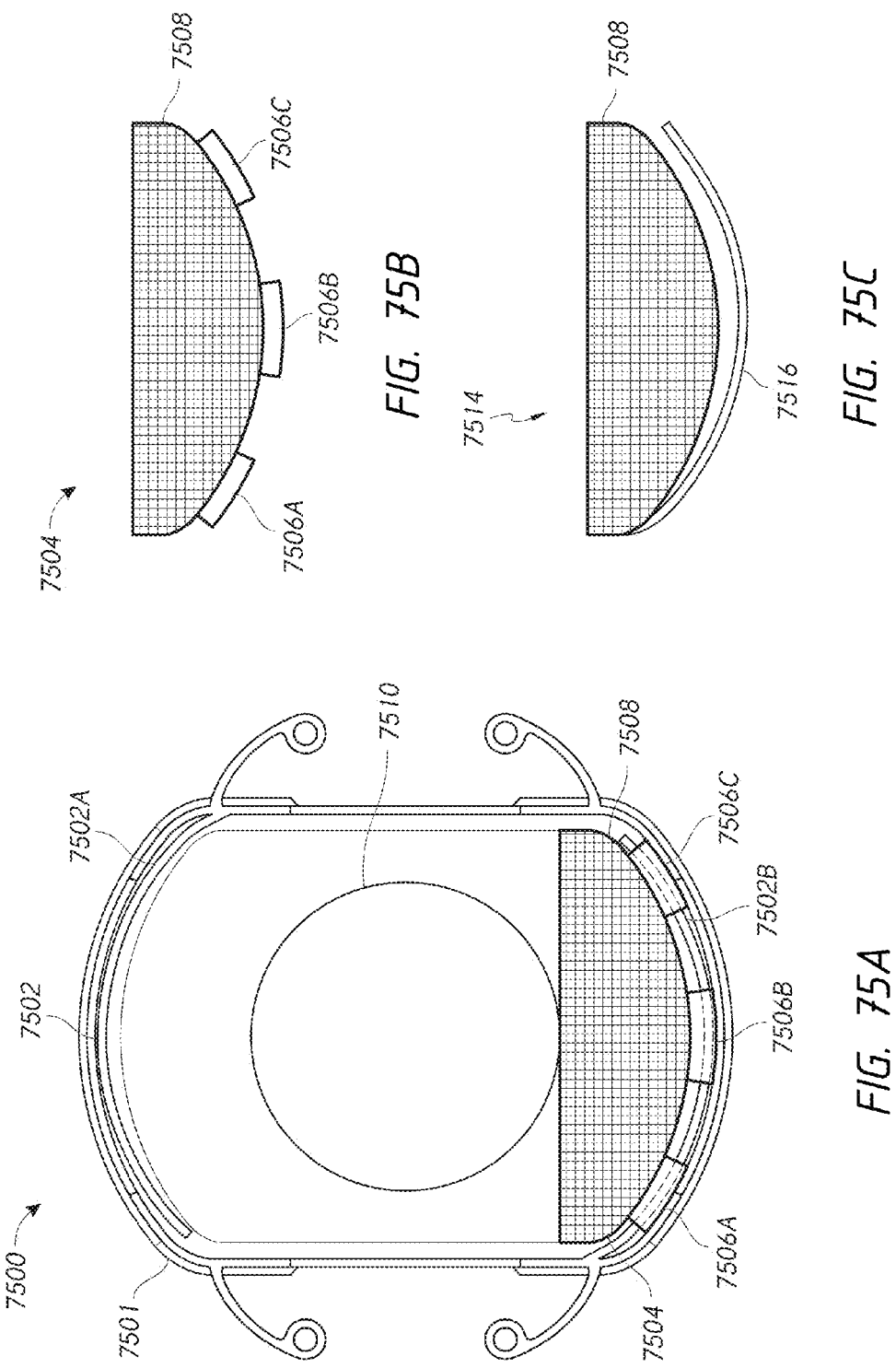

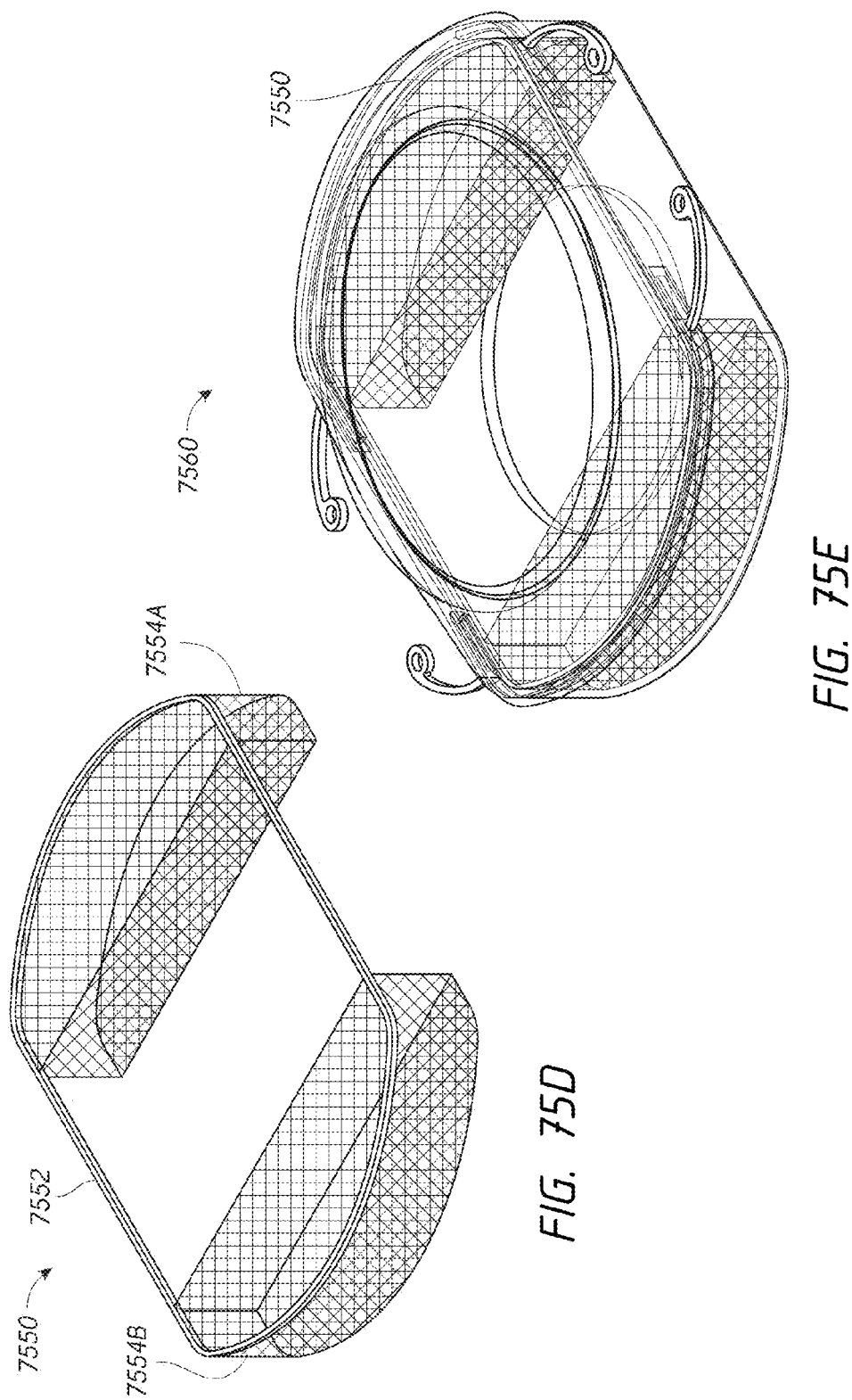

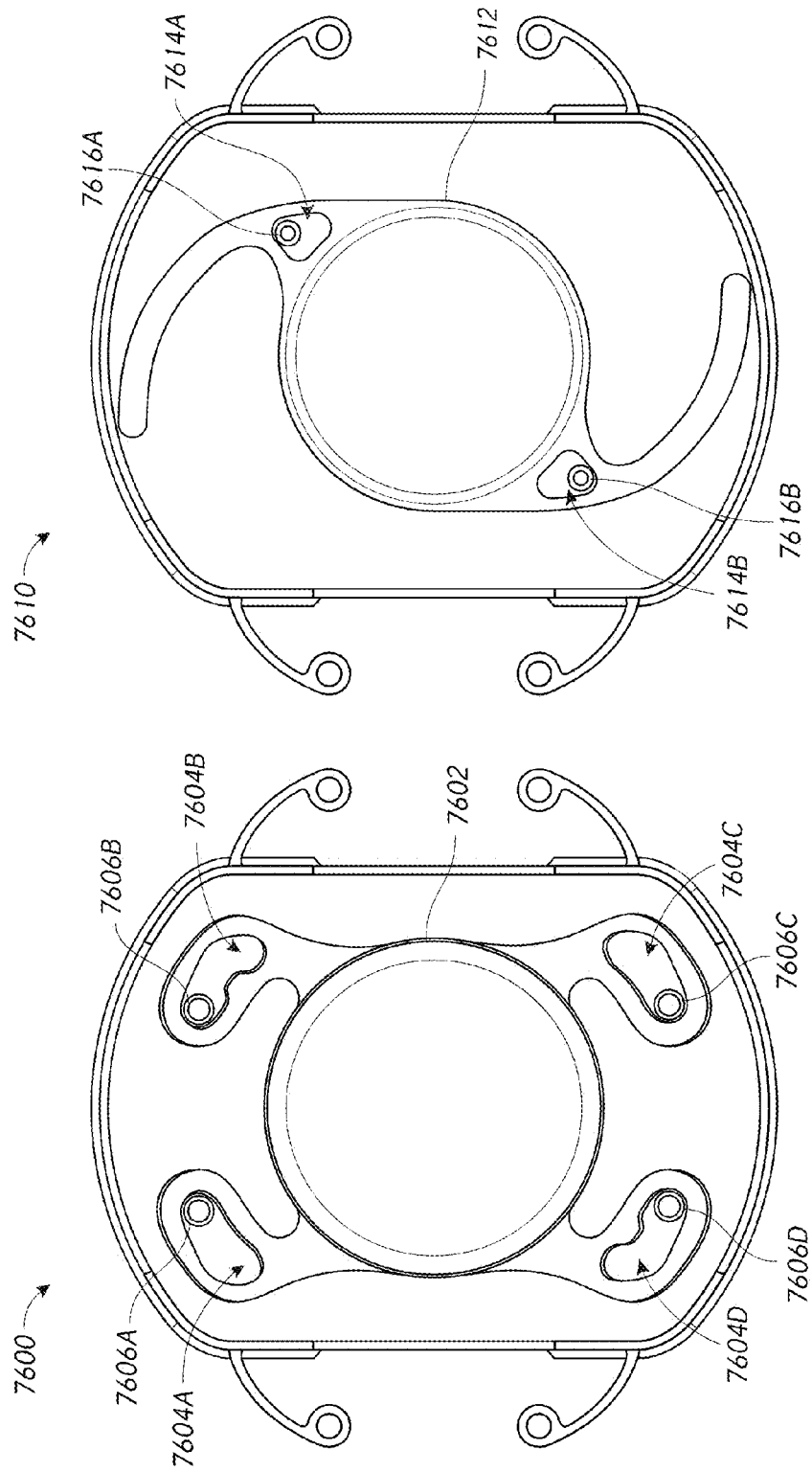

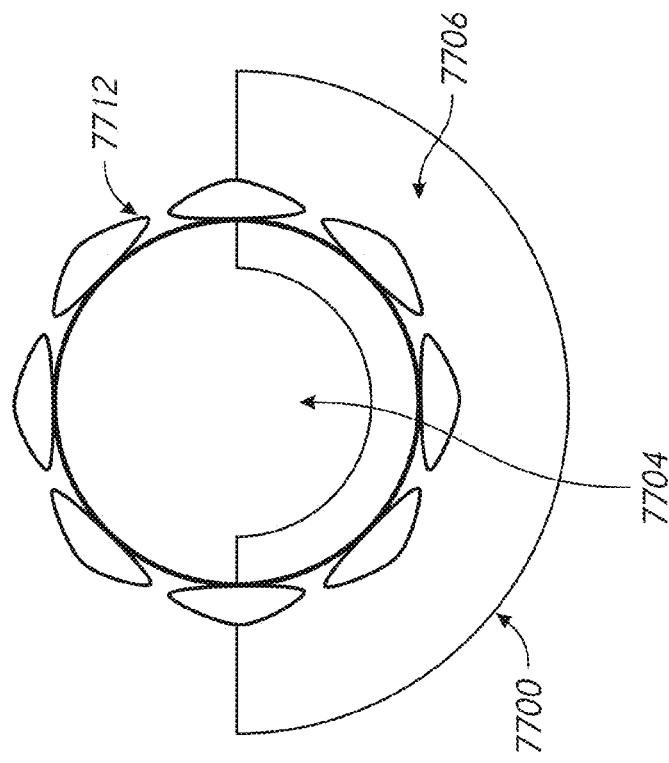
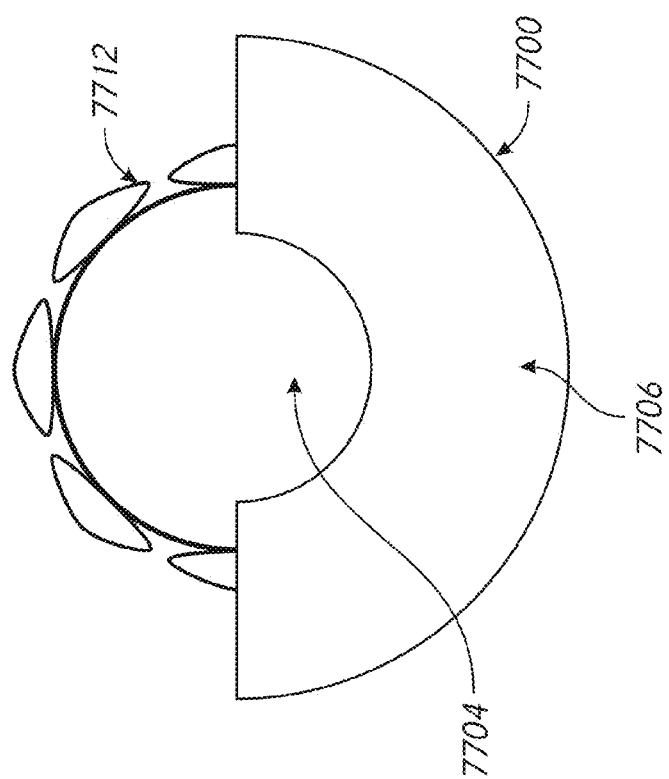
FIG. 77F
FIG. 77E

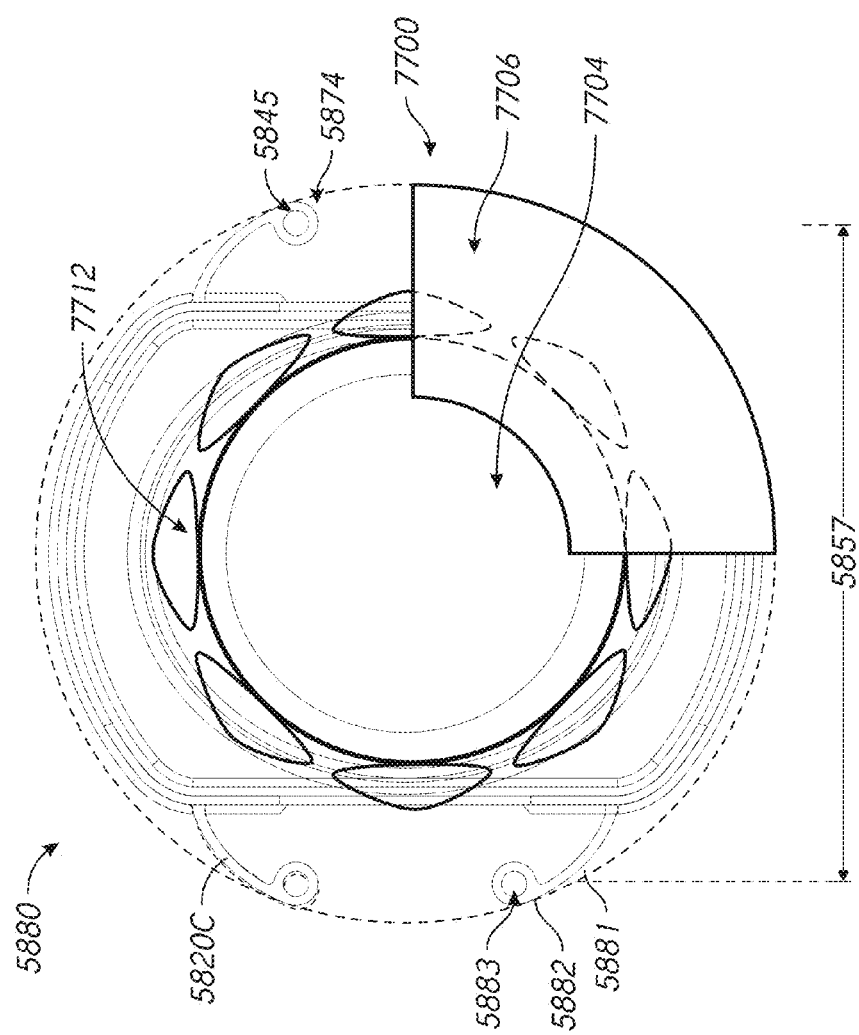

PROSTHETIC CAPSULAR DEVICES, SYSTEMS, AND METHODS

INCORPORATION BY REFERENCE TO ANY PRIORITY APPLICATIONS

This application is a continuation of U.S. patent application Ser. No. 14/968,427, filed Dec. 14, 2015 and issued as U.S. Pat. No. 9,358,103 on Jun. 7, 2016, which claims priority benefit of U.S. Provisional Patent Application No. 62/216,591, filed Sep. 10, 2015, U.S. Provisional Patent Application No. 62/168,493, filed May 29, 2015, and U.S. Provisional Patent Application No. 62/114,231, filed Feb. 10, 2015, each of which is incorporated herein by reference in its entirety. Any and all applications for which a foreign or domestic priority claim is identified in the Application Data Sheet as filed with the present application are hereby incorporated by reference under 37 C.F.R. §1.57.

BACKGROUND

Technical Field

The present application relates to prosthetic capsular devices including wearable electronic technology device(s), and methods for insertion into the eye.

Description of the Art

Cataract surgery is one of the most successfully and most frequently performed surgical procedures in the United States. Each year, millions of people achieve a dramatic improvement in their visual function thanks to this procedure. With the increasing proportion of the U.S. population reaching their retirement years, there is expected to be an almost doubling of the demand for cataract surgery over the next twenty years from 3.3 million to over 6 million annually. In response to the increased demand, more ophthalmologists may be trained and certified to perform cataract surgery, and each trained and certified ophthalmologist may perform more cataract surgeries each year.

In addition to the increase in demand for cataract surgery, technological advances have increased patient expectations for the surgery. The procedure takes a short amount of time to perform, and patients expect quick recovery of visual function. Patients are also asking their ophthalmologist to give them the restoration of more youthful vision without glasses through the use multifocal intraocular lenses, presbyopia correcting lenses, toric lenses, and monovision, to name a few. Despite accurate preoperative measurements and excellent surgical technique, the desired refractive outcome requires a dose of good fortune as there are numerous uncontrolled variables involved. As many as 20-50% of post-operative cataract patients may benefit from glasses or follow-up refractive surgical enhancements to achieve their desired refractive endpoint. The reason for this high amount of refractive unpredictability is believed to be the final resting position of the lens implant in the eye, mathematically expressed as the effective lens position (ELP), which can be quite variable and unpredictable in the current state of cataract surgery. Recently, hundreds of millions of dollars have been invested into developing highly sophisticated femtosecond laser systems that are able to more precisely control the size and shape of the capsulotomy and corneal incisions with the stated goal of lessening the variability of the ELP and thus aiding in better refractive outcomes. Unfortunately, the increased precision of the femtosecond laser systems have not been able to account for the major problem plaguing the variability of the ELP, which is the volumetric difference between the cataract, natural capsular bag, and intraocular lens implant (IOL).

A device and method that helps provide the desired refractive endpoint in cataract surgery is described in PCT Published Patent Application No. WO 2013/126380, Wortz, published on Aug. 29, 2013, which is incorporated herein by reference in its entirety.

All patents and other documents referred to in this application are incorporated by reference herein in their entirety.

SUMMARY

Over the past few years, there has been a major increase in the presence of and reliance on small electronic devices, such as smartphones and related wearable technology, which can provide the user with functions such as internet access, computational ability, computer functionality, e-mail, games, and global positioning system (GPS) function. Some of these devices are being miniaturized and are sometimes worn on the body, such as Google Glass, Microsoft HoloLens, and other head-mounted displays. Additionally, wearable technology that provides biometric data such as blood glucose levels, electrolyte balance, heart rate, electrocardiogram (EKG), intraocular pressure, sensing ciliary muscle contraction for accommodation stimulus, dynamic pupil change, and retinal prostheses have been developed to assist in technology-assisted health care. Such body-mounted devices can be awkward to wear and some users might prefer the positioning of the device in the body. Certain implementations described herein can provide methods and devices for placing an electronic device in the eye.

Certain implementations described herein relate to prosthetic capsular devices (e.g., bags as defined in WO 2013/126380) that can be inserted into an eye. A prosthetic capsular device may comprise an anterior surface including an opening, and a posterior surface. At least a portion of the posterior surface includes or is a refractive surface. The device includes a wearable electronic technology device (e.g., a technology device). The prosthetic capsular device or a system comprising the prosthetic capsular device may include an intraocular lens or features similar to an IOL, such as may be used in cataract surgery to replace the natural lens. The technology device and the intraocular lens may be positioned (e.g., in, around, etc. the prosthetic capsular device) such that the technology device does not interfere with (e.g., block, distort) the sight lines through the intraocular lens.

A retinal prosthesis may be positioned in a prosthetic capsular device, and data collected by the prosthesis may be remotely transmitted to the optic nerve and/or optionally transmitted directly to the visual cortex, for example wirelessly. In some implementations in which the retinal prosthesis can function as the end receptor of light, the retinal prosthesis may interfere with (e.g., block, distort) the sight lines through the IOL.

A method for inserting a wearable technology device (e.g., a technology device) into an eye of a patient may comprise surgically removing a lens or cataract from a natural capsule, leaving the natural capsule in an empty state; inserting a prosthetic capsular device into the eye of the patient (e.g., the prosthetic capsular device including an anterior surface having an opening, and a posterior surface, wherein at least a portion of the posterior surface includes or is a refractive surface); and inserting an electronic technology device into the prosthetic capsular device.

An intraocular lens may also be inserted into the prosthetic capsular device, and may be placed in the prosthetic capsular device such that the technology device does not interfere with (e.g., block, distort) sight lines through the intraocular lens, except optionally in the case of a retinal prosthesis.

In some embodiments, a prosthetic capsular device that is configured to be inserted in an eye comprises a housing structure and a ring structure. The housing structure comprises a first material. The housing structure includes a first flat side, a second flat side opposite the first flat side, a third arcuate side extending between the first end of the first flat side and the first end of the second flat side, a fourth arcuate side extending between the second end of the first flat side and the second end of the second flat side and the fourth arcuate side opposite the third arcuate side, a posterior side, an anterior side opposite the posterior side, and a longitudinal axis. The first flat side includes a first end and a second end. The second flat side includes a first end and a second end. The posterior side includes a refractive surface and a posterior fin. The anterior side includes an opening and a round lip around the opening. The first flat side, the second flat side, the third arcuate side, the fourth arcuate side, the posterior side, and the anterior side at least partially define a cavity configured to contain an intraocular device (e.g., an IOL). The ring structure comprises a second material different than the first material. The ring structure is transverse to the longitudinal axis and at a position along the longitudinal axis. The ring structure includes a first ring structure portion extending from proximate to the first end of the first flat side radially outward and towards the second end of the first flat side, a second ring structure portion extending from proximate to the second end of the first flat side radially outward and towards the first end of the first flat side, a third ring structure portion extending from proximate to the first end of the second flat side radially outward and towards the first end of the second flat side, and a fourth ring structure portion extending from proximate to the second end of the second flat side radially outward and towards the first end of the second flat side. The first ring structure portion is anchored in the first flat side and the third arcuate side. The second ring structure portion is anchored in the first flat side and the fourth arcuate side. The third ring structure portion is anchored in the second flat side and the third arcuate side. The fourth ring structure portion is anchored in the second flat side and the fourth arcuate side. Each of the first ring structure portion, the second ring structure portion, the third ring structure portion, and the fourth ring structure portion includes an anterior-posterior opening (e.g., an eyelet) proximate to a terminal end. The housing structure further comprises a bulge extending radially outward from anchor points of the ring structure. Each of the first flat side, the second flat side, the third arcuate side, and the fourth arcuate side includes a first portion extending parallel to the longitudinal axis from the posterior side towards the anterior side to at least the position of the ring structure along the longitudinal axis and a second portion extending radially inwardly from the first portion towards the lip of the anterior side. The first material may comprise silicone. The second material may comprise polyimide. The refractive surface may have a refractive power between −35 D and +35 D. The opening may be oblong.

In some embodiments, a prosthetic capsular device that is configured to be inserted in an eye comprises a housing structure and a ring structure. The housing structure includes a first flat side, a second flat side opposite the first side, a third arcuate side extending between the first end of the first flat side and the first end of the second flat side, a fourth arcuate side extending between the second end of the first flat side and the second end of the second flat side and the fourth arcuate side opposite the third arcuate side, a posterior side including a refractive surface, an anterior side opposite the posterior side, and a longitudinal axis. The first flat side includes a first end and a second end. The second flat side includes a first end and a second end. The anterior side includes an opening. The first flat side, the second flat side, the third arcuate side, the fourth arcuate side, the posterior side, and the anterior side at least partially define a cavity configured to contain an intraocular device (e.g., an IOL). The ring structure includes a first ring structure portion extending from proximate to the first end of the first flat side radially outward and towards the second end of the first flat side, a second ring structure portion extending from proximate to the second end of the first flat side radially outward and towards the first end of the first flat side, a third ring structure portion extending from proximate to the first end of the second flat side radially outward and towards the first end of the second flat side, and a fourth ring structure portion extending from proximate to the second end of the second flat side radially outward and towards the first end of the second flat side. The housing structure may comprise a first material. The ring structure may comprise a second material different than the first material. The first material may comprise silicone. The second material may comprise polyimide. The refractive surface may have a refractive power between −35 D and +35 D. One, two, three, or each of the first flat side, the second flat side, the third arcuate side, and the fourth arcuate side may include a portion extending parallel to the longitudinal axis from the posterior side towards the anterior side. One, two, three, or each of the first flat side, the second flat side, the third arcuate side, and the fourth arcuate side may include a second portion extending radially inwardly from the first portion towards the opening of the anterior side. The housing structure may comprise a bulge extending radially outward from anchor points of the ring structure. One, two, three, or each of the first ring structure portion, the second ring structure portion, the third ring structure portion, and the fourth ring structure portion may include an anterior-posterior opening (e.g., an eyelet) proximate to a terminal end.

In some embodiments, a prosthetic capsular device that is configured to be inserted in an eye comprises a housing structure and a ring structure. The housing structure includes a first side, a second side opposite the first side, a third side extending between the first end of the first side and the first end of the second side, a fourth side extending between the second end of the first side and the second end of the second side and the fourth side opposite the third side, a posterior side including a refractive surface, an anterior side opposite the posterior side, and a longitudinal axis. The first side includes a first end and a second end. The second side includes a first end and a second end. The anterior side includes an opening. The first side, the second side, the third side, the fourth side, the posterior side, and the anterior side at least partially define a cavity configured to contain an intraocular device (e.g., an IOL). The ring structure includes a ring structure portion extending radially outward from proximate one of the first end of the first side, the second end of the first side, the first end of the second side, and the second end of the second side. The housing structure may comprise a first material. The ring structure may comprise a second material different than the first material. The first material may comprise silicone. The second material may comprise polyimide. The refractive surface may have a refractive power between −35 D and +35 D. The opening may be oblong. The device may further comprise a lip around the opening. One, two, three, or each of the first side, the second side, the third side, and the fourth side may include a portion extending parallel to the longitudinal axis from the posterior side towards the anterior side. One, two, three, or each of the first side, the second side, the third side, and the fourth side may include a second portion extending radially inwardly from the first portion towards the opening of the anterior side. The posterior side may comprise a posterior fin. The housing structure may comprise a bulge extending radially outward from anchor points of the ring structure. The ring structure may comprise a plurality of ring structure portions including the ring structure portion. The ring structure portion may be a first ring structure portion extending from proximate to the first end of the first flat side radially outward and towards the second end of the first flat side. The plurality of ring structure portions may include a second ring structure portion extending from proximate to the second end of the first flat side radially outward and towards the first end of the first flat side, a third ring structure portion extending from proximate to the first end of the second flat side radially outward and towards the first end of the second flat side, and a fourth ring structure portion extending from proximate to the second end of the second flat side radially outward and towards the first end of the second flat side. The ring structure portion may include an anterior-posterior opening (e.g., an eyelet) proximate to a terminal end.

The methods summarized above and set forth in further detail below may describe certain actions taken by a practitioner; however, it should be understood that these steps can also include the instruction of those actions by another party. Thus, actions such as "inserting an intraocular lens into a prosthetic capsular device" include "instructing the insertion of an intraocular lens into a prosthetic capsular device."

BRIEF DESCRIPTION OF THE DRAWINGS

A better understanding of the devices and methods described herein will be appreciated upon reference to the following description in conjunction with the accompanying drawings, wherein:

FIG. 12A depicts a cross-sectional view of an eye including an example prosthetic capsular device containing including both a technology device and an IOL;

FIG. 12B depicts a front view of an example intraocular lens usable in the example prosthetic capsular device shown in FIG. 12A in which the technology device surrounds the outer edge of the IOL (e.g., surrounds the outer edge of the optical surface of the IOL);

FIG. 12C depicts a top front perspective of the example intraocular lens of FIG. 12B;

FIGS. 48A-48E are photographs of animal study results for a left eye of the second rabbit;

FIGS. 49A-49E are photographs of animal study results for a right eye of a third rabbit;

FIGS. 50A-50E are photographs of animal study results for a left eye of the third rabbit;

FIGS. 51A-51E are photographs of animal study results for a right eye of a fourth rabbit;

FIGS. 53A-53E are photographs of animal study results for a right eye of a fifth rabbit;

FIGS. 54A-54E are photographs of animal study results for a left eye of the fifth rabbit;

FIG. 57C illustrates a cross-sectional view of the example kit of FIG. 57A along the line 57C-57C of FIG. 57B;

FIG. 59A illustrates a side view of an example prosthetic capsular device;

FIGS. 59B and 59C illustrate an example method of use of the example prosthetic capsular device of FIG. 59A FIGS. 60A-60N illustrate an example method of loading and ejecting the example prosthetic capsular device of FIG. 58E;

FIG. 61A illustrates an anterior side perspective view of an example prosthetic capsular device;

FIG. 61B illustrates an anterior plan view of the example prosthetic capsular device of FIG. 61A;

FIG. 61C illustrates a side view of the example prosthetic capsular device of FIG. 61A;

FIG. 61D illustrates a side view of an example prosthetic capsular device;

FIG. 63A illustrates an anterior side perspective view of an example prosthetic capsular device;

FIG. 63B illustrates an anterior plan view of the example prosthetic capsular device of FIG. 63A;

FIG. 63C illustrates a side view of the example prosthetic capsular device of FIG. 63A;

FIG. 65A illustrates an anterior side perspective view of an example prosthetic capsular device;

FIG. 65B illustrates an anterior plan view of the example prosthetic capsular device of FIG. 65A;

FIG. 65C illustrates a side view of the example prosthetic capsular device of FIG. 65A;

FIG. 66A illustrates an anterior side perspective view of an example prosthetic capsular device;

FIG. 66B illustrates an anterior plan view of the example prosthetic capsular device of FIG. 66A;

FIG. 66C illustrates a side view of the example prosthetic capsular device of FIG. 66A;

FIG. 67A illustrates an anterior side perspective view of an example prosthetic capsular device;

FIG. 67B illustrates an anterior plan view of the example prosthetic capsular device of FIG. 67A;

FIG. 67C illustrates a side view of the example prosthetic capsular device of FIG. 67A;

FIG. 68A illustrates an anterior side perspective view of an example prosthetic capsular device;

FIG. 68B illustrates an anterior plan view of the example prosthetic capsular device of FIG. 68A;

FIG. 68C illustrates a side view of the example prosthetic capsular device of FIG. 68A;

Figures 70A, 70B, 70C:
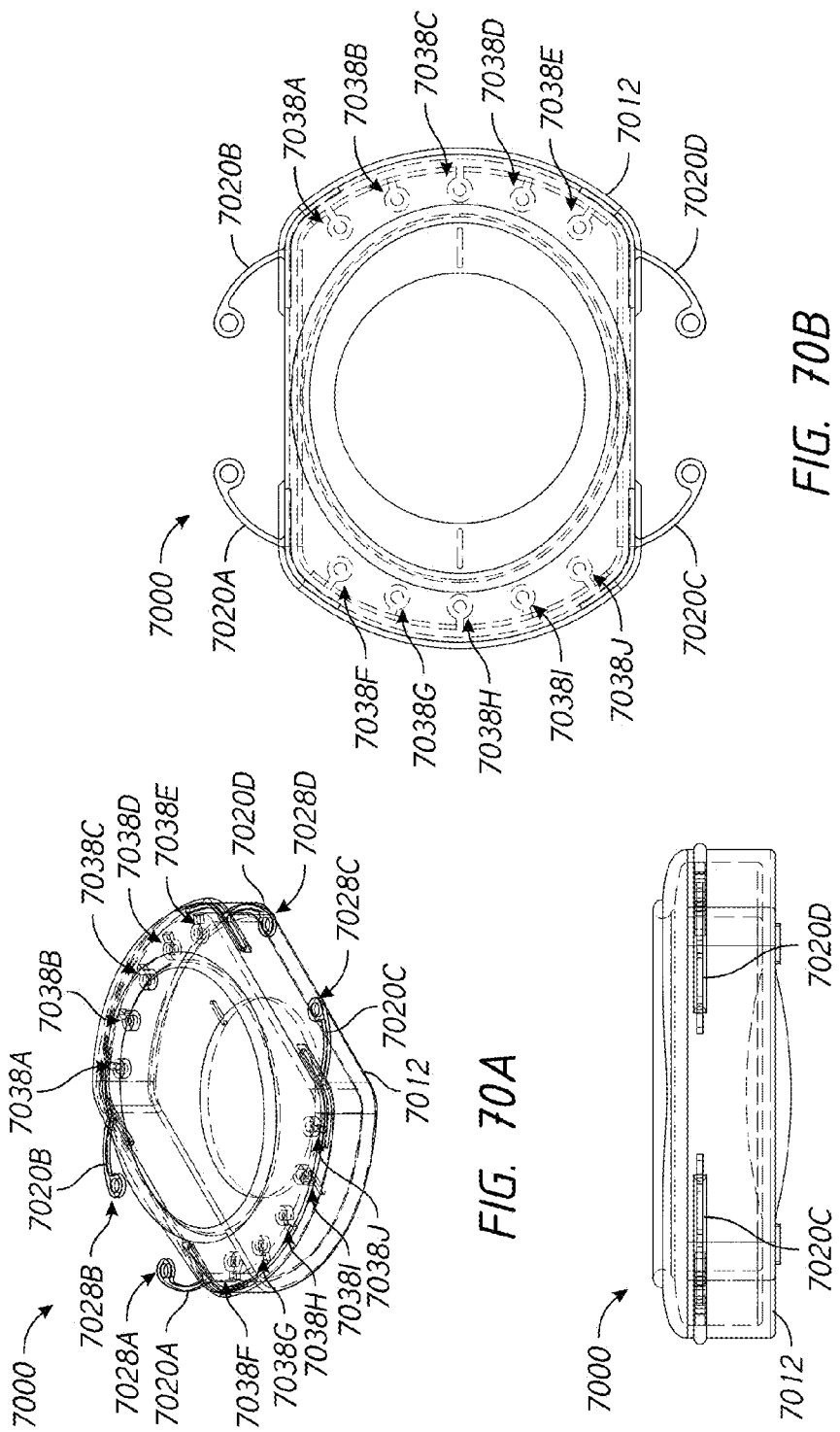
Figure 73A:
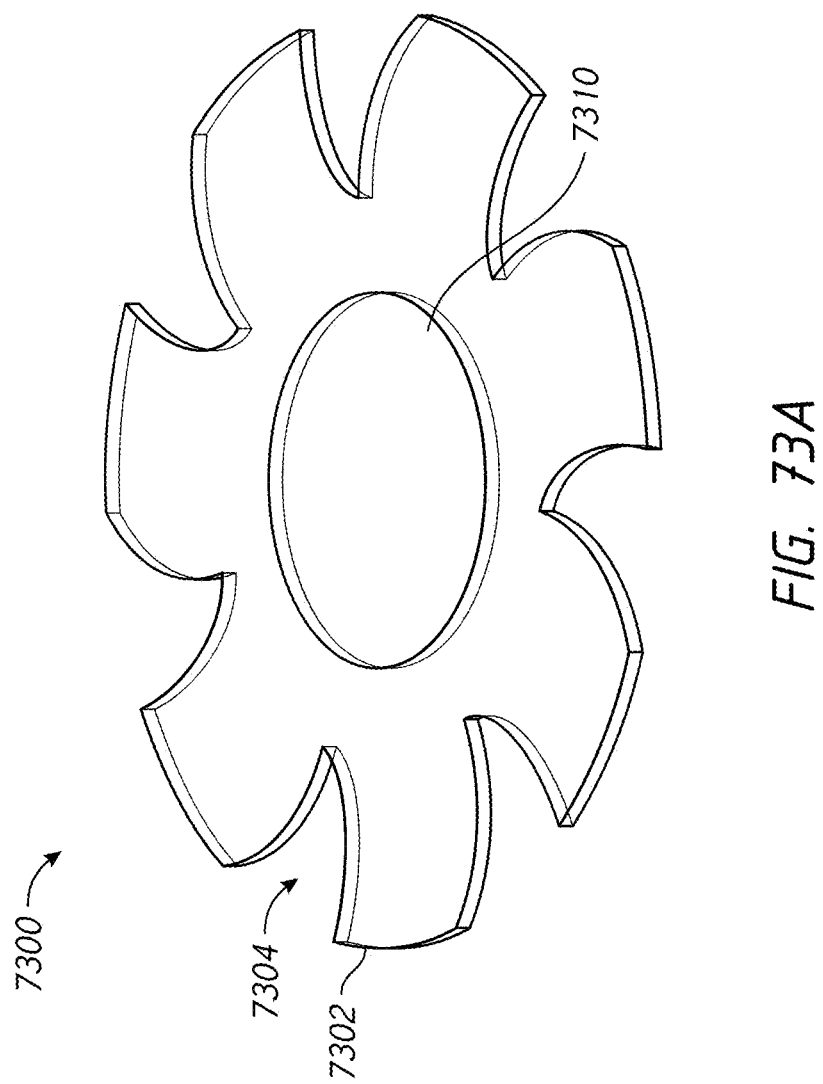
Figure 73B:
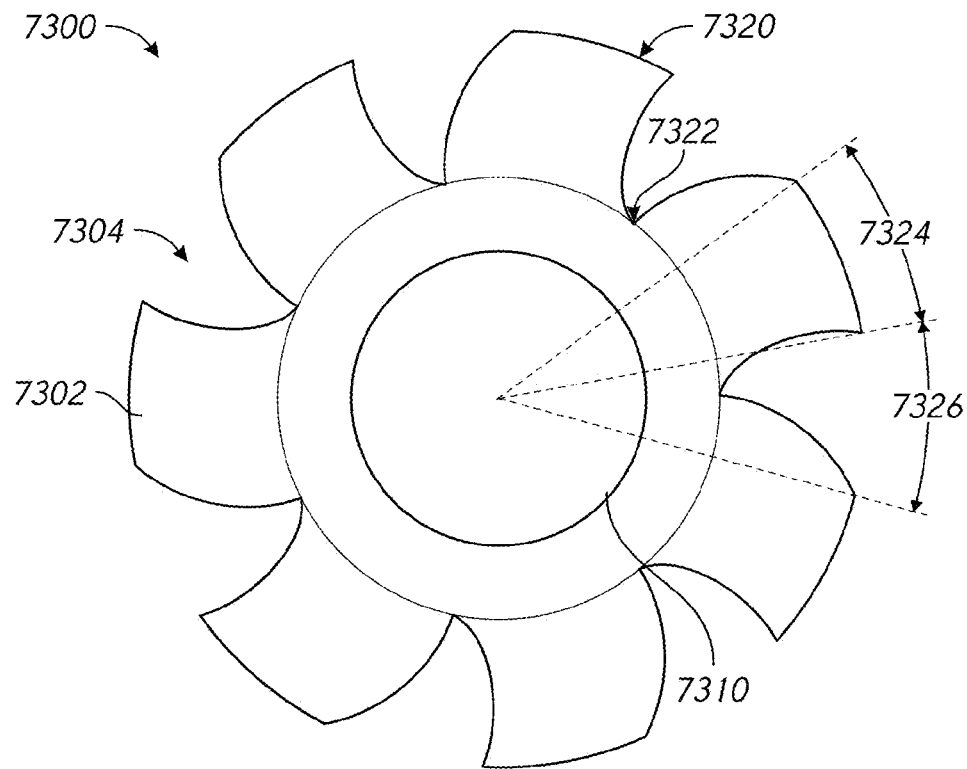
Figure 73C:
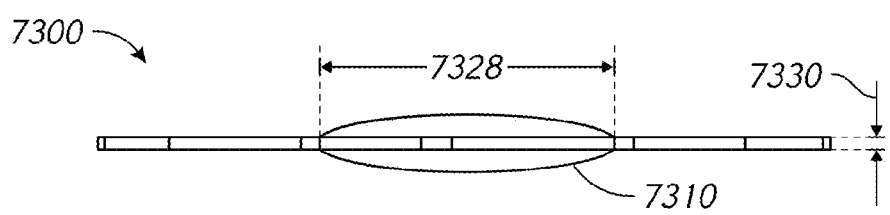
Figure 73E:
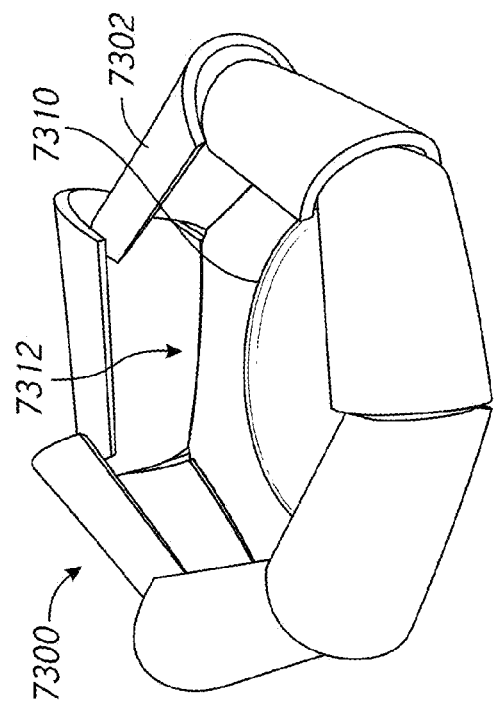
Figure 73D:
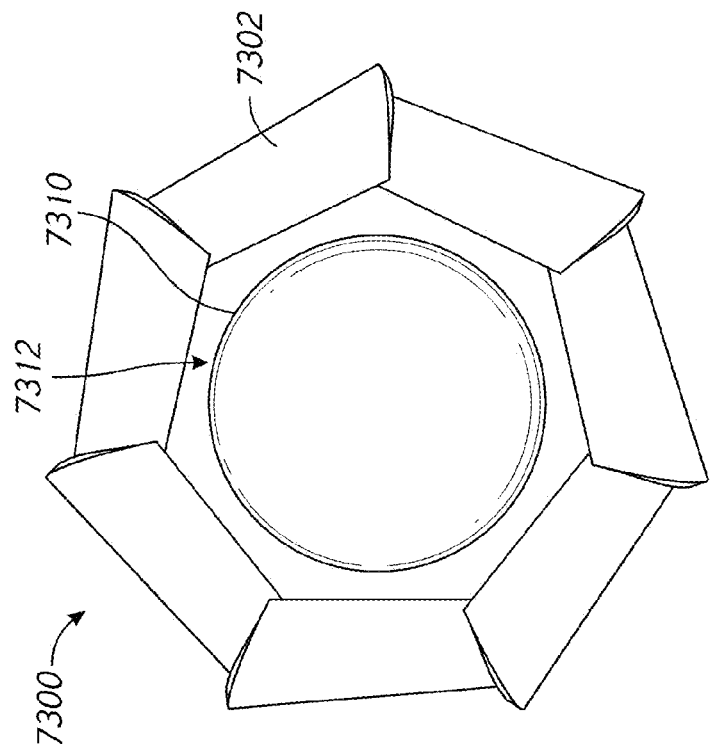
Figure 74A:
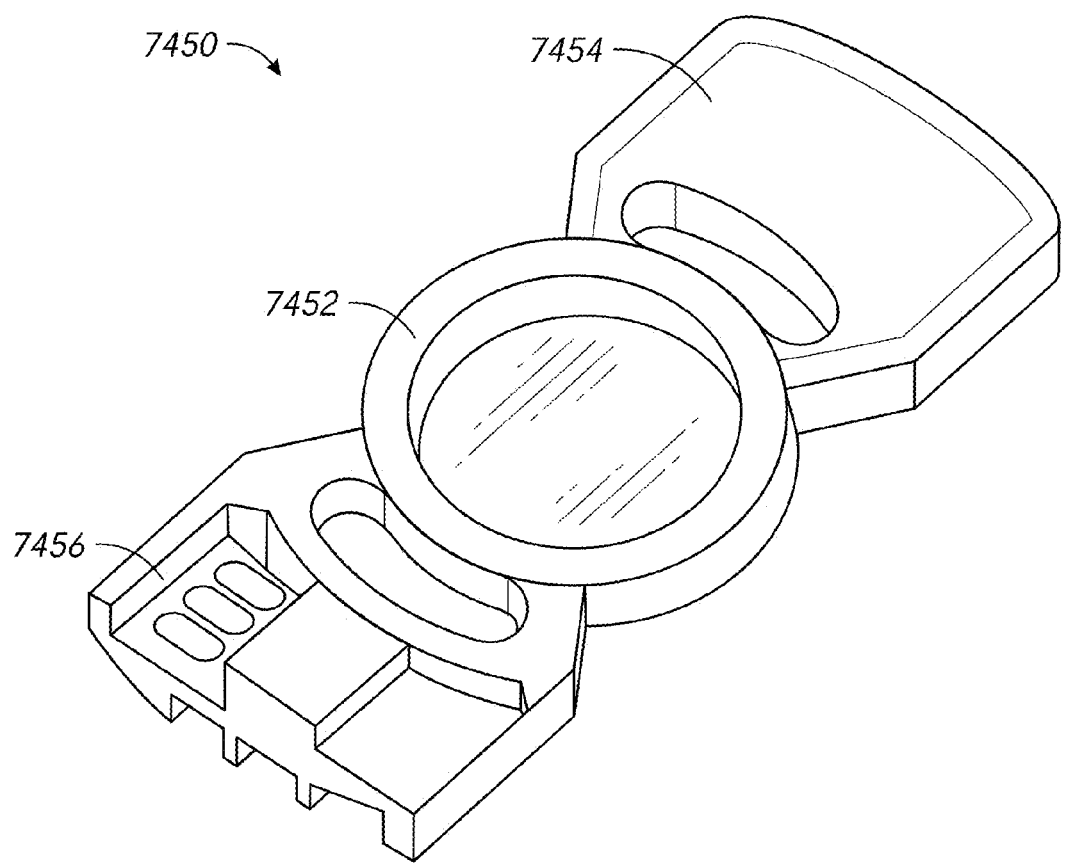
Figure 74D:
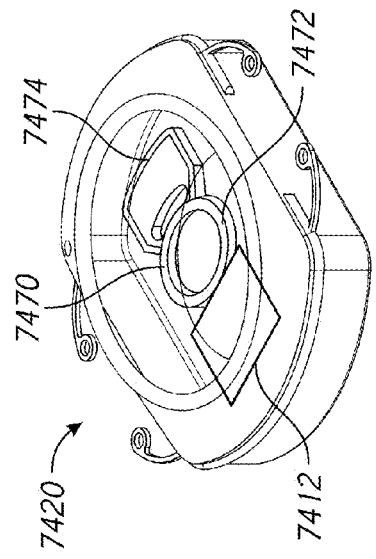
Figure 74E:
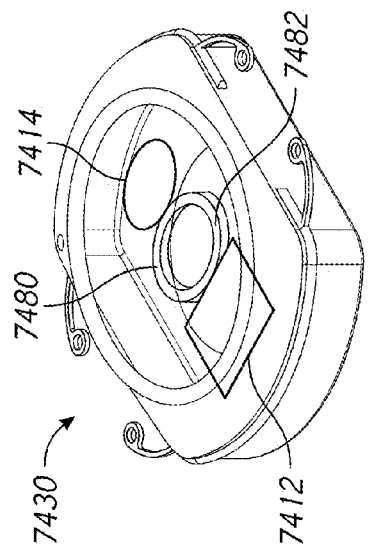
Figure 74B:
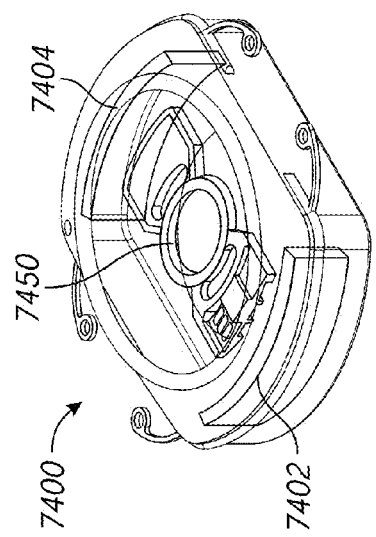
Figure 74C:
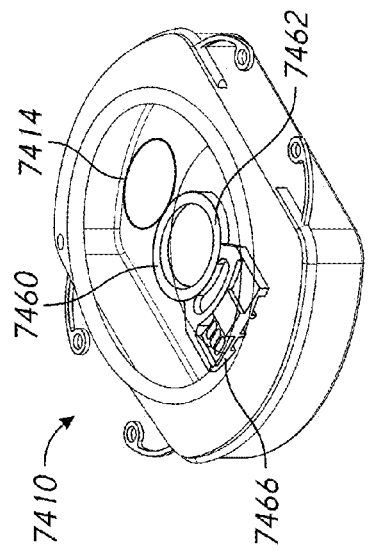
Figure 76D:
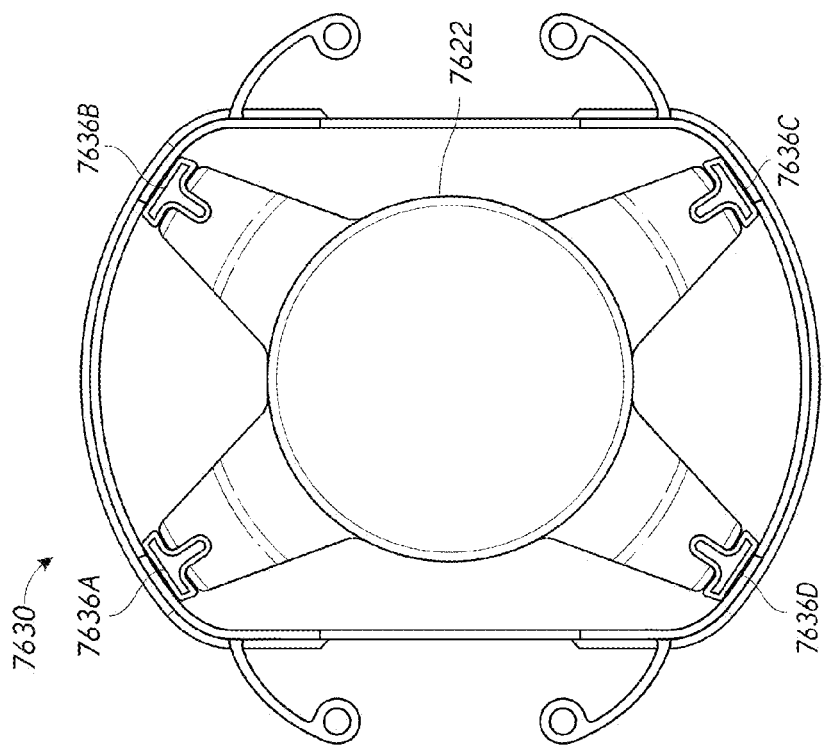
Figure 76C:
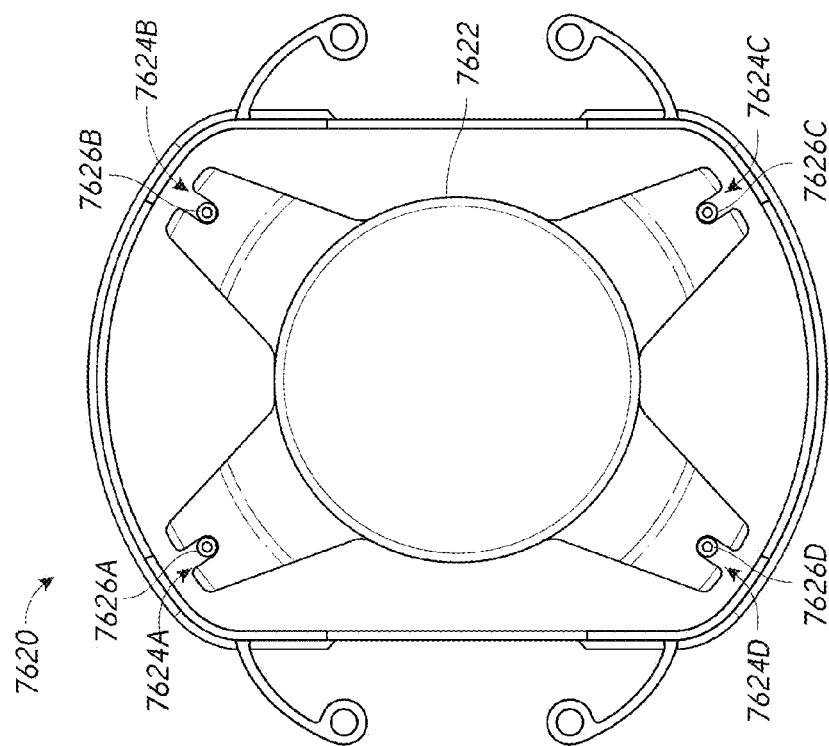
Figure 76F:
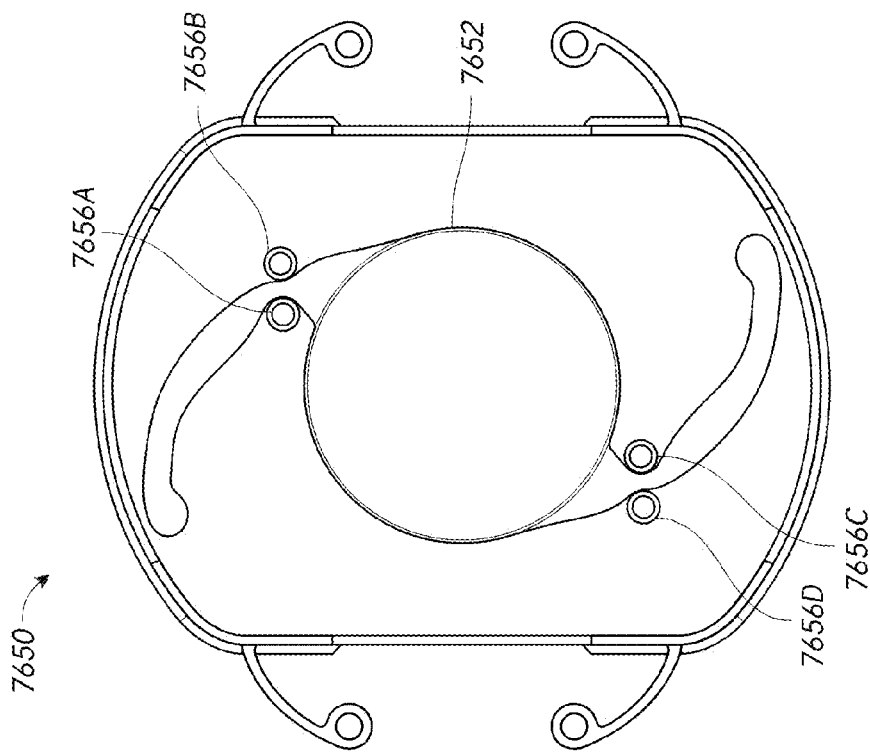
Figure 76E:
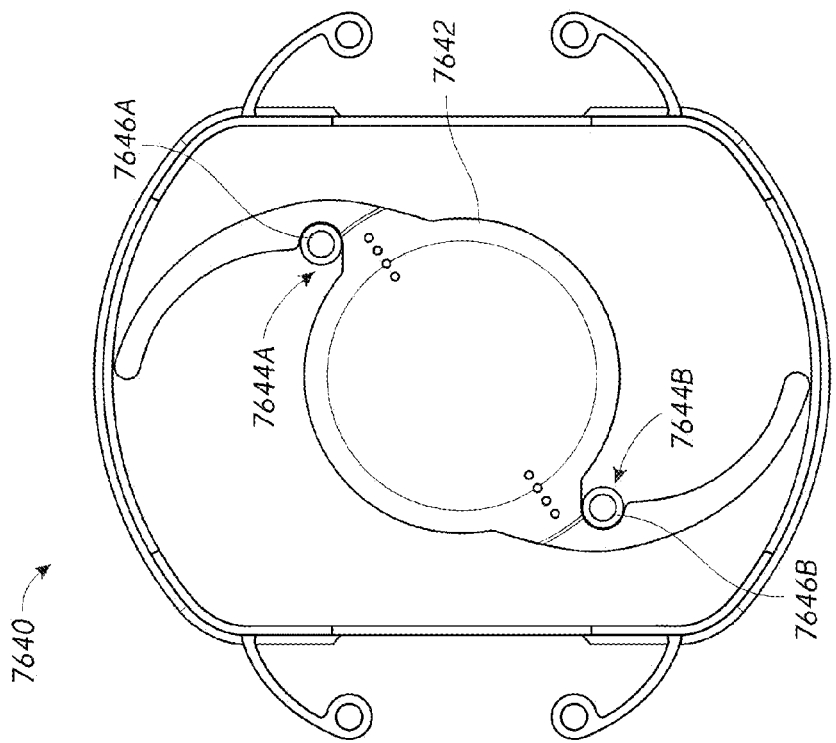
Figure 77B:
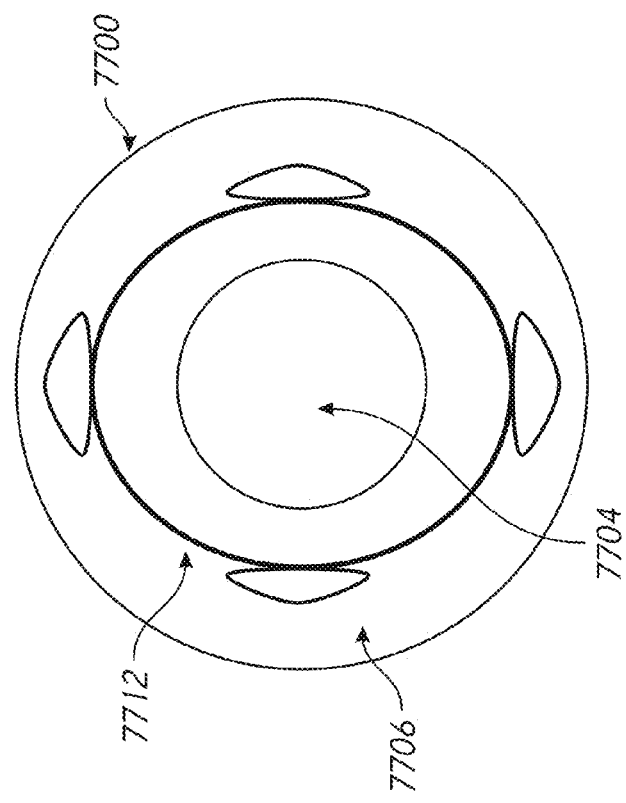
Figure 77A:
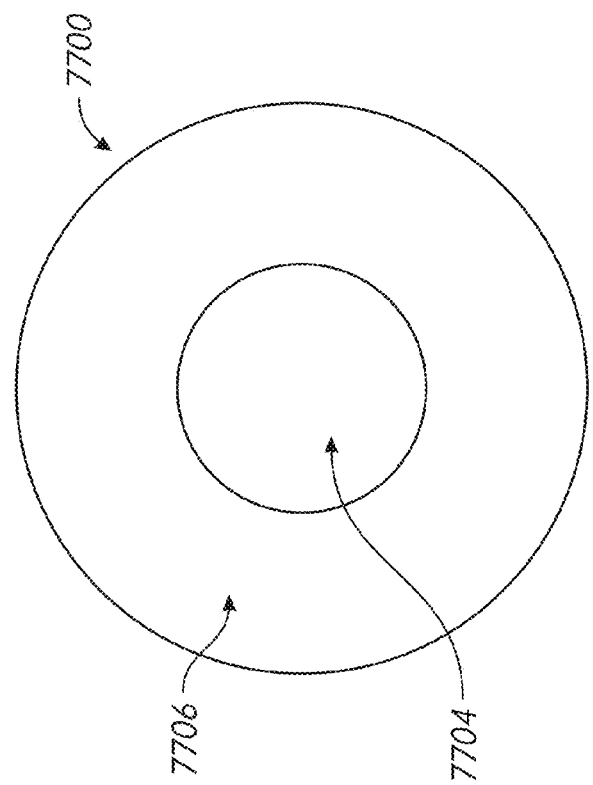
Figure 77C:
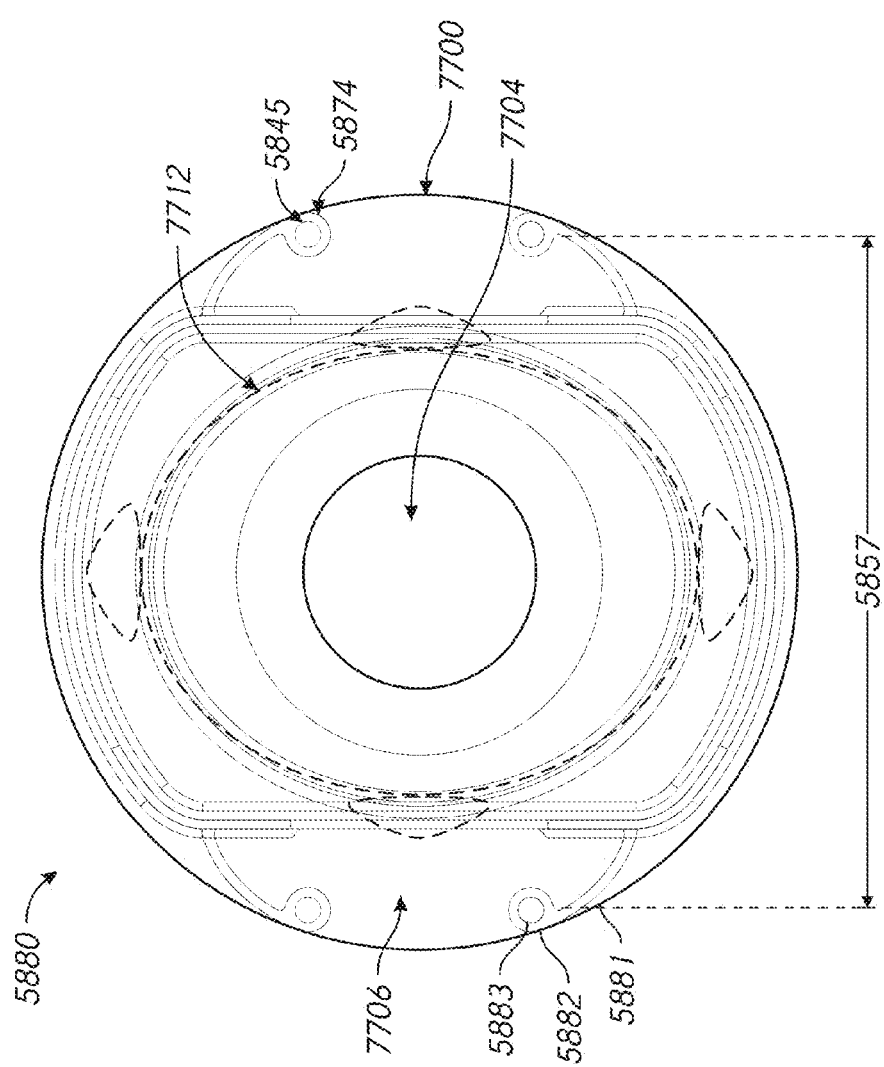
Figure 77D:
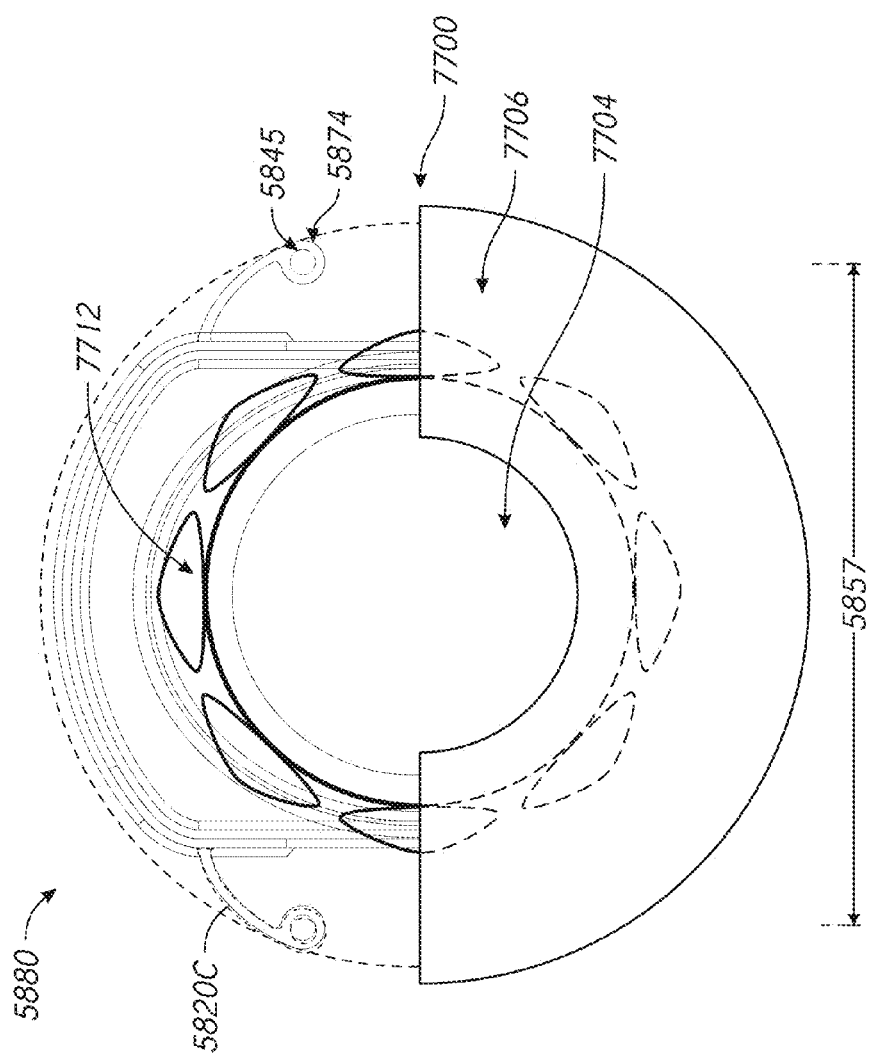
Figure 77H:
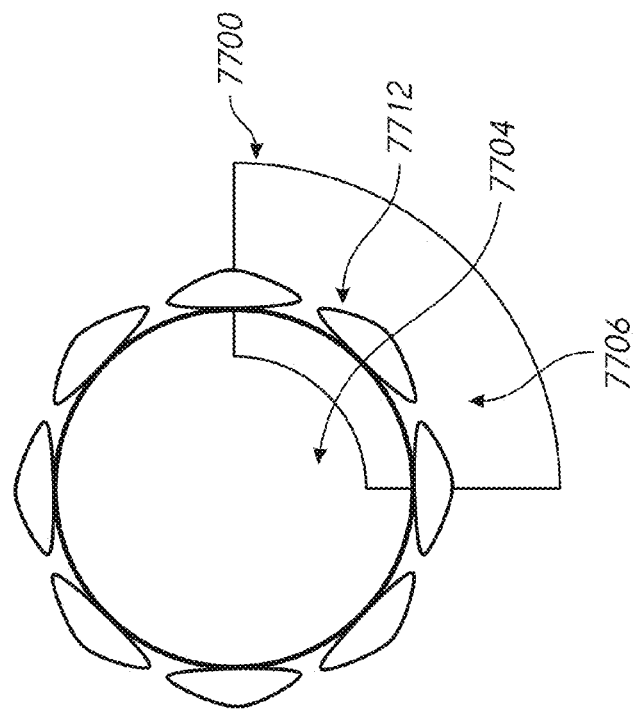
Figure 77G:
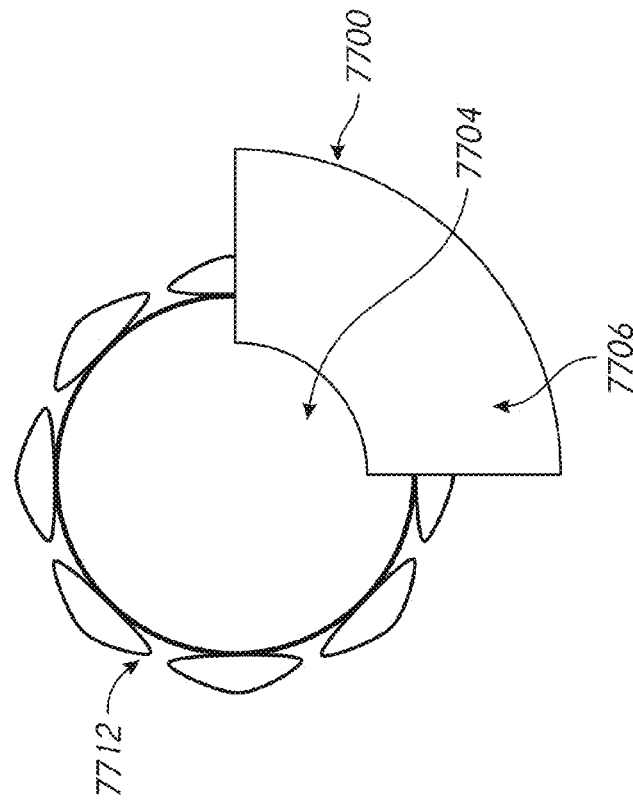

FIG. 68D illustrates a side view of an example prosthetic capsular device system including the example prosthetic capsular device of FIG. 68A;

FIG. 69A illustrates an anterior side perspective view of an example prosthetic capsular device;

FIG. 69B illustrates an anterior plan view of the example prosthetic capsular device of FIG. 69A;

FIG. 69C illustrates a side view of the example prosthetic capsular device of FIG. 69A;

FIG. 69D illustrates a side view of an example prosthetic capsular device system including the example prosthetic capsular device of FIG. 69A;

FIG. 70A illustrates an anterior side perspective view of an example prosthetic capsular device;

FIG. 70B illustrates an anterior plan view of the example prosthetic capsular device of FIG. 70A;

FIG. 70C illustrates a side view of the example prosthetic capsular device of FIG. 70A;

FIG. 71A illustrates a perspective view of an example device for coupling to a prosthetic capsular device;

FIG. 71B illustrates an example coupling of the example device of FIG. 71A with an example portion of a prosthetic capsular device;

FIG. 71C illustrates an example coupling of an example device with an example portion of a prosthetic capsular device;

FIG. 71D illustrates an example coupling of an example device with an example portion of a prosthetic capsular device;

FIG. 72A illustrates an anterior side perspective view of an example prosthetic capsular device;

FIG. 72B illustrates a magnified side view of an example portion of the example prosthetic capsular device of FIG. 71B;

FIG. 73A illustrates an anterior side perspective view of an example prosthetic capsular device in an unfolded state;

FIG. 73B illustrates an anterior plan view of the example prosthetic capsular device of FIG. 73A in an unfolded state;

FIG. 73C illustrates a side view of the example prosthetic capsular device of FIG. 73A in an unfolded state;

FIG. 73D illustrates an anterior plan view of the example prosthetic capsular device of FIG. 73A in a folded state;

FIG. 73E illustrates an anterior side perspective view of the example prosthetic capsular device of FIG. 73A in a folded state;

FIG. 74A illustrates an anterior side perspective view of an example intraocular lens;

FIG. 74B illustrates an anterior side perspective view of an example prosthetic capsular device containing the intraocular lens of FIG. 74A;

FIG. 74C illustrates an anterior side perspective view of an example prosthetic capsular device containing an example intraocular lens;

FIG. 74D illustrates an anterior side perspective view of an example prosthetic capsular device containing an example intraocular lens;

FIG. 74E illustrates an anterior side perspective view of an example prosthetic capsular device containing an example intraocular lens;

FIG. 75A illustrates an anterior plan view of an example prosthetic capsular device system;

FIG. 75B illustrates an anterior plan view of an example medicament delivery device of the prosthetic capsular device system of FIG. 75A;

FIG. 75C illustrates an anterior plan view of another example medicament delivery device of a prosthetic capsular device system;

FIG. 75D illustrates an anterior side perspective view of another example medicament delivery device of a prosthetic capsular device system;

FIG. 75E illustrates an anterior side perspective view of an example prosthetic capsular device system including the medicament delivery device of FIG. 75D;

FIG. 76A illustrates an anterior plan view of an example prosthetic capsular device;

FIG. 76B illustrates an anterior plan view of an example prosthetic capsular device;

FIG. 76C illustrates an anterior plan view of an example prosthetic capsular device;

FIG. 76D illustrates an anterior plan view of an example prosthetic capsular device;

FIG. 76E illustrates an anterior plan view of an example prosthetic capsular device;

FIG. 76F illustrates an anterior plan view of an example prosthetic capsular device;

FIG. 77A illustrates an anterior plan view of an example prosthetic iris device;

FIG. 77B illustrates a posterior plan view of the example prosthetic iris device of FIG. 77A;

FIG. 77C illustrates a plan view of the example prosthetic iris device of FIG. 77A coupled to an example prosthetic capsular device disclosed herein;

FIG. 77D illustrates a plan view of an example prosthetic iris device coupled to an example prosthetic capsular device disclosed herein;

FIG. 77E illustrates an anterior plan view of an example prosthetic iris device;

FIG. 77F illustrates a posterior plan view of the example prosthetic iris device of FIG. 77E;

FIG. 77G illustrates an anterior plan view of an example prosthetic iris device;

FIG. 77H illustrates a posterior plan view of the example prosthetic iris device of FIG. 77G; and FIG. 77I illustrates a plan view of the example prosthetic iris device of FIG. 77G coupled to an example prosthetic capsular device disclosed herein.

The patent or application file contains at least one drawing executed in color. Copies of this patent or patent application publication with color drawing(s) will be provided by the Office upon request and payment of the necessary fee.

DETAILED DESCRIPTION

Some prosthetic capsular enclosure devices (e.g., prosthetic capsular bags) that can be used in the eye can hold at least one of a technology device (e.g., an electronic technology device (e.g., a wearable electronic technology device (e.g., a miniaturized wearable electronic technology device))) and an intraocular lens.

Examples of preferred prosthetic capsular devices that may be compatible with certain implementations described herein are disclosed in PCT Published Patent Application No. WO 2013/126380, which is incorporated herein by reference in its entirety. Some preferred prosthetic capsular devices are described herein.

Figure 2:
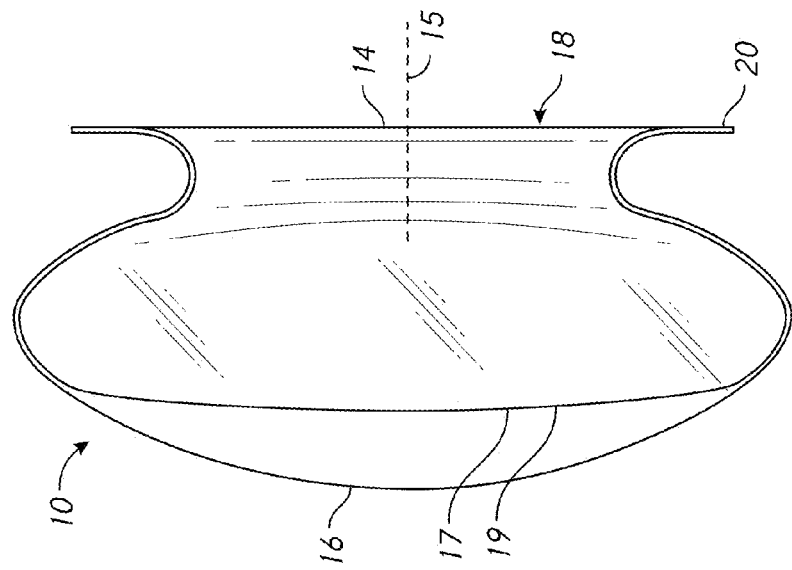
FIG. 2 depicts a side view of the example prosthetic capsular device shown in FIG. 1.
Figure 1:
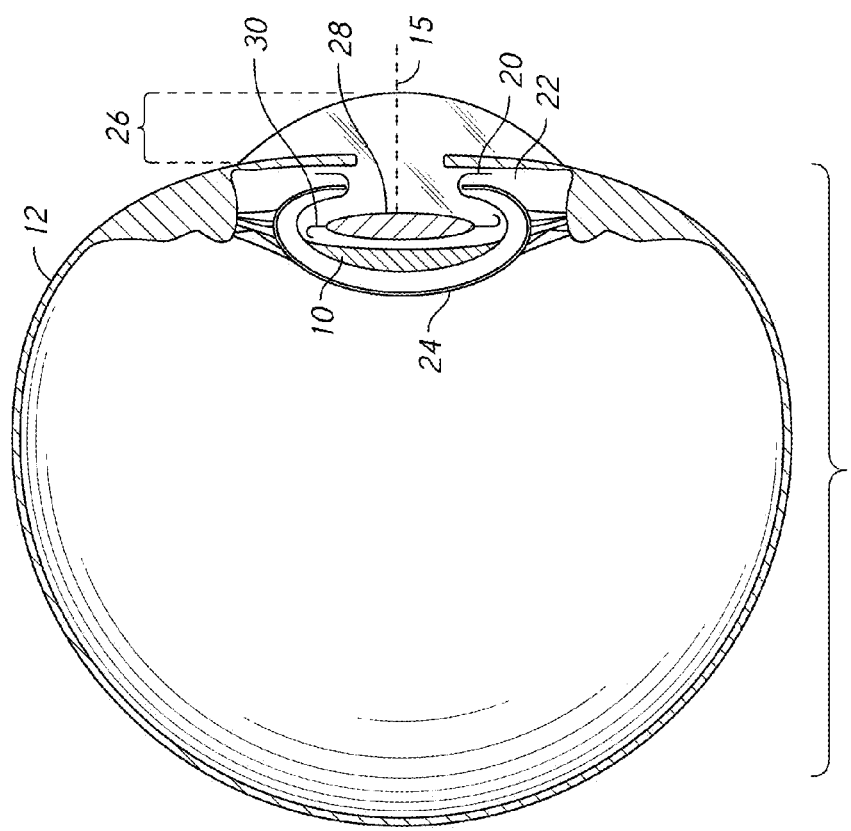
FIG. 1 depicts a cross-sectional side view of an eye including an example of a prosthetic capsular device including an IOL.
Figure 3:
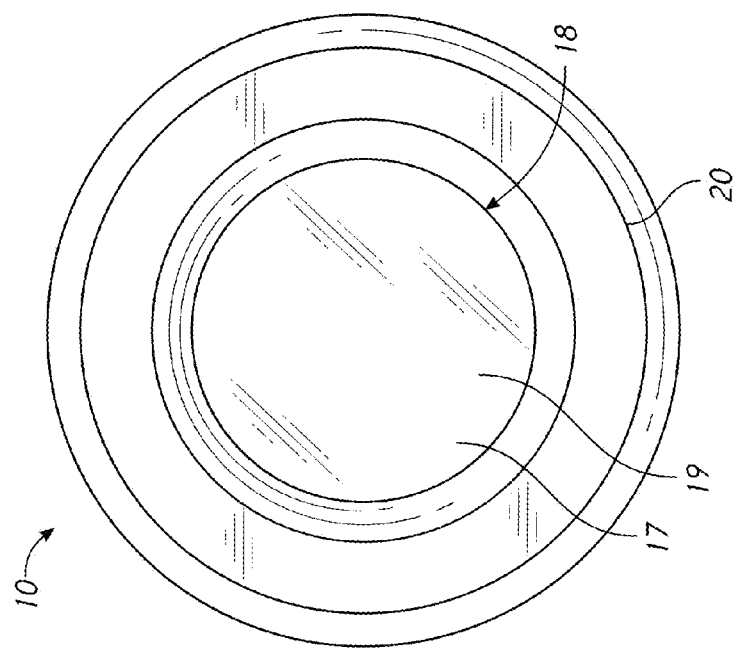
FIG. 3 depicts an anterior plan view of the example prosthetic capsular device shown in FIG. 1.

With reference to FIGS. 1-3, a prosthetic capsular device or PPL-C 10 is shown approximating the size, shape, and volume of a natural human lens. The dimensions of the prosthetic capsular device 10 may be variable, so that physicians may order an implant that most closely matches the lens of the eye 12 being operated on. The human lens varies in thickness from about 3.5 millimeters (mm) to about 5.5 mm. A natural lens tends to be thicker in more hyperopic eyes and thinner in more myopic eyes. A natural lens thickens over time, and increased age is associated with a thicker lens on average. The diameter of the human lens is about 9 mm. In some implementations, the prosthetic capsular device 10 comprises a substantially discoid (e.g., a substantially flat, substantially circular disc) and/or spheroid (e.g., prolate spheroid, oblate spheroid) shape having a thickness between about 1.5 mm and about 5.5 mm (e.g., about 2.5 mm) and a diameter between about 8.5 mm and about 10 mm (e.g., about 9 mm). For purposes of clarity, the thickness of the prosthetic capsular device 10 is the distance between the anterior surface 14 and posterior surface 16 of the prosthetic capsular device 10 along the visual axis 15 (FIG. 2), for example in contrast with the thickness of walls of the device 10. The anterior surface 14 includes an arcuate (e.g., circular, oval) opening 18 having a diameter between about 5 mm and about 7 mm (e.g., about 6 mm), and has an exterior contour, such as, for example, a flange 20 (e.g., having a thickness between about 0.5 mm and about 1.5 mm (e.g., about 1 mm), substantially surrounding (e.g., surrounding) and extending radially outwardly from the opening 18. The flange 20 can assist in stabilization and/or centration of the prosthetic capsular device 10 by extending into and fitting in the ciliary sulcus 22 (FIG. 1). The flange 20 may lack or be substantially free of perforations, which may increase stability and apposition surface area of the flange 20. The prosthetic capsular device 10 may be dimensioned to fit precisely in a capsulorhexis created by a femtosecond laser.

At least a portion of the inner face or side 17 of the posterior surface or portion 16 of the prosthetic capsular device 10 may comprise a refractive surface, which may, for example, allow a pseudophakic refraction to be performed intraoperatively with a known lens already inside the eye 12, e.g., the posterior refractive surface 19. In the implementation shown in FIGS. 1-3, substantially the entire inner face 17 comprises a low power refractive surface (e.g., about +1 diopter (D)). While the posterior refractive surface 19 is generally discussed herein in terms of a +1 D surface, the posterior refractive surface 19 may comprise any and all lens powers and designs that are currently known in the art of intraocular lenses, including, but not limited to: spherical, aspheric, wavefront, convex, concave, multifocal (diffractive, refractive, zonal), toric, accommodative, ultraviolet (UV) filtering, diffractive chromatic aberration reducing lenses, light adjustable lenses (ultraviolet light adjustable, femtosecond phase wrapping), and optical powers ranging from any positive diopter value (e.g., including +35 D and above) to any negative diopter value (e.g., including −35 D and below).

The posterior refractive surface 19 may advantageously reduce the refractive power of the IOL to be placed in the device 10. For example, if the device did not include a posterior surface (e.g., comprised a simple or modified ring), then one or more IOL devices would provide all of the refractive power, which could increase the volume of the IOL, leading to a larger incision and associated complications. A posterior refractive surface implanted in the eye can advantageously allow for a second refractive device to be coupled with (e.g., placed within, next to, and/or on top of) the posterior refractive surface. The posterior refractive surface 19 can allow the ELP of the eye to be determined along with any residual refractive error. If any further refractive error is discovered, a second refractive device can be added to the posterior refractive surface 19 (e.g., immediately), which can neutralize the deficit and help ensure that the desired outcome is achieved. The posterior refractive surface 19 being integrally formed with the remainder of the device 10, which can be accurately placed and anchored, can inhibit or prevent shifting of lateral and/or posterior-anterior position, rotation, tilt, etc. of the posterior refractive surface 19 that could lead to degradation of vision. The continuous nature of the device 10 on all sides except for the anterior opening 18 can inhibit, reduce, or prevent ingrowth of lens epithelial cells, and thereby can inhibit or prevent formation of intra-lenticular opacifications.

The device 10 comprising a refractive surface 19, rather than being a through hole of an annulus, for example, can reduce the volume of an IOL inserted therein, which may advantageously reduce incision size. The posterior refractive surface 19 may provide protection for the natural capsular bag 24 during placement of an IOL. For example, the IOL is inhibited or prevented from directly contacting the natural capsular bag 24 because the IOL instead contacts the device 10. For another example, vitreous is inhibited or prevented from contacting the IOL. Sidewalls of the device 10 that do not include apertures large enough for a portion (e.g., a haptic) of an IOL to prolapse through may provide protection for the natural capsular bag 24 during placement of an IOL, for example because the IOL is inhibited or prevented from directly contacting the natural capsular bag 24.

The prosthetic capsular device 10 is adapted to be implanted in the eye 12. The prosthetic capsular device 10 preferably comprises a biologically-compatible material that would be inserted inside the eye 12. The prosthetic capsular device 10 is preferably deformable so as to be folded and inserted via an injection system through a corneal incision ranging between about 0.1 mm and about 10 mm, preferably between about 1.5 mm and about 3 mm. The size of the corneal incision varies based on several factors, including, for example, the volume of the prosthetic capsular device 10, the plasticity of the prosthetic capsular device 10, the volume of the injection cartridge through which the prosthetic capsular device 10 will be delivered, frictional forces, combinations thereof, and the like. The capsulorhexis is preferably between about 4 mm and about 7 mm (e.g., about 6 mm), although, if a femtosecond laser is used, the capsulorhexis should be less than the dilated diameter of the patient's pupil, as a femtosecond laser generally cannot create a capsulotomy through the iris. A capsulorhexis created manually may be about the same size as a capsulorhexis created by a femtosecond laser, as direct visualization of the rhexis boundary is advisable throughout the creation process. The capsulorhexis ranges between about 3 mm and about 8 mm, preferably between about 4 mm and about 7 mm. During implantation, the folded prosthetic capsular device 10 passes through the corneal incision, through the capsulorhexis, and into the patient's natural capsular bag 24 (FIG. 1). The natural capsular bag 24 may be fully, partially, or not intact, or is missing or a remnant, although it is preferred to place the device 10 in an intact natural capsular bag 24 other than the continuous curvilinear capsulorhexis, devoid of natural lens material, with intact zonules. If the natural capsular bag 24 is not sufficiently intact, alternative techniques may be employed, for example to secure the device 10 to the posterior chamber (e.g., suturing the device 10 to the scleral wall). The prosthetic capsular device 10 preferably possesses sufficient elasticity to resume its pre-folded shape, for example by self-expanding, once positioned inside the eye 12. Intraocular lenses comprising materials including silicone, polyimide, collamer, and acrylic can have one or more of these capabilities. In some implementations, the prosthetic capsular device 10 comprises a biologically-compatible, optically clear material similar or identical to those used in foldable intraocular lenses.

The prosthetic capsular device 10 is preferably inserted in the natural capsular bag 24 of the eye 12 of a patient through the use of an injection system. The injection system can allow the prosthetic capsular device 10 to be folded or automatically folded into a smaller shape as the prosthetic capsular device 10 is advanced through the injection system so as to allow the prosthetic capsular device 10 to fit through an incision much smaller than the diameter of the unfolded prosthetic capsular device 10. Injection systems through which IOLs are injected into the eye, for example comprising a cylindrical cartridge and an advancement rod on a screw type advancement system or plunger advancement system, would be suitable for use with the prosthetic capsular device 10. Other injection systems are also possible.

The prosthetic capsular device 10 is preferably inserted in a natural capsular bag 24 of the eye 12 of a patient who has had cataract surgery with the use of a laser (e.g., a femtosecond laser) to create a capsulorhexis, although insertion into natural capsular bag 24 after manual creation of the capsulorhexis is also possible. A femtosecond laser may be used to create the capsulorhexis, for example after the same femtosecond laser or a different femtosecond laser or a different device was used to make the other incisions including the main wound, the paracentesis, and any corneal or limbal relaxing incisions. The patient's natural lens, for example clouded by a cataract such that it may be itself termed a "cataract," may be removed using techniques known in the art. For example, the natural lens material may be broken up and vacuumed out, leaving the natural capsular bag 24 partially, fully, or not intact, or being missing or a remnant. The residual cortex may be removed using techniques known in the art such as via irrigation/aspiration. An aphakic refraction may be completed using an intraocular refracting device such as, for example, the ORA System, available from Alcon Surgical, Ft. Worth, Tex. (formerly WaveTec of Aliso Viejo, Calif., or the Holos IntraOp system available from Clarity Medical Systems, Inc. of Pleasanton, Calif. An IOL calculation may be performed using an algorithm such as, for example, the Mackool algorithm. The patient's natural capsular bag 24 and anterior segment 26 may be inflated with a viscoelastic material, such as sodium hyaluronate (e.g., Provisc, Healon, Viscoat). The prosthetic capsular device 10 may be loaded into an injection device, for example by being folded into a small tubular shape, and injected into the natural capsular bag 24. The viscoelastic material may be removed from behind the prosthetic capsular device 10 and from the anterior segment 26. A pseudophakic refraction may be performed with a system similar to a standard auto-refractor or the intraoperative refracting system. This calculation is preferably performed using approved protocols. An intraoperative Optical Coherence Tomography system, such as the Zeiss OMPI Lumera 700 with ReScan 700, could be used to measure the exact position of the prosthetic capsular device 10 in the eye 12, relative to the cornea and the retina. Along with pre-operative measurements of the cornea and axial length, the position of prosthetic capsular device 10 as determined by the OCT measurement could allow the surgeon to determine the power of a lens that would provide the desired refraction using a vergence formula.

An example refraction using an approved protocol, and accompanying background information, is discussed herein. Current state of the art requires multiple independent variables to be measured so that the dependent variable of effective lens position can be estimated. The seven independent variables in the Holladay 2 formula (one of the most popular modern formulas) are, in decreasing order of importance: (1) axial length, (2) average keratometric power, (3) horizontal white to white, (4) refraction, (5) anterior segment depth, (6) lens thickness, and (7) age. These variables are then used to estimate the Effective Lens Position. However, this position is simply an estimation or prediction. If the estimation or prediction of the position is incorrect, the post-operative refractive outcome will be compromised. Therefore, emphasis should be placed on the ability to determine the ELP rather than estimating the ELP. The prosthetic capsular device 10 can help determine the ELP in one, two, or more different ways, as described herein.

Figure 4A:
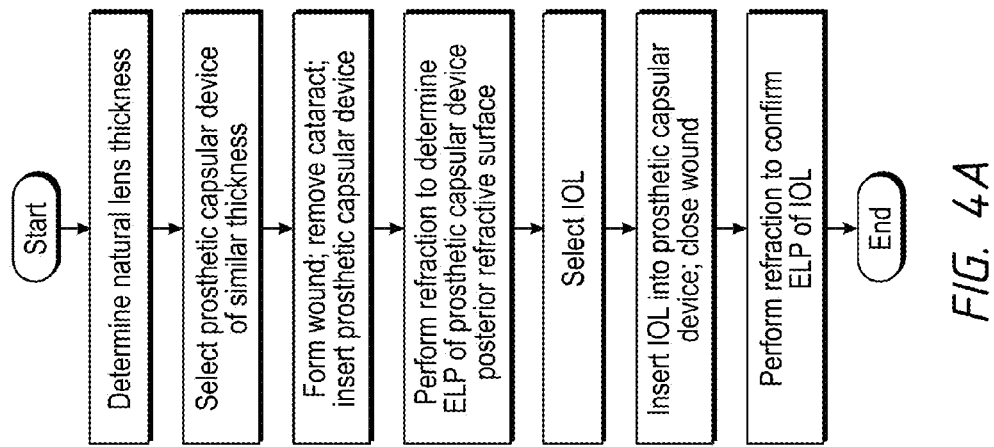
FIG. 4A is a flow chart of an example method for inserting and positioning a prosthetic capsular device into an eye.

FIG. 4A is a flow chart of an example method for inserting and positioning a prosthetic capsular device 10 into a patient's eye 12, with continued reference to FIGS. 1-3. First, the lens thickness of a patient's natural lens is determined preoperatively using known techniques. Next, a prosthetic capsular device 10 having a thickness similar to the thickness of the patient's natural lens is selected. Selection of a prosthetic capsular device 10 sized such that the inner face 17 of the prosthetic capsular device 10 is at the same location as the posterior surface of the patient's natural lens is preferred such that, when an IOL 28 is inserted in the prosthetic capsular device 10, that IOL 28 will be positioned in substantially the identical location previously occupied by the patient's natural lens. Although the natural capsular bag 24 remains open, a combination of very thin lenses may be used such that lenses may be positioned slightly differently than the natural lens as measured from cornea to lens surface or back surface to retina. The prosthetic lens of ideal power can be appropriately identified and inserted in the eye 12 to provide the desired refractive endpoint.

A femtosecond laser and/or manual keratome may be used to form the main wound, the paracentesis, any corneal or limbal relaxing incisions. The femtosecond laser and/or manual technique may be used to create the capsulorhexis. The patient's natural lens or cataract is then removed using techniques known in the art. The residual cortex is removed using techniques known in the art, such as via irrigation/aspiration. Then, the patient's natural capsular bag 24 and anterior segment 26 are filled with viscoelastic material, and the prosthetic capsular device 10 is inserted into the natural capsular bag 24. The viscoelastic material is then removed from behind the prosthetic capsular device 10 and from the anterior segment 26 in preparation for performing a pseudophakic refraction.

By being able to identify and control the position of the IOL 28, choosing an IOL 28 may be independent of the seven variables used for ELP in the Holladay 2 formula. Rather, via theoretical vergence formulas, the exact IOL 28 that can provide a desired refractive outcome can be specifically calculated using keratometric power, effective lens position, and axial length. The weakness of the formulas currently used is the inability to accurately estimate or predict ELP. To confirm that the pre-operative theoretical calculation is correct, a refraction may be performed in the operating room once the prosthetic capsular device 10 is implanted in the patient's eye via an intraoperative refracting system, retinoscopy, or by other known methods. The refraction will technically be a pseudophakic refraction, as the posterior refractive surface 19 of the prosthetic capsular device 10 has a refractive power, such as, for example, +1 diopter.

A method to determine the correct intraocular power for a piggyback lens may be calculated by first determining the power of the IOL 28 to be implanted using Equation 1:

$$IOLe = \frac{1336}{\frac{1336}{\frac{1000}{\frac{1000}{PreRx} - V} + Ko} - ELPo} - \frac{1336}{\frac{1336}{\frac{1000}{\frac{1000}{DPostRx} - V} + Ko} - ELPo} \qquad \text{(Eq. 1)}$$

wherein: IOLe=IOL power; ELPo=effective lens position; Ko=net corneal power; V=vertex distance; PreRx=pre-op refraction (also can represent the intra-operative refraction after the prosthetic capsular device has been placed); and DPostRx=desired post-operative refraction.

The Effective Lens Position (ELP or ELPo) is the distance from the secondary principal plane of the cornea to the principal plane of the thin-IOL equivalent. The keratometric power of the cornea (Kk) can be converted to the net optical power of the cornea (Ko) using Equation 2:

$$Ko = Kk \times 0.98765431 \qquad \text{(Eq. 2)}$$

For example, if the Kk is 44.50 D, Ko=44.50 D×0.98765431=43.95 D. The net optical power of the cornea would then be 43.95 D.

By comparing the pre-operative theoretical IOL calculations with the aphakic refraction, the prosthetic capsular device refraction, and the post-IOL implantation refraction, surgeons can greatly improve the accuracy of their post-operative refractive outcomes.

Still referring to FIG. 4A, once the appropriate IOL 28 is selected, the prosthetic capsular device 10 and anterior segment 26 are refilled with viscoelastic material and, based on the residual refractive error, the appropriate IOL 28 is selected and inserted into the prosthetic capsular device 10. The viscoelastic material is then removed from the eye 12, and the wounds are closed through standard methods such as hydration, suturing, etc. A final confirmatory refraction may be completed while ensuring normal intraocular pressure, which can affect the position of the prosthetic capsular device 10 and IOL 28 inside the eye 12. If significant error was found at this point, the surgeon may remove the implanted IOL and replace the implanted IOL with a more desirable IOL (e.g., having a more desirable refractive power), substantially without risking damage to the fragile natural capsular bag 24, due to the protective nature of having the IOL 28 contained in the prosthetic capsular device 10. The ability provided by the natural capsular device 10 to remove and insert IOLs is described further herein.

The device 10 may be used as a stand-alone intraocular lens for the primary correction of aphakia. A device 10 including a particular lens may be chosen based on pre-operative measurements and/or theoretical formulae. Intraoperative aberommetry could also be used in the aphakic mode to help aid in the selection of the device 10 including its lens or posterior refractive surface 19. While this technique and implementation does not necessarily take advantage of the improvement of ELP prediction and identification, use the device 10 as a stand alone intraocular lens, with the ability to contain other technology of various types for implantation in the future, is a reasonable solution.

The following method or surgical procedure for implanting a prosthetic capsular device as described herein has been successfully used in animal studies using three New Zealand white rabbits of same sex and weighing between 2.4 kg and 3.2 kg and in animal studies using five New Zealand white rabbits of same sex and weighing between 3.2 kg and 3.6 kg. The animals were quarantined for at least seven days and grossly checked for the presence of any anomalies prior to the beginning of the procedure. Each animal was prepared for surgery by pupil dilation with 1% cyclopentolate hydrochloride and 2.5% phenylephrine drops, applied topically three times each spaced by a duration of five minutes. Anesthesia was obtained with an intramuscular injection of ketamine hydrochloride (50 mg/kg) and xylazine (7 mg/Kg) in a mixture of 7:1, respectively. One drop of topical proparacaine hydrochloride anesthetic was also placed in each eye prior to beginning surgery. Eye movement and animal respiration were monitored intraoperatively to ensure that adequate levels of anesthesia were maintained. Supplemental anesthetics were given intramuscularly as needed during the operation. The area around the eye was draped in an aseptic manner. A lid speculum was placed to retract the lids. One drop of povidone-iodine (PVP-I) 5% and a drop of antibiotic was placed on the surface of the eye just before beginning surgery. Using aseptic technique and a Zeiss surgical microscope, a fornix-based conjunctival flap was fashioned. A corneal-scleral incision was made using a crescent blade, and an initial 3.0 mm limbal incision was made using a 3.0 mm keratome to enter the anterior chamber. Capsulorhexis forceps were used to create a well centered continuous curvilinear capsulotomy (CCC), with a diameter between about 5.0 mm and about 5.5 mm.

After hydrodissection, a phacoemulsification handpiece (Alcon Infiniti system) was inserted into the posterior chamber for removal of lens nucleus and cortical material. One milliliter (mL) of epinephrine 1:1000 and 0.5 mL of heparin (10,000 USP units/mL) were added to each 500 mL of irrigation solution to facilitate pupil dilation and control inflammation. The endocapsular technique was used with the phacoemulsification to take place entirely within the natural capsular bag. The residual cortex was then removed with the an irrigation/aspiration (I/A) handpiece. After removal of the natural lens, an ophthalmic viscosurgical device (OVD) (Amvisc Plus, Bausch & Lomb) was used to inflate the natural capsular bag.

Figure 4D:
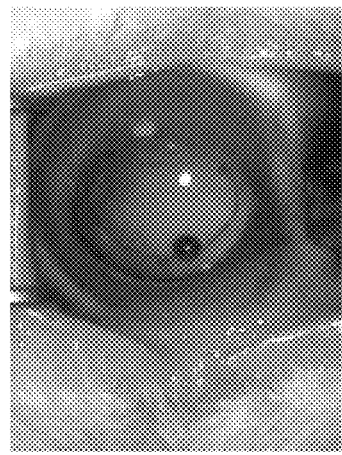
FIGS. 4B-4G are photos of an example method for inserting and positioning a prosthetic capsular device into an eye.
Figure 4C:
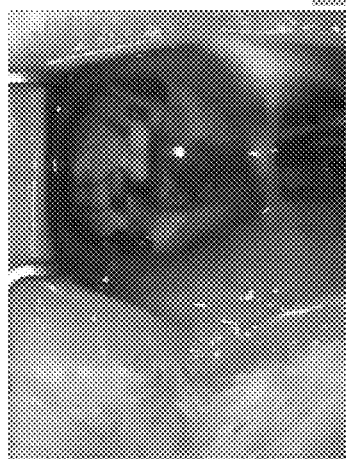
Figure 4B:
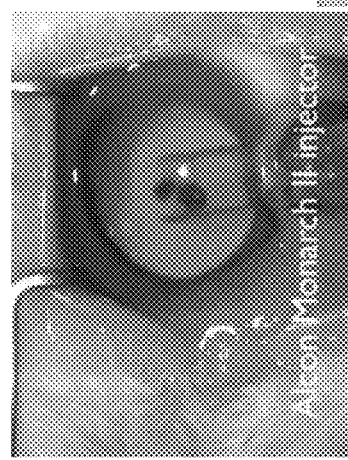

As shown in FIGS. 4B-4D, the prosthetic capsular device was then injected by using an appropriate injector system ("A" cartridge and Monarch II injector from Alcon Laboratories; Accuject 2.2-1P injector set from Medicel), after the surgeon slightly increased the incision size. Loading of the prosthetic capsular device into the injectors was found to be uneventful. If the prosthetic capsular device was injected partially out of the natural capsular bag (e.g., due to fibrin formation, papillary restriction, injector limitation, etc.), the prosthetic capsular device was able to be manipulated with a collar button hook to complete in-the-bag fixation. Careful control of the injector may inhibit or prevent rapid or uncontrolled release of the prosthetic capsular device from the injector. Even when the plunger of an injector overrode the prosthetic capsular device inside the plunger, injection in the natural capsular bag was possible.

Figure 4G:
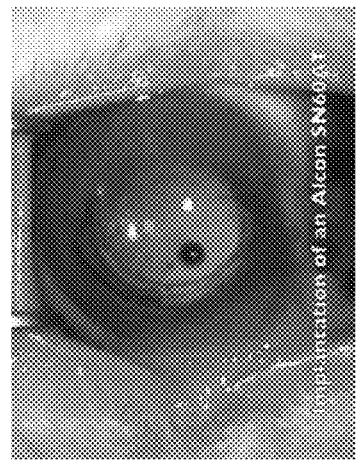
Figure 4F:
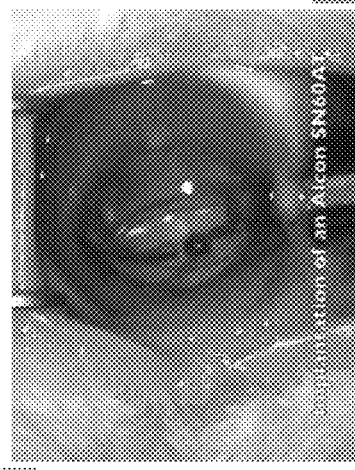
Figure 4E:
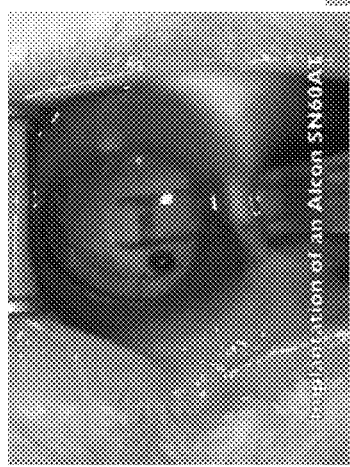

As shown in FIGS. 4E-4G, this was followed by insertion of IOLs (AcrySof SN60AT, a single-piece hydrophobic acrylic IOL manufactured by Alcon) using the Monarch II injector and "C" cartridges. The AcrySof lens was fully fixated within the prosthetic capsular device in all instances, uneventfully. The device and IOL were carefully inspected under high magnification for any possible damage that might have occurred during the loading/implantation process. Centration of the prosthetic capsular device and of the IOL inside of the prosthetic capsular device was found to be excellent in all cases. In three eyes, the natural capsular bag containing the prosthetic capsular device and the AcrySof lens was slightly oval.

Combination antibiotics/steroid ointment (neomycin and polymyxin B sulfates, and dexamethasone) was applied to the eyes following surgery. The same ointment was placed in the eyes four times per day for the first postoperative week. Ointment was discontinued after one week. In the second postoperative week, each animal received topical prednisolone acetate drops four times per day. In the third postoperative week, each animal received topical prednisolone acetate drops two times per day, with discontinuation of the drops following the third postoperative week.

The eyes were evaluated grossly at day one, and by slit lamp examination with scoring for ocular inflammatory response at one, two, three, and four weeks postoperatively (±2 days) and photographs were taken (see below). At each of these examinations, the rabbit eyes were dilated using a combination of cyclopentolate hydrochloride solution and phenylephrine. A standard scoring method in eleven specific categories was used at each examination, including assessment of corneal edema, as well as the presence of cell and flare within the anterior chamber. Retro-illumination images with the pupil fully dilated were obtained for the purpose of photographic documentation regarding CCC size, anterior capsule opacification (ACO), posterior capsule opacification (PCO), and any observed capsular fibrosis at the discretion of the study directors. The images are provided and discussed in further detail herein.

After the clinical examination at four weeks, the animals were anesthetized using a 1 to 2 $cm^3$ (cc) intramuscular injection of a 7:1 mixture of ketamine hydrochloride and xylazine, and then humanely euthanized with a 1 mL intravenous injection of pentobarbital sodium/phenytoin sodium. The globes were enucleated and placed in 10% neutral buffered formalin. The globes were then bisected coronally just anterior to the equator. Gross examination and photographs from the posterior aspect (Miyake-Apple view) were performed to assess the ACO and PCO development, as well as IOL fixation. The extent and severity of ACO and PCO were scored according to established methods.

After gross examination and photographs, all globes were sectioned and the anterior segments including the capsular bags were processed for standard light microscopy and stained with hematoxylin and eosin (H & E). Features such as cell type, extent and route of growth, etc. were documented by serial photomicrographs.

Figure 4H:
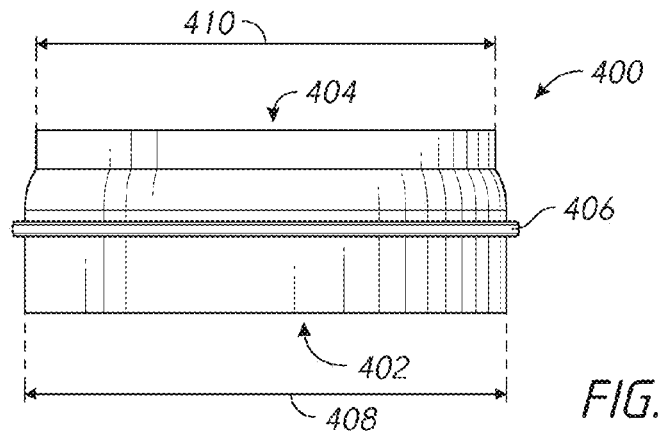
FIG. 4H is a side view of an example prosthetic capsular device.
Figure 4I:
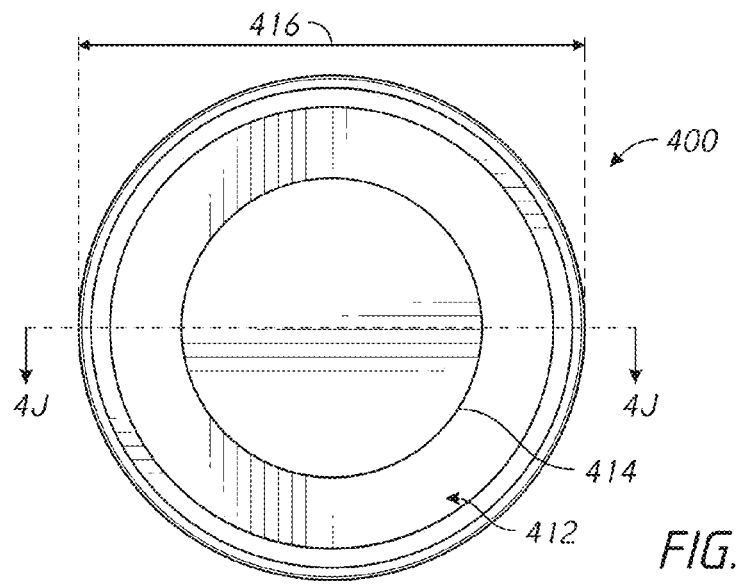
FIG. 4I is an anterior view of the prosthetic capsular device of FIG. 4H.
Figure 4J:
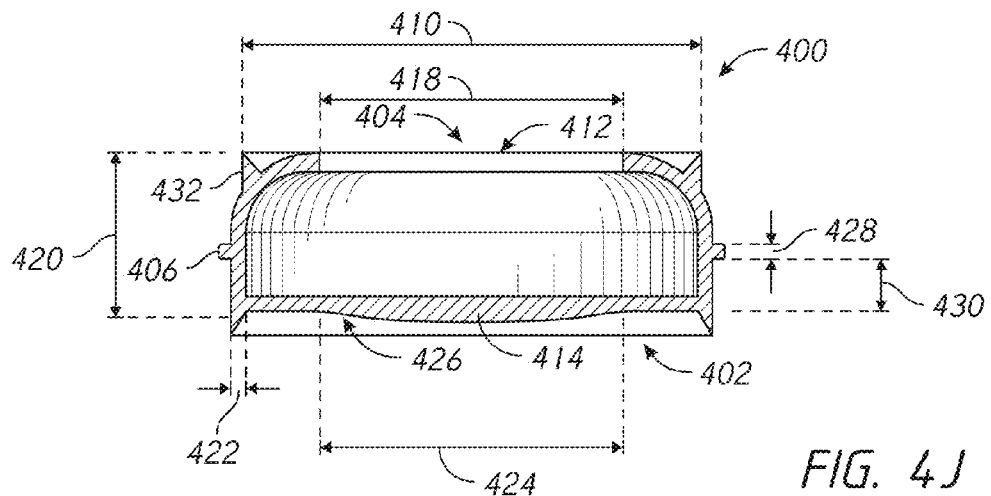
FIG. 4J is a cross-sectional view of the prosthetic capsular device of FIG. 4H along the line 4J-4J of FIG. 4I.

FIGS. 4H-4J illustrate another example prosthetic capsular device 400, in which FIG. 4H is a side view, FIG. 4I is an anterior plan view, and FIG. 4J is a cross-sectional view of along the line 4J-4J of FIG. 4I. The device 400 is illustrative of the prosthetic capsular devices used in the animal studies described herein, with certain modifications where indicated.

The device 400 comprises a posterior side 402 and an anterior side 404. The posterior side 402 has a diameter 408 between about 5 mm and about 10 mm (e.g., about 9.5 mm). The anterior side 404 has a diameter 410 between about 5 mm and about 10 mm (e.g., about 9 mm). The diameter 410 of the anterior side 404 may be between about 0.25 mm and about 1 mm (e.g., about 0.5 mm) less than the diameter 408 of the posterior side. The device 400 comprises a generally cylindrical portion having the diameter 408 from the posterior side 402 to the flange 406, a tapered portion tapering from the diameter 408 to the diameter 410 anterior to the flange 406, and another generally cylindrical portion having the diameter 410 from the tapered portion to the anterior side 404. The tapered portion may be straight, arcuate, and/or combinations thereof.

The posterior side 402 has a generally flat end shape and a rounded refractive portion 414 inwardly set back from the end of the posterior side 402, as best seen in FIG. 4J. The refractive portion 414 provides a refractive property to the device 400. The refractive portion 414 has a diameter 424 between about 4 mm and about 9 mm (e.g., about 5.9 mm). The illustrated refractive portion 414 has a refractive power of 5 D with a radius of curvature 426 of about 19.32 mm) although other refractive powers (e.g., 0 D, <0 D, >0 D, ±35 D, etc.) and radii of curvature (e.g., at least partially depending on one or more of refractive power, the diameter 424, material, etc.) are also possible.

The anterior side 404 comprises an opening 410, which allows the insertion of an IOL as discussed herein. The opening 410 may have a diameter 418 between about 5 mm and about 10 mm (e.g., about 9 mm). The sidewalls of the device 400 optionally do not extend radially inwardly such that the opening 410 may have a large or maximum diameter (e.g., based on the diameter of the inner surface of the sidewalls of the device 400). A larger opening 410 may aid insertion of the IOL and/or reduce volume and/or mass, which can aid insertion into small incisions (e.g., by being easier to compress into and/or advance through an injection device). A smaller opening 410 may aid in containment of an IOL (e.g., better defining the interior volume of the device 400 and/or inhibiting anterior drift on an inserted IOL). The anterior side 404 and/or the posterior side 402 may comprise a lip or ridge 432 on a radial exterior.

The distance 430 between the flange 406 and the refractive portion 414 may be between about 0.5 mm and about 2 mm (e.g., about 1 mm). The distance 420 between the anterior end 404 and the refractive portion 414 may be between about 1 mm and about 5 mm (e.g., about 2.5 mm). As described herein, in devices comprising a flange, the flange may be anywhere along the longitudinal axis of the device.

The device 400 comprises sidewalls between the posterior end 402 and the anterior end 404. The sidewalls may have a radial thickness 422 between about 0.1 mm and about 0.5 mm (e.g., about 0.26 mm). The sidewalls optionally extend posterior to the refractive portion 414 and/or anterior to or substantially longitudinally even with the opening 412. The sidewalls may extend towards the anterior side 404 and/or the posterior side 402 to form a lip or ridge 432.

The device 400 illustrated in FIGS. 4H-4J includes a flange or ring 406 having an anterior-posterior thickness 428 of about 0.3 mm and a radial thickness ((diameter 416–diameter 408)/2) of about 0.25 mm, but the flange 406 was removed from the devices used in the animal studies such that the outer diameter of the devices was the diameter 408. If the flange 406 is not removed, other thicknesses are also possible. For example, a flange 406 having thicker dimensions may be less prone to tearing upon loading in a delivery syringe and/or insertion in an eye.

The prosthetic capsular device 10 can enhance the ability to achieve desired refractive targets, with a side benefit of increased safety. The prosthetic capsular devices (e.g., the prosthetic capsular device 10 and/or variants thereof) described herein can provide one or more of these advantages in one or more of several ways. Although various numbered potential advantages are listed, each advantage may include sub-advantages or alternative advantages, and not all devices 10 need to accomplish every enumerator or otherwise described potential advantage.

First, with reference again the FIGS. 1-3, the prosthetic capsular device 10 can provide centration of the IOL 28 along the visual axis 15. A femtosecond cataract laser system has the ability to center the capsulorhexis around the visual axis 15 of the patient rather than the optical center of the cataract. The capsulorhexis is ultimately what will center the prosthetic capsular device 10 as the capsulorhexis is the opening through which the prosthetic capsular device 10 will be inserted. The capsulorhexis is juxtaposed at the center of the prosthetic capsular device 10, centering the prosthetic capsular device 10. The prosthetic capsular device 10 may optionally be stabilized via the flange 20 extending into and fitting in the ciliary sulcus 22. The flange 20 can mechanically retain the prosthetic capsular device 10 centered on the patient's visual axis 15 and inhibit or prevent future movement or migration of the prosthetic capsular device 10, although centering and inhibited movement are also possible without a flange 20.

Centration of the IOL 28 on the visual axis 15 can be important to the visual function of the IOL 28 and the benefit the patient receives. Aspheric lenses have made decentration more tolerable, however improved centration can be advantageous to the increase or optimize visual performance of multifocal intraocular lenses. Decentration by less than 1 mm can cause significant morbidity, so much so that surgical intervention including laser pupiloplasty, IOL repositioning, and IOL exchange are often performed. The prosthetic capsular device 10 is centered along the visual axis 15 via the capsulorhexis. An IOL 28 commonly includes haptics 30 which can engage opposed interior surfaces in the prosthetic capsular device 10 to maintain the centered position of the IOL 28. The outer diameter of the IOL 28, when unfolded and including the haptics 30, may be substantially equal to or less than the inner diameter of the prosthetic capsular device 10. The IOL 28 can be centered by being in physical contact with the peripheral internal surface of the prosthetic capsular device 10 that is centered in the visual axis 15, which maintains the centered position of the IOL 28 in the prosthetic capsular device 10 and also in the visual axis 15.

Second, the prosthetic capsular device 10 can provide a prosthetic barrier between the anterior segment 26 and posterior segment 32 of the eye 12 in the case of inadvertent rupture of the posterior surface of the natural capsular bag 24, or after planned neodymium-doped yttrium aluminum garnet (Nd:YAG) laser posterior capsulotomy. Despite the overall success of cataract surgery, there is still about 2% surgical complication rate utilizing modern techniques, although this varies among individual surgeons. Residents in ophthalmology training programs have historically had complication rates around 4-7%. Most complications from cataract surgery are caused by inadvertent rupture of the natural capsular bag 24, which houses the cataract. The natural capsular bag 24 also provides an important anatomical barrier within the eye 12 by dividing the anterior segment 26 from the posterior segment 32. The posterior segment 32 contains the vitreous body, retina, optic nerve, and the central retinal artery and vein. A violation of the integrity of the barrier provided by the natural capsular bag 24 allows fluid communication between the anterior segment 26 and the posterior segments 32, and potentially the ocular surface. Vitreous may flow out of the posterior segment 32 according to pressure gradients, flowing from high pressure (e.g., in the posterior segment 32) toward low pressure (e.g., the anterior segment 26). A pressure gradient can cause vitreous to flow directly to the surgical incision site in the lower pressure anterior segment 26. Vitreous can inhibit or prevent wound healing if present at the surgical incision site, and more significantly can provide a conduit for microbial infections to proceed directly to the posterior segment 32. In addition to the problems caused by vitreous, a break or tear in the natural capsular bag 24 can inhibit or prevent the stable implantation of an IOL 28 in the posterior segment 32. Surgeons can place an IOL 28 in the ciliary sulcus 22 or the anterior chamber, although each of these alternatives has their own potential complications associated with them. The natural capsular bag 24 is desirably maintained intact, as there are currently no methods to consistently reestablish the integrity of the natural capsular bag 24 once it has been compromised. Should the natural capsular bag 24 be compromised, the prosthetic capsular device 10 may serve as a prosthetic barrier between the anterior segment 26 and posterior segment 32.

About 30% of all implanted intraocular lenses develop visually significant posterior capsular opacification. If this develops, a Nd:YAG laser may be used to create an opening in the posterior surface of the natural capsular bag 24 to remove this opaque membrane. If the IOL 28 is to be removed after a Nd:YAG laser posterior capsulotomy has been performed, the chances for serious complications rise dramatically because the barrier between the vitreous and the anterior segment 26 has been lost due to the Nd:YAG-created opening in the posterior surface of the natural capsular bag 24. If a prosthetic capsular device 10 is placed in the natural capsular bag 24 and Nd:YAG laser posterior capsulotomy has been performed, the prosthetic capsular device 10 can provide an adequate barrier for the vitreous, inhibiting or preventing vitreous from flowing out of the posterior segment 32. The haptics 30, which hold the IOL 28 in place inside the prosthetic capsular device 10, are not prone to scar formation or fibrosis because they contact the prosthetic capsular device 10 rather than the natural capsular bag 24, which can make future lens removal easier and decrease the risk for complications during IOL 28 exchange. The prosthetic capsular device 10 can provide a platform for routine IOL 28 exchange, as described further herein.

Third, the prosthetic capsular device 10 can limit chronic capsular opacification that takes place in the natural capsular bag 24 and that can cause refractive shifts due to ELP change, anterior capsular phimosis, and visually significant posterior capsular opacification. After cataract surgery has been performed, the natural capsular bag 24 undergoes chronic changes. These changes are largely due to the presence of lens epithelial cells that remain on the natural capsular bag 24 after surgery. These epithelial cells continue to grow and can cause problems. For example, the anterior surface of the natural capsular bag 24 can fibrose and contract over time, causing a progressively smaller aperture overtop of the lens. If the entire natural capsular bag 24 becomes fibrotic, and phimosis persists, there can be zonular dehiscence and changes to the effective lens position over time. About 30% of the time, the posterior surface of the natural capsular bag 24 becomes significantly opacified, which may be remedied by a Nd:YAG laser posterior capsulotomy. The effect of limiting epithelial cell migration and propagation can be mediated by the type of material that the prosthetic capsular device 10 comprises (e.g., hydrophobic acrylic materials, which tend to be most efficacious of all currently known and used IOL materials).

Fourth, the prosthetic capsular device 10 can help maintain the effective lens position of an IOL 28 implanted into the eye 12. Precisely matching the preoperative dimensions of the cataract with the prosthetic capsular device 10 can enhance the ability to predict the ELP of the lens implant 28. Currently, the ELP of an IOL 28 is estimated or predicted based on a number of factors, including the depth of the anterior segment 26, lens thickness, and white to white diameter, among others. The accuracy of the prediction is actually quite low, resulting in only 50% of patients being within a tolerable level of their refractive goal post-cataract surgery. While other dimensions of the eye required for standard IOL calculation can be measured quite precisely and accurately, the ELP has remained the elusive last great variable to conquer in the quest for highly accurate and predictable IOL calculations for cataract surgery.

The reason for the great variability in the ELP is due to the volumetric difference between the cataract and the IOL 28. The average thickness of the human cataract at age 65 is approximately 4.5 mm, but varies from patient to patient. In contrast, an IOL 28 is typically less than 1 mm thick and/or produces no or substantially no anterior-posterior (Z-axis) stabilization inside the natural capsular bag. The thickness of the IOL generally does not match the thickness of the cataract due to deliverability issues, as thicker IOLs generally use a larger incision. The resulting volumetric difference allows for pressure differentials between the posterior segment 32 and the anterior segment 26, as well as contraction of the natural capsular bag 24, which can shift the final resting position of the IOL 28. The lens thickness may be measured preoperatively and a prosthetic capsular device 10 with a corresponding volume and thickness may be implanted. By implanting a prosthetic capsular device 10, the volume of the natural capsular bag 24 may effectively be held constant and/or in accordance with the cataract. The natural capsular bag 24, buttressed by the prosthetic capsular device 10, can resist forces that would otherwise shift the natural capsular bag 24 and its contents anteriorly or posteriorly. This stability of lens capsule volume and/or Z-axis stabilization of the lens inside the prosthetic capsular bag and the natural capsular bag can increase or significantly increase the accuracy of IOL calculations.

Fifth, the prosthetic capsular device 10 can allow for an intraoperative pseudophakic refraction while still allowing another IOL to be implanted without explanting an originally implanted lens. Recently, there have been advances in IOL calculation methodologies that use intraoperative refraction devices, such as the WaveTec ORA System, the WaveTec Orange System, the HOLOS IntraOp from Clarity Medical Systems, Inc., etc., to provide better refractive outcomes. These devices can perform aphakic refractions, pseudophakic refractions, and assist with the alignment of toric IOLs 28 and assist with Limbal Relaxing Incisions.

Aphakic refractions do not have the benefit of a lens inside the eye, so ELP is still a variable for which this data cannot account. Pseudophakic refractions can be helpful, but provide the information only after the IOL 28 has been implanted. If the data shows that a different IOL 28 would be more beneficial, the physician would explant the less beneficial IOL 28 and implant a more beneficial IOL 28. Explanting an IOL 28 takes time, effort, and skill, and can cause damage to the natural capsular bag 24, zonules, cornea, and/or other structures within the eye 12. Using a prosthetic capsular device 10 with a low power lens incorporated into its posterior surface (e.g., the posterior refractive surface 19) can allow a physician to perform a pseudophakic refraction with this refractive surface, and still provides the physician the ability to implant a second lens (e.g., the IOL 28) within the prosthetic capsular device 10 that will make up the refractive difference as measured by an intraoperative refraction device, such as the WaveTec ORA System and Clarity HOLOS.

Stabilization of the natural capsular bag 24 by insertion of the prosthetic capsular device 10 can be leveraged to perform an intraoperative optical coherence tomography (OCT) measurement and/or A or B scan ultrasound, for example using commercially available systems such as the Zeiss RESIGHT OCT and/or any of a multitude of ophthalmic A/B scan ultrasound systems. Once the prosthetic capsular device 10 is inserted into the natural capsular bag 24, the anterior and posterior capsule can be stented open into a stable configuration, which should be unlikely to significantly change post operatively. By knowing the corneal power, the distance from the cornea to the refractive surface of the prosthetic capsular device 10, and the distance from the refractive surface of the prosthetic capsular device 10 to the surface of the retina, the ELP can be determined. By knowing the ELP, the power of the cornea, the refractive power built in to the posterior aspect of the prosthetic capsular device 10, and the axial length of the eye 12 (e.g., from the surface of the corneal epithelium to the internal limiting membrane (ILM) (ultrasonic technique), the retinal pigment epithelial (RPE) layer (laser interferometry technique), from cornea to retina), an appropriate second lens (e.g., of an IOL) can be selected and implanted into the open space in the prosthetic capsular device 10 to provide the desired refractive outcome.

Sixth, the prosthetic capsular device 10 may serve as a means for pharmaceutical delivery. Pharmaceuticals, drugs, and medications, such as, for example, slow release fully or partially dissolvable medicine pellets, non-dissolvable prostheses coated with slow release pharmaceutical agents, and/or other substances intended for introduction into the eye 12 may be placed in and/or on prosthetic capsular device 10 outside of the visual axis 15 in a location that is not subject to sequestration by membrane formation. There is a tremendous amount of research and demand for a slow release implant that would essentially eliminate the need for post-cataract surgery eye drops. The prosthetic capsular device 10 would be a suitable receptacle for such an implant, as the periphery of the interior of the prosthetic capsular device 10 provides a location outside of the visual axis 15, in constant contact with the aqueous humor, substantially without risk of becoming encapsulated by scarring. Due to the prosthetic material of the prosthetic capsular device 10, there would be little to no risk of membrane formation or encapsulation. Dissolved or suspended pharmaceuticals would not affect the patient's vision and could be introduced directly into the prosthetic capsular device 10 during the implantation surgery. Larger pharmaceuticals, such as slow release medicine pellets, may be shaped to mechanically maintain their position with respect to the prosthetic capsular device 10. For example, a slow release medicine pellet may be constructed with a generally toroidal shape sized to fit within the prosthetic capsular device 10, while remaining in the peripheral space and not obstructing the visual axis 15. Alternatively, slow release pharmaceutical agents may be placed inside a carrier that is mechanically configured to fit inside the prosthetic capsular device in order to ensure the agent remains in place and/or do not migrate into the visual axis and/or outside of the prosthetic device even after substantial dissolution.

Seventh, the prosthetic capsular device 10 may provide physicians with the ability to perform a lens exchange in the future that can reduce or minimize the risk of damage to the natural capsular bag 24 and zonular apparatus, which ultimately can substantially reduce or minimize the risk of serious vision threatening sequlae such as macular edema, macular hole, retinal tear, retinal detachment, proliferative vitreoretinopathy, and/or loss of capsular support leading to less favorable lens implantation techniques (e.g., a sutured or glued IOL 28, an anterior chamber IOL 28, a posterior chamber IOL 28, etc.). As stated above, if a prosthetic capsular device 10 is placed in the natural capsular bag 24 and a Nd:YAG laser posterior capsulotomy has been performed, the prosthetic capsular device 10 provides an adequate barrier for the vitreous. The haptics 30 which hold the IOL 28 in place inside the prosthetic capsular device 10 are not prone to scar formation, making future removal and/or exchange of the IOL 28 easier.

Figure 6:
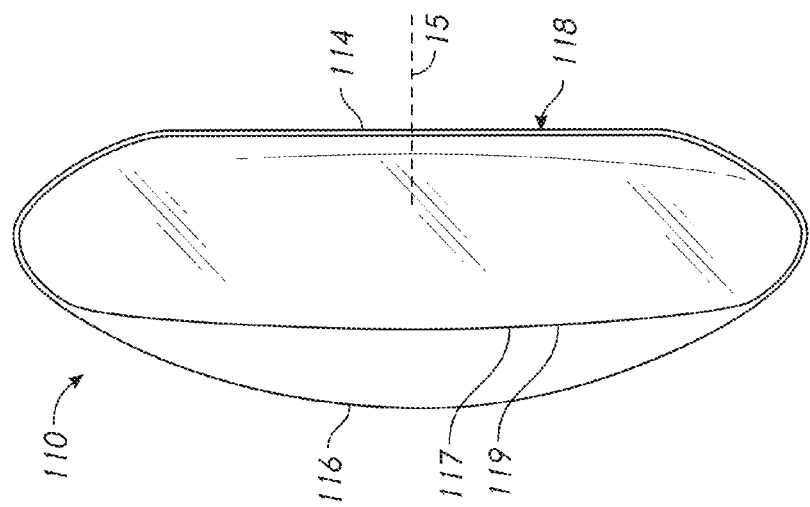
FIG. 6 depicts a side view of the example prosthetic capsular device shown in FIG. 5.
Figure 5:
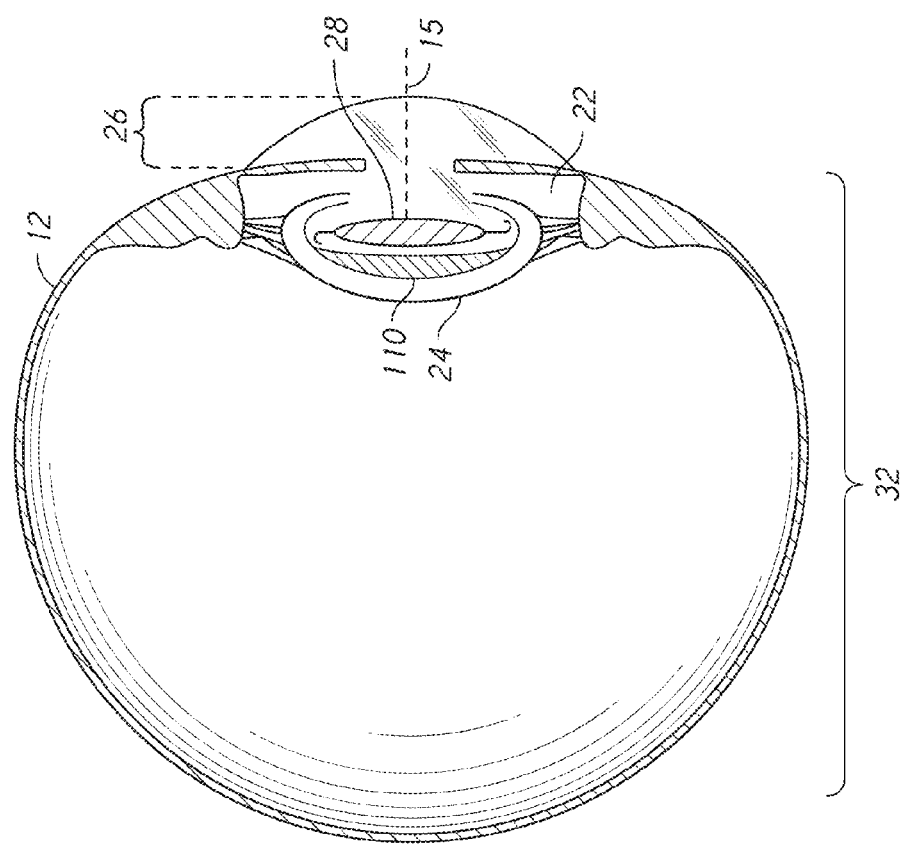
FIG. 5 depicts a cross-sectional side view of an eye including another example of a prosthetic capsular device containing including an IOL.
Figure 7:
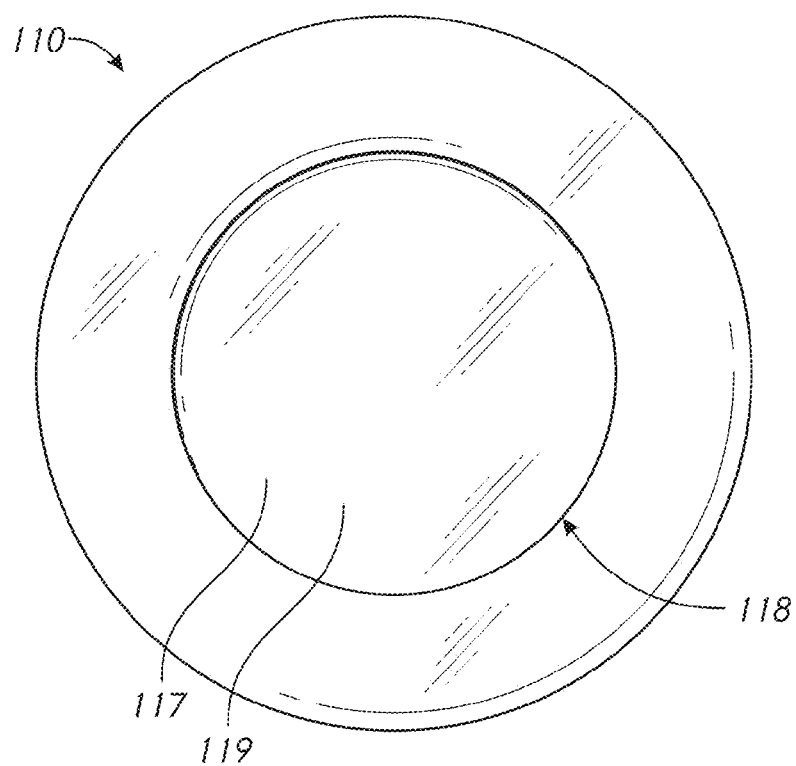
FIG. 7 depicts an anterior plan view of the example prosthetic capsular device shown in FIG. 5.

FIGS. 5-7 depict another example prosthetic capsular device 110. The prosthetic capsular device 110 is a substantially discoid shape having a thickness between about 2.5 mm and about 4.5 mm and a diameter of about 9 mm, although other dimensions, for example as described herein with respect to the prosthetic capsular device 10, 400, are also possible. The thickness of the prosthetic capsular device 110 is the distance between the anterior surface 114 and posterior surface 116 of the prosthetic capsular device 110 along the visual axis 15. The anterior surface 114 contains a circular opening 118 having a diameter of about 6 mm. At least a portion of the inner face 117 of the posterior surface 116 of the prosthetic capsular device 110 comprises a refractive surface, e.g., the posterior refractive surface 119. The prosthetic capsular device 110 lacks or is free of a flange 20 (as in the prosthetic capsular device 10) that could mechanically fixate or center the prosthetic capsular device 110 on the capsulorhexis. The volume of the prosthetic capsular device 110 relative to the opening of the capsulorhexis may keep the device in place similar to the manner in which current single piece IOLs 28 are folded and placed within the natural capsular bag 24.

The prosthetic capsular device 110 may sacrifice a measure of stability as compared to the prosthetic capsular device 10 comprising a flange 20. Without a flange, the prosthetic capsular device 110 may be usable for non-femtosecond laser cataract removal (e.g., traditional manual phacoemulsification), and may be particularly useful for surgeons who lack access to a femtosecond laser.

The lenticular surface on the posterior aspect of a prosthetic capsular device may have a plano powered lens. Some extreme myopes would not benefit from a +1 D refractive surface, as they may benefit from a negative IOL 28 power. For patients with these conditions, a prosthetic capsular device may be used with a plano or zero power posterior lenticular surface.

The prosthetic capsular device may have a negative posterior refractive lenticular surface (e.g., −1 D, −2 D, −3 D, −4 D, −5 D, −6 D, −7 D, −8 D, −9 D, −10 D, or more), as some extreme axial myopes (about 30 mm and beyond) may benefit from this type of lens.

The posterior refractive surface of a prosthetic capsular device may comprise a multifocal lenticular surface, which could aid in presbyopia correction. This multifocal lenticular surface may include, but is not limited to, refractive, diffractive, and zonal multifocal refractive technology. A multifocal lens may be designed to provide multiple focal points generally ranging from plano (e.g., 0 D) to +3 D or greater at the spectacle plane.

The posterior refractive surface of a prosthetic capsular device may include a spherical, aspheric, and/or cylindrical (astigmatic) lenticular surface so as to aid in the correction of pre-existing and surgically induced corneal astigmatism. As most surgeons induce between −0.25 D and −0.50 D of astigmatism with their corneal incisions required for cataract surgery, it would be beneficial even for most patients with spherical corneas to have this neutralized. The diopteric power of the toric correction could increase up to 6 diopters for patients with even higher amounts of astigmatism.

Figure 8:
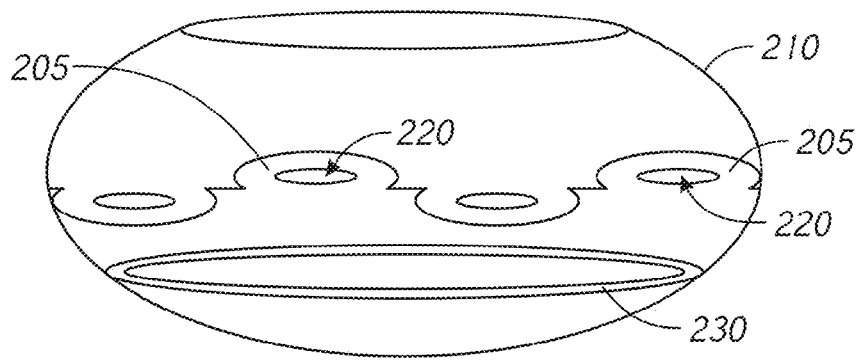
FIG. 8 depicts a side view of an example prosthetic capsular device comprising an outer surface including, around a perimeter of the outer surface, a continuous outer rim of tabs (e.g., comprising silicone) each tab including an opening in a center of the tab, and the capsular device including an internal lip configured to hold haptics of an IOL.

In some implementations described herein (e.g., the prosthetic capsular device 110 shown in FIG. 6, the prosthetic capsular device 400 with the flange 406 removed or never formed), the prosthetic capsular device (e.g., bag, bowl, housing, structure, cage, frame) does not include or is free of a flange. Certain such implementations may include, around a perimeter of the prosthetic capsular device 210, an outer rim comprising tabs or haptics 205. The rim may be continuous, and tabs 205 that are in contact may be considered continuous. Tabs 205 that are continuous may provide better apposition with the natural capsular bag and/or be more form fitting than a device in which the tabs 205 are not continuous. The tabs 205 may position (e.g., center) the device 210 in a desired position. Some or all of the tabs 205 may include an opening or hole 220, for example in the approximate center of the tab 205. An example prosthetic capsular device 210 comprising a continuous outer rim comprising tabs 205 each including an opening or hole 220 is illustrated in FIG. 8. The rim, tabs 205, and/or openings 220 can assist the prosthetic capsular device 210 to fit inside natural capsular bags of many sizes and shapes. The prosthetic capsular device 210 preferably allows for some fibrosis through the openings 220, which can stabilize the capsule 210 in the event of a Nd:YAG laser posterior capsulotomy. The tabs 205 can comprise, for example, silicone, silicone derivatives, acrylic, acrylic derivatives, biocompatible methacrylates (e.g., poly(methyl methacrylate) (PMMA)), collamer, olefins (e.g., polypropylene), polyimide, combinations thereof, and the like. The tabs 205 may comprise the same material as (e.g., be integrally formed with) the remainder of the device 210 or may comprise a different material than the remainder of the device 210 (e.g., being overmolded over the remainder of the device 210). The device 210, like other prosthetic capsular devices described herein, may comprise a plurality of pieces and/or materials, which may advantageously allow selection or use of a material suitable for the function of that component, as opposed to selection or use of a material having compromising suitability for several functions. If the remainder of the device 210 comprises opaque material, the tabs 205 may comprise opaque and/or transparent material, for example because the opaque material of the remainder of the device 210 can reduce or minimize intraocular scattering and/or glare such that light may not reach the tabs 205. The prosthetic capsular device 210 can include an internal lip 230. The internal lip 230 can run partially, intermittently, or completely around the inside of the prosthetic capsular device 210. The lip 230 may be designed to hold the haptics of an IOL stable, inhibiting or preventing the lens from rotating or shimmering during eye movements.

In some implementations, the prosthetic capsular device intentionally moves away from natural form fitting conformation of the posterior aspect of the device. This can allow for the posterior aspect of the prosthetic capsular device to have a larger diameter (e.g., the largest diameter possible for the physiology), potentially allowing for implants with a wider diameter to be implanted, and to have a more stabilizing effect on the lens that the device will be holding.

In some implementations, the prosthetic capsular device 210 comprises at least one of the following: external form-fitting elements (e.g., the tabs 205 shown in FIG. 8); openings in the external form-fitting elements through which fibrosis can take place, thereby allowing stabilization of the positioning of the device (e.g., the openings 220 in the tabs 205 shown in FIG. 8); and an internal lip/sulcus configured to secure the haptics of a standard IOL (e.g., the lip 230 shown in FIG. 8).

Figure 9A:
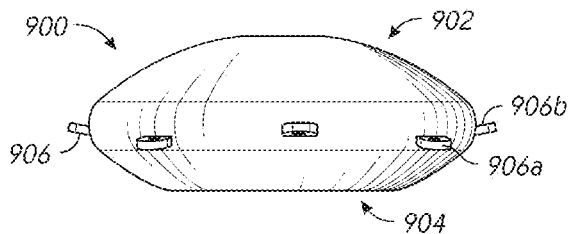
FIG. 9A depicts a side view of another example prosthetic capsular device.
Figure 9B:
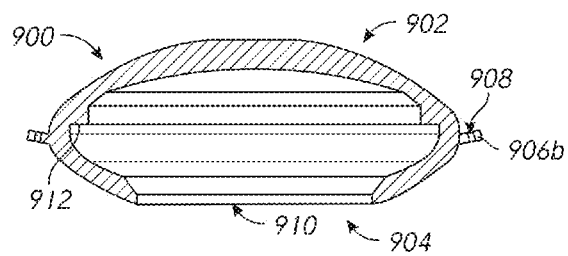
FIG. 9B depicts a side cross-sectional view of the prosthetic capsular device of FIG. 9A.
Figure 9C:
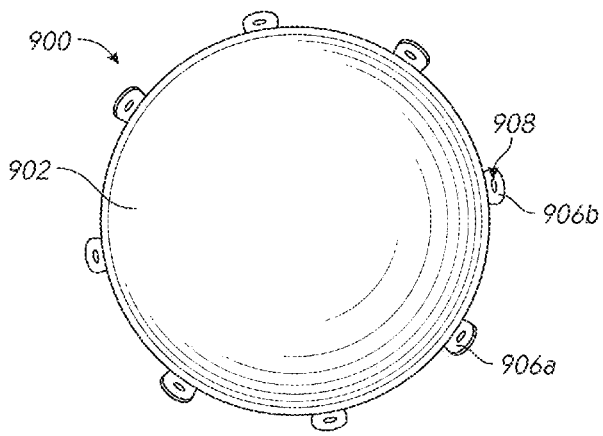
FIG. 9C depicts a posterior plan view of the prosthetic capsular device of FIG. 9A.
Figure 9D:
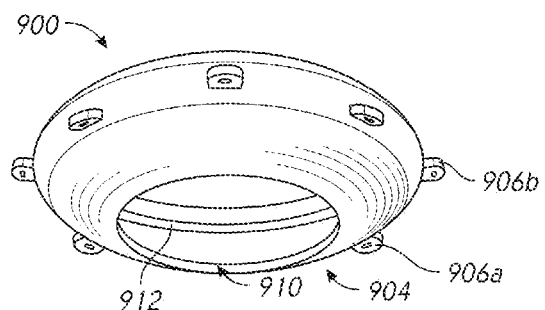
FIG. 9D depicts an anterior side perspective view of the prosthetic capsular device of FIG. 9A.

FIGS. 9A-9D illustrate another example prosthetic capsular device 900, in which FIG. 9A is a side view, FIG. 9B is a side cross-sectional view, FIG. 9C is a posterior plan view, and FIG. 9D is an anterior side perspective view. The prosthetic capsular device (e.g., bag, bowl, housing, structure, cage, frame) 900 does not include or is free of a flange, although combination with a flange (e.g., the flange 20) is also possible. The device 900 comprises a posterior side 902 and an anterior side 904. The posterior side 902 has a generally rounded shape. As shown in FIG. 9B, the posterior side 902 comprises a refractive portion, which provides a refractive property to the device 900.

As shown in FIGS. 9B and 9D, the anterior side 904 comprises an opening 910, which allows the insertion of an IOL as discussed herein. The opening 910 may have sharp edges (e.g., as depicted in FIGS. 9B and 9D), rounded edges (e.g., as shown in other implementations herein), etc. Sharp edges may reduce material volume and allow insertion of the device 900 through a smaller incision. The opening 910 may have a diameter between about 5 mm and about 10 mm (e.g., between about 6 mm and about 9 mm). The sidewalls of the device 900 optionally do not extend radially inwardly such that the opening 910 may have a large or maximum diameter (e.g., based on the diameter of the inner surface of the sidewalls of the device 900). A larger opening 910 may aid insertion of the IOL and/or reduce volume and/or mass, which can aid insertion into small incisions (e.g., by being easier to compress into and/or advance through an injection device). A smaller opening 910 may aid in containment of an IOL (e.g., better defining the interior volume of the device 900 and/or inhibiting anterior drift on an inserted IOL).

As shown in FIGS. 9B and 9D, the device 900 comprises an internal lip 912. The internal lip 912 can run partially, intermittently, or completely around the inside of the prosthetic capsular device 900. The lip 912 may be designed to hold the haptics of an IOL stable, inhibiting or preventing the lens from rotating or shimmering during eye movements. The lip 912 is proximate to a midpoint of the device 900, for example being proximate to a plane about half way between the posterior side 902 and the anterior side 904. The lip 912 may be proximate to the anterior side 902, proximate to the anterior side 904, etc., and can be designed and/or selected based on the IOL to be inserted into the device 900. The device 900 may comprise a plurality of lips 912, for example configured to engage a plurality of IOLs and/or to provide a plurality of alternative positions to engage one IOL. The lip 912 may comprise a tubular structure, for example configured to lockingly engage haptics of an IOL (e.g., by insertion of end portions of one or more haptics into a lumen of the tubular structure, by resilient compression of the tubular structure by a haptic, etc.). Rather than extending radially inwardly (e.g., as shown in FIGS. 9B and 9D), the lip 912 could extend radially outwardly, for example comprising a groove in the inner sidewalls of the device 900. A lip 912 comprising a groove may be integrally formed (e.g., during molding of the device 900) and/or formed after (e.g., by laser milling or diamond lathe cutting). Combinations of the lips 912 described herein are also possible. For example, the lip 912 could comprise: one or a plurality of lips 912; position(s) proximate to a surface and/or a midpoint; continuous and/or intermittent; filled and/or tubular; a groove extending into the sidewalls of the device 900; and combinations thereof.

The device 900 comprises, around a perimeter of the device 900, a plurality of tabs or haptics 906. The tabs 906 are not in contact and may be considered not continuous. Tabs 906 that are not continuous may use less material and impart less volume and/or mass to the device 900, allowing the device 900 to be easier to insert into small incisions. Use of less material may reduce costs due to use of less material. As discussed above, tabs that are continuous may provide better apposition with the natural capsular bag and/or be more form fitting, but may use more material and impart more volume and/or mass to a device, which can inhibit insertion into small openings. Depending on the application, the devices described herein that include tabs may include tabs that are continuous, not continuous, and combinations thereof (e.g., comprising continuous tabs over a portion of the perimeter).

The tabs 906 comprise an opening or hole or aperture 908. The openings 908 illustrated in FIGS. 9A-9D extend all of the way through the tabs 906, but could extend only partially through the tabs 906. The openings 908 may assist in suturing the device 908, allow fibrosis therethrough, etc. The tabs 906 include tabs 906a that are anteriorly biased and tabs 906b that are posteriorly biased. Biased tabs 906 (e.g., tabs 906a, 906b having alternating bias) can inhibit preferential torqueing and tilt. In addition and/or alternatively to being differently biased, the tabs 906 may have other differences (e.g., shape, material, absence of an opening 908, anterior-posterior position, orientation, combinations thereof, and the like).

Figure 10A:
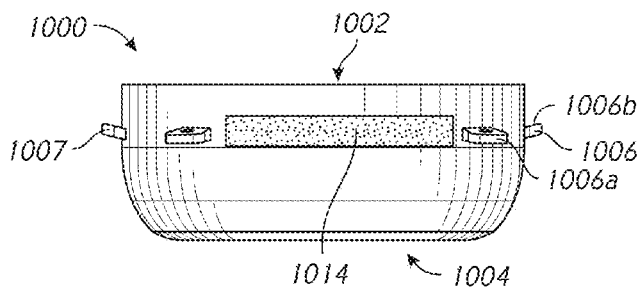
FIG. 10A depicts a side view of yet another example prosthetic capsular device.
Figure 10B:
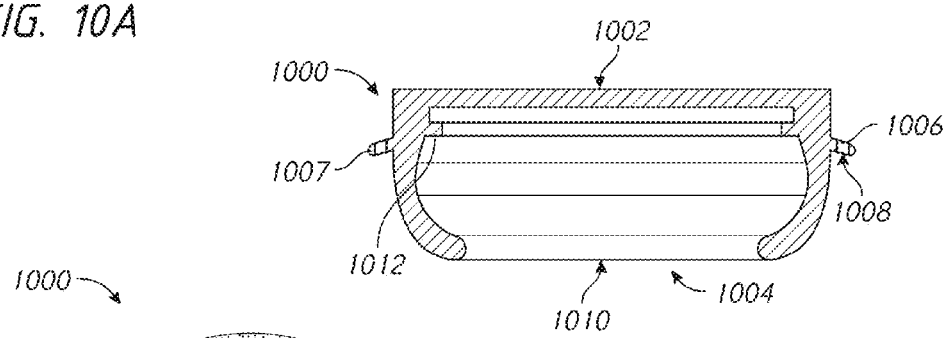
FIG. 10B depicts a side cross-sectional view of the prosthetic capsular device of FIG. 10A.
Figure 10C:
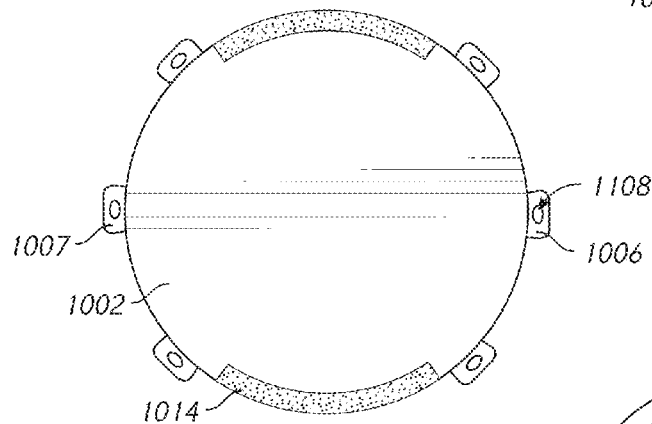
FIG. 10C depicts a posterior plan view of the prosthetic capsular device of FIG. 10A.
Figure 10D:
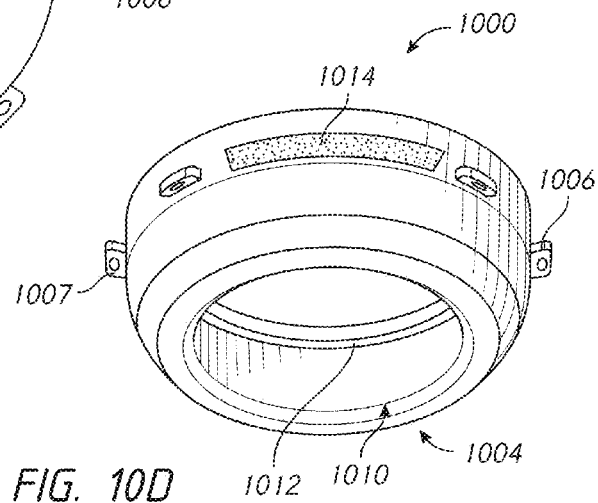
FIG. 10D depicts an anterior side perspective view of the prosthetic capsular device of FIG. 10A.

FIGS. 10A-10D illustrate yet another example prosthetic capsular device 1000, in which FIG. 10A is a side view, FIG. 10B is a side cross-sectional view, FIG. 10C is a posterior plan view, and FIG. 10D is an anterior side perspective view. The prosthetic capsular device (e.g., bag, bowl, housing, structure, cage, frame) 1000 does not include or is free of a flange, although combination with a flange (e.g., the flange 20) is also possible. The device 1000 comprises a posterior side 1002 and an anterior side 1004. The posterior side 1002 has a generally flat shape. As shown in FIG. 10B, the posterior side 1002 comprises a solid surface, but substantially constant thickness and parallel planar surfaces are indicative of a lack of a refractive portion, which may be useful if the IOL provides sufficient refractive power (e.g., if the diopter value is low). Although the posterior side 1002 is flat, the interior surface of the posterior part of the device 1000 could be curved such that the device 1000 can provide refractive power even though the outer surface is flat.

As shown in FIGS. 10B and 10D, the anterior side 1004 comprises an opening 1010, which allows the insertion of an IOL as discussed herein. The opening 1010 may have sharp edges (e.g., as shown in other implementations herein), rounded edges (e.g., as depicted in FIGS. 10B and 10D), etc. Curved surfaces are more likely to transmit light than sharp surfaces, so an opening 1010 comprising rounded edges may reduce refraction of light and inhibit or prevent unwanted reflections or dysphotopsias.

As shown in FIGS. 10B and 10D, the device 1000 comprises an internal lip 1012. The internal lip 1012 can comprise the same options and/or features as discussed herein (e.g., with respect to the lip 912). The lip 1012 is proximate to the posterior side 1002, for example being posterior to a plane half way between the posterior side 1002 and the anterior side 1004 and/or being posterior to the tabs 1006. Consistent with the lip 1012 comprising the options of other lips described herein, the lip 1012 may be proximate to the anterior side 1004, proximate to a midpoint, etc., and can be based on the IOL to be inserted into the device 1000.

The device 1000 comprises, around a perimeter of the device 1000, a first plurality of tabs or haptics 1006 and a second plurality of tabs or haptics 1007. The tabs 1006, 1007 can comprise the same options and/or features as discussed herein (e.g., with respect to the tabs 906). The pluralities of tabs 1006, 1007 are not in contact and may be considered not continuous. The pluralities of tabs 1006, 1007 are spaced from each other about a perimeter of the device 1000, bunched at two opposite sides of the device 1000. Pluralities of tabs may be bunched at one side, two sides (e.g., as shown in FIGS. 10A-10D), three sides, etc. Pluralities of tabs may be evenly circumferentially spaced (e.g., as shown in FIGS. 10A-10D) or unevenly circumferentially spaced. Pluralities of tabs may comprise the same types of tabs (e.g., as shown in FIGS. 10A-10D) or different types of tabs (e.g., comprising different anterior-posterior bias, shape, material, absence of an opening 1008, anterior-posterior position, orientation, continuousness, combinations thereof, and the like). Tabs within a plurality of tabs may be the same or different (e.g., comprising different anterior-posterior bias (e.g., as shown by the tabs 1006a, 1006b in the plurality of tabs 1006), shape, material, absence of an opening 1008, anterior-posterior position, orientation, continuousness, combinations thereof, and the like). In implementations in which the tabs comprise circumferentially spaced pluralities of tabs (e.g., the tabs 1006, 1007), the tabs may be configured to provide more engagement (e.g., by being larger, by being continuous, combinations thereof, and the like) than if the tabs extend all around the perimeter of the device. Use of fewer tabs by circumferentially spacing pluralities of tabs 1006, 1007 may reduce volume and/or mass, which can aid insertion into small incisions (e.g., by being easier to compress into and/or advance through an injection device). Use of fewer tabs by circumferentially spacing pluralities of tabs 1006, 1007 may reduce costs due to use of less material. As discussed above, tabs that are continuous may provide better apposition with the natural capsular bag and/or be more form fitting, but have increased volume and/or mass. Depending on the application, the devices described herein that include tabs may include tabs that are continuous, not continuous, and combinations thereof (e.g., comprising continuous tabs over a portion of the perimeter).

The tabs 1006, 1007 are illustrated as being generally short, rounded-edge rectangular structures. Other shapes are also possible, for example arcuate (e.g., semicircular), elongate (e.g., spiraling out of the device 1000), having end features (e.g., loops, hooks), etc. When pluralities of tabs 1006, 1007 are circumferentially spaced, the perimeter of the device 1000 may have room for more voluminous tabs 1006, 1007.

As shown in FIGS. 10A, 10C, and 10D, the device 1000 comprises textured surfaces 1014. The textured surfaces 1014 may comprise pores (e.g., extending partially through the walls of the device, extending fully through the walls of the device 1000, circular, spherical, elongate, having an undulating pattern, etc.), surface texture patterns, combinations thereof, and the like. The textured surfaces 1014 may be configured to capture, engage, and/or promote fibrosis (e.g., by not being smooth). The textured surfaces 1014 may be formed during forming the device 1000 (e.g., by being integrated into a mold) and/or formed after forming the device 1000 (e.g., by laser drilling). The device 1000 and/or other prosthetic capsular devices may lack or be free of tabs 1006, 1007, and the textured surfaces 1014 may provide engagement with the natural capsular bag, allow fibrosis, etc. The device 1000 may comprise tabs 1006, 1007 comprising openings or holes 1008 that may assist in suturing the device 908, allow fibrosis therethrough, etc. and textured surfaces 1014 that may allow fibrosis. The textured surfaces 1014 of the device 1000 are positioned between the pluralities of tabs 1006, 1007, but any portion of the device 1000 may comprise a textured surface, preferably not in the optical path, which can permit strategic fibrosis. The textured surfaces 1014 may be continuous around the perimeter, circumferentially spaced (e.g., as shown in FIG. 10C), in patches, etc. If the device 1000 comprises tabs, the tabs may comprise textured surfaces.

Figure 11A:
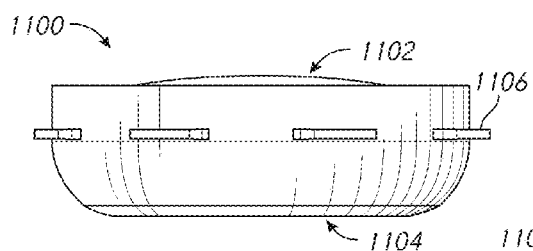
FIG. 11A depicts a side view of still another example prosthetic capsular device.
Figure 11B:
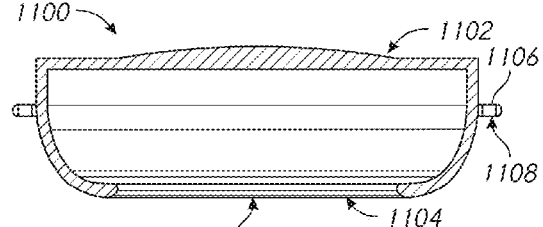
FIG. 11B depicts a side cross-sectional view of the prosthetic capsular device of FIG. 11A.
Figure 11C:
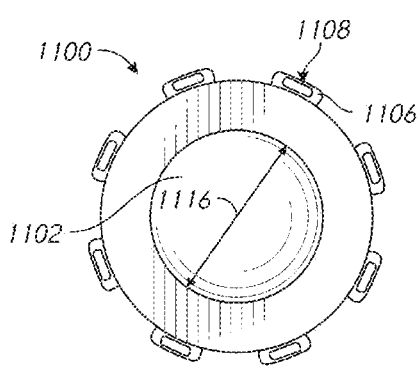
FIG. 11C depicts a posterior plan view of the prosthetic capsular device of FIG. 11A.
Figure 11D:
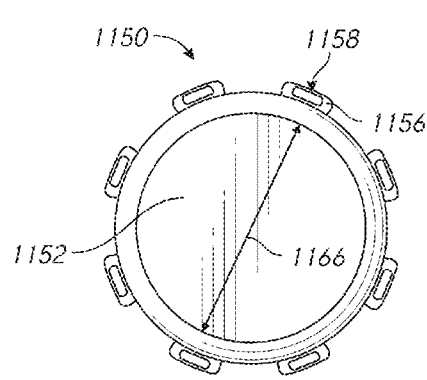
FIG. 11D depicts a posterior plan view of still yet another example prosthetic capsular device.
Figure 11E:
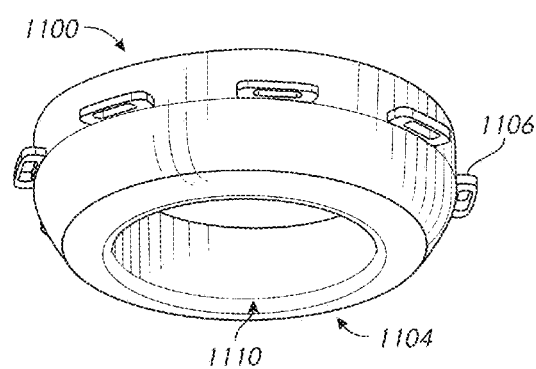
FIG. 11E depicts an anterior side perspective view of the prosthetic capsular device of FIG. 11A.

FIGS. 11A-11C and 11E illustrate still another example prosthetic capsular device 1100, in which FIG. 11A is a side view, FIG. 11B is a side cross-sectional view, FIG. 11C is a posterior plan view, and FIG. 11E is an anterior side perspective view. FIG. 11D depicts a posterior plan view of still yet another example prosthetic capsular device 1150 that is similar to the device 1100 except for the refractive portion, as described in further detail below. The prosthetic capsular device (e.g., bag, bowl, housing, structure, cage, frame) 1100 does not include or is free of a flange, although combination with a flange (e.g., the flange 20) is also possible. The device 1100 comprises a posterior side 1102 and an anterior side 1104.

The posterior side 1102 has a generally flat edge with a convex central portion. As shown in FIG. 11C, convex central portion of the posterior side 1102 comprises a refractive portion, which provides a refractive property to the device 1100 for refractive powers >0 D (positive or converging lens power). The posterior side 1102 can include a concave central portion for refractive powers <0 D (negative or diverging lens power). As shown in FIG. 11C, the refractive portion of the device 1100 has a diameter 1116 that is about 6 mm. As shown in FIG. 11C, the refractive portion of a similar device 1150 has a diameter 1166 that is about 8 mm. Most IOL optics have a diameter between 5.5 mm and 6 mm since the refractive power range of IOLs is typically ±35 D, and IOLs are designed to be substantially the same throughout the refractive power range such that even low refractive power IOLs have a diameter similar to that of a high refractive power IOL. The diameters of the refractive portion of the devices 1100, 1150 are not limited by refractive power value, which can allow larger diameter refractive portions as evidenced by the device 1150. The devices 1100, 1150 could provide a small refractive power value to aid an IOL, which could allow IOLs with smaller refractive powers to be used, resulting in a total refractive power, which could potentially increase the diameter of such IOLs if no longer designed based on a full refractive power range. The devices 1100, 1150 could provide a refractive surface that has sufficient refractive power that no IOL providing additional refractive power is inserted into device 1100, 1150.

As shown in FIGS. 11B and 11D, the anterior side 1104 comprises an opening 1110, which allows the insertion of an IOL as discussed herein. The opening 1110 may have sharp edges (e.g., as shown in other implementations herein), rounded edges (e.g., as depicted in FIGS. 11B and 11E), etc. Sharp edges may reduce material volume and allow insertion of the device through a smaller incision. Curved surfaces are more likely to transmit light than sharp surfaces, so an opening comprising rounded edges may reduce refraction of light and inhibit or prevent unwanted reflections or dysphotopsias.

As shown in FIGS. 11B and 11E, the device 1100 lacks or is free of an internal lip. Lack of an internal lip may reduce volume and/or mass, which can aid insertion into small incisions (e.g., by being easier to compress into and/or advance through an injection device). Lack of an internal lip may reduce costs due to use of less material. Alternatively, the device 1100 may comprise an internal lip, as the features described with respect to the devices described in the present application may be optionally substituted, interchanged, rearranged, etc. when compatible.

The device 1100 comprises, around a perimeter of the device 1100, a plurality of tabs or haptics 1106. The device 1150 comprises, around a perimeter of the device 1150, a plurality of tabs or haptics 1156. The tabs 1106, 1156 can comprise the same options and/or features as discussed herein (e.g., with respect to the tabs 906, 1006, 1007). The pluralities of tabs 1106, 1156 are not in contact and may be considered not continuous. The tabs 1106, 1156 are not biased in an anterior and/or posterior direction, which may be easier to manufacture than biased tabs. The tabs 1106, 1156 are larger than the tabs 906, 1006, 1007 described herein. Larger tabs 1106, 1156 may increase apposition of the device 1100, 1150 to a natural capsular bag and/or increase fibrosis surface area. Larger tabs 1106, 1156 may also allow the formation of larger openings 1108, 1158. Openings that extend all the way through a tab, if desired, may be difficult to produce in small tabs, so the larger tabs 1106, 1156 may enable easier formation of larger openings 1108, 1158 that fully extend through the tabs 1106, 1156. Larger openings 1108, 1158 may aid in suturing.

The prosthetic capsular devices described herein or similar prosthetic capsular devices may be compatible with any IOLs that are currently commercially available or developed in the future, regardless of manufacturer (e.g., AcrySof platform of lenses from Alcon, TECNIS ZCB00, ZKB00, ZLB00, ZMB00, ZCT, and Symfony extended depth of focus lenses from Abbott Medical Optics, enVista, TRULIGN, Akreos, SofPort, and Crysalens from Bausch and Lomb, iSert from Hoya Corporation, ELENZA Sapphire from Elenza, Calhoun light adjustable lens from Calhoun Vision, and others), material (e.g., comprising PMMA, silicone, relatively hydrophobic acrylic, relatively hydrophilic acrylic, other acrylic, collamer, combinations thereof, and the like), product type (e.g., aphakic, pseudophakic), refractive power (e.g., negative, planar, and positive), number of pieces (e.g., one, two, three, and more), accommodation (e.g., accommodating and non-accommodating), size (e.g., diameter, thickness), shape (e.g., disc, toroid, symmetric, and asymmetric), haptic type and quantity, delivery system, delivery profile, expansion profile, combinations thereof, and the like.

Referring again to the potential advantages described above, the prosthetic capsular devices described herein or similar prosthetic capsular devices can increase the options for IOL replacement. A physician may be less reluctant to perform IOL replacement if the initially-implanted lens fails due to the reduce risk of complications, such that the physician will more readily replace the initially-implanted lens with a more appropriate lens, thereby providing a better outcome (e.g., initial outcome). Even without replacement, the IOL selection capability provided by the refractive portion of the prosthetic capsular device and/or the positioning capability provided by the prosthetic capsular device and can improve outcome (e.g., initial outcome). Certain prosthetic capsular devices described herein may be able to provide more accurate refractive outcomes after initial surgery every or almost every time.

Since IOL replacement from a prosthetic capsular device involves less risk than IOL replacement without a prosthetic capsular device, physicians and patients may also be more open to replacement of the IOL over time. For example, IOL replacement may be potentially advantageous for medical reasons (e.g., due to changing physiological conditions (e.g., development of macular degeneration, glaucomatous optic neuropathy), refractive reasons (e.g., change of corneal power due to corneal dystrophy, the progressive hyperopic shift associated with previous refractive keratotomy), the patient's desire to access new intraocular technology (e.g., powered accommodating IOL, implantable intraocular wireless input/output computerized devices)), such that replacement of an IOL in a prosthetic capsular device can provide improved outcomes even after the initial surgery. The reduced risk of complications due to removal from and placement in a prosthetic capsular device may even permit physicians and patients to exchange the IOL as often as desirable. The ability to change the IOL more often due to a prosthetic capsular device may also permit surgery at an earlier age, as the physician may dispossess concerns that the initially-implanted IOL must last the rest of the patient's life or risk serious complications upon replacement. Such IOL replacement procedures may even be able to substitute for removable corrective devices such as glasses and contact lenses.

The prosthetic capsular devices described herein or similar prosthetic capsular devices may provide a platform by which a technology device (e.g., a wearable miniaturized electronic technology device) can be inserted and carried in the eye independent of or in combination with an IOL. As used herein, the phrase "technology device" is a broad term including any device that generally provides biometric measurement functions, computer functions (e.g., digital data input directly via wireless signals and/or indirectly through sensors, data analysis, input, and/or output), image generation and projection onto the retina, and/or internet/WiFi capabilities and is small enough to fit functionally within the eye (e.g., having a diameter less than or equal to about 11 mm and a thickness less than or equal to about 6 mm), some of which can be used to perform useful electronic functions for the wearer. Examples of such devices include, but are not limited to, computers (e.g., Google Glass, Microsoft Hololens), virtual reality devices, augmented reality devices, head-mounted displays (such as graphic or image displays, map displays), devices with WiFi and/or internet connectivity, image receivers (e.g., television or movies), game devices, projectors (including image viewers, image readers, or image senders), GPS devices, biometric measurement devices (e.g., aqueous humor glucose and electrolyte sensor, Intraocular VEGF sensor, blood glucose level sensors, electrolyte sensors, heart rate sensors, basal metabolic rate sensors, temperature sensors, EEG, EKG, intraocular pressure sensors, ciliary muscle contraction sensors, dynamic pupil change sensors), retinal prostheses, camera functions (e.g., still image and/or video recording), and e-mail senders or receivers. Such devices do not necessarily have to be characterizable as wearable (e.g., because they are implanted rather than "worn"), miniaturized (e.g., because they may have already been a certain size), or electronic (e.g., because they may be mechanical), but would still be a "technology device" as described herein.

In use, the technology device is in the prosthetic capsular device, and the output from the electronic device is provided to the user, either through viewing of the output visually through the eye or otherwise (e.g., wireless transmission to an external computing device). Data from the outside of the body can be transmitted to and/or from the technology device in a wireless electromagnetic energy format including, but not limited to, currently available modalities such as Bluetooth, radio signals, WiFi, and/or analog and/or digital cellular format signals. This data may be processed and output in the form of a visual display that could be projected onto the retina, creating the perception of a digital heads-up display, for example how Google Glass employed this technology in an external device. For technology devices configured to sense biometric data (for example, but not limited to, glucose level, electrolyte level, VEGF level, basal metabolic rate, temperature, EEG, EKG, heart rate, intraocular pressure (e.g., for glaucoma patients or glaucoma candidates), ciliary muscle contraction, papillary construction or dilation, eye movement, blink rate, combinations thereof, and the like), the data could be collected by the technology device and transmitted wirelessly by the technology device to an external device configured to receive the data The electronic technology or the external device may be configured to process the data. For example, before transmission, the technology device may transform the data for privacy, security, data transfer efficiency, etc. The external device may be configured to process the data, for example because the external device may more easily be linked to a power source, cooled, etc. The external device can be configured to provide the data in a format that can be utilized in a health care decision. The data may be accessible by the wearer and/or a doctor or other healthcare professional, for example locally and/or through via a secure (e.g., HIPAA-compliant) network.

Another application of this technology could be use by people in environmentally challenging environments, for example intelligence agents, special forces soldiers, astronauts, police officers, and/or firefighters. Various sensors (e.g., external environmental sensors (e.g., for oxygen level, atmospheric pressure, temperature, infrared heat sensors) and/or internal biometric sensors (e.g., for oxygen level, temperature, heart rate, heart rhythm, glucose level, etc.) could be centrally assessed in an external computing device (e.g., a smartphone), and then transmitted to the intraocular lens to project information onto the retina in a dashboard type configuration. This information could be used to help them avoid danger and/or more effectively perform their duties. The technology could also be advantageous to performing any tasks that could benefit from a heads-up display such as surgery (e.g., recognition and labeling of anatomical structures), mechanical repair (e.g., recognition and labeling of mechanical elements), translation (e.g., from a first language to a second language), business identification (e.g., based on user ratings, health ratings, etc.), directions, design, etc.

Generally, as blood glucose increases, the optical properties of the aqueous humor change in a corresponding way, and such change is optically detectable through a plurality of methods, such as Raman spectroscopy, optical polarimetry and other methods. Additionally, changes in glucose concentration in the aqueous humor can interact with other devices comprised on or in the system, for example through oncotic pressure/osmotic gradients which can be measured through a plurality of ways, including through a fluorescence resonance energy transfer system based on Concanavalin A chemistry. Additionally, the system can comprise a passive sensor, and an electric transmitter that can be configured to harness the glucose induced osmotic changes in the aqueous humor by placing sensors in the system such that their relative distance would change (increase or decrease) in a corresponding manner (for example, the sensors (potentially using two or more capacitor plates) could be configured to move closer to each other as glucose levels increased and further apart when glucose levels decreased. This relative distance would be quantifiable (for example as an increase or decrease in electrical charge of capacitors), and the data could be transmitted for correlation to a secondary device). In an example implementation of an electronic device, a blood glucose monitor may comprise an optical detector configured to monitor the optical properties of the aqueous humor, such as refractive index, optical polarity, and/or spectroscopic properties in vivo, for example, using an optical detector such as a camera, light sensor, spectrometer, and/or optical polarimeter. An advantage of having the optical polarimeter based glucose sensor housed within the anterior segment of the eye (and particularly housed inside the capsular prosthesis device is that it overcomes the artifact induced by the corneal birefringence and the motion artifact, two of the most significant obstacles to accurate measurement methodology in external devices. In another example, the optical detector (spectroscopy unit) can be used to measure the changes of wavelength of light produced in a glucose sensitive fluorescence unit. The changes in optical properties of the aqueous humor and/or secondary changes induced in a glucose sensitive fluorescence unit can be correlated to blood glucose level via in situ electronics and/or raw data (e.g., images, histograms, etc.) can be transmitted to an external device configured to perform the correlation. The results can be available on and/or transmitted to an external device (e.g., smartphone, smartwatch), which could trigger an alarm if the blood glucose value is above and/or below certain thresholds. The blood glucose value can inform the user about the need to ingest sugar, take an insulin shot, etc or could be directly integrated into an insulin pump that could automatically dose the patient according to an algorithm based on a determined dose response as directed by a physician. Intraocular pressure can also be measured in vivo through a secondary device for insertion into the prosthetic capsular device. For example, a secondary device having a passive sensor and an electric transmitter can be positioned in or on the prosthetic device. The secondary device can be configured to harness the changing intraocular pressure by placing sensors on the secondary device such that their relative distance would change (increase or decrease) in a corresponding manner (for example, the sensors (potentially using two or more capacitor plates) would move closer to each other as the intraocular pressure increased and further apart when intraocular pressure decreased. This relative distance would be quantifiable (for example as an increase or decrease in electrical charge of capacitors), and the data could be transmitted for correlation to a secondary device which would account for atmospheric barometric pressure, record the difference and store and/or transmit the data to other devices). Other bodily parameters that can be measured in the eye include, but are not limited to, body temperature, heart rate, VEGF levels in macular degeneration patients, diabetic retinopathy, and retinal vein occlusion. One or all of these values may be visualizable on an external device (e.g., smartphone, smartwatch) and/or via an internal display system (e.g., a heads-up display). These technologies can all be engineered in such a way as to be housed within the described prosthetic capsular device without interfering with the optical properties of the refractive portion of the device.

The technology device can be used in combination with an intraocular lens. For example, the technology device can be used to control the properties of the intraocular lens (e.g., the refractive power, ultraviolet (UV) or visual light transmission properties of the IOL, etc.) and/or the properties of the prosthetic capsular device. For example, the technology device could be used to control the properties of a Calhoun adjustable lens (e.g., as described in U.S. Pat. No. 7,988,285, which is hereby incorporated by reference in its entirety), an Elenza lens (e.g., as described in further detail below), etc. When used in combination with an IOL, the technology device and the IOL may be positioned such that the technology device does not interfere with the sight lines of the IOL (e.g., the technology device does not block or interfere with light and images transmitted through the IOL and, ultimately, to the retina). The technology device may be around the outside perimeter edge of the intraocular lens. For example, two separate devices, (1) an IOL and (2) the technology device, may each be attached at the outer edge of the IOL. For another example, the IOL can be manufactured or adapted to have the technology device integral to the IOL at the outer perimeter edge of the IOL. If an IOL has a diameter of about 6 mm, a technology device having a width of about 2 mm may be added around the outer perimeter of the IOL, resulting in the IOL and technology device having a total diameter of about 10 mm. Such devices can vary in size, but the center is preferably at least about 1 mm to serve as the optic, and the entire device (technology device and optic) is preferably small enough to be implanted through an incision into the eye (e.g., the entire device may be similar in size to an IOL).

FIGS. 12A-12C illustrate example prosthetic capsular devices including technology devices and IOLs, and a manner of positioning the technology device and the IOL within a prosthetic capsular device. FIG. 12A shows a cross-section of a ring-like technology device 1202 inside a prosthetic capsular device 1200. FIG. 12A also depicts an IOL 1204 in the prosthetic capsular device 1200. FIG. 12B depicts a front view of an example intraocular lens 1250 usable in the example prosthetic capsular device 1200 shown in FIG. 12A in which the technology device 1250 surrounds the outer edge of the IOL 1250 (e.g., surrounds the outer edge of the optical surface of the IOL 1250). FIG. 12C depicts a top front perspective of the example intraocular lens 1250. The optical surface 1260 is not blocked by the technology device elements of the IOL 1250. The technology device 1250 includes an element 1252 for data output, an element 1254 for data input or receiving, and an element 1256 for data processing.

The prosthetic capsular device can comprise a material configured to shield the other internal eye structures from the small amount of heat or electromagnetic waves that might be generated by the technology device. Examples of such materials include silicone and silicone derivatives, acrylic, acrylic derivatives, collamer, biocompatible methacrylates (e.g., PMMA), biocompatible polymers, olefins (e.g., polypropylene), polyimide, combinations thereof (e.g., silicone and polyimide), and the like. A device comprising a thermally insulating material such as silicone, polyimide, acrylic, silicon dioxide, flexible glass, aerogels, combinations thereof (e.g., silicone and polyimide), and/or the like may be used to inhibit or prevent heat transfer due to conduction. Certain device dimensions can be increased to increase heat insulation, although injectability concerns may also be considered. A reflective and/or opaque material such as polyimide may be used to inhibit or prevent heat transfer due to radiation. Since the device is capsular, the device can be configured to shield (e.g., selectively shield) the ciliary body from heat. In some implementations, the prosthetic capsular device may comprise a combination of silicone and polyimide (e.g., polyimide overmolded on silicone).

The prosthetic capsular device can comprise a material or have a configuration configured to protect the interior of the eye from unwanted transmission of light. For example, the prosthetic capsular device can be designed to shield the posterior segment of the eye from UV light (for example, therapeutic UV light that is used in high concentration during procedures such as corneal cross-linking and in the refractive change that occurs through UV light modification of the Calhoun light adjustable lens). There are reports of retinal toxicity to UV exposure during these treatments because the pupil commonly dilates beyond the borders of the optic (e.g., greater than about 6 mm), and the UV filter coating on the posterior aspect of these lenses is prone to being rubbed off during folding and injecting, leaving the retina exposed to high doses of UV light transmittance through areas in which the coating is scratched off and around the outer border between the pupil edge and the rim of the IOL. By using a prosthetic capsular device which is larger than the pupil (about 6-10.5 mm in minimal width, there would be no gap between the border of the iris and the IOL. Other sizes of prosthetic capsular devices can also provide UV benefits. Using established materials and methods well known in the art of intraocular lens manufacturing, the UV chromophore could be substantially incorporated into the material of the prosthetic capsular device so this property would not be susceptible to failure due to inadvertent mechanical removal (e.g., scratching and/or scraping off) during folding, insertion, and/or unfolding of the prosthetic capsular device.

The prosthetic capsular device can have a near-UV and UV blocking ability, which can protect the eye from energy or radiation in the form of near-UV or UV light emanating from the environment and utilized for therapeutic and refractive purposes. Intraocular lenses have been made with coatings that include UV blocking chromaphores, which can suffer from scratching issues upon implantation and other issues, as described above. There are currently multiple ophthalmic therapies that utilize UV light as a treatment modality. For example, the Calhoun light adjustable lens (available from Calhoun Vision, Inc. of Pasadena, Calif.) is an intraocular lens in which the refractive power can be changed post-operatively through the targeted application of near-UV and UV light of a specific wavelength for various time periods using a proprietary exposure algorithm. The back surface of the Calhoun light adjustable lens has a UV blocking layer, but that UV blocking layer is prone to being mechanically damaged (e.g., rubbed or scratched off) upon insertion of the lens, rendering the UV blocking layer potentially ineffective such that when the near-UV or UV light treatment is performed to adjust the lens power post-operatively, the patients are prone to near-UV and UV radiation exposure related complications to the contents of the posterior segment (ciliary body, retina, optic nerve, etc.). The diameter of the Calhoun lens optic is 6.0 mm, which for many patients is smaller than the dilated pupil such that UV light may pass by the edges of the lens. For these patients, applying a wide beam of near-UV or UV light to the lens has the potential to cause UV radiation exposure related complications to the contents of the posterior segment (ciliary body, retina, optic nerve, etc.). If this light adjustable lens is placed inside a prosthetic capsular device that is larger or much larger than the dilated pupil and that has the ability to block near-UV and UV light, there could be a reduced likelihood of UV radiation related complications during the post-operative treatment.

In some implementations, a capacitor, series of capacitors, and/or a rechargeable battery that can be recharged by a device from outside the eye (such as by external induction methods or other electromagnetic radiation energy such as radio waves) may supply power to the technology device. The battery changer could be incorporated into or adapted to be affixed to a sleeping device such as a facemask, pillow, mattress, headboard, or bed linen to charge the battery during a user's sleep, sunglasses, a headband, or a hat to charge the battery while the user is outdoors, and/or spectacle frames or other appropriate devices for when the user is indoors. Preferably, the transfer of electricity to power a technology device either directly or through the charging of a battery is via an inductive charging system such as through resonant inductive coupling. For example, the external device could contain an induction coil and would be connected to a power source in order to generate an alternating electromagnetic field, and the technology device could contain a second induction coil configured to harness power from the alternating electromagnetic field generated by the external device and to convert the power into electricity to charge the battery. The prosthetic capsular device can be designed to shield the posterior segment structures, such as the iris, zonules, ciliary body, ciliary process, etc., from heat generated by the charging of batteries through external induction, or the discharge of heat generated by a technology device, for example using certain materials and techniques as described above. Increased local temperatures can result in inflammation and uveitis, and ultimately limit the biocompatibility of technology device. Utilizing a prosthetic capsular device having optical clarity and with thermal insulating properties (e.g., comprising silicone, silicone derivatives, polyimide, combinations thereof, the like, and/or other appropriate materials) could provide appropriate thermal insulation without adversely affecting visual function.

FIG. 74A illustrates an anterior side perspective view of an example intraocular lens 7450. The IOL comprises an optic 7452, a battery 7454 on a first radial side of the optic 7452, and electronics 7456 on a second radial side of the optic 7452. The electronics 7456, provided with energy from the battery 7454, can affect optical properties of the optic 7452.

FIG. 74B illustrates an anterior side perspective view of an example prosthetic capsular device 7400 containing the intraocular lens 7450 of FIG. 74A. The device 7400 may include the properties of other devices described herein, for example but not limited to the devices 5800, 6100, 6200, 6300, 6400, 6500, 6600, 6700, 6800, 6900, 7000, 7200. The device 7400 comprises a first insulated area 7402 and a second insulated area 7404. The insulated areas 7402, 7404 are configured to provide thermal insulation for parts of a device such as the device 7450 that may heat up. The insulated areas 7402, 7404 may be the same or different (e.g., having a different thickness or other dimension(s), comprising a different material, comprising a different shape, etc.). In some implementations, the insulated areas 7402, 7404 comprise polyimide.

FIG. 74C illustrates an anterior side perspective view of an example prosthetic capsular device 7410 containing an example intraocular lens 7460. The device 7410 may include the properties of other devices described herein, for example but not limited to the device 7400. The IOL 7460 is similar to the IOL 7450, for example including an optic 7462 and electronics 7466, but does not include a battery. The device 7410 may comprise or be configured to contain (e.g., comprising sufficient space radially outward of an optical path and/or contours) a modular battery 7414. The battery 7414 may interact with electrical leads extending from the device 7460. The battery 7414 may be rechargeable (e.g., using inductive charging, for example as described herein). The battery 7414 may be modularly exchanged, for example using an anchoring system as described herein. The device 7460 may be modularly exchanged, for example each new device 7460 powered by the battery 7414, and/or the battery 7414 may be changed with the device 7460.

FIG. 74D illustrates an anterior side perspective view of an example prosthetic capsular device 7420 containing an example intraocular lens 7470. The device 7420 may include the properties of other devices described herein, for example but not limited to the device 7400. The IOL 7470 is similar to the IOL 7450, for example including an optic 7472 and a battery 7474, but does not include electronics. The device 7420 may comprise or be configured to contain (e.g., comprising sufficient space radially outward of an optical path and/or contours) modular electronics 7412. The electronics 7412 may interact with electrical leads extending from the device 7470. The electronics 7412 may be modularly exchanged, for example using an anchoring system as described herein, which can allow upgrading of electronics configured to control the optic 7472. The device 7470 may be modularly exchanged, for example each new device 7470 powered by a new battery 7474, and/or the electronics 7412 may be changed with the device 7470.

FIG. 74E illustrates an anterior side perspective view of an example prosthetic capsular device 7430 containing an example intraocular lens 7480. The device 7430 may include the properties of other devices described herein, for example but not limited to the device 7400. The IOL 7480 is similar to the IOL 7450, for example including an optic 7482, but does not include electronics or a battery. The device 7430 may comprise or be configured to contain (e.g., comprising sufficient space radially outward of an optical path and/or contours) a modular battery 7414 and/or modular electronics 7412. The battery 7414 may interact with electrical leads extending from the device 7480. The battery 7414 may be rechargeable (e.g., using inductive charging, for example as described herein). The battery 7414 may be modularly exchanged, for example using an anchoring system as described herein, which can allow upgrading of electronics configured to control the optic 7482. The electronics 7412 may interact with electrical leads extending from the device 7480. The electronics 7412 may be modularly exchanged, for example using an anchoring system as described herein, which can allow upgrading of electronics 7412 configured to control the optic 7482. The device 7480 may be modularly exchanged. Each new device 7480 may powered by the battery 7414 and/or a new battery 7414. Each new device 7480 may be controlled by the electronics 7412 and/or new electronics 7412.

In some implementations, the device 7410, 7420, 7430 may comprise electrical leads configured to connect electrical components such as electronics, batteries, and controllable optics. Although schematically illustrated as rectangular and square, modular components may be adapted to utilize the volume at an end of the device 7410, 7420, 7430.

Referring again to the discussion of virtual and augmented reality devices herein, the prosthetic capsular devices described herein can be configured to contain one or more virtual and/or augmented reality devices. In some implementations, the devices can include insulation (e.g., thicker and/or different material) generally or specifically where virtual and/or augmented reality devices may be inserted. In some implementations, the devices can include walls, flanges, posts, rails, eyelets, openings, slits, etc. configured to interact with virtual and/or augmented reality devices that can be inserted separate from insertion of the prosthetic capsular device. In some implementations, the devices can include walls, flanges, posts, rails, eyelets, openings, slits, etc. configured to interact with modular insulating structures containing virtual and/or augmented reality devices that can be inserted separate from insertion of the prosthetic capsular device. In some implementations, the devices can include a heat sink (e.g., comprising fins on an outside of the housing structure). Miniature devices or components for virtual and/or augmented that may be shrunk or otherwise optimized to be inserted into or interact with the devices described herein include, for example, sensors (e.g., six-axis position sensors, glucose sensors, light sensors, motion sensors, etc.), display devices (e.g., retinal projectors, stereoscopic displays, external light dimmers, etc.), data sending and/or receiving devices, and the like. Potential uses for such devices include virtual reality (e.g., a method of transitioning between a transparent lens and an opaque lens with a screen used for virtual reality), augmented reality (e.g., a heads-up display that is implantable into the human capsule for augmented reality, gaming, etc.), enterprise applications (e.g., a heads-up display for training purposes), medical applications (e.g., a method for inserting time-released drugs into the human capsule; blood glucose monitoring using the fluids naturally present in the eye; a heads-up display to assist surgeons with a patient's vital signs, device instructions for use, drug interaction warnings, etc.; pressure measurement for early warning of potential glaucoma; liquid lenses allowing autofocus, optical zoom, etc.), gaming applications (e.g., controls based on eye and/or head movement, focusing, light levels, etc.), directions applications (e.g., a heads-up display that overlays direction and navigation cues such as turn-by-turn directions, business listings, etc. on top of real-world visual elements), virtual retinal display applications (e.g., a virtual retinal display paired with eye movement mapping), etc.

The prosthetic capsular device can be designed to be photo-responsive so as to shield the retina from unwanted light, which could provide a number of uses.

For a first example, people with chronic light-sensitivity may want a permanent decrease in the light transmitted. This would function like permanent internal sunglasses. A light blocking chromophore of any and all various wavelengths, and of any and all densities of transmission could be added to the material formulation, baked into material, contained in a film that can be added as a self-expanding and/or self-contained implant, and/or layered and/or bonded to the prosthetic capsular device, and/or absorbed/adsorbed into/onto the prosthetic capsular device.

For a second example, people might want to have a device in the eye that darkens in the light and becomes more clear/transparent in the dark (photogrey, photobrown). Photochromatic materials (e.g., silver chloride, silver halide), which change shape and light absorption profile in response to the presence or absence of UV light, could be added to the material formulation, baked into material, contained in a film that can be added as a self-expanding and/or self-contained implant, and/or layered and/or bonded to the prosthetic capsular device, and/or absorbed/adsorbed into/onto the prosthetic capsular device. Photochromatic materials may be combined with light blocking chromophores.

For a third example, people might want to take advantage of the pinhole effect that can be created by using a small aperture, which can extend the depth of focus of a given optical system. This can be achieved by darkening all but the central 1-2 mm (approximately) of the prosthetic capsular device. This effect could be permanent (e.g., comprising an opaque annular mask (e.g., comprising polyvinylidene fluoride (PVDF) and carbon nanoparticles) embedded in and/or on one or both surfaces of the refractive portion) or transient (e.g., using a color shifting photogrey, photobrown, and/or liquid crystal technology to create an annular mask that is opaque or has reduced transmittance). The mask could have an outer diameter between about 3 mm and about 3.5 mm (e.g., about 3.25 mm). The mask could have an inner diameter between about 1 mm and about 1.5 mm (e.g., about 1.35 mm). The mask could have a thickness between about 4 µm and about 6 µm (e.g., about 5 µm), although thickness may vary based on the number of masks. The mask may comprise a plurality of microperforations, for example small enough to not allow substantial light passage or to create diffractive dispersion, but removing enough material to increase flexibility of the mask. In the transient pinhole mask modality where there is good lighting, the patient would be able to read due to the transient pinhole effect that would be created. In low lighting, the pinhole effect would be removed. Such a device could improve near and intermediate vision, increase depth of focus (e.g., by at least about 1.5 D), maintain good distance vision, inhibit creation of competing focal points, glare, halos, night-vision problems, double vision, ghosting, etc., maintain binocularity for distance, and/or maintain binocular contrast sensitivity.

With reference to FIGS. 77A-77I, other patients with iris defects may wish to have an iris prosthesis placed at the time of cataract or lens replacement surgery, or perhaps at a later date following an intraocular injury. Iris prostheses can be bulky and/or difficult to implant. The prosthetic capsular devices disclosed herein can be configured to provide a defined and/or stable anterior opening upon which an iris prosthesis could be positioned to fit on top of the prosthetic capsular device and attach to it through a tongue and groove mechanism. The iris prosthesis can be made out of biocompatible materials, and can be made of various sizes, shapes, and colorings to match the size, shape and desired cosmetic appearance of the pupil and iris. This could be an entire 12 clock hour prosthetic iris in the case of total or near total aniridia or loss of iris tissue. Another implementation could be an iris prosthesis that is subtotal (11 clock hours, 10 clock hours, 9 clock hours, 8 clock hours, 7 clock hours, 6 clock hours, 5 clock hours, 4 clock hours, 3 clock hours, 2 clock hours, 1 clock hours, or any combination or variation thereof). Notwithstanding the size of the prosthesis, all would have an element to affix the prosthetic iris to the prosthetic device.

FIG. 77A-77I illustrates an example prosthetic iris device 7700 configured to be coupled to any of the prosthetic capsular devices 5880 disclosed herein. In an embodiment, the prosthetic iris device can be implanted in patients with total or partial loss of iris tissue (for example, aniridia or iridodialysis). The prosthetic iris device 7700 can be configured to treat light sensitivity, photophobia, glare, and/or cosmetic flaws in patients. In general, the use of a prosthetic iris device configured to be fixated in the sulcus and/or to the sclera can in some instances result in complications and/or may require adequate capsular support, and therefore such prosthetic iris devices may not be suitable for all patients. In an embodiment, the prosthetic iris device 7700 can reduce postoperative complications because the device 7700 does not require fixation or suturing to the sulcus and/or the sclera because the device 7700 is removably coupled to the prosthetic capsular device 7702, and/or may not require attachment to eye tissue. In an embodiment, the prosthetic iris device 7700 can be utilized whether or not there is adequate eye tissue capsular support because the device 7700 can be configured to be supported and maintained by the prosthetic capsular device 5880.

In an embodiment, the prosthetic iris device 7700 comprises a biocompatible material, for example, silicone, silicone derivatives, acrylic, acrylic derivatives, PMMA, collarmer, polymer, other biocompatible optically transparent, semi-transparent and/or opaque material, combinations thereof, and the like. In an embodiment, the prosthetic iris device 7700 comprises a circumference of about or that is no more than 10 mm. In some embodiments, the circumference of the prosthetic iris device 7700 is about or no more than 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, 10.5 mm, 11.0 mm, 11.5 mm, 12.0 mm, 12.5 mm, 13.0 mm, 13.5 mm, 14.0 mm, or 14.5 mm. In an embodiment, the prosthetic iris device 7700 can comprise an iris portion 7706 that is optically partially transparent and/or opaque. In an embodiment, the iris portion 7706 can comprise a color and/or pattern. In an embodiment, the color and/or pattern of the iris portion 7706 can be configured to have a similar appearance to a human iris. In an embodiment, the iris portion 7706 is only partially colored and/or patterned to cover only an affected area of the eye of a patient. In an embodiment, the iris portion 7706 is entirely colored and/or patterned to cover affected and non-affected areas of the eye. In an embodiment, the prosthetic iris device 7700 is not entirely circular in order to cover only portions of the eye where there exists iris tissue loss, for example, the prosthetic iris device can be an arc or a partial circle of 45 degrees, 90 degrees, 135 degrees, 180 degrees, 225 degrees, 270 degrees, or 315 degrees, as illustrated in FIGS. 77D, 77E, 77F (illustrating a 180 degree arc), 77G, 77H, 77I (illustrating a 90 degree arc).

In an embodiment, the prosthetic iris device 7700 comprises an opening 7704 having a diameter of about or no more than 4 mm. In some embodiments, the opening 7704 comprises a diameter of about or no more than 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, or 11 mm. In an embodiment, the prosthetic iris device 7700 can comprise an optically transparent portion in lieu of opening 7704. In an embodiment, the optically transparent portion is integral with respect to the iris portion 7706 to be a single monolithic piece. In an embodiment, the optically transparent portion is removably coupled to the iris portion 7706. In an embodiment, the optically transparent portion and the iris portion 7706 are part of a single transparent device wherein the iris portion 7706 is colored or adapted to be partially transparent and/or opaque.

In an embodiment, the prosthetic device 7700 comprises a circular or a substantially circular shape; however, other shapes are possible, such as square, oval, elliptical, or any other shape. In an embodiment, the iris portion 7706 is circular or substantially circular to resemble that of a natural human iris shape. In an embodiment, the prosthetic device 7700 comprises a curvature that curves toward the opening 7704; however, in other embodiments, the prosthetic device 7700 comprises a substantially planar configuration. In an embodiment, the prosthetic device 7700 is flexible and can adapt to the space and shape allocated by the surgical site. In an embodiment, the prosthetic device 7700 is configured to be rolled up, folded, or otherwise deformed for injection into the eye through an injector apparatus or otherwise inserted into the eye. In an embodiment, the prosthetic iris device 7700 is configured to self-expand to a pre-folded shape. In an embodiment, the prosthetic iris device 7700 is configured to be expanded by fluid upon implantation in the eye. In an embodiment, the prosthetic device 7700 is sufficiently rigid and/or resilient to withstand external pressures and/or forces exerted by the eye, fluid, eye movement, or the like in order to maintain or substantially maintain its shape and/or dimension.

In an embodiment, the prosthetic iris device 7700 comprises a ring structure 7712. In an embodiment, the ring structure 7712 is positioned on the posterior side and/or outer and/or inner perimeter and/or a middle portion of the prosthetic iris device 7700. In an embodiment, the ring structure 7712 is affixed, attached, embedded, overmolded, integrated, glued, or otherwise coupled to the prosthetic capsular device. In an embodiment, the ring structure 7712 can comprise an oval, circular, elliptical, or other shape. In an embodiment, a circular shaped ring structure 7712 can be advantageous in order to be able to rotate the prosthetic iris device 7700 to a particular orientation, especially, when the iris portion 7706 is an arc or partial circle. In an embodiment, an oval shaped ring structure that is configured to be the same or similar shape as the anterior opening to the prosthetic device can be advantageous in order to prevent the ring structure 7712 from rotating on the prosthetic device thereby keeping the prosthetic iris in a fixed position. In an embodiment, the ring structure 7712 is configured to fit lock and key with the anterior opening of the prosthetic capsular device 7702. In an embodiment, the ring structure 7712 can form a friction fit with the anterior opening of the prosthetic capsular device 7702. In an embodiment, the ring structure 7712 can be configured to be sutured or other otherwise fixed to the anterior opening of the prosthetic capsular device 7702. In embodiment, the prosthetic iris device 7700 can comprise an outer rim having one or more flanges and/or tabs that can be sutured to and/or form a friction fit with and/or tuck in and/or under the anterior opening of the prosthetic capsular device 7702. In an embodiment, the one or more flanges and/or tabs comprises the same material as the of the prosthesis iris device 7700 and/or the one or more flanges and/or tabs can comprise polyimide/prolene haptic type material that could secure the device into place.

In certain non-limiting examples, the prosthetic capsular devices described herein could perform one or more of the following functions: provide a protected prosthetic receptacle having refractive properties, for an intraocular electronic technology device having the ability to send and receive wireless data, and/or interact with internal or external controls through external eye movements, pupil movement, ciliary body contraction, voice, and or controls from other prostheses (contacts, glasses, computer screens, projectors); provide a protected prosthetic receptacle for battery storage, designed to power electronic intraocular technology; provide a protected prosthetic receptacle for an electric powered accommodating intraocular lens (such as the Elenza lens); and/or provide a protected prosthetic receptacle for the repair or replacement of intraocular technology including traditional lenses, and electric powered devices as described above.

Figure 13:
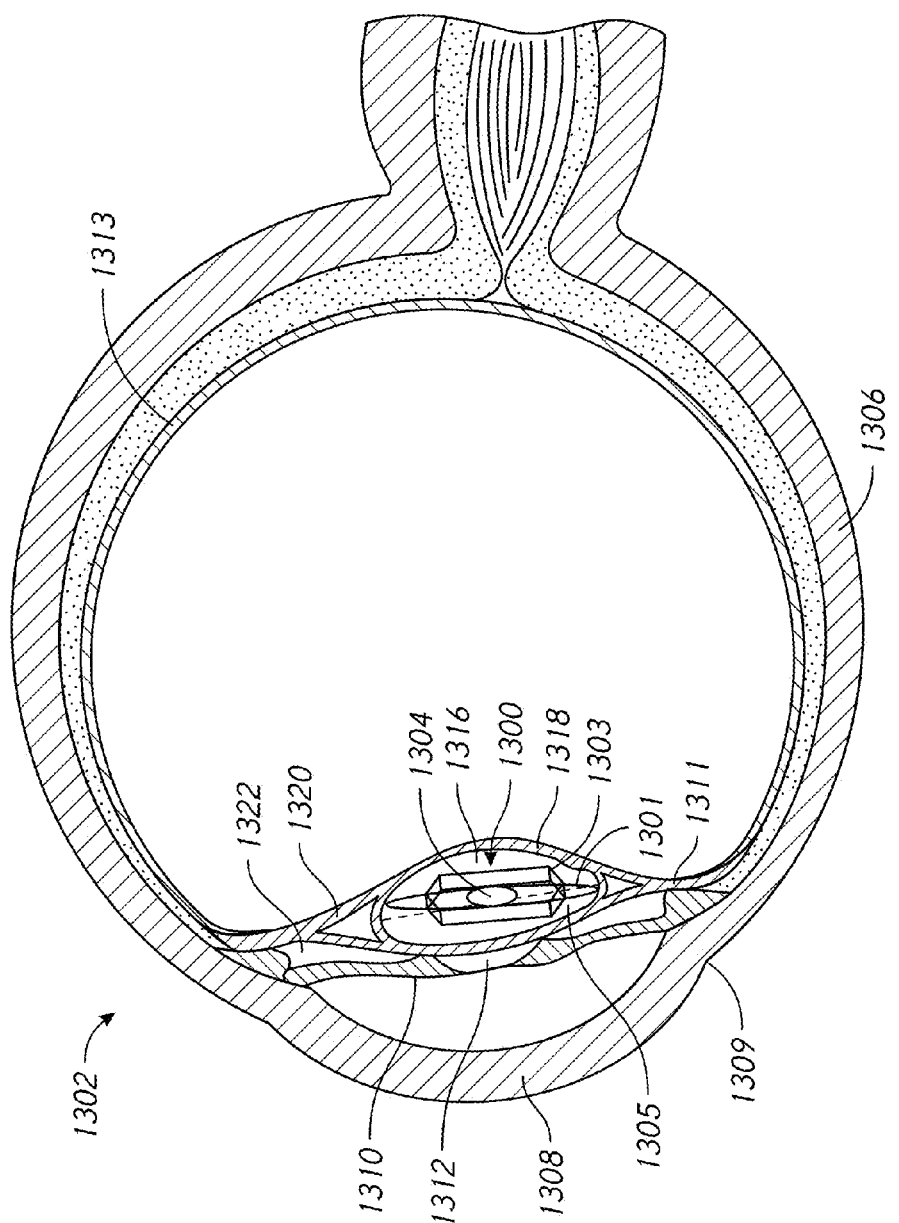
FIG. 13 illustrates a side cross-sectional side view of an eye including an example of a prosthetic capsular device and an IOL.
Figure 14A:
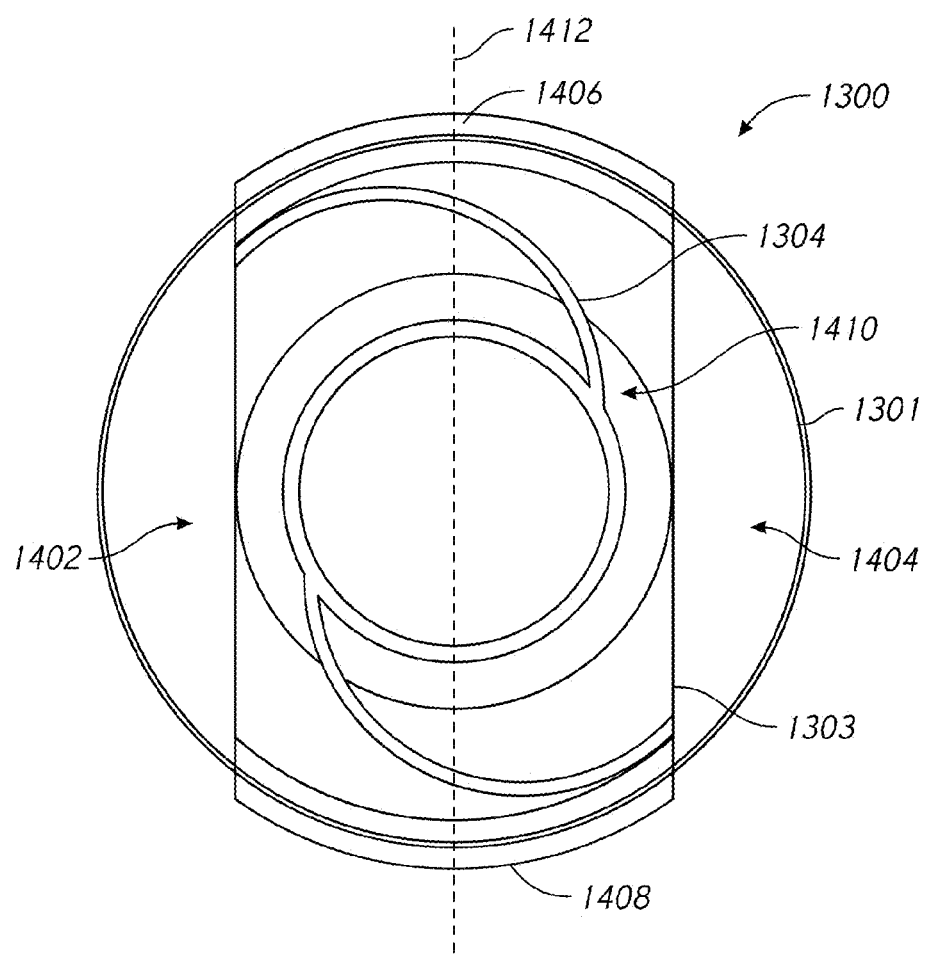
FIG. 14A illustrates an anterior plan view of the example prosthetic capsular device of FIG. 13 with an optional secondary IOL positioned inside the prosthetic capsular device.
Figure 14B:
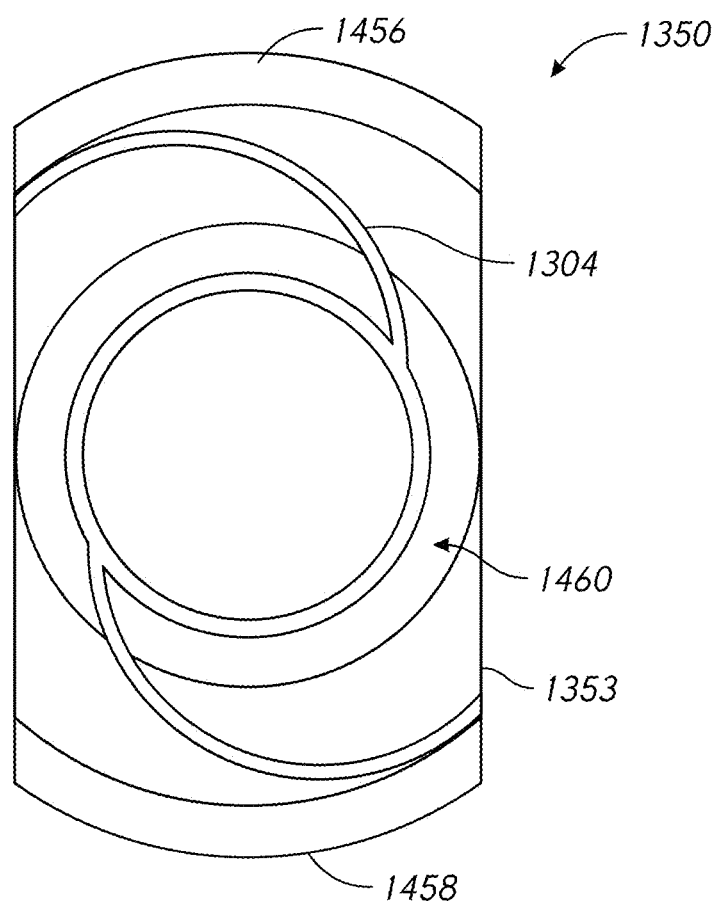
FIG. 14B illustrates an anterior plan view of another example prosthetic capsular device with an optional secondary IOL positioned inside the prosthetic capsular device.
Figure 15:
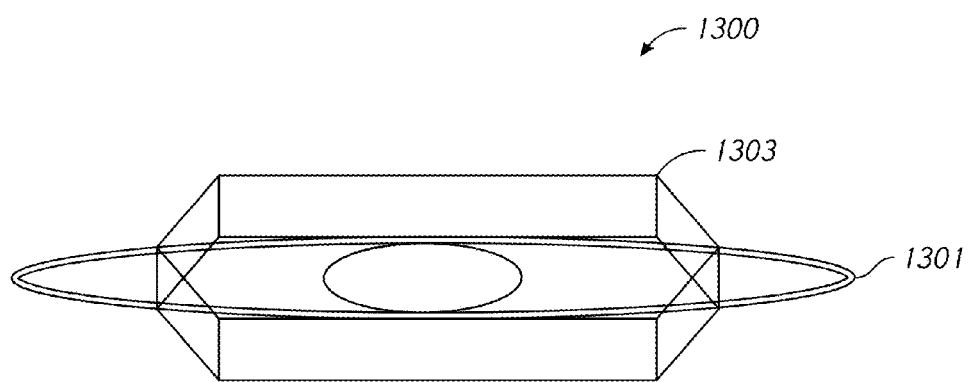
FIG. 15 illustrates a side perspective view of the example prosthetic device of FIG. 13.

FIGS. 13-15 illustrate an example of a prosthetic capsular device 1300 positioned in an eye 1302. FIG. 13 illustrates a side cross-sectional side view of an eye 1302 including a prosthetic capsular device 1300. In some implementations, the prosthetic capsular device 1300 can be configured to receive an IOL 1304. The anatomy of the eye 1302 comprises an outermost layer including the sclera 1306 and the cornea 1308, which meet at the cornea-scleral junction or limbus 1309. The iris 1310 is visible through the transparent cornea 1308 and forms the outer diameter of the pupil 1312, which is an opening in the opaque iris 1310. The aqueous humor is between the cornea 1308 and the iris 1310. Behind the iris 1310 and pupil 1312 typically (e.g., without prior surgery or physical issues) sits a natural lens or cataract that occupies the space 1316. The natural lens is held in place or suspended by suspensory ligaments (zonules) 1320 connected to the ciliary body 1311. The natural lens comprises lens fibers surrounded by a natural capsular bag 1318, which generally comprises a thin transparent membrane. The space anterior to the ciliary body 1311 is the sulcus 1322. The vitreous is a clear gel that fills the vitreous humor between the natural capsular bag 1318 and the retina 1313 of the eye 1302. As discussed herein, the natural lens can be surgically removed for various reasons (e.g., clouding) and the prosthetic device 1300 can be implanted in the natural capsular bag 1318.

In some implementations, the prosthetic device 1300 comprises a ring structure 1301 coupled to a housing structure 1303. In some implementations, the ring structure 1301 comprises a material that is sufficiently strong to maintain the circumference 1305 or volume of the natural capsular bag 1318. In some implementations, the ring structure 1301 is configured to be sufficiently flexible to adjust and conform to the natural shape or volume of the natural capsular bag 1318, which can be asymmetrical. In some implementations, the ring structure 1301 is configured to secure the prosthetic device 1300 within the natural capsular bag 1318 or other eye region through a friction fit. For example, the ring structure 1301 can comprise polyimide, materials known in intraocular lens manufacturing such as silicone (e.g., MED-6820, available from NuSil Technology LLC of Carpinteria, Calif.), collamer, PMMA, acrylic, and acrylates, materials used in permanent suture applications such as polypropylene, nylon, polytetrafluoroethylene (PTFE), and polyester, shape memory or thermal memory materials such as nitinol, chromium cobalt, and shape memory polymers, combinations thereof, and the like. In some implementations, the ring structure 1301 comprises hydrophilic and/or hydrophobic materials.

In some implementations, the housing structure 1303 comprises a material sufficiently flexible and strong to mechanically maintain and expand the natural capsular bag 1318 (e.g., to a natural volume of the capsule prior to removal of the natural lens) and/or to house an IOL 1304 or other device within the housing structure 1303. For example, the housing structure 1303 can comprise and/or be manufactured from PMMA, acrylic, silicone, collamer, polymer, other biocompatible optically transparent materials, combinations thereof, and the like. In some implementations, the housing structure 1303 comprises hydrophilic and/or hydrophobic materials.

As illustrated in FIG. 14A, the prosthetic device 1300 can comprise a ring structure 1301 that is a continuous loop or circle. In some implementations, the housing structure 1303 is coupled to the ring structure 1301 by embedding and/or overmolding (e.g., insert molding, double shot molding, co-injection molding, 2-times injection molding) the ring structure 1301 into the outer edges of the housing structure 1303. Compared to bonding (e.g., adhering) the ring structure 1301 and the housing structure 1303 to each other, overmolding the ring structure 1301 to the housing structure 1303 can reduce costs, reduce production duration, and/or provide a more secure coupling. The material of the housing structure 1303 (e.g., silicone) can be configured to surround or encase or envelop a portion of the ring structure 1301 at junction points 1406, 1408. In some implementations, the housing structure 1303 comprises an opening 1410 in the anterior portion of the housing structure 1303. In some implementations, the opening 1410 can be configured to receive an IOL 1304 and/or other device therethrough to be positioned in the housing structure 1303.

The prosthetic device 1300 can advantageously comprise less mass and be less bulky relative to other example prosthetic devices disclosed herein. In some implementations, the prosthetic device 1300 is advantageous because the device 1300 is smaller and stronger relative to other example prosthetic devices disclosed herein. For example, the prosthetic device 1300 can be configured to allow for increased structural stability to self-retain structural shape and integrity through the ring structure 1301 while also reducing volume by reducing the amount of material used to construct the housing structure 1303. For example, the prosthetic device 1300 comprises open space 1402, 1404 on each side of the housing structure 1303. The prosthetic device 1300 thereby can comprise less volume and mass of material than devices that are diametrically continuous. In some implementations, the open spaces 1402, 1404 can allow for and/or promote fibrosis around the ring structure 1301 and/or in the open spaces 1402, 1404. In some implementations, fibrosis around the ring structure 1301 and/or in the open spaces 1402, 1404 can help secure or anchor the prosthetic device 1300 to the eye and/or maintain the prosthetic device 1300 in a fixed position in the eye. In some implementations, fibrosis around the prosthetic device 1300 can reduce or eliminate the need for suturing the prosthetic device 1300 to the eye.

As illustrated in FIG. 14B, the prosthetic device 1350 can lack or be free of a ring structure (e.g., the ring structure 1301). The material of the housing structure 1353 (e.g., comprising silicone) can be configured to appose interior sidewalls of the natural capsular bag at junction points 1456, 1458. In some implementations, the housing structure 1353 comprises an opening 1460 in the anterior portion of the housing structure 1353. In some implementations, the opening 1460 can be configured to receive an IOL 1304 and/or other device therethrough to be positioned in the housing structure 1353. The prosthetic device 1350 can advantageously comprise less mass and be less bulky relative to other example prosthetic devices disclosed herein. The prosthetic device 1350 can be combined with a second component such as a capsular tension ring configured to hold the device 1350. For example, the ring could be implanted first, and then the device 1350 could be coupled to the ring in situ.

During implantation, the prosthetic device 1300 can generally be folded or rolled up along the axis 1412 of the prosthetic device 1300. After the device 1300 is rolled up or folded, the prosthetic device 1300 can be positioned within a insertion or injector device. In some implementations, the insertion or injector device comprises a wide first end opening and becomes progressively narrower until terminating at a narrow second end opening. In some implementations, the wide first end opening comprises a substantially oval configuration and the narrow second end opening comprises an arcuate (e.g., substantially circular, elliptical, etc.) configuration. In some implementations, the wide first end opening is configured to receive the prosthetic device 1300 and, as the prosthetic device 1300 is pushed through the funnel or tapering portion of the insertion or injector device, the prosthetic device 1300 is compressed as the device advances towards the narrow second end opening.

In some implementations, the prosthetic device 1300 is inserted or squeezed or compressed into the insertion device without folding or rolling up the prosthetic device 1300. After positioning the distal end of the insertion device in the natural capsular bag 1318 of the eye 1302, an implantation tool can be positioned within the insertion device to push the prosthetic device 1300 through and out of the insertion device and into the natural capsular bag 1318. By having less mass, in particular lateral to the axis 1412, the prosthetic device 1300 can be inserted through a narrower insertion device because the prosthetic device 1300 can be rolled up, folded, or compressed into a more compact form. A narrower insertion device allows a smaller incision in the eye, which can be beneficial to the patient. Generally, smaller incisions in the eye require less healing time and, in some cases, may be closed without sutures.

As illustrated in FIG. 14A, the prosthetic device 1300 comprises a housing structure 1303 that is narrower than other examples of prosthetic devices disclosed herein. In some implementations, the narrower configuration of the housing structure 1303 can be advantageous for insertion of an IOL into the housing structure 1303. For example, a narrower housing structure 1303 can inhibit or limit or prevent rotation of an IOL 1304 within the housing structure 1303. By limiting, inhibiting, or preventing the rotation of the IOL 1304 within the housing structure 1303, a surgeon or other user can be substantially certain that the position of the IOL 1304 will remain substantially constant over time. In some cases, changes in the IOL 1304 position over time can cause the patient to experience blurred or unclear vision. Limiting rotational freedom of the IOL 1304 within the housing structure 1303 can advantageously inhibit or prevent vision issues that might otherwise develop over time. For example, in toric IOLs, every 1 degree of rotation causes loss of approximately 3% of astigmatic correction such that if the lens rotates 15°, almost half of the corrective effect can be lost. In some instances, a surgeon or other user may not need to rotate an IOL 1304 within the housing structure 1303 to achieve a particular orientation if the surgeon or user can align the prosthetic device 1300 such that an IOL 1304 positioned in the device 1300 automatically or necessarily assumes the orientation.

With reference to FIGS. 15-18, the housing structure of the prosthetic device can have various shapes and/or sizes. Housing structures having various shapes and/or sizes can be advantageous because different shapes and/or sizes can accommodate different types of IOLs and/or other devices to be positioned within the housing structure. Some patients may benefit from a housing structure that is as compact as possible. For example, compact housing structures can include, without limitation, housing structures having a shape that is more spherical or circular or rounded in nature, or having tapered or angled sides. In these types of situations, implanting a prosthetic device having a housing structure that is as compact as possible can advantageously accommodate the surgical needs of the patient. For example, some patients have smaller natural capsular bags may benefit from a prosthetic device having a compact housing structure.

In some situations, a patient may benefit from two or more IOLs and/or devices to be positioned in the housing structure of the prosthetic device. In these types of situations, it could be beneficial for the prosthetic device to comprise a housing structure that provides for as much capacity as possible. For example, some patients may require or desire two or more IOLs to be positioned within the housing structure. Therefore, it may be beneficial to provide a housing structure that is less compact and is more cylindrical in order to provide more space for receiving two or more IOLs or other devices within the housing structure. In certain implementations, a housing structure that allows for the positioning of one or more IOLs or other devices at specific positions in the x, y, and/or z planes within the housing structure may be advantageous. For example, the surgeon can advantageously position an IOL in the anterior portion of the housing structure, or in the posterior portion of the housing structure, or in the middle portion of the housing structure.

In certain cases, the surgeon may find it difficult to ensure that the IOL is positioned within a desired portion of the housing structure. In certain implementations, the housing structure comprises ridges or grooves within the interior portion of the housing structure, which can help ensure that an IOL maintains a specific position within the housing structure. In some implementations, the housing structure comprises a pyramid-like configuration (e.g., frusto-pryamidal), which can help ensure that the IOL maintains a certain position within the housing structure. For example, the housing structure can have a width that is narrower at the anterior portion than at the posterior portion. In certain instances, an IOL or other device may comprise a certain diameter or width that inhibits or prevents the IOL or other device from moving past a certain point in the anterior portion due to the narrow width of the anterior portion of the housing structure. The housing structure may comprise a configuration wherein the posterior portion of the housing structure is narrower in width than the anterior portion of the housing structure.

Figure 16:
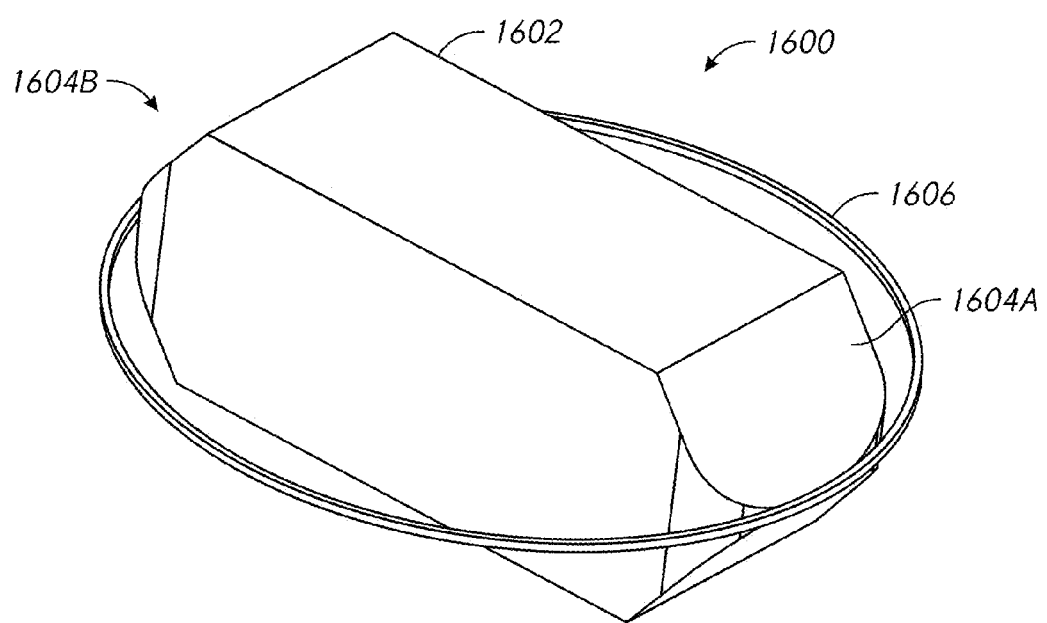
FIG. 16 illustrates a side perspective view of another example of a prosthetic capsular device.

FIG. 16 illustrates a prosthetic device 1600 comprises a housing structure 1602 having tapered sides 1604A, 1604B. The housing structure 1602 is coupled to the ring structure 1606 at the apices of the tapered sides 1604A, 1604B. As described above with respect to the ring structure 1301, the ring structure 1606 can be embedded or attached or otherwise coupled to the housing structure 1602. As discussed above, the prosthetic device 1600 can be advantageous in certain situations where a compact housing structure is required. By having tapered sides 1604A, 1604B, the housing structure 1602 occupies less volume. This type of configuration may be well-suited for natural capsular bags having small volume capacity, or having tapered side regions, or other conditions that may benefit from a prosthetic device 1600 having a compact housing structure 1602. The prosthetic device 1600 can be advantageous for positioning an IOL and/or other device within the housing structure 1602 at a particular position in the housing structure 1602. For example, the tapered sides 1604A, 1604B can be configured to inhibit or prevent migration of the IOL and/or other devices into the anterior and/or posterior regions of the housing structure 1602. Although not illustrated, as described herein, the anterior end or face or surface of the device 1600 may comprise an opening through which an IOL and/or other devices can be inserted. The opening can be circular (e.g., like the opening 1410), may conform to the shape of the anterior surface, or take other shapes. The absence of illustration of an opening in an anterior face of example prosthetic devices herein is for clarity of other aspects of such devices and does not mean that such device lacks such an opening.

Figure 17:
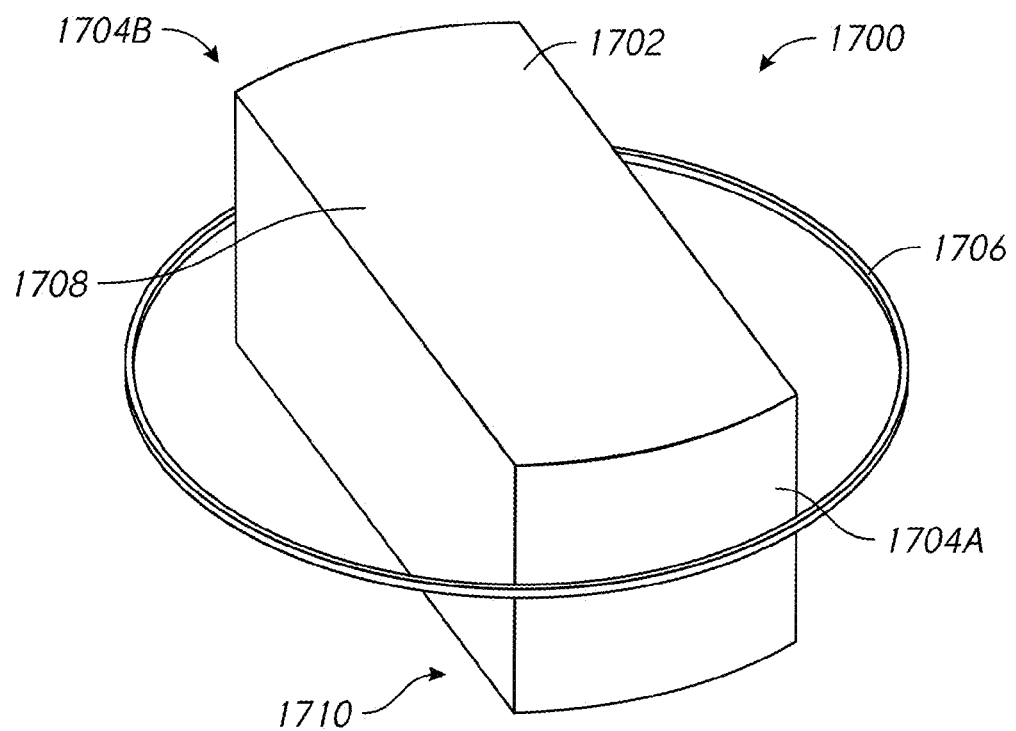
FIG. 17 illustrates a side perspective view of yet another example of a prosthetic capsular device.

FIG. 17 illustrates a prosthetic device 1700 comprising a housing structure 1702 having a generally cylindrical (e.g., without material on two opposite sides of the cylinder) configuration in which the side walls 1704A, 1704B are perpendicular or substantially perpendicular to at least one of the anterior face 1708 and the posterior face 1710 of the housing structure 1702. As discussed above, it can be advantageous for the housing structure 1702 to be configured with a shape that increases or maximizes internal volume of or capacity within the housing structure 1702 while still maintaining possible benefits of a ring structure 1706 and housing structure 1702. By increasing or maximizing capacity, the housing structure 1702 can be configured to receive two or more IOLs and/or other devices that may be implanted in an eye of a patient. The configuration of the prosthetic device 1700 can be advantageous for patients having natural capsular bags that have large volume capacity. The housing structure 1702 can be configured to take up additional space within the natural capsular bag, for example mechanically expanding to maintain the shape or volume of the natural capsular bag. In some implementations, the housing structure 1702 comprises side walls 1704A, 1704B that have a curvature that is the same or substantially the same as the curvature of the ring structure 1706. In some implementations, the housing structure 1702 is coupled to the ring structure 1706 at the side walls 1704A, 1704B. In some implementations, the side walls 1704A, 1704B are embedded, attached, or otherwise coupled to the ring structure 1706.

Figure 18:
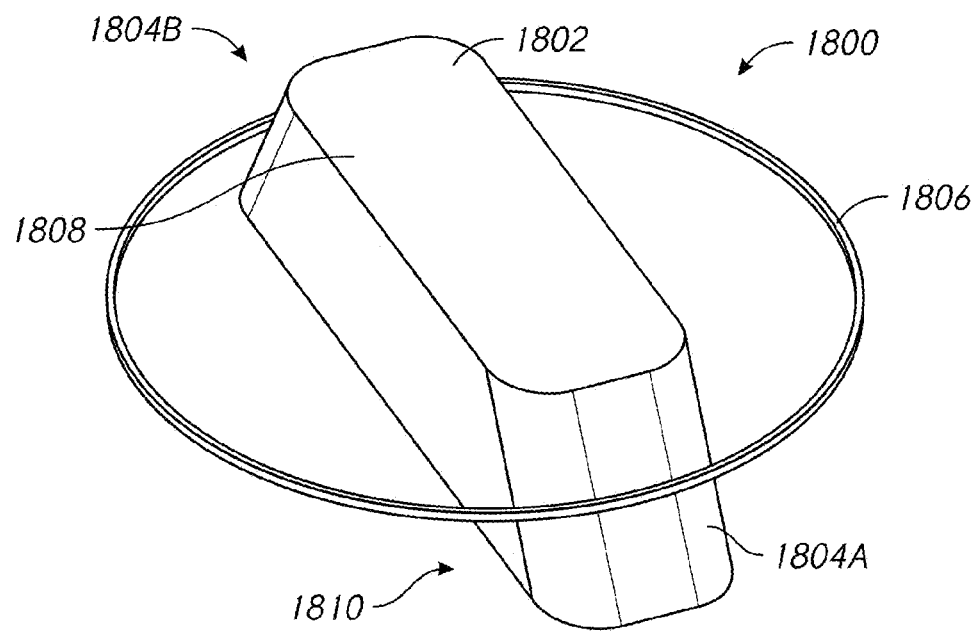
FIG. 18 illustrates a side perspective view of still another example of a prosthetic capsular device.

FIG. 18 illustrates a prosthetic device 1800 comprising a housing structure 1802 having side walls 1804A, 1804B that form an angle with respect to the anterior face 1808 that is obtuse or greater than 90°, and the side walls 1804A, 1804B form an anterior angle with respect to the posterior face of the housing structure 1802 that is acute or less than 90°. The angles formed by the faces 1804A, 1804B may be the same or different. As discussed above, it can be advantageous for the housing structure 1802 to comprise a pyramid-like configuration in which a width at the anterior portion of the housing structure 1802 is smaller than the width at the posterior portion of the housing structure 1802. For example, certain IOLs and/or other devices may comprise a diameter or width or other dimension that interacts with the housing structure 1802 to inhibit or prevent the IOL and/or other device from migrating beyond a certain point within a certain portion of the housing structure 1802. For example, the narrower anterior portion of the housing structure 1802 can be configured to inhibit or prevent an IOL and/or other device having a certain dimension from migrating anteriorly beyond a certain point within the housing structure 1802.

In some implementations, a surgeon or other user may desire to implant two or more IOLs and/or other devices within the housing structure 1802. The surgeon or other user may desire that a first IOL or other device be spaced from a second IOL or other device within the housing structure 1802. To accommodate the foregoing, the first IOL or other device can be positioned in the posterior portion of the housing structure 1802, but is inhibited from migrating towards the anterior portion of the housing structure 1802 (e.g., by comprising a width, diameter, or other dimension that is too large for the smaller anterior portion), and the second IOL or other device can be positioned in the anterior portion of the housing structure 1802 (e.g., by comprising a width, diameter, or other dimension that is small enough to fit in the smaller anterior portion). As illustrated in FIG. 18, the housing structure 1802 can be coupled to a ring structure 1806. In certain implementations, the ring structure 1806 is embedded, attached, or otherwise coupled to the housing structure 1802 (e.g., to the side walls 1804A, 1804B of the housing structure 1802). In certain implementations, the housing structure 1802 comprises side walls 1804A, 1804B having curvatures that are the same or substantially the same as the curvature of the ring 1806. In certain implementations, the sidewalls 1804A, 1804B are generally flat between rounded edges and the housing structure 1802 is attached to the ring structure 1806 at edge points of the housing structure 1802.

FIGS. 19-22C illustrate example prosthetic devices comprising a housing structure that is coupled to a sinusoidal or zigzag or undulating or wave-like ring structure as opposed to a circular, oval, or otherwise arcuate configuration. In certain implementations, the ring structure is in a plane that is substantially parallel to the anterior surface of the housing structure. In some implementations, the ring structure comprises a shape that ripples in a direction perpendicular or substantially perpendicular to the anterior surface. In some implementations, the ring structure comprises a shape that ripples both in a plane that is parallel to the anterior surface and in a direction substantially perpendicular to the anterior surface. The ring structure can be configured to have a sinusoidal shape in a horizontal direction relative to the anterior surface, in a vertical direction relative to the anterior surface, or in both a horizontal direction and a vertical direction relative to the anterior surface.

Figure 21:
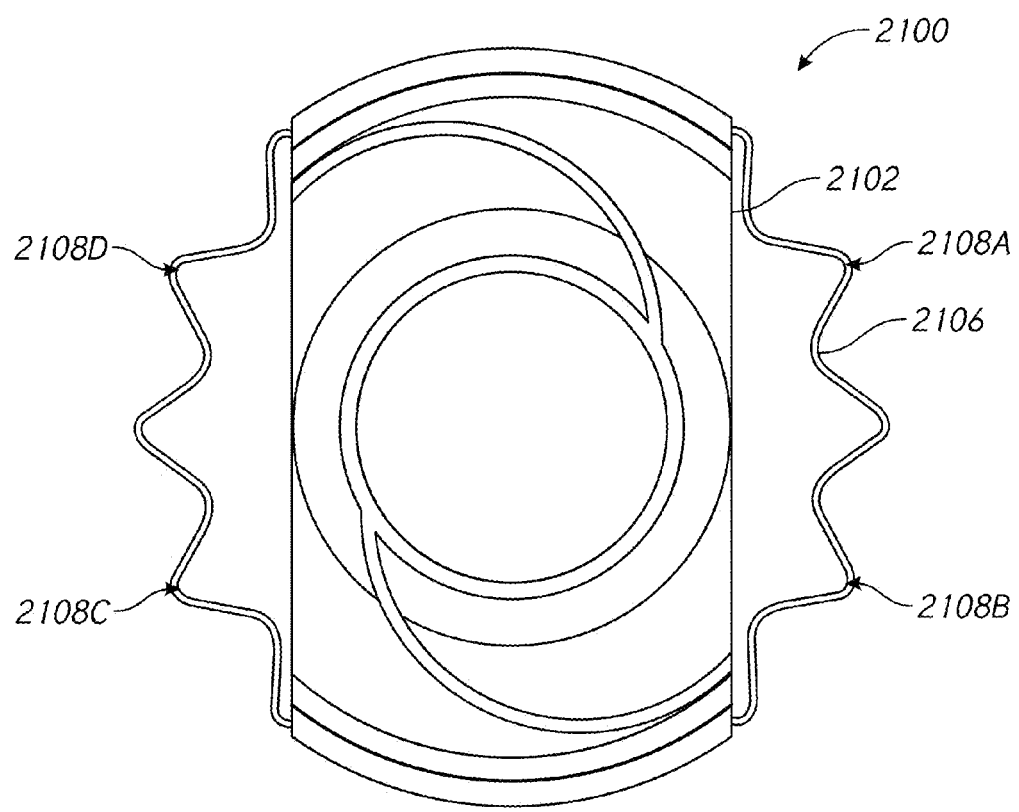
FIG. 21 is an anterior plan view of yet another example of a prosthetic capsular device with an optional secondary IOL positioned inside the prosthetic capsular device.
Figure 22A:
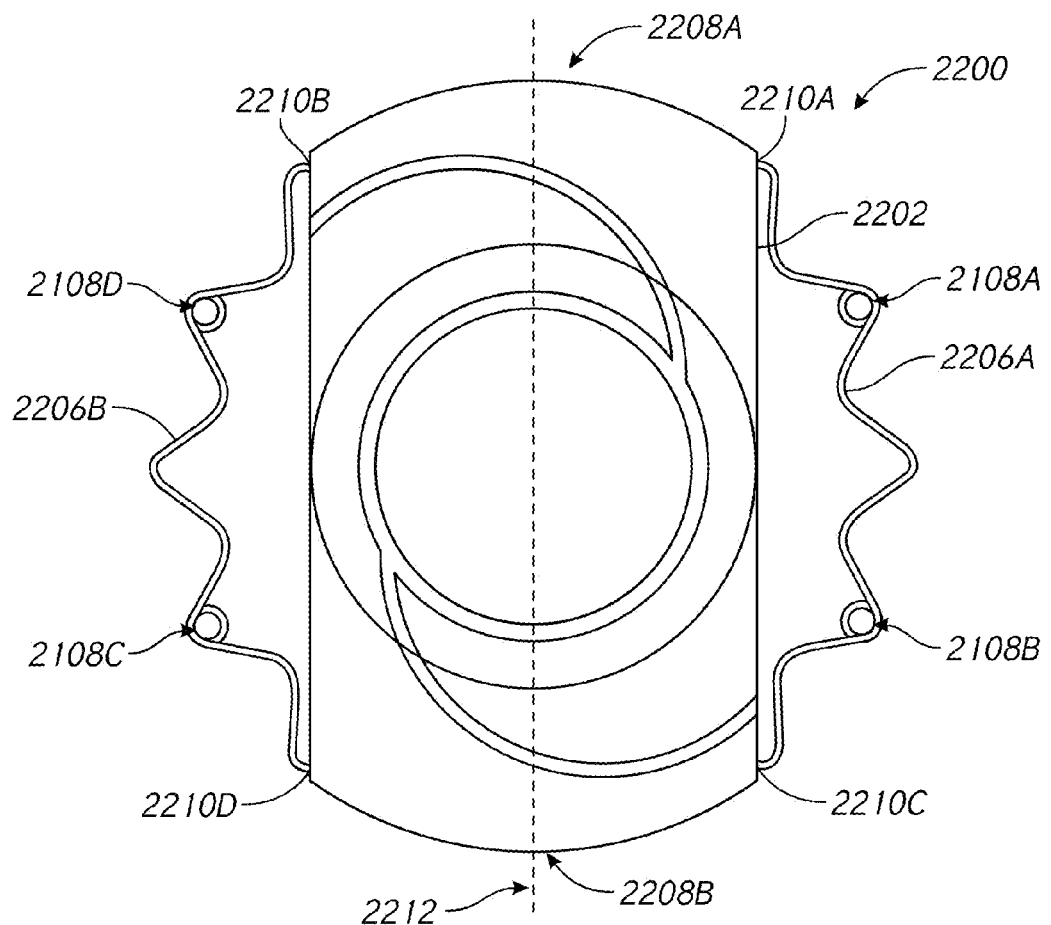
FIG. 22A is an anterior plan view of still another example of a prosthetic capsular device with an optional secondary IOL positioned inside the prosthetic capsular device.

The sinusoidal shape of the ring structure may increase securement or anchoring of the ring structure to the natural capsular bag. For example, the shape and dimensions of the natural capsular bag varies greatly from patient to patient. In some instances, the shape of the natural capsular bag of a patient is not completely circular or oval or elliptical in shape. In some instances, the shape of the natural capsular bag is irregular and/or asymmetrical. A ring structure having a sinusoidal shape can flex and conform to the shape of the natural capsular bag, which can provide improved positioning within an irregular natural capsular bag shape. In certain implementations, the tips or apices or radially outward portions of the sinusoidal wave are configured to engage the natural capsular bag. The shape of the sinusoidal ring structure may be substantially regular (e.g., as shown in FIGS. 19-22C) or may vary. For example, some apices may have a larger diameter than other apices. For another example, some apices may be biased in an anterior direction and other apices may be biased in a posterior direction. For another example, some apices may comprise a bend and other apices may comprise a coil or ring (e.g., as shown in FIGS. 21-22C). In certain implementations, a ring structure having a substantially circular or oval or elliptical configuration may not be able to conform to an irregular and/or asymmetrical shape of a natural capsular bag as well as a ring structure having a sinusoidal shape.

In some implementations, the sinusoidal shape of the ring structure can be substituted with a coil structure that forms the ring structure around the housing structure.

Figure 19:
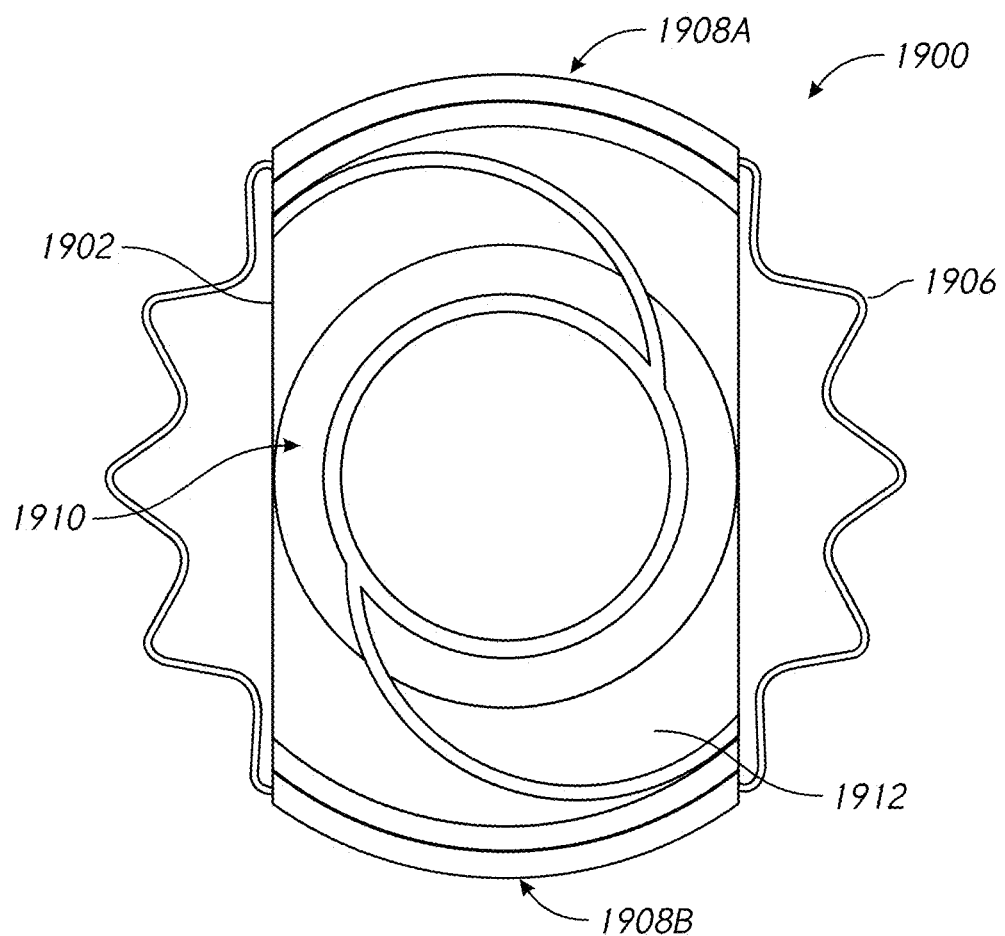
FIG. 19 illustrates an anterior plan view of yet still another example of a prosthetic capsular device with an optional secondary IOL positioned inside the prosthetic capsular device.

FIG. 19 illustrates an example prosthetic device 1900 comprising a sinusoidal ring structure 1906 and a housing structure 1902. The housing structure 1902 can comprise an opening 1910 in the anterior surface 1912. The opening 1910, as described in other examples herein, can be configured to receive an IOL or other device (e.g., technology device) therethrough in order to position the IOL or other device in the housing structure 1902. In some implementations, the ring structure 1906 is configured to be coupled to the housing structure 1902. In the example device 1900 illustrated in FIG. 19, the ring structure 1906 is embedded within the housing structure 1902 at portions 1908A, 1908B such that the ring structure 1906 is partially encapsulated by the housing structure 1902. In certain implementations, the ring structure 1906 is attached or coupled to the housing structure 1902. In certain implementations, the housing structure 1906 is attached to the interior portion of the housing structure 1902. In certain implementations, the ring structure 1906 is attached to the exterior portion of the housing structure 1902. The ring structure 1906 may be non-undulating or substantially arcuate where the ring structure 1906 is configured to be coupled to the housing structure 1902, for example to reduce manufacturing complexity. The ring structure 1906 may continue the sinusoidal shape for engagement of more material with the housing structure 1902 at the portions 1908A, 1908B. The ring structure 1906 may have a different sinusoidal shape for engagement with the housing structure 1902 at the portions 1908A, 1908B, for example to lock into place at a particular orientation.

Figure 20:
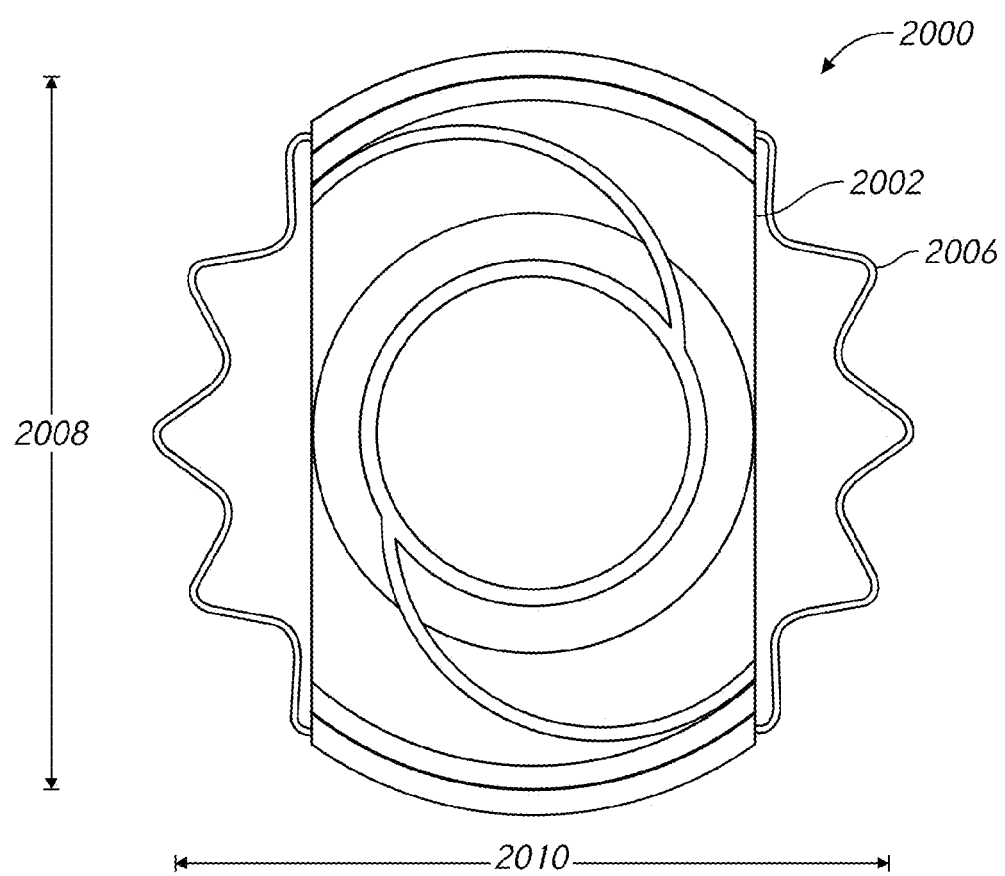
FIG. 20 is an anterior plan view of another example of a prosthetic capsular device with an optional secondary IOL positioned inside the prosthetic capsular device.

FIG. 20 illustrates an example of a prosthetic device 2000. In some implementations, the prosthetic device 2000 comprises a housing structure 2002 that is coupled to a ring structure 2006. In contrast to the prosthetic device 1900 of FIG. 19, the prosthetic device 2000 can be configured to have an elongate housing structure 2002 that has an even larger length along the axis 2008 than width along the axis 2010, or length to width ratio. As described above, it can be advantageous to have a prosthetic device 2000 having a housing structure 2002 that is elongate in the axis 2008 in order to accommodate IOL and/or other devices to be positioned in the housing structure 2002. A housing structure 2002 that is elongate in the axis 2008 may advantageously take up additional space within the natural capsular bag such that the housing structure 2002 can be better suited for mechanically expanding and/or maintaining the natural shape of the natural capsular bag, but the smaller dimensions in the axis 2010 can reduce the volume of the device 2000 for insertion. The housing structure 2002 can be configured to be elongate in the axis 2010. As discussed above, a housing structure 2002 that is wider along the axis 2010 than the axis 2008, or vice versa, can be configured to receive IOLs and other devices having a wider diameter or width or other dimension. In some implementations, the prosthetic device 2000 can be elongate both in the axial direction 2008 and the axial direction 2010 (e.g., having a shape of a rounded square).

Figure 22B:
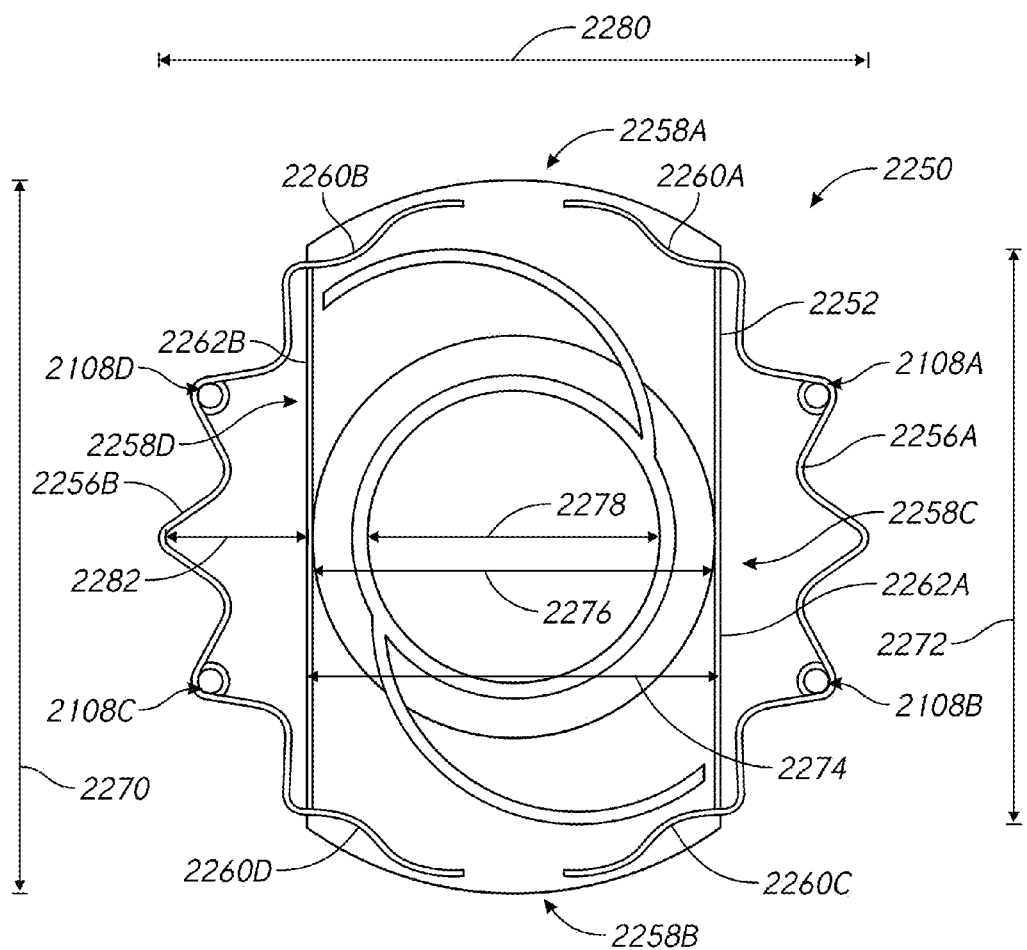
FIG. 22B is an anterior plan view of still yet another example of a prosthetic capsular device with an optional secondary IOL positioned inside the prosthetic capsular device.
Figure 22C:
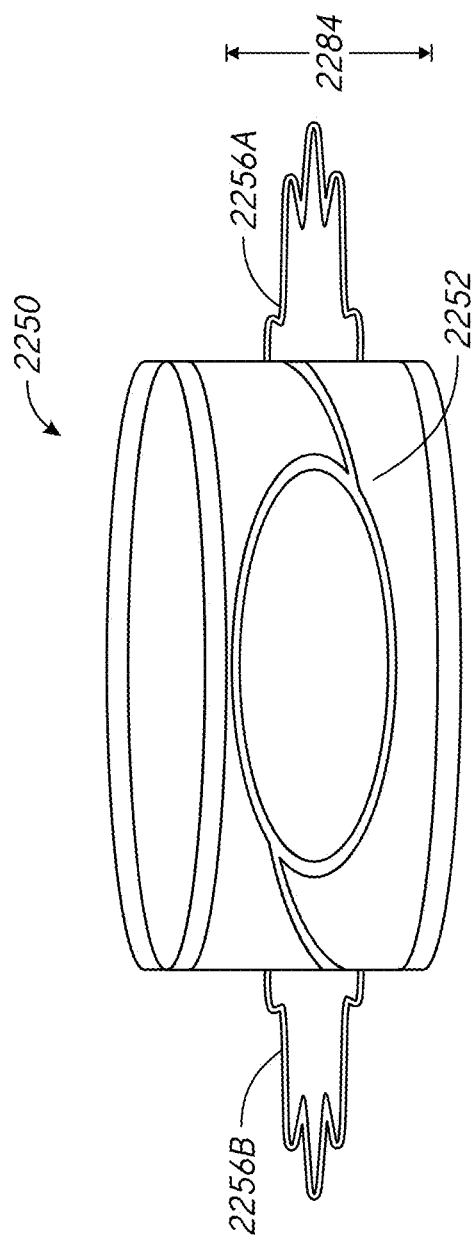
FIG. 22C is a side perspective view of the example prosthetic capsular device of FIG. 22B with an optional secondary IOL positioned inside the prosthetic capsular device.

FIGS. 21-22B illustrate examples of prosthetic devices 2100, 2200, 2250, respectively, comprising a housing structure 2102, 2202 that is coupled to a ring structure 2106, 2206. In some implementations, the ring structure 2106, 2206 comprises eyelets 2108A, 2108B, 2108C, 2108D. In certain implementations, the eyelets 2108A, 2108B, 2108C, 2108D can be configured to receive a suture to allow the surgeon or other user to suture the ring structure 2106 to the natural capsular bag, iris, ciliary body, sclera, or other eye tissue. In some implementations, the eyelets 2108A, 2108B, 2108C, 2108D can be configured to allow and/or promote fibrosis formation within the eyelets 2108A, 2108B, 2108C, 2108D to secure or anchor the prosthetic device 2100, 2200, 2250 in the natural capsular bag. In certain implementations, the prosthetic device 2100, 2200, 2250 comprising eyelets 2108A, 2108B, 2108C, 2108D can be advantageous in situations in which the prosthetic device 2100, 2200, 2250 is implanted in the eye of a patient for long periods of time. As the eye ages, the eye changes in shape and elasticity. Eyelets 2108A, 2108B, 2108C, 2108D that allow a surgeon or other used to secure the ring structure 2106, 2206 to an eye by suturing may advantageously properly secure the prosthetic device 2100, 2200, 2250 to the eye of a patient throughout these changes. By suturing the ring structure 2106, 2206 to the eye, the prosthetic device 2100, 2200, 2250 can be inhibited or prevented from migrating to a different position in the eye as the eye changes shape and/or elasticity due to age. The eyelets 2108A, 2108B, 2108C, 2108D may comprise bends that are at least 360° at an exterior point or loops or coils or in the ring 2106, which can increase spring force at the apices, which can provide increased conformation to the natural capsular bag.

FIG. 22A illustrates an example of a prosthetic device 2200. In some implementations, the prosthetic device 2200 comprises a housing structure 2202 that is coupled to at least two ring portions 2206A, 2206B. In contrast to the device 2100 in which the ring structure 2106 is embedded in the housing structure 2102, the ring portions 2206A, 2206B can be attached or coupled to the housing structure 2202 at junction points 2210A, 2210B, 2210C, 2210D such that the ring portions 2206A, 2206B are not substantially embedded in the housing structure 2202. In some implementations, the housing structure 2202 can comprise edge portions 2208A, 2208B that do not comprise or lack or are free of ring portions 2206A, 2206B along substantially the entire length of the edge portions 2208A, 2208B. In some implementations, the edge portions 2208A, 2208B are configured to be more easily folded by not embedding or being coupled to a ring portions 2206A, 2206B across the entire length of the edge portions 2208A, 2208B. The ring portions 2206A, 2206B may be the same or different, for example comprising different shapes, materials, dimensions, bend types, combinations thereof, and the like. The ring portions 2206A, 2206B may be configured for a specific orientation in the eye (e.g., the ring portion 2206A medial, the ring portion 2206A being dorsal, etc.).

In some implementations, the edge portions 2208A, 2208B comprise sufficient mechanical structural support to inhibit or prevent the housing structure 2202 from collapsing under the forces exerted by the natural capsular bag of the eye. For example, the edge portions 2208A, 2208B may comprise one or more raised ridge regions along a length of the edge portions 2208A, 2208B. As discussed above, reducing the amount of mass and/or material utilized to construct the prosthetic device 2200 can allow the device 2200 to be rolled up or folded along the lengthwise axis 2212 in such a way that the prosthetic device 2200 may be inserted into an insertion tool having a small diameter. By utilizing an insertion tool having a small diameter, the surgeon or other user can make an incision in the eye that is less than about 3.5 mm, less than about 3.4 mm, less than about 3.3 mm, less than about 3.2 mm, less than about 3.1 mm, less than about 3 mm, less than about 2.9 mm, less than about 2.8 mm, less than about 2.7 mm, less than about 2.6 mm, less than about 2.5 mm, less than about 2.4 mm, less than about 2.3 mm, less than about 2.2 mm, less than about 2.1 mm, less than about 2 mm, less than about 1.9 mm, or less than about 1.8 mm.

FIG. 22B illustrates an example of a prosthetic device 2250. In some implementations, the prosthetic device 2250 comprises a housing structure 2252 that is coupled to at least two ring portions 2256A, 2256B. In contrast to the device 2100 in which the ring structure 2106 is embedded across an entire length of a portion of the housing structure 2102, and in contrast to the device 2200 in which the ring portions 2206A, 2206B are attached or coupled to the housing structure 2202 at junction points 2210A, 2210B, 2210C, 2210D such that the ring portions 2206A, 2206B are not substantially embedded in the housing structure 2202, the device 2250 comprises ring portions 2256A, 2256B that are partially embedded in the housing structure 2252 by at least one of end anchors 2260A, 2260B, 2260C, 2260D (e.g., into end portions 2258A, 2258B of the housing structure 2252) and longitudinal anchors 2262A, 2262B (e.g., into side portions 2258C, 2258D of the housing structure 2252). The end anchors 2260A, 2260B, 2260C, 2260D can extend into edge portions 2258A, 2258B of the housing structure 2252 by the same amount or by different amounts. In some implementations, at least one of the end anchors 2260A, 2260B, 2260C, 2260D comprises an arcuate shape that changes direction at least once (e.g., an "S" shape). The shapes of the end anchors 2260A, 2260B, 2260C, 2260D may be the same or different. The longitudinal anchors 2262A, 2262B can extend along an entire length of the side portions 2258C, 2258D of the housing structure 2252 (e.g., as shown in FIG. 22B) or partially along a length of the side portions 2258C, 2258D of the housing structure 2252. The longitudinal anchors 2262A, 2262B can extend along the side portions 2258C, 2258D of the housing structure 2252 by the same amount or by different amounts. In some implementations, at least one of the longitudinal anchors 2262A, 2262B comprises a shape that changes direction at least once (e.g., turning towards a longitudinal center of the housing structure 2250). The shapes of the longitudinal anchors 2262A, 2262B may be the same or different. One or more of the end anchors 2260A, 2260B, 2260C, 2260D and/or the longitudinal anchors 2262A, 2262B may comprise a shape configured to provide secure anchoring in the housing structure 2252 (e.g., an undulating shape, a coil shape, a direction-changing shape, etc.). The end anchors 2260A, 2260B, 2260C, 2260D and the longitudinal anchors 2262A, 2262B may be connected in one or more locations. For example, instead of or in addition to being connected proximate to the points of entry into the housing structure 2252, the end anchors 2260A, 2260B, 2260C, 2260D and the longitudinal anchors 2262A, 2262B may be connected in the housing structure 2252 inward of the edges of the housing structure 2252.

FIG. 22B also illustrates example dimensions of the device 2250. The external length 2270 of the housing structure 2252 may be between about 9 mm and about 11 mm (e.g., between about 9.5 mm and about 10 mm). The internal length 2272 of the housing structure 2252 may be between about 8 mm and about 10 mm (e.g., about 9 mm). The external width 2274 of the housing structure 2252 may be between about 6 mm and about 8 mm (e.g., about 7 mm). The external length to width ratio (e.g., 2270/2274) may be between about 1.125:1 and about 2:1 (e.g., about 1.4:1). The internal width 2276 of the housing structure 2252 may be between about 6 mm and about 7 mm (e.g., about 6.5 mm). The length or width 2278 of the opening in the anterior side may be between about 5 mm and about 7 mm (e.g., about 6 mm). As discussed herein, the opening may have shapes other than circular and appropriate dimensions in accordance with such shapes. The external width 2280 of the device 2250 (e.g., including the housing structure 2252 and the ring portions 2256A, 2256B) may be between about 9 mm and about 11 mm (e.g., between about 9.5 mm and about 10 mm). The distance 2282 between the housing structure 2252 and the outermost part of the ring portions 2256A, 2256B may be between about 1 mm and about 2 mm (e.g., about 1.5 mm). Referring to FIG. 22C, which is a side perspective view of the device 2250, the external thickness or depth or height 2284 of the housing structure 2252 may be between about 2 mm and about 3 mm (e.g., about 2.5 mm).

Figure 23:
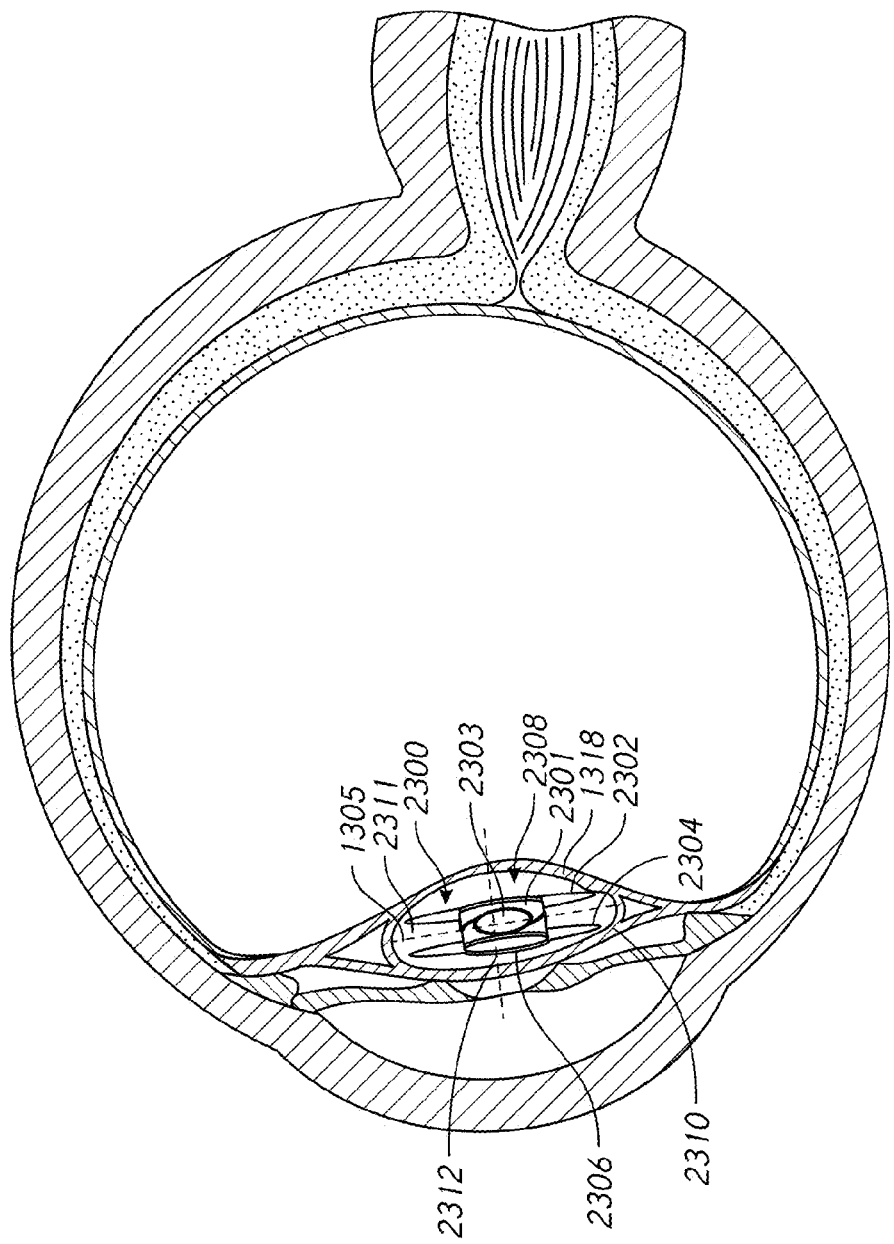
FIG. 23 illustrates a side cross-sectional side view of an eye including an example of a prosthetic capsular device and an IOL.
Figure 24:
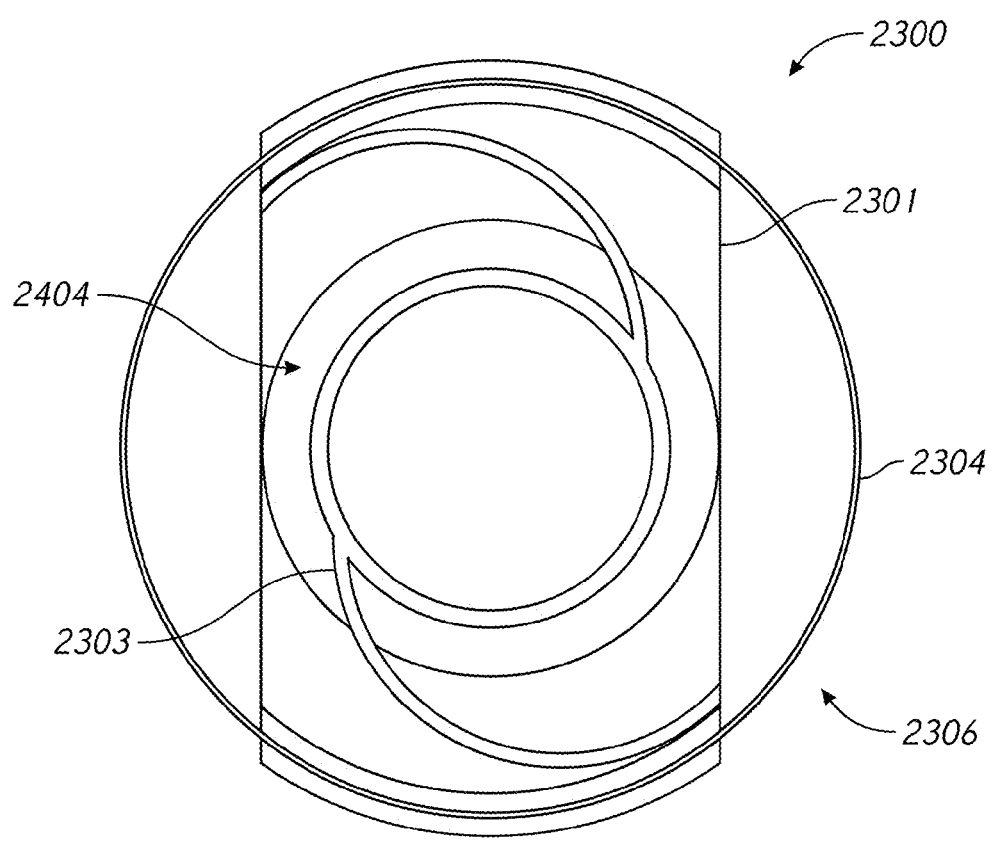
FIG. 24 illustrates an anterior plan view of the example prosthetic capsular device of FIG. 23 with an optional secondary IOL positioned inside the prosthetic capsular device.
Figure 25:
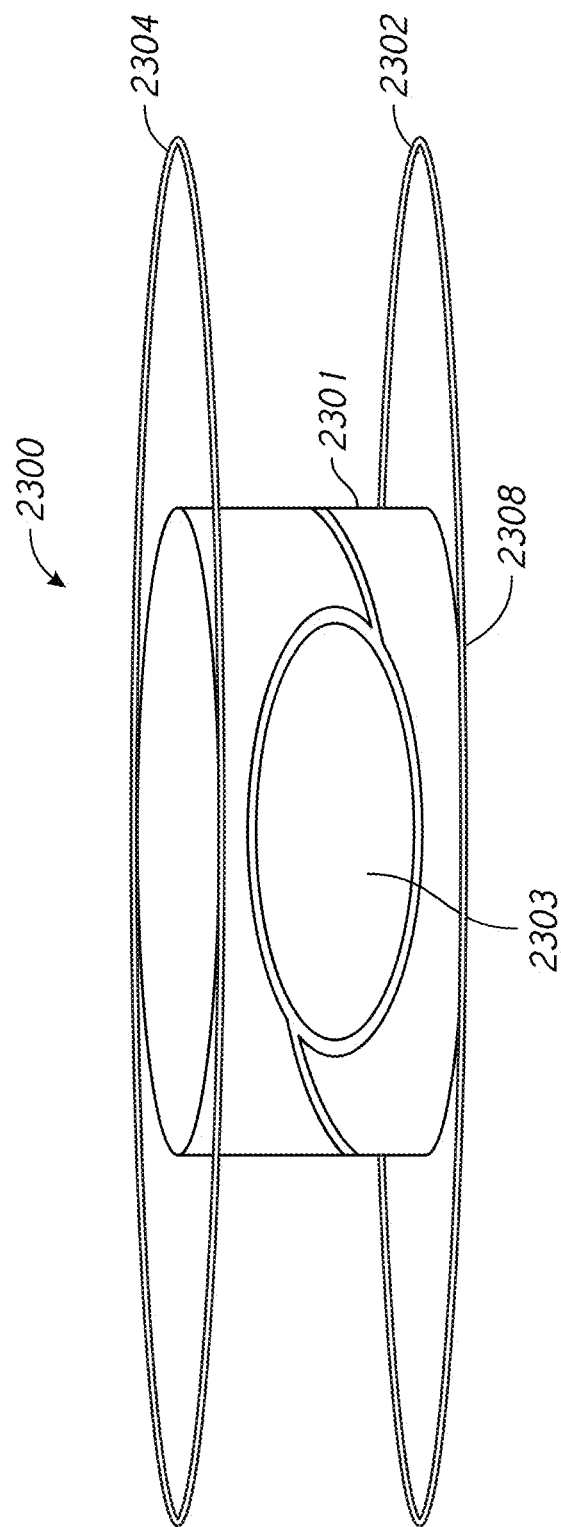
FIG. 25 illustrates a side perspective of the example prosthetic capsular device of FIG. 23 with an optional secondary IOL positioned inside the prosthetic capsular device.

FIGS. 23-25 illustrate an example of a prosthetic device 2300 comprising a housing structure 2301 that is coupled to an anterior ring structure 2304 and a posterior ring structure 2302. In some implementations, the anterior ring structure 2304 is coupled to the anterior portion of the housing structure 2301 and the posterior ring structure 2302 is coupled to the posterior portion of the housing structure 2301. In some implementations, the ring structures 2304, 2302 can be coupled to other areas of the housing structure 2301. For example, the anterior ring structure 2304 can be positioned slightly posterior from the anterior edge of the anterior portion of the housing structure 2301 and the posterior ring structure 2302 can be positioned slightly anterior from the posterior edge of the posterior portion of the housing structure 2301. As described above, the ring structures 2304, 2302 can be embedded in the housing structure 2301 or the ring structures 2304, 2302 can be attached or coupled in some other fashion to the housing structure 2301. In some implementations, the housing structure 2301 can comprise an opening 2404 in the anterior surface of the housing structure 2301. In some implementations, the opening 2404 can be configured to receive therethrough an IOL 2303 or other device that is to be positioned within the housing structure 2301.

As illustrated in FIG. 23, the prosthetic device 2300 can be configured to be positioned in the natural capsular bag 1318 such that the ring structures 2304, 2302 are oriented parallel or substantially parallel to the plane of the circumference 1305 of the natural capsular bag 1318. As illustrated in FIG. 23, the prosthetic device 2300 is not positioned such that the ring structures 2304, 2302 are oriented in an anterior-posterior direction 2312; however, in some implementations, the prosthetic device can be configured such that the ring structures 2304, 2302 can be oriented in an anterior-posterior direction 2312. If the ring structures 2304, 2302 are positioned in an anterior-posterior direction, the ring structures 2304, 2302 may be configured to be smaller, oval, and have dimensions less than the diameter of the ring structures shown in FIG. 23 and/or may be positioned substantially near the top region 2311 and the bottom region 2310 of the natural capsular bag 1318 (e.g., radially outward of the pupil such that the ring structures 2304, 2302 are not in the optical path). In some implementations, the ring structures 2304, 2302 can advantageously be configured to provide the prosthetic device 2300 with sufficient mechanical force to mechanically expand and/or maintain the natural shape of the natural capsular bag 1318 and to inhibit or prevent the capsular bag 1318 from collapsing. In some implementations, the ring structures 2304, 2302 can be helpful in securing the housing structure 2301 in the natural capsular bag 1318 in a fixed or substantially fixed position.

In some implementations, the ring structures 2304, 2302 can be helpful in maintaining the shape and/or size of the housing structure 2301 and/or can inhibit or prevent the housing structure 2301 from at least partially or fully collapsing (e.g., radially inwardly contracting) due to the forces exerted by or on the natural capsular bag 1318. In some implementations, the ring structures 2304, 2302 can be helpful in causing the prosthetic device 2300 to return to an expanded configuration (e.g., to self-expand) after the prosthetic device 2300 has been rolled up and inserted into the insertion tool for implantation in the natural capsular bag 1318. As discussed above, the prosthetic device 2300 is an advantageous design because the prosthetic device 2300 comprises less mass and housing material as compared to other examples disclosed herein. A prosthetic device 2300 having less mass and material can be rolled up into a more compact form for placement in a smaller insertion tool, thereby allowing a smaller incision in the eye.

FIGS. 26-30 illustrate an example of a prosthetic device 2600 comprising a housing structure 2608 that is coupled to an anterior ring structure 2606 at an anterior portion of the housing structure 2608, that is coupled to a posterior ring structure 2602 at a posterior portion 2612 of the housing structure 2608, and that is coupled to an intermediate ring structure 2604 at an intermediate portion of the housing structure 2608 between the anterior portion of the housing structure and the posterior portion of the housing structure. The intermediate portion of the housing structure 2608 may be at a substantial midpoint between the anterior and posterior portions of the housing structure 2608, may be closer to the anterior portion of the housing structure 2608, or may be closer to the posterior portion of the housing structure 2608. In some implementations, the anterior and posterior ring structures 2606, 2602 comprise a diameter or dimension that is substantially the same whereas the intermediate ring structure 2604 comprises a diameter or dimension that is greater than the diameters or dimensions of the posterior and anterior ring structures 2606, 2602. In some implementations, the ring structures 2602, 2604, 2606 each comprises a diameter or dimension that is substantially the same. In some implementations, the anterior ring structure 2606, the posterior ring structure 2602, and the intermediate ring structure 2604 each comprises a diameter or dimension that is different from each other.

Figure 26:
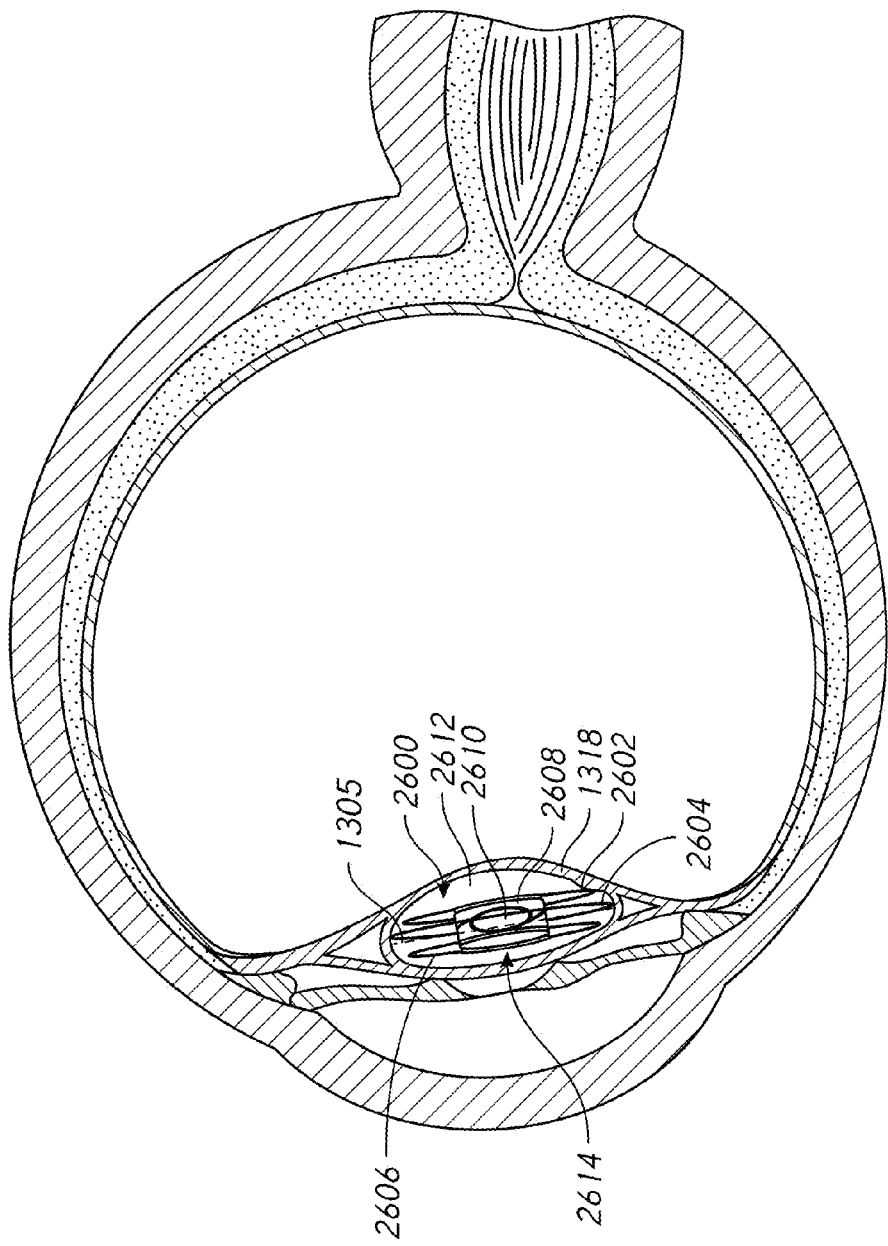
FIG. 26 illustrates a side cross-sectional side view if an eye including another example of a prosthetic capsular device and an IOL.
Figure 27:
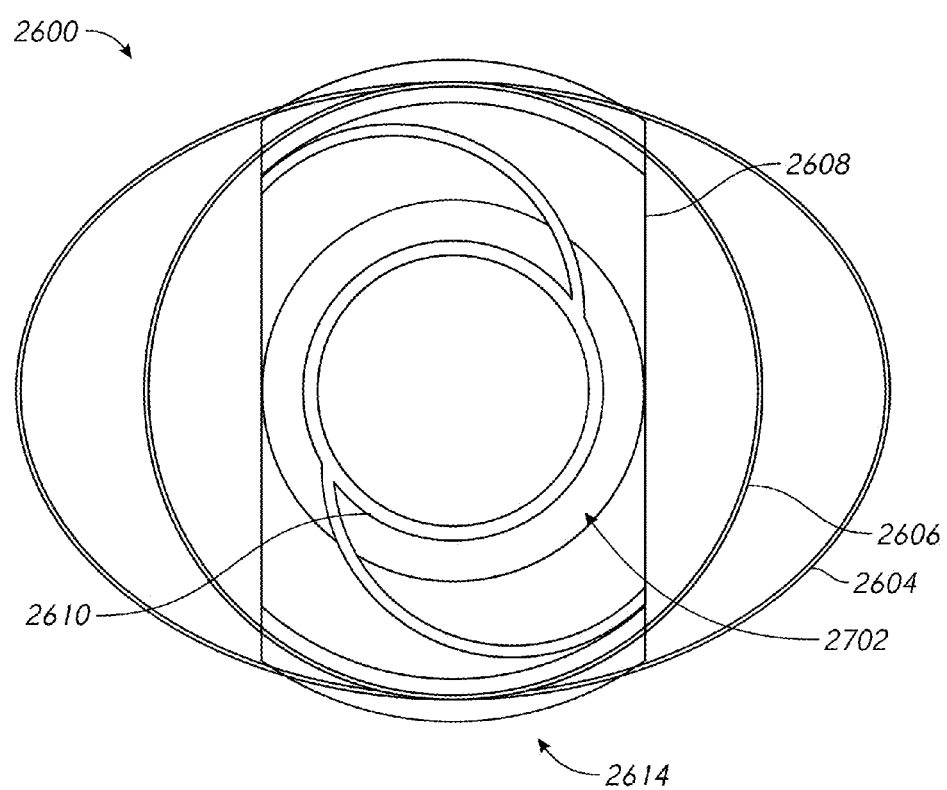
FIG. 27 illustrates an anterior plan view of the example prosthetic capsular device of FIG. 26 with an optional secondary IOL positioned inside the prosthetic capsular device.
Figure 28:
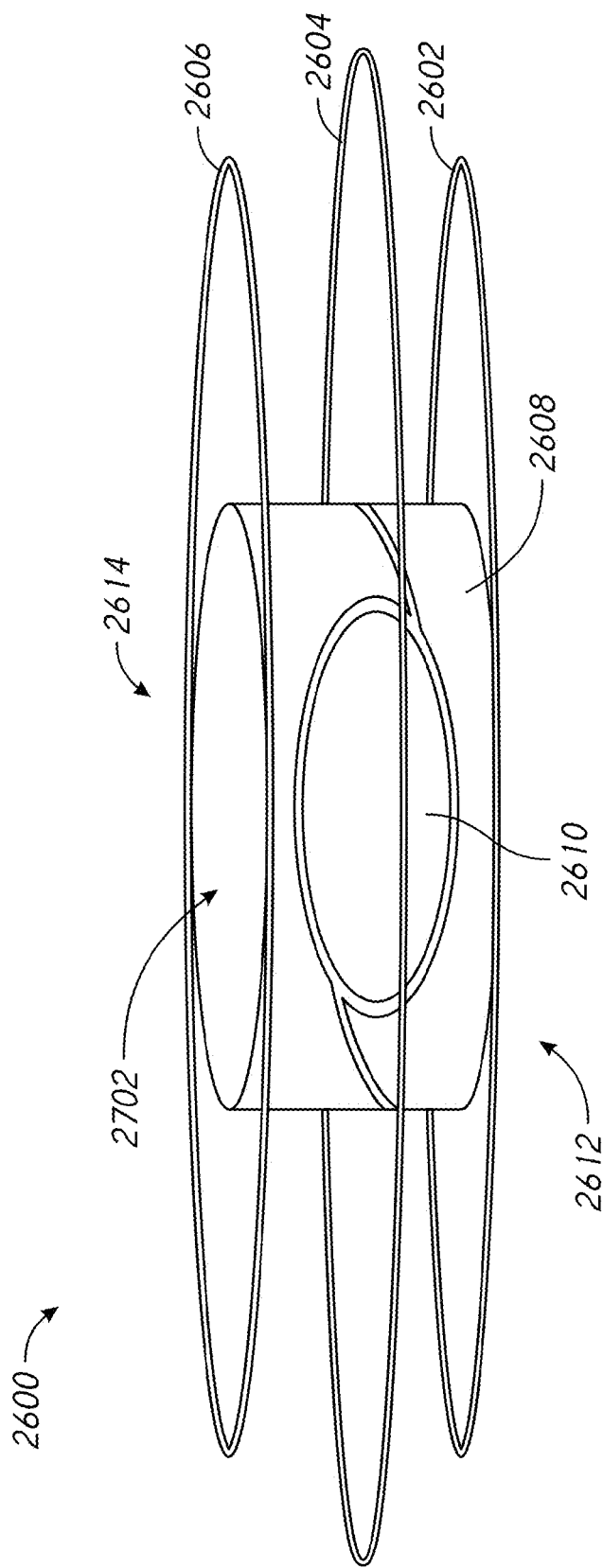
FIG. 28 illustrates a side perspective of the example prosthetic capsular device of FIG. 26 with an optional secondary IOL positioned inside the prosthetic capsular device.

In some implementations, the prosthetic device 2600 is positioned within the natural capsular bag 1318 in a plane that is parallel or substantially parallel to the plane of the circumference 1305 of the natural capsular bag 1318. As illustrated in FIG. 26, the prosthetic device 2600 is not positioned in an anterior-posterior direction. In some implementations, the prosthetic device 2600 comprises an opening 2702 in the anterior surface 2614. In some implementations, the opening 2702 is configured to receive therethrough an IOL 2610 and/or other device to be positioned in the housing structure 2608.

In some implementations, the three ring structures 2602, 2604, 2606 coupled to the housing structure 2608 can better secure the prosthetic device 2600 within the natural capsular bag 1318, for example due to increased surface area with which the prosthetic device 2600 can contact the interior surface of the natural capsular bag 1318. In some implementations, the ring structures 2602, 2604, 2606 can be configured to provide greater mechanical force to expand and maintain the natural shape of the natural capsular bag 1318 and inhibit or prevent the natural capsular bag 1318 from collapsing under the forces of or on the natural capsular bag 1318. In some implementations, the three ring structures 2602, 2604, 2606 can be configured to take up additional volume and space within the natural capsular bag 1318 to expand and maintain the natural shape of the natural capsular bag 1318.

Figure 29:
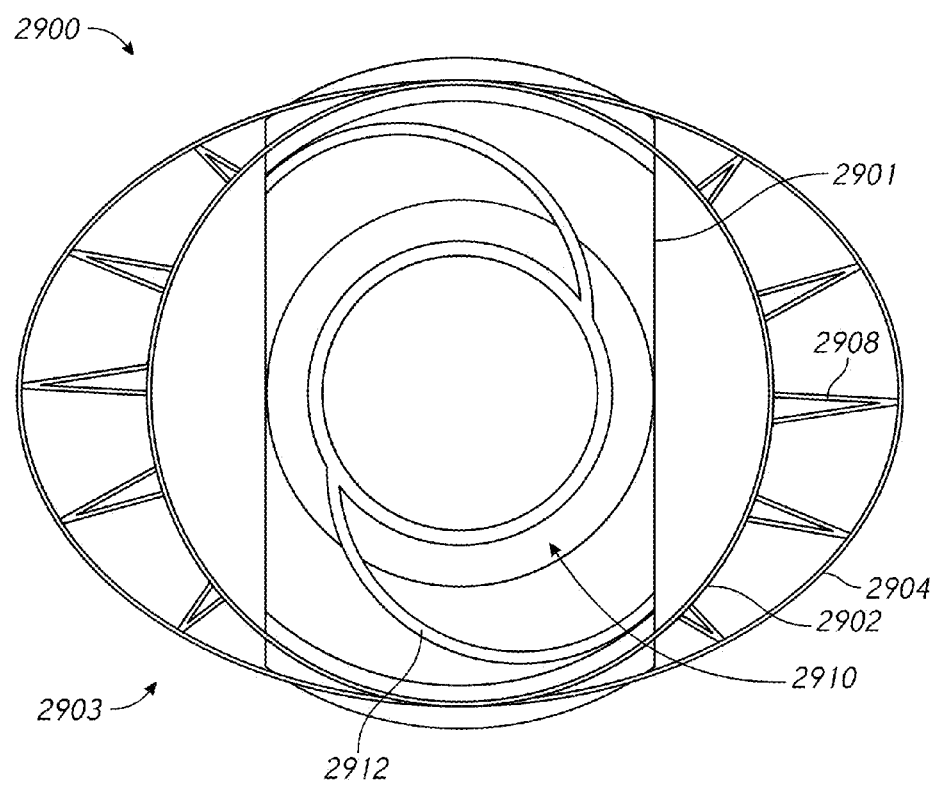
FIG. 29 illustrates an anterior plan view of another example of a prosthetic capsular device with an optional secondary IOL positioned inside the prosthetic capsular device.
Figure 30:
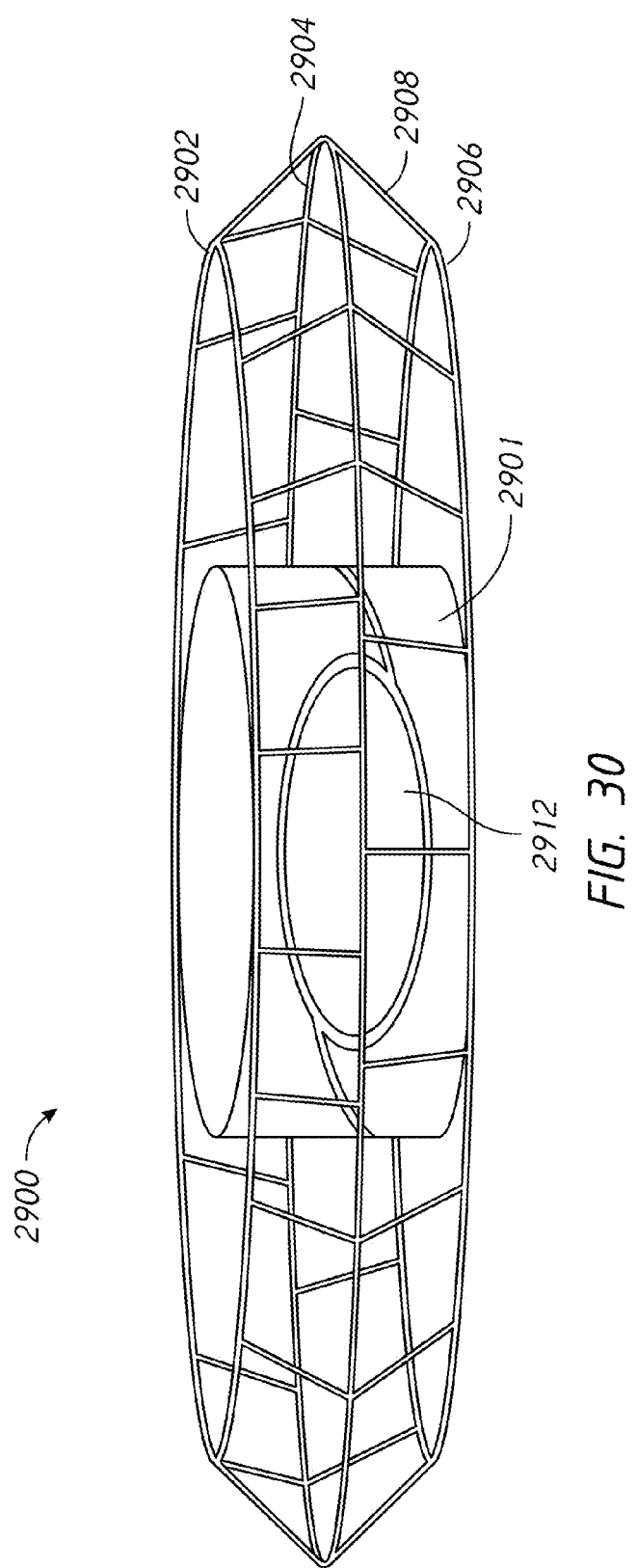
FIG. 30 illustrates a side perspective view of the example prosthetic capsular device of FIG. 29 with an optional secondary IOL positioned inside the prosthetic capsular device.

FIGS. 29 and 30 illustrate an example of a prosthetic device 2900. The prosthetic device 2900 is similar to the prosthetic device 2600 in that the prosthetic device 2900 comprises three ring structures 2902, 2904, 2906 that are coupled to a housing structure 2901. The three ring structures 2902, 2904, 2906 are also connected to each other through a plurality of connecting structures or struts 2908. In some implementations, the connecting structures 2908 are configured to stabilize and maintain the position and/or structure of the three ring structures 2902, 2904, 2906. In some implementations, stabilizing the three ring structures 2902, 2904, 2906 can allow the prosthetic device 2900 to better mechanically expand and maintain the natural shape and/or size of the natural capsular bag. The connecting structures 2908 can be helpful in inhibiting or preventing the housing structure 2901 from collapsing under the forces of the natural capsular bag. Similar to the other examples of the prosthetic device disclosed herein, the housing structure 2901 can be configured to receive an IOL 2912 and/or other devices in the housing structure 2901. The connecting structures 2908 may comprise straight bars, coils, sinusoidal structures, other appropriate shapes, combinations thereof, and the like. The connecting structures 2908 may be oriented substantially in an anterior-posterior direction, may be circumferentially angled like triangle supports, may be radially angled to account for diameter differences, combinations thereof, and the like. The connecting structures 2908 between the rings 2902, 2904 may be aligned (e.g., in a same circumferential position) with the connecting structures 2908 between the rings 2902, 2904, misaligned (e.g., in different circumferential positions) with the connecting structures 2908 between the rings 2902, 2904, and combinations thereof. The prosthetic device 2900 may comprise connecting structures connecting the rings 2902, 2906. The connecting structures 2908 may comprise a same material as the ring structures 2902, 2904, 2906 (e.g., making manufacturing and/or coupling easier) or a different material than the ring structures 2902, 2904, 2906 (e.g., allowing material more suitable for support such as having high rigidity to be used for the connecting structures 2908).

Figure 31:
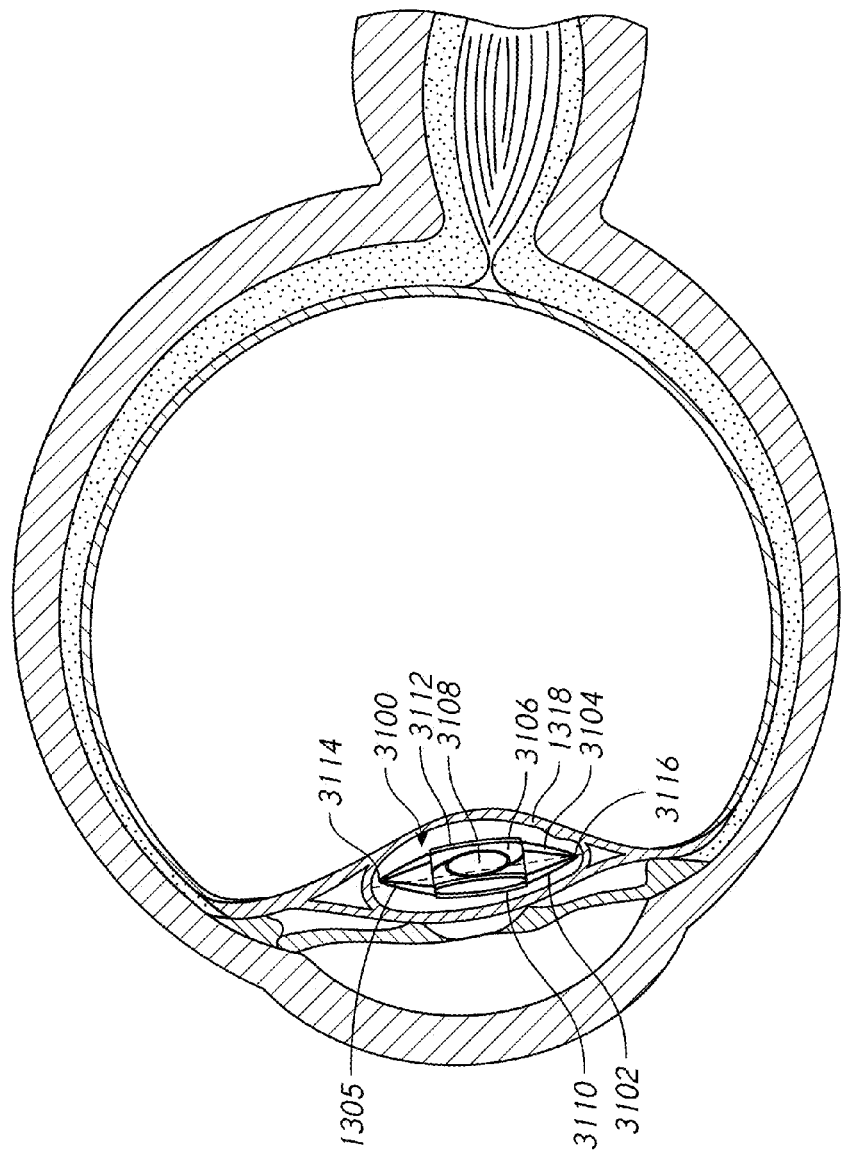
FIG. 31 illustrates a side cross-sectional side view of an eye including an example of a prosthetic capsular device and an IOL.
Figure 32:
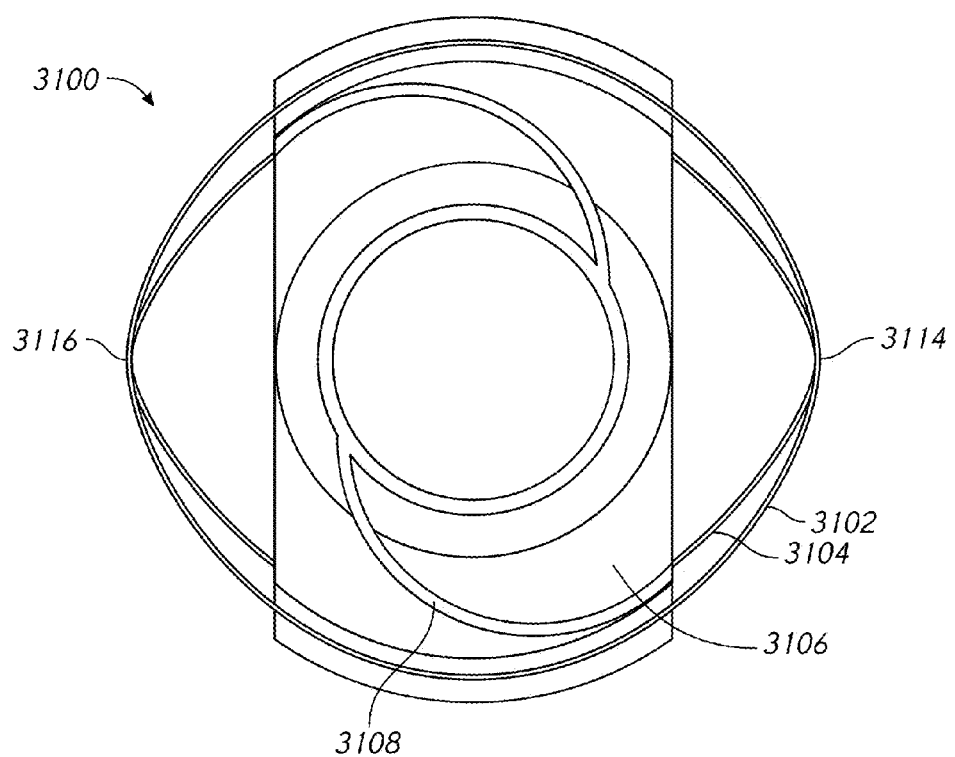
FIG. 32 illustrates an anterior plan view of the example prosthetic capsular device of FIG. 31.
Figure 33:
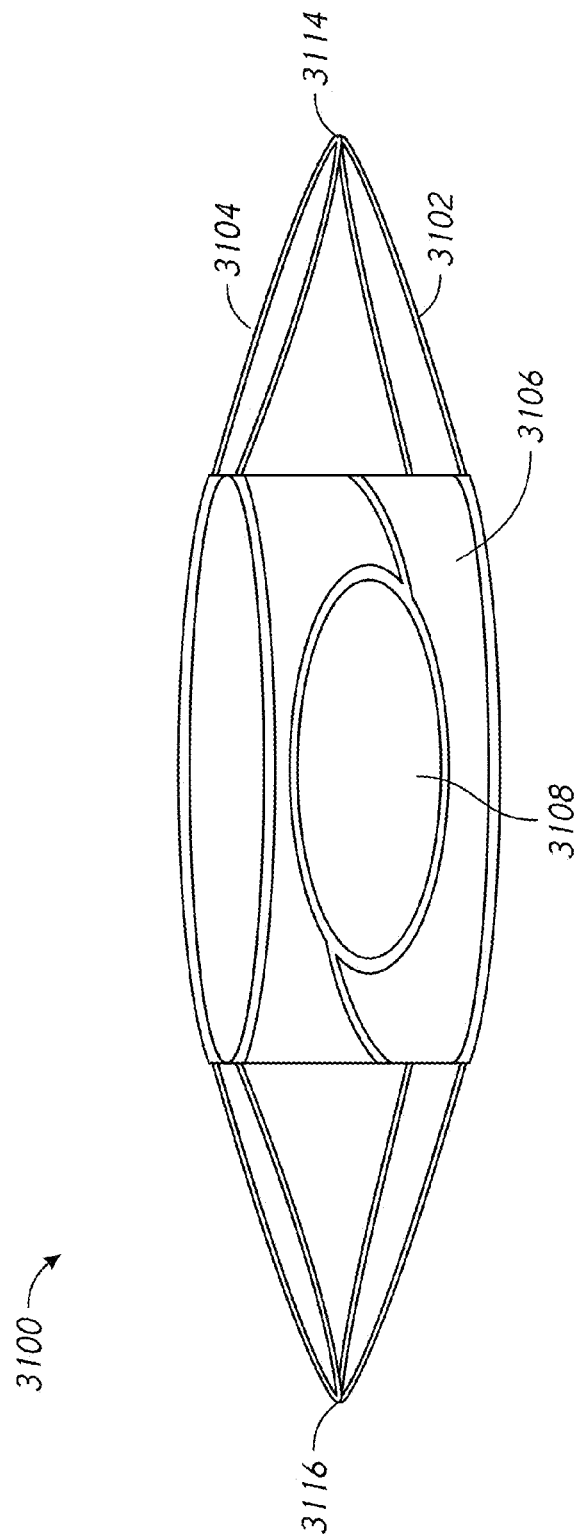
FIG. 33 illustrates a side perspective view of the example prosthetic capsular device of FIG. 31.

FIGS. 31-33 illustrate an example of a prosthetic device 3100. The prosthetic device 3100 comprises a housing structure 3106 coupled to an anterior ring structure 3102 and a posterior ring structure 3104. The ring structures 3102, 3104 connect with each other at junction points 3114, 3116. The junction points 3114, 3116 can be substantially evenly spaced or opposite about the circumference of the ring structures 3102, 3104 or asymmetrically spaced about the circumference of the ring structures 3102, 3104. Fewer (e.g., one) or more (e.g., greater than two) junction points are also possible. In some implementations, the anterior ring structure 3102 is coupled to an anterior portion of the housing structure 3106 and the posterior ring structure 3104 is coupled to a posterior portion of the housing structure 3106. In some implementations, the ring structures 3102, 3104, where connected to the housing structure 3106, are in planes that are parallel or substantially parallel with each other. Portions of the ring structures 3102, 3104 that are not connected to the housing structure 3106 are intersect each other at the junction points 3114, 3116. In some implementations, the ring structures 3102, 3104 are continuous monolithic structures. In some implementations, the ring structures 3102, 3104 comprise two, three, or more components that are coupled or fused together to form the ring structures 3102, 3104.

In some implementations, ring structures 3102, 3104 connected at junction points 3116, 3114 can provide better structural support and integrity for the prosthetic device 3100. By strengthening the structural integrity, the prosthetic device 3100 can be configured to better mechanically maintain and/or expand the natural capsular bag 1318. The structural integrity provided by the connected ring structures 3102, 3104 can help inhibit or prevent the housing structure 3106 from collapsing under the forces of the natural capsular bag 1318. In some implementations, the ring structures 3102, 3104 can be configured to be spring-like such that the ring structures 3102, 3104 can be configured to flex radially in and out depending on the forces exerted on the prosthetic device 3100. In this regard, the ring structures 3102, 3104 can be configured to better hold the shape of the natural capsular bag 1318 and/or can be configured to inhibit or prevent or mitigate the tendency for the prosthetic device 3100 to rotate in the natural capsular bag 1318 or eye.

Figure 34:
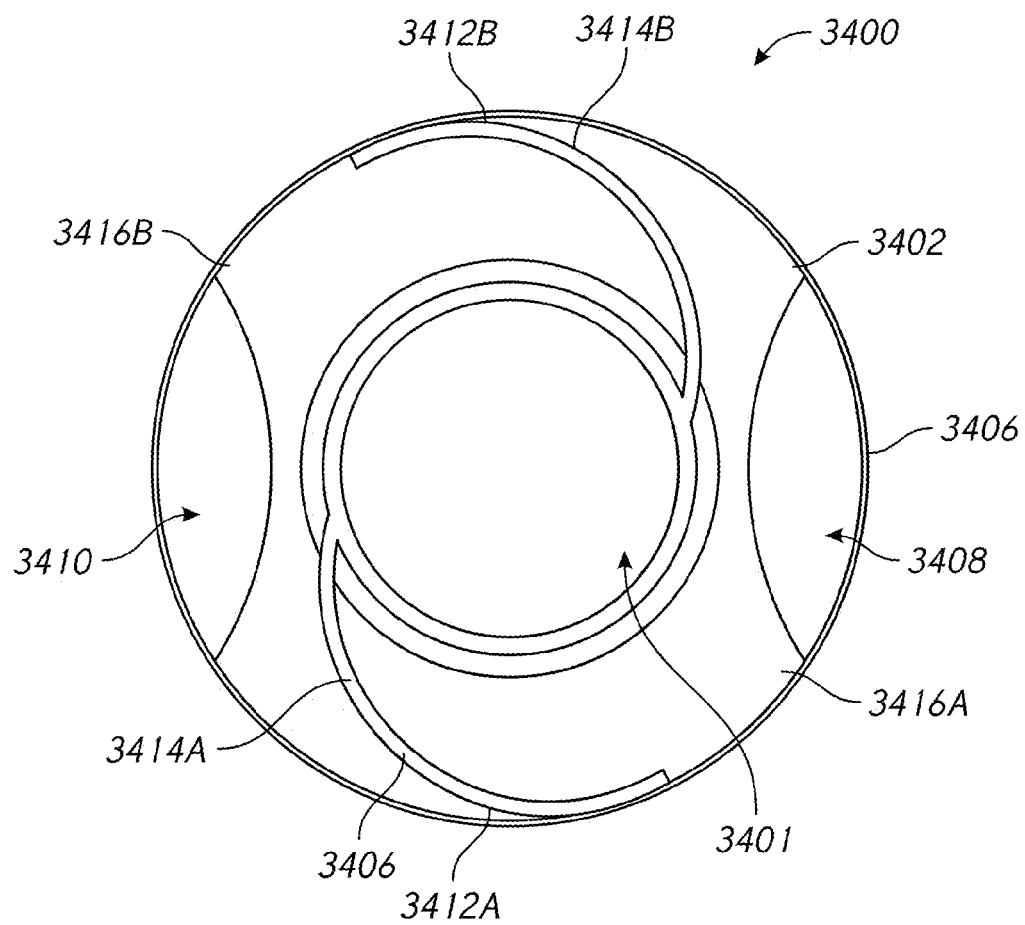
FIG. 34 illustrates an anterior plan view of another example of a prosthetic capsular device.
Figure 35:
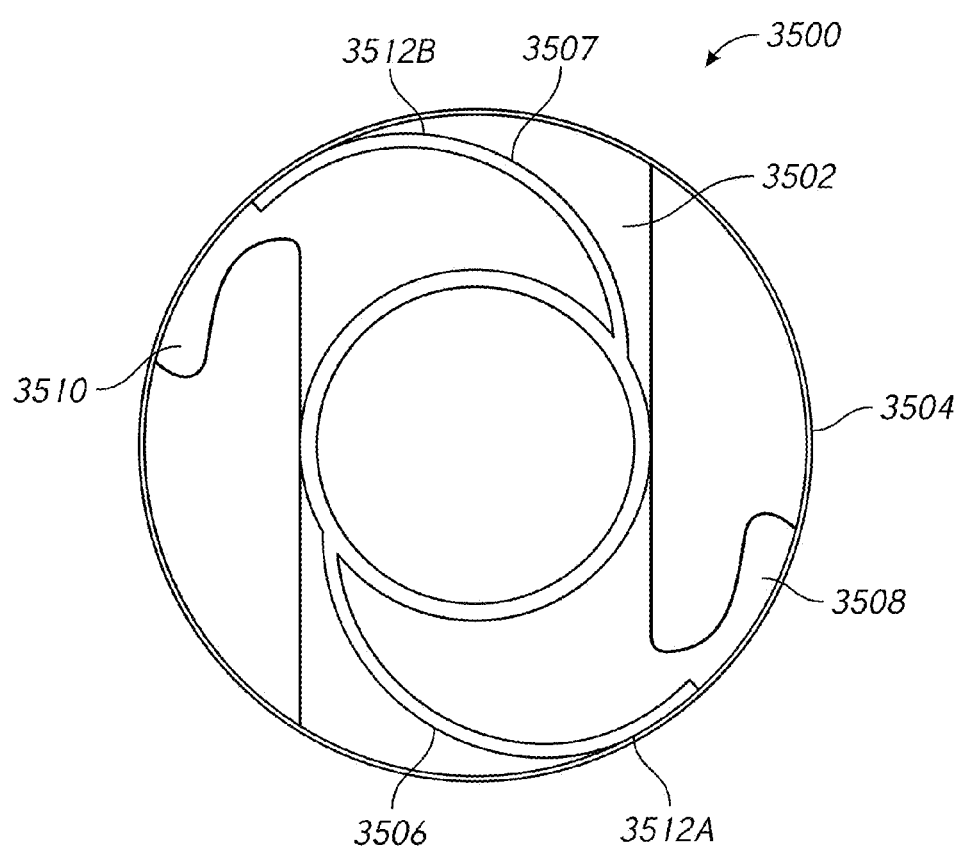
FIG. 35 illustrates an anterior plan view of yet another example of a prosthetic capsular device.

FIGS. 34 and 35 illustrate examples of prosthetic devices 3400, 3500, respectively. With reference to FIG. 34, the prosthetic device 3400 comprises a housing structure 3402 that is coupled to a ring structure 3406. In some implementations, the housing structure 3402 comprises an opening 3401 that is configured to receive therethrough an IOL 3406 and/or other devices to be positioned in the housing structure 3402. In some implementations, the housing structure 3402 is configured to have an hourglass configuration such that the prosthetic device 3400 comprises arced or almond-shaped cutout portions 3408, 3410. The prosthetic device 3400 can be advantageous because the hourglass shape of the housing structure 3402 can allow for the distal portions 3412A, 3412B of the haptics 3414A, 3414B, respectively, of an IOL 3406 to be moved to various positions within the housing structure 3402. For example, the IOL 3406 can be rotated counterclockwise until the distal tips 3412A, 3412B of the haptics 3414A, 3414B, respectively, touch the arc edge portions 3416A, 3416B, respectively. The IOL 3406 can be inhibited or prevented from rotating clockwise, providing rotational certainty. Alternatively, the IOL 3406 could be rotated clockwise into another (e.g., opposite) position. The IOL 3406 may be rotated differently if the haptics 3414A, 3414B are shaped differently.

By providing rotational flexibility and certainty for the IOL 3406 positioned in the housing 3402, the surgeon or other user can better position the IOL 3406 in the eye to achieve good or best performance or results for the patient. With reference to FIG. 35, the prosthetic device 3500 can provide similar rotational flexibility as disclosed for the prosthetic device 3400. In some implementations, the prosthetic device 3500 comprises a housing structure 3502 that is coupled to a ring structure 3504. The housing structure 3502 can comprise wing portions 3508, 3510. In some implementations, the wing portions 3508, 3510 are configured to receive the distal portions 3512A, 3512B of the haptics 3506, 3507, respectively, of an IOL 3506. The wing portions 3508, 3510 may include a bulbous end (e.g., as illustrated in FIG. 35), may taper to a point or a blunt end, or have any other shape suitable for interacting with the haptics 3506, 3507. The surgeon or other user can rotate the IOL 3506 in a counterclockwise direction, for example until the haptics 3506, 3507 engage or interact with the wing portions 3508, 3510, in order to better position the IOL 3506 within the eye to achieve good or best performance or results for the patient. In an embodiment, the wing portions 3508, 3510 may also be designed to engage the housing structure 3502 more proximally, substantially decreasing the volume of the prosthetic device 3500. In an embodiment, the prosthetic device can be form fitted to the IOL. This configuration of the prosthetic device can be limited in application to a prosthetic device 3500 capable of simply housing another IOL 3506 without the ability to rotate said IOL 3506 or haptics 3506, 3507, or distal portions 3512A, 3512B within said prosthetic device 3500 or to contain much additional technology. In an embodiment, the peripheral outline of such a device can be configured to substantially follow the shape of a traditional IOL 3506. Additionally, the ring structure may or may not be present in such an implementation.

Figure 36:
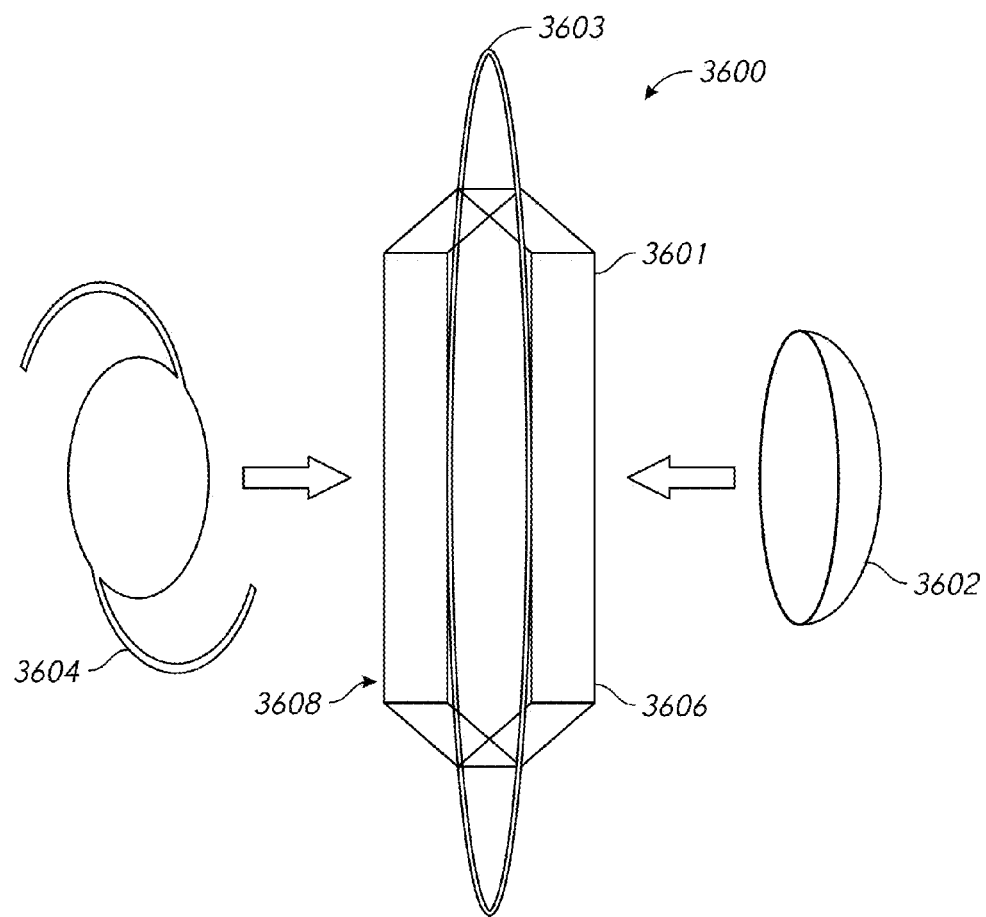
FIG. 36 illustrates an exploded side perspective view of still another example of a prosthetic capsular device.

FIG. 36 illustrates a prosthetic device 3600 comprising a housing structure 3601 that is coupled to a ring structure 3603. In some implementations, the housing structure 3601 comprises an opening in the posterior portion 3606 of the housing structure 3601. In some implementations, the posterior portion 3606 of the housing structure can be configured to receive a lens structure 3602. As described herein, the lens structure 3602 can serve as a refractive lens that provides a reference point for the surgeon or other user to select an appropriate IOL and to position the IOL in the housing structure 3601 to achieve good or best performance or results for the patient. In some implementations, the housing structure 3601 comprises a second opening in the anterior portion 3608 of the housing structure 3601. As described herein, the second opening in the anterior portion 3608 can be configured to receive therethrough an IOL 3604 and/or other devices to be positioned in the housing structure 3601.

The prosthetic device 3600 can be advantageous because, by including a separate lens structure, the prosthetic device 3600, more specifically the housing structure 3601, can have a reduced mass versus devices comprising an integral or coupled refractive posterior portion. With less mass in the housing structure 3601, the prosthetic device 3600 can be rolled up or folded in a more compact fashion for positioning into an insertion tool. A surgeon or other user may be able to utilize a smaller insertion tool that uses a smaller incision. The surgeon or other user can couple the prosthetic device 3600 to the lens 3602 while each component is in the natural capsular bag, for example after being delivered through an incision in series. After the components have expanded (e.g., self-expanded) into their expanded states, the surgeon or user can position the lens 3602 into the opening of the posterior portion 3606. The surgeon may create a posterior capsulorhexis while still supporting the housing structure 3601 (e.g., in combination with a ring structure 3603) and the posterior segment 3602, which could enhance the ease or reduce the difficulty of performing a procedure for inserting the device 3600 through manual means, and can inhibit or prevent vitreous prolapse. The device 3600 may be used in conjunction with a femtosecond laser to create the posterior capsulorhexis. After the posterior capsulorhexis is created, the posterior capsular material can be removed from the eye, which can inhibit or prevent (e.g., forever) development of a posterior capsular opacification, and which can possibly inhibit or prevent long term shifts in IOL position through capsular contraction. Before or after the housing structure 3601 is inserted, the lens 3602 of the prosthetic capsular device 3600 could be inserted.

In some implementations, the lens 3602 can be configured to be coupled to the opening in the posterior portion 3606 using a friction fit. In some implementations, the lens 3602 is coupled to the opening in the posterior portion 3606 through sutures or other mechanisms for attaching the lens 3602 to the posterior portion 3606. As described in other examples herein, the prosthetic device 3600 can comprise an opening in the anterior portion 3608 of the housing structure 3601. In some implementations, the opening in the anterior portion 3608 can be configured to receive therethrough an IOL 3604 and/or other devices for positioning in the housing structure 3601.

Figure 37A:
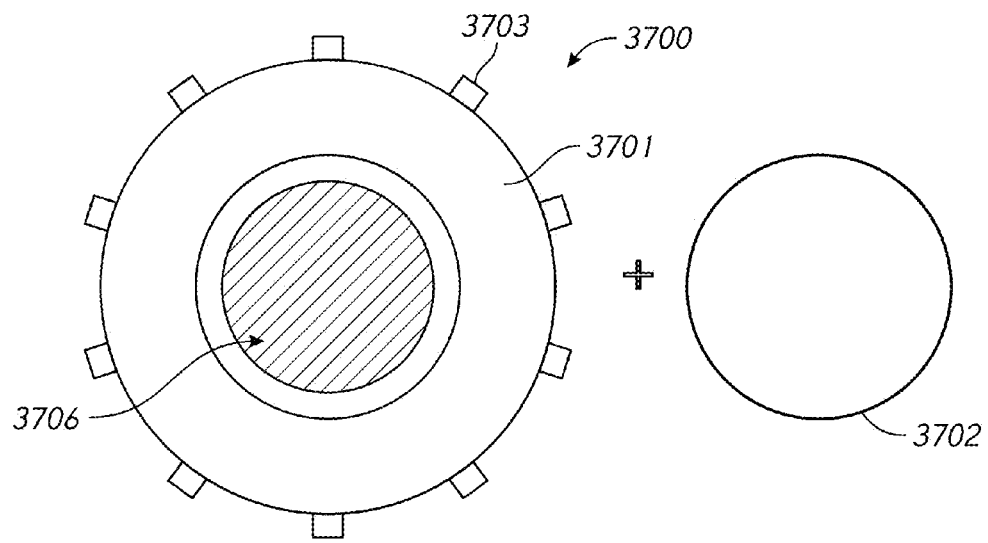
FIG. 37A illustrates an exploded anterior plan view of yet still another example of a prosthetic capsular device.
Figure 37B:
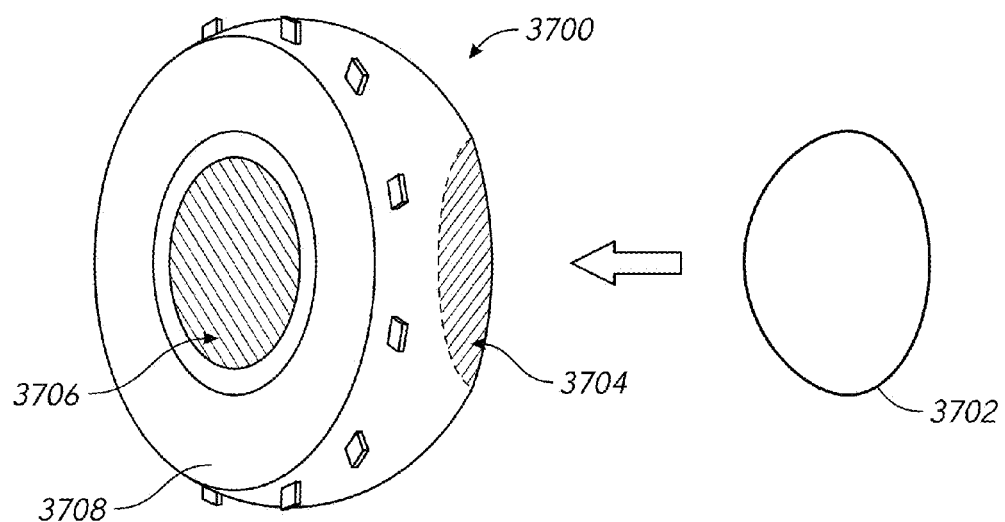
FIG. 37B illustrates an exploded side perspective view of the example prosthetic capsular device of FIG. 37A.

FIGS. 37A and 37B illustrate an example of a prosthetic device 3700. The prosthetic device 3700 comprises a housing structure 3701 comprising a plurality of tabs 3703. In some implementations, the housing structure 3701 comprises an opening 3704 in the posterior portion of the housing structure 3701 for receiving a separate lens 3702. In some implementations, the housing structure 3701 comprises an opening 3706 in the anterior portion 3708 of the housing structure 3701. In some implementations, the opening 3706 in the anterior portion 3708 can be configured to receive therethrough an IOL and/or other devices for positioning in the housing structure 3701.

Figure 38A:
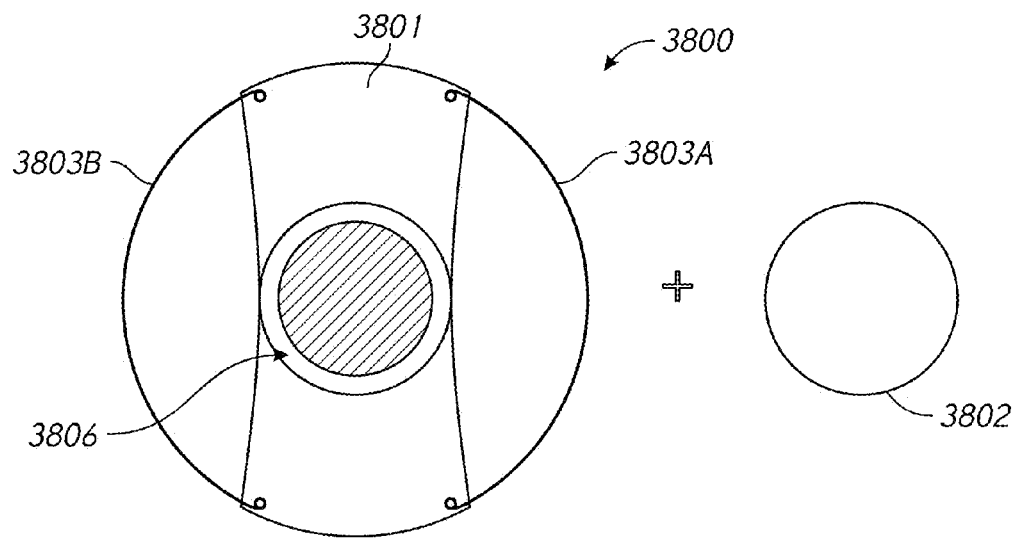
FIG. 38A illustrates an exploded anterior plan view of another example of a prosthetic capsular device.
Figure 38B:
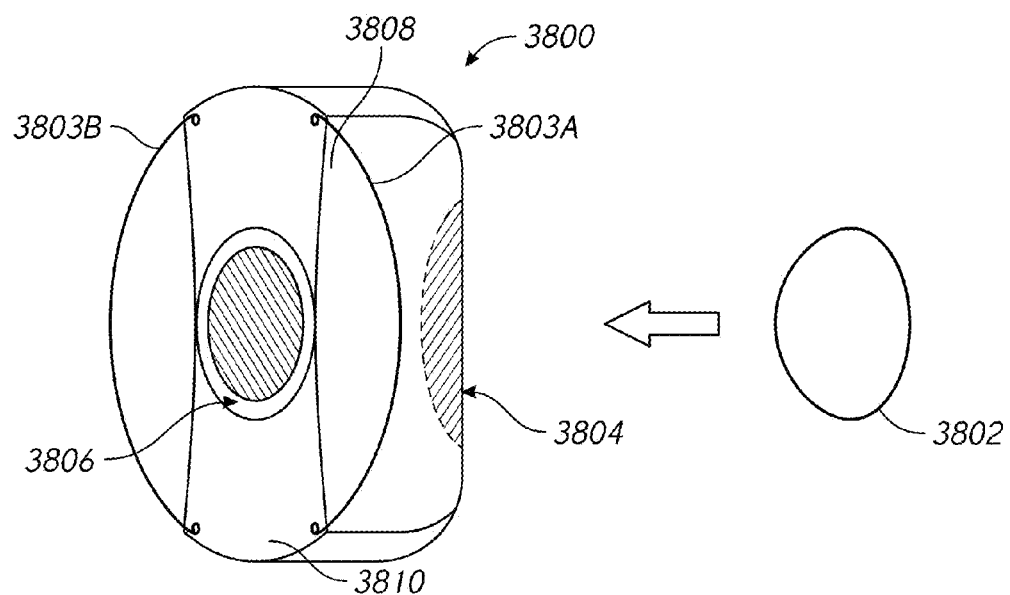
FIG. 38B illustrates an exploded side perspective view of the example prosthetic capsular device of FIG. 38A.

FIGS. 38A-38B illustrate an example of a prosthetic device 3800. The prosthetic device 3800 comprises a housing structure 3801 that is coupled to a ring structure 3803A, 3803B. In some implementations, the housing structure 3801 comprises an opening 3804 in the posterior portion 3808 of the housing structure 3801. In some implementations, the opening 3804 is configured to receive a lens structure 3802. In some implementations, the housing structure 3801 comprises an opening 3806 in the anterior portion 3810 of the housing structure 3801. In some implementations, the opening 3806 can be configured to receive therethrough an IOL and/or other devices for positioning in the housing structure 3801.

In some implementations of a multi-component prosthetic capsular device assembly comprising a separate posterior optic, the posterior optic may be coupled to a housing structure without a posterior optic (e.g., instead comprising a posterior opening, a non-refractivity powered membrane, or a reflectively powered optic configured to provide partial refractive power). For example, the housing structure may include one or more openings or slits and the posterior optic can include a post having a lip, vice versa, or combinations thereof. In some implementations, a pattern of openings and posts can be a proprietary lock and key configuration, for example to ensure quality control. The posterior optic can be inserted separately from (e.g., before or after) the housing structure, which could reduce material volume during each injection, reducing incision size. When the post is inserted through an opening, the lip can inhibit or prevent the posterior optic from uncoupling from the housing structure. If desired, the posterior optic can be exchanged, for example by forcing the lip through the opening, which can allow flexibility for a variety of potentially desired optics (e.g., multifocal, toric, higher power, lower power, etc.). In some implementations, the pattern can include threads (e.g., external threads on the optic and internal threads on the opening, or vice versa) having a particular winding density, helical width, etc.

Figure 39:
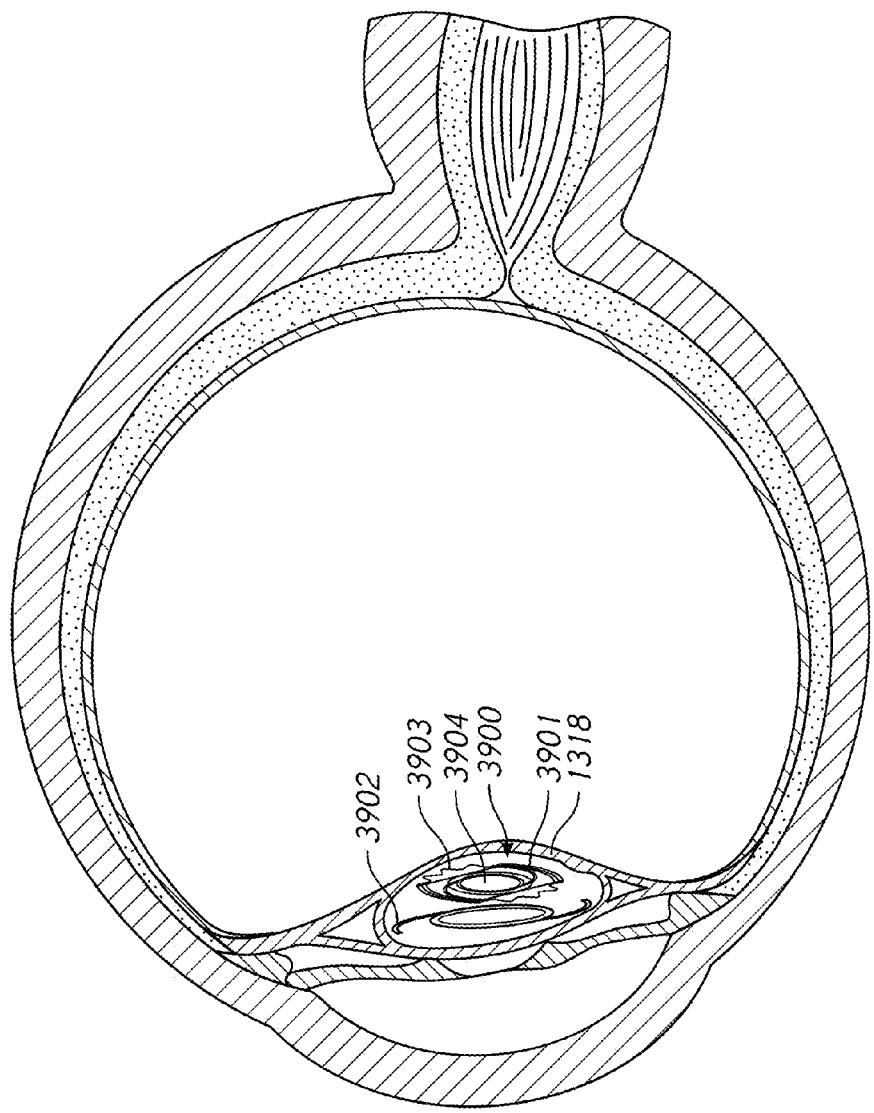
FIG. 39 illustrates a side cross-sectional side view of an eye including an example of a prosthetic device.

FIG. 39 illustrates an example of a prosthetic device 3900. In some implementations, the prosthetic device 3900 comprises a substantially planar housing structure 3901 that is coupled to a ring structure 3903 (e.g., comprising a polyimide loop structure). The ring structure 3903 may include features described herein (e.g., arcuate or sinusoidal shape, coupling or anchoring to the housing structure 3901). In some implementations, the substantially planar housing structure 3901 comprises a refractive portion 3904. Unlike other examples disclosed herein, the prosthetic device 3900 is not configured to receive an IOL and/or other devices for positioning in the substantially planar housing structure

3901. Rather, the substantially planar housing structure 3901 is configured to retain the refractive portion 3904 within the natural capsular bag 1318.

Similar to the posterior refractive portion of the housing structures within the prosthetic devices described herein, the refractive portion 3904 can be used by a surgeon or other user as a point of reference in determining or selecting an IOL 3902 for implantation in the natural capsular bag 1318. The prosthetic device 3900 can be advantageous because without a three-dimensional housing structure, further mass and material can be removed from the prosthetic device 3900. With additional mass and material removed from the prosthetic device 3900, the device can be rolled up or folded in a more compact fashion for insertion into the insertion tool. With a more compact folded configuration, the surgeon can utilize a insertion tool with a smaller diameter and can make a smaller incision in the eye. The housing structure 3901 may still provide other advantages described herein such as providing a barrier to contact with the vitreous humor, housing electronics and other structures, etc.

Figure 40:
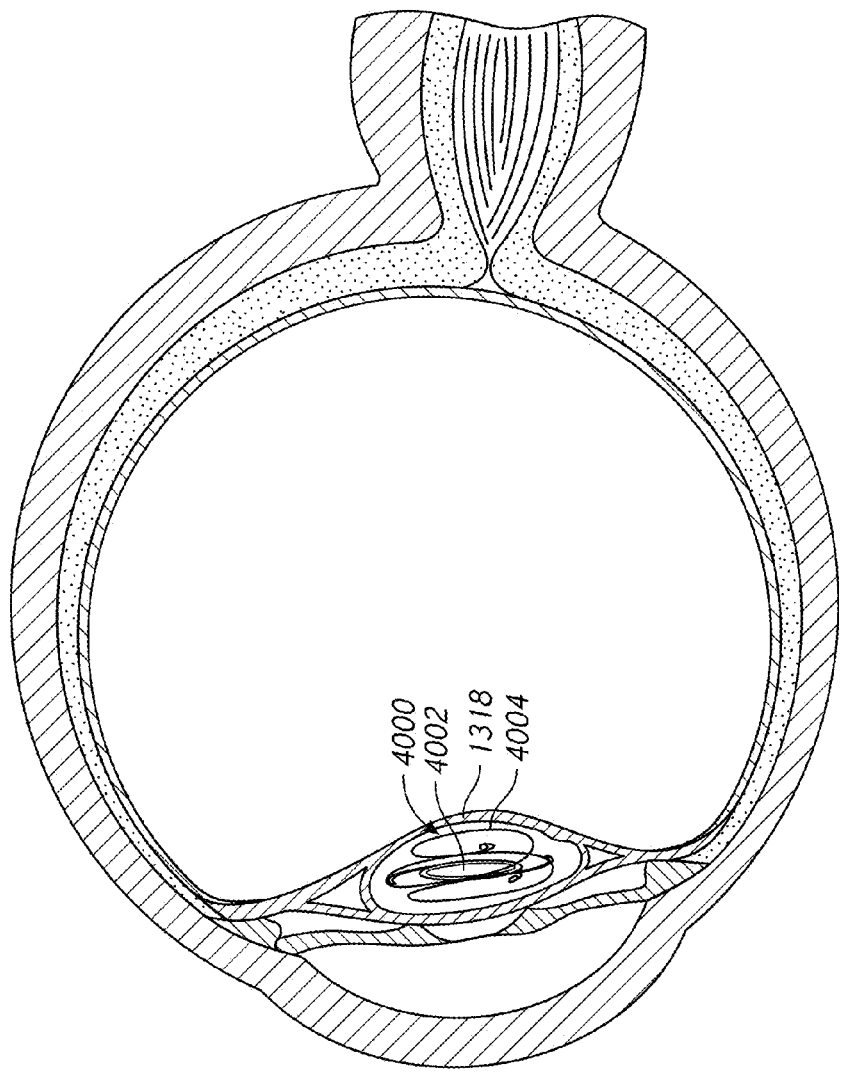
FIG. 40 illustrates a side cross-sectional side view of an eye including another example of a prosthetic device and an IOL.

FIG. 40 illustrates an example of a prosthetic device 4000. The device 4000 may be substantially similar in composition to a capsular tension ring. The prosthetic device 4000 comprises a wire frame 4004. The wire frame 4004 comprise or can be made of a single material or combination of materials that are biocompatible within the eye, including, but not limited to, PMMA, acrylic, silicone, collamer, nitinol, nylon, polypropylene, polyimide, PTFE, polyester, combinations thereof, and the like. In some implementations, the wire frame 4004 comprises a curled up shape configured to encircle the natural capsular bag 1318 multiple times, which can create volumetric separation of the anterior and posterior capsules while providing stability to the capsular bag in instances where zonules may be weak, torn, damaged and/or absent. In some implementations, the wire frame 4004 is configured to expand in the natural capsular bag 1318 to mechanically expand and/or maintain the size of the natural capsular bag 1318. In some implementations, the prosthetic device 4000 is configured to receive an IOL 4002 and/or other devices for implantation in the natural capsular bag 1318. In some implementations, the wire frame 4004 of the prosthetic device 4000 is curled in a fashion so as to not interfere with the optical path. In some implementations, the lack of a housing structure of the prosthetic device 4000 may advantageously allow mass and material to be omitted from the prosthetic device 4000. With less mass and material, the prosthetic device 4000 can be more compactly rolled up or folded into an insertion tool. Having a more compact form can allow the surgeon to utilize an insertion tool having a smaller diameter and/or can allow the surgeon or other user to make a smaller incision in the eye. The prosthetic device 4000 may still provide other advantages described herein such as providing a barrier to contact with the vitreous humor, housing electronics and other structures, etc. In some implementations, the prosthetic device 4000 comprises a refractive surface.

Figure 41:
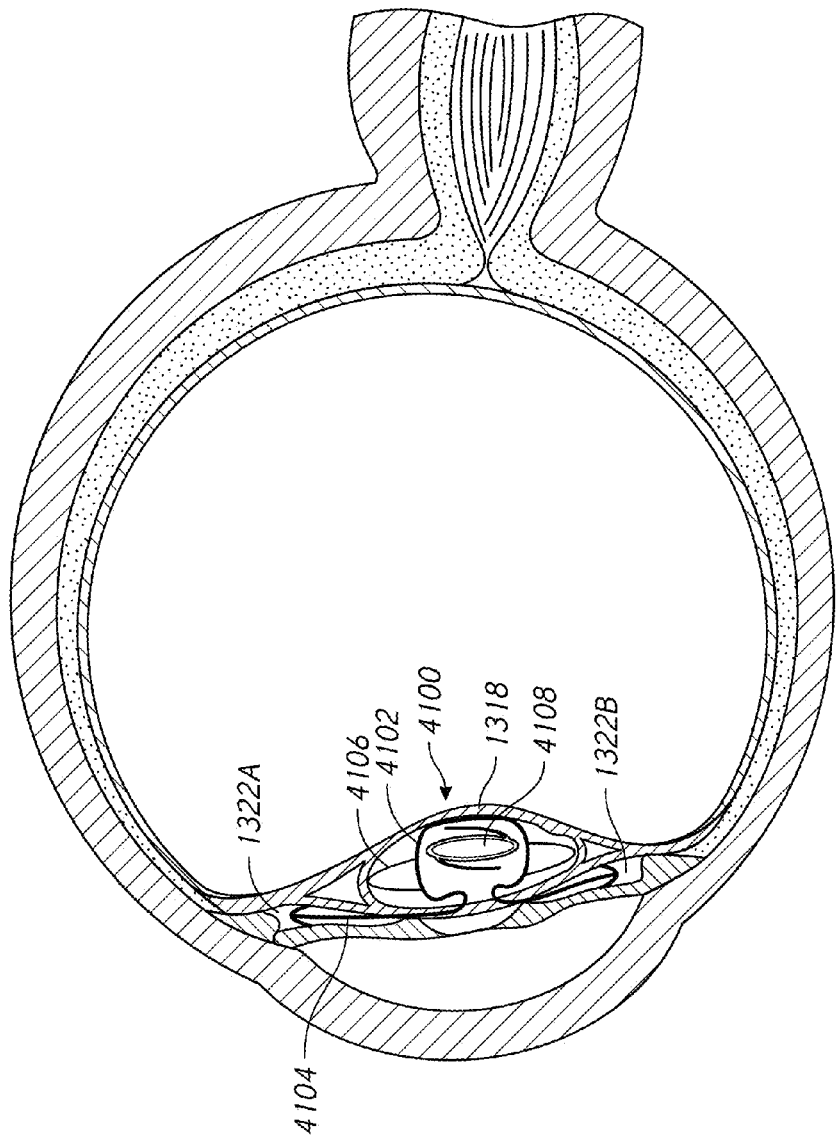
FIG. 41 illustrates a side cross-sectional side view of an eye including yet another example of a prosthetic device and an IOL.

FIG. 41 illustrates an example of a prosthetic device 4100. The prosthetic device 4100 comprises a housing structure 4102 that is coupled to an outer ring structure 4104 and an inner ring structure 4106. In some implementations, the outer ring structure 4104 is configured to be positioned in the sulcus 1322A, 1322B of the eye (e.g., as described herein with respect to the flange 20). In some implementations, the inner ring structure 4106 is configured to be positioned in the natural capsular bag 1318. In some implementations, the prosthetic device 4100 can be advantageous because by positioning the outer ring structure 4104 in the sulcus 1322A, 1322B, the housing structure 4102 can be securely positioned in the natural capsular bag 1318. In some implementations, the outer ring structure 4104 can be configured to inhibit or prevent the housing structure 4102 of the prosthetic device 4100 from migrating in or out of the natural capsular bag 1318. By maintaining the position of the housing structure 4102, the prosthetic device 4100 can be maintained in the eye at a fixed position even as the eye changes over time. In some implementations, the inner ring structure 4106 can be configured to mechanically expand and/or maintain the natural volume of the natural capsular bag 1318. In some implementations, the housing structure 4102 can be configured to receive through an opening in an anterior surface an IOL 4108 and/or other devices for positioning in the housing structure 4102.

Figure 42:
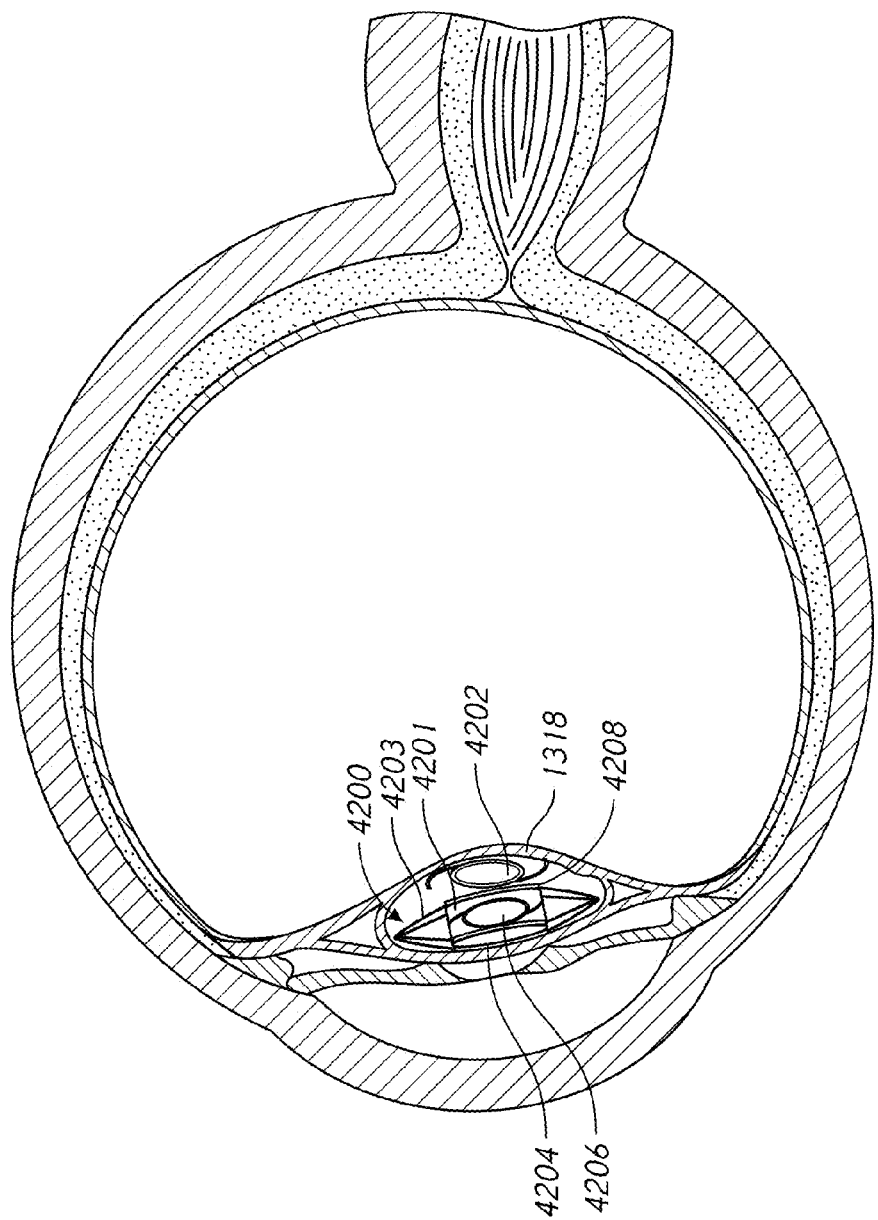
FIG. 42 illustrates a side cross-sectional side view of an eye including still another example of a prosthetic device.

FIG. 42 illustrates an example of a prosthetic device 4200. The prosthetic device 4200 comprises a housing portion 4201 that is coupled to one or more ring structures 4203. In some implementations, the housing structure 4201 comprises an anterior portion 4204. Unlike in other examples disclosed herein, the anterior portion 4204 does not comprise an opening but rather comprises a refractive portion. In some implementations, the housing portion 4201 comprises a posterior portion 4208. Unlike in other examples disclosed herein, the posterior portion 4208 does not comprise a refractive portion but rather comprises an opening for receiving an IOL 4206 and/or other devices for positioning in the housing structure 4201. In some implementations, the prosthetic device 4200 can be advantageous because the prosthetic device 4200 can be combined with an IOL 4202 to act like a telescope or an apparatus for magnifying the visibility of objects. In order to produce the magnification of objects, the prosthetic device 4200 is utilized to create space between the IOL 4202 and the refractive portion in the anterior portion 4204 and/or the IOL 4206 positioned within the housing structure 4201.

Figure 43A:
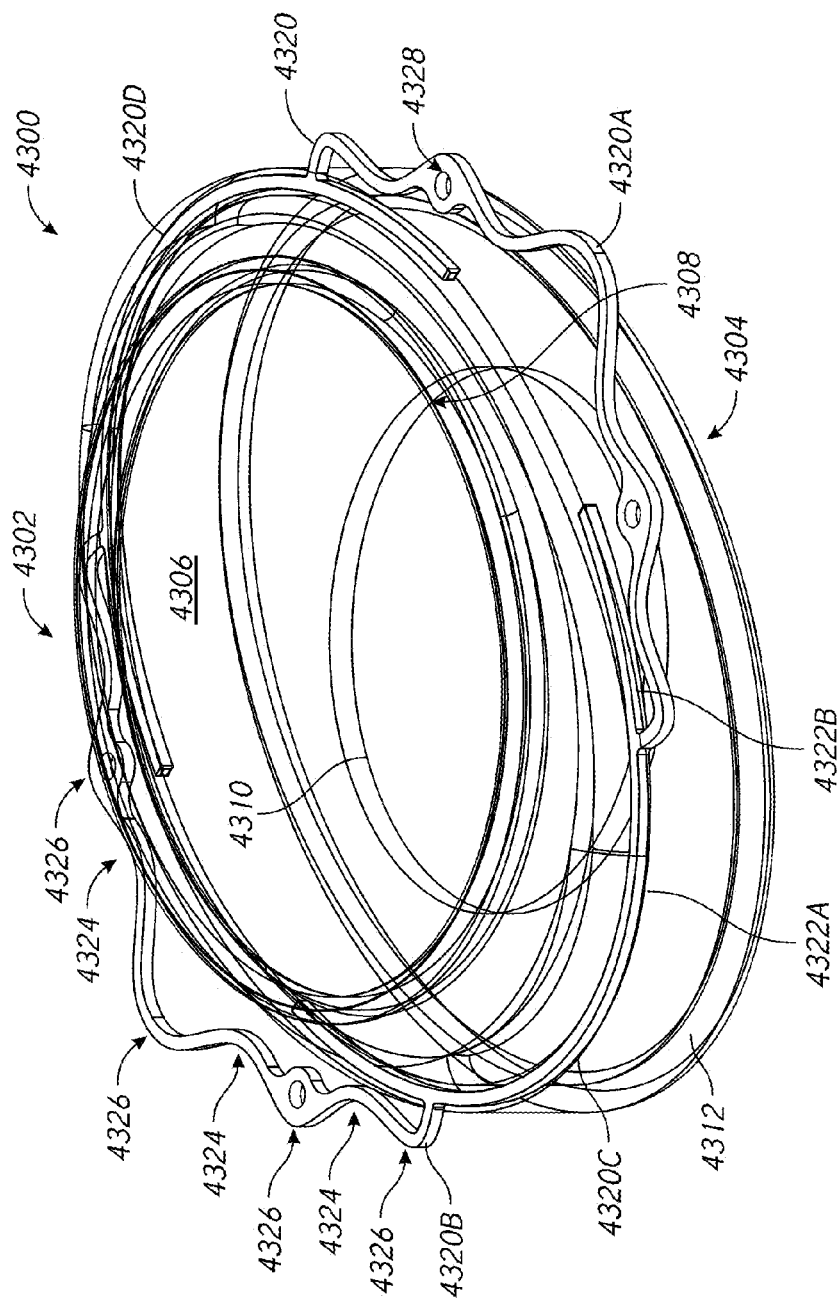
FIG. 43A illustrates an anterior side perspective view of an example of a prosthetic capsular device.

FIG. 43A illustrates an anterior side perspective view of an example of a prosthetic capsular device 4300. The device 4300 comprises an anterior side 4302, a posterior side 4304, and sidewalls 4306 extending between the anterior side 4302 and the posterior side 4304. The anterior side 4302 comprises an opening 4308. The posterior side 4304 optionally comprises a refractive surface 4310. In some implementations, the prosthetic device 4300 comprises a ring structure 4320 coupled to a housing structure 4312 comprising the anterior side 4302, posterior side 4304, and sidewalls 4306. In some implementations, the ring structure 4320 comprises a material that is sufficiently strong to maintain the circumference of a natural capsular bag. In some implementations, the ring structure 4320 is configured to be sufficiently flexible to adjust and conform to the natural shape of a natural capsular bag, which can be asymmetrical. In some implementations, the ring structure 4320 is configured to secure the prosthetic device 4300 within the natural capsular bag or other eye region through a friction fit. For example, the ring structure 4320 can comprise polyimide, materials known in intraocular lens manufacturing such as silicone, collamer, PMMA, acrylic, and acrylates, materials used in permanent suture applications such as polypropylene, nylon, polytetrafluoroethylene (PTFE), and polyester, shape memory or thermal memory materials such as nitinol, chromium cobalt, and shape memory polymers, combinations thereof, and the like. In some implementations, the ring structure 4320 comprises hydrophilic and/or hydrophobic materials.

Figure 43B:
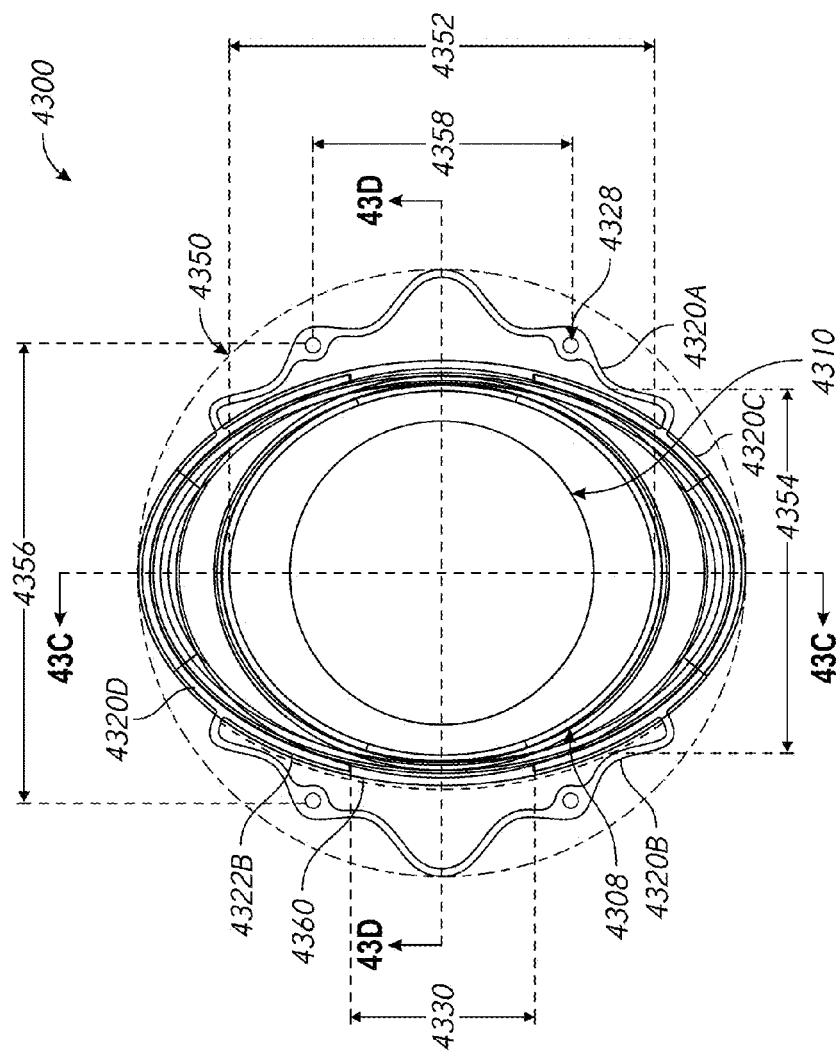
FIG. 43B illustrates an anterior plan view of the example prosthetic capsular device of FIG. 43A.

In some implementations, the ring structure 4320 comprises at least two ring portions 4320A, 4320B. Like the device 2100 in which the ring structure 2106 is embedded across an entire length of a portion of the housing structure 2102, the ring structure 4320 is embedded in at least a portion of the housing structure 4312 by anchors 4320C, 4320D. The anchors 4320C, 4320D comprise a first portion 4322A that extends between the ring portions 4320A, 4320B and a second portion 4322B that extends along side portions of the housing structure 4312. The first portion 4322A and the second portion 4322B may comprise the same or similar properties or at least one property that is different (e.g., material, composition, dimension, cross-sectional shape, combinations thereof, etc.). The anchors 4320C, 4320D and the ring portions 4320A, 4320B may comprise the same or similar properties or at least one property that is different (e.g., material, composition, dimension, cross-sectional shape, combinations thereof, etc.). As discussed as an optional variant of FIG. 22B, the longitudinal anchors 4322B extend partially along a length of the side portions of the housing structure 4312. Referring to FIG. 43B, the distance 4330 the anchor portions 4322B are spaced along the major axis is between about 2 mm and about 4 mm (e.g., about 2 mm, about 2.5 mm, about 3 mm, about 3.5 mm, about 4 mm, ranges between such values, etc.). The longitudinal anchors 4322B could extend along the entire length of the side portions of the housing structure 4312, along the side portions by different amounts, change direction, etc.

The ring structure 4320 comprises an undulating or sinusoidal shape including alternating radially inward troughs 4324 and radially outward peaks or apices 4326. As described with respect to FIGS. 19-22C, a ring structure 4320 having a sinusoidal shape can flex and conform to the shape of the natural capsular bag, which can provide improved positioning within an irregular natural capsular bag shape. In certain implementations, the tip or apex radially outward portions 4327 of the sinusoidal wave are configured to engage the natural capsular bag. As discussed as an optional variant of FIGS. 19-22C, the shape of the sinusoidal ring structure 4320 comprises some apices 4326 having a larger diameter than other apices 4326. In certain implementations, a ring structure having a substantially circular or oval or elliptical configuration may not be able to conform to an irregular and/or asymmetrical shape of a natural capsular bag as well as a ring structure having a sinusoidal shape.

The ring portions 4320A, 4320B comprise holes or apertures or openings or eyelets 4328. The openings 4328 may be used, for example, to suture the device 4300 to an eye. The openings 4328 illustrated in FIGS. 43A and 43B extend all of the way through the ring structure 4320, but could extend only partially through the ring structure 4320. The openings 4328 may assist in suturing the device 4300, allow fibrosis therethrough, etc. The ring structure 4320 may comprise more or fewer openings 4328, openings 4328 at different locations (e.g., at troughs 4324, at other apices 4326), etc. The openings 4328 may be formed, for example, by photo-etching and/or laser milling polyimide.

Figure 43C:
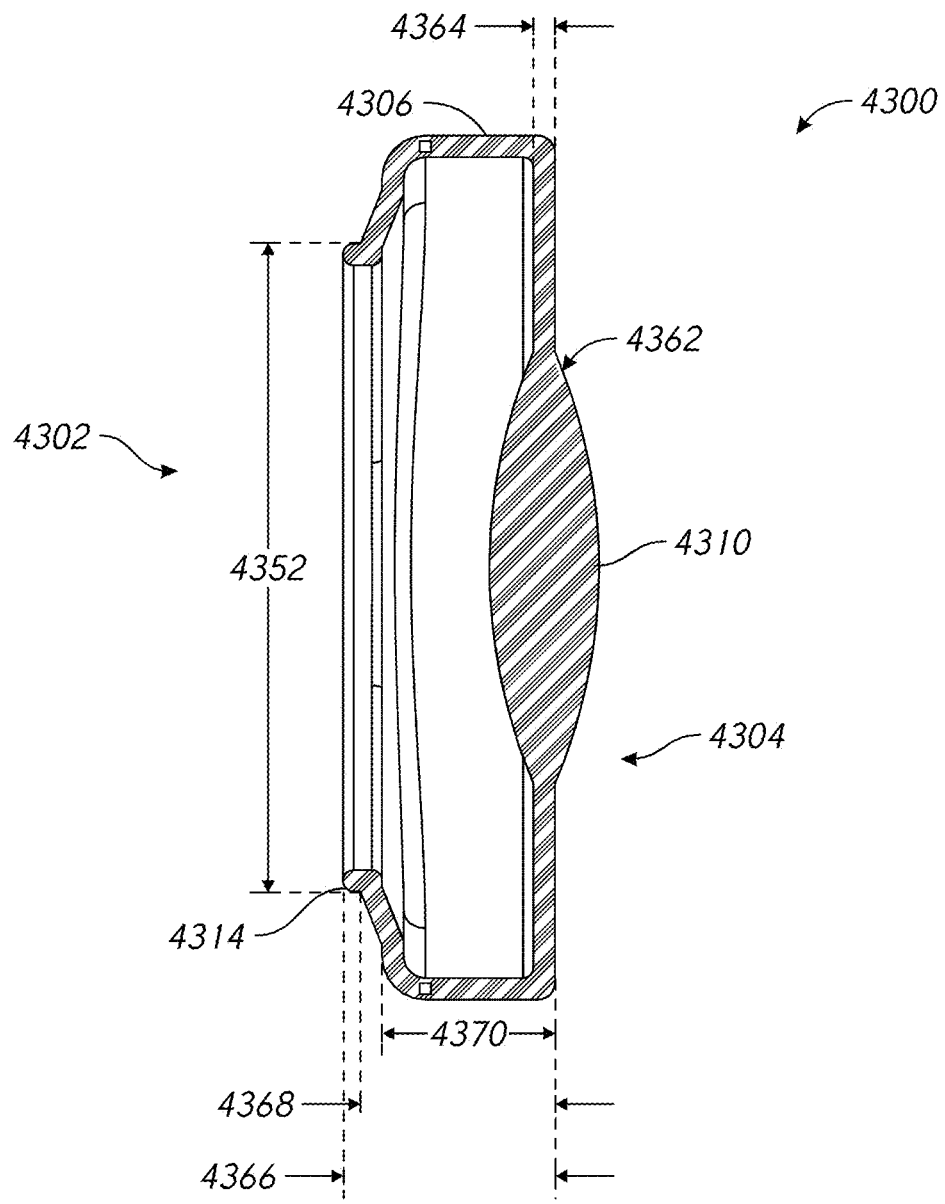
FIG. 43C illustrates a cross-sectional view of the example prosthetic capsular device of FIG. 43A along the line 43C-43C of FIG. 43B.
Figure 43D:
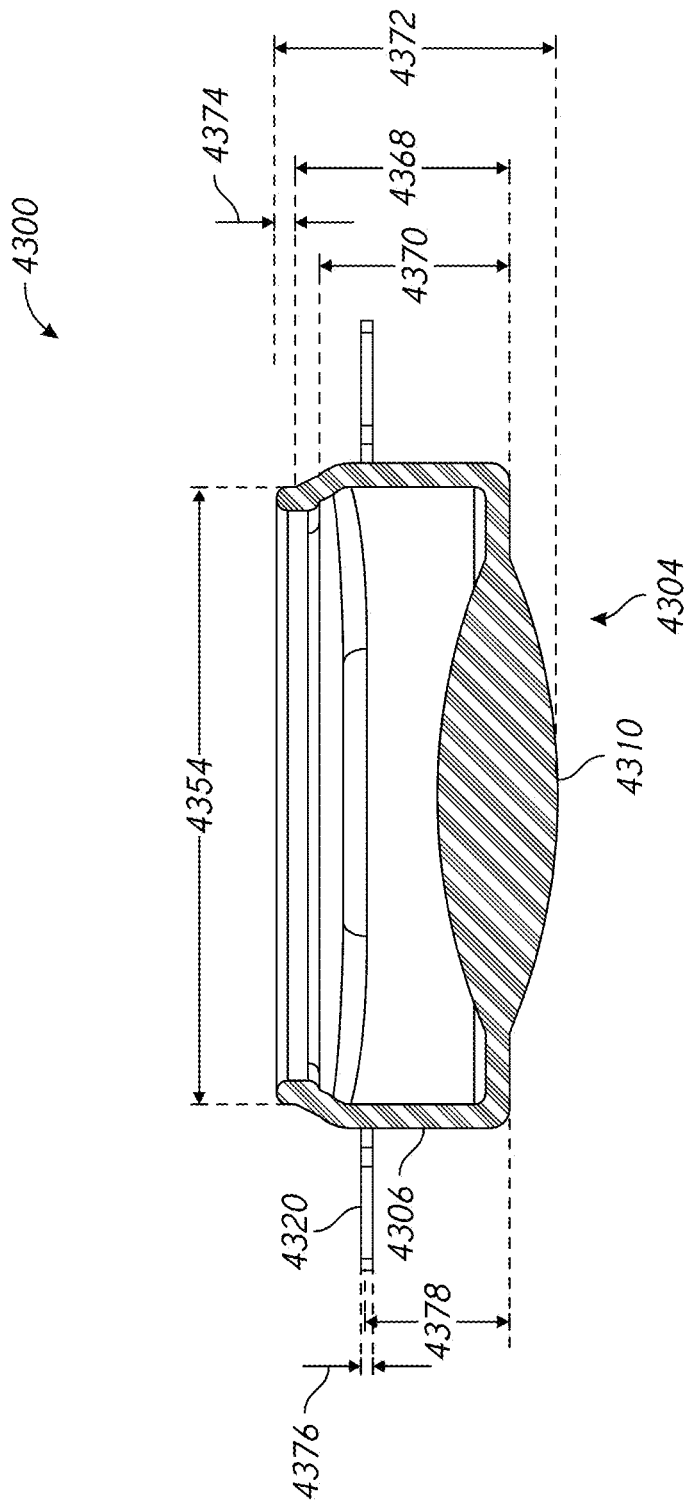
FIG. 43D illustrates a cross-sectional view of the example prosthetic capsular device of FIG. 43A along the line 43D-43D of FIG. 43B.

FIG. 43B illustrates an anterior plan view of the example prosthetic capsular device 4300 of FIG. 43A. The prosthetic capsular device 4300 has a major axis along the line 43C-43C and a minor axis along the line 43D-43D. FIG. 43C illustrates a cross-sectional view of the example prosthetic capsular device 4300 of FIG. 43A along the line 43C-43C of FIG. 43B. FIG. 43D illustrates a cross-sectional view of the example prosthetic capsular device 4300 of FIG. 43A along the line 43D-43D of FIG. 43B.

FIGS. 43B-43D illustrate example dimensions of the device 4300. The outer or under certain circumstances maximum diameter 4350 of the device 4300 may be between about 9 mm and about 11 mm (e.g., about 9 mm, about 9.5 mm, about 10 mm, about 10.5 mm, about 11 mm, ranges between such values, etc.). The length 4352 of the opening 4308 in the anterior side 4302 along the major axis may be between about 7 mm and about 8 mm (e.g., about 7 mm, about 7.5 mm, about 8 mm, ranges between such values, etc.). The length 4354 of the opening 4308 in the anterior side 4302 along the minor axis may be between about 6 mm and about 7 mm (e.g., about 6 mm, about 6.5 mm, about 7 mm, ranges between such values, etc.). The opening 4308 illustrated in FIGS. 43A-43D is oblong, with the length 4352 being greater than the length 4354, but is not as oblong as the housing structure 4312. In some implementations, the opening 4308 may be circular, more oblong, less oblong, and/or include straight portions. The diameter of the refractive surface 4310 of the posterior side 4304 may be between about 4 mm and about 6 mm (e.g., about 4 mm, about 4.5 mm, about 5 mm, about 5.5 mm, about 6 mm, ranges between such values, etc.).

The distance 4356 between the openings 4328 of the ring portion 4320A and the openings 4328 of the ring portion 4320B along the minor axis may be between about 7 mm and about 8 mm (e.g., about 7 mm, about 7.25 mm, about 7.5 mm, about 7.75 mm, about 8 mm, ranges between such values, etc.). The distance 4358 between the openings 4328 of the ring portion 4320A and the openings 4328 of the ring portion 4320B along the major axis may be between about 4 mm and about 5 mm (e.g., about 4 mm, about 4.25 mm, about 4.5 mm, about 4.75 mm, about 5 mm, ranges between such values, etc.). The dimensions described herein can affect position of the device 4300 with respect to the circumference of the scleral wall. For example, if the holes 4328 are used to suture the device 4300 to the scleral wall, the holes 4328 are preferably spaced or far enough away from each other to provide stable anchor points that are preferably symmetrical.

As the device 4300 is folded along the major axis for insertion in an eye, the refractive surface 4310 can stretch along the minor axis. In some implementations, the refractive surface 4310 can stretch at least about 110%, about 120%, about 130%, about 140%, about 150%, about 160%, about 170%, about 180%, about 190%, about 200%, or more. In some implementations, the refractive surface 4310 can stretch between about 110% and about 600% (e.g., about 110%, about 120%, about 130%, about 140%, about 150%, about 160%, about 170%, about 180%, about 190%, about 200%, about 250%, about 300%, about 350%, about 400%, about 450%, about 500%, about 550%, about 600%, ranges between such values, less than about 110% (e.g., between about 0% and about 110%), greater than about 200%, greater than about 300%, greater than about 400%, greater than about 500%, greater than about 600%, etc.). As the devices 4300 is unfolded (e.g., self-expands), the ring structure 4320 can also stretch due to straightening of the undulations. The length of an arc between the attachment points between the ring portions 4320A, 4320B shown by the dotted line 4360 is about 7.7 mm. The length of the outer edge of each ring portion 4320A, 4320B is about 10.46 mm. The ring portions 4320A, 4320B can stretch along the major axis to a length greater than the housing structure arc, reducing the danger that the ring structure 4320 may be pulled out of the housing structure 4312.

The radius of curvature of a refractive portion 4310 having a diameter of 5 mm is between about 6.39 mm for a 30 diopter equi-convex lens. The radius of curvature may be different for larger or smaller diopters, a refractive portion

4310 with a different diameter, a non-equiconvex lens, etc. The thickness of a wall of the posterior side 4304 radially outward of the refractive surface 4310 and the sidewalls 4306 may be between about 0.1 mm and about 0.4 mm (e.g., about 0.1 mm, about 0.15 mm, about 0.2 mm, about 0.25 mm, about 0.3 mm, about 0.35 mm, about 0.4 mm, ranges between such values, etc.). In some implementations, the sidewalls 4306 may be thicker or thinner than the posterior wall. The thickness 4366 of the device 4300 between the anterior side 4302 and the posterior side 4304 may be between about 2 mm and about 3 mm (e.g., about 2 mm, about 2.25 mm, about 2.5 mm, about 2.75 mm, about 3 mm, ranges between such values, etc.). The thicknesses 4368, 4370 between inflection points or design features and the posterior side 4304 may be less than the thickness 4366 because they are closer to the posterior side 4304. For example, the anterior side 4302 may comprise a lip 4314 having a thickness 4374 of about 0.2 mm such that the thickness 4366 may be about 0.2 mm greater than the thickness 4368. Other lip 4314 thicknesses 4374 are also possible, for example being the same as or different than wall and/or sidewall thicknesses. For another example, the anterior side 4302 may comprise a radially inward taper, and the thickness 4370 between the start of the taper (e.g., where the sidewalls 4306 are generally parallel to a longitudinal axis of the device 4300) and the lip 4314 may be about 0.25 mm such that the thickness 4366 may be about 0.45 mm greater than the thickness 4368. The thickness 4372 between the end of the refractive surface 4310 and the anterior side 4304 may be greater than the thickness 4366 because the refractive surface 4310 extends outwardly of the wall of the posterior side 4304. For example, the refractive surface 4310 may protrude about 0.509 mm such that the thickness 4372 may be about 0.509 mm greater than the thickness 4366, and may vary by diopter value, lens type, lens diameter, etc.

The ring structure 4320 may have a thickness 4376 between about 0.1 mm and about 0.15 mm (e.g., about 0.1 mm, about 0.11 mm, about 0.12 mm, about 0.125 mm, about 0.13 mm, about 0.14 mm, about 0.15 mm, ranges between such values, etc.). A distance between the ring structure 4320, for example measured at an approximate midpoint, and the posterior side 4304 may be between about 0.25 mm and about 2.5 mm (e.g., about 0.25 mm, about 0.5 mm, about 0.75 mm, about 1 mm, about 1.25 mm, about 1.5 mm, about 1.75 mm, about 2 mm, about 2.5 mm, ranges between such values, etc.). The longitudinal position of the ring structure 4320 may be more proximate to the anterior side 4302 or the posterior side 4304, for example based on expected interaction with a natural capsular bag.

Figure 43E:
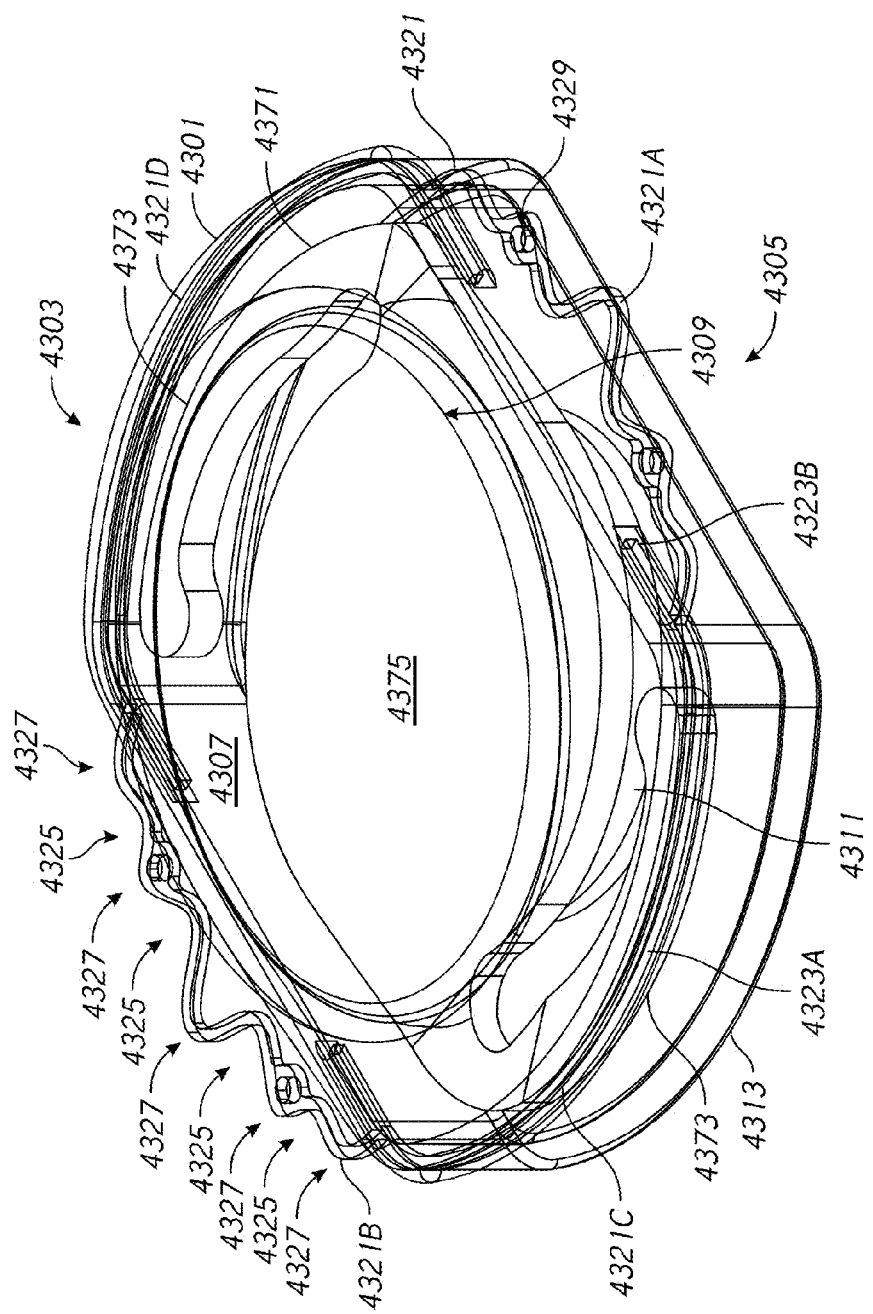
FIG. 43E illustrates an anterior side perspective view of an example of a prosthetic capsular device system.
Figure 43F:
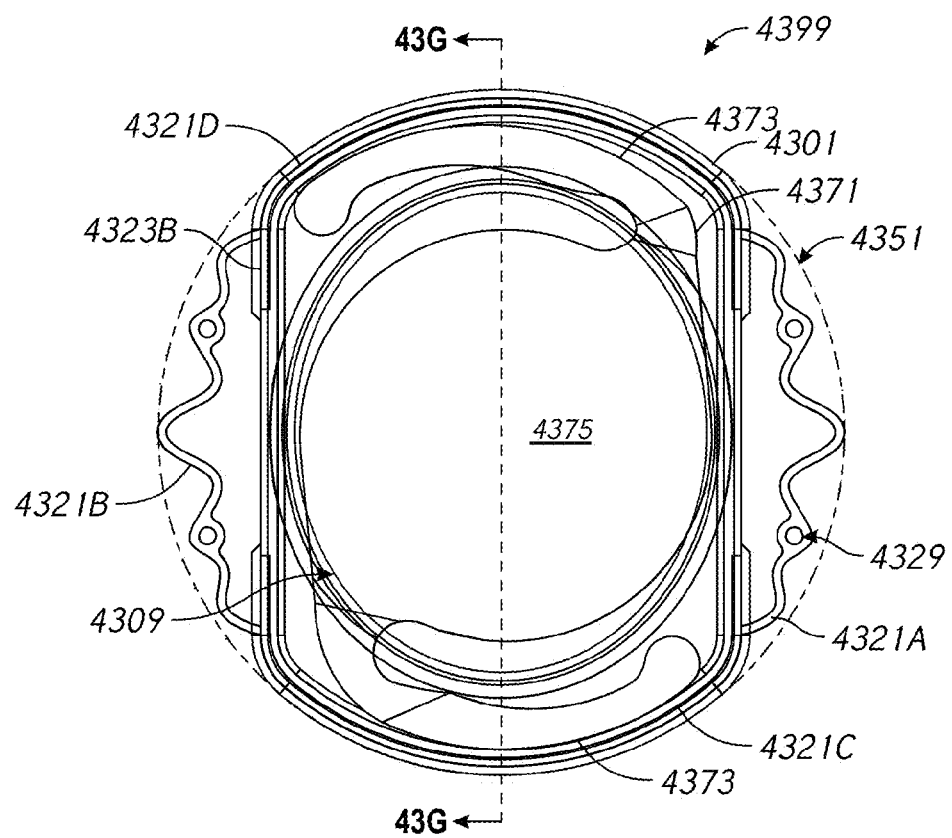
FIG. 43F illustrates an anterior plan view of the example prosthetic capsular device system of FIG. 43E.
Figure 43G:
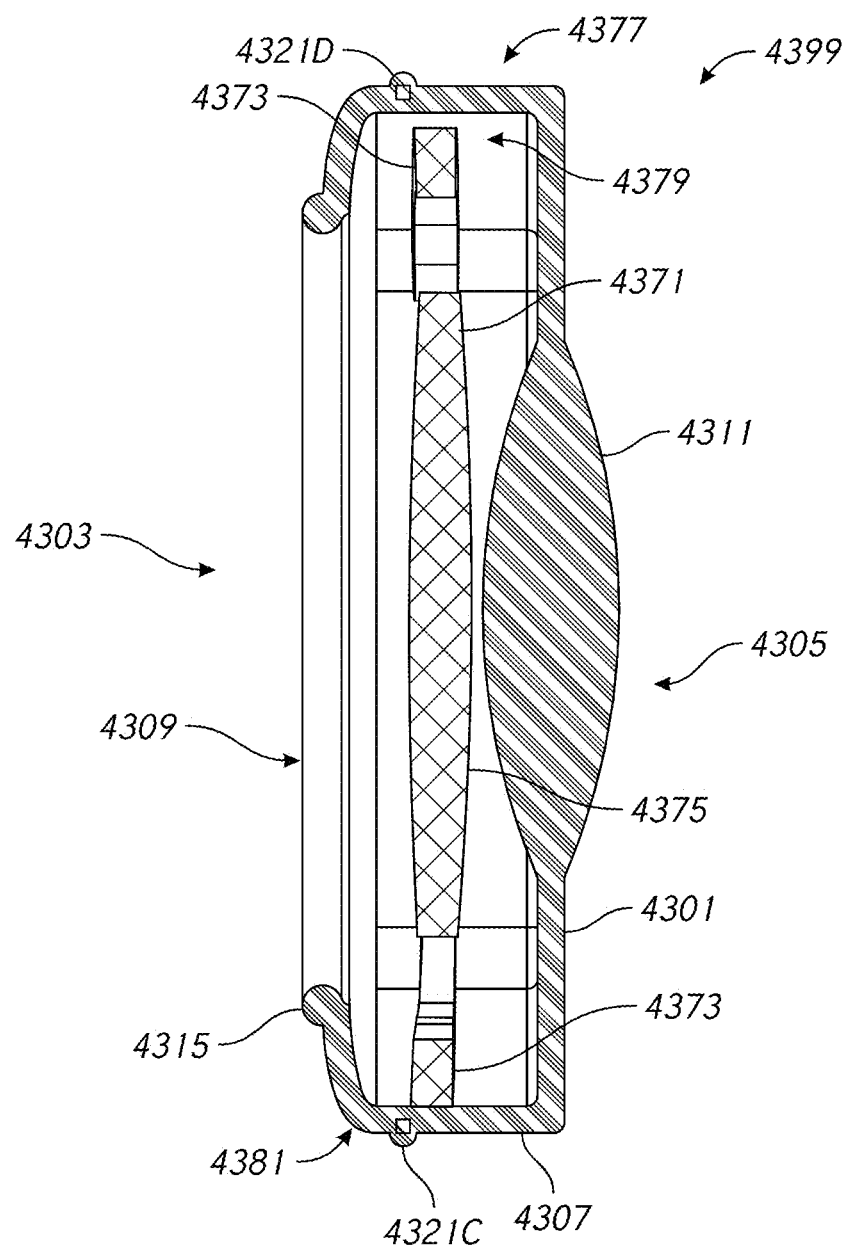
FIG. 43G illustrates a cross-sectional view of the example prosthetic capsular device system of FIG. 43E along the line 43G-43G of FIG. 43F.
Figure 43H:
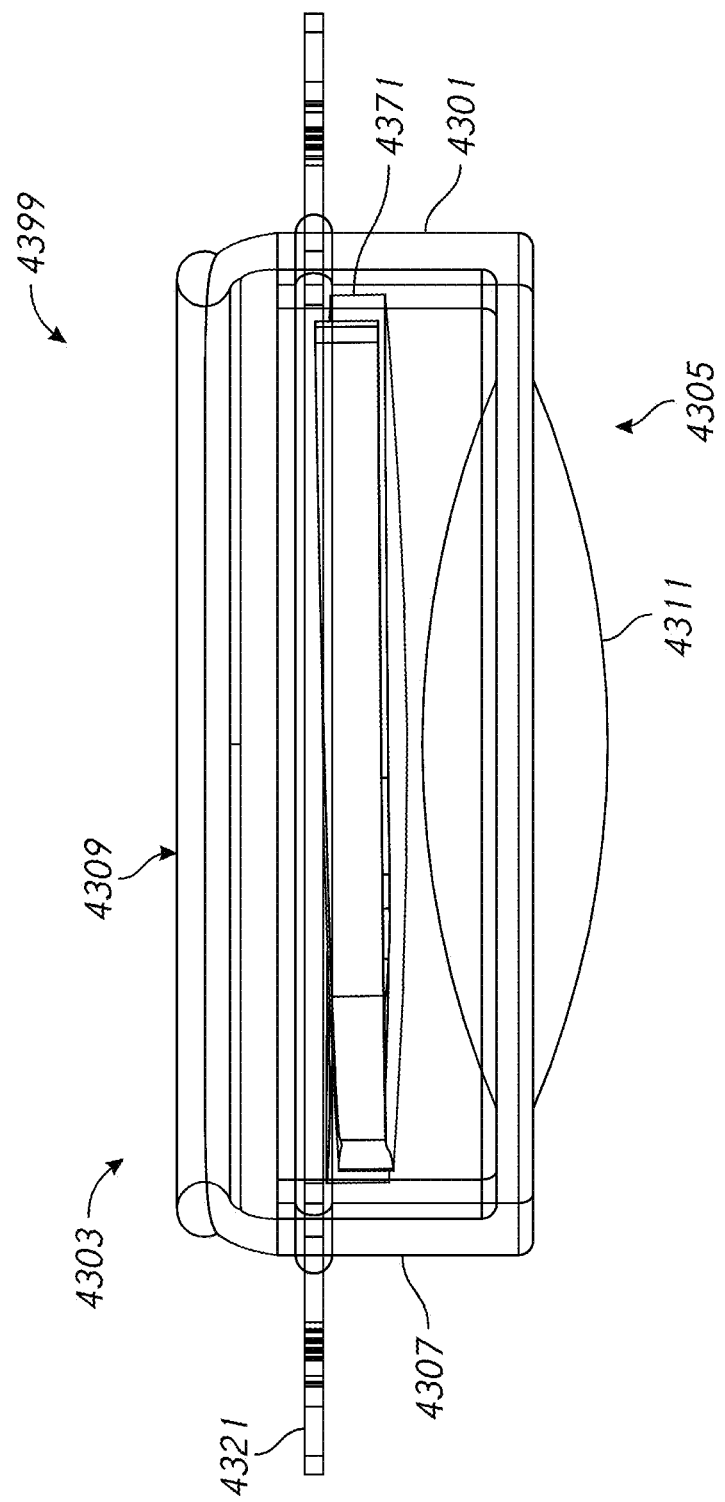
FIG. 43H illustrates a side view of the example prosthetic capsular device system of FIG. 43E.

FIG. 43E illustrates an anterior side perspective view of an example of a prosthetic capsular device system 4399. FIG. 43F illustrates an anterior plan view of the example prosthetic capsular device system 4399 of FIG. 43E. FIG. 43G illustrates a cross-sectional view of the example prosthetic capsular device system 4399 of FIG. 43E along the line 43G-43G of FIG. 43F. FIG. 43H illustrates a side view of the example prosthetic capsular device system 4399 of FIG. 43E. The system 4399 comprises a prosthetic capsular device 4301 and an intraocular lens 4371.

The intraocular lens 4371 comprises haptics 4373 extending radially outward from a refractive portion 4375. The haptics 4373 then turn generally coaxial with the refractive portion 4375 to be radially outward of and spaced from the refractive portion 4375. The system 4399 may comprise other types of intraocular lenses 4371 including, but not limited to: spherical, aspheric, wavefront, convex, concave, multifocal (diffractive, refractive, zonal), toric, accommodative, ultraviolet (UV) filtering, diffractive chromatic aberration reducing lenses, and light adjustable lenses (ultraviolet light adjustable, femtosecond phase wrapping), with optical powers ranging from any positive diopter value (e.g., including +35 D and above) to any negative diopter value (e.g., including −35 D and below), and including any prism power (including 60 Prism Diopters and above). The system 4399 may include a component of an optical system designed to work in conjunction with the refractive lens of the prosthetic capsular device, which can create a polypseudophakic optical system such as a telescope, or provide modification of multiple refractive qualities (e.g. astigmatism, spherical aberration, extended depth of focus, and/or multifocality).

The prosthetic capsular device 4301 has a major axis along the line 43G-43G and a minor axis orthogonal to the line 43G-43G. The device 4301 comprises an anterior side 4303, a posterior side 4305, and sidewalls 4307 extending between the anterior side 4303 and the posterior side 4305. The anterior side 4303 comprises an opening 4309. The posterior side 4305 optionally comprises a refractive surface 4311. In some implementations, the prosthetic device 4301 comprises a ring structure 4321 coupled to a housing structure 4313 comprising the anterior side 4303, posterior side 4305, and sidewalls 4307. The intraocular device 4371 abuts interior surfaces 4379 of the sidewalls 4307. The device 4301 is devoid of or lacks an interior lip.

The sidewalls 4307 have an outer surface 4377 and an inner surface 4379. Like the sidewalls of the devices 400, 1000, 1100, 1150, 1250, 2250, 2300, 2900, 3100, 4300, for example, the sidewalls 4307 include a first straight-walled portion extending anteriorly from the posterior surface 4305 and a second part that tapers radially-inwardly toward the opening 4309 of the anterior surface 4303. The first and second parts may be identified by a transition point 4381, or may be identified based on the properties (e.g., shape, function, etc.) of the parts. The straight-walled portion of the sidewalls 4307 may be parallel or substantially parallel with a longitudinal axis of the device 4301. The straight-walled portion of the sidewalls 4307 may be orthogonal or substantially orthogonal to a flat portion of the posterior surface of the device 4301. The straight-walled portion of the sidewalls 4307 may be orthogonal or substantially orthogonal to the opening 4309. The straight-walled portion of the sidewalls 4307 can increase space in the cavity of the device 4301. The space can be used for intraocular lenses, other optical devices, drug eluting devices, electronic devices, and the like. The device 4301 provides a platform for insertion, and even removal, of various articles into an eye.

In some implementations, a prosthetic capsular device comprising convex or dual-tapered sidewalls (e.g., as in the devices 10, 110, 210, 900) includes an interior lip configured to inhibit or prevent anterior movement of the IOL. In some embodiments, the interior lip is proximate to the posterior end of the device. In some embodiments, the device may be configured to interact with a particular type of IOL, type of haptics, and/or IOL diopter value.

In some implementations, the ring structure 4321 comprises a material that is sufficiently strong to maintain the circumference of a natural capsular bag. In some implementations, the ring structure 4321 is configured to be sufficiently flexible to adjust and conform to the natural shape of a natural capsular bag, which can be asymmetrical. In some implementations, the ring structure 4321 is configured to secure the prosthetic device 4301 within the natural capsular bag or other eye region through a friction fit. For example, the ring structure 4321 can comprise polyimide, materials known in intraocular lens manufacturing such as silicone, collamer, PMMA, acrylic, and acrylates, materials used in permanent suture applications such as polypropylene, nylon, polytetrafluoroethylene (PTFE), and polyester, shape memory or thermal memory materials such as nitinol, chromium cobalt, and shape memory polymers, combinations thereof, and the like. In some implementations, the ring structure 4321 comprises hydrophilic and/or hydrophobic materials.

In some implementations, the ring structure 4321 comprises ring portions 4321A, 4321B. Other numbers of ring portions are also possible, (e.g., one, three, four, etc.). The ring structure 4321 is embedded in at least a portion of the housing structure 4313 by anchors 4321C, 4321D. The anchors 4321C, 4321D comprise a first portion 4323A that extends between the ring portions 4321A, 4321B and a second portion 4323B that extend along side portions of the housing structure 4313. The first portion 4323A and the second portion 4323B may comprise the same or similar properties or at least one property that is different (e.g., material, composition, dimension, cross-sectional shape, combinations thereof, etc.). The anchors 4321C, 4321D and the ring portions 4321A, 4321B may comprise the same or similar properties or at least one property that is different (e.g., material, composition, dimension, cross-sectional shape, combinations thereof, etc.). As discussed as an optional variant of FIG. 22B and as discussed with respect to FIG. 43A, the longitudinal anchors 4323B extend partially along a length of the side portions of the housing structure 4313. The longitudinal anchors 4323B could extend along the entire length of the side portions of the housing structure 4313, along the side portions by different amounts, change direction, etc.

The ring structure 4321 comprises an undulating or sinusoidal shape including alternating radially inward troughs 4325 and radially outward peaks or apices 4327. As described with respect to FIGS. 19-22C and 43A-43D, a ring structure 4321 having a sinusoidal shape can flex and conform to the shape of the natural capsular bag, which can provide improved positioning within an irregular natural capsular bag shape. In certain implementations, the tip or apex radially outward portions 4327 of the sinusoidal wave are configured to engage the natural capsular bag. The shape of the sinusoidal ring structure 4321 comprises some apices 4327 having a larger diameter than other apices 4327. In certain implementations, a ring structure having a substantially circular or oval or elliptical configuration may not be able to conform to an irregular and/or asymmetrical shape of a natural capsular bag as well as a ring structure having a sinusoidal shape.

The ring portions 4321A, 4321B comprise holes or apertures or openings or eyelets 4329. The openings 4329 may be used, for example, to suture the device 4301 to an eye. The openings 4329 illustrated in FIGS. 43E and 43F extend all of the way through the ring structure 4321, but could extend only partially through the ring structure 4321. The openings 4329 may assist in suturing the device 4301, allow fibrosis therethrough, etc. The ring structure 4321 may comprise more or fewer openings 4329, openings 4329 at different locations (e.g., at troughs 4325, at other apices 4327), etc. The openings 4329 may be formed, for example, by photo-etching and/or laser milling polyimide.

Example dimensions of the device 4301, some of which are provided below, may be the same or similar to the example dimensions of the device 4300, modifications thereof, and/or other devices described herein. The outer or under certain circumstances maximum diameter 4351 of the device 4301 may be between about 9 mm and about 11 mm (e.g., about 9 mm, about 9.5 mm, about 10 mm, about 10.5 mm, about 11 mm, ranges between such values, etc.). The length of the opening 4309 in the anterior side 4303 along the major axis may be between about 7 mm and about 8 mm (e.g., about 7 mm, about 7.5 mm, about 8 mm, ranges between such values, etc.). The length of the opening 4309 in the anterior side 4303 along the minor axis may be between about 6 mm and about 7 mm (e.g., about 6 mm, about 6.5 mm, about 7 mm, ranges between such values, etc.). The opening 4309 may be oblong (e.g., longer along the major axis), circular, and/or other shapes. The diameter of the refractive surface 4311 of the posterior side 4305 may be between about 4 mm and about 6 mm (e.g., about 4 mm, about 4.5 mm, about 5 mm, about 5.5 mm, about 6 mm, ranges between such values, etc.).

The distance between the openings of the ring portion 4321A and the openings 4329 of the ring portion 4321B along the minor axis may be between about 7 mm and about 8 mm (e.g., about 7 mm, about 7.25 mm, about 7.5 mm, about 7.75 mm, about 8 mm, ranges between such values, etc.). The distance between the openings 4329 of the ring portion 4321A and the openings 4329 of the ring portion 4321B along the major axis may be between about 4 mm and about 5 mm (e.g., about 4 mm, about 4.25 mm, about 4.5 mm, about 4.75 mm, about 5 mm, ranges between such values, etc.). The dimensions described herein can affect position of the device 4301 with respect to the circumference of the scleral wall. For example, if the holes 4329 are used to suture the device 4301 to the scleral wall, the holes 4329 are preferably spaced or far enough away from each other to provide stable anchor points that are preferably symmetrical.

As the device 4301 is folded along the major axis for insertion in an eye, the refractive surface 4311 can stretch along the minor axis. In some implementations, the refractive surface 4311 can stretch at least about 110%, about 120%, about 130%, about 140%, about 150%, about 160%, about 170%, about 180%, about 190%, about 200%, or more. In some implementations, the refractive surface 4311 can stretch between about 110% and about 600% (e.g., about 110%, about 120%, about 130%, about 140%, about 150%, about 160%, about 170%, about 180%, about 190%, about 200%, about 250%, about 300%, about 350%, about 400%, about 450%, about 500%, about 550%, about 600%, ranges between such values, less than about 110% (e.g., between about 0% and about 110%), greater than about 200%, greater than about 300%, greater than about 400%, greater than about 500%, greater than about 600%, etc.). As the devices 4301 is unfolded (e.g., self-expands), the ring structure 4321 can also stretch due to straightening of the undulations. The ring portions 4321A, 4321B can stretch along the major axis to a length greater than the housing structure arc, reducing the danger that the ring structure 4321 may be pulled out of the housing structure 4313.

The thickness of a wall of the posterior side 4305 radially outward of the refractive surface 4311 and the sidewalls 4307 may be between about 0.1 mm and about 0.4 mm (e.g., about 0.1 mm, about 0.15 mm, about 0.2 mm, about 0.25 mm, about 0.3 mm, about 0.35 mm, about 0.4 mm, ranges between such values, etc.). In some implementations, the sidewalls 4307 may be thicker or thinner than the posterior wall. The thickness of the device 4301 between the anterior side 4303 and the posterior side 4305 may be between about 2 mm and about 3 mm (e.g., about 2 mm, about 2.25 mm, about 2.5 mm, about 2.75 mm, about 3 mm, ranges between such values, etc.).

The ring structure 4321 may have a thickness between about 0.1 mm and about 0.15 mm (e.g., about 0.1 mm, about 0.11 mm, about 0.12 mm, about 0.125 mm, about 0.13 mm, about 0.14 mm, about 0.15 mm, ranges between such values, etc.). A distance between the ring structure 4321, for example measured at an approximate midpoint, and the posterior side 4305 may be between about 0.25 mm and about 2.5 mm (e.g., about 0.25 mm, about 0.5 mm, about 0.75 mm, about 1 mm, about 1.25 mm, about 1.5 mm, about 1.75 mm, about 2 mm, about 2.5 mm, ranges between such values, etc.). The longitudinal position of the ring structure 4321 may be more proximate to the anterior side 4303 or the posterior side 4305, for example based on expected interaction with a natural capsular bag.

Figure 57A:
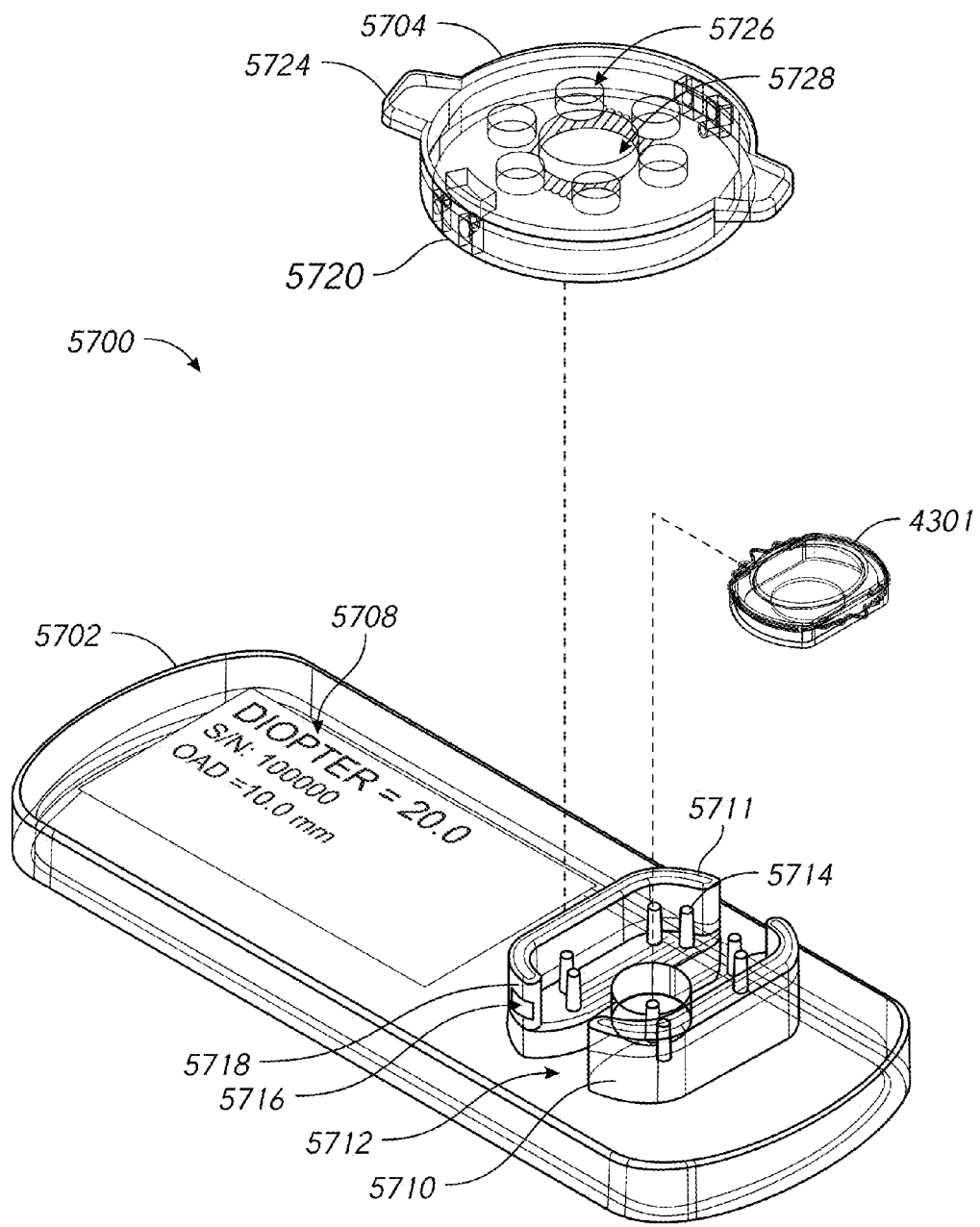
FIG. 57A is an exploded perspective view of an example kit including a prosthetic capsular device.
Figure 57B:
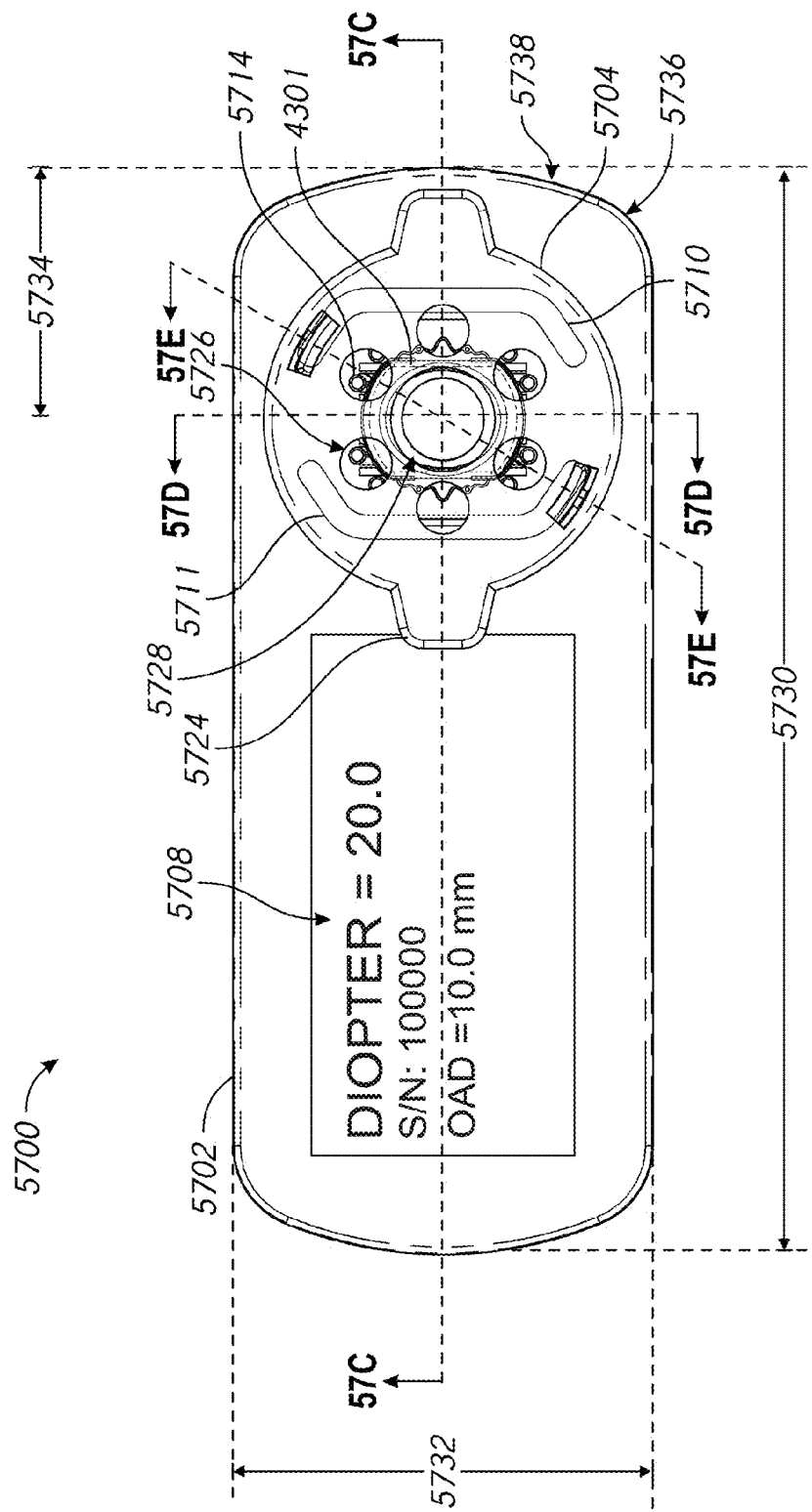
FIG. 57B is a top plan view of the example kit of FIG. 57A.
Figure 57D:
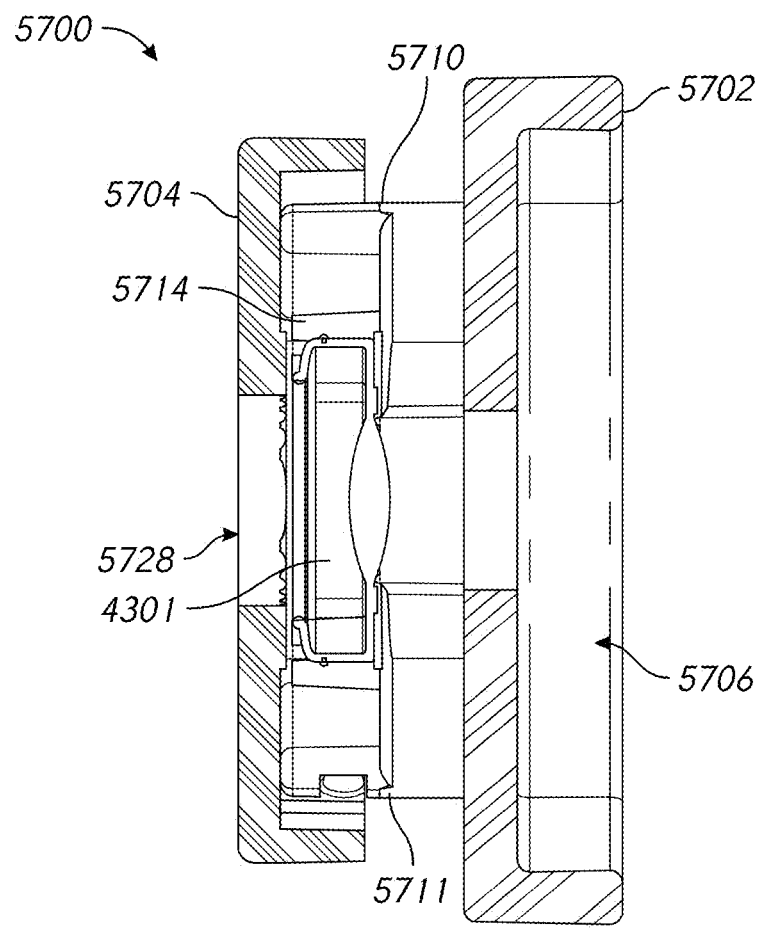
FIG. 57D illustrates a cross-sectional view of the example kit of FIG. 57A along the line 57D-57D of FIG. 57B.
Figure 57E:
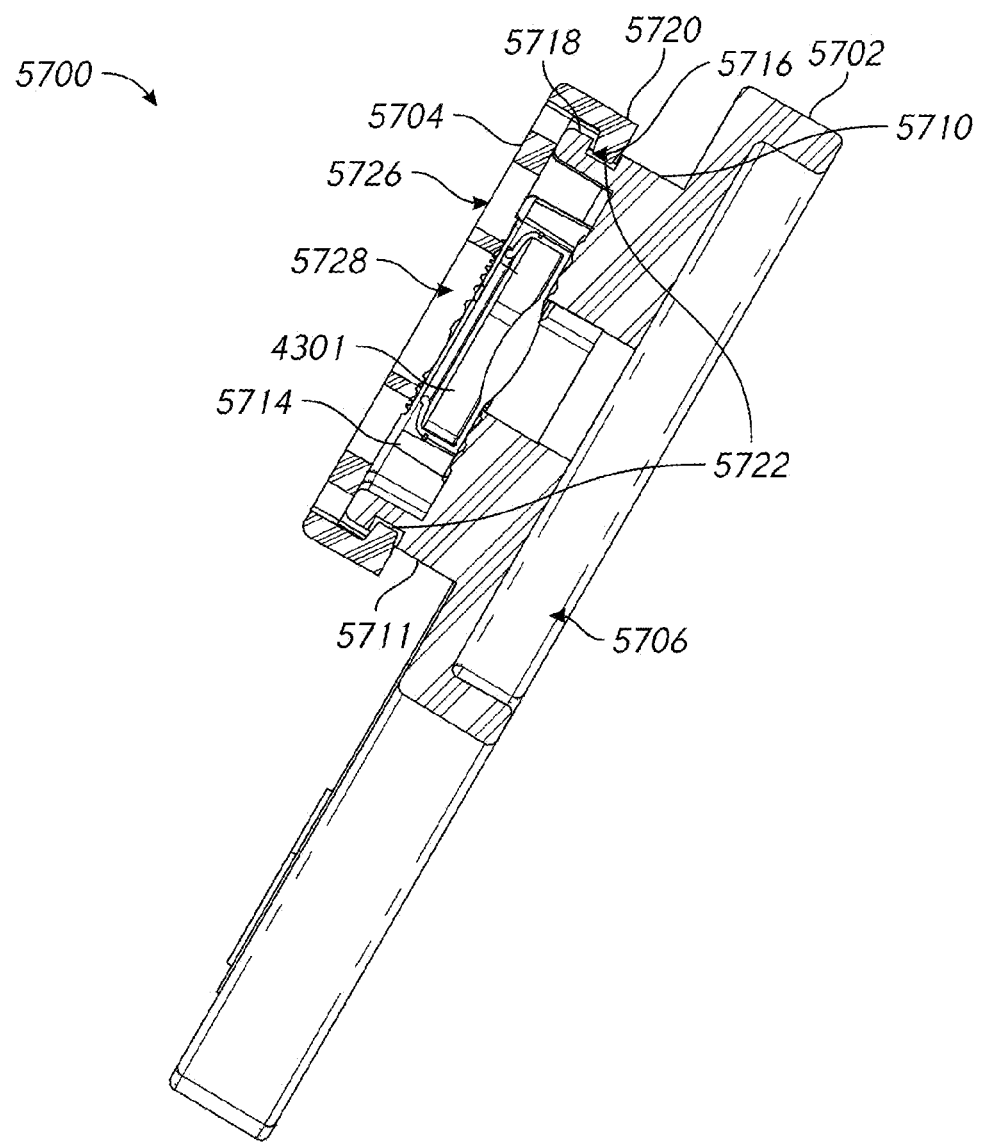
FIG. 57E illustrates a cross-sectional view of the example kit of FIG. 57A along the line 57E-57E of FIG. 57B.

FIG. 57A is an exploded perspective view of an example kit 5700 including a prosthetic capsular device 4301. FIG. 57B is a top plan view of the example kit of FIG. 57A. FIG. 57C illustrates a cross-sectional view of the example kit of FIG. 57A along the line 57C-57C of FIG. 57B. FIG. 57D illustrates a cross-sectional view of the example kit of FIG. 57A along the line 57D-57D of FIG. 57B. FIG. 57E illustrates a cross-sectional view of the example kit of FIG. 57A along the line 57E-57E of FIG. 57B. Although illustrated and described herein with respect to the device 4301, the kit 5700 may comprise any of the devices described herein, other prosthetic devices, intraocular lenses, other types of implants, fluids, instruments, and the like. The kit includes a case 5702 and a lid 5704.

Figure 57F:
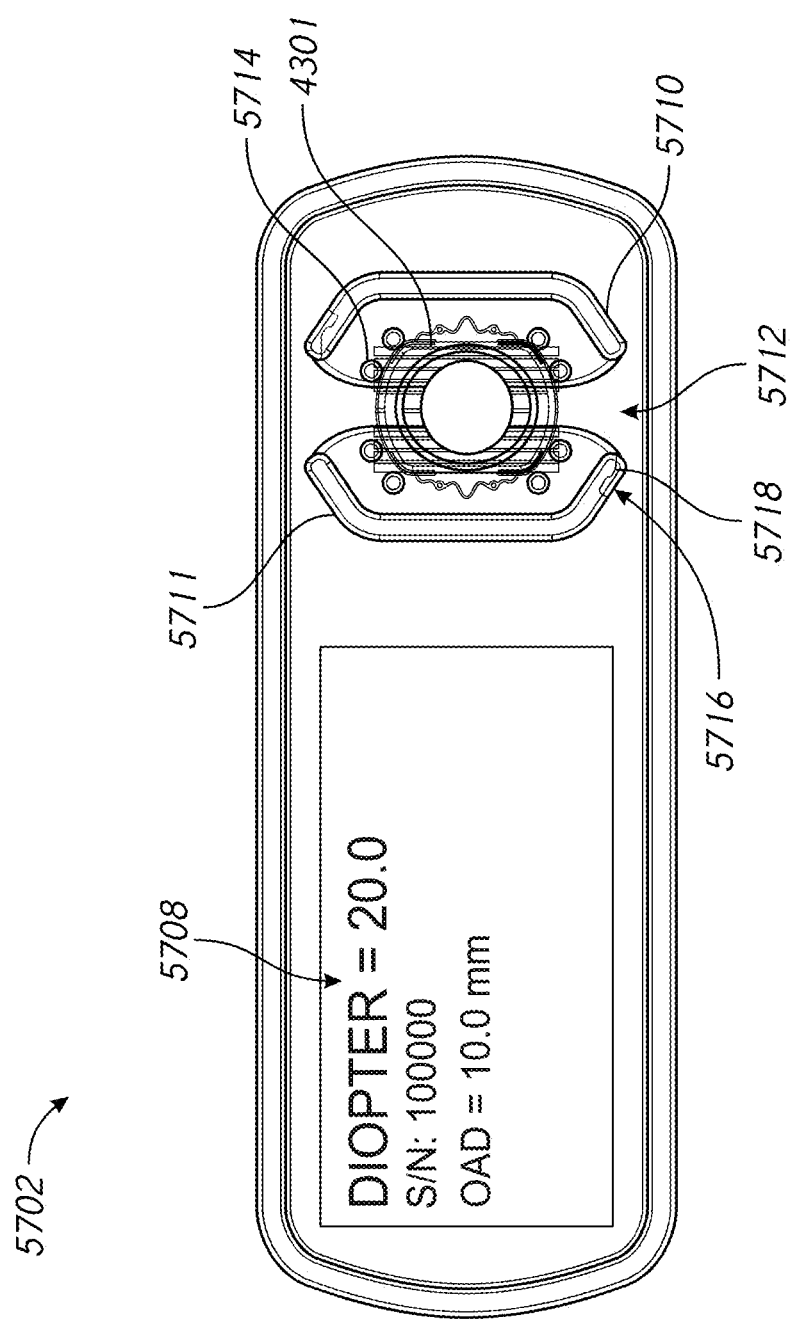
FIG. 57F is a top plan view of a component of the example kit of FIG. 57A.

FIG. 57F is a top plan view of a component, the base 5702, of the example kit 5700 of FIG. 57A holding a device 4301. The case 5702 comprises rounded rectangular shape. In some implementations, the case 5702 comprises a shape corresponding to or reminiscent of the device 4301 (e.g., without the ring structure 4321).

The case 5702 comprises a cavity 5706. The cavity 5706, which can be seen in the cross-sections of FIGS. 57C-57E, can reduce weight, reduce material usage to save costs, provide stacking interlock, provide grip, and/or provide other possible advantages.

An upper surface of the case 5702 identification indicia 5708. The indicia 5708 can include information about the device 4301, such as diopter value, serial number, outer diameter, refractive surface diameter, thickness manufacturer, shape, material, etc.). The indicia 5708 may be grouped together, placed around the device 4301, on different surfaces of the case 5702, on the lid 5704, etc.

The case 5702 comprises a lid engagement structure extending from the upper surface. The lid engagement structure comprises a first part 5710 and a second part 5711. The first part 5710 is spaced from the second part 5711 by a gap 5712. Each of the first part 5710 and the second part 5711 comprises a plurality of frustoconical posts 5714. As best seen in FIG. 57B, the posts 5714 can help to securely hold the device 4301. More or fewer posts or other shapes (e.g., arcs) may be used. The posts may be configured to be interact with the housing 4313 (e.g., as illustrated in FIG. 57B), the ring structure 4321, the openings 4329, and/or other parts of the device 4301 and/or other devices. For example, in the outer diameter of the device 4301 is 10 mm, the inner edges of the posts 5714 may be slightly greater than 10 mm (e.g., about 10.01 mm to about 11 mm).

As best seen in FIG. 57E, each of the first part 5710 and the second part 5711 comprises a C-shaped or (-shaped upwardly projecting wall including a cutout 5716 forming an outwardly projecting lip 5718. The lid 5704 comprises a plurality of teeth 5720 each including an inwardly projecting lip 5722. The lips 5722 are configured to interact with the lips 5718 to secure the lid 5704 to the base 5702 by positioning the lid 5704 with the lips 5722 in the gap 5712 and rotating clockwise until the lips 5722 are under the lips 5718. The teeth 5720 may provide radial flexibility to the lip 5722 and/or identification of the location of the lip 5722. In some implementations, the lid 5704 is devoid of the teeth 5720 but includes the lips 5722. The base 5702 may comprise cutouts 5716 on other segments of the parts 5710, 5711, for example to allow interlocking of the lid 5704 to the base 5702 by turning in a counterclockwise direction.

The lid 5704 comprises a hollow generally round body including a plurality of outwardly projecting tabs 5724. The tabs 5724 may provide a gripping surface. More or fewer tabs 5724 and/or tabs 5724 having a different shape can be used. The tabs 5724 may correspond to a shape on the base 5702, for example to indicate a locked state. In some implementations, the lid 5704 is devoid of tabs 5724. In certain such embodiments, the lid 5704 may comprise a roughened edge surface. In some implementations, the lid 5704 is comprises a shape corresponding to the device 4301, for example an outer edge of the device 4301, with or without the ring structure 4321. In some implementations in which the device comprises tabs, the tabs 5724 of the lid 5704 correspond to the tabs of the device (e.g., indicative of continuousness, bias, openings, etc.).

The lid 5704 comprises a plurality of openings 5726 and a central opening 5728. The openings 5726, 5728 can allow sterilization of the device 4301 (e.g., using ethylene oxide), for example through cavity 5706. The openings 5726 may allow a user to view the shape of the housing 4313, ring structure 4321, and/or other features of the device 4301. The lid 5704 may be partially or totally opaque. The opening 5728 may allow a user to view the refractive surface of the device 4301. For example, each of the base 5702 and the lid 5704 may be open to the refractive surface (e.g., the base 5702 via the cavity 5706 and the lid 5704 via the opening 5728).

FIG. 57B illustrates example dimensions of the kit 5700. The base 5702 may have a length 5730 between about 20 mm and about 100 mm (e.g., about 20 mm, about 40 mm, about 50 mm, about 60 mm, about 66 mm, about 70 mm, about 75 mm, about 100 mm, ranges between such values, etc.). The base 5702 may have a width 5732 between about 20 mm and about 30 mm (e.g., about 20 mm, about 22 mm, about 24 mm, about 25 mm, about 25.4 mm, about 26 mm, about 27 mm, about 30 mm, ranges between such values, etc.). A length 5734 from a minor edge of the base 5702 to a position in the middle of the gap 5712 may be between about 10 mm and about 20 mm (e.g., about 10 mm, about 12 mm, about 14 mm, about 15 mm, about 15.2 mm, about 16 mm, about 20 mm, ranges between such values, etc.). The minor edges of the base 5702 may have a first radius of curvature 5736 and a second radius of curvature 5738. The first radius of curvature 5736 may be between about 2 mm and about 10 mm (e.g., about 2.5 mm, about 3 mm, about 4 mm, about 5 mm, about 5.1 mm, about 6 mm, about 7.5 mm, about 10 mm, ranges between such values, etc.). The first radius of curvature 5736 may be between about 20 mm and about 30 mm (e.g., about 20 mm, about 22 mm, about 24 mm, about 25 mm, about 25.4 mm, about 26 mm, about 27 mm, about 30 mm, ranges between such values, etc.).

FIG. 57C illustrates further example dimensions of the kit 5700. A distance or thickness 5740 between an upper surface of the base 5702 and a top surface of the lid 5704 may be between about 5 mm and about 20 mm (e.g., about 5 mm, about 7.5 mm, about 10 mm, about 11 mm, about 11.6 mm, about 12 mm, about 15 mm, about 20 mm, ranges between such values, etc.). A thickness of the base 5702 from a lower end to the upper surface may be between about 2 mm and about 8 mm (e.g., about 2 mm, about 3 mm, about 4 mm, about 4.8 mm, about 5 mm, about 6 mm, about 7 mm, about 8 mm, ranges between such values, etc.).

Figure 58A:
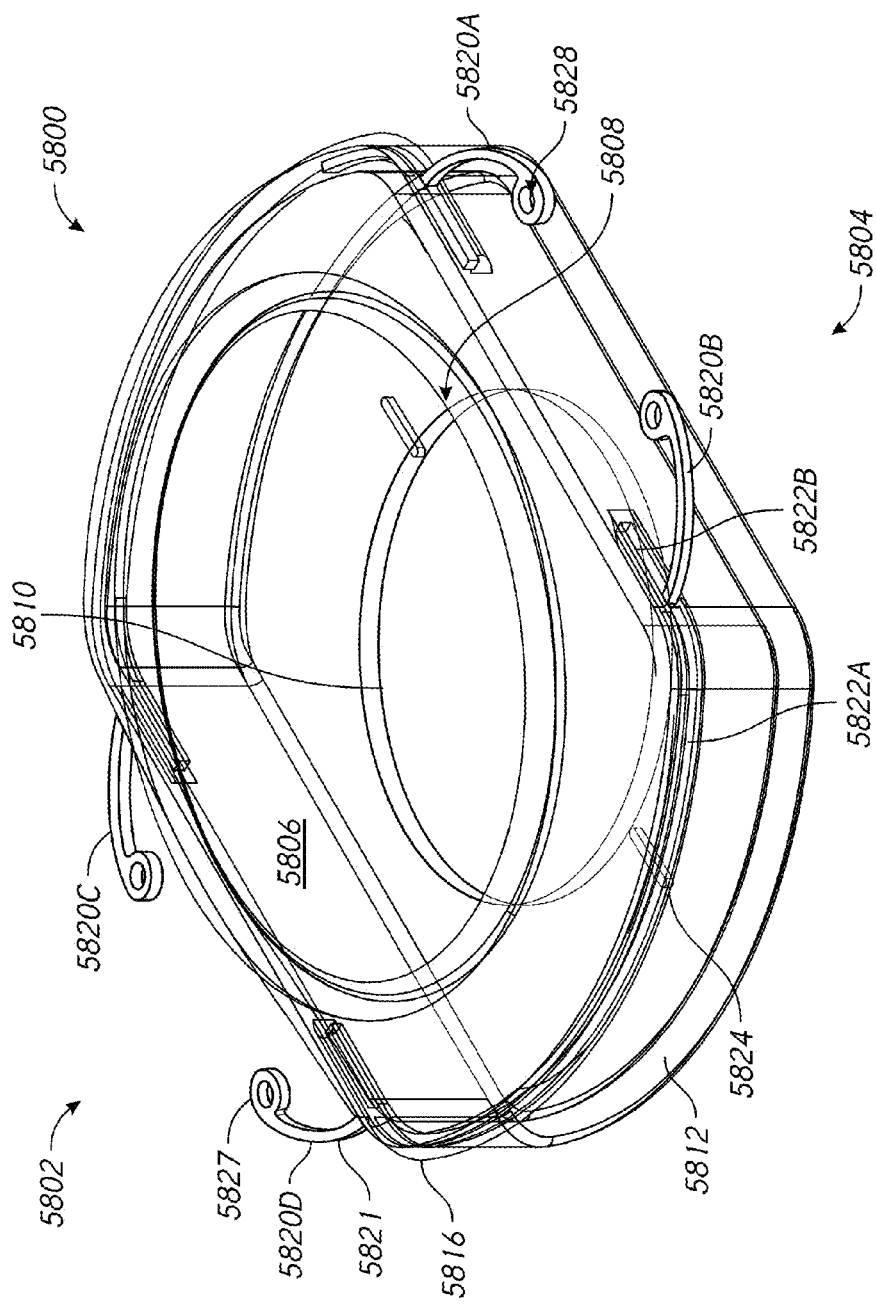
FIG. 58A illustrates an anterior side perspective view of an example of a prosthetic capsular device.

FIG. 58A illustrates an anterior side perspective view of an example of a prosthetic capsular device 5800. The device 5800 comprises an anterior side 5802, a posterior side 5804, and sidewalls 5806 extending between the anterior side 5802 and the posterior side 5804. The anterior side 5802 comprises an opening 5808. The posterior side 5804 optionally comprises a refractive surface 5810. The refractive surface 5810 may have a diameter between about 4 mm and about 9 mm (e.g., about 4 mm, about 5 mm, about 6 mm, about 7 mm, about 8 mm, about 9 mm, ranges between such values, etc.).

In some implementations, the prosthetic device 5800 comprises a ring structure 5820 (e.g., comprising ring structure portions 5820A, 5820B, 5820C, 5820D) coupled to a housing structure 5812 comprising the anterior side 5802, posterior side 5804, and sidewalls 5806. In some implementations, the ring structure 5820 comprises a material that is sufficiently strong to maintain the circumference of a natural capsular bag. In some implementations, the ring structure 5820 is configured to be sufficiently flexible to adjust and conform to the natural shape of a natural capsular bag, which can be asymmetrical. In some implementations, the ring structure 5820 is configured to secure the prosthetic device 5800 within the natural capsular bag or other eye region through a friction fit. For example, the ring structure 5820 can comprise polyimide, materials known in intraocular lens manufacturing such as silicone, collamer, PMMA, acrylic, and acrylates, materials used in permanent suture applications such as polypropylene, nylon, polytetrafluoroethylene (PTFE), and polyester, shape memory or thermal memory materials such as nitinol, chromium cobalt, and shape memory polymers, combinations thereof, and the like. In some implementations, the ring structure 5820 comprises hydrophilic and/or hydrophobic materials. The ring structure 5820 may comprise the same or similar properties or at least one property that is different (e.g., material, composition, dimension, cross-sectional shape, combinations thereof, presence of an aperture, aperture properties, etc.).

In some implementations, the ring structure 5820 comprises four ring portions or haptics 5820A, 5820B, 5820C, 5820D. Other numbers of ring portions are also possible, (e.g., one, two, three, etc.). The ring portions 5820A, 5820B, 5820C, 5820D comprise a radially-outwardly extending arm 5821 and an aperture section 5827. The arm 5821 may have a single radius of curvature, a plurality of radii of curvature, be straight, change direction, have an undulating or sinusoidal shape (e.g., including alternating radially inward troughs and radially outward peaks or apices such as in the devices 4300, 4301), and/or the like. The ring structure 5820, which is not continuous between points on the housing structure 5812, may use less material and impart less volume and/or mass to the device 5800, allowing the device 5800 to be easier to insert into small incisions. Use of less material may reduce costs due to use of less material. The arms 5821 can independently move, which can provide more flexibility than a ring structure that is continuous between points on a housing structure.

In implementations in which a device comprises a stretchable housing structure (e.g., comprising MED-6820 silicone, which is stretchable up to about 200% without damage) and a non-stretchable ring structure (e.g., comprising polyimide) having a ring shape coupled to the housing structure at two ends (e.g., as in the device 4300), stretching forces due to loading or advancing of the device, for example through a delivery syringe or injector cartridge, may break or tear the non-stretchable ring structure. The ring structure 5820 of the device 5800 can inhibit or prevent tearing of the ring structure 5820 and/or the housing structure 5812.

The ring portions 5820A, 5820B, 5820C, 5820D are individually anchored to the housing structure 5812 and are not coupled to the housing structure 5812 at two ends such that stretching forces are independent and generally unidirectional for each ring portion 5820A, 5820B, 5820C, 5820D. Individual anchoring or not being connected to each other can also inhibit or prevent the possibility of crimping the ring structure material as the device is folded and advanced through an injector.

The amount of stretch can increase exponentially from the end portions towards the center of the device 5800. Each of the ring portions 5820A, 5820B, 5820C, 5820D is anchored on a side portion of the device 5800 between the end portions and proximate to the end portions. Anchoring the ring portions 5820A, 5820B, 5820C, 5820D proximate to the end portions reduces the amount of stretch experienced by the ring portions 5820A, 5820B, 5820C, 5820D at their anchor points.

The curvature of the arms 5821 of the ring portions 5820A, 5820B, 5820C, 5820D may be configured to maintain a natural capsular bag in an open position in the area outside the walls of the device 5800. The curvature of the arms 5821 can maintain an effective diameter 5842 that is similar to or the same as other devices described herein having a circular housing structure, having a circular ring structure, etc. The design of the device 5800 reduces the volume of material at the center, for example compared to other devices including housing structure material and/or ring structure material at the center, where the relatively thick or bulky refractive portion 5810 already resides and where stretching forces are the highest. Reducing the volume of structural materials of the device 5800 near the center of the major axis can allow the device 5800 to fit through a small incision size.

The ring portions 5820A, 5820B, 5820C, 5820D comprise aperture sections 5827 comprising holes or apertures or openings or eyelets 5828. The openings 5828 may be used, for example, to suture the device 5800 to an eye. The openings 5828 illustrated in FIGS. 58A, 58B, and 58E extend all of the way through the aperture sections 5827, but could extend only partially through the aperture sections 5827. The openings 5828 may assist in suturing the device 5800, allow fibrosis therethrough, etc. The ring structure 5820 may comprise more or fewer openings 5828, openings 5828 at different locations (e.g., along an arm 5821 between the housing structure 5812 and the aperture section 5827), etc. The openings 5828 may be formed, for example, by photo-etching and/or laser milling polyimide.

Like the device 4300 in which the ring structure 4320 is embedded in at least a portion of the housing structure 4312 by anchors 4320C, 4320D, the ring structure 5820 is embedded in at least a portion of the housing structure 5812 by anchors 5822. In the device 5800, each of the ring portions 5820A, 5820B, 5820C, 5820D comprises an anchor 5822 comprising a first anchor portion 5822A that extends in a first direction (e.g., from the ring portion 5820B towards the ring portion 5820D) and a second portion 5822B that extends in a second direction different than the first direction (e.g., along side portions of the housing structure 5812; from the ring portion 5820B towards the ring portion 5820A). The first anchor portion 5822A and the second anchor portion 5822B may comprise the same or similar properties or at least one property that is different (e.g., material, composition, dimension, cross-sectional shape, combinations thereof, etc.). The anchor portions 5822 may comprise the same or similar properties or at least one property that is different (e.g., material, composition, dimension, cross-sectional shape, combinations thereof, etc.). The anchors 5822 and the radially outward projections or haptics of the ring structure 5820 may comprise the same or similar properties or at least one property that is different (e.g., material, composition, dimension, cross-sectional shape, combinations thereof, etc.). As discussed with respect to the end anchors 2260 of FIG. 22B, the longitudinal anchors 5822A extend partially along a length of the end portions of the housing structure 5812. The longitudinal anchors 5822A could extend along the entire length of the end portions of the housing structure 5812, along the end portions by different amounts, change direction, etc. As discussed as an optional variant of FIG. 22B, the longitudinal anchors 5822B extend partially along a length of the side portions of the housing structure 5812. The longitudinal anchors 5822B could extend along the entire length of the side portions of the housing structure 5812, along the side portions by different amounts, change direction, etc. In some implementations, at least one of the ring portions 5820A, 5820B, 5820C, 5820D may comprise an anchor portion 5822 that is different than at least one other anchor portion 5822.

The device 5800 optionally comprises a bulge 5816 extending radially outward of the sidewalls 5806. The device 5800 shown in FIGS. 58A-58E includes a bulge 5816 on each end portion. The housing structure 5812 may comprise the bulge 5816 (e.g., the bulge 5816 being integral with the housing structure 5812). In some implementations, the ring structure 5820 is placed in a mold and the housing structure 5812 is overmolded around the ring structure 5820. The bulge 5816 may be coupled to the housing structure 5812. The bulge 5816 may comprise the same material as the housing structure 5812 or a different material than the housing structure 5812. The bulge 5816 may allow the anchors 5822 to be substantially radially aligned with the sidewalls 5806. The bulge 5816 may provide extra material in which the ring structure 5820 may anchor, for example maintaining a wall thickness (e.g., about 0.2 mm) on one or both sides of the ring structure 5820 with or without the use of a primer. The bulge 5816 may allow the material of the housing structure 5812 to surround (e.g., completely surround) the anchoring portions 5822 of the ring portion 5820, which can avoid an area of weakness and/or discontinuity of the housing structure 5812. The device 5800 includes bulges 5816 that extend along the entire edge portions of the housing structure 5812, even beyond the termination of the anchor portions 5822A. In some implementations, the device includes bulges 5816 that extend slightly beyond the termination of the anchor portions 5822A.

The device 5800 optionally comprises a posterior fin 5824. The device 5800 shown in FIGS. 58A-58E includes two posterior fins 5824. The posterior fins 5824 are aligned along a diameter of the refractive surface 5810 and in line with the major axis of the prosthetic device 5800. In some implementations, a plurality of posterior fins 5824 (e.g., 2, 3, 4, 5, 6, or more fins 5824) may be circumferentially offset (e.g., by about 180°, by about 120°, by about 90°, by about 72°, by about 60°, and the like). In some implementations, at least some or all of a plurality of posterior fins 5824 (e.g., 2, 3, 4, 5, 6, or more fins 5824) may be unaligned. The posterior fins 5824 are aligned along a major axis of the device 5800. In some implementations, the posterior fins 5824 may be aligned along a minor axis of the device 5800. In some implementations, the posterior fins 5824 may be unaligned along an axis of the device 5800 (e.g., at an angle with respect to the major axis and/or the minor axis). The housing structure 5812 may comprise the posterior fin 5824 (e.g., the posterior fin 5824 being integral with the housing structure 5812). The posterior fin 5824 may be coupled to the housing structure 5812. The posterior fin 5824 may comprise the same material as the housing structure 5812 or a different material than the housing structure 5812. The posterior fin 5824 may help to space a posterior surface of a natural capsular bag from the posterior end 5804 of the housing structure 5812 radially outward of the refractive surface 5810. Spacing the posterior surface of the natural capsular bag from the posterior end 5804 of the housing structure 5812 radially outward of the refractive surface 5810 may allow fluid flow radially outward of the refractive surface 5810, which may help to reduce opacification. Spacing the posterior surface of the natural capsular bag from the posterior end 5804 of the housing structure 5812 radially outward of the refractive surface 5810 may reduce the chance of retaining viscoelastic that has some residual trapped fibrin or inflammatory precipitate contained within it.

In embodiments in which the fins 5824 are aligned with the major axis of the device 5800, the device 5800 can be strategically aligned in an eye. For example, if an eye has astigmatism, a device 5800 in which the refractive surface 5810 comprises a toric lens can be used to at least partially correct the astigmatism if the device 5800 is properly oriented (e.g., with the steep axis of a cornea). In some implementations, at least one of the fins 5824 can be different (e.g., different shape, dimensions, etc.) to indicate a top or bottom of the device 5800. In devices allowing any rotational orientation of an IOL inserted therein, a toric IOL can be rotated. The device 5800 includes truncated sides, reducing volume and in some cases advantageously limiting rotation of an IOL inserted therein. Aligning the device 5800 for alignment of a toric refractive surface 5810 and/or a toric IOL contained in the device 5800 can advantageously provide the advantages of limited IOL rotation, reduced volume, and astigmatism correction.

Figure 58B:
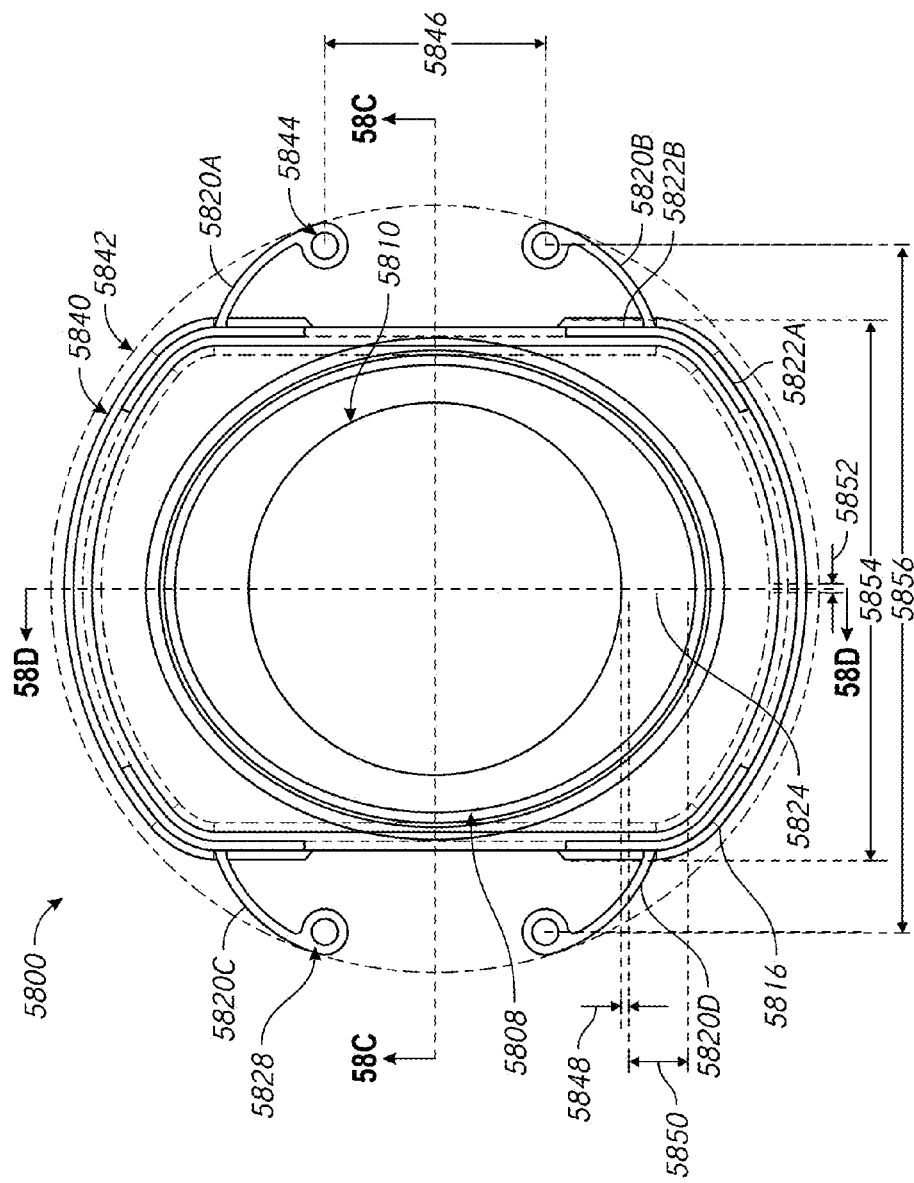
FIG. 58B illustrates an anterior plan view of the example prosthetic capsular device of FIG. 58A.
Figure 58C:
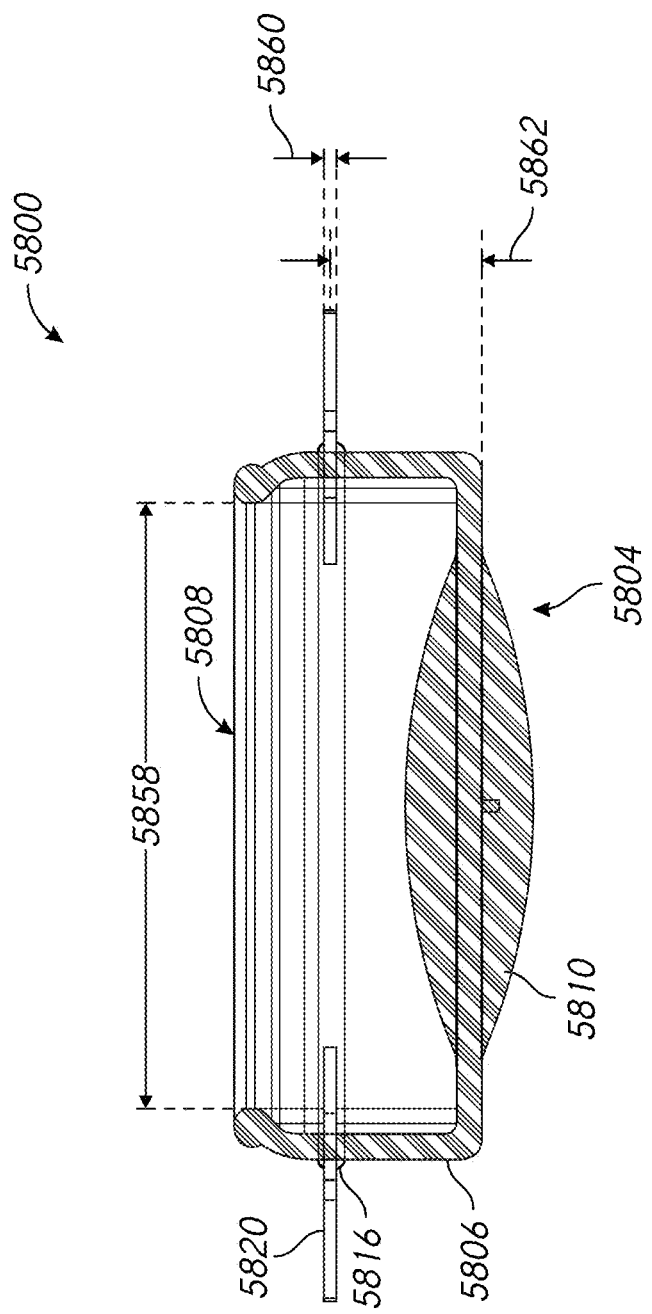
FIG. 58C illustrates a cross-sectional view of the example prosthetic capsular device of FIG. 58A along the line 58C-58C of FIG. 58B.
Figure 58D:
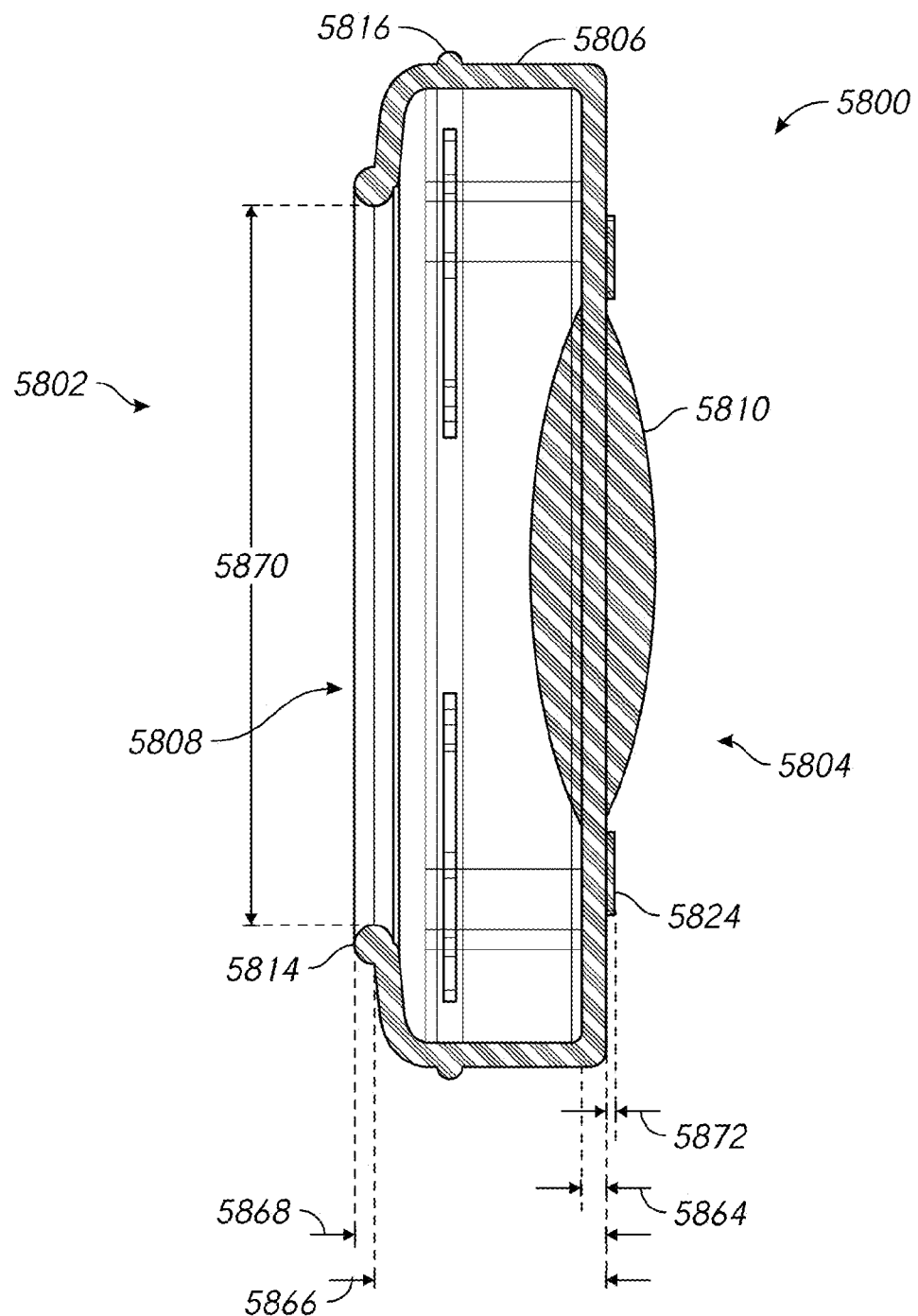
FIG. 58D illustrates a cross-sectional view of the example prosthetic capsular device of FIG. 58A along the line 58D-58D of FIG. 58B.

FIG. 58B illustrates an anterior plan view of the example prosthetic capsular device 5800 of FIG. 58A. The prosthetic capsular device 5800 has a major axis along the line 58C-58C and a minor axis along the line 58D-58D. FIG. 58C illustrates a cross-sectional view of the example prosthetic capsular device 5800 of FIG. 58A along the line 58C-58C of FIG. 58B. FIG. 58D illustrates a cross-sectional view of the example prosthetic capsular device 5800 of FIG. 58A along the line 58D-58D of FIG. 58B. FIGS. 58B-58D illustrate example dimensions of the device 5800.

As seen in FIG. 58A, but perhaps best seen in FIGS. 58C and 58D, the ring structure 5820 extends from the housing structure 5812 at a position anterior to a longitudinal midline of the device 5800, which may inhibit or prevent the anterior capsule and the posterior capsule from fusing. The fins 5824 may also help to spatially separate the anterior capsule and the posterior capsule to inhibit or prevent the anterior capsule and the posterior capsule from fusing.

The outer diameter 5840 of the housing structure 5812, including the bulge 5816, may be between about 9 mm and about 11 mm (e.g., about 9 mm, about 9.5 mm, about 10 mm, about 10.5 mm, about 11 mm, ranges between such values, etc.). The thickness 5854 of the housing structure 5812, including the bulge 5816, along the minor axis may be between about 6 mm and about 8 mm (e.g., about 6 mm, about 6.25 mm, about 6.5 mm, about 6.75 mm, about 7 mm, about 7.25 mm, about 7.5 mm, about 7.75 mm, about 8 mm, ranges between such values, etc.). The outer or under certain circumstances maximum diameter 5842 of the device 5800, for example accounting for extension of the ring structure 5820, may be between about 9 mm and about 12 mm (e.g., about 9 mm, about 9.5 mm, about 10 mm, about 10.3 mm, about 10.5 mm, about 11 mm, about 12 mm, ranges between such values, etc.). In some implementations, a diameter greater than 10 mm may impart outward forces on a natural capsular bag that may tear the bag such that a diameter of about 10 mm or less may be preferred.

The length 5870 of the opening 5808 in the anterior side 5802 along the major axis may be between about 6 mm and about 8 mm (e.g., about 6 mm, about 6.5 mm, about 7 mm, about 7.5 mm, about 8 mm, ranges between such values, etc.). The length 5858 of the opening 5808 in the anterior side 5802 along the minor axis may be between about 5 mm and about 7 mm (e.g., about 5 mm, about 5.5 mm, about 6 mm, about 6.5 mm, about 7 mm, ranges between such values, etc.). The opening 5808 illustrated in FIGS. 58A-58D is oblong, with the length 5870 being greater than the length 5858, but is not as oblong as the housing structure 5812. In some implementations, a ratio of a major axis opening length to a minor axis opening length is between about 1:2 and 2:1 (e.g., 1:2, 2:3, 3:4, 4:5, 5:6, 6:7, 7:8, 8:9, 9:10, 10:9, 9:8, 8:7, 7:6, 6:5, 5:4, 4:3, 3:2, 2:1, ranges between such values, etc.). For example, major axis opening length may be shorter than the minor axis opening length. In some implementations, the opening 5808 may be circular, more oblong, less oblong, and/or include straight portions. A larger opening 5808 may allow more light to pass to the refractive surface 5810 and/or an IOL in the device 5800 such that light is less likely to refract off anterior surfaces and create dysphotopsias.

The distance 5856 between the centers of the openings 5828 of the ring portions 5820 on opposite sides of the major axis may be between about 8 mm and about 10 mm (e.g., about 8 mm, about 8.25 mm, about 8.5 mm, about 8.75 mm, about 9 mm, about 9.25 mm, about 9.5 mm, about 9.75 mm, about 10 mm, ranges between such values, etc.). The distance 5846 between the openings 5828 of the ring portions 5820 on opposite sides of the minor axis may be between about 2 mm and about 4 mm (e.g., about 2 mm, about 2.25 mm, about 2.5 mm, about 2.75 mm, about 3 mm, about 3.25 mm, about 3.5 mm, about 3.75 mm, about 4 mm, ranges between such values, etc.). The diameter 5844 of the openings 5828 may be between about 0.2 mm and about 0.3 mm (e.g., about 0.2 mm, about 0.25 mm, about 0.3 mm, ranges between such values, etc.). The diameters 5844 of the openings 5828 may be the same or different. The dimensions described herein can affect position of the device 5800 with respect to the circumference of the scleral wall. For example, if the holes 5828 are used to suture the device 5800 to the scleral wall, the holes 5828 are preferably spaced or far enough away from each other to provide stable anchor points that are preferably symmetrical.

As the device 5800 is folded along the major axis for insertion in an eye, the refractive surface 5810 can stretch along the minor axis. In some implementations, the refractive surface 5810 can stretch at least about 110%, about 120%, about 130%, about 140%, about 150%, about 160%, about 170%, about 180%, about 190%, about 200%, or more. In some implementations, the refractive surface 5810 can stretch between about 110% and about 600% (e.g., about 110%, about 120%, about 130%, about 140%, about 150%, about 160%, about 170%, about 180%, about 190%, about 200%, about 250%, about 300%, about 350%, about 400%, about 450%, about 500%, about 550%, about 600%, ranges between such values, less than about 110% (e.g., between about 0% and about 110%), greater than about 200%, greater than about 300%, greater than about 400%, greater than about 500%, greater than about 600%, etc.).

The ring structure 5820 may have a thickness 5860 between about 0.1 mm and about 0.15 mm (e.g., about 0.1 mm, about 0.11 mm, about 0.12 mm, about 0.125 mm, about 0.13 mm, about 0.14 mm, about 0.15 mm, ranges between such values, etc.). A distance 5862 between the ring structure 5820, for example measured at an approximate midpoint, and the posterior side 5804 may be between about 0.25 mm and about 2.5 mm (e.g., about 0.25 mm, about 0.5 mm, about 0.75 mm, about 1 mm, about 1.25 mm, about 1.5 mm, about 1.75 mm, about 2 mm, about 2.5 mm, ranges between such values, etc.). The longitudinal position of the ring structure 5820 may be more proximate to the anterior side 5802 or the posterior side 5804, for example based on expected interaction with a natural capsular bag. At least one of the ring portions 5820A, 5820B, 5820C, 5820D may have a different longitudinal position than at least one other of the ring portions 5820A, 5820B, 5820C, 5820D.

The thickness 5864 of a wall of the posterior side 5804 radially outward of the refractive surface 5810 may be between about 0.1 mm and about 0.4 mm (e.g., about 0.1 mm, about 0.15 mm, about 0.2 mm, about 0.25 mm, about 0.3 mm, about 0.35 mm, about 0.4 mm, ranges between such values, etc.). In some implementations, the sidewalls 5806 may be thicker or thinner than the posterior wall. The posterior fin 5824 may protrude from the posterior wall by a distance 5872 between about 0.05 mm and about 0.2 mm (e.g., about 0.05 mm, 0.1 mm, about 0.15 mm, about 0.2 mm, about 0.25 mm, about 0.3 mm, about 0.35 mm, about 0.4 mm, ranges between such values, etc.). The thickness 5866 of the device 5800 between the anterior side 5802 and the posterior side 5804 may be between about 2 mm and about 3 mm (e.g., about 2 mm, about 2.25 mm, about 2.5 mm, about 2.75 mm, about 3 mm, ranges between such values, etc.). The thickness 5868 of the device 5800 between the anterior side 5802 under the lip 5814 and the inside of the posterior wall may be between about 2 mm and about 3 mm (e.g., about 2 mm, about 2.25 mm, about 2.5 mm, about 2.75 mm, about 3 mm, ranges between such values, etc.).

The posterior fin 5824 may be spaced from the refractive surface 5810 by a spacing or distance 5848 between about 0.05 mm and about 0.2 mm (e.g., about 0.05 mm, 0.1 mm, about 0.15 mm, about 0.2 mm, about 0.25 mm, about 0.3 mm, about 0.35 mm, about 0.4 mm, ranges between such values, etc.). The posterior fin 5824 may have a thickness 5850 between about 0.5 mm and about 2 mm (e.g., about 0.5 mm, about 0.6 mm, about 0.7 mm, about 0.8 mm, about 0.9 mm, about 1 mm, about 1.25 mm, about 1.5 mm, about 1.75 mm, about 2 mm, ranges between such values, etc.). The posterior fin 5824 may have a thickness 5852 between about 0.05 mm and about 0.2 mm (e.g., about 0.05 mm, 0.1 mm, about 0.15 mm, about 0.2 mm, about 0.25 mm, about 0.3 mm, about 0.35 mm, about 0.4 mm, ranges between such values, etc.). The spacing 5848, length 5850, thickness 5852, and/or distance 5872 may vary, for example based on the properties of the refractive surface 5810 (e.g., a larger distance 5872 for a larger diopter value).

Figure 58E:
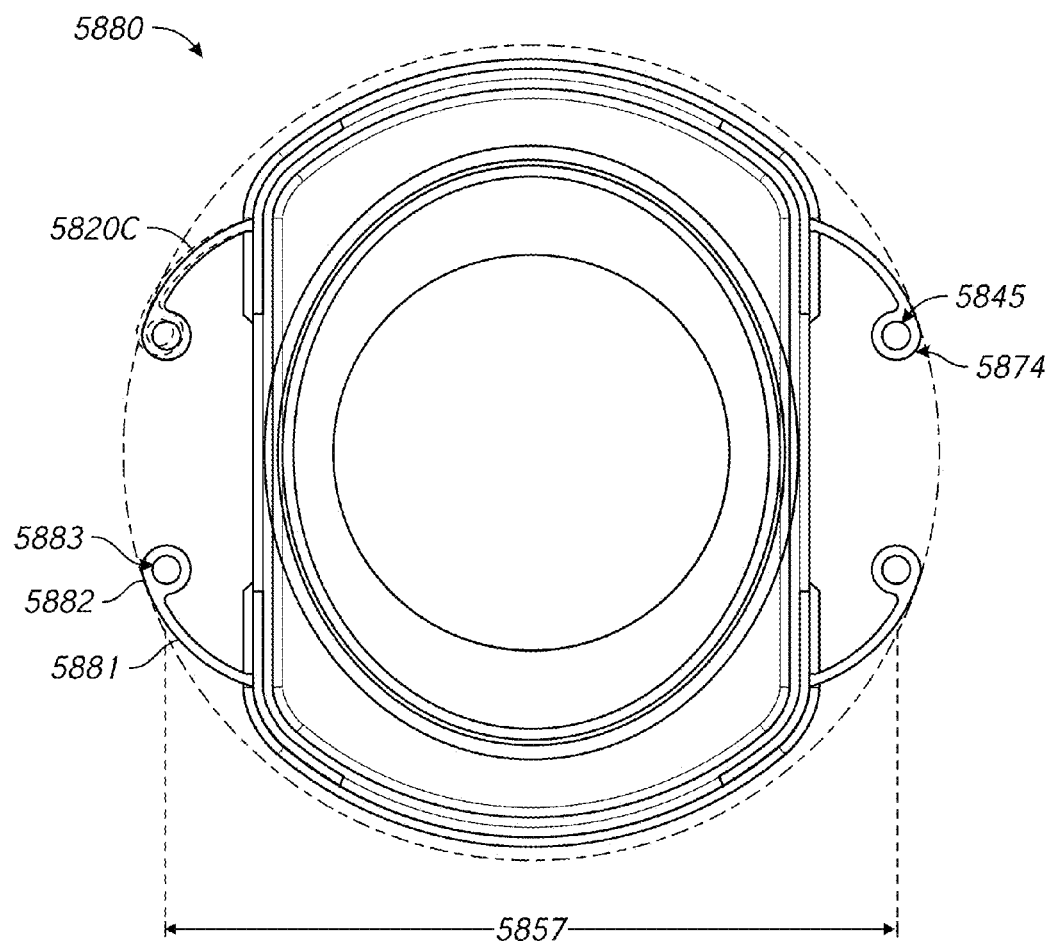
FIG. 58E illustrates an anterior plan view of an example prosthetic capsular device.

FIG. 58E illustrates an anterior plan view of an example prosthetic capsular device 5880. The device 5880 is similar to the device 5800 except for the ring structure 5820. The arms 5881 may be different than the arms 5821, the aperture sections 5882 may be different than the aperture sections 5827, and/or the holes 5883 may be different than the holes 5828. A ring portion 5820C of the device 5800 is shown in phantom for comparison to the ring portions of the device 5880.

The diameter 5845 of the openings 5883 may be between about 0.3 mm and about 0.4 mm (e.g., about 0.3 mm, about 0.35 mm, about 0.4 mm, ranges between such values, etc.). The diameters 5845 of the openings 5883 may be the same or different. The diameter 5845 may be less than the diameter 5844. The diameter difference may be between about 0.05 mm and about 0.2 mm (e.g., about 0.05 mm, 0.1 mm, about 0.15 mm, about 0.2 mm, about 0.25 mm, about 0.3 mm, about 0.35 mm, about 0.4 mm, ranges between such values, etc.). Larger openings 5883 may provide more surface area for fibrosis therethrough. The diameter 5874 of the aperture sections 5882 may be between about 0.4 mm and about 0.8 mm (e.g., about 0.4 mm, 0.5 mm, about 0.6 mm, about 0.7 mm, about 0.8 mm, ranges between such values, etc.). The diameter 5874 may be larger than the diameter of the aperture sections 5827 of the device 5800, for example to accommodate larger openings 5883.

Larger openings 5883 may provide easier suturing and/or be better able to securely hold a suture (e.g., comprising PTFE) for the potential scleral fixation of the device 5800 to the sclera. For example, one pass of a suture may go under the device 5800 and through a first opening 5833 and another pass of the suture may go over top the device 5800, through a second opening 5833 (e.g., the opening on the same side of the major axis), under the device 5800 and through a third opening 5833 (e.g., the opening on the same side of the minor axis as the second opening), and over the top of the device 5800 and through a fourth opening 5833 (e.g., the opening on the same side of the major axis as the third opening), passing through the midvitreous cavity after a vitrectomy. Once the suture(s) has/have been passed, suture slack can be reduced and a 3-1-1 suture placement tie can be performed using a straight tie, a kelman tie, etc. may be used to secure the suture to the sclera. Knots may be tucked into the sclerotomy. The ability to affix the device 5800 to the sclera may be particularly advantageous, for example, for subjects who have had a total loss of capsular support due to surgical trauma, unintended eye trauma, congenital weakness of the zonules, etc.

In embodiments in which the openings 5883 have a diameter of at least about 0.35 mm, the openings 5883 are large enough to allow a surgeon to engage the openings 5883 with a standard IOL positioning tool such as a Lester IOL manipulator, which may include a tip that is angled up to 90° and have a diameter between 0.2 mm and 0.25 mm.

The distance 5857 between the centers of the openings 5883 of the ring portions on opposite sides of the major axis may be between about 8 mm and about 10 mm (e.g., about 8 mm, about 8.25 mm, about 8.5 mm, about 8.75 mm, about 9 mm, about 9.25 mm, about 9.5 mm, about 9.75 mm, about 10 mm, ranges between such values, etc.).

The distance 5857 may be less than the distance 5856, indicative that the centers of the openings 5883 are closer to the housing structure in the device 5880 than the centers of the openings 5828 are to the housing structure 5812 in the device 5800. The aperture sections 5882 may have the same radial extension as the device 5800, but the larger size of the aperture sections 5882 and the openings 5883 may extend radially inward such that the centers of the openings are also radially inward. The distance difference may be between about 0.05 mm and about 0.2 mm (e.g., about 0.05 mm, 0.1 mm, about 0.15 mm, about 0.2 mm, about 0.25 mm, about 0.3 mm, about 0.35 mm, about 0.4 mm, ranges between such values, etc.). The distance between the openings 5883 of the ring portions on opposite sides of the minor axis may be the same as or different than the device 5800.

The dimensions described herein can affect position of the device 5880 with respect to the circumference of the scleral wall. For example, if the holes 5883 are used to suture the device 5880 to the scleral wall, the holes 5883 are preferably spaced or far enough away from each other to provide stable anchor points that are preferably symmetrical.

Figure 58F:
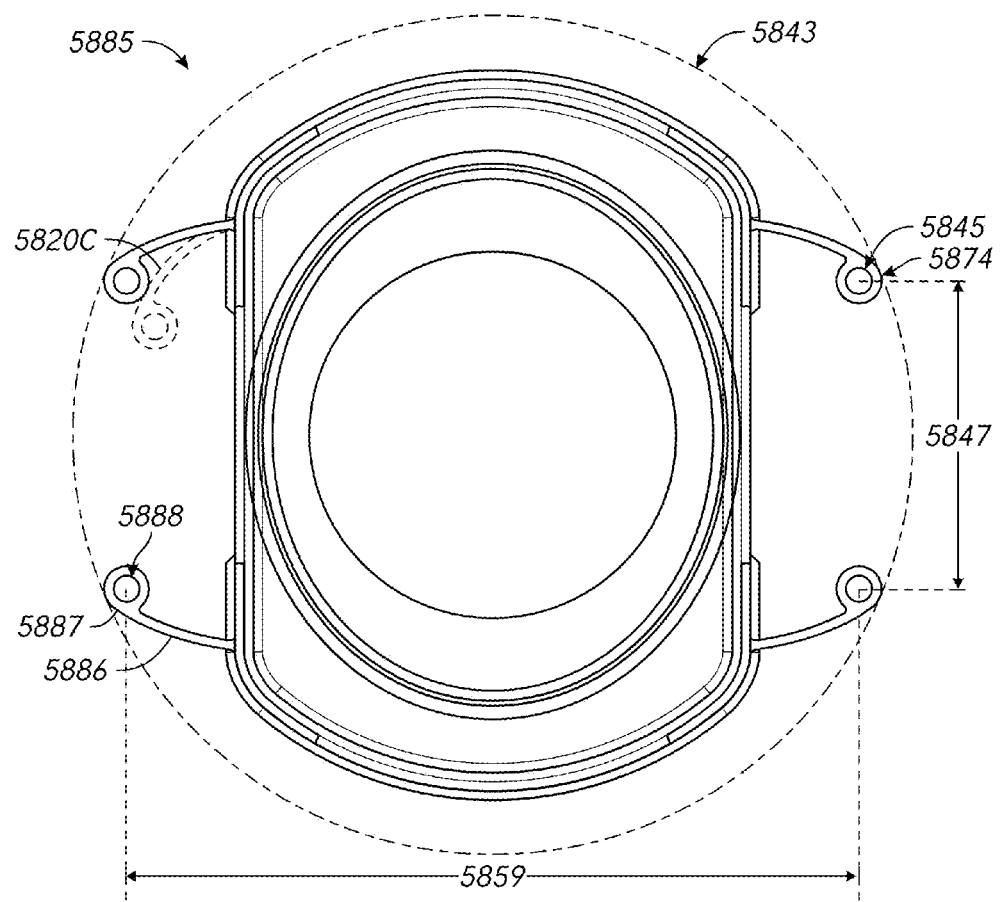
FIG. 58F illustrates an anterior plan view of the example prosthetic capsular device.

FIG. 58F illustrates an anterior plan view of the example prosthetic capsular device 5885. The device 5885 is similar to the devices 5880, 5880 except for the ring structure. The arms 5886 may be different than the arms 5821 and/or the arms 5881, the aperture sections 5887 may be different than the aperture sections 5827 and/or the aperture sections 5882, and/or the holes 5888 may be different than the holes 5828 and/or the holes 5883. A ring portion 5820C of the device 5800 is shown in phantom for comparison to the ring portions of the device 5885.

The outer or under certain circumstances maximum diameter 5843 of the device 5885, for example accounting for extension of the ring structure, may be between about 10 mm and about 13 mm (e.g., about 10 mm, about 10.5 mm, about 11 mm, about 11.5 mm, about 12 mm, about 12.5 mm, about 13 mm, ranges between such values, etc.). The housing structure may have the same dimensions as the housing structure 5812 of the device 5800, indicative that the change in maximum diameter due to extension of the ring structure. The device 5885 can provide a larger maximum diameter, which may better conform to a natural capsular bag (e.g., providing tension on and/or increasing stability in a natural capsular bag having a larger than average diameter), while also maintaining advantages due to the use of less material for the housing structure (e.g., insertion through a smaller incision size).

The diameter 5845 of the openings 5888 may the same as the diameter 5845 of the openings 5883 and/or the diameter 5874 of the aperture sections 5887 may be the same as the diameter 5874 of the aperture sections 5882.

The distance 5847 between the centers of the openings 5888 of the ring portions on opposite sides of the minor axis may be between about 3 mm and about 5 mm (e.g., about 3 mm, about 3.25 mm, about 3.5 mm, about 3.75 mm, about 4 mm, about 4.25 mm, about 4.5 mm, about 4.75 mm, about 5 mm, ranges between such values, etc.). The distance 5859 between the centers of the openings 5888 of the ring portions on opposite sides of the major axis may be between about 9 mm and about 11 mm (e.g., about 9 mm, about 9.25 mm, about 9.5 mm, about 9.75 mm, about 10 mm, about 10.25 mm, about 10.5 mm, about 10.75 mm, about 11 mm, ranges between such values, etc.).

The distance 5847 may be greater than the distance 5846, indicative that the centers of the openings 5888 are farther from each other than the centers of the openings 5828 are from each other. The aperture sections 5887 have further radial extension than in the device 5800, for example due to a different angle and/or curvature of the arms 5886. The distance difference may be between about 0.05 mm and about 0.2 mm (e.g., about 0.05 mm, 0.1 mm, about 0.15 mm, about 0.2 mm, about 0.25 mm, about 0.3 mm, about 0.35 mm, about 0.4 mm, ranges between such values, etc.).

The distance 5859 may be greater than the distance 5856 and/or the distance 5857, indicative that the centers of the openings 5888 are farther from the housing structure in the device 5885 than the centers of the openings 5828 are to the housing structure 5812 in the device 5800 and the centers of the openings 5883 are to the housing structure in the device

5880. The aperture sections 5887 have further radial extension than in the device 5800, for example due to a different angle and/or curvature of the arms 5886. The distance difference may be between about 0.05 mm and about 0.2 mm (e.g., about 0.05 mm, 0.1 mm, about 0.15 mm, about 0.2 mm, about 0.25 mm, about 0.3 mm, about 0.35 mm, about 0.4 mm, ranges between such values, etc.).

The dimensions described herein can affect position of the device 5885 with respect to the circumference of the scleral wall. For example, if the holes 5888 are used to suture the device 5885 to the scleral wall, the holes 5888 are preferably spaced or far enough away from each other to provide stable anchor points that are preferably symmetrical.

Figure 58G:
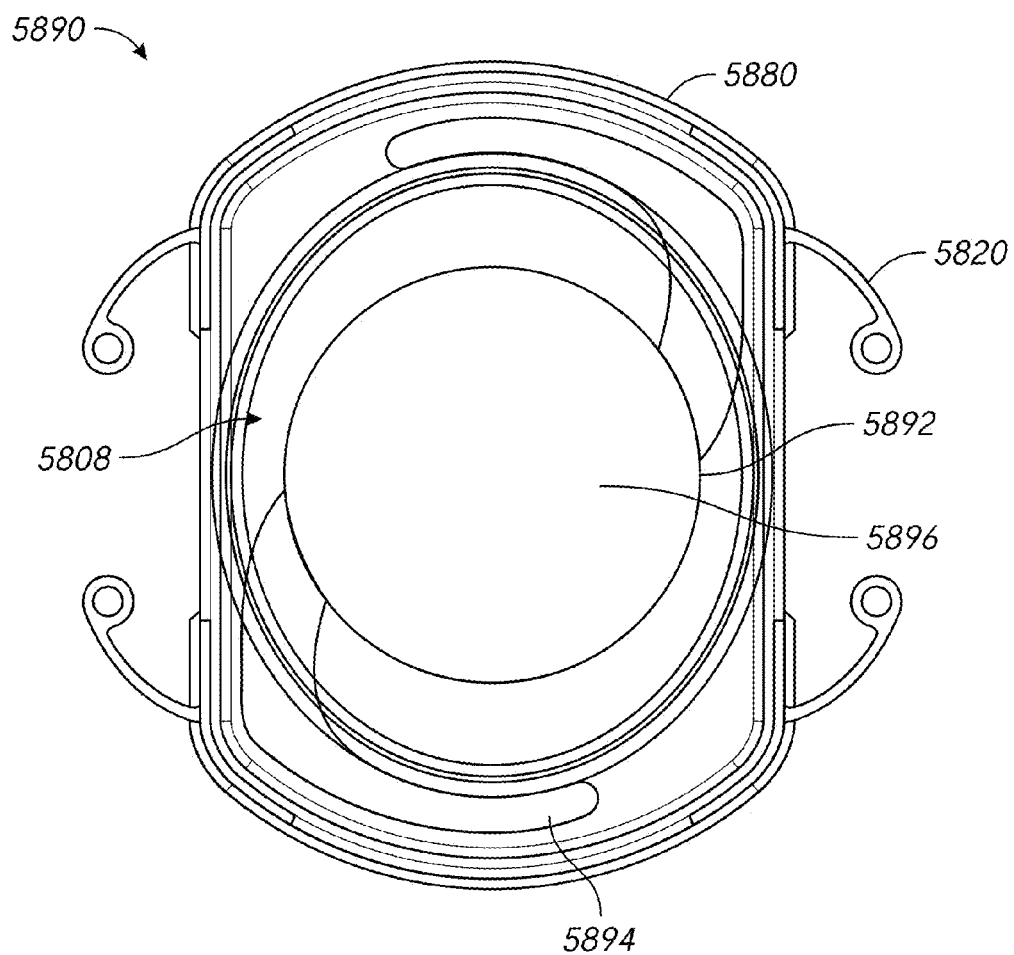
FIG. 58G illustrates an anterior plan view of an example prosthetic capsular device system.

FIG. 58G illustrates an anterior plan view of an example prosthetic capsular device system 5890. The prosthetic capsular device system 5890 comprises the prosthetic capsular device 5880 and an intraocular lens 5892. The intraocular lens 5892 comprises haptics 5894 extending radially outward from a refractive portion 5896. The haptics 5894 then turn generally coaxial with the refractive portion 5896 to be radially outward of and spaced from the refractive portion 5896. The system 5890 may comprise other types of intraocular lenses 5892 including, but not limited to: spherical, aspheric, wavefront, convex, concave, multifocal (diffractive, refractive, zonal), toric, accommodative, ultraviolet (UV) filtering, and diffractive chromatic aberration reducing lenses, and light adjustable lenses (ultraviolet light adjustable, femtosecond phase wrapping) and optical powers ranging from any positive diopter value (e.g., including +35 D and above) to any negative diopter value (e.g., including −35 D and below), and including any prism power (including 60 Prism Diopters and above). The system 5890 may include a component of an optical system designed to work in conjunction with the refractive lens of the prosthetic capsular device, which can create a polypseudophakic optical system such as a telescope, or provide modification of multiple refractive qualities (e.g. astigmatism, spherical aberration, extended depth of focus, and/or multifocality).

All of the prosthetic capsular devices described herein can provide for the creation of a complex refractive system comprising one or a plurality of components. For example, a refractive surface comprising a toric lens may be able to correct sphere or sphere and astigmatism and/or create multifocal vision. The prosthetic capsular device can include other optical components instead of or in addition to a spherical and/or toric lens. A plurality of components can fine tune the vision to levels previously impossible. For example, the refractive surface of the prosthetic capsular device can correct sphere; then, astigmatism, spherical aberration, multifocality, and/or chromatic aberrations could be further corrected with the addition of lenses stacked on top of the refractive surface. If the optic contains a light adjustable material, the optical power can be changed through the external light application. A plurality of other lenses inside the prosthetic capsular device can create complex optical systems. For another example, a telescope can be created to allow magnification of images in subjects with severe retinal pathologies such as macular degeneration. In some implementations, a telescope implant, such as available from VisionCare Ophthalmic Technologies of Saratoga, Calif., a dual-lens system that creates magnification through telescopic principles, etc., can be contained in the prosthetic capsular device. For example, the prosthetic capsular device could comprise a strongly negative lens and a strongly positive lens could be placed in the ciliary sulcus or in the prosthetic capsular device. If the subject cannot adapt to or tolerate the change, the assembly is totally reversible. The device allows removal of components such as IOLs, additional components, telescope implants, etc. and provides a barrier to vitreous, even after a Nd:YAG laser posterior capsulotomy. The "plug-and-play" abilities provided by the prosthetic capsular device can allow the creation of different vision tuning at different times, for example based on physiological changes and technological updates. The prosthetic capsular device can comprise a prism (e.g., the refractive surface can comprise a prism), which may shift images away from a damaged retina (e.g., in ARMD or other maculopathy patients). In subjects having eyes that are misaligned, a prism could help resolve double vision.

Like the sidewalls of the devices 400, 1000, 1100, 1150, 1250, 2250, 2300, 2900, 3100, 4300, 4301, for example, the sidewalls 5806 of the devices 5800, 5880, 5885 include a first straight-walled portion extending anteriorly from the posterior surface 5804 and a second part that tapers radially-inwardly toward the opening 5808 of the anterior surface 5802. The first and second parts may be identified by a transition point, or may be identified based on the properties (e.g., shape, function, etc.) of the parts. The straight-walled portion of the sidewalls 5806 may be parallel or substantially parallel with a longitudinal axis of the device 5800. The straight-walled portion of the sidewalls 5806 may be orthogonal or substantially orthogonal to a flat portion of the posterior surface (e.g., radially outward of the refractive portion 5810). The straight-walled portion of the sidewalls 5806 may be orthogonal or substantially orthogonal to the opening 5808. The straight-walled portion of the sidewalls 5806 can increase space in the cavity of the device 5800. The space can be used for intraocular lenses, other optical devices, drug eluting devices, electronic devices, and the like. The device 5800, like other devices described herein, provides a platform for insertion, and even removal, of various articles into an eye, and increased cavity space opens that platform to more articles.

Figure 58H:
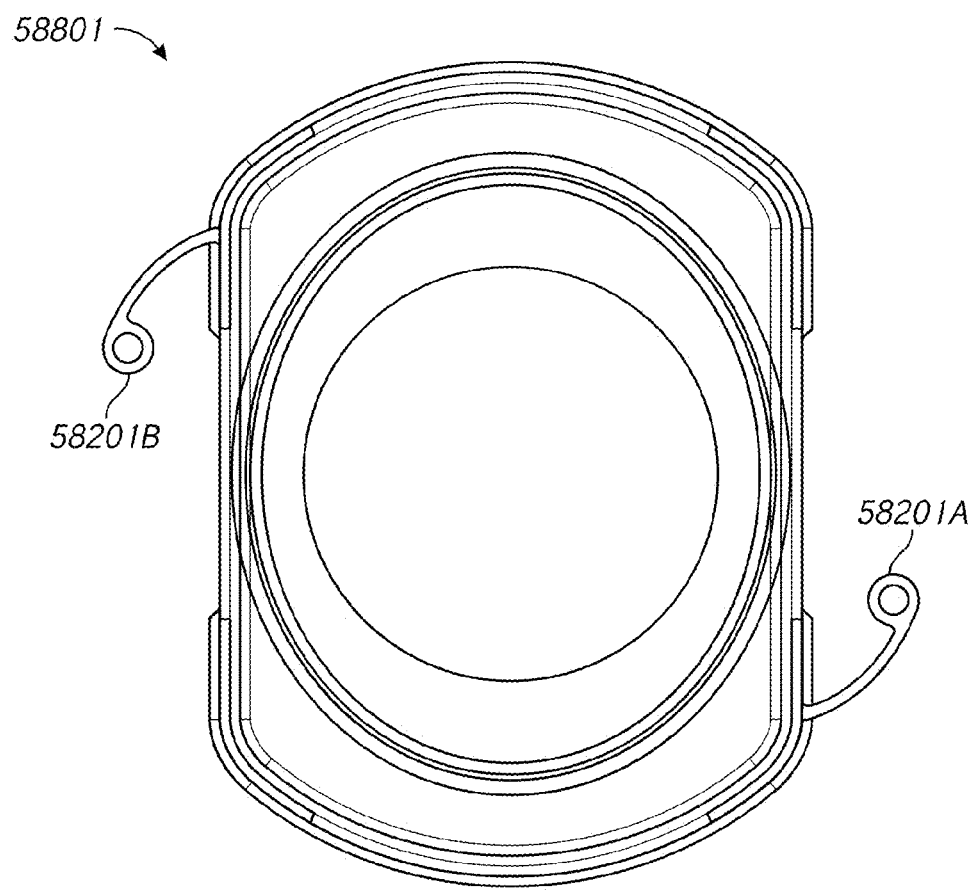
FIGS. 58H-58L illustrate anterior plan views of example prosthetic capsular devices.
Figure 58I:
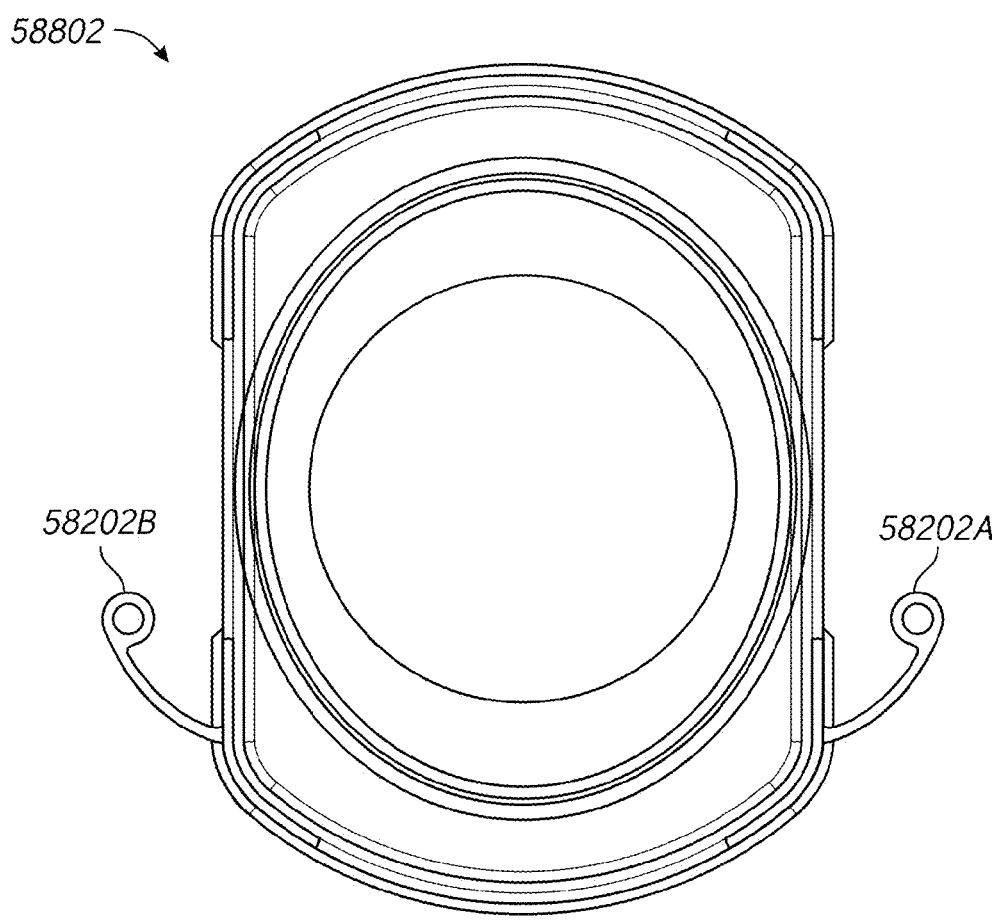
Figure 58J:
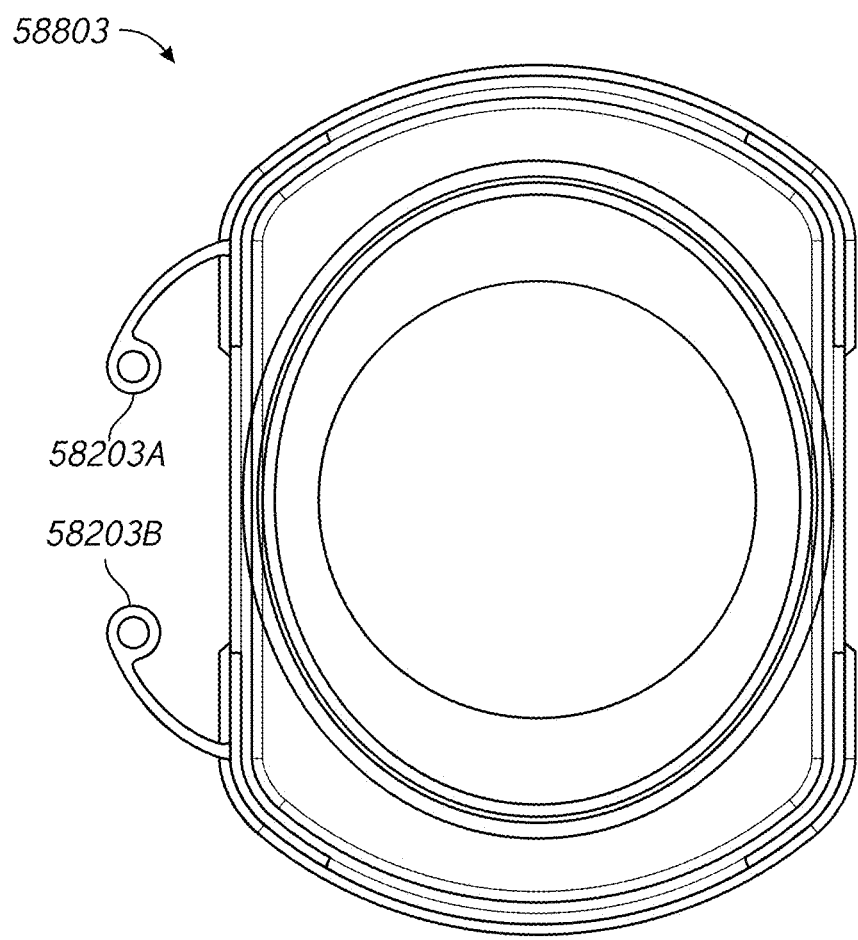
Figure 58K:
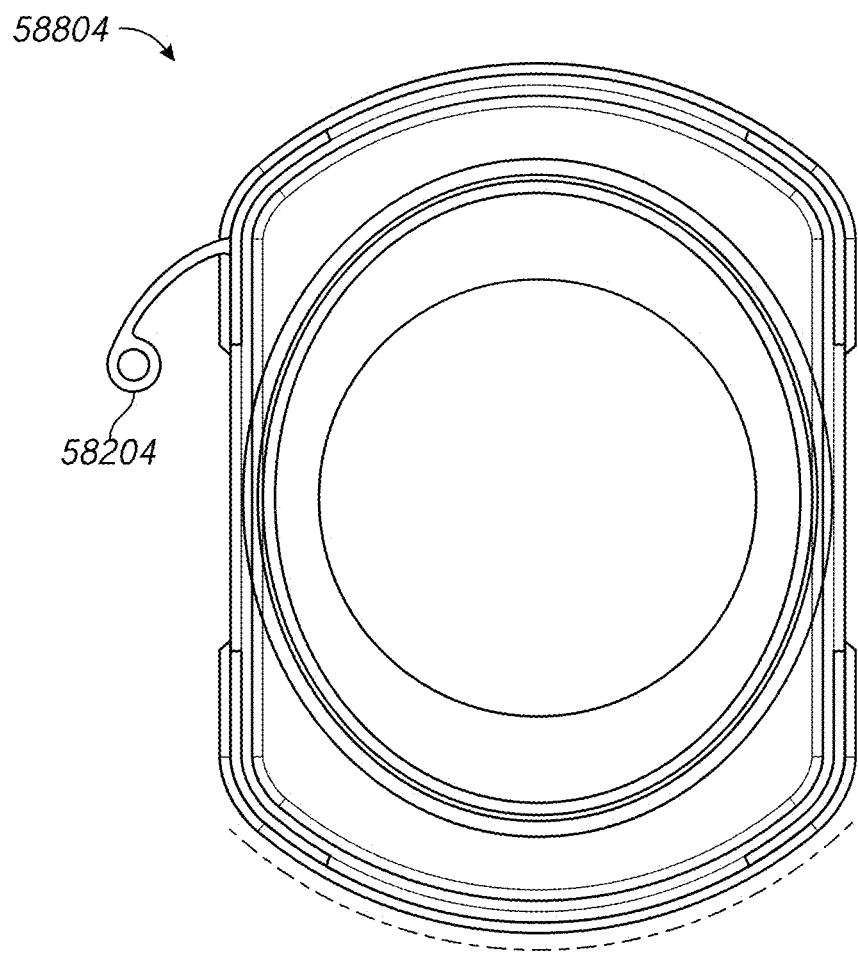
Figure 58L:
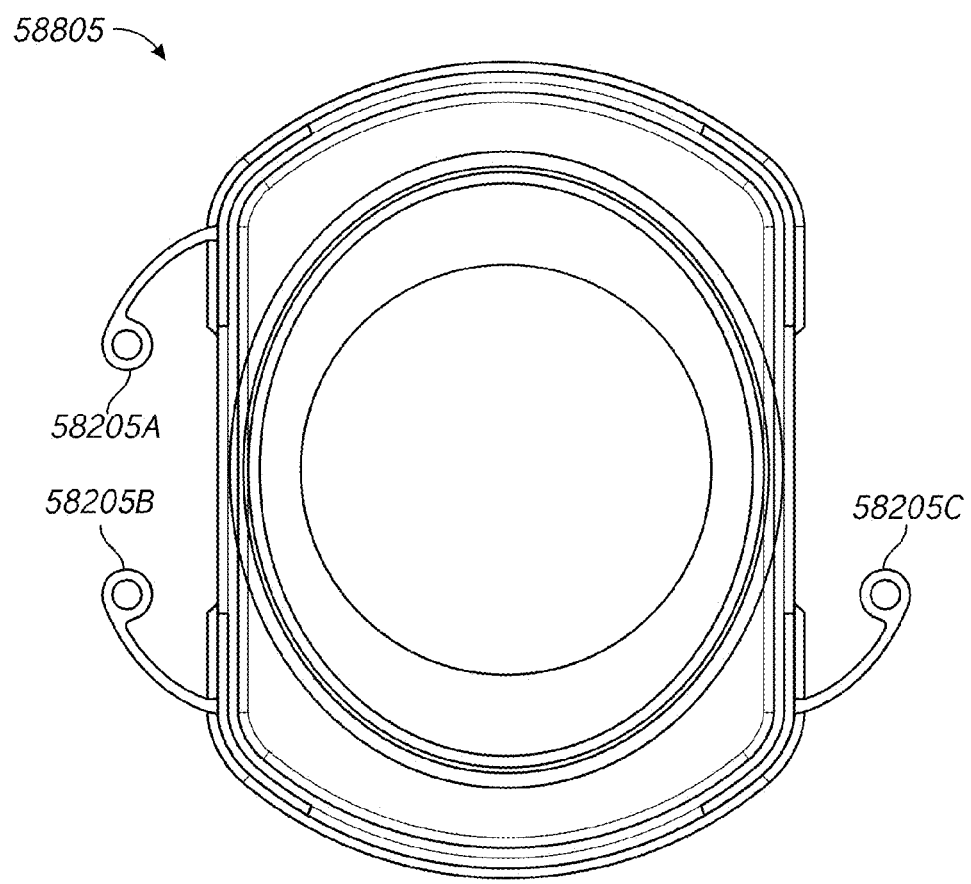

FIGS. 58H-58L illustrate anterior plan views of example prosthetic capsular devices comprising different numbers of ring portions. In FIG. 58H, the device 58801 comprises two ring portions 58201A, 58201B that are on opposite sides of the major axis and on opposite sides of the minor axis. In FIG. 58I, the device 58802 comprises two ring portions 58202A, 58202B that are on opposite sides of the major axis and on the same side of the minor axis. In FIG. 58J, the device 58803 comprises two ring portions 58203A, 58203B that are on the same side of the major axis and on opposite sides of the minor axis. In FIG. 58K, the device 58804 comprises one ring portion 58204. In FIG. 58L, the device 58805 comprises three ring portions 58205A, 58205B, 58205C in which the ring portions 58205A, 58205B are on the same side of the major axis and on opposite sides of the minor axis, the ring portions 58205A, 58205C are on opposite sides of the major axis and on opposite sides of the minor axis, and the ring portions 58205B, 58205C are on opposite sides of the major axis and the same side of the minor axis. Other numbers and configurations of ring portions are also possible. In some implementations comprising one ring structure on a side of the major axis, the arm of the ring structure may be longer, including extending up to or even abutting but not anchored in the housing structure on the other side of the minor axis.

FIG. 61A illustrates an anterior side perspective view of an example prosthetic capsular device 6100. FIG. 61B illustrates an anterior plan view of the example prosthetic capsular device 6100 of FIG. 61A. FIG. 61C illustrates a side view of the example prosthetic capsular device 6100 of FIG. 61A. The device 6100 comprises openings 6126A, 6126B in the housing structure 6112. The opening 6126A may be the same or different than the opening 6126B. An inserted device (e.g., an intraocular lens or other device) may be inside the housing structure 6112 of the device 6100 and/or project through one or both of the openings 6126A, 6126B to the unoccupied capsular recess. The openings 6126A, 6126B may allow rotation of the inserted device, for example comprising a lens that needs to be rotated (e.g., for astigmatism correction). The openings 6126A, 6126B may allow delivery of a medicament (including but not limited to therapeutic agents in the form of pharmaceuticals, biologic agents, monoclonal antibodies, gene therapy and gene vectors, radiation therapy, chemotherapeutic agents, engineered cell culture products) from an inserted drug delivery platform (including but not limited to traditional platforms and non-traditional platforms engineered cell culture biologic agent monoclonal antibody and/or protein producing implants) through one or both of the openings 6126A, 6126B into the natural capsular bag and into the vitreous or posterior segment. The openings 6126A, 6126B may provide access the unoccupied space of the housing structure 6112, for example to store a battery, microchip, or other opaque piece of technology that is desirably held outside of the visual axis or pupillary aperture.

The openings 6126A, 6126B illustrated in FIGS. 61A-61C are between the ring structure portions 6120A, 6120B and between the ring structure portions 6120C, 6120D, respectively. Other positions, quantities, and shapes of the openings are also possible. For example, the device 6100 may also or alternatively comprise openings between the ring structure portions 6120A, 6120C and/or between the ring structure portions 6120B, 6120D. The device 6100 may comprise only one opening, only two openings, or more than two openings. The device 6100 may comprise a first plurality of openings between the ring structure portions 6120A, 6120B and/or a second plurality of openings between the ring structure portions 6120C, 6120D. A plurality of openings smaller than the openings 6126A, 6126B may increase the structural integrity of the device 6100 and/or inhibit lens epithelial cell growth into the cavity of the housing structure 6112 while still providing at least one of the potential advantages described herein.

The openings 6126A, 6126B are illustrated as being mirror-image oval openings, but other shapes are also possible (e.g., polygonal (e.g., rectangular), arcuate (e.g., circular, ellipsoid, oval), slits, combinations thereof, and the like). For example, the openings 6126A, 6126B may comprise oval openings with a series of struts 6152 aligned with the longitudinal axis (e.g., as shown with respect to the opening 6176B of the device 6150 of FIG. 61D) and/or a series of triangular struts.

The openings 6126A, 6126B may be formed during formation of the housing structure 6112 (e.g., as part of a molding process) and/or formed after formation of the housing structure 6112 (e.g., by a laser, chemical, or mechanical removal process). In some implementations, the housing structure 6112 may comprise a different material around the openings 6126A, 6126B (e.g., the housing structure 6212 comprising silicone and the opening surrounding material comprising polyimide). In some implementations, the housing structure 6112 may comprise thicker material around the openings 6126A, 6126B (e.g., to buttress the openings 6126A, 6126B, for example if another device is to be anchored to the opening 6126A, 6126B). In some implementations, the housing structure 6112 may comprise thinner material around the openings 6126A, 6126B (e.g., for easier removal of material and/or opening formation).

Figure 62B:
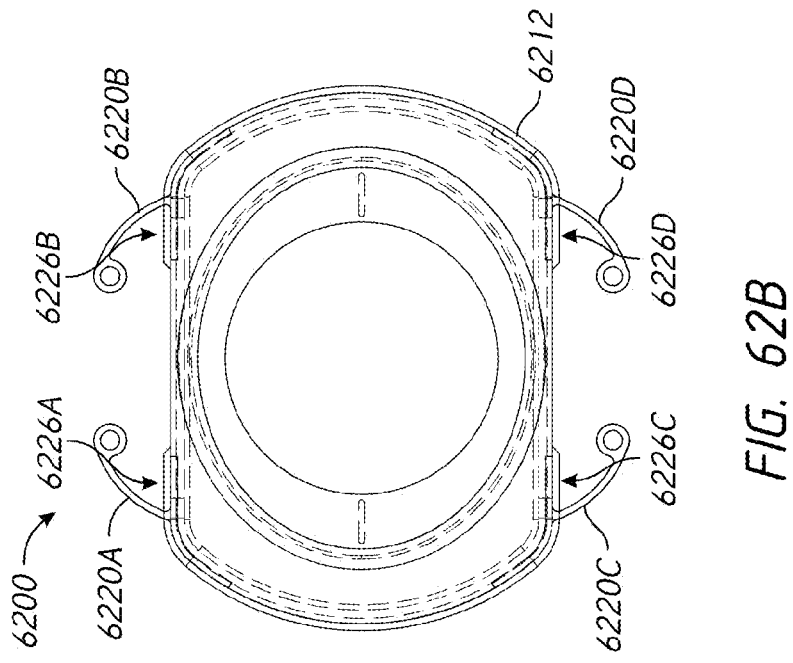
FIG. 62B illustrates an anterior plan view of the example prosthetic capsular device of FIG. 62A.
Figure 62A:
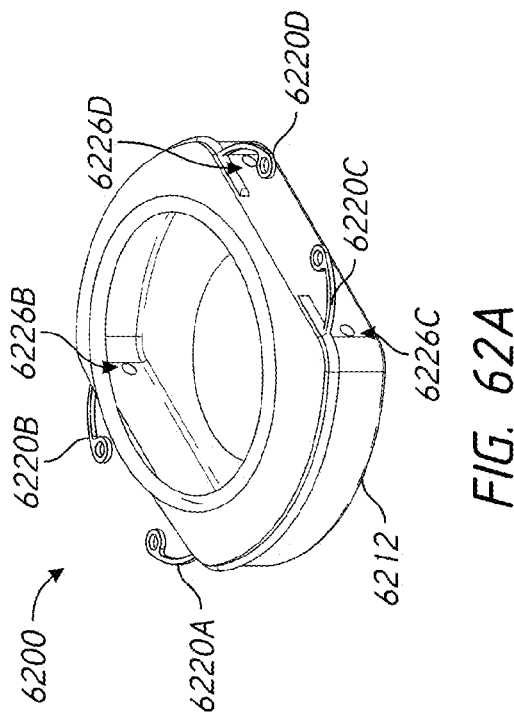
FIG. 62A illustrates an anterior side perspective view of an example prosthetic capsular device.
Figure 62C:
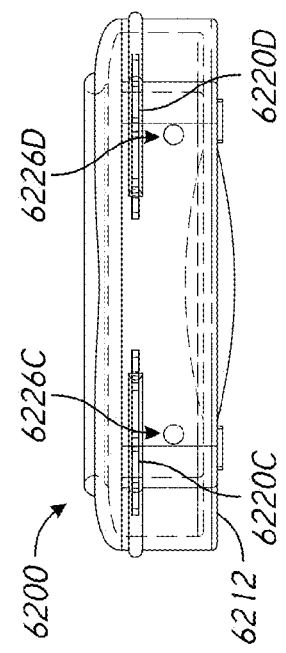
FIG. 62C illustrates a side view of the example prosthetic capsular device of FIG. 62A.

FIG. 62A illustrates an anterior side perspective view of an example prosthetic capsular device 6200. FIG. 62B illustrates an anterior plan view of the example prosthetic capsular device 6200 of FIG. 62A. FIG. 62C illustrates a side view of the example prosthetic capsular device 6200 of FIG. 62A. The device 6200 comprises openings 6226A, 6226B, 6226C, 6226D in the housing structure 6212. Each of the openings 6226A, 6226B, 6226C, 6226D may be the same as the others of the openings 6226A, 6226B, 6226C, 6226D. At least one of the openings 6226A, 6226B, 6226C, 6226D may be different than at least one of the other openings 6226A, 6226B, 6226C, 6226D. The openings 6226A, 6226B, 6226C, 6226D, which are smaller than the openings 6126A, 6126B described above, may increase the structural integrity of the device 6200 and/or inhibit lens epithelial cell growth into the cavity of the housing structure 6212. The openings 6226A, 6226B, 6226C, 6226D may allow delivery of a medicament from an inserted drug delivery platform through one, some, or all of the openings 6226A, 6226B, 6226C, 6226D into the natural capsular bag and into the vitreous or posterior segment. The openings 6226A, 6226B, 6226C, 6226D may provide access the unoccupied space of the housing structure 6212, for example to store a battery, microchip, or other opaque piece of technology that is desirably held outside of the visual axis or pupillary aperture. The openings 6226A, 6226B, 6226C, 6226D illustrated in FIGS. 62A-62C are posterior to the ring structure portions 6220A, 6220B, 6220C, 6220D, respectively. Other positions, quantities, and shapes of the openings are also possible. For example, the device 6200 may comprise only one opening, only two openings, only three openings, only four openings, or more than four openings. The openings 6226A, 6226B, 6226C, 6226D may be at a position other than posterior to the ring structure portions 6220A, 6220B, 6220C, 6220D. The device 6200 may comprise a plurality of openings posterior to the ring structure portions 6220A, 6220B, 6220C, 6220D or in another position. The openings 6226A, 6226B, 6226C, 6226D are illustrated as being mirror-image circular openings, but other shapes are also possible (e.g., polygonal (e.g., rectangular), arcuate (e.g., circular, ellipsoid, oval), slits, combinations thereof, and the like). The openings 6226A, 6226B, 6226C, 6226D may provide an anchor point, for example interacting with a protrusion, for another device to be held in the capsule of the device 6200 or outside the device 6200. The openings 6226A, 6226B, 6226C, 6226D may be formed during formation of the housing structure 6212 (e.g., as part of a molding process) and/or formed after formation of the housing structure 6212 (e.g., by a laser, chemical, or mechanical removal process). In some implementations, the housing structure 6212 may comprise a different material around the openings 6226A, 6226B, 6226C, 6226D (e.g., the housing structure 6212 comprising silicone and the opening surrounding material comprising polyimide). In some implementations, the housing structure 6212 may comprise thicker material around the openings 6226A, 6226B, 6226C, 6226D (e.g., to buttress the openings 6226A, 6226B, 6226C, 6226D, for example if another device is to be anchored to the opening 6226A, 6226B, 6226C, 6226D). In some implementations, the housing structure 6212 may comprise thinner material around the openings 6226A, 6226B, 6226C, 6226D (e.g., for easier removal of material and/or opening formation).

FIG. 63A illustrates an anterior side perspective view of an example prosthetic capsular device 6300. FIG. 63B illustrates an anterior plan view of the example prosthetic capsular device 6300 of FIG. 63A. FIG. 63C illustrates a side view of the example prosthetic capsular device 6300 of FIG. 63A. The device 6300 comprises openings 6326A1, 6326B1, 6326C1, 6326D1, 6326A2, 6326B2, 6326C2, 6326D2 in the housing structure 6312. The openings 6326A1, 6326B1, 6326C1, 6326D1 illustrated in FIGS. 63A-63C are posterior to the ring structure portions 6320A, 6320B, 6320C, 6320D, respectively. The openings 6326A2, 6326B2, 6326C2, 6326D2 illustrated in FIGS. 63A-63C are anterior to the ring structure portions 6320A, 6320B, 6320C, 6320D, respectively. In some implementations, the openings 6326A1, 6326B1, 6326C1, 6326D1 may provide better access to the natural capsular bag (e.g., for transmission of medicaments). In some implementations, the openings 6326A2, 6326B2, 6326C2, 6326D2 may be easier to access from an anterior incision. Other positions, quantities, and shapes of the openings are also possible. For example, the device 6300 may comprise only one opening, only two openings, only three openings, only four openings, only five openings, only six openings, only seven openings, only eight openings, or more than eight openings. The openings 6326A1, 6326B1, 6326C1, 6326D1 may be at a position other than posterior to the ring structure portions 6320A, 6320B, 6320C, 6320D. The openings 6326A2, 6326B2, 6326C2, 6326D2 may be at a position other than anterior to the ring structure portions 6320A, 6320B, 6320C, 6320D. The device 6300 may comprise a plurality of openings posterior to the ring structure portions 6320A, 6320B, 6320C, 6320D, a plurality of openings anterior to the ring structure portions 6320A, 6320B, 6320C, 6320D, or in another position. The openings 6326A1, 6326B1, 6326C1, 6326D1 and the openings 6326A2, 6326B2, 6326C2, 6326D1 are each illustrated as being mirror-image circular openings, but other shapes are also possible (e.g., polygonal (e.g., rectangular), arcuate (e.g., circular, ellipsoid, oval), slits, combinations thereof, and the like). Each of the openings 6326A1, 6326B1, 6326C1, 6326D1, 6326A2, 6326B2, 6326C2, 6326D2 may be the same as the others of the openings 6326A1, 6326B1, 6326C1, 6326D1, 6326A2, 6326B2, 6326C2, 6326D2. At least one of the openings 6326A1, 6326B1, 6326C1, 6326D1, 6326A2, 6326B2, 6326C2, 6326D2 may be different than at least one of the other openings 6326A1, 6326B1, 6326C1, 6326D1, 6326A2, 6326B2, 6326C2, 6326D2. The openings 6326A1, 6326B1, 6326C1, 6326D1, 6326A2, 6326B2, 6326C2, 6326D2, which are smaller than the openings 6126A, 6126B described above, may increase the structural integrity of the device 6300 and/or inhibit lens epithelial cell growth into the cavity of the housing structure 6312. The openings 6326A1, 6326B1, 6326C1, 6326D1, 6326A2, 6326B2, 6326C2, 6326D2 may allow delivery of a medicament from an inserted drug delivery platform through one, some, or all of the openings 6326A1, 6326B1, 6326C1, 6326D1, 6326A2, 6326B2, 6326C2, 6326D2 into the natural capsular bag and into the vitreous or posterior segment. The openings 6326A1, 6326B1, 6326C1, 6326D1, 6326A2, 6326B2, 6326C2, 6326D2 may provide access the unoccupied space of the housing structure 6312, for example to store a battery, microchip, or other opaque piece of technology that is desirably held outside of the visual axis or pupillary aperture. The openings 6326A1, 6326B1, 6326C1, 6326D1, 6326A2, 6326B2, 6326C2, 6326D2 may provide an anchor point, for example interacting with a protrusion, for another device to be held in the capsule of the device 6300 or outside the device 6300. The openings 6326A1, 6326B1, 6326C1, 6326D1, 6326A2, 6326B2, 6326C2, 6326D2 may be formed during formation of the housing structure 6312 (e.g., as part of a molding process) and/or formed after formation of the housing structure 6212 (e.g., by a laser, chemical, or mechanical removal process). In some implementations, the housing structure 6312 may comprise a different material around the openings 6326A1, 6326B1, 6326C1, 6326D1, 6326A2, 6326B2, 6326C2, 6326D2 (e.g., the housing structure 6312 comprising silicone and the opening surrounding material comprising polyimide). In some implementations, the housing structure 6312 may comprise thicker material around the openings 6326A1, 6326B1, 6326C1, 6326D1, 6326A2, 6326B2, 6326C2, 6326D2 (e.g., to buttress the openings 6326A1, 6326B1, 6326C1, 6326D1, 6326A2, 6326B2, 6326C2, 6326D2, for example if another device is to be anchored to the opening 6326A1, 6326B1, 6326C1, 6326D1, 6326A2, 6326B2, 6326C2, 6326D2). In some implementations, the housing structure 6312 may comprise thinner material around the openings 6326A1, 6326B1, 6326C1, 6326D1, 6326A2, 6326B2, 6326C2, 6326D2 (e.g., for easier removal of material and/or opening formation).

Figure 64B:
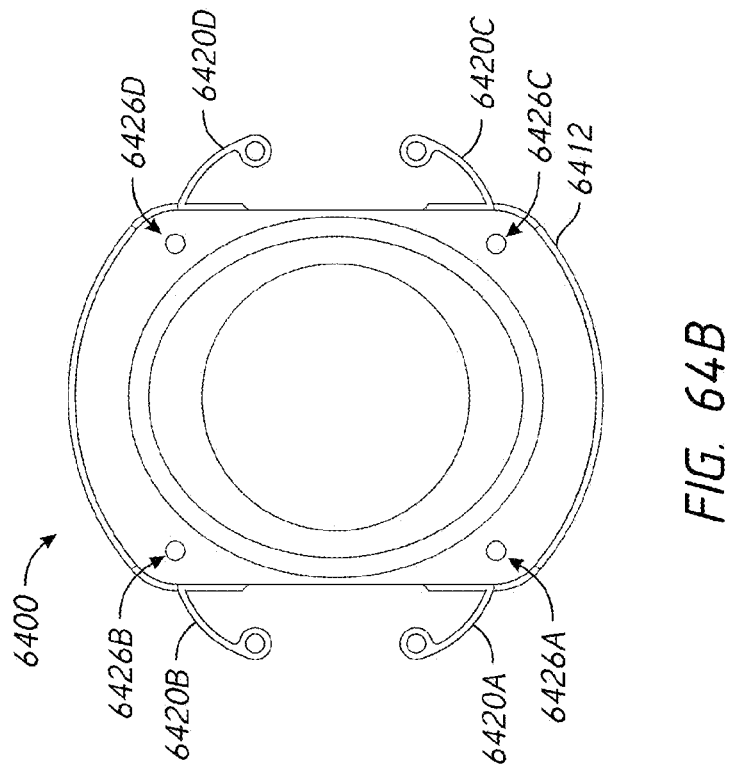
FIG. 64B illustrates an anterior plan view of the example prosthetic capsular device of FIG. 64A.
Figure 64A:
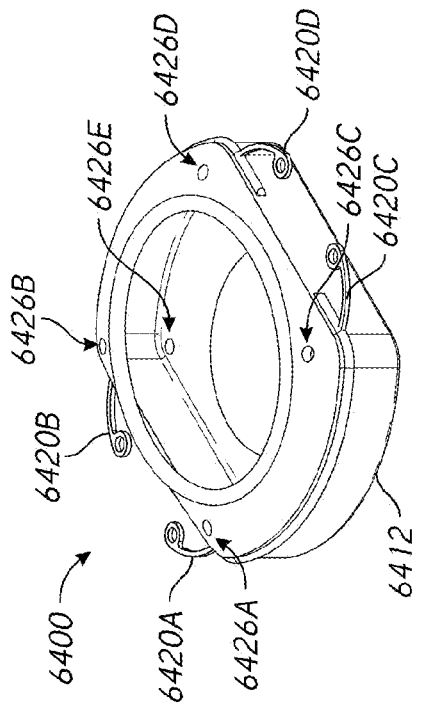
FIG. 64A illustrates an anterior side perspective view of an example prosthetic capsular device.
Figure 64C:
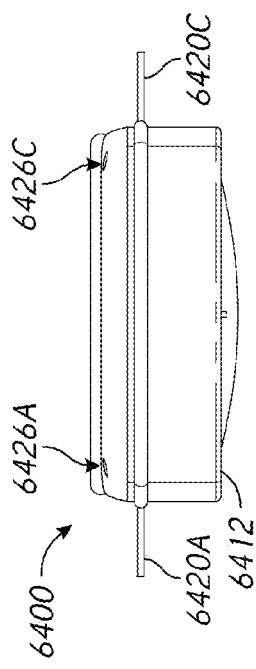
FIG. 64C illustrates a side view of the example prosthetic capsular device of FIG. 64A.

FIG. 64A illustrates an anterior side perspective view of an example prosthetic capsular device 6400. FIG. 64B illustrates an anterior plan view of the example prosthetic capsular device 6400 of FIG. 64A. FIG. 64C illustrates a side view of the example prosthetic capsular device 6400 of FIG. 64A. The device 6400 comprises openings 6426A, 6426B, 6426C, 6426D in the housing structure 6412. Each of the openings 6426A, 6426B, 6426C, 6426D may be the same as the others of the openings 6426A, 6426B, 6426C, 6426D. At least one of the openings 6426A, 6426B, 6426C, 6426D may be different than at least one of the other openings 6426A, 6426B, 6426C, 6426D. The openings 6426A, 6426B, 6426C, 6426D, which are smaller than the openings 6126A, 6126B described above, may increase the structural integrity of the device 6400 and/or inhibit lens epithelial cell growth into the cavity of the housing structure 6412. The openings 6426A, 6426B, 6426C, 6426D may allow delivery of a medicament from an inserted drug delivery platform through one, some, or all of the openings 6426A, 6426B, 6426C, 6426D into the natural capsular bag and into the vitreous or posterior segment. The openings 6426A, 6426B, 6426C, 6426D may provide access the unoccupied space of the housing structure 6412, for example to store a battery, microchip, or other opaque piece of technology that is desirably held outside of the visual axis or pupillary aperture. The openings 6426A, 6426B, 6426C, 6426D may provide an anchor point, for example interacting with a protrusion, for another device to be held in the capsule of the device 6500 or outside the device 6500. The openings 6426A, 6426B, 6426C, 6426D illustrated in FIGS. 64A-64C are anterior to the ring structure portions 6420A, 6420B, 6420C, 6420D, respectively. In some implementations, the openings 6426A, 6426B, 6426C, 6426D may provide access from an anterior incision. Other positions, quantities, and shapes of the openings are also possible. For example, the device 6400 may comprise only one opening or more than four openings. The openings 6426A, 6426B, 6426C, 6426D may be at a position other than anterior to the ring structure portions 6420A, 6420B, 6420C, 6420D. The device 6400 may comprise a plurality of openings anterior to the ring structure portions 6420A, 6420B, 6420C, 6420D or in another position. The openings 6426A, 6426B, 6426C, 6426D are illustrated as being mirror-image circular openings, but other shapes are also possible (e.g., polygonal (e.g., rectangular), arcuate (e.g., circular, ellipsoid, oval), slits, combinations thereof, and the like). In some implementations, the posterior surface of the device 6400 includes an opening that is longitudinally aligned with one, some, or all of the openings 6426A, 6426B, 6426C, 6426D (e.g., the opening 6426E illustrated in FIG. 64A).

In some implementations, the opening 6426E and other such openings can provide one or more advantages. The opening 6426E may inhibit or prevent entrapment of fluid or potentially residual viscoelastic material after implantation of the device 6400, for example by allowing anterior-posterior fluid flow. The opening 6426E may allow a drug contained in the device 6400 to reach a posterior segment of the eye (e.g., vitreous, retina, choroid). The opening 6426E may allow a slow release anti-VEGF injectable (e.g., ranibizuman (e.g., Lucentis® from Genentech), aflibercept (e.g., Eylea® from Regerneron Pharmacueticals) or anti-VEGF produced from cells (e.g., from Neurotech) contained in the device 6400 to reach a posterior segment of the eye (e.g., vitreous, retina, choroid) for treatment of macular degeneration. The opening 6426E may be sized such that there is little or no pressure gradient from posterior to anterior, for example during anterior decompression. In some implementations, the posterior portion of the natural capsular bag may be opened at a point corresponding to the opening 6426E to facilitate the communication of the posterior segment with the anterior segment to aid in the diffusion of pharmaceutical agents. The opening of the capsule and the opening 6426E may be small enough in size that there is a low likelihood of vitreous prolapse through the openings 6426E.

The openings 6426A, 6426B, 6426C, 6426D may be formed during formation of the housing structure 6412 (e.g., as part of a molding process) and/or formed after formation of the housing structure 6412 (e.g., by a laser, chemical, or mechanical removal process). In some implementations, the housing structure 6412 may comprise a different material around the openings 6426A, 6426B, 6426C, 6426D (e.g., the housing structure 6412 comprising silicone and the opening surrounding material comprising polyimide). In some implementations, the housing structure 6412 may comprise thicker material around the openings 6426A, 6426B, 6426C, 6426D (e.g., to buttress the openings 6426A, 6426B, 6426C, 6426D, for example if another device is to be anchored to the opening 6426A, 6426B, 6426C, 6426D). In some implementations, the housing structure 6412 may comprise thinner material around the openings 6426A, 6426B, 6426C, 6426D (e.g., for easier removal of material and/or opening formation).

FIG. 65A illustrates an anterior side perspective view of an example prosthetic capsular device 6500. FIG. 65B illustrates an anterior plan view of the example prosthetic capsular device 6500 of FIG. 65A. FIG. 65C illustrates a side view of the example prosthetic capsular device 6500 of FIG. 65A. The device 6500 comprises slots or slits 6526A1, 6526B1, 6526C1, 6526D1, 6526A2, 6526B2, 6526C2, 6526D2 in the housing structure 6512. When the device 6500 in an unfolded state, the slits 6526A1, 6526B1, 6526C1, 6526D1, 6526A2, 6526B2, 6526C2, 6526D2 may generally be in a closed unless acted upon. For example, pressure (e.g., physical pressure such as from a device to be inserted therethrough, fluid pressure) applied to a slit can force the slit open. For another example, the slits may allow the flow of small amounts of drug, proteins, fluid, etc. The slits 6526A1, 6526B1, 6526C1, 6526D1, 6526A2, 6526B2, 6526C2, 6526D2 may be opened by applying opposing forces, for example like a squeeze coin holder.

The slits 6526A1, 6526B1, 6526C1, 6526D1 illustrated in FIGS. 65A-65C are posterior to the ring structure portions 6520A, 6520B, 6520C, 6520D. The slits 6526A2, 6526B2, 6526C2, 6526D2 illustrated in FIGS. 65A-65C are anterior to the ring structure portions 6520A, 6520B, 6520C, 6520D. The slits 6526A1, 6526A2, 6526C1, 6526C2 illustrated in FIGS. 65A-65C are circumferentially between the ring structure portions 6520A, 6520C. The slits 6526B1, 6526B2, 6526D1, 6526D2 illustrated in FIGS. 65A-65C are circumferentially between the ring structure portions 6520B, 6520D. Other positions, quantities, and shapes of the slits are also possible. For example, the device 6500 may comprise only one slit, only two slits, only three slits, only four slits, only five slits, only six slits, only seven slits, only eight slits, or more than eight slits. The slits 6526A1, 6526B1, 6526C1, 6526D1 may be at a position other than posterior to the ring structure portions 6520A, 6520B, 6520C, 6520D. The slits 6526A2, 6526B2, 6526C2, 6526D2 may be at a position other than anterior to the ring structure portions 6520A, 6520B, 6520C, 6520D. The device 6500 may comprise a plurality of slits posterior to the ring structure portions 6520A, 6520B, 6520C, 6520D, a plurality of slits anterior to the ring structure portions 6520A, 6520B, 6520C, 6520D, or in another position. The slits 6526A1, 6526B1, 6526C1, 6526D1 and the slits 6526A2, 6526B2, 6526C2, 6526D1 are each illustrated as being mirror-image straight slits, but other shapes are also possible (e.g., polygonal, arcuate, combinations thereof, and the like). Each of the slits 6526A1, 6526B1, 6526C1, 6526D1, 6526A2, 6526B2, 6526C2, 6526D2 may be the same as the others of the slits 6526A1, 6526B1, 6526C1, 6526D1, 6526A2, 6526B2, 6526C2, 6526D2. At least one of the slits 6526A1, 6526B1, 6526C1, 6526D1, 6526A2, 6526B2, 6526C2, 6526D2 may be different than at least one of the other slits 6526A1, 6526B1, 6526C1, 6526D1, 6526A2, 6526B2, 6526C2, 6526D2. The slits 6526A1, 6526B1, 6526C1, 6526D1, 6526A2, 6526B2, 6526C2, 6526D2, which are smaller than the slits 6126A, 6126B described above, may increase the structural integrity of the device 6500 and/or inhibit lens epithelial cell growth into the cavity of the housing structure 6512. The slits 6526A1, 6526B1, 6526C1, 6526D1, 6526A2, 6526B2, 6526C2, 6526D2 may allow delivery of a medicament from an inserted drug delivery platform through one, some, or all of the slits 6526A1, 6526B1, 6526C1, 6526D1, 6526A2, 6526B2, 6526C2, 6526D2 into the natural capsular bag and into the vitreous or posterior segment. The slits 6526A1, 6526B1, 6526C1, 6526D1, 6526A2, 6526B2, 6526C2, 6526D2 may provide access the unoccupied space of the housing structure 6512, for example to store a battery, microchip, or other opaque piece of technology that is desirably held outside of the visual axis or pupillary aperture. The slits 6526A1, 6526B1, 6526C1, 6526D1, 6526A2, 6526B2, 6526C2, 6526D2 may provide an anchor point, for example interacting with a protrusion, for another device to be held in the capsule of the device 6500 or outside the device 6500. The slits 6526A1, 6526B1, 6526C1, 6526D1, 6526A2, 6526B2, 6526C2, 6526D2 may be formed during formation of the housing structure 6512 (e.g., as part of a molding process) and/or formed after formation of the housing structure 6512 (e.g., by a laser, chemical, or mechanical removal process). In some implementations, the housing structure 6512 may comprise a different material around the slits 6526A1, 6526B1, 6526C1, 6526D1, 6526A2, 6526B2, 6526C2, 6526D2 (e.g., the housing structure 6512 comprising silicone and the opening surrounding material comprising polyimide). In some implementations, the housing structure 6512 may comprise thicker material around the slits 6526A1, 6526B1, 6526C1, 6526D1, 6526A2, 6526B2, 6526C2, 6526D2 (e.g., to buttress the slits 6526A1, 6526B1, 6526C1, 6526D1, 6526A2, 6526B2, 6526C2, 6526D2, for example if another device is to be anchored to the slits 6526A1, 6526B1, 6526C1, 6526D1, 6526A2, 6526B2, 6526C2, 6526D2). In some implementations, the housing structure 6512 may comprise thinner material around the slits 6526A1, 6526B1, 6526C1, 6526D1, 6526A2, 6526B2, 6526C2, 6526D2 (e.g., for easier removal of material, slit formation, slit opening, etc.).

FIG. 66A illustrates an anterior side perspective view of an example prosthetic capsular device 6600. FIG. 66B illustrates an anterior plan view of the example prosthetic capsular device 6600 of FIG. 66A. FIG. 66C illustrates a side view of the example prosthetic capsular device 6600 of FIG. 66A. The device 6600 comprises slits 6626A1, 6626B1, 6626C1, 6626D1, 6626A2, 6626B2, 6626C2, 6626D2 in the housing structure 6612. The slits 6626A1, 6626B1, 6626C1, 6626D1 illustrated in FIGS. 66A-66C are posterior to the ring structure portions 6620A, 6620B, 6620C, 6620D. The slits 6626A2, 6626B2, 6626C2, 6626D2 illustrated in FIGS. 66A-66C are anterior to the ring structure portions 6620A, 6620B, 6620C, 6620D. The slits 6626A1, 6626A2, 6626B1, 6626B2, 6626C1, 6626C2, 6626D1, 6626D2 illustrated in FIGS. 66A-66C are circumferentially proximate to the anchor portions of the ring structure portions 6620A, 6620B, 6620C, 6620D, respectively. Other positions, quantities, and shapes of the slits are also possible. For example, the device 6600 may comprise only one slit, only two slits, only three slits, only four slits, only five slits, only six slits, only seven slits, only eight slits, or more than eight slits. The slits 6626A1, 6626B1, 6626C1, 6626D1 may be at a position other than posterior to the ring structure portions 6620A, 6620B, 6620C, 6620D. The slits 6626A2, 6626B2, 6626C2, 6626D2 may be at a position other than anterior to the ring structure portions 6620A, 6620B, 6620C, 6620D. The device 6600 may comprise a plurality of slits posterior to the ring structure portions 6620A, 6620B, 6620C, 6620D, a plurality of slits anterior to the ring structure portions 6620A, 6620B, 6620C, 6620D, or in another position. The slits 6626A1, 6626B1, 6626C1, 6626D1 and the slits 6626A2, 6626B2, 6626C2, 6626D1 are each illustrated as being mirror-image slits, but other shapes are also possible (e.g., polygonal, arcuate, combinations thereof, and the like). Each of the slits 6626A1, 6626B1, 6626C1, 6626D1, 6626A2, 6626B2, 6626C2, 6626D2 may be the same as the others of the slits 6626A1, 6626B1, 6626C1, 6626D1, 6626A2, 6626B2, 6626C2, 6626D2. At least one of the slits 6626A1, 6626B1, 6626C1, 6626D1, 6626A2, 6626B2, 6626C2, 6626D2 may be different than at least one of the other slits 6626A1, 6626B1, 6626C1, 6626D1, 6626A2, 6626B2, 6626C2, 6626D2. The slits 6626A1, 6626B1, 6626C1, 6626D1, 6626A2, 6626B2, 6626C2, 6626D2, which are smaller than the slits 6126A, 6126B described above, may increase the structural integrity of the device 6600 and/or inhibit lens epithelial cell growth into the cavity of the housing structure 6612. The slits 6626A1, 6626B1, 6626C1, 6626D1, 6626A2, 6626B2, 6626C2, 6626D2 may allow delivery of a medicament from an inserted drug delivery platform through one, some, or all of the slits 6626A1, 6626B1, 6626C1, 6626D1, 6626A2, 6626B2, 6626C2, 6626D2 into the natural capsular bag and into the vitreous or posterior segment. The slits 6626A1, 6626B1, 6626C1, 6626D1, 6626A2, 6626B2, 6626C2, 6626D2 may provide access the unoccupied space of the housing structure 6612, for example to store a battery, microchip, or other opaque piece of technology that is desirably held outside of the visual axis or pupillary aperture. The slits 6626A1, 6626B1, 6626C1, 6626D1, 6626A2, 6626B2, 6626C2, 6626D2 may provide an anchor point, for example interacting with a protrusion, for another device to be held in the capsule of the device 6600 or outside the device 6600. The slits 6626A1, 6626B1, 6626C1, 6626D1, 6626A2, 6626B2, 6626C2, 6626D2 may be formed during formation of the housing structure 6612 (e.g., as part of a molding process) and/or formed after formation of the housing structure 6612 (e.g., by a laser, chemical, or mechanical removal process). In some implementations, the housing structure 6612 may comprise a different material around the slits 6626A1, 6626B1, 6626C1, 6626D1, 6626A2, 6626B2, 6626C2, 6626D2 (e.g., the housing structure 6612 comprising silicone and the slit surrounding material comprising polyimide). In some implementations, the housing structure 6612 may comprise thicker material around the slits 6626A1, 6626B1, 6626C1, 6626D1, 6626A2, 6626B2, 6626C2, 6626D2 (e.g., to buttress the slits 6626A1, 6626B1, 6626C1, 6626D1, 6626A2, 6626B2, 6626C2, 6626D2, for example if another device is to be anchored to the slits 6626A1, 6626B1, 6626C1, 6626D1, 6626A2, 6626B2, 6626C2, 6626D2). In some implementations, the housing structure 6612 may comprise thinner material around the slits 6626A1, 6626B1, 6626C1, 6626D1, 6626A2, 6626B2, 6626C2, 6626D2 (e.g., for easier removal of material, slit formation, slit opening, etc.).

The housing structure openings and slits described herein can be used to provide an anchor point, a pathway through the housing structure (e.g., for wires or leads from a battery exterior to the device to electronics inside the device), for other device(s) to be held in the capsule of the device or outside the device. The other devices can include electronic devices, medicament delivery systems, etc. In some implementations, the device comprises one or more interior and/or exterior protrusions configured to interact with an element of another device.

FIG. 67A illustrates an anterior side perspective view of an example prosthetic capsular device 6700. FIG. 67B illustrates an anterior plan view of the example prosthetic capsular device 6700 of FIG. 67A. FIG. 67C illustrates a side view of the example prosthetic capsular device 6700 of FIG. 67A. The device 6700 comprises ring structure portions 6720A, 6720B, 6720C, 6720D. The ring structure portions 6720A, 6720B, 6720C, 6720D comprise openings 6728A1, 6728B1, 6728C1, 6727D1, respectively, which may provide one or more of the advantages discussed herein with respect to openings of other ring structure portions. The device 6700 further comprises openings or eyelets or grommets 6628A2, 6628B2, 6628C2, 6628D2, 6628A3, 6628B3, 6628C3, 6628D3. The openings 6628A2, 6628B2, 6628C2, 6628D2 are radially outward of and coupled to the ring structure portions 6720A, 6720B, 6720C, 6720D, respectively. The openings 6628A2, 6628B2, 6628C2, 6628D2 are radially inward of and separate from the ring structure portions 6720A, 6720B, 6720C, 6720D, respectively. Other positions, quantities, and shapes of the openings are also possible. For example, the device 6700 may comprise only one opening, only two openings, only three openings, only four openings, only five openings, only six openings, only seven openings, only eight openings, only nine openings, only ten openings, only eleven openings, only twelve openings, or more than twelve openings. Each of the openings 6728A1, 6728B1, 6728C1, 6728D1, 6728A2, 6728B2, 6728C2, 6728D2, 6728A3, 6728B3, 6728C3, 6728D3 may be the same as the others of the openings 6728A1, 6728B1, 6728C1, 6728D1, 6728A2, 6728B2, 6728C2, 6728D2, 6728A3, 6728B3, 6728C3, 6728D3. At least one of the openings 6728A1, 6728B1, 6728C1, 6728D1, 6728A2, 6728B2, 6728C2, 6728D2, 6728A3, 6728B3, 6728C3, 6728D3 may be different than at least one of the other openings 6728A1, 6728B1, 6728C1, 6728D1, 6728A2, 6728B2, 6728C2, 6728D2, 6728A3, 6728B3, 6728C3, 6728D3. The openings 6728A1, 6728B1, 6728C1, 6728D1, 6728A2, 6728B2, 6728C2, 6728D2, 6728A3, 6728B3, 6728C3, 6728D3 may provide an anchor point, for example interacting with a protrusion, for another device to be held outside the device 6700, for suturing to parts of an eye such as a natural capsular bag, zonules, ciliary muscles, scleral wall, etc., and/or for allowing epithelial cell growth, allow fibrosis therethrough, and/or the like. Other devices can be coupled to one or more of the openings 6728A1, 6728B1, 6728C1, 6728D1, 6728A2, 6728B2, 6728C2, 6728D2, 6728A3, 6728B3, 6728C3, 6728D3 after the device 6700 has been positioned in a natural capsular bag of an eye. Coupling the other device(s) after positioning of the device 6700, for example as opposed to coupling or integrally forming the other device(s) to the device 6700 before positioning the device 6700 in an eye, can allow the device 6700 to be injected through a smaller opening as described herein. Coupling other device(s), for example as opposed to coupling or integrally forming the other device(s) with the device 6700, can allow a variety of other devices to be used. In some implementations, the other device(s) may be removed and a replacement or other device may optionally be coupled during a later procedure. In some implementations, the other device(s) may be absorbed over time, and a replacement or other device may optionally be coupled during a later procedure. The positions of the openings 6728A1, 6728B1, 6728C1, 6728D1, 6728A2, 6728B2, 6728C2, 6728D2, 6728A3, 6728B3, 6728C3, 6728D3 can allow functional use of other devices in the volume of the natural capsular bag radially outward of the housing structure 6812. The openings 6728A1, 6728B1, 6728C1, 6728D1, 6728A2, 6728B2, 6728C2, 6728D2, 6728A3, 6728B3, 6728C3, 6728D3 may be formed during formation of the device 6700 (e.g., as part of a molding process) and/or formed after formation of the device 6700 (e.g., by a laser, chemical, or mechanical removal process). In some implementations, the housing structure 6712 may comprise a different material than the material surrounding the openings 6728A1, 6728B1, 6728C1, 6728D1, 6728A2, 6728B2, 6728C2, 6728D2, 6728A3, 6728B3, 6728C3, 6728D3 (e.g., the housing structure 6712 comprising silicone and the opening surrounding material comprising polyimide).

FIG. 68A illustrates an anterior side perspective view of an example prosthetic capsular device 6800. FIG. 68B illustrates an anterior plan view of the example prosthetic capsular device 6800 of FIG. 68A. FIG. 68C illustrates a side view of the example prosthetic capsular device 6800 of FIG. 68A. The device 6800 comprises ring structure portions 6820A, 6820B, 6820C, 6820D. The device 6800 further comprises a sliding retainer 6830A posterior to and circumferentially between the ring structure portions 6820A, 6820B and a sliding retainer 6830B posterior to and circumferentially between the ring structure portions 6820C, 6820D. The sliding retainer 6830A comprises an upper or anterior portion and a lower or posterior portion forming a retaining cavity 6832A, and the sliding retainer 6830B comprises an upper or anterior portion and a lower or posterior portion forming a retaining cavity 6832B. The positions between the ring structure portions can allow functional use of other devices in the volume of the natural capsular bag radially outward of the housing structure 6812. Other positions, quantities, and shapes of the sliding retainers are also possible. For example, the device 6800 may comprise only one sliding retainer, only two sliding retainers, or more than two sliding retainers. In some implementations, a sliding retainer comprises a dovetail-shaped retaining cavity, for example configured to interact with a dovetail-shaped protrusion of another device.

The sliding retainers 6830A, 6830B are configured to receive a slot protrusion of another device. For example, FIG. 68D schematically shows an example of another device 6850 interacting with the sliding retainer 6830B. One or more devices may interact with one or both of the sliding retainers 6830A, 6830B (e.g., sliding in from one or either end of the sliding retainers 6830A, 6830B). The example device 6850 includes a slot protrusion 6852 and a radially outwardly projecting part 6854. The projecting part 6854 may take any variety of shapes and sizes. The device 6850 can be slid into the retaining cavity of the structure 6830B after the device 6800 has been positioned in a natural capsular bag of an eye. Coupling the device 6850 after positioning of the device 6800, for example as opposed to coupling or integrally forming the device 6850 to the device 6800 before positioning the device 6800 in an eye, can allow the device 6800 to be injected through a smaller opening as described herein. Coupling the device 6850, for example as opposed to coupling or integrally forming the device 6850 with the device 6800, can allow a variety of other devices 6850 to be used. In some implementations, the other device may be removed (e.g., by sliding out the side of the sliding retainer, by radially pulling out if the sliding retainer material is resilient, etc.) and a replacement or other device may optionally be coupled during a later procedure. In some implementations, the other device may be absorbed over time, and a replacement or other device may optionally be coupled during a later procedure.

The sliding retainers 6830A, 6830B may be formed during formation of the device 6800 (e.g., as part of a molding process) and/or formed after formation of the device 6800 (e.g., by a laser, chemical, or mechanical removal process). In some implementations, the housing structure 6812 may comprise a different material than the sliding retainers 6830A, 6830B (e.g., the housing structure 6812 comprising silicone and the sliding retainers 6830A, 6830B comprising polyimide). The sliding retainers 6830A, 6830B may be integral with or separate from the ring structure portions 6820A, 6820B, 6820C, 6820D.

FIG. 69A illustrates an anterior side perspective view of an example prosthetic capsular device 6900. FIG. 69B illustrates an anterior plan view of the example prosthetic capsular device 6900 of FIG. 69A. FIG. 69C illustrates a side view of the example prosthetic capsular device 6900 of FIG. 69A. The device 6900 comprises ring structure portions 6920A, 6920B, 6920C, 6920D. The device 6900 further comprises a sliding retainer 6930A radially inward of and circumferentially between the ring structure portions 6920A, 6920B and a sliding retainer 6930B radially inward of and circumferentially between the ring structure portions 6920C, 6920D. The sliding retainer 6930A comprises a first portion radially inward of the ring structure portion 6920A and a second portion radially inward of the ring structure portion 6920B, the first portion and the second portion forming a retaining cavity 6932A. The sliding retainer 6930B comprises a first portion radially inward of the ring structure portion 6920C and a second portion radially inward of the ring structure portion 6920D, the first portion and the second portion forming a retaining cavity 6932B. The positions circumferentially between the ring structure portions can allow functional use of other devices in the volume of the natural capsular bag radially outward of the housing structure 6912. Other positions, quantities, and shapes of the sliding retainers are also possible. For example, the device 6900 may comprise only one sliding retainer, only two sliding retainers, or more than two sliding retainers. In some implementations, a sliding retainer comprises a dovetail-shaped retaining cavity, for example configured to interact with a dovetail-shaped protrusion of another device.

The sliding retainers 6930A, 6930B are configured to receive a slot protrusion of another device. For example, FIG. 69D schematically shows an example of another device 6950 interacting with the sliding retainer 6930B. One or more devices may interact with one or both of the sliding retainers 6930A, 6930B (e.g., sliding in from one or either end of the sliding retainers 6930A, 6930B). The example device 6950 includes a slot protrusion 6952 and a radially outwardly projecting part 6954. The projecting part 6954 may take any variety of shapes and sizes. The device 6950 can be slid into the retaining cavity of the structure 6930B after the device 6900 has been positioned in a natural capsular bag of an eye. Sliding the device 6950 anterior to posterior may be physically less difficult than, for example, sliding a device 6850 from a side, particularly in a later procedure. Coupling the device 6950 after positioning of the device 6900, for example as opposed to coupling or integrally forming the device 6950 to the device 6900 before positioning the device 6900 in an eye, can allow the device 6900 to be injected through a smaller opening as described herein. Coupling the device 6950, for example as opposed to coupling or integrally forming the device 6950 with the device 6900, can allow a variety of other devices 6950 to be used. In some implementations, the other device may be removed (e.g., by sliding out the side of the sliding retainer, by radially pulling out if the sliding retainer material is resilient, etc.) and a replacement or other device may optionally be coupled during a later procedure. In some implementations, the other device may be absorbed over time, and a replacement or other device may optionally be coupled during a later procedure.

The sliding retainers 6930A, 6930B may be formed during formation of the device 6900 (e.g., as part of a molding process) and/or formed after formation of the device 6900 (e.g., by a laser, chemical, or mechanical removal process). In some implementations, the housing structure 6912 may comprise a different material than the sliding retainers 6930A, 6930B (e.g., the housing structure 6912 comprising silicone and the sliding retainers 6930A, 6930B comprising polyimide). The sliding retainers 6930A, 6930B may be integral with or separate from the ring structure portions 6920A, 6920B, 6920C, 6920D.

FIG. 70A illustrates an anterior side perspective view of an example prosthetic capsular device 7000. FIG. 70B illustrates an anterior plan view of the example prosthetic capsular device 7000 of FIG. 70A. FIG. 70C illustrates a side view of the example prosthetic capsular device 7000 of FIG. 70A. The device 7000 comprises ring structure portions 7020A, 7020B, 7020C, 7020D. The ring structure portions 7020A, 7020B, 7020C, 7020D comprise openings 7028A, 7028B, 7028C, 7027D, respectively, which may provide one or more of the advantages discussed herein with respect to openings of other ring structure portions. The device 7000 further comprises interior openings or eyelets or grommets 7038A, 7038B, 7038C, 7038D, 7038E, 7038F, 7038G, 7038H, 7038I, 7038J. The openings 7038A, 7038B, 7038C, 7038D, 7038E, 7038F, 7038G, 7038H, 7038I, 7038J are in the capsule of the housing structure 7012 of the device 7000. The openings 7038A, 7038B, 7038C, 7038D, 7038E, 7038F, 7038G, 7038H, 7038I, 7038J may be formed from the same material as (e.g., integral with) the ring structure portions 7020A, 7020B, 7020C, 7020D. Other positions, quantities, and shapes of the openings are also possible. For example, the device 7000 may comprise only one interior opening, only two interior openings, only three interior openings, only four interior openings, only five interior openings, only six interior openings, only seven interior openings, only eight interior openings, only nine interior openings, only ten interior openings, or more than ten interior openings. The openings 7038A, 7038B, 7038C, 7038D, 7038E, 7038F, 7038G, 7038H, 7038I, 7038J are illustrated as being extending inwardly from ends of the housing structure 7012, but the openings may extend inwardly from sides of the housing structure 7012 and/or outwardly from the housing structure 7012. The openings 7038A, 7038B, 7038C, 7038D, 7038E, 7038F, 7038G, 7038H, 7038I, 7038J may be longitudinally aligned or parallel to the ring structure portions 7020A, 7020B, 7020C, 7020D, anterior to the ring structure portions 7020A, 7020B, 7020C, 7020D, and/or posterior to the ring structure portions 7020A, 7020B, 7020C, 7020D. Each of the openings 7038A, 7038B, 7038C, 7038D, 7038E, 7038F, 7038G, 7038H, 7038I, 7038J may be the same as the others of the openings 7038A, 7038B, 7038C, 7038D, 7038E, 7038F, 7038G, 7038H, 7038I, 7038J. At least one of the openings 7038A, 7038B, 7038C, 7038D, 7038E, 7038F, 7038G, 7038H, 7038I, 7038J may be different than at least one of the other openings 7038A, 7038B, 7038C, 7038D, 7038E, 7038F, 7038G, 7038H, 7038I, 7038J. The openings 7038A, 7038B, 7038C, 7038D, 7038E, 7038F, 7038G, 7038H, 7038I, 7038J may provide an anchor point, for example interacting with a protrusion, for another device to be held inside the device 7000. Other devices can be coupled to one or more of the openings 7038A, 7038B, 7038C, 7038D, 7038E, 7038F, 7038G, 7038H, 7038I, 7038J after the device 7000 has been positioned in a natural capsular bag of an eye. Coupling the other device(s) after positioning of the device 7000, for example as opposed to coupling or integrally forming the other device(s) to the device 7000 before positioning the device 7000 in an eye, can allow the device 7000 to be injected through a smaller opening as described herein. Coupling other device(s), for example as opposed to coupling or integrally forming the other device(s) with the device 7000, can allow a variety of other devices to be used. In some implementations, the other device(s) may be removed and a replacement or other device may optionally be coupled during a later procedure. In some implementations, the other device(s) may be absorbed over time, and a replacement or other device may optionally be coupled during a later procedure. The openings 7038A, 7038B, 7038C, 7038D, 7038E, 7038F, 7038G, 7038H, 7038I, 7038J may be formed during formation of the device 7000 (e.g., as part of a molding process) and/or formed after formation of the device 7000. In some implementations, the housing structure 7012 may comprise a different material than the material surrounding the openings 7038A, 7038B, 7038C, 7038D, 7038E, 7038F, 7038G, 7038H, 7038I, 7038J (e.g., the housing structure 7012 comprising silicone and the opening surrounding material comprising polyimide).

FIG. 71A illustrates a perspective view of an example device 7140 for coupling to a prosthetic capsular device. The device 7140 comprises a first attachment portion 7142 and a second functional portion 7144. The first attachment portion 7142 illustrated in FIG. 71A comprises a hairpin structure. The hairpin structure 7142 extends from the second functional portion 7144 then turns back towards the second functional portion 7144. As illustrated in FIG. 71A, the hairpin structure 7142 turns approximately 270°, then reverses 180° three times to form undulations like a hairpin.

The first turn may be larger than the later turns. The hairpin structure 7142 may comprise fewer turns, including a single turn that may be less than 270°. The second functional portion 7144 may comprise a drug eluting device. For example, the second functional portion 7144 may comprise a cage configured to hold medicament pellets. The medicament may elute through sidewalls of the cage. The cage may comprise an opening 7146, for example allowing for the insertion and/or removal of medicament pellets. In some implementations, the second functional portion 7144 comprises a different type of medicament device, an electronic device, etc.

FIG. 71B illustrates an example coupling of the example device 7140 of FIG. 71A with an example portion 7138 of a prosthetic capsular device. The portion 7138 may be similar, for example, to the openings 6728A1, 6728B1, 6728C1, 6728D1, 6728A2, 6728B2, 6728C2, 6728D2, 6728A3, 6728B3, 6728C3, 6728D3 of the device 6700, the openings 7038A, 7038B, 7038C, 7038D, 7038E, 7038F, 7038G, 7038H, 7038I, 7038J, or other openings or attachment structures. The tail end of the hairpin structure 7142 is inserted through the opening 7138 and slid until the opening 7138 is proximate to the first turn, which can lock the device 7140 in position. In some implementations, a plurality of devices can be directly coupled to a single opening 7138. In some implementations, a plurality of devices can be coupled to a single opening 7138, for example a first device 7140 anchoring to the opening 7138 and then at least one other device anchoring to anchor structure 7142 (e.g., along different longitudinal positions of the anchor structure 7142).

FIG. 71C illustrates an example coupling of an example device 7150 with an example portion 7138 of a prosthetic capsular device. The device 7150 comprises a first attachment portion 7152 and a second functional portion (not shown) extending from the first attachment portion 7152. The first attachment portion 7152 comprises a carabiner structure 7152. The carabiner structure 7152 comprises a C-shaped frame 7153 and a gate 7154. The gate 7154 is coupled to the frame 7153 at a hinge 7155. In an open configuration in which the gate 7154 pivots inside the frame 7153, an opening or gap 7158 is formed between the end 7156 of the gate 7154 and the end 7157 of the frame 7153, allowing the frame 7153 to be positioned in an opening 7138. In a closed configuration in which the gate 7154 pivots outward, the gap 7158 is removed and the end 7156 of the gate 7154 and the end 7157 of the frame 7153 make contact, inhibiting or preventing the frame 7153 from sliding out of the opening 7138. The frame 7153 may comprise shapes other than C-shaped. The gate 7155 may comprise shapes other than substantially linear. In some implementations, the ends 7156, 7157 are configured to enhance interaction in the closed position (e.g., comprising complementary shapes). The second functional portion may comprise a drug eluting device, for example similar to the second functional portion 7144 of FIGS. 71A and 71B. The portion 7138 may be similar, for example, to the openings 6728A1, 6728B1, 6728C1, 6728D1, 6728A2, 6728B2, 6728C2, 6728D2, 6728A3, 6728B3, 6728C3, 6728D3 of the device 6700, the openings 7038A, 7038B, 7038C, 7038D, 7038E, 7038F, 7038G, 7038H, 7038I, 7038J, or other openings or attachment structures. In some implementations, a plurality of devices can be directly coupled to a single opening 7138. In some implementations, a plurality of devices can be coupled to a single opening 7138, for example a first device 7150 anchoring to the opening 7138 and then at least one other device anchoring to carabener structure 7152.

FIG. 71D illustrates an example coupling of an example device 7160 with an example portion 7138 of a prosthetic capsular device. The device 7160 comprises a first attachment portion 7162 and a second functional portion 7166. The first attachment portion 7162 extends from the second functional portion 7166 by a member 7165. The first attachment portion 7162 comprises an arrowhead structure 7162. The arrowhead structure 7162 comprises a point 7163 and barbs 7164 pointing away from the point 7163. The arrowhead structure 7162 may be at least partially deformable in a first direction of the point 7163 and generally non-deformable in a second direction away from the point 7163.

The second functional 7166 portion may comprise a drug eluting device, for example similar to the second functional portion 7144 of FIGS. 71A and 71B. The portion 7138 may be similar, for example, to the openings 6728A1, 6728B1, 6728C1, 6728D1, 6728A2, 6728B2, 6728C2, 6728D2, 6728A3, 6728B3, 6728C3, 6728D3 of the device 6700, the openings 7038A, 7038B, 7038C, 7038D, 7038E, 7038F, 7038G, 7038H, 7038I, 7038J, or other openings or attachment structures. The point 7163 is inserted through the opening 7138 until the barbs 1764 are on the opposite side of the opening 7138, which can lock the device 7160 in position.

Examples of drugs or medicaments that may be compatible with one or more of the devices described herein are non-limiting. Further and more creative solutions may be developed for the delivery of pharmaceutical, biologic, monoclonal antibodies, chemotherapeutic, radiation emitting and/or genetic (e.g., stem cell) therapies inside the eye. Certain devices described herein are designed with the future in mind by preserving and protecting an open space in the anterior segment of the eye (e.g., the internal volume of the device that outside the optical path) for the potential placement of controlled distribution devices for treatment of pathologic, refractive, aesthetic, etc. conditions. The ease of access to this space through an anterior segment approach (cornea, limbus, or scleral tunnel) can advantageously allow placement, modification, exchange, replacement, and/or removal of such medicament delivery devices, providing long-term viability to implants that may have a finite duration of effectiveness.

Bimatoprost SR (Lumigan® from Allergan, Inc.) is an example of a time released drug that is effective (e.g., has been shown to successfully reduce intraocular pressure for treatment of glaucoma and/or ocular hypertension), but non-reversible (e.g., not able to be removed from the eye and/or potentially requiring rescue therapy) and impractical to implement. The drug pellet is placed into the anterior chamber of the eye through a small needle (e.g., intracameral injection) and left to float and drift inside the anterior segment without sequestration. Adverse outcomes could include loss of endothelial cells, cataract formation, iritis, and allergic reaction to one of the components in the implant (drug and/or vehicle). Drugs having a cosmetic or aesthetic effect may also be used. For example, a higher dosage version of bimatoprost is sold by Allergan as an eyelash growth serum, which may be developed into an implant form. Other non-limiting examples of medicaments include a fluocinolone acetonide implant (Iluvien® from Alimera Sciences, Inc. of Alpharetta, Ga.) and a dexamethasone intravitreal implant (Ozurdex® from Allergan, Inc.). These examples are slowly dissolving steroid implants that are injected into the vitreous cavity, left to float in the vitreous with no control over migration. Traditionally, steroids have also been injected into the vitreous as a bolus of the steroid suspension (such as triamcinolone), which can cause a visual disturbance since the drug suspension can form a white opaque cloud covering vast portions of the visual field. Drugs implants designed for long term delivery have also been developed with surgically implanted carriers. For example, the ganciclovir intravitreal implant (Vitrasert® from Auritec Pharmaceuticals, Inc.) for treatment of CMV retinitis and the fluocinolone acetonide (Retisert® from Bausch & Lomb Inc.) are both designed as slowly dissolvable drug inside a carrier that must be surgically implanted through the sclera directly into the vitreous, requiring suture fixation to the sclera. These are not technically easy to perform, even by a skilled ophthalmic surgeon, and carry associated morbidity such as retinal detachment, infection, and blindness.

Neurotech Pharmaceuticals, Inc. of Cumberland, R.I. is developing an implant (NT-503) for its encapsulated cell therapy that is designed to be sutured to the sclera. The Neurotech implant contains a live cell culture that has been modified to produce proteins that function as a vascular endothelial growth factor (VEGF) trap. The cell culture is kept alive through nutrients available inside the eye, effectively acting as an implantable biologic drug producing factory.

FIG. 75A illustrates an anterior plan view of an example prosthetic capsular device system 7500. The system 7500 includes a prosthetic capsular device 7501 (e.g., having features of the device 5800, other devices described herein, etc.). For example, the device 7501 may comprise openings to allow medicament to flow into the anterior chamber and/or the posterior chamber. The device 7501 includes an anchoring structure 7502 configured to interact with a medicament delivery device. The anchoring structure 7502 includes a first pole or rod or bar or rail 7502A and a first pole or rod or bar or rail 7502B. The system 7500 is illustrated in FIG. 75A as comprising one medicament delivery device 7504 interacting with the second rail 7502B to better illustrate the first rail 7502A, but the system 7500 could include two medicament delivery devices 7504 (e.g., one on each lateral side of a posterior optic 7510) or a plurality of medicament delivery devices (e.g., a plurality on one lateral side of the posterior optic 7510). The first rail 7502A is anchored to the housing structure of the device 7501 and extends, as illustrated in FIG. 75A, to the left, with a free end on the left side. The first rail 7502A may comprise a same material as and/or integral with a ring structure portion. The first rail 7502A may be the same as the rail 7502B (e.g., a mirror image (e.g., both anchored on the right), reversed (identical but the rail 7502B anchored on the left), etc.). The first rail 7502A may be different than the rail 7502B. For example, the first rail 7502A may have a different property (e.g., length, cross-sectional area (e.g., diameter), lateral position, anchor point, shape, material, etc.) than the second rail 7502B. In some implementations, the device 7501 comprises a plurality of rails on one side of the optic 7510. For example, the device 7501 may comprise a first rail extending laterally from left to right and a second rail extending laterally from right to left. The device 7501 may also or alternatively comprise one or more rails on the left and/or right sides of the optic 7510. The device 7501 may be deployed in a capsulorhexis. In some implementations, the system 7500 may be used as a medicament delivery system without containing an IOL.

FIG. 75B illustrates an anterior plan view of an example medicament delivery device 7504 of the prosthetic capsular device system 7500 of FIG. 75A. The medicament delivery device 7504 comprises a shell or cage 7508 containing or configured to contain a medicament. In some implementations, the cage 7508 comprises a mesh structure configured to interact with fluid (e.g., anterior chamber fluid) in the device 7501. In some implementations, the medicament may comprise a bacterial culture configured to provide a protein as a waste product. In certain such implementations, the bacteria may derive nutrients from the anterior chamber fluid. In some implementations, the cage 7508 comprises a selective membrane (e.g., an osmotic membrane) configured to allow medicament to flow out to the device 7501. The details of the cage 7508 may vary based on the medicament. The medicament delivery device 7504 maybe inserted into the device 7501 before and/or after an IOL. The medicament delivery device 7504 may be folded for insertion into the device 7501, then unfold (e.g., self-expand, be unfolded) in the capsule of the device 7501. The medicament delivery device 7504 includes a plurality of tubes or ducts or pipes or sleeves 7506A, 7506B, 7506C configured to interact with the second rail 7502B. The free end of the rail 7502B, on the right side in FIG. 75A, can be inserted into an open end of the first sleeve 7506A, through the first sleeve 7506A, into an open end of the second sleeve 7506B, through the second sleeve 7506B, into an open end of the third sleeve 7506C, and through the third sleeve 7506C, for example by rotating the medicament delivery device 7504 clockwise. The rail 7502B inhibits or prevents the medicament delivery device 7504 from migrating in the device 7501, for example because the sleeves 7506A, 7506B, 7506C, which are coupled to the device body 7508, are inhibited from moving. More or fewer sleeves are also possible. In some implementations, features other than sleeves can be configured to interact with a rail.

The cage 7508 may include an opening or slit configured to allow insertion of medicament after insertion into the device 7501. For example, the cage 7508 may be inserted empty, and then a drug may be inserted through the opening or slit, thereafter inhibited or prevented from migrating out of the medicament delivery device 7504. In some implementations, the cage 7508 may be inserted with a first drug implant inside, and once that drug loses effectiveness, a second drug implant, which may be the same or different than the first drug implant, may be inserted. In some implementations, the medicament delivery device 7504 may be removed (e.g., by rotating counter-clockwise to disengage the rail 7502B from the sleeves 7506A, 7506B, 7506C) and a second medicament delivery device 7504 may be inserted in the device 7501. In some implementations, a second medicament delivery device 7504 may be inserted in the device 7501 while the first medicament delivery device 7504 remains (e.g., interacting with the rail 7502A or also interacting with the rail 7502B). For example, the full benefit of the medicament in the first medicament delivery device 7504 may be realized (e.g., exhausting all of the active ingredient(s)) without a reduction in effectiveness over time due to decreasing dosage.

FIG. 75C illustrates an anterior plan view of another example medicament delivery device 7514 of a prosthetic capsular device system. The device 7514 comprises a cage 7508 and a pole or rod or bar or rail 7516. The rail 7516 may be configured to interact with one or a plurality of tubes or ducts or pipes or sleeves of a prosthetic capsular device (e.g., an inverse of the system 7500). In some implementations, a first side of a prosthetic capsular device comprises a rail and a second side of the prosthetic capsular device comprises a plurality of sleeves.

FIG. 75D illustrates an anterior side perspective view of another example medicament delivery device 7550 of a prosthetic capsular device system. The device 7550 includes a framework 7552, a first cage 7554A, and a second cage 7554B. The framework 7552 may comprise a ring (e.g., as illustrated in FIG. 75D), a plurality of rings (e.g., an upper ring, a lower ring, an intermediate ring, a partial ring in the area of the cage 7554B), struts between rings, broken rings (e.g., to aid flexibility for insertion), combinations thereof, and the like. The framework 7552 may comprise a flexible material capable of or configured to revert to an original shape once inserted into the cavity of a prosthetic capsular device. For example, the framework 7552 may comprise polyimide, polyamide, PLLA, PLGA, superelastic alloys (e.g., nitinol, chromium-cobalt), etc. The cages 7554A, 7554B may be, for example, similar to the cage 7508. The device 7550 may comprise only one cage, two cages, or more than two cages. One or both of the cages 7554A, 7554B may be coupled to the framework 7552, for example, by threading a rail of the framework 7552 through sleeves (e.g., as described with respect to FIGS. 75A and 75B). One or both of the cages may be coupled to the framework 7552, for example, by adhesive, welding, chemical adhesion, intertwining, combinations thereof, and the like. The device 7550 is capable of or configured to be inserted into a prosthetic capsular device that does not necessarily include any features configured to interact with the device 7550. The framework may self-expand within a cavity of the prosthetic capsular device radially outward of an anterior opening, anchoring the device 7550 in place. The device 7550 can be removed from the prosthetic capsular device, for example after medicament in the cages 7554A, 7554B has been exhausted. A second device 7550 may be inserted after removal of the first device 7550. In some implementations, multiple devices 7550 (e.g., having a smaller thickness, different shapes of devices 7550 that may be configured to fit together, etc.) may be inserted into a prosthetic capsular device.

FIG. 75E illustrates an anterior side perspective view of an example prosthetic capsular device system 7560 including the medicament delivery device 7550 of FIG. 75D. The device 7550 has been inserted into the prosthetic capsular device. The cages 7554A, 7554B are out of the visual axis, for example at least partially defined by a portion of or the entire posterior refractive surface. The prosthetic capsular device need not have any special features configured to engage the device 7550 apart from a cavity. In some implementations, the prosthetic capsular device may include a lip, posts, or the like configured to interact with the device 7550. In some implementations, the shape of the framework 7552 may correspond or substantially correspond to a lateral cross-sectional shape or a volume of the cavity of the prosthetic capsular device, for example to increase or maximize the internal volume available for the cages 7554A, 7554B.

FIG. 76A illustrates an anterior plan view of an example prosthetic capsular device 7600. To aid understanding, the device 7600 is shown holding an IOL 7602 (e.g., Akreos® Adapt AO from Bausch and Lomb). The IOL 7602 comprises a plurality of openings or holes or apertures 7604A, 7604B, 7604C, 7604D. The device 7600 comprises a plurality of poles or columns or pillars or posts 7606A, 7606B, 7606C, 7606D. The posts 7606A, 7606B, 7606C, 7606D are configured to interact with the apertures 7604A, 7604B, 7604C, 7604D. The interaction may inhibit or prevent rotation of the IOL 7602 within the device 7600, for example because the posts 7606A, 7606B, 7606C, 7606D bear against the insides of the apertures 7604A, 7604B, 7604C, 7604D. The device 7600 may comprise more or fewer posts 7606A, 7606B, 7606C, 7606D. For example, the posts 7606B, 7606D, the posts 7606A, 7606C, or other combinations may be omitted. For another example, additional posts may be added, for example inward of the rounded recesses formed between the outward protrusions and the optic of the IOL 7602. Although illustrated as generally cylindrical, the posts 7606A, 7606B, 7606C, 7606D may take other shapes (e.g., oblong, polygonal, configured to match the shapes of the apertures 7604A, 7604B, 7604C, 7604D, etc.).

FIG. 76B illustrates an anterior plan view of an example prosthetic capsular device 7610. To aid understanding, the device 7610 is shown holding an IOL 7612 (e.g., enVista™ from Bausch and Lomb). The IOL 7612 comprises a plurality of openings or holes or apertures 7614A, 7614B. The device 7610 comprises a plurality of poles or columns or pillars or posts 7616A, 7616B. The posts 7616A, 7616B are configured to interact with the apertures 7614A, 7614B. The interaction may inhibit or prevent rotation of the IOL 7612 within the device 7610, for example because the posts 7616A, 7616B bear against the insides of the apertures 7614A, 7614B. The device 7610 may comprise more or fewer posts 7616A, 7616B. For example, the post 7616A or the post 7616B may be omitted. For another example, additional posts may be added, for example inward of the haptics of the IOL 7612. Although illustrated as generally cylindrical, the posts 7616A, 7616B may take other shapes (e.g., oblong, polygonal, configured to match the shapes of the apertures 7614A, 7614B, etc.).

FIG. 76C illustrates an anterior plan view of an example prosthetic capsular device 7620. FIG. 76D illustrates an anterior plan view of an example prosthetic capsular device 7630. To aid understanding, the devices 7620, 7630 are each shown holding an IOL 7622 (e.g., Akreos® MICS from Bausch and Lomb). The IOL 7622 comprises a plurality of openings or holes or apertures 7624A, 7624B, 7624C, 7624D. The device 7620 comprises a plurality of poles or columns or pillars or posts 7626A, 7626B, 7626C, 7626D at the radially outward edges of the haptics. The posts 7626A, 7626B, 7626C, 7626D are configured to interact with the apertures 7624A, 7624B, 7624C, 7624D. The interaction may inhibit or prevent rotation of the IOL 7622 within the device 7620, for example because the posts 7626A, 7626B, 7626C, 7626D bear against the insides of the apertures 7624A, 7624B, 7624C, 7624D. The device 7620 may comprise more or fewer posts 7626A, 7626B, 7626C, 7626D. For example, the posts 7626B, 7626D, the posts 7626A, 7626C, or other combinations may be omitted. For another example, additional posts may be added, for example configured to interact with the apices between the haptics of the IOL 7622. Although illustrated as generally cylindrical in FIG. 76C, the posts 7626A, 7626B, 7626C, 7626D may take other shapes (e.g., oblong, polygonal, configured to match the shapes of the apertures 7624A, 7624B, 7624C, 7624D (e.g., as the posts 7636A, 7636B, 7636C, 7636D of the device 7630), etc.).

FIG. 76E illustrates an anterior plan view of an example prosthetic capsular device 7640. To aid understanding, the device 7640 is shown holding an IOL 7642 (e.g., Tecnis® Toric from Abbott Medical Optics). The IOL 7642 comprises a plurality of rounded recesses 7644A, 7644B. The device 7640 comprises a plurality of poles or columns or pillars or posts 7646A, 7646B. The posts 7646A, 7646B are configured to interact with the apertures 7644A, 7644B. In some implementations, the rounded recesses 7644A, 7644B can snap around the posts 7646A, 7646B. The interaction may inhibit or prevent rotation of the IOL 7642 within the device 7640, for example because the posts 7646A, 7646B bear against the insides of the recesses 7644A, 7644B. The device 7640 may comprise more or fewer posts 7646A, 7646B. For example, the post 7646A or the post 7646B may be omitted. For another example, additional posts may be added. Although illustrated as generally cylindrical, the posts 7646A, 7646B may take other shapes (e.g., oblong, polygonal, configured to match the shapes of the apertures 7644A, 7644B, etc.).

FIG. 76F illustrates an anterior plan view of an example prosthetic capsular device 7650. To aid understanding, the device 7650 is shown holding an IOL 7652 (e.g., AcrySof® IQ Toric from Alcon). The IOL 7652 does not comprise openings or recesses of note. The device 7650 comprises a plurality of poles or columns or pillars or posts 7656A, 7656B, 7656C, 7656D. The posts 7656A, 7656B, 7656C, 7656D are configured to interact with the haptics of the IOL 7652. The interaction may inhibit or prevent rotation of the IOL 7652 within the device 7650, for example because the posts 7656A, 7656B, 7656C, 7656D bear against the sides of the haptics. The device 7650 may comprise more or fewer posts 7656A, 7656B, 7656C, 7656D. For example, the posts 7656A, 7656B, the posts 7656C, 7656D, or other combinations may be omitted. For another example, additional posts may be added, for example configured to act with other portions of the haptics and/or the optic portion of the IOL 7652. Although illustrated as generally cylindrical, the posts 7656A, 7656B, 7656C, 7656D may take other shapes (e.g., oblong, polygonal, configured to match the shapes of haptic features, etc.).

Several examples of prosthetic capsular device features configured to interact with example IOL features are explicitly provided herein, other housing shapes, posts, openings, insulated areas, combinations thereof, etc. may be adapted for other IOLs or other devices that may be contained in the device.

FIG. 72A illustrates an anterior side perspective view of an example prosthetic capsular device 7200. The device 7200 comprises interior structures or hairpins 7238A, 7238B, 7238C, 7238D. The hairpins 7238A, 7238B, 7238C, 7238D are in the capsule of the housing structure 7212 of the device 7200. FIG. 72B illustrates a magnified side view of an example portion 7038, representative of one of the hairpins 7238A, 7238B, 7238C, 7238D, of the example prosthetic capsular 7200 device of FIG. 72B. The hairpin 7238 comprises an anchor portion 7240, for example configured to anchor the hairpin 7238 in the housing structure 7212. The hairpin 7238 further comprises a pin portion 7042 extending radially inward from the anchor portion 7240 and then turning to extend radially outward. As illustrated in FIG. 72B, the hairpin 7038 turns approximately 270°, then reverses 180° three times to form undulations like a hairpin. The first turn may be larger than the later turns. The hairpin 7238 may comprise fewer turns, including a single turn that may be less than 270°. FIG. 72B shows interaction of the hairpin 7238 with a loop structure 7252 of another device 7250 (which could include a container formed out of any biocompatible material including but not limited to surgical suture material such as silk, prolene, gortex, nylon, vicryl, or the like). The loop structure 7252 can be positioned proximate to the radially inward extension of the hairpin 7238 and slid radially inward to be proximate to the first turn, which can lock the device 7250 into position. In some implementations, a plurality of other devices can be coupled to a single hairpin 7238, for example all anchoring proximate to the first turn or anchoring along different longitudinal positions of the radially inward extension. The hairpin 7238 may be compatible with other types of attachment structures, for example the hairpin structure 7142 of FIGS. 71A and 71B, the carabiner 7150 of FIG. 71C, the arrowhead structure 7162 of FIG. 71D, etc.

The hairpins 7238A, 7238B, 7238C, 7238D may be formed from the same material as (e.g., integral with) the ring structure portions 7220A, 7220B, 7220C, 7220D. Other positions, quantities, and shapes of the openings are also possible. For example, the device 7200 may comprise only one hairpin, only two hairpins, only three hairpins, only four hairpins, or more than four hairpins. The hairpins 7238A, 7238B, 7238C, 7238D are illustrated as being extending inwardly from ends of the housing structure 7212, but the hairpins may extend inwardly from sides of the housing structure 7212 (e.g., like the hairpins 7238E, 7238F of FIG. 72A) and/or outwardly from the housing structure 7212. Each of the hairpins 7238A, 7238B, 7238C, 7238D may be the same as the others of the hairpins 7238A, 7238B, 7238C, 7238D. At least one of the hairpins 7238A, 7238B, 7238C, 7238D may be different than at least one of the other hairpins 7238A, 7238B, 7238C, 7238D. The hairpins 7238A, 7238B, 7238C, 7238D may provide an anchor point, for example interacting with a protrusion, for another device to be held inside the device 7200. Other devices can be coupled to one or more of the hairpins 7238A, 7238B, 7238C, 7238D after the device 7200 has been positioned in a natural capsular bag of an eye. Coupling the other device(s) after positioning of the device 7200, for example as opposed to coupling or integrally forming the other device(s) to the device 7200 before positioning the device 7200 in an eye, can allow the device 7200 to be injected through a smaller opening as described herein. Coupling other device(s), for example as opposed to coupling or integrally forming the other device(s) with the device 7200, can allow a variety of other devices to be used. In some implementations, the other device(s) may be removed and a replacement or other device may optionally be coupled during a later procedure. In some implementations, the other device(s) may be absorbed over time, and a replacement or other device may optionally be coupled during a later procedure. The hairpins 7238A, 7238B, 7238C, 7238D may be formed during formation of the device 7200 (e.g., as part of a molding process) and/or formed after formation of the device 7200. In some implementations, the housing structure 7212 may comprise a different material than the material surrounding the hairpins 7238A, 7238B, 7238C, 7238D (e.g., the housing structure 7212 comprising silicone and the hairpins 7238A, 7238B, 7238C, 7238D comprising polyimide).

As seen in FIG. 58A, but perhaps best seen in FIGS. 58C and 58D, the ring structure 5820 extends from the housing structure 5812 at a position anterior to a longitudinal midline of the device 5800, which may create separation between the anterior capsule and posterior capsule, which could play a role in use of the device 5800 to provide accommodation.

FIG. 59A illustrates a side view of an example prosthetic capsular device 5900. The device 5900 can provide accommodation, as explained in further detail below. The device 5900 comprises a housing structure 5912, a ring structure 5920, and a refractive surface 5910. The ring structure 5920 may be similar, for example, to the ring structure 5820. In some implementations, the ring structure 5920 can allow the device 5900 to be sutured to parts of an eye such as a natural capsular bag, zonules, ciliary muscles, etc. The refractive surface 5910 may be similar, for example, to the refractive surface 5810. The housing structure 5912 may be similar to, for example, the housing structure 5812. The end portions of the housing structure 5912 may arch posterior to the central plane of the central plane of the refractive surface 5910, placing the refractive surface 5910 in a relatively anterior position (e.g., compared to the refractive surface 5810), in the absence of outside forces (e.g., capsular forces). The housing structure can have an arch amount 5930 that may be measured by angle, distance, and/or percentage. In some implementations, the arch amount 5930 is between about 10° and about 50° (e.g., about 10°, about 20°, about 25°, about 30°, about 35°, about 40°, about 50°, ranges between such values, etc.).

The device 5900 comprises an opening 5908 spaced from the refractive surface 5910. Different longitudinal or anterior-posterior positions of the refractive surface 5910, which may be at least partially measured by distance from the relatively stable positioning of the opening 5908, provide different effective lens powers.

FIGS. 59B and 59C illustrate an example method of use of the example prosthetic capsular device 5900 of FIG. 59A. The device 5900 has been positioned in a natural capsular bag after a phacoemulsification. The natural capsular bag is surrounded by zonules 5942, which are connected to ciliary muscles 5940. In a natural eye, the ciliary muscles 5940 contract radially inward to focus on close objects (accommodation or accommodated state), which allows the zonules 5942 to relax, allowing the lens to relax and expand longitudinally; the ciliary muscles 5940 relax radially outward when not focused on close objects (disaccomodation or dis-accomodated state), which tightens the zonules 5942, longitudinally compressing the natural lens. The changes in lens shape alter the lens power, which provides focus abilities.

In FIG. 59B, the ciliary muscles 5940 are in a contracted state with the zonules 5942 relaxed for accommodation. Without forces from tightened zonules 5942, the device 5900 can be in substantially the shape shown in FIG. 59A. The refractive surface 5910 is spaced from the opening 5808 by a distance 5946, which provides a first effective lens power. In FIG. 59C, the ciliary muscles 5940 are in a relaxed or resting state with the zonules 5942 tightened for dis-accommodation. The outward forces from the tightened zonules 5942, as indicated by the arrow 5948, causes the device 5900 to stretch radially outwardly, resulting in a reduction in arch of the housing structure 5912. Reducing the arch of the housing structure 5912 moves the refractive surface 5910 posterior, as indicated by the arrow 5952. The position of the refractive surface 5910 is spaced from the opening 5908 by a distance 5954, which provides a second effective lens power less than the first effective lens power. If a subject focuses on a close object, the ciliary muscles 5940 will contract, allowing the zonules 5942 to relax, as indicated by the arrow 5950, and the refractive surface 5910 to move anterior, as indicated by the arrow 5944, thereby increasing effective lens power. The effective lens power of the device 5900 is thereby adjustable during natural accommodation. Rather than changing lens shape and actual lens power as in a natural lens, the same anatomy acts to change the position of the refractive surface 5910 and the effective lens power of the device 5900.

FIGS. 60A-60N illustrate an example method of loading and ejecting the example prosthetic capsular device 5880 of FIG. 58E. FIG. 60A shows the device 5880 in a case 6002, for example similar to the case 5702. The case 6002 includes a first part 6010 and a second part 6011. The first part 6010 is spaced from the second part 6011 by a gap 6012. Each of the first part 6010 and the second part 6011 comprises a plurality of frustoconical posts 6014. The device 5880 is radially inward of the posts 6014. In FIGS. 60B and 60C, forceps 6004 (e.g., Cumming CrystaLens Forceps from Miltex, Inc. of Plainsboro, N.J.) are used to remove the device 5880 from the case 6002. The gap 6012 allows one arm of the forceps 6004 to reach under the device 5880. In FIGS. 60D-60F, the device 5880 is loaded into an injector 6006 (e.g., Accuject 2.6 BL (back load) from Medicel AG of Wolfhalden, Switzerland). The forceps 6004 continue to hold the device 5880 while the device 5880 is loaded into a cavity of the injector 6006. The injector 6008 includes a snap lock mechanism 6008 to secure the device 5880 after loading. In FIGS. 60D and 60E, the mechanism 6008 is open. In FIG. 60F, the mechanism 6008 is snapped closed. FIG. 60D also shows the distal tip 6016 of the injector 6006.

FIGS. 60G-60M show the device 5880 being ejected from the distal tip 6016 of the injector 6006 by longitudinal advancement of a plunger 6018, as indicated by the arrow 6019. The device 5880 stretches longitudinally as the device 5880 is advanced through the injector 6006, which tapers towards the distal tip 6016. In FIG. 60G, the distance 6020 between the ring portions of the device 5880 is indicative of a first level of stretching. In FIG. 60H, the distance 6022 between the ring portions of the device 5880 is indicative of a second level of stretching. The distance 6022 is longer than the distance 6020 (as drawn, about 73% longer). In FIG. 60I, just before the device 5880 is about to start to exit the distal tip 6016 of the injector 6006, the distance 6024 between the ring portions of the device 5880 is indicative of a third level of stretching. The distance 6024 is longer than the distance 6020 (as drawn, about 287% longer) and the distance 6022 (as drawn, about 65% longer). The stretching of the device 5880 is exponential as the device 5880 advances through the taper of the injector 6006. Different amounts of stretching may be achieved by use of different materials, different injectors, etc.

In FIG. 60J, the device 5880 is starting to exit the distal tip 6016 of the injector 6006. The device 5880 begins to self-expand to resume a pre-folded shape (see FIG. 60A) upon release from the injector 6006. The sequence from FIGS. 60J to 60M can take less than one second, and the self-expansion or elastic spring back shown from FIG. 60L to FIG. 60M is fast enough to be almost imperceptible.

In FIG. 60N, the injector 6006 has been retracted. If the device 5880 was in a natural capsular bag of an eye, a user may engage the openings of the ring portions with a standard IOL positioning tool such as a Lester IOL manipulator, for example to align the fins along a specific rotational axis.

Referring again to FIGS. 4B-4G and the description of example animal study procedures, FIGS. 44A-54E are photographs of results of an animal study conducted along the same lines. In five rabbits, a prosthetic capsular device 400 as shown in FIGS. 4G-4I and described above, and then an IOL (AcrySof SN60AT, a single-piece hydrophobic acrylic IOL manufactured by Alcon) were inserted into the right eye of each rabbit, and only an IOL was inserted into the left eye of each rabbit. The procedure for the prosthetic capsular device and IOL eyes was as described above, and the procedure for the IOL-only eyes was substantially the same without the prosthetic capsular device steps.

Figure 44A:
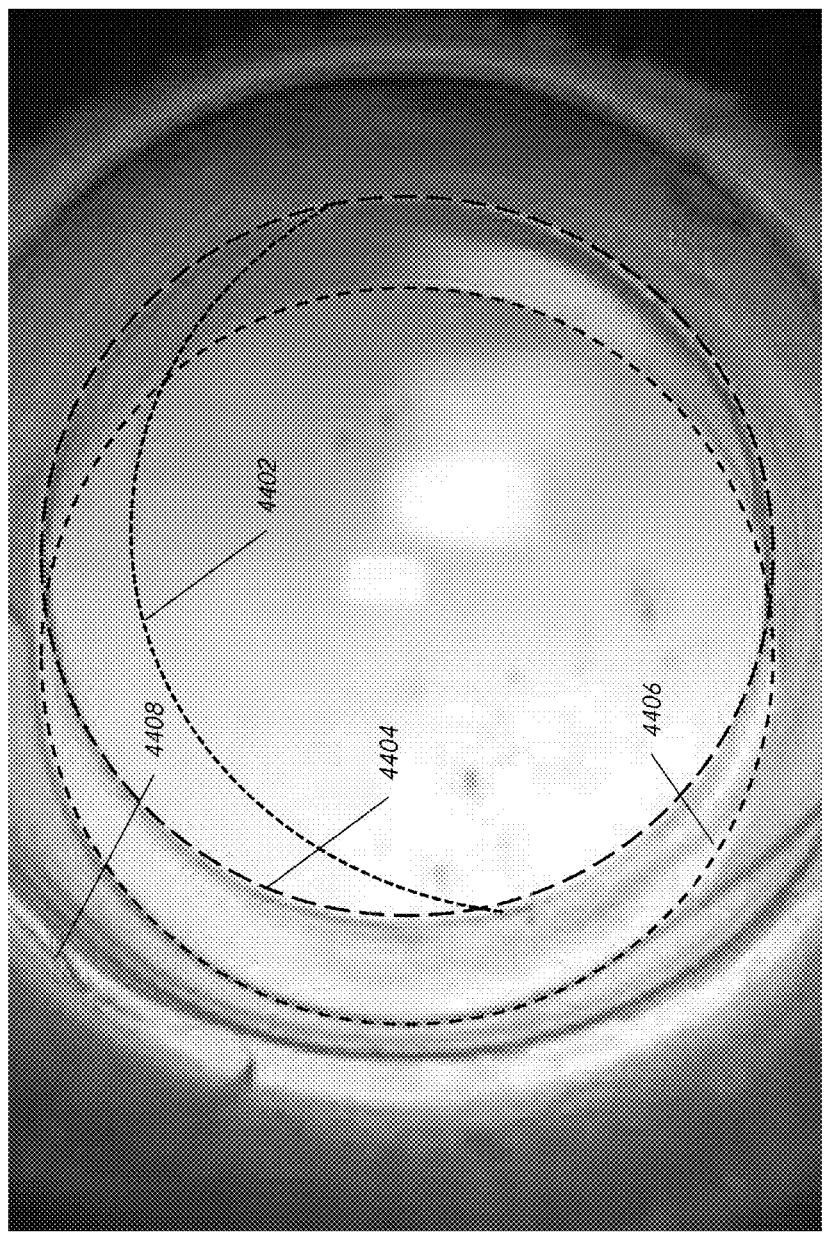
FIGS. 44A and 44B are photographs of animal study results annotated to highlight certain features.
Figure 44B:
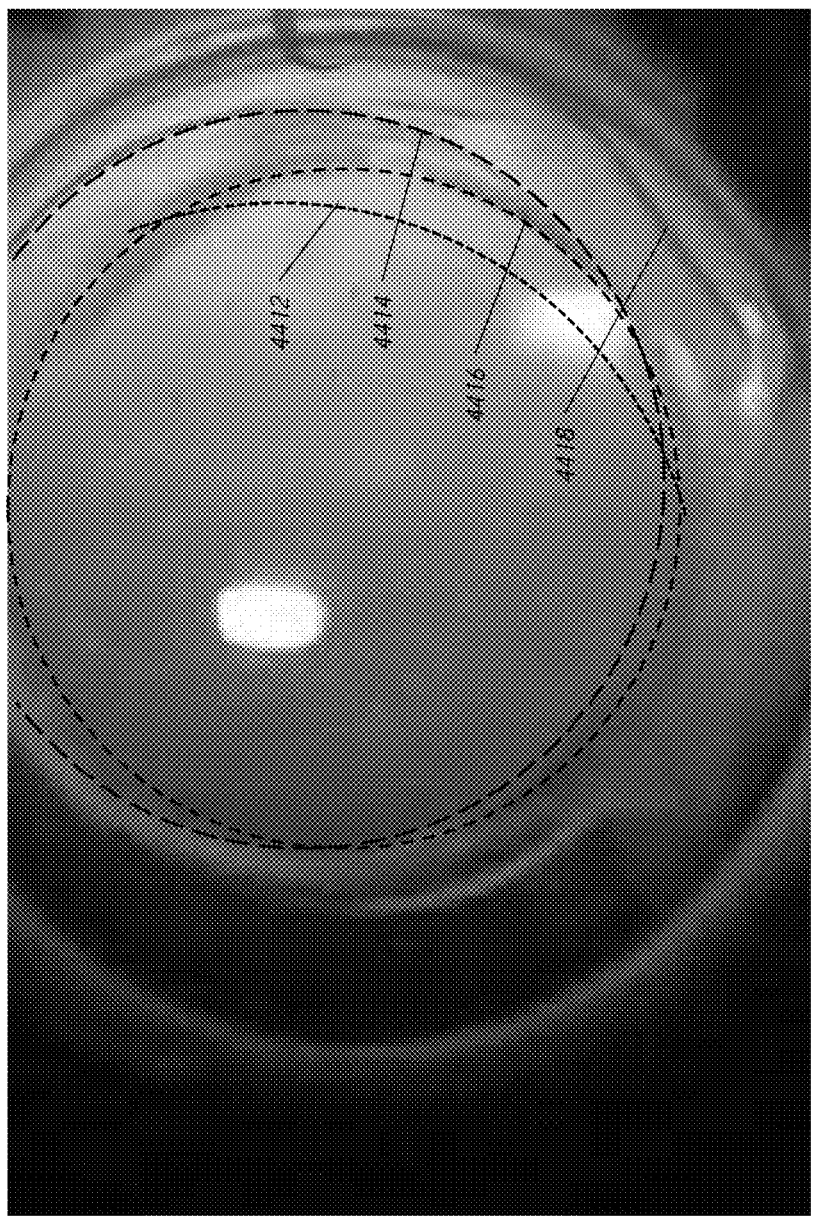

FIGS. 44A and 44B are photographs of animal study results annotated to highlight certain features. Since the location, shading, coloration, etc. can vary based on variations in device location, lighting, anatomy, and the like, FIGS. 44A and 44B are somewhat redundantly provided to provide the reader with the ability to identify the identified features in the variety of photographs described herein. In FIGS. 45A-54C, four photographs are provided for each figure with different lighting conditions, focal points, angles, etc. to provide at least one figure illustrative of the condition of the eye; however, the photographs in each figure are of the same eye at the same time (e.g., after one week, after two weeks, after three weeks, or after four weeks).

Figure 49A:
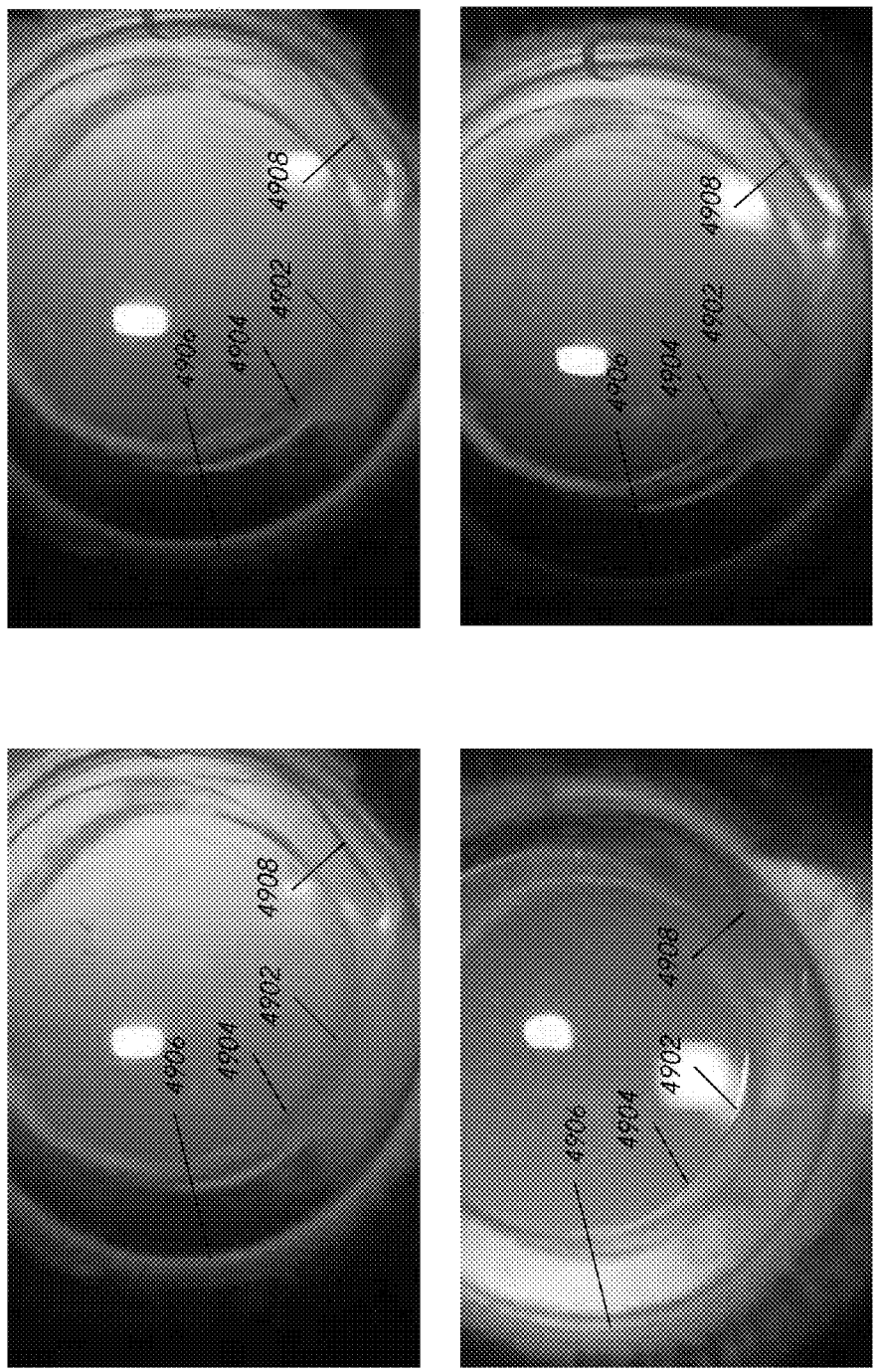
Figure 49B:
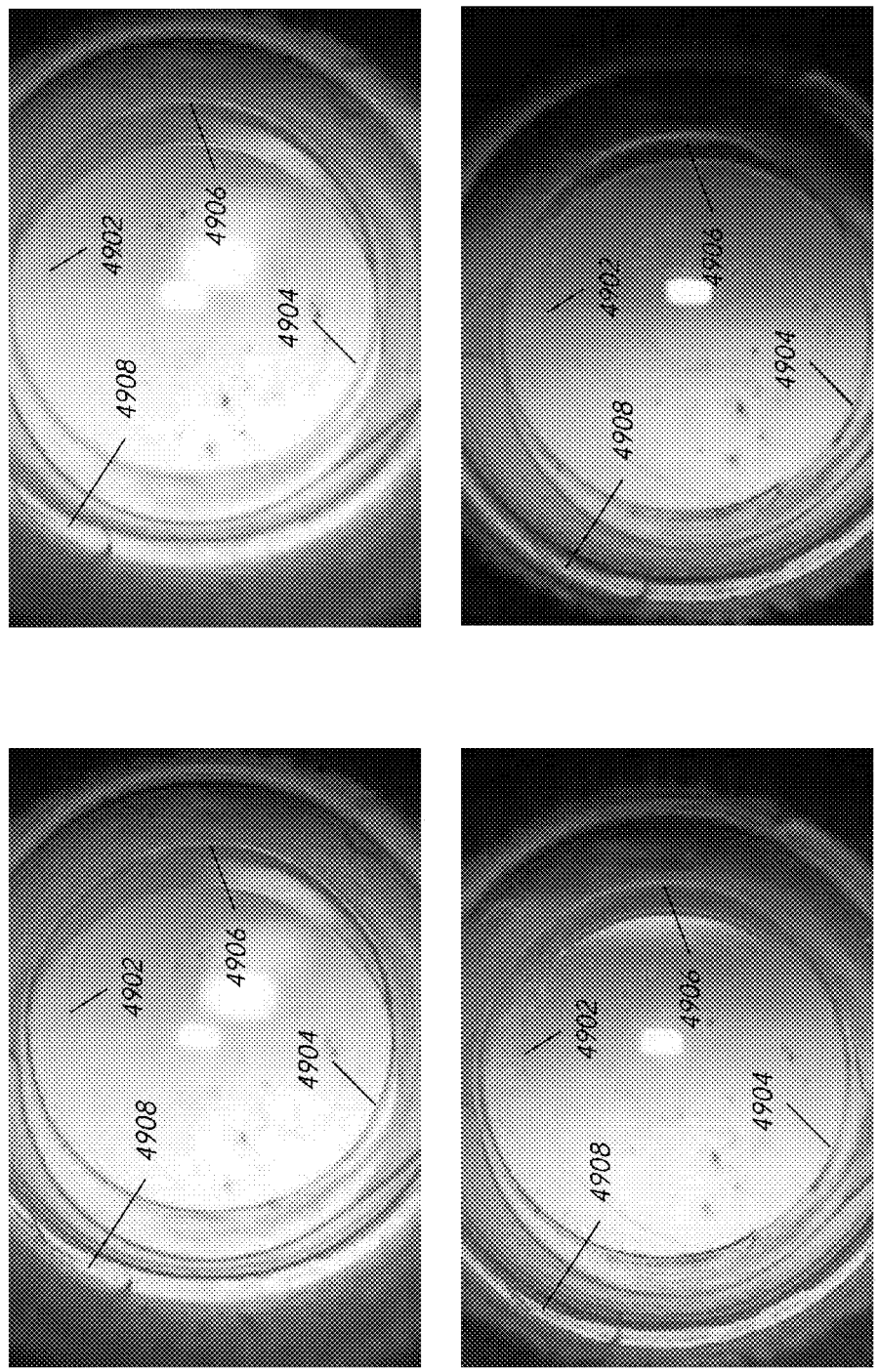

FIG. 44A, which is an annotated version of FIG. 49B (upper left photograph), illustrates an anterior capsulorhexis 4402 (shown by short dashes), a refractive surface 4404 (shown by long dashes) of an IOL, an anterior opening 4406 (shown by intermediate dashes) of a prosthetic capsular device containing the IOL, and IOL haptics 4408. FIG. 44B, which is an annotated version of FIG. 49A (upper right photograph), illustrates an anterior capsulorhexis 4412 (shown by short dashes), a refractive surface 4414 (shown by long dashes) of an IOL, an anterior opening 4416 (shown by intermediate dashes) of a prosthetic capsular device containing the IOL, and IOL haptics 4418. Photographs of eyes used for control (e.g., consisting essentially of an IOL) do not show an anterior opening of a prosthetic capsular device.

Rabbit eyes are highly inflammatory such that each week in a rabbit is approximately six months in a human. Four weeks in a rabbit, the last two sets of photographs in each figure set (e.g., "D" and "E"), is substantially equivalent to the effects after approximately two years in a human.

Figure 45A:
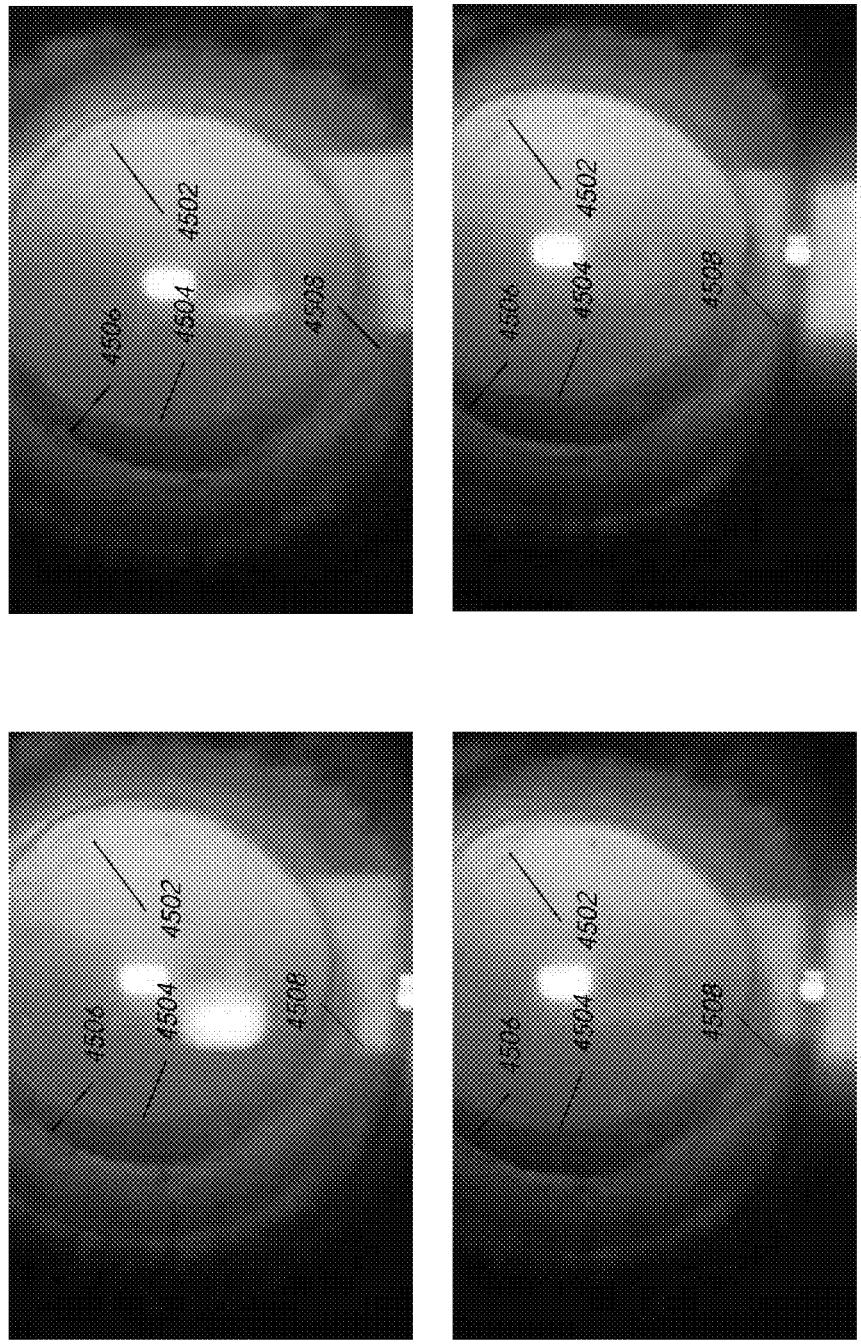
FIGS. 45A-45E are photographs of animal study results for a right eye of a first rabbit.
Figure 45B:
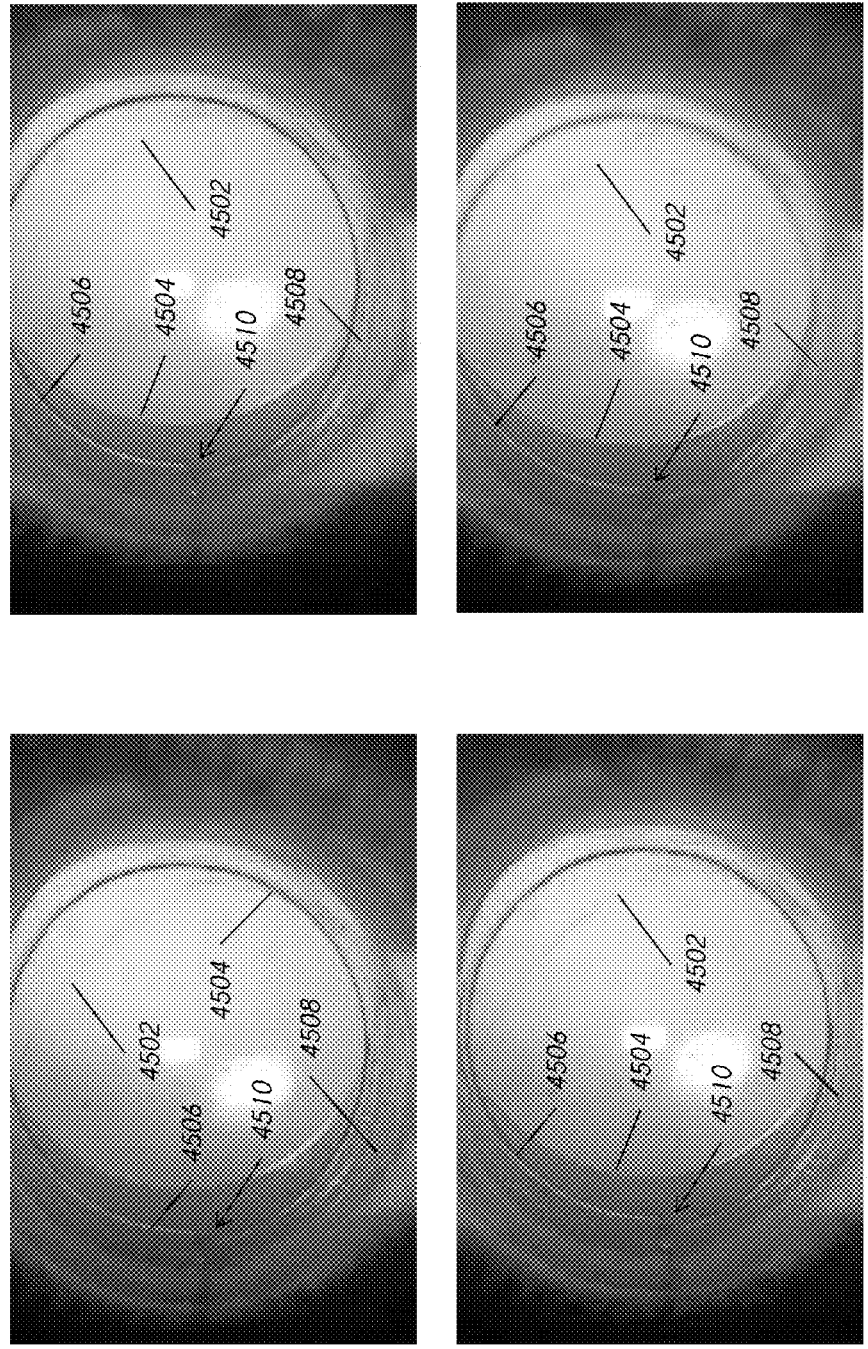
Figure 45C:
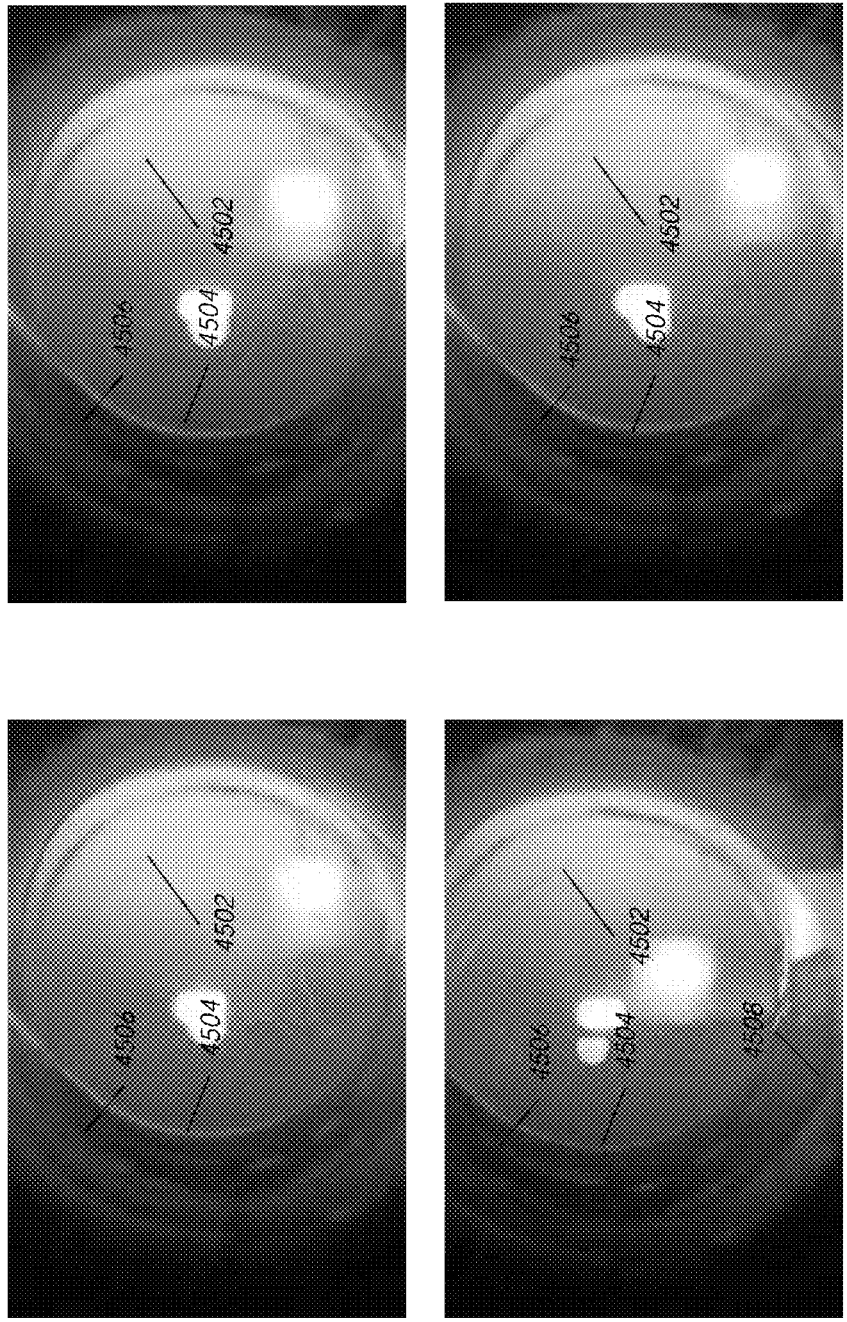
Figure 45D:
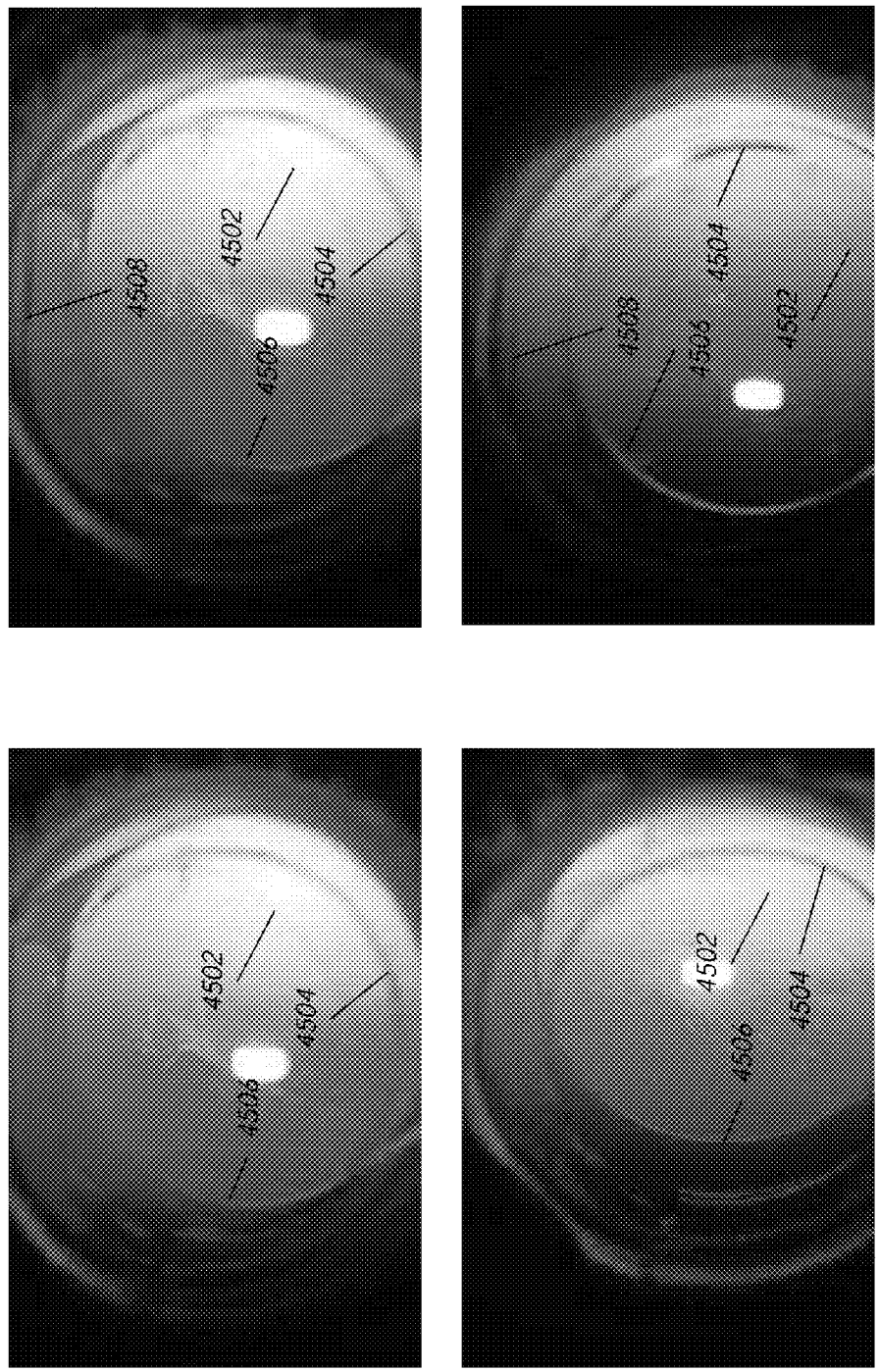
Figure 45E:
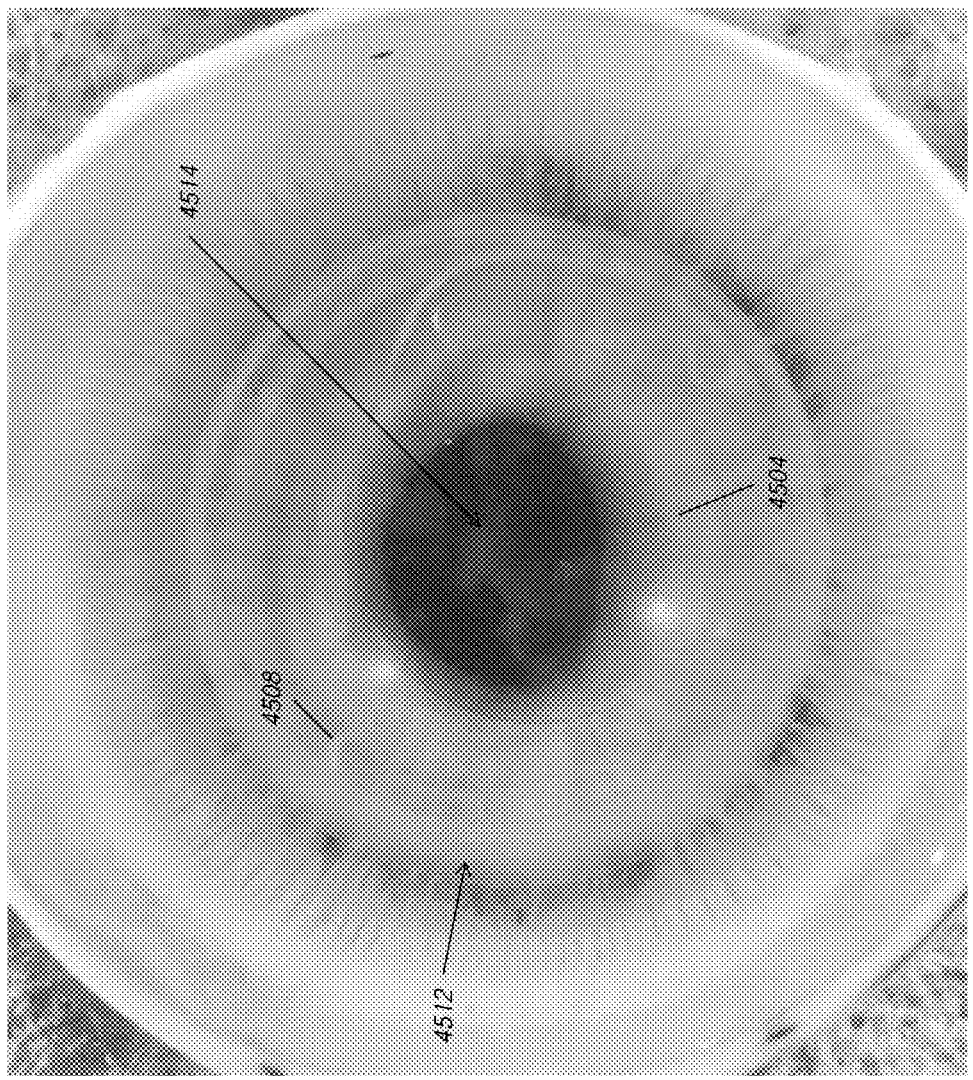

FIGS. 45A-45E are photographs of animal study results for a right eye of a first rabbit. FIG. 45A is after one week, FIG. 45B is after two weeks, FIG. 45C is after three weeks, and FIGS. 45D and 45E are after four weeks. FIGS. 45A-45E illustrate an anterior capsulorhexis 4502, a refractive surface 4504 of an IOL, an anterior opening 4506 of a prosthetic capsular device containing the IOL, and IOL haptics 4508. The IOL haptics 4508 are not visible in some figures, although the position of the haptics may be assumed based on other figures and/or the position of any visible portions of the IOL flared radially outwardly to form the start of the haptics.

As described above, the natural capsular bag undergoes chronic changes after cataract surgery believed to be largely due to the presence and continued growth of epithelial cells remaining on the natural capsular bag. If the entire natural capsular bag becomes fibrotic, and phimosis persists, there can be zonular dehiscence and changes to the effective lens position over time. Significant opacification of the natural capsular bag may be remedied by a Nd:YAG laser posterior capsulotomy. FIGS. 45A-45C show that epithelial cell migration and propagation has been successfully mediated by use of the prosthetic capsular device. Even after four weeks, the natural capsular bag is substantially free of PCO, which is best seen by comparison to FIGS. 46A-46D, which show the left eye of the same rabbit during the same time periods. Without being bound by any particular theory, the Applicant believes that the prosthetic capsular device filling or substantially filling the natural space or volume of the natural capsular bag inhibits or prevents PCO.

FIG. 45B shows a small tear 4510 in the prosthetic capsular device at approximately a 9 o'clock position. Even with this small defect, which was not present in the other four eyes containing a prosthetic capsular device and which is not believed to be a chronic problem, no irritation or opacification is evidenced in eyes containing a prosthetic capsular device. The eyes containing a prosthetic capsular device show some irritation of the vitreous.

FIG. 45E shows a Soemmering's ring 4512 and material 4514 on a posterior surface of the IOL. The Soemmering's ring 4512 is a toroidal collection of lens epithelial cells that have transformed and grown after the cataract has been removed. This occurs in the natural capsular bag after removal of the natural lens as a result of mesenchymal epithelial transformation thought to be caused by a combination of inflammatory mediators and contact between the anterior capsule and the posterior capsule.

Figure 46A:
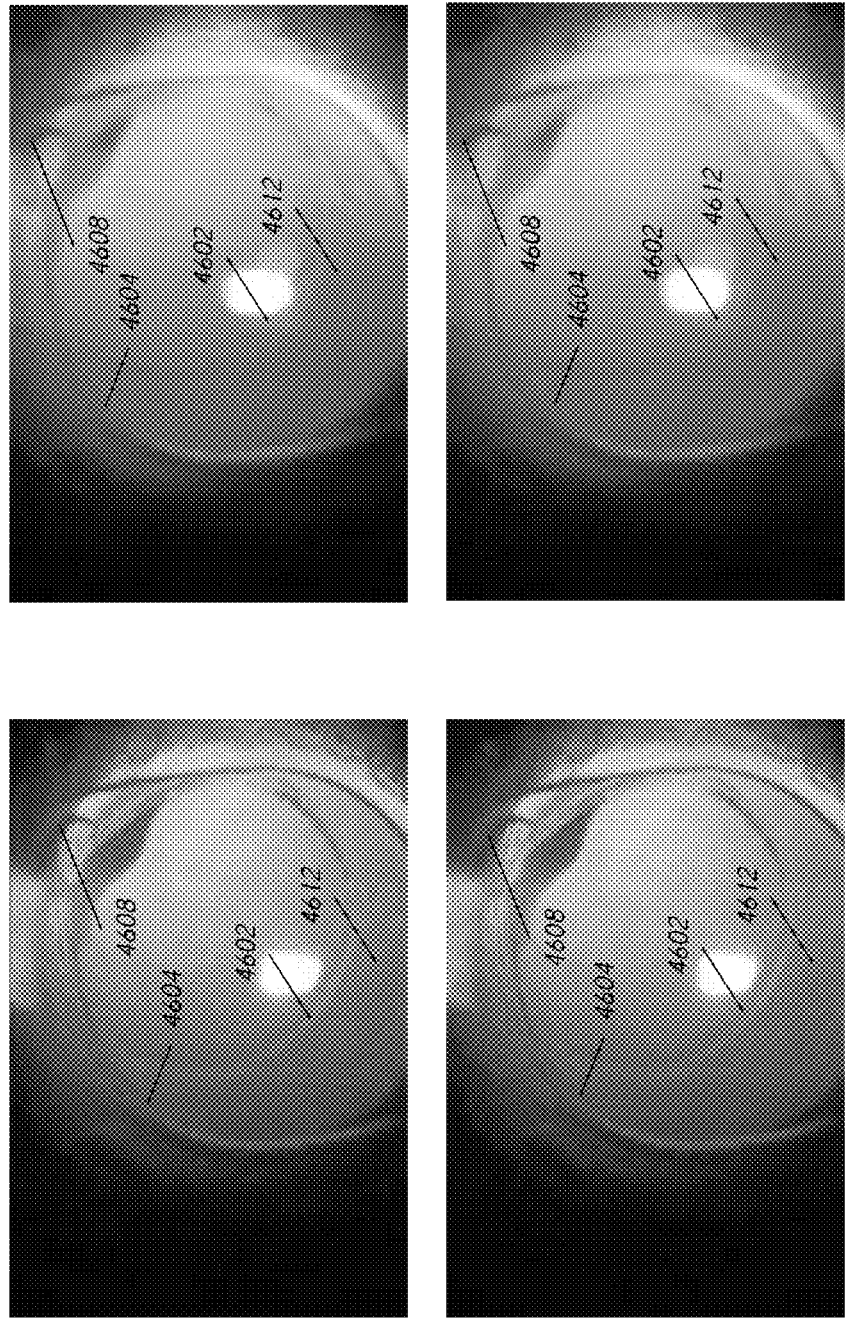
FIGS. 46A-46E are photographs of animal study results for a left eye of the first rabbit.
Figure 46B:
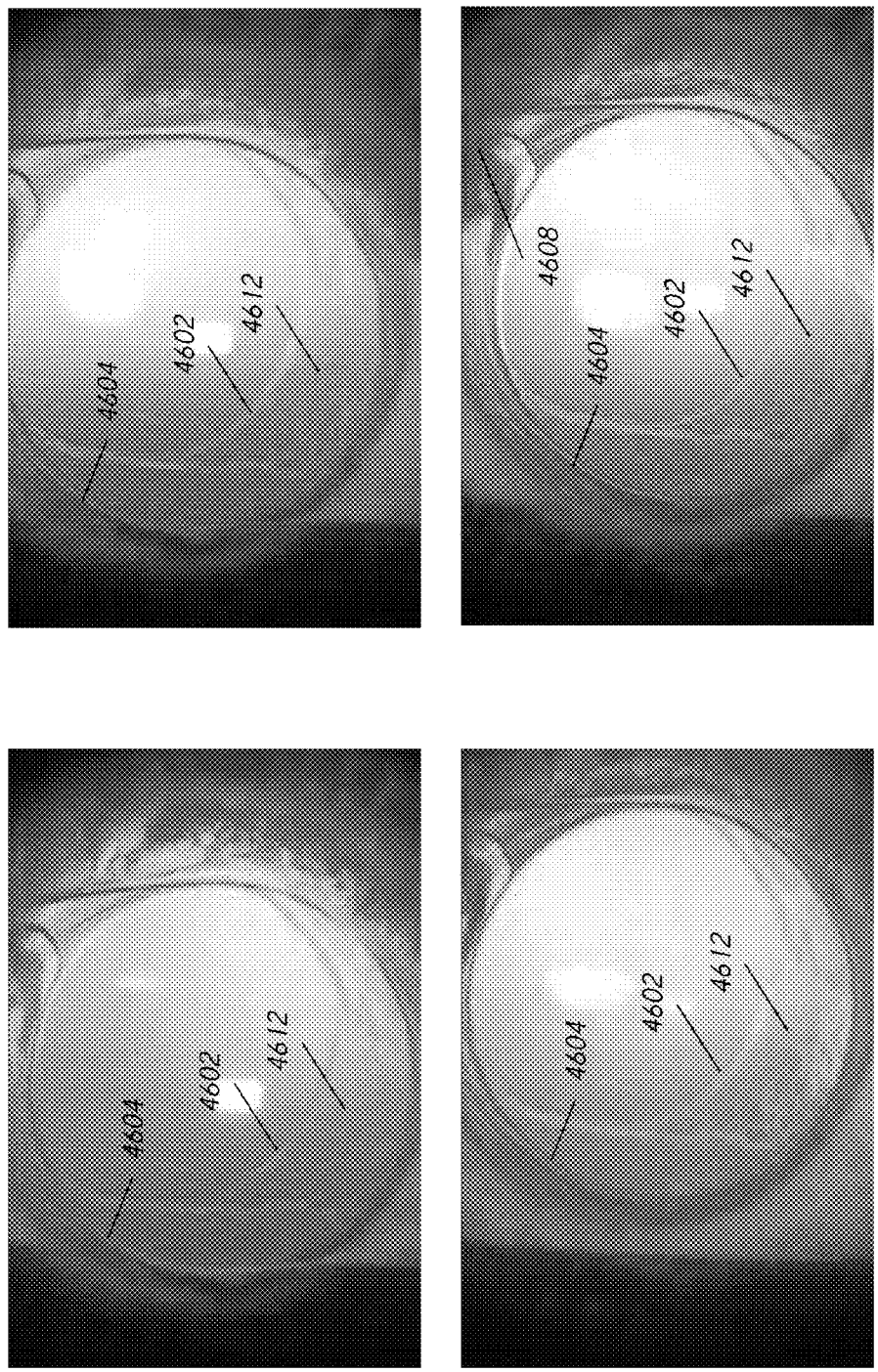
Figure 46C:
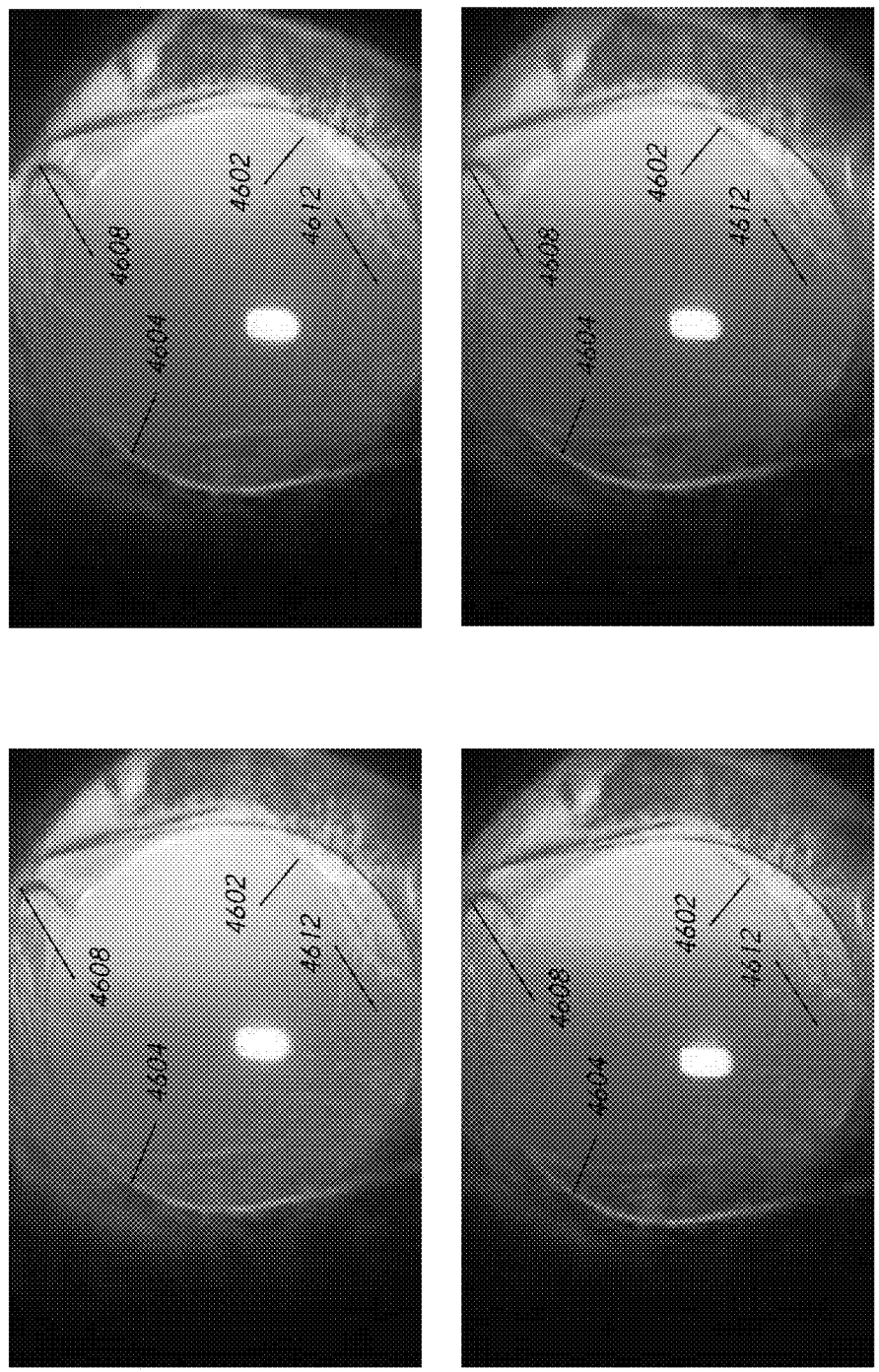
Figure 46D:
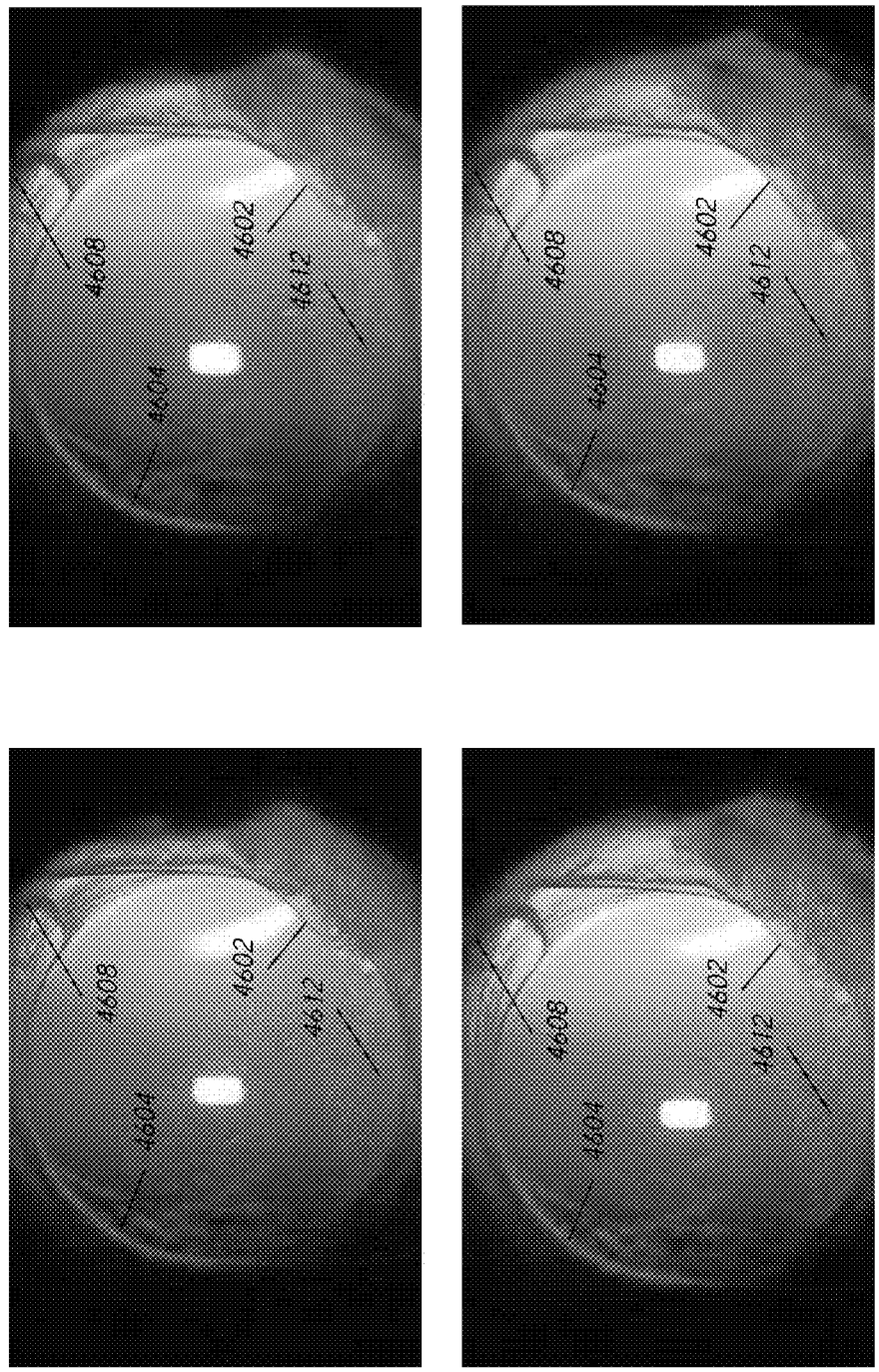
Figure 46E:
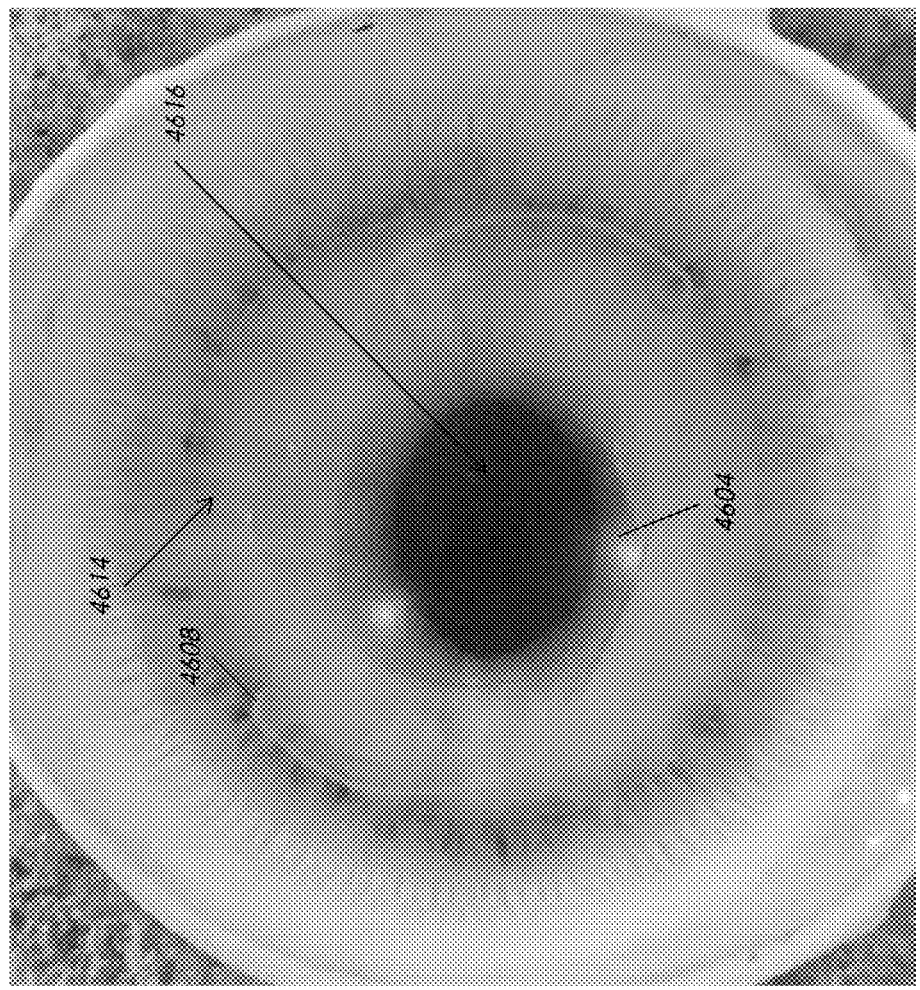

FIGS. 46A-46E are photographs of animal study results for a left eye of the first rabbit. FIG. 46A is after one week, FIG. 46B is after two weeks, FIG. 46C is after three weeks, and FIGS. 46D and 46E are after four weeks. FIGS. 46A-46E illustrate an anterior capsulorhexis 4602, a refractive surface 4604 of an IOL, and IOL haptics 4608. The IOL haptics 4608 are not visible in some figures, although the position of the haptics may be assumed based on other figures and/or the position of any visible portions of the IOL flared radially outwardly to form the start of the haptics.

The first easily identifiable difference between the right eye of FIGS. 45A-45D and the left eye of FIGS. 46A-46D is the significant fibrosis 4612 of the natural capsular bag, even after only two weeks (FIG. 46B). Fibrosis, the epithelial-mesenchymal transition of the lens epithelial cells to muscle cells (or contractile tissue or myofibroblast tissue), can cause opacification and/or can increase the elasticity of the natural capsular bag, which can cause contraction. Each are undesirable, but in combination, contraction and opacification can reduce an amount of light that can pass through the eye to the retina, reducing vision.

A normal eye under normal lighting conditions takes in light between about 3 mm and about 6 mm. Under bright light conditions, the normal eye may reduce light intake to between about 1 mm and about 2 mm. Under low light conditions, the normal eye may increase light intake to between about 7 mm and about 8 mm. Due to the contraction and fibrosis, the effective diameter at which the left eye of FIGS. 46A-46D can take in light is about 4.1 mm, which significantly impairs the vision in that eye except under the best lighting conditions. The effective diameters provided herein are rough approximations based on the photographs, but are precise enough to show visual impairment.

The second easily identifiable difference between the right eye of FIGS. 45A-45D and the left eye of FIGS. 46A-46D is the migration or shifting of the position of the IOL. The last figure ("E") for each set of eye figures, which is a gross section, best shows the centering of the IOL. The IOLs in the right eyes, which also include a prosthetic capsular device, were generally more centered and sat more posterior than the IOLs in the left eyes, in which the IOL is more flat in line with the collapsed natural capsular bag.

FIG. 46E shows a Soemmering's ring 4614 and the inception of PCO 4616. As described in further detail herein, PCO is the formation of a partially opaque membrane by the reproduction of lens epithelial cells along the posterior of the natural capsular bag. In contrast, material on the posterior surface, for example as described with respect to FIG. 45E, is most likely retrained viscoelastic that has some residual trapped fibrin or inflammatory precipitate contained within it.

Figure 47A:
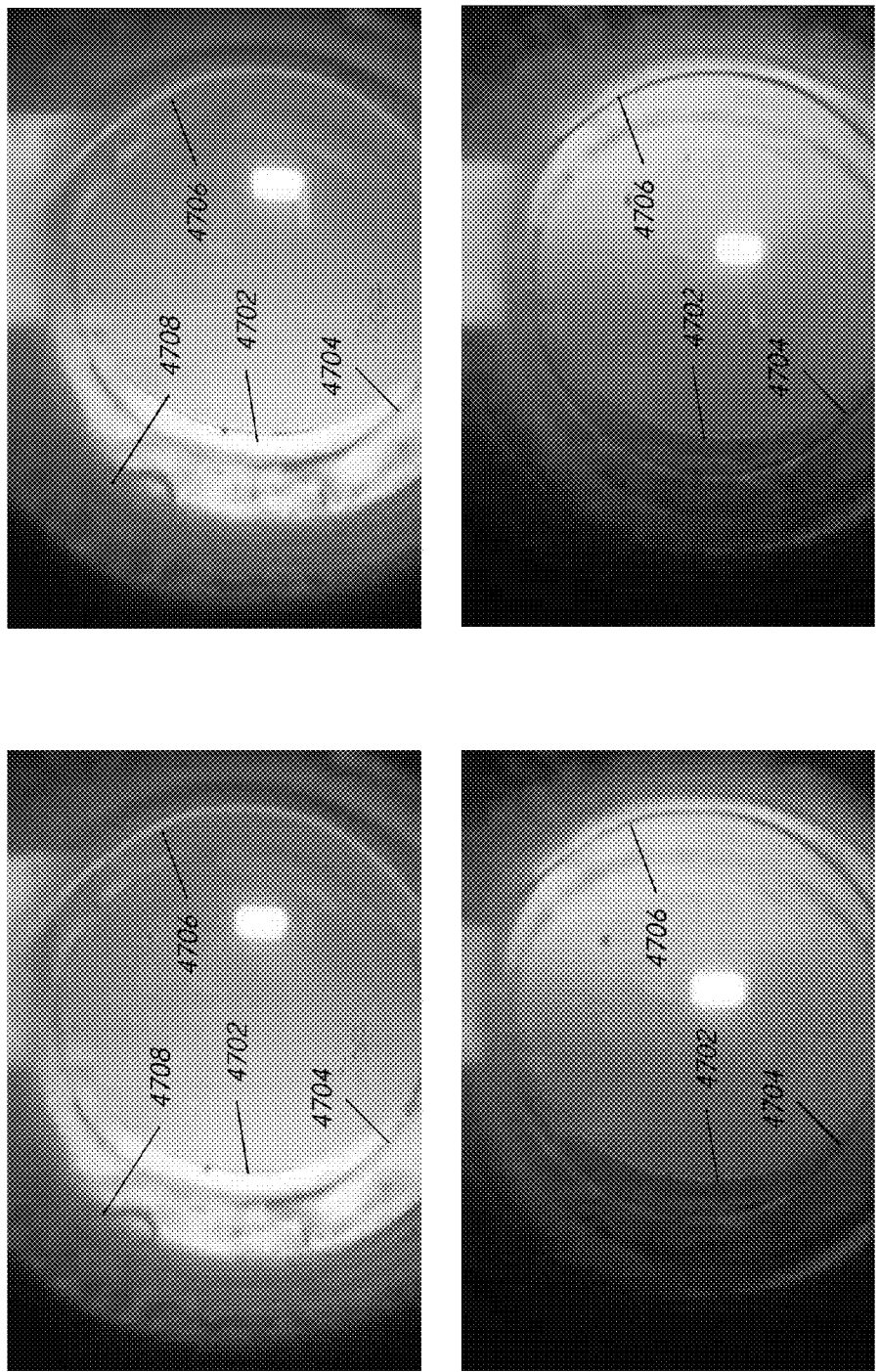
FIGS. 47A-47E are photographs of animal study results for a right eye of a second rabbit.
Figure 47B:
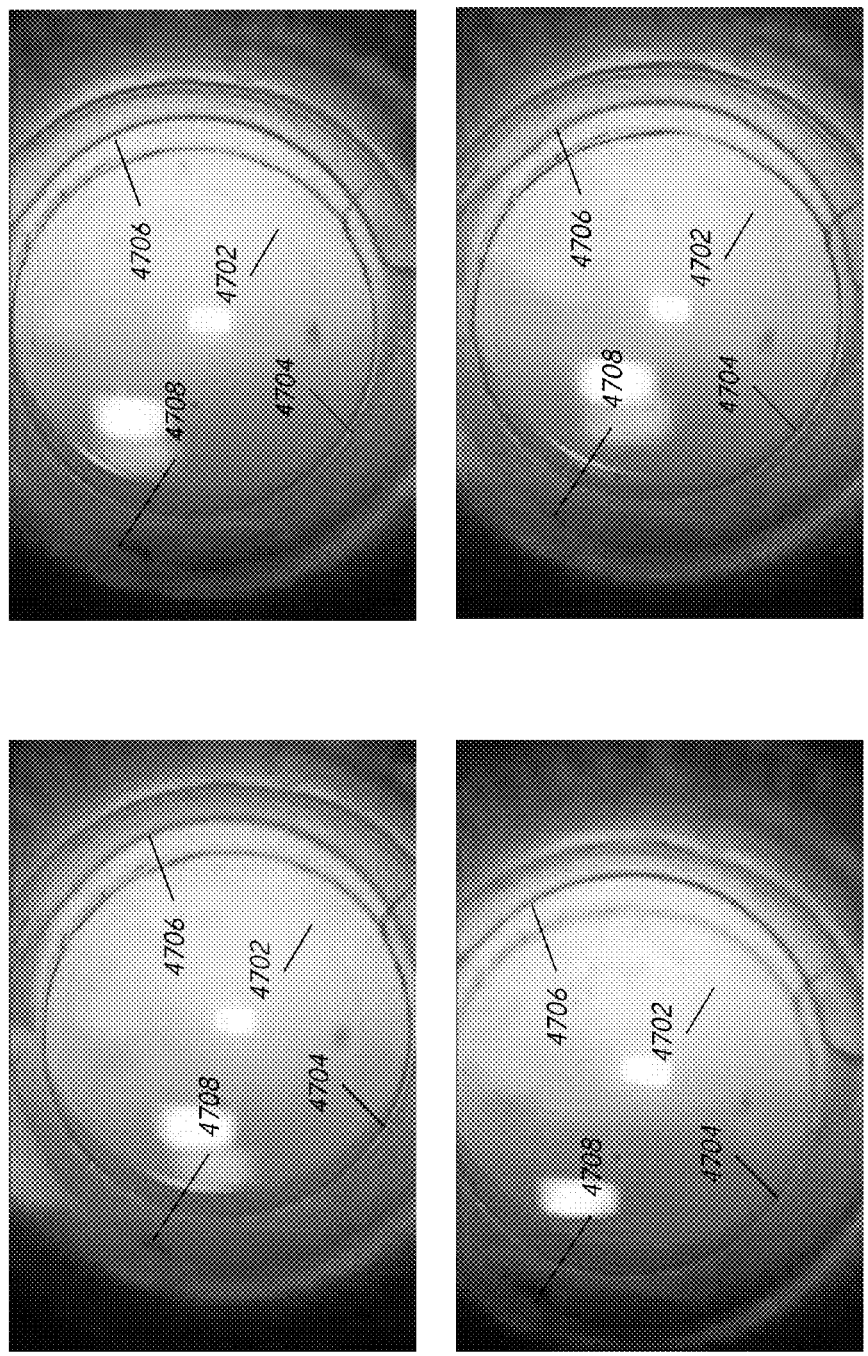
Figure 47C:
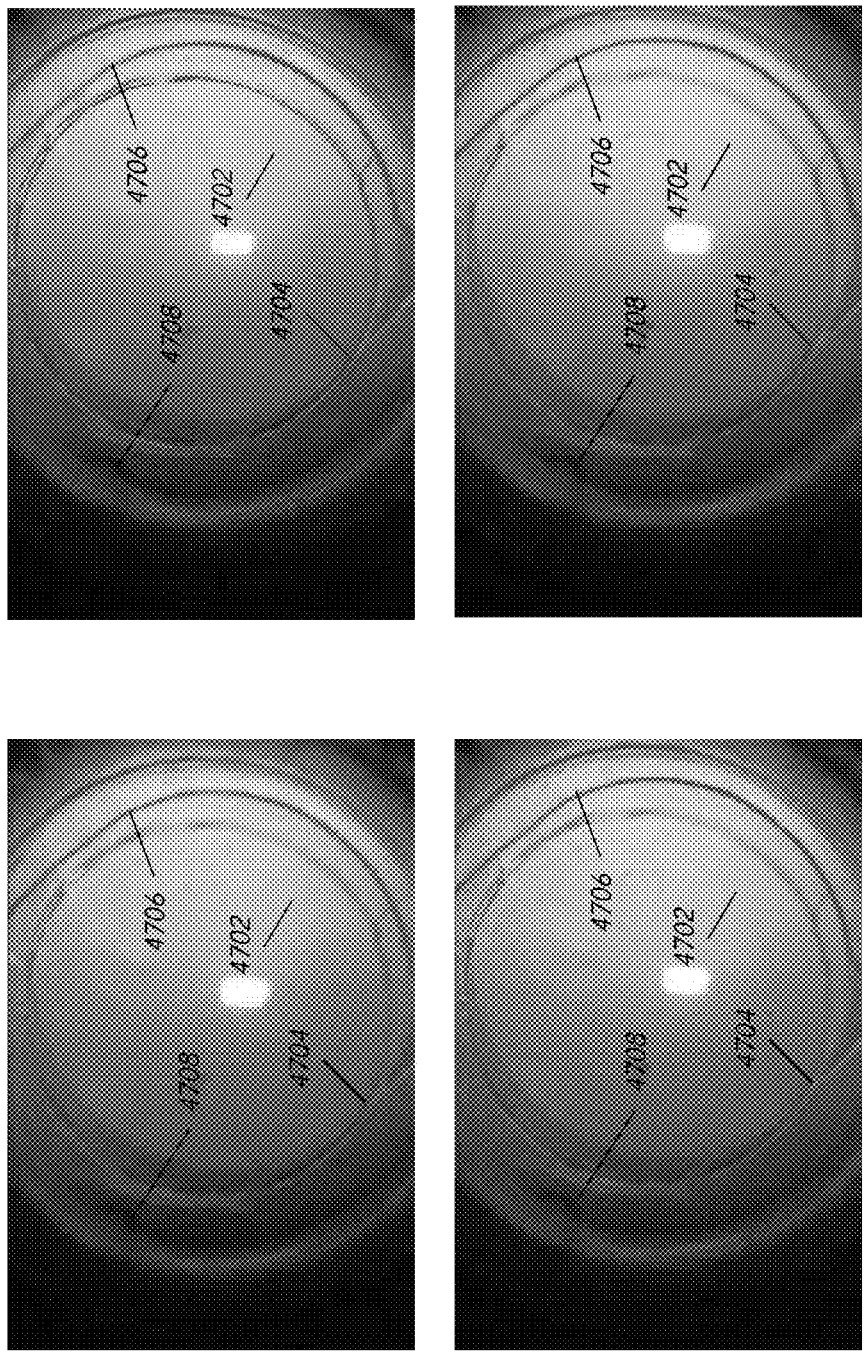
Figure 47D:
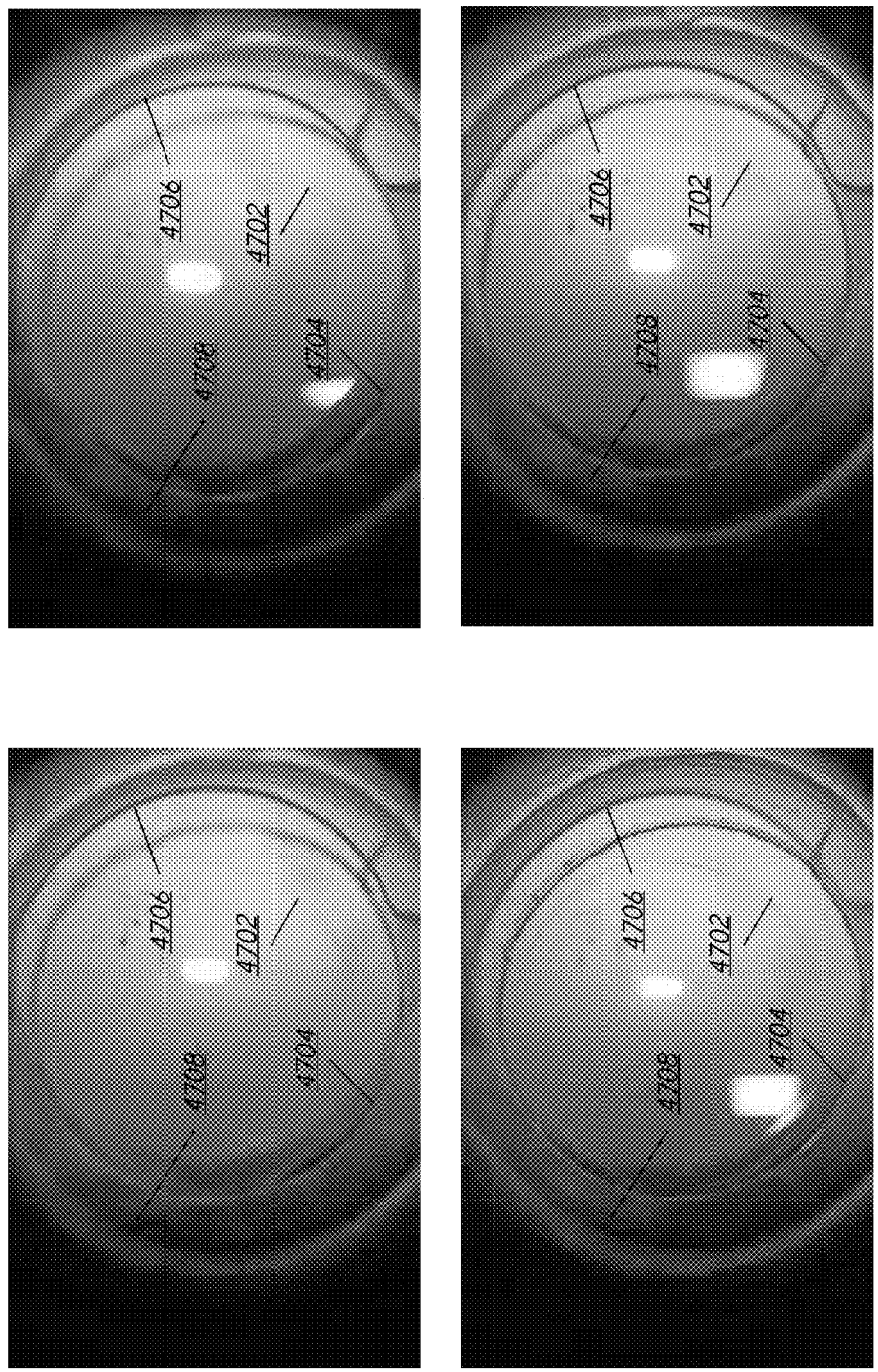
Figure 47E:
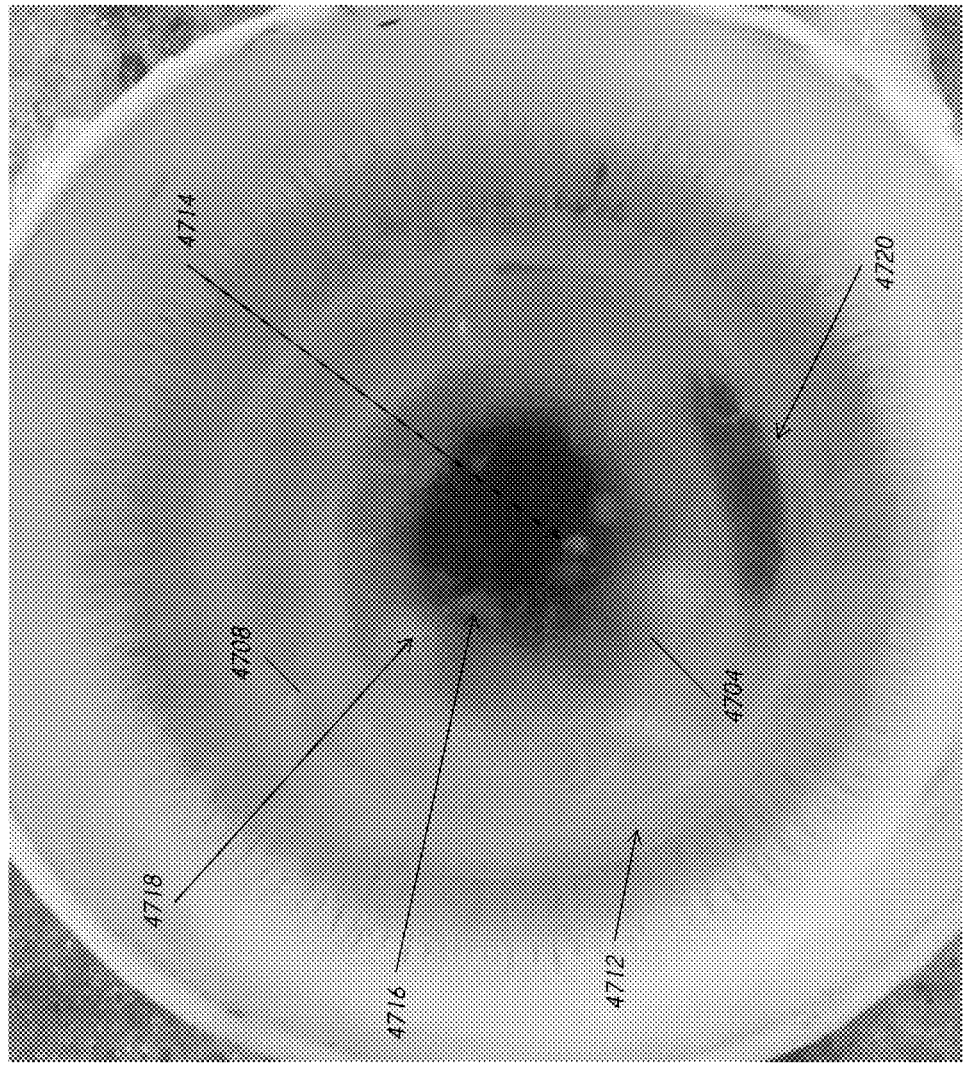

FIGS. 47A-47E are photographs of animal study results for a right eye of a second rabbit. FIG. 47A is after one week, FIG. 47B is after two weeks, FIG. 47C is after three weeks, and FIGS. 47D and 47E are after four weeks. FIGS. 47A-47E illustrate an anterior capsulorhexis 4702, a refractive surface 4704 of an IOL, an anterior opening 4706 of a prosthetic capsular device containing the IOL, and IOL haptics 4708. The IOL haptics 4708 are not visible in some figures, although the position of the haptics may be assumed based on other figures and/or the position of any visible portions of the IOL flared radially outwardly to form the start of the haptics. The IOL is well centered in the prosthetic capsular device, which can be seen by the positions of the refractive surface 4704 of the IOL and the anterior opening 4706 of the prosthetic capsular device. In contrast to FIGS. 45A-45D, FIGS. 47A-47D, as well as FIGS. 49A-49D, 51A-51D, and 53A-53D, show that the prosthetic capsular device was not torn, which is generally preferably even though tearing did not cause irritation in the eye of the first rabbit. The natural capsular bag is substantially free of fibrosis.

FIG. 47E shows a Soemmering's ring 4712, material 4714 on the posterior surface of the IOL, material 4716 attached to the posterior capsule at the vitreous face, and the inception of peripheral PCO 4718. FIG. 47E also shows a mild reaction in the anterior vitreous with some small clumps of lymphocytes 4720 in the anterior vitreous, indicative of a low-grade vitritis.

Figure 48A:
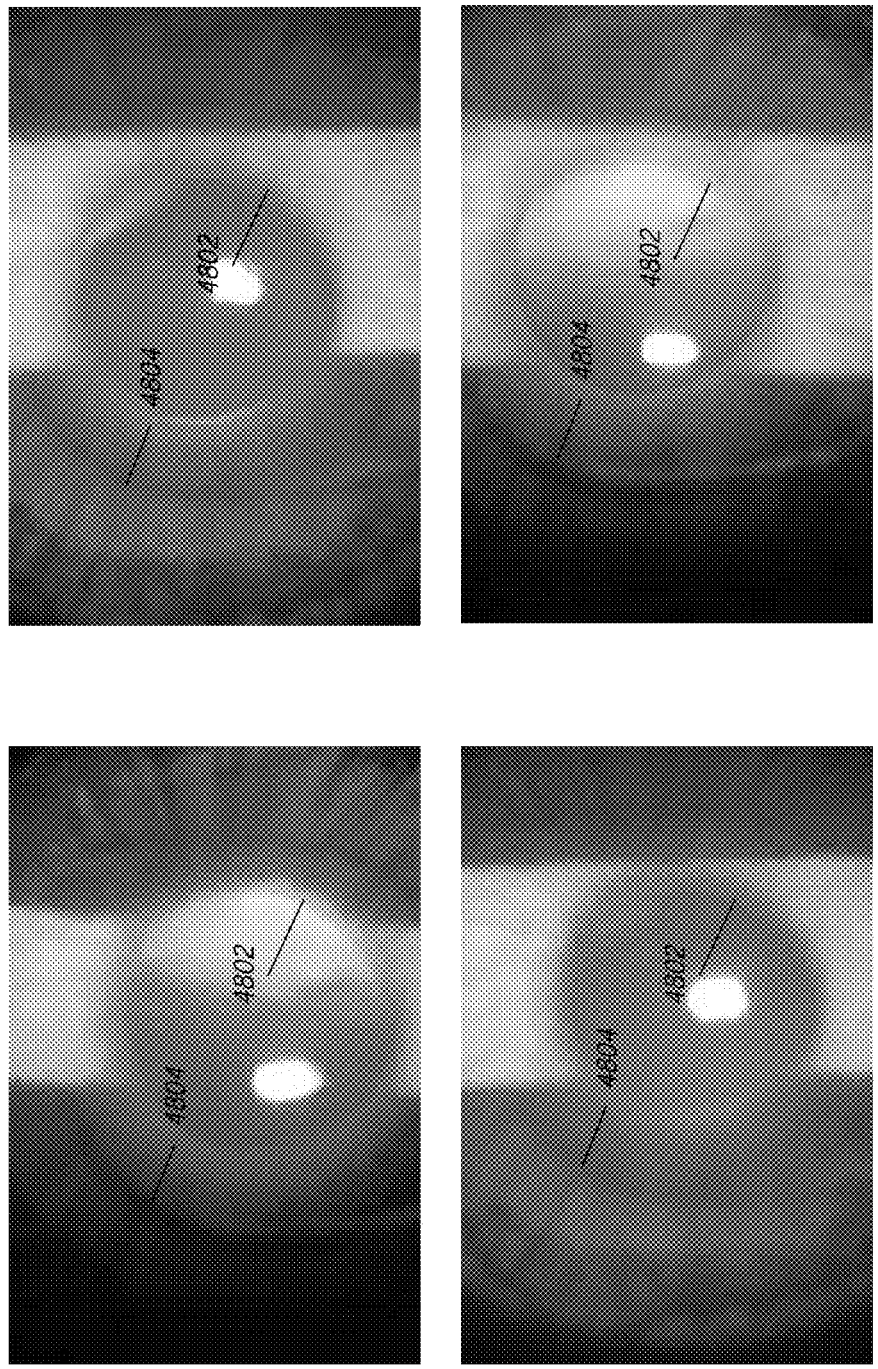
Figure 48C:
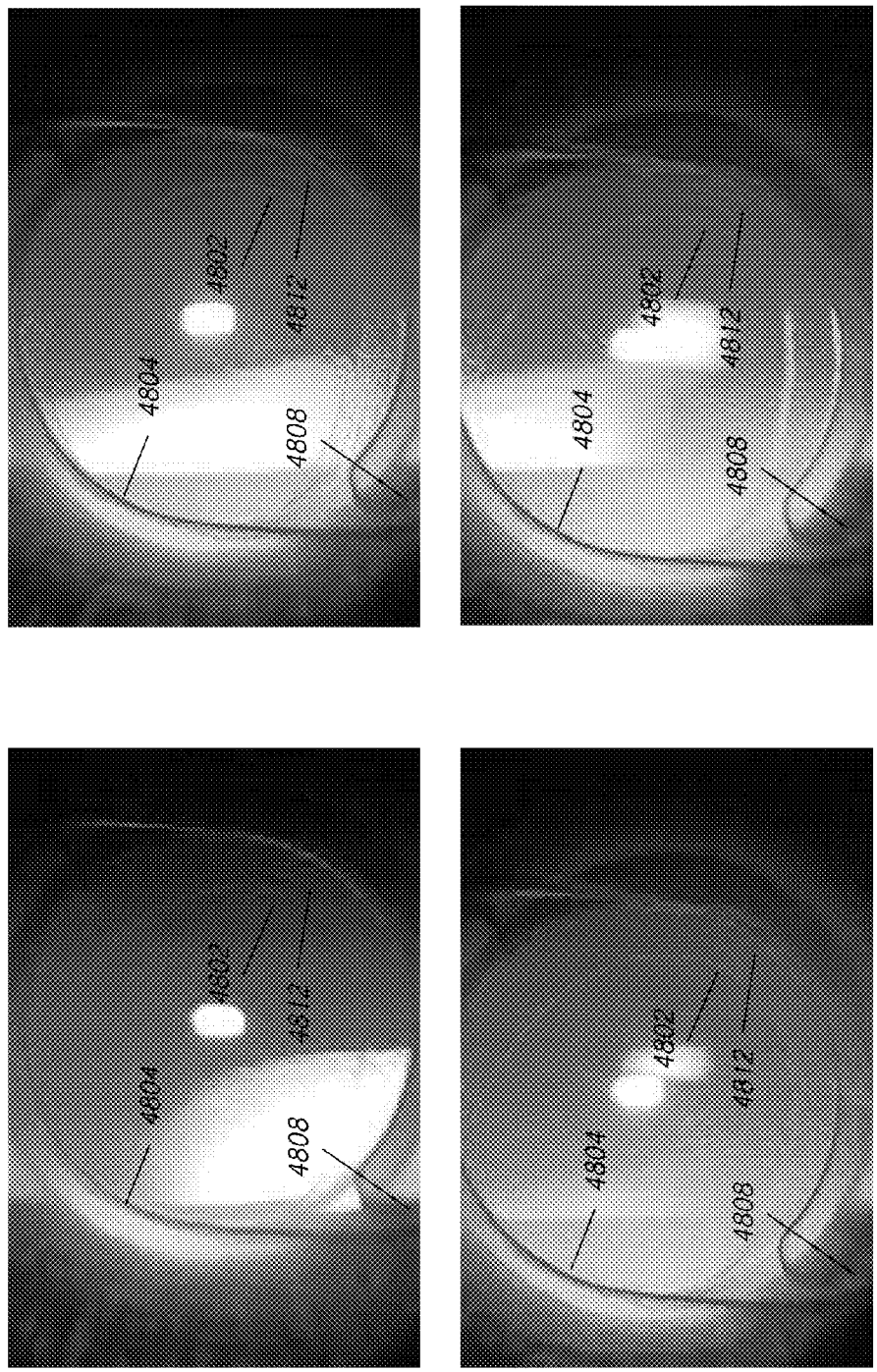
Figure 48D:
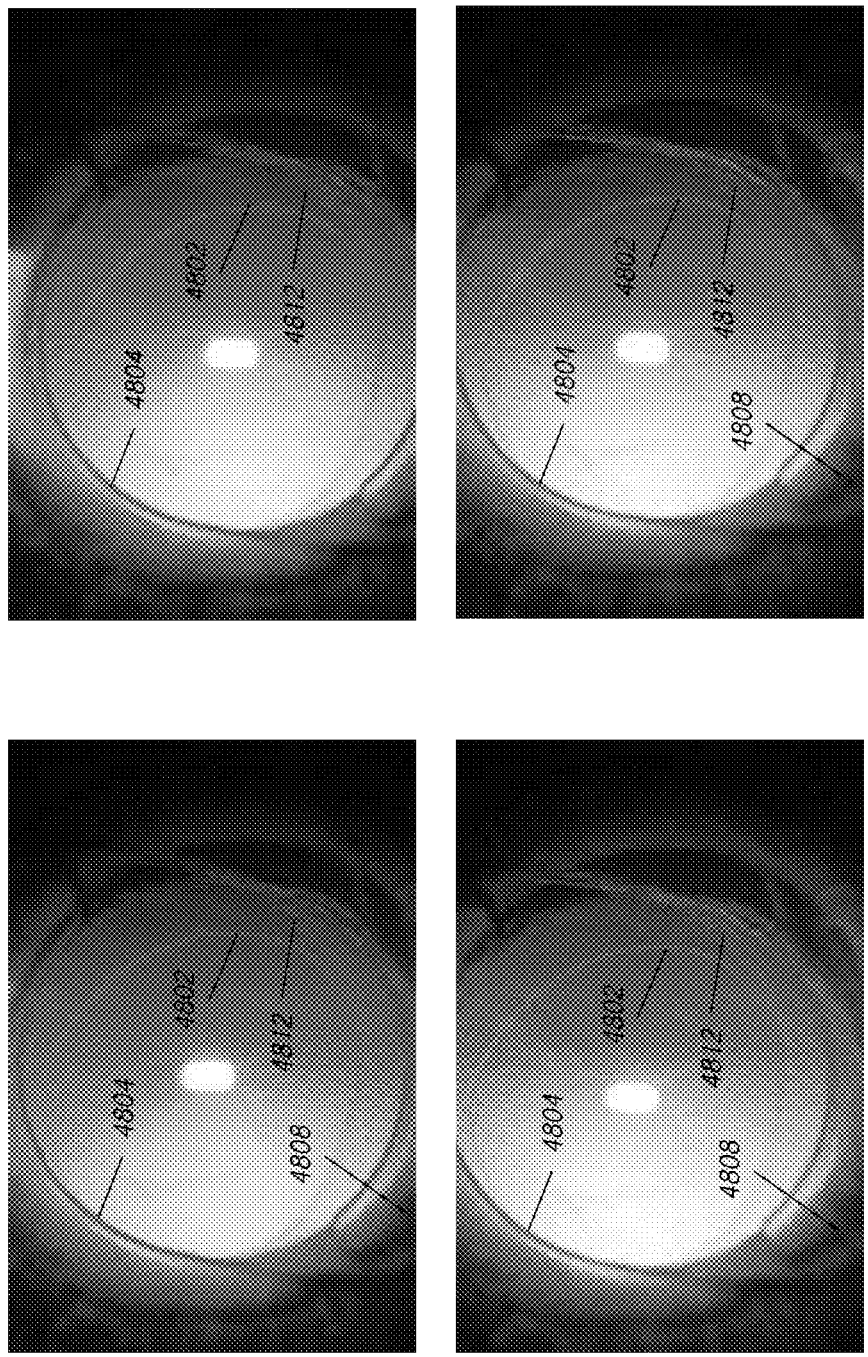
Figure 48E:
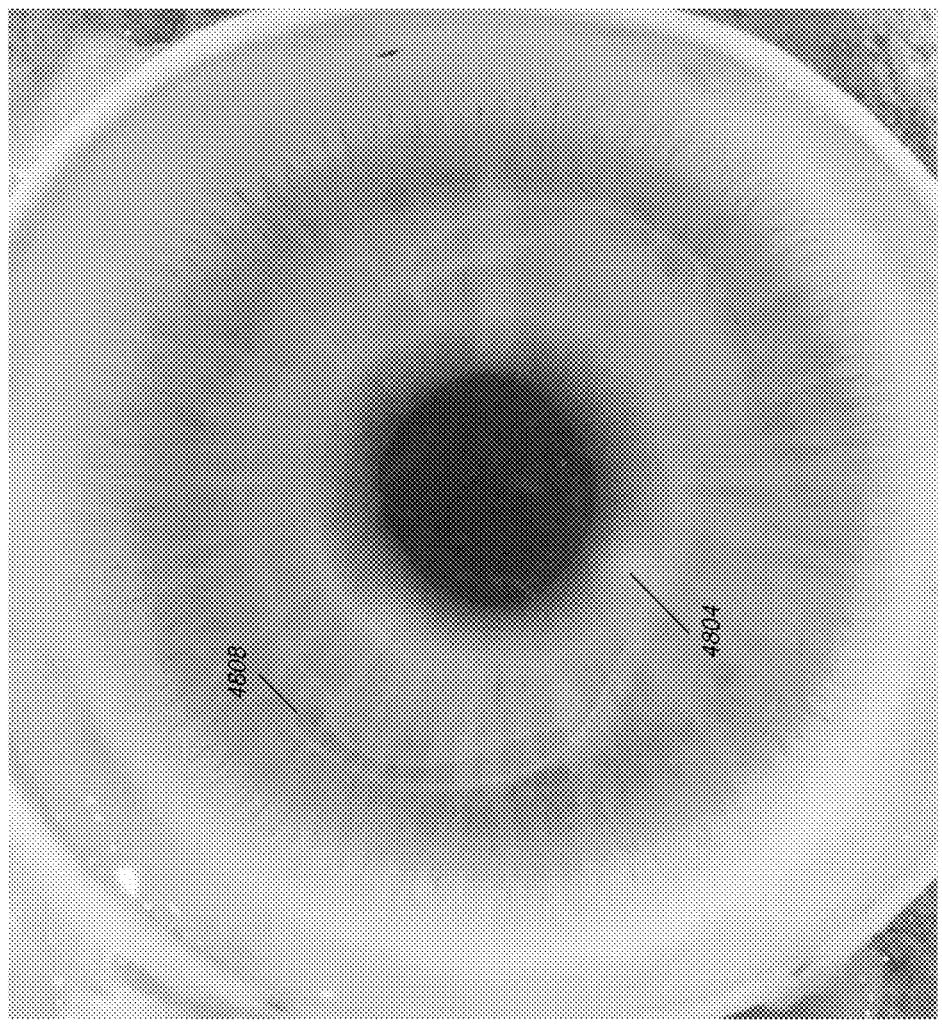

FIGS. 48A-48E are photographs of animal study results for a left eye of the second rabbit. FIG. 48A is after one week, FIG. 48B is after two weeks, FIG. 48C is after three weeks, and FIGS. 48D and 48E are after four weeks. FIGS. 48A-48E illustrate an anterior capsulorhexis 4802, a refractive surface 4804 of an IOL, and IOL haptics 4808. The IOL haptics 4808 are not visible in some figures, although the position of the haptics may be assumed based on other figures and/or the position of any visible portions of the IOL flared radially outwardly to form the start of the haptics. As in FIGS. 46A-46E, and in stark contrast to the right eye of FIGS. 47A-47E, the left eye of FIGS. 48A-48E evidence significant fibrosis 4812 of the natural capsular bag, best seen in FIG. 48C. FIGS. 46A-46E also shown contraction of the anterior capsulorhexis 4802. Due to the contraction and fibrosis, the effective diameter at which the left eye of FIGS. 48A-48E can take in light is about 4.3 mm, which significantly impairs the vision in that eye except under the best lighting conditions.

Figure 49C:
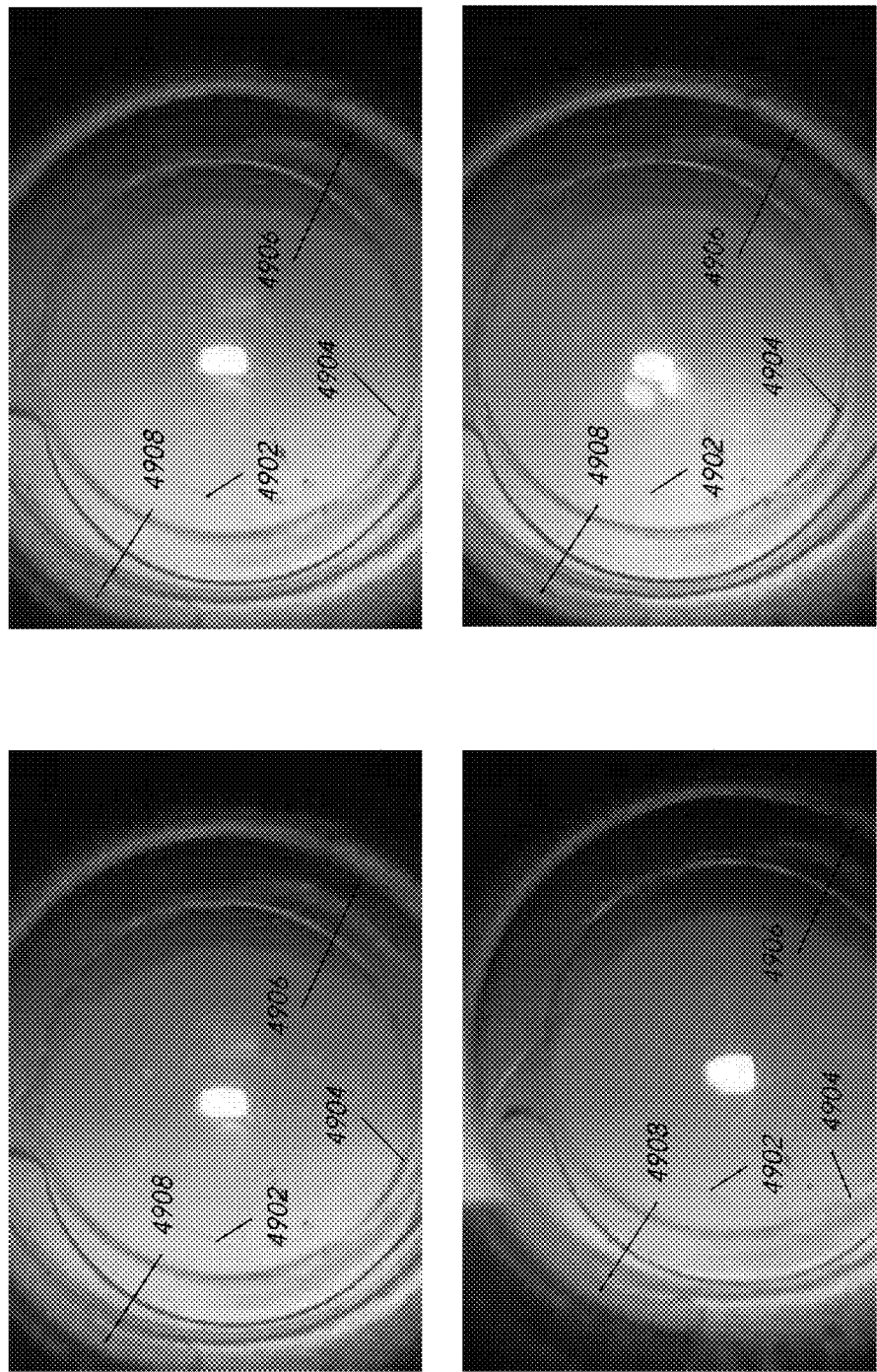

FIGS. 49A-49E are photographs of animal study results for a right eye of a third rabbit. FIG. 49A is after one week, FIG. 49B is after two weeks, FIG. 49C is after three weeks, and FIGS. 49D and 49E are after four weeks. FIGS. 49A-49E illustrate an anterior capsulorhexis 4902, a refractive surface 4904 of an IOL, an anterior opening 4906 of a prosthetic capsular device containing the IOL, and IOL haptics 4908. The IOL haptics 4908 are not visible in some figures, although the position of the haptics may be assumed based on other figures and/or the position of any visible portions of the IOL flared radially outwardly to form the start of the haptics. The natural capsular bag is substantially free of fibrosis. FIG. 49E shows material 4912 on a posterior surface of the IOL and the inception of peripheral PCO 4614.

Figure 50A:
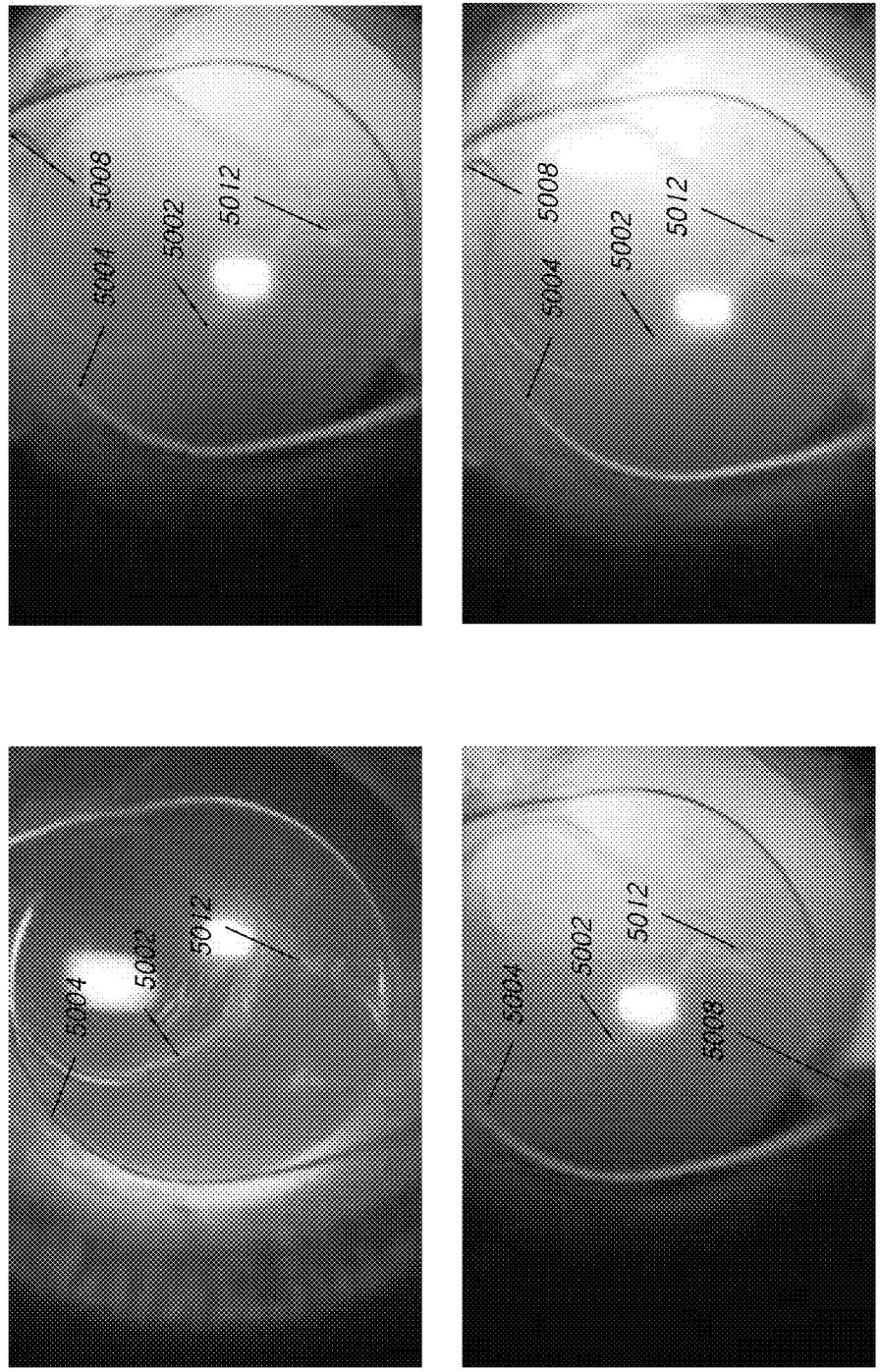
Figure 50B:
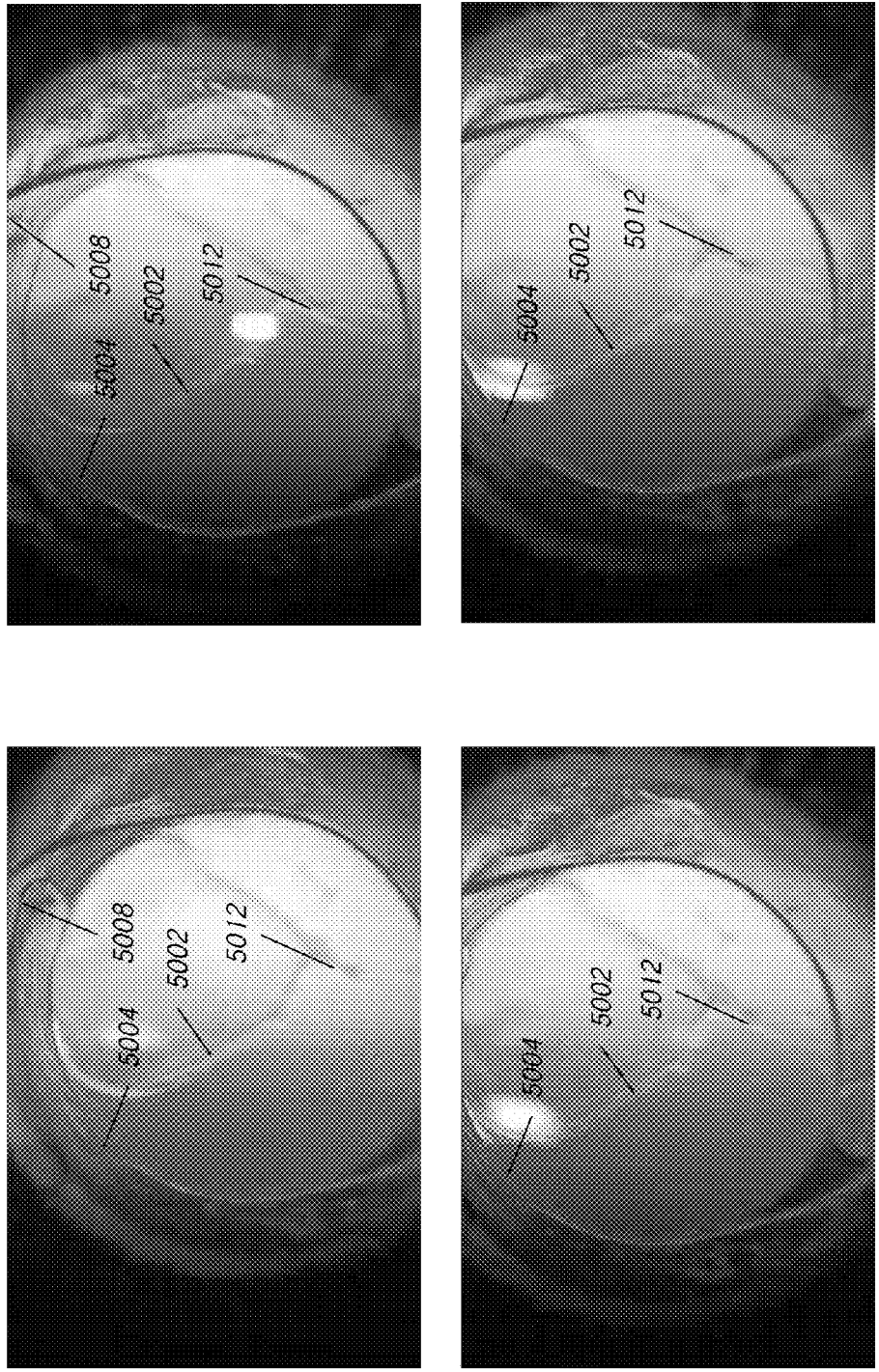
Figure 50C:
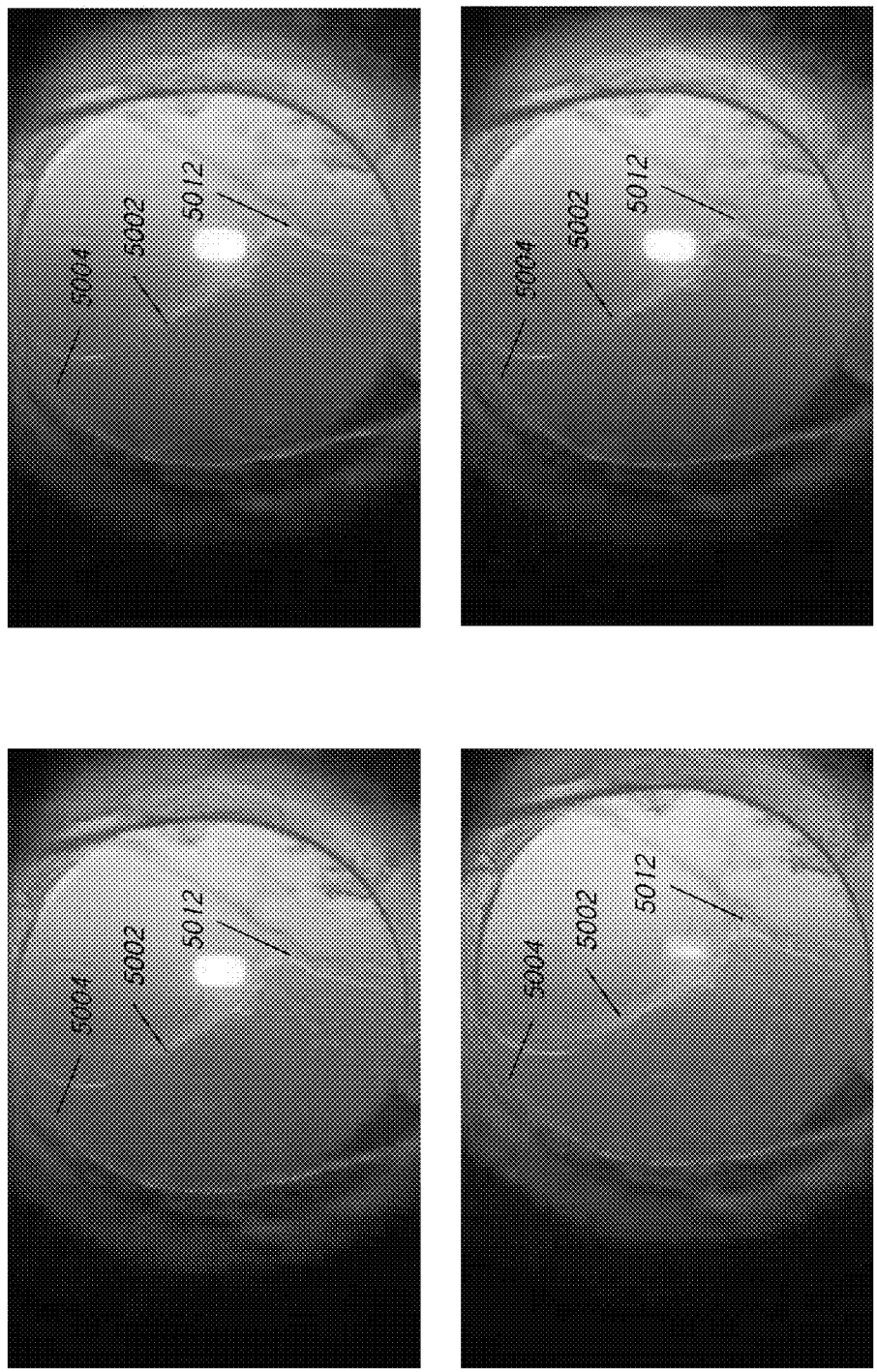
Figure 50E:
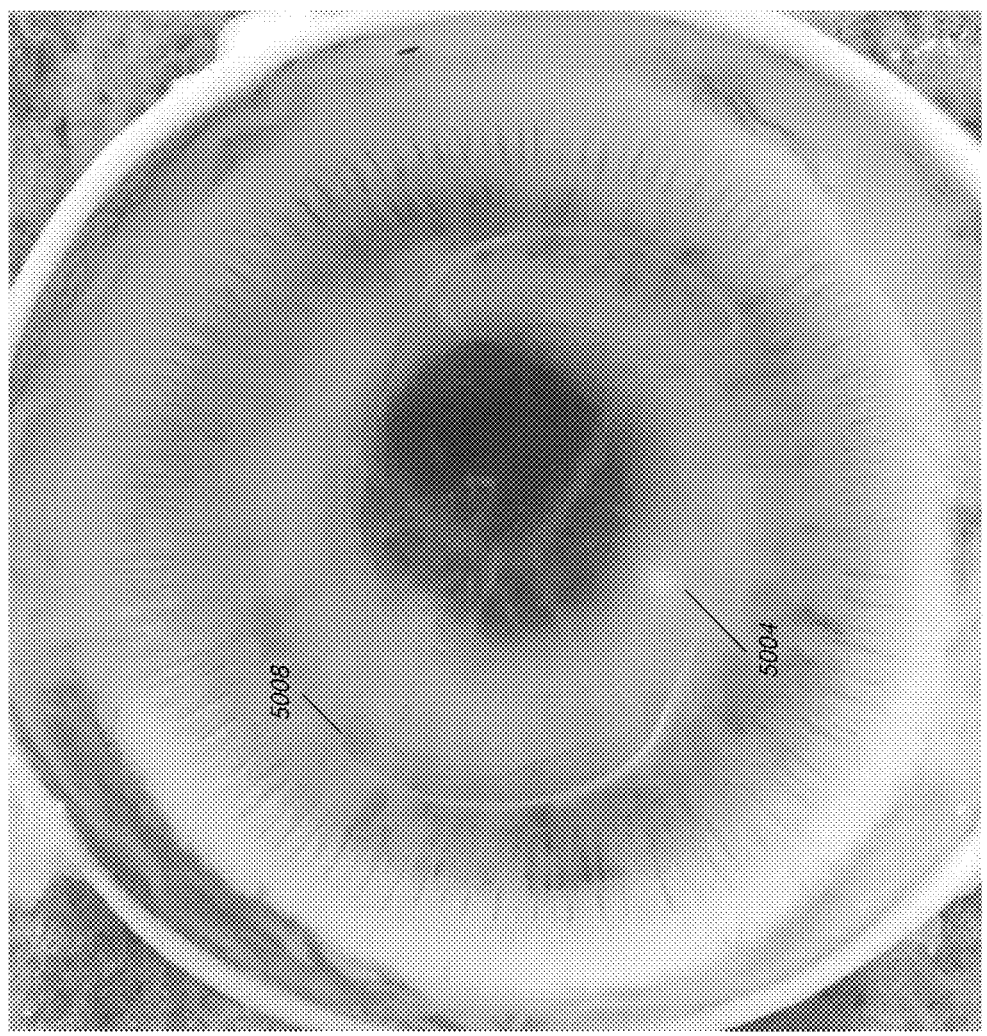

FIGS. 50A-50E are photographs of animal study results for a left eye of the third rabbit. FIG. 50A is after one week, FIG. 50B is after two weeks, FIG. 50C is after three weeks, and FIGS. 50D and 50E are after four weeks. FIGS. 50A-50E illustrate an anterior capsulorhexis 5002, a refractive surface 5004 of an IOL, and IOL haptics 5008. The IOL haptics 5008 are not visible in some figures, although the position of the haptics may be assumed based on other figures and/or the position of any visible portions of the IOL flared radially outwardly to form the start of the haptics. Out of all the left eyes, FIGS. 50A-50E show the most dramatic contraction of the natural capsular bag, which can be seen by the size of the anterior capsulorhexis 4902. Due to the contraction and fibrosis, the effective diameter at which the left eye of FIGS. 50A-50E can take in light is about 4.2 mm, which significantly impairs the vision in that eye except under the best lighting conditions. FIG. 50E also shows PCO.

Figure 51A:
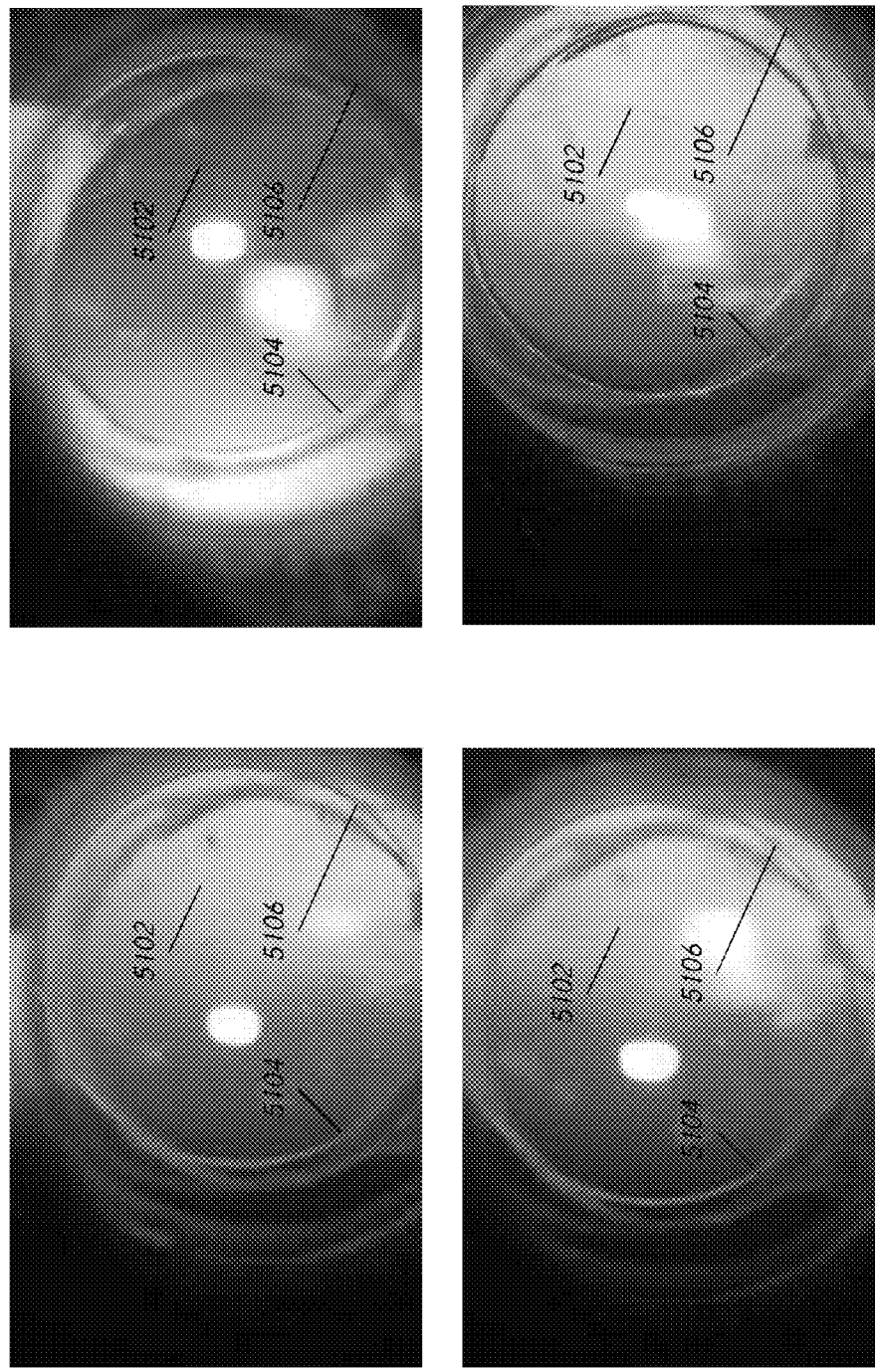
Figure 51C:
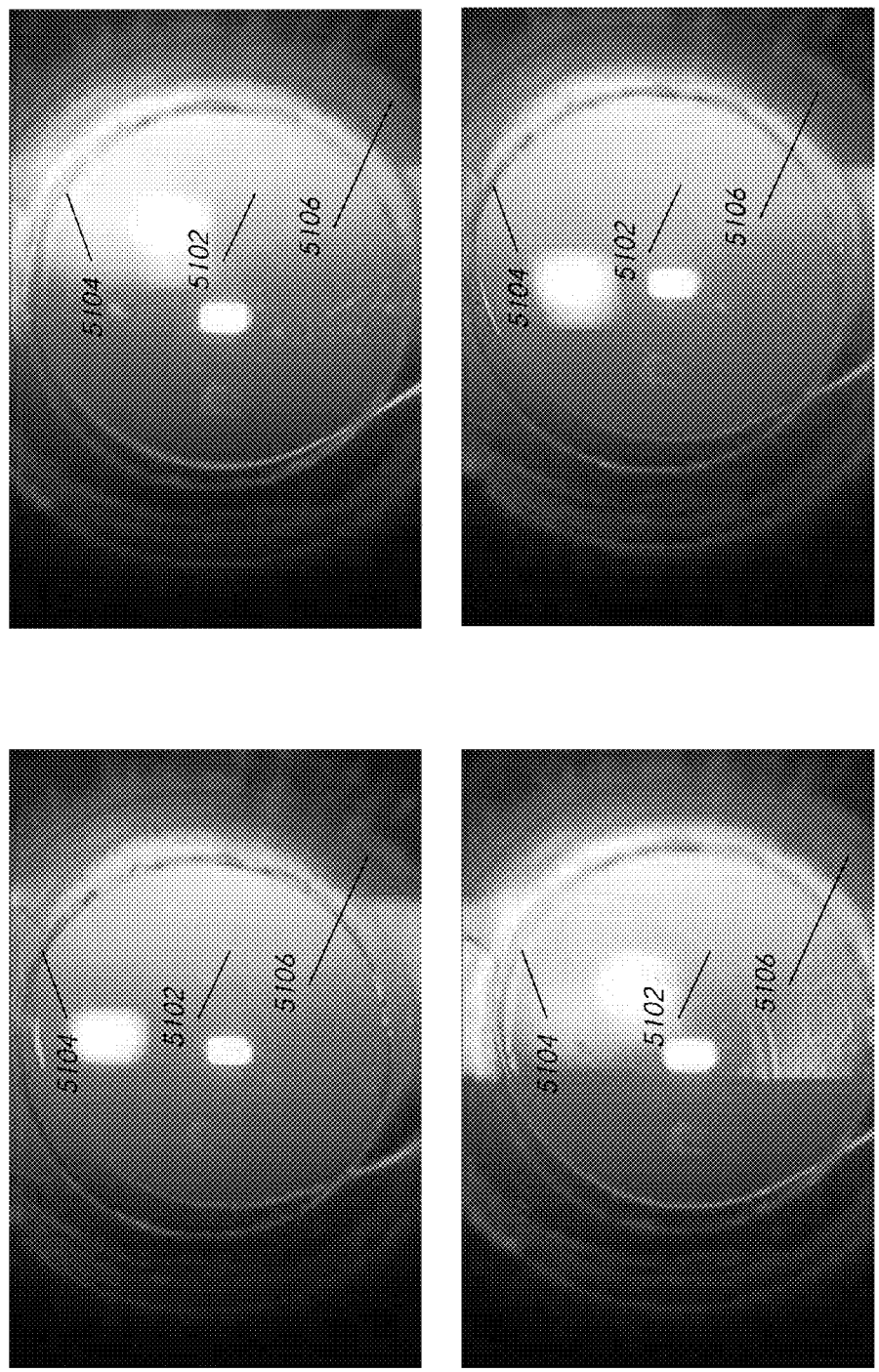
Figure 51D:
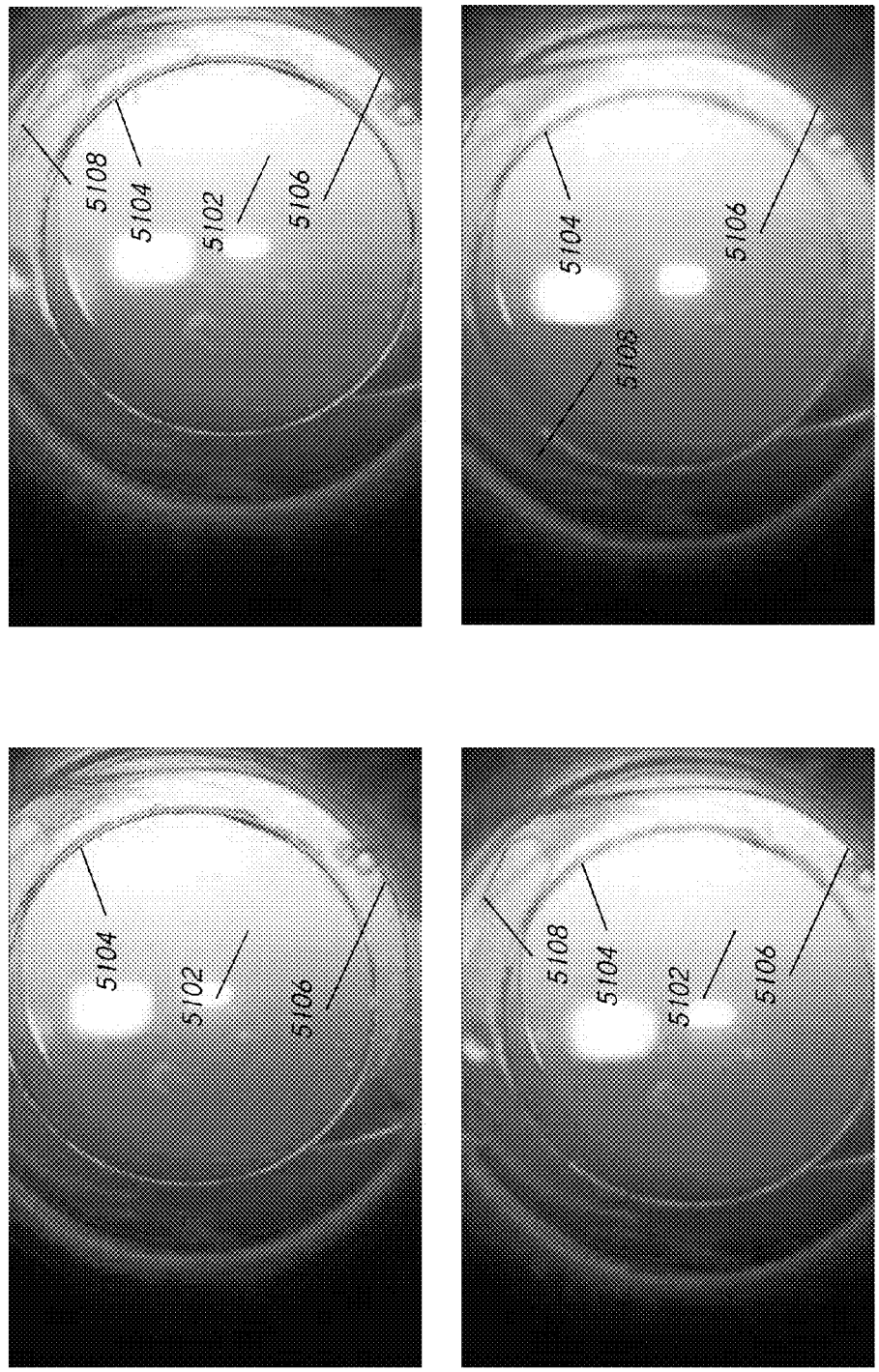

FIGS. 51A-51E are photographs of animal study results for a right eye of a fourth rabbit. FIG. 51A is after one week, FIG. 51B is after two weeks, FIG. 51C is after three weeks, and FIGS. 51D and 51E are after four weeks. FIGS. 51A-51E illustrate an anterior capsulorhexis 5102, a refractive surface 5104 of an IOL, an anterior opening 5106 of a prosthetic capsular device containing the IOL, and IOL haptics 5108. The IOL haptics 5108 are not visible in some figures, although the position of the haptics may be assumed based on other figures and/or the position of any visible portions of the IOL flared radially outwardly to form the start of the haptics. FIGS. 51A-51E show that the prosthetic capsular device may have been poorly centered in the natural capsular bag and/or that the natural capsular bag contracted, but the natural capsular bag is substantially free of fibrosis such that mis-centering and/or contraction does not present a serious issue, as light may pass through the still-epithelial natural capsular bag cells. FIG. 51E shows material 5112 on a posterior surface of the IOL. The right eye of the fourth rabbit also shows a small amount of fibrin peripherally between the prosthetic capsular device and the IOL, discussed in further detail below.

Figure 52A:
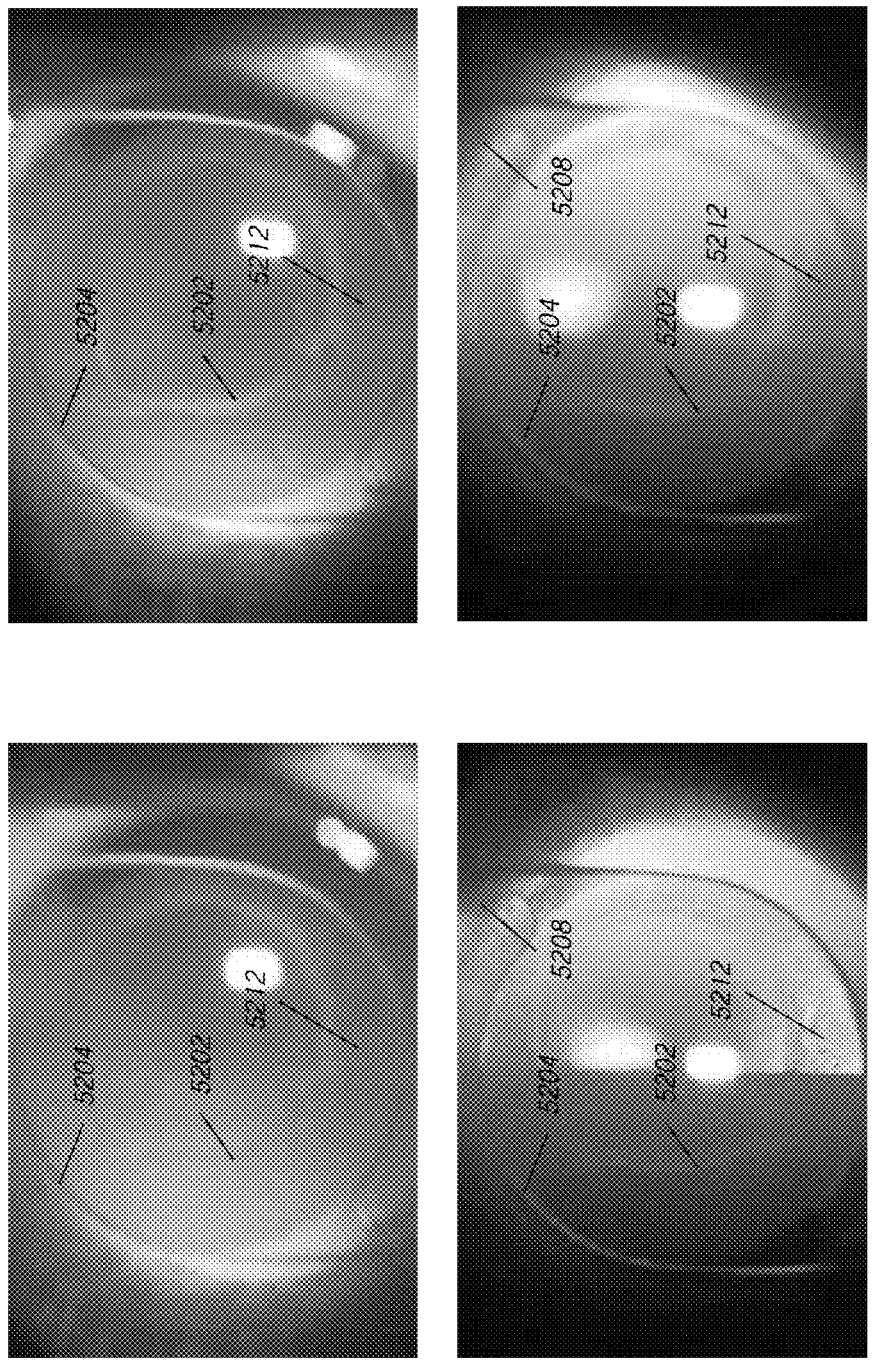
FIGS. 52A-52E are photographs of animal study results for a left eye of the fourth rabbit.
Figure 52B:
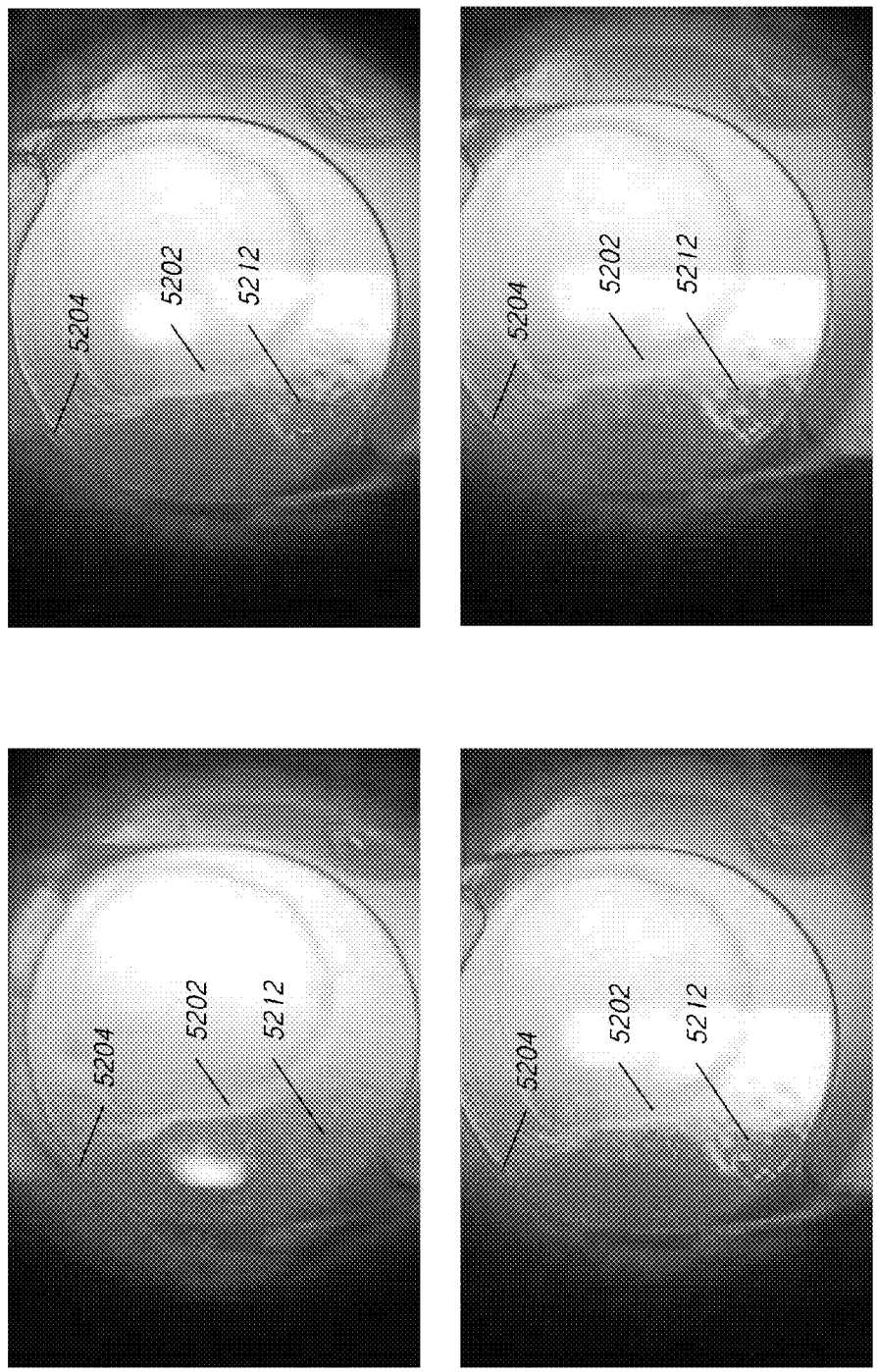
Figure 52C:
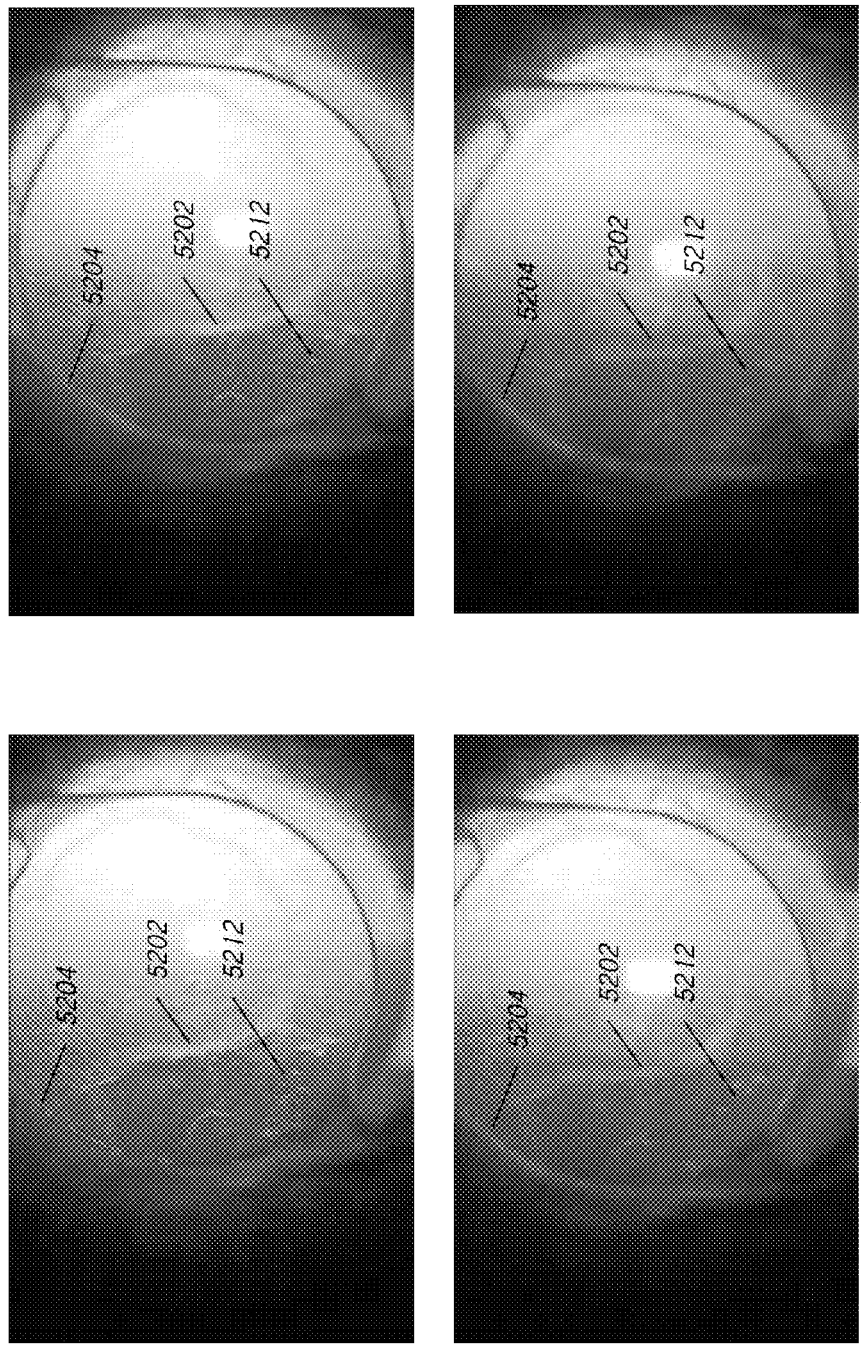
Figure 52D:
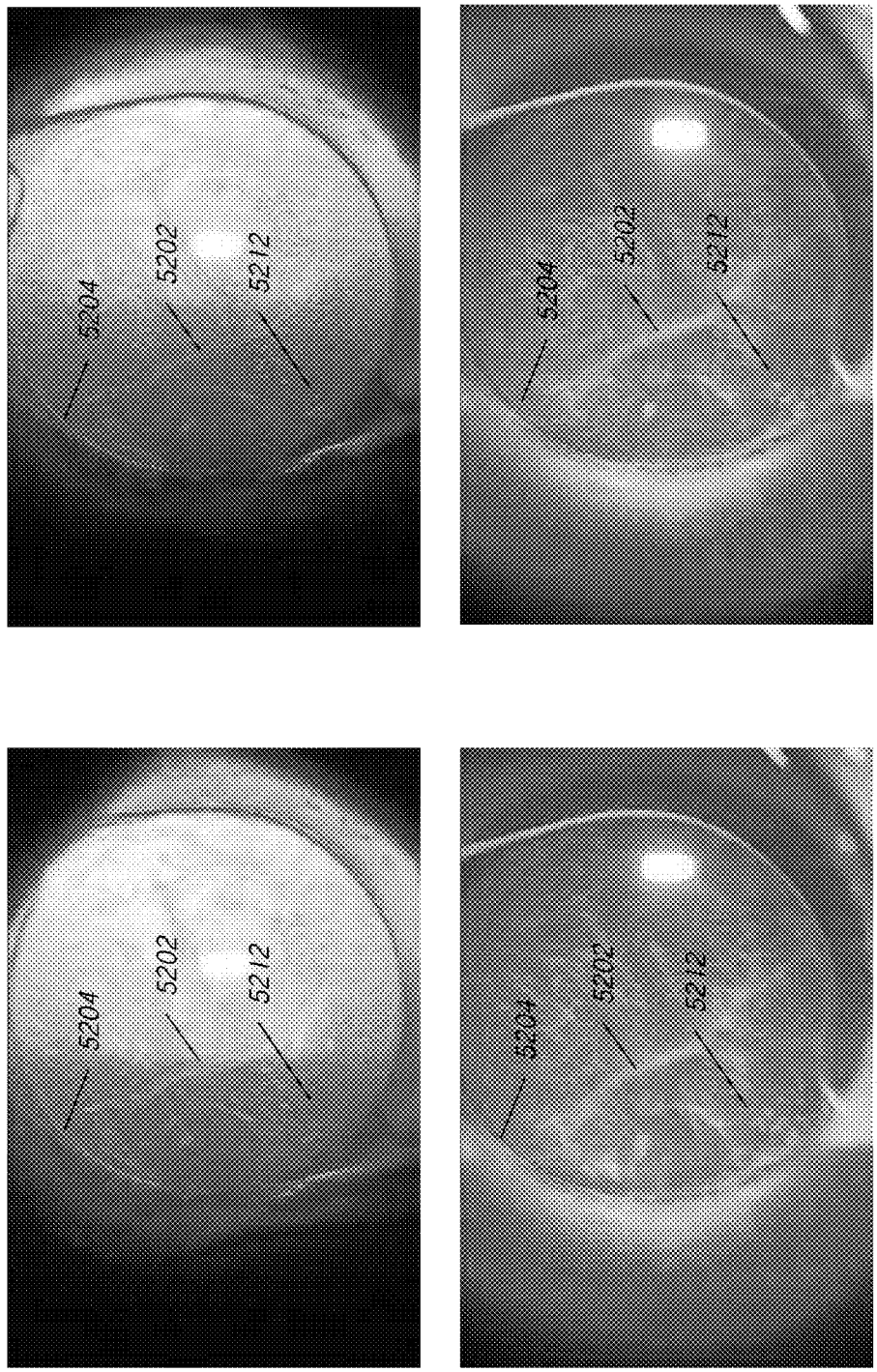
Figure 52E:
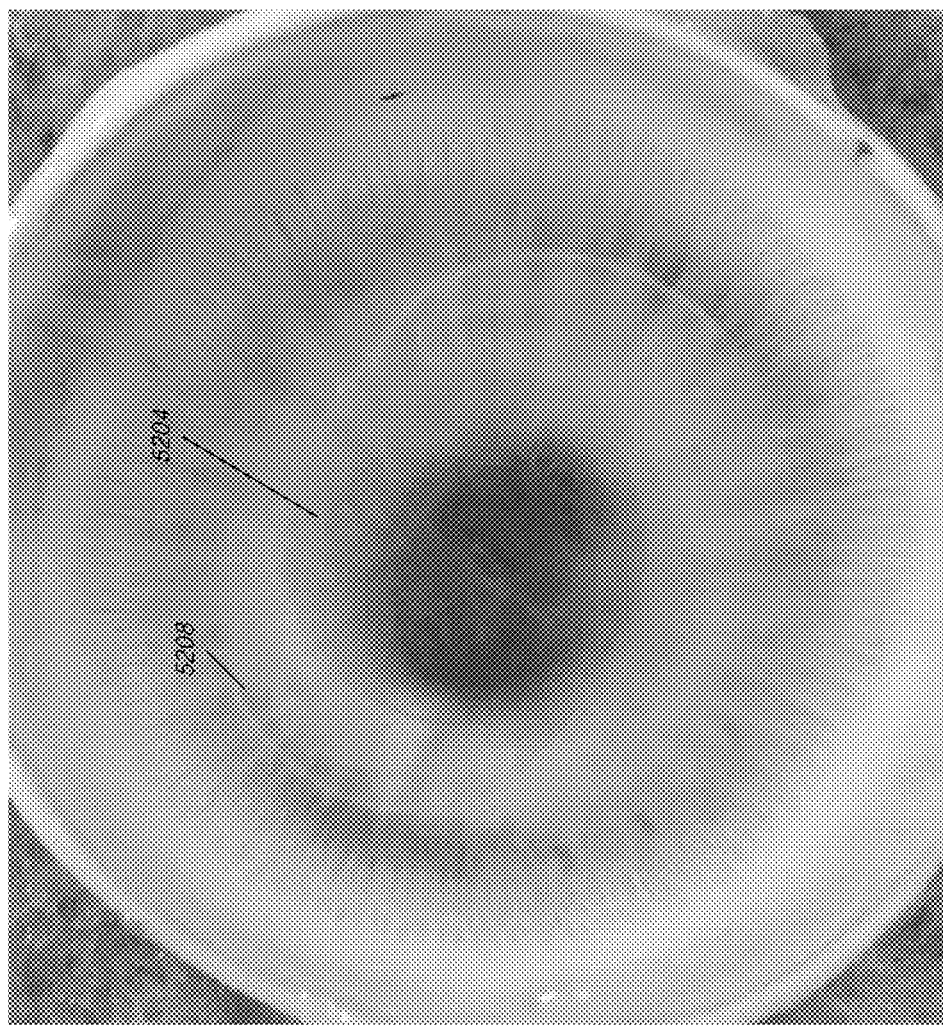

FIGS. 52A-52E are photographs of animal study results for a left eye of the fourth rabbit. FIG. 52A is after one week, FIG. 52B is after two weeks, FIG. 52C is after three weeks, and FIGS. 52D and 52E are after four weeks. FIGS. 52A-52E illustrate an anterior capsulorhexis 5202, a refractive surface 5204 of an IOL, and IOL haptics 5208. The IOL haptics 5208 are not visible in some figures, although the position of the haptics may be assumed based on other figures and/or the position of any visible portions of the IOL flared radially outwardly to form the start of the haptics. Like several of the other left eyes, FIGS. 52A-52E show significant fibrosis and contraction. Due to the contraction and fibrosis, the effective diameter at which the left eye of FIGS. 52A-52E can take in light is about 2.6 mm, which significantly impairs the vision in that eye except under the best lighting conditions. FIG. 52E also shows PCO.

Figure 53A:
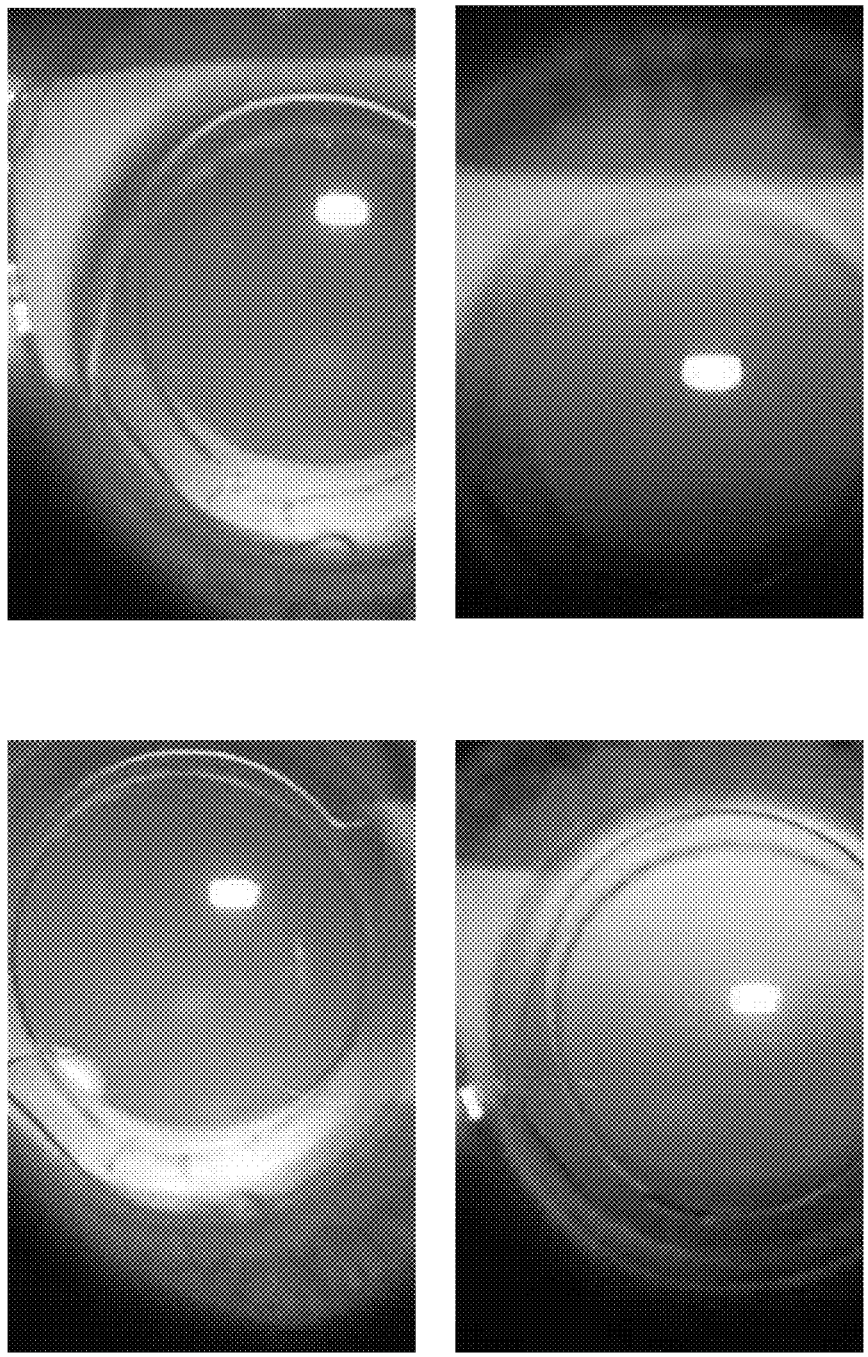
Figure 53C:
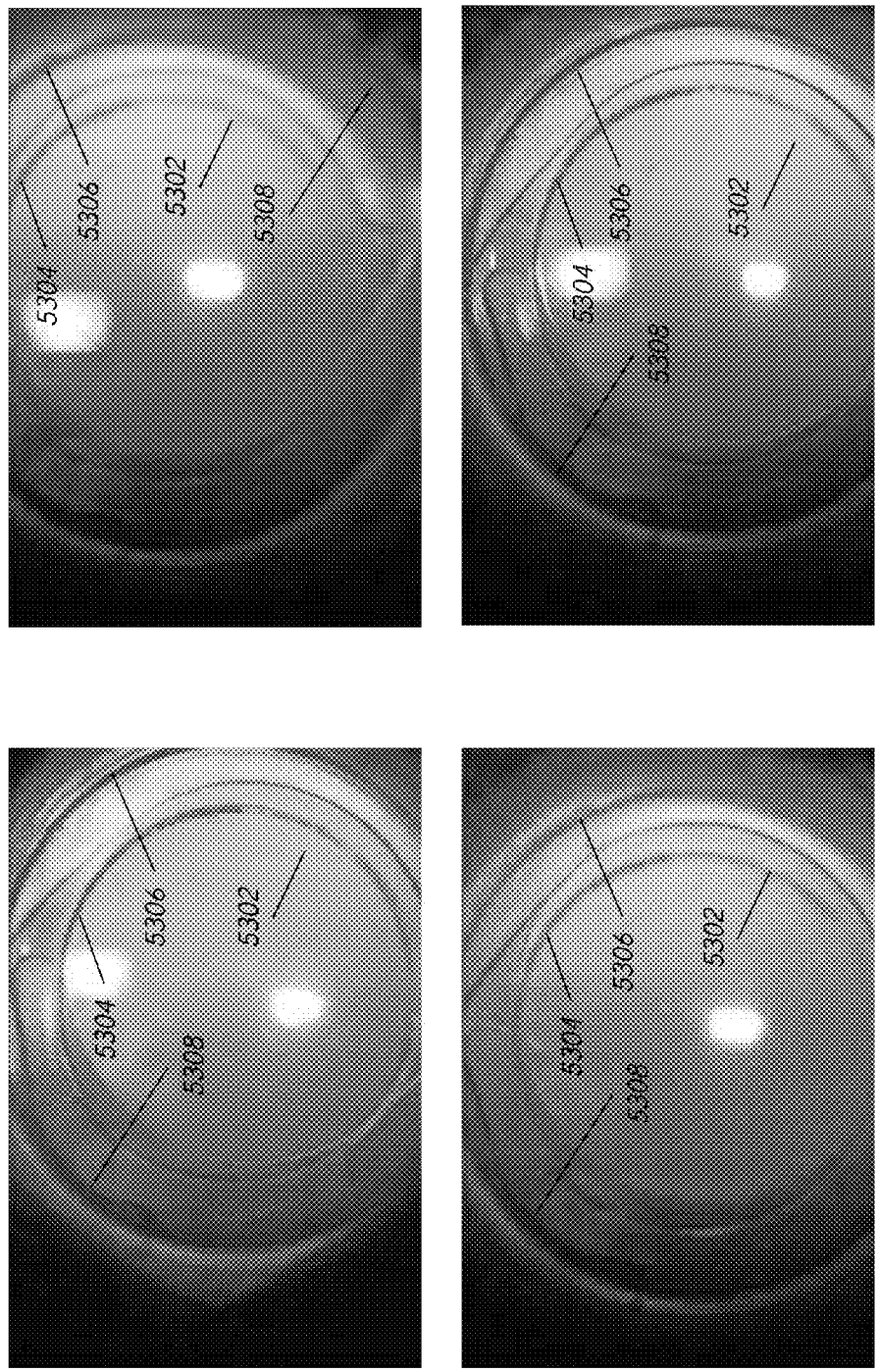
Figure 53D:
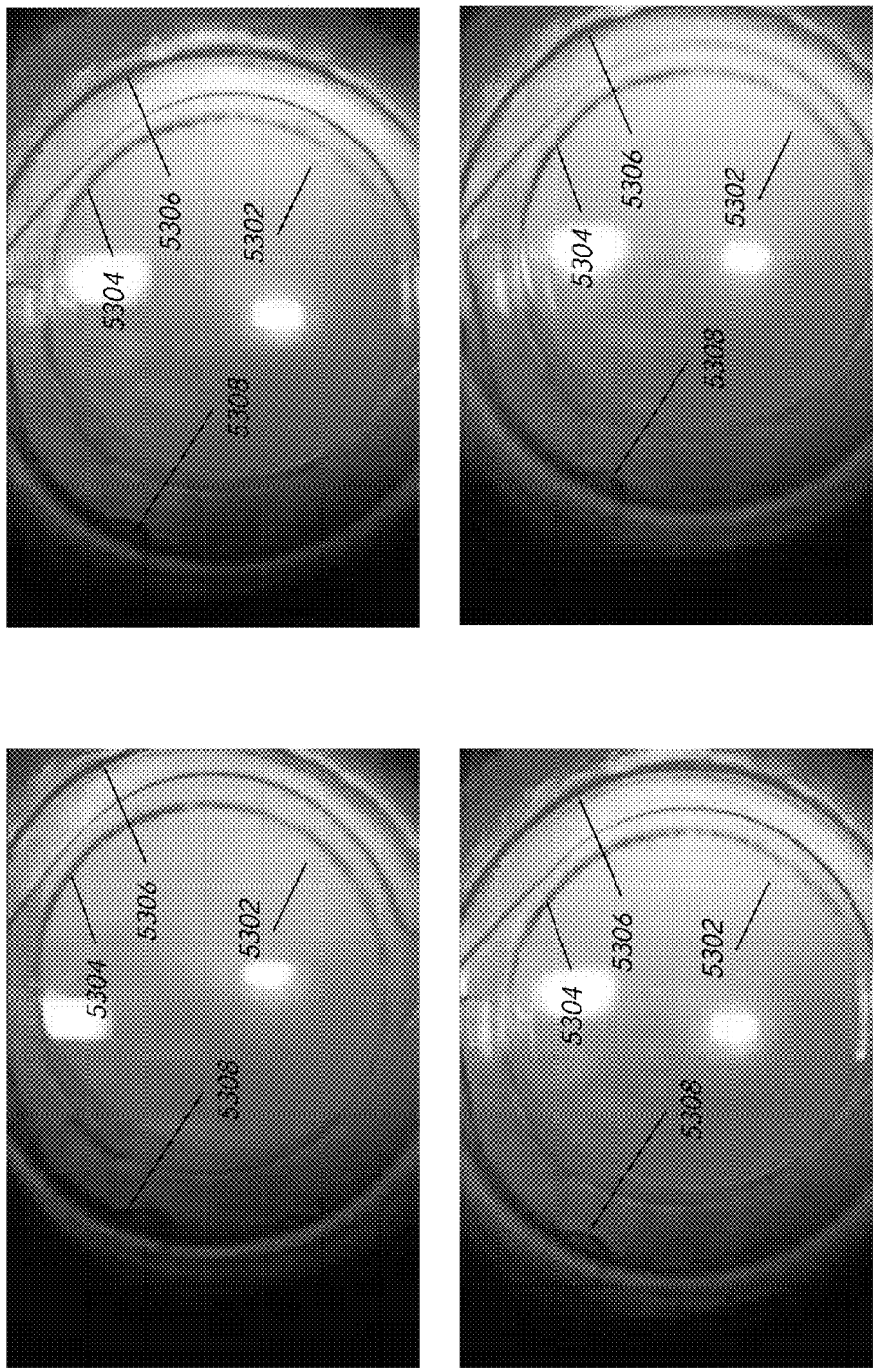
Figure 53E:
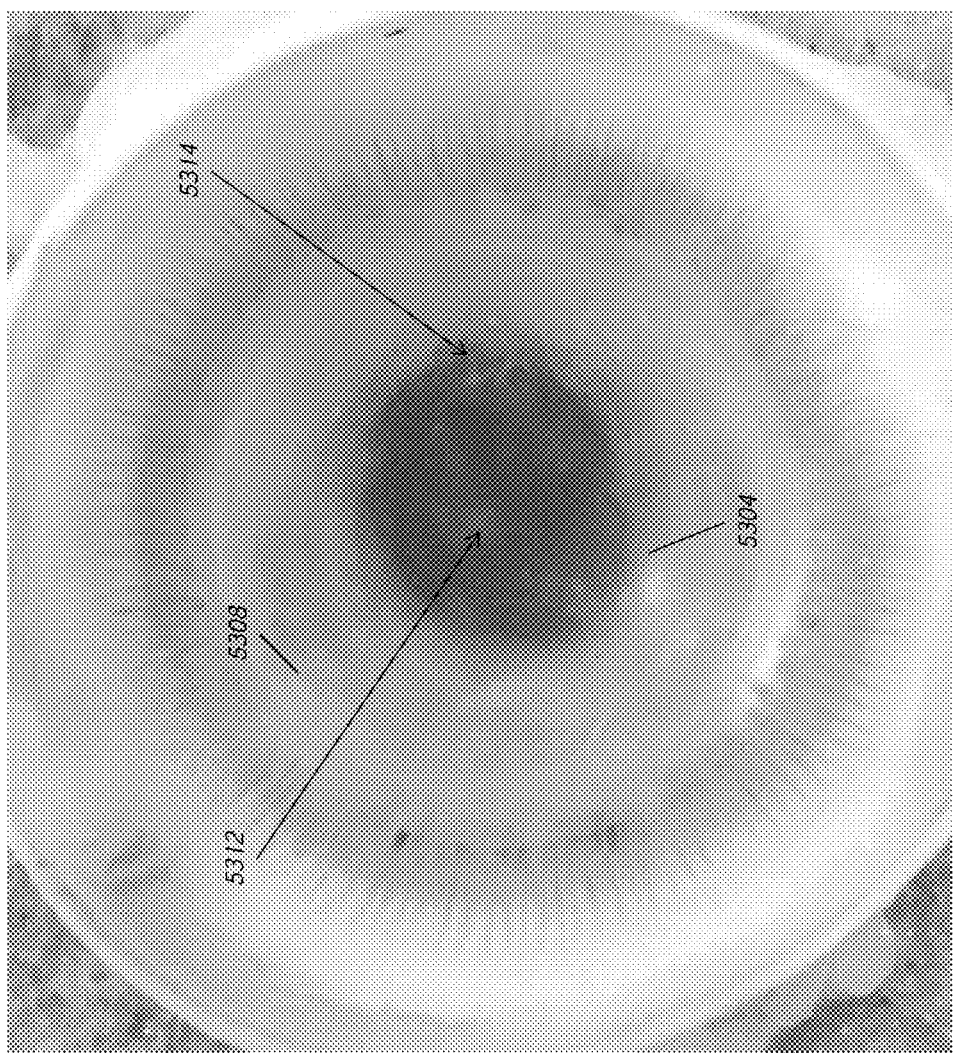

FIGS. 53A-53E are photographs of animal study results for a right eye of a fifth rabbit. FIG. 53A is after one week, FIG. 53B is after two weeks, FIG. 53C is after three weeks, and FIGS. 53D and 53E are after four weeks. FIGS. 53A-53E illustrate an anterior capsulorhexis 5302, a refractive surface 5304 of an IOL, an anterior opening 5306 of a prosthetic capsular device containing the IOL, and IOL haptics 5308. The IOL haptics 5308 are not visible in some figures, although the position of the haptics may be assumed based on other figures and/or the position of any visible portions of the IOL flared radially outwardly to form the start of the haptics. Like FIGS. 49A-49E, FIGS. 53A-53E show good centering of the prosthetic capsular device in the natural capsular bag, and lack of fibrosis. FIG. 53E shows material 5312 on a posterior surface of the IOL and peripheral PCO 5314.

Figure 54A:
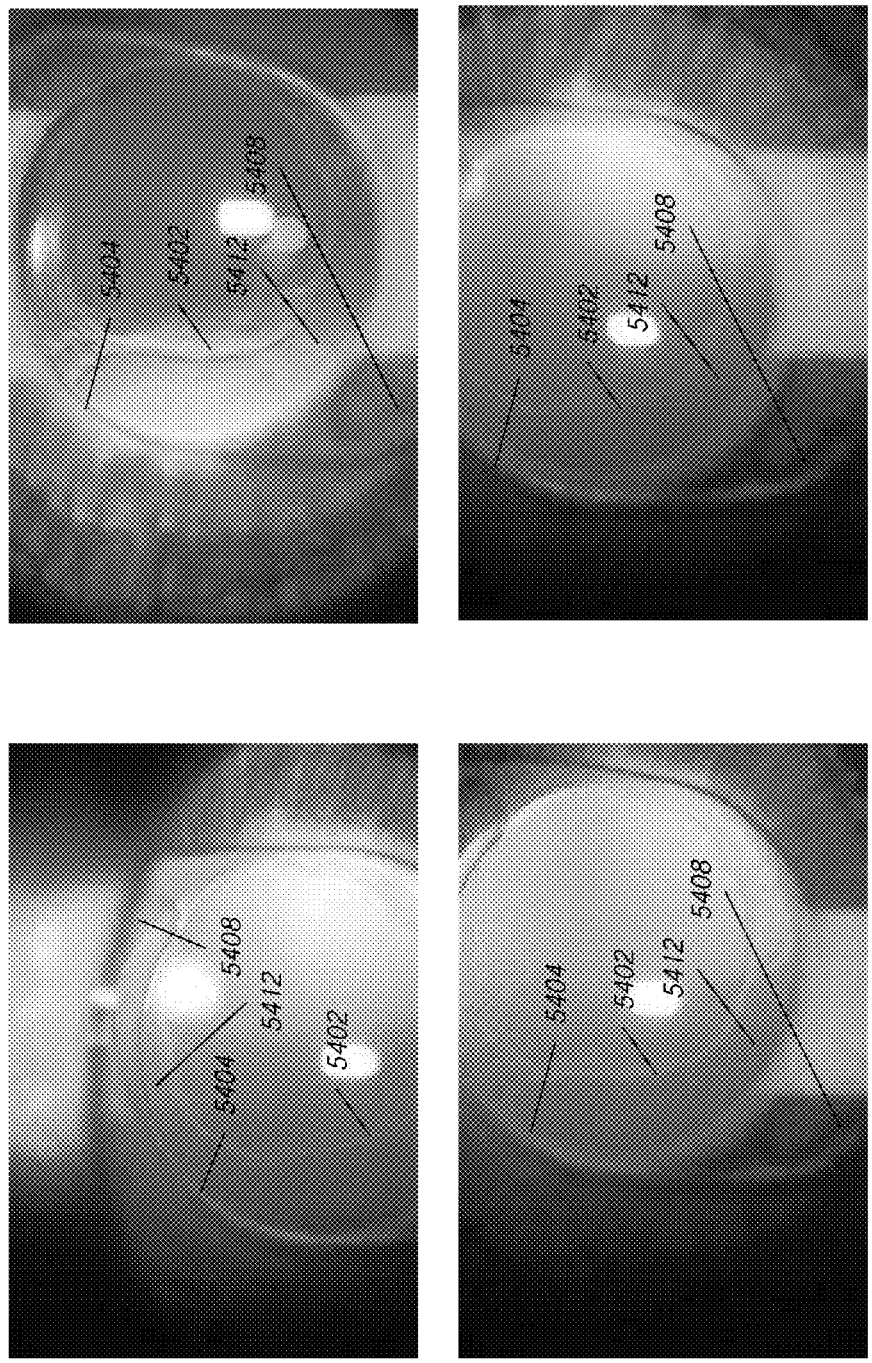
Figure 54C:
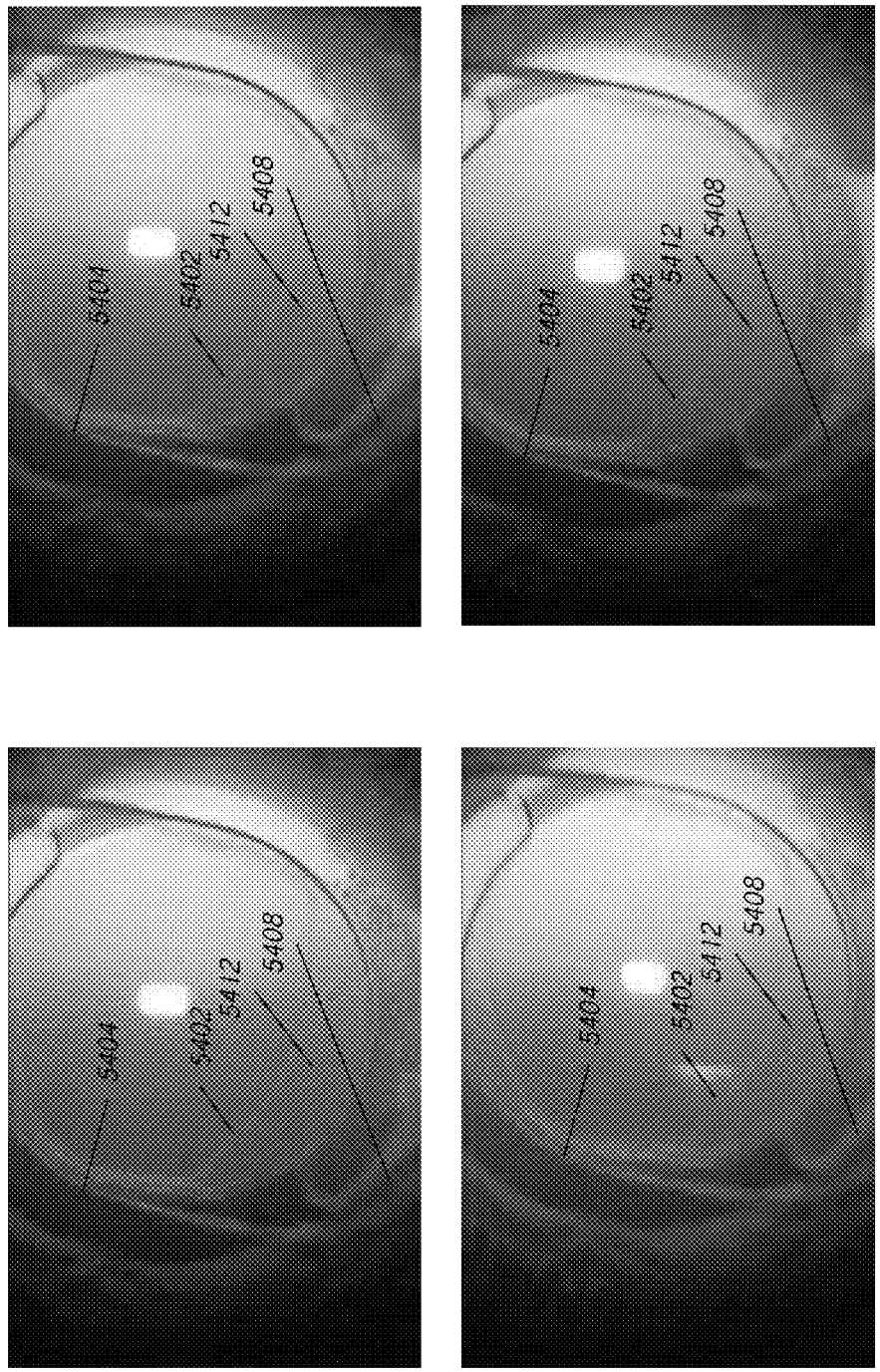
Figure 54D:
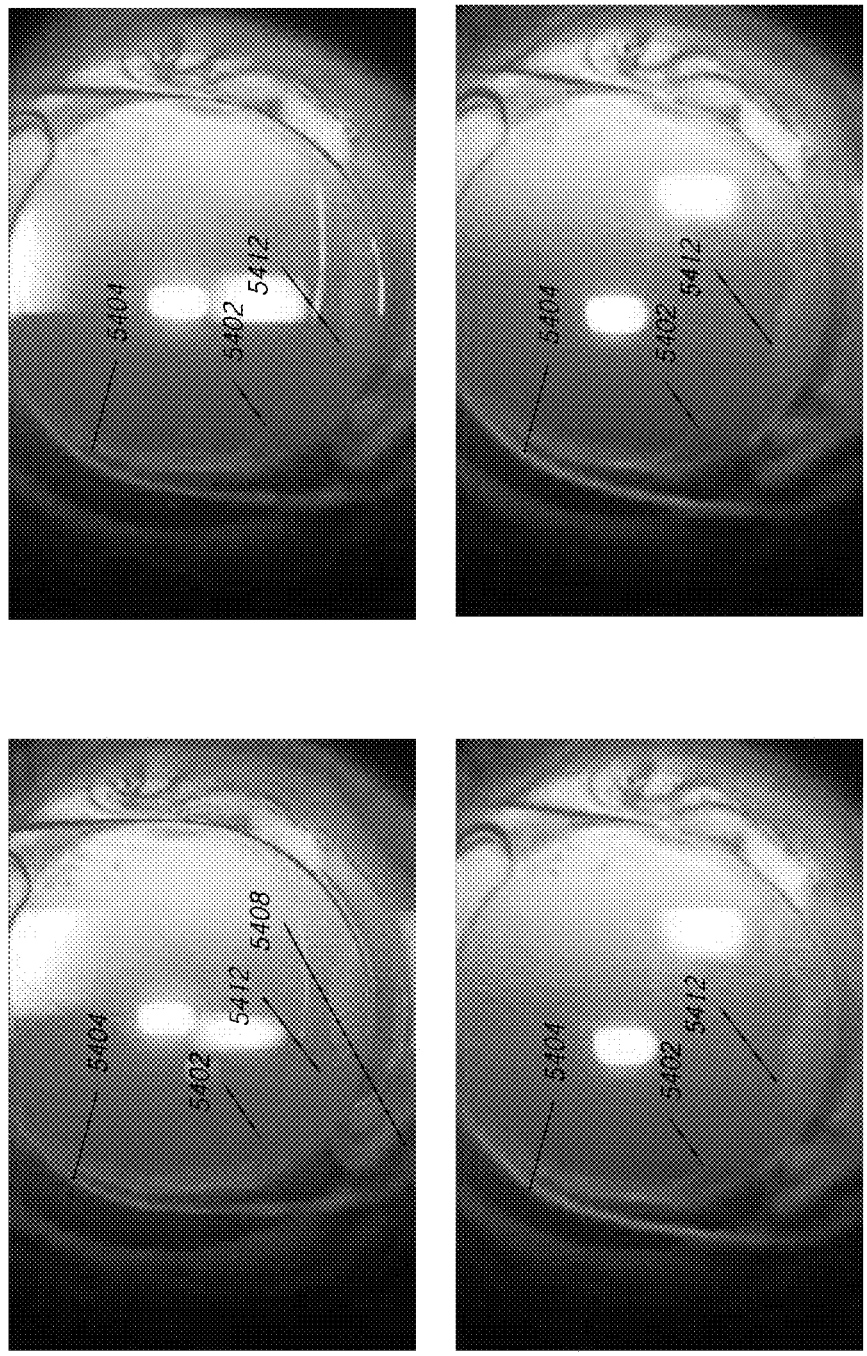

FIGS. 54A-54E are photographs of animal study results for a left eye of the fifth rabbit. FIG. 54A is after one week, FIG. 54B is after two weeks, FIG. 54C is after three weeks, and FIGS. 54D and 54E are after four weeks. FIGS. 54A-54E illustrate an anterior capsulorhexis 5402, a refractive surface 5404 of an IOL, and IOL haptics 5408. The IOL haptics 5408 are not visible in some figures, although the position of the haptics may be assumed based on other figures and/or the position of any visible portions of the IOL flared radially outwardly to form the start of the haptics. Like several of the other left eyes, FIGS. 52A-52E show significant fibrosis and contraction. Due to the contraction and fibrosis, the effective diameter at which the left eye of FIGS. 54A-54E can take in light is about 4.5 mm, which significantly impairs the vision in that eye except under the best lighting condition.

The reduction in the effective diameter shows why PCO can be so detrimental and preferably reduced or prevented. As described above, a Nd:YAG laser may be used to ablate the natural capsular bag to remove the opaque membrane. If the natural capsular bag separating the vitreous is removed, then post-PCO treatment operation on an IOL absent a prosthetic capsular device could result in anterior flow of vitreous. A careful user may be able to viscodissect an IOL from an eye and place a prosthetic capsular device comprising a posterior surface into the eye to inhibit or prevent the flow of vitreous. The eye of a post-PCO subject with an existing IOL issue may be salvageable using a prosthetic capsular device, providing another potential advantage and/or use.

One goal of the animal studies of FIGS. 45A-54E was to show that use of a prosthetic capsular device was not worse for the eye than use of an IOL alone. The right eyes were all substantially free of fibrosis (e.g., almost totally pristine), IOL position shift, and anterior capsulorhexis contraction. By contrast, the left eyes generally showed significant fibrosis, IOL migration, and significant asymmetric contraction of the capsulorhexis. The animal studies empirically show that the use of a prosthetic capsular device can provide at least some of the advantages discussed herein.

Slight damage to the prosthetic capsular devices such as small tears in the edge of the anterior opening may have occurred due to insertion through the Accuject 2.2 mm injectors. Upon any incomplete injection of the prosthetic capsular device into the natural capsular bag, the prosthetic capsular device was manipulated with a collar button hook after injection to complete in-the-bag fixation. The manipulation and/or a hard push on the injector may have caused the damage. Injection of the prosthetic capsular device fully into the natural capsular bag (e.g., without further manipulation or repositioning), for example using a different injector, may reduce the risk of tearing the prosthetic capsular device.

Inflammation of the vitreous in right eyes, starting after about two weeks and then decreasing throughout the follow up, may have been due to the material of the prosthetic capsular device being sterilized, but not having undergone an extensive extraction process such that uncrosslinked siloxane monomers can leach out of the material over time. Extraction prior to sterilization and packaging of the prosthetic capsular device, for example single, double, triple, or more extractions to promote crosslinking (e.g., substantially total crosslinking), may reduce such inflammation.

Fibrin formation between the prosthetic capsular device and the IOL may have been due to incomplete viscoelastic removal and/or residual OVD remained trapped behind the IOL. More aggressive viscoelastic evacuation after the implantation, use of a more cohesive viscoelastic material, which may be easier to remove than dispersive viscoelastic materials, and/or an OVD removal technique may reduce the such fibrin formation. There was little change in the fibrin material throughout the four weeks. Fibrin was also generally observed at the level of the capsulorhexis edge in the left eyes, which was resolved within two weeks.

Dilation or significant dilation of the natural capsular bag was generally associated with the presence of the prosthetic capsular device. However, ACO was absent, for example due to lack of contact between the residual anterior capsule and the anterior surface of the prosthetic capsular device, such that the dilation was not a negative result.

The right eyes, in which a prosthetic capsular device was placed before an IOL, showed significantly reduced Soemmering's ring formation compared to the left eyes, in which only an IOL was placed. The right eyes showed reduced central and peripheral PCO compared to the left eyes. A different edge profile (e.g., square) of a prosthetic capsular device, for example as described herein, may provide a better effect against PCO. PCO at week 4 of the examination was scored as a 0 in the right eyes and as $2\pm1$ in the left eyes (two-tail P=0.01; t-Test: Paired Two Sample for Means). ACO was found to be absent in the right eyes and was mile (0.5 or 1) in the left eyes.

Central PCO was scored (two-tail P=0.05; t-Test: Paired Two Sample for Means,) as $0.1\pm0.22$ for right eyes and $1.2\pm0.75$ for left eyes. Peripheral PCO was scored (two-tail P=0.23; t-Test: Paired Two Sample for Means) as $0.8\pm0.83$ for right eyes and $1.8\pm0.83$ for left eyes; the amount of PCO varied from a trace to moderate PCO. Soemmering's ring formation was scored (two-tail P=0.006; t-Test: Paired Two Sample for Means) as $2.8\pm0.83$ for right eyes and $8.6\pm2.19$ for left eyes; the left eyes all showed a moderate Soemmering's ring formation with proliferation of cortical material in the periphery. In all cases, a lower number indicates better results. In all parameters, eyes with a prosthetic capsular device scored better than eyes without a prosthetic capsular device.

All prosthetic capsular devices were found to be fully fixated inside of the natural capsular bag and centered. The IOL in FIGS. 45A-45E was very slightly decentered inside of the prosthetic capsular device. Mild IOL decentration (0.5 or 1) inside of the prosthetic capsular device was observed in two left eyes.

There was no sign of untoward inflammation or toxicity on any of the left eyes. There was no sign of any toxicity or inflammation on four of the five right eyes. As mentioned above with respect to FIG. 47E, one right eye showed a mild anterior vitritis.

Figure 55B:
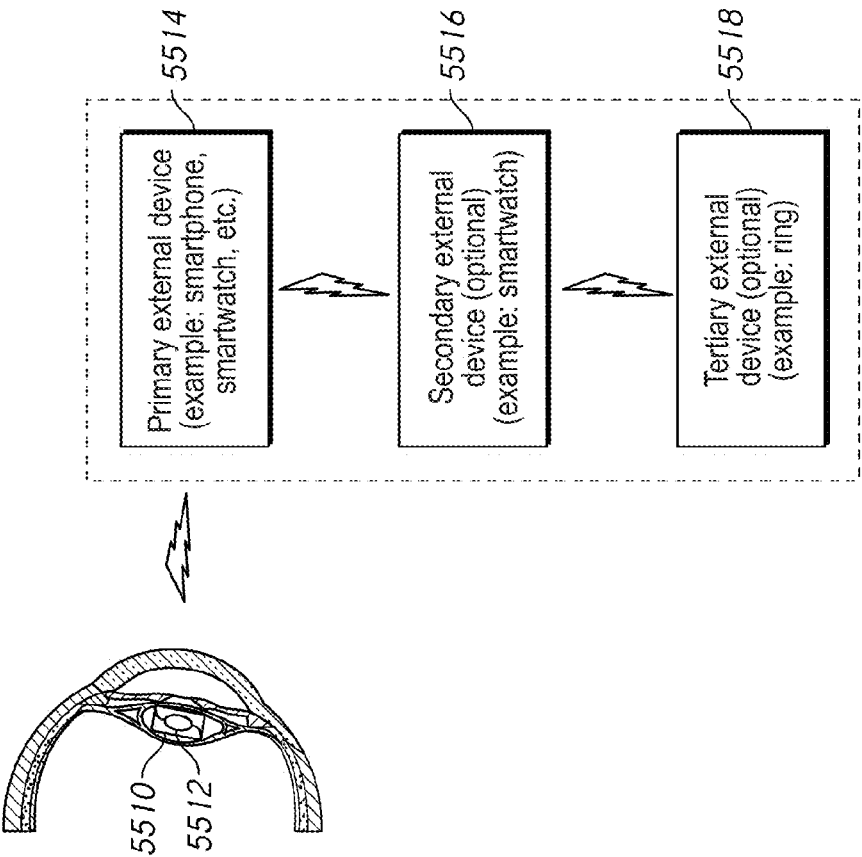
FIG. 55B is a schematic of a system for controlling an electronic device using an external device.
Figure 55A:
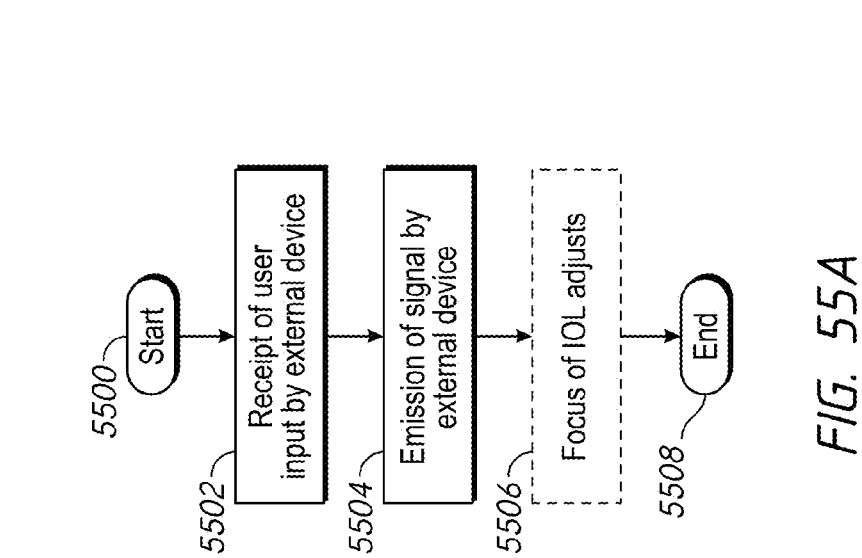
FIG. 55A is a flowchart of an example of controlling focus of an IOL using an external device.

Referring again to the disclosure regarding use of the technology device to control the properties of an IOL, FIG. 55A is a flowchart of an example of controlling focus of an IOL using an external device. Starting at block 5500, the external device receives input from a user at block 5502. An example of user input is control of an external device (e.g., external to the eye) such as a smartwatch, smartphone, and the like. In some implementations, control of the external device is with a second external device. For example, a user wearing a ring on one hand may touch a smartwatch worn on the opposite wrist to complete a circuit, send a signal (e.g., via near-field communication (NFC)), or otherwise communicate. In some implementations, the user operation 5502 does not require full attention of the user (e.g., attention to a display) such that the focus can be controlled without the user deviating from another activity such as driving or communicating with someone. For example, a user may initiate an operation by a series of taps on a smartwatch or a voice command based on built-in voice recognition such as Ski on Apple devices or OK Google on Android devices. In some implementations, features of a smartphone (e.g., volume buttons) and/or a smartwatch (e.g., a rotatable knob) can be manipulated, which may provide fine tuning of and/or adjusting of the focus. Operation of a software application running on an external device that is configured to control the IOL is also possible.

Upon receipt of the user input at block 5502, the external device wirelessly transmits an electronic message at block 5504 to the IOL. The wireless transmission may be in accordance with a standard wireless protocol such as Bluetooth or a specialized wireless protocol, for example to enhance security and/or safety. As described above, the external device may be a single device or a series of devices operating in conjunction with each other. For example, the external device that emits the wireless transmission at block 5504 may be a smartwatch. For another example, the external device that emits the wireless transmission at block 5504 may be a smartphone that received a first wireless transmission from a smartwatch. The wireless transmission is configured to be received by a technology device and/or an IOL configured to process the wireless transmission and cause focus adjustment.

In some implementations, the wireless transmission is received by the technology device of the prosthetic capsular device, which then controls operation of an adjustable-focus IOL in the prosthetic capsular device. In some implementations, the wireless transmission is received by the adjustable-focus IOL in the prosthetic capsular device directly (e.g., if the prosthetic capsular device lacks a suitable technology device or any technology device, or in the absence of the use of a prosthetic capsular device for suitable IOLs). In some implementations, the wireless transmission is received by another device that communicates with the technology device of the prosthetic capsular device and/or the adjustable-focus IOL in the prosthetic capsular device. For example, the smartwatch may send a wireless transmission to a smartphone, which emits a secondary wireless transmission that may be received by the IOL, the technology device, etc. One or more of the wireless transmissions may be sent over a network. Intraocular communication may be wireless (e.g., based on the same or different wireless standard) or wired (e.g., based on electrical contact between an exterior of the IOL haptics and an interior of the prosthetic capsular device).

In response to the wireless transmission or a secondary wireless transmission, the IOL focus adjusts at block 5506. The block 5506 is shown in dashed outline because the process may be performed by another device (e.g., the IOL). The focus may adjust for near objects by increasing refractive power (e.g., to allow the user to focus on near objects) and/or adjust for intermediate to distance vision by decreasing refractive power (e.g., to allow the user to focus on intermediate and/or distant objects).

An example of an IOL that may be focus adjusted at block 5504 is ELENZA Sapphire from Elenza. Upon sensing a change in the natural pupil, the Elenza IOL can accommodate, or focus. For example, upon sensing that the natural pupil is constricting, the Elenza IOL can myopically accommodate. As another example, upon sensing that the natural pupil is dilating, an IOL may return to the dis-accommodated state for emmetropia. As another example, upon sensing that the natural pupil is dilating, an IOL may return adjust focus for intermediate and/or distant object viewing. In some implementations, the transmission at block 5506 may effect accommodation regardless of a state of the natural pupil. In some implementations, the transmission at block 5506 may effect accommodation in combination with sensing of a change in a natural pupil.

Another example of focus adjustment at block 5504 is by a technology device comprising an artificial pupil or electronically-controlled iris diaphragm configured to selectively block light transmission into the eye. The transmission at block 5506 can instruct the artificial pupil to constrict and/or dilate. In some implementations, an artificial pupil could effectively work for patients with damaged or missing iris tissue and/or to provide increased depth of focus, creating a hyperfocality by decreasing the effective aperture size. In some implementations, an artificial pupil allows the user to achieve better near and intermediate vision in adequate lighting, without the loss of distance vision. An example of a static device that could achieve these refractive benefits is the Acufocus Kamra. This device is typically implanted either in the cornea or upon an IOL, and heretofore not been controllable by the user, for example in a manner that can increase or optimize functionality. In some implementations, upon application of an electrical wireless transmission, the technology device works similarly to a camera aperture, closing circumferentially from the limbal toward the visual axis. In some implementations, upon application of an electrical wireless transmission, the molecular configuration of liquid crystals in the technology device orient to make an edge opaque, akin to the result of pupil constriction. The artificial pupil may work in combination with the natural pupil, or may provide beneficial refractive effects independent of the natural pupil. In some implementations, an artificial pupil may work in combination with accommodation of an IOL such as the Elenza IOL. In some implementations, a technology device of the prosthetic capsular device comprises the artificial pupil, which may be used in combination with an IOL, an accommodating IOL, or without an IOL.

Another example of an IOL that may be focus adjusted at block 5504 is Light Adjustable Lens (LAL) from Calhoun Vision that has not been locked in. Upon application of an electrical wireless transmission, light is directed to cause photopolymerization of macromers and swelling in an illuminated area, causing a change in power. The focus of the IOL may be changed using a microsolenoid (e.g., application of an electrical wireless transmission to a coil creates a magnetic field that attracts or repels a magnetic material coupled to a refractive surface), MEMS (e.g., application of an electrical wireless transmission creates an electrostatic charge that attracts a hinged metallic material coupled to a refractive surface), etc. The entire IOL or portions thereof (e.g., a refractive surface) may move within the prosthetic capsular device, providing a focusing mechanism to non-adjustable IOLs.

In some implementations, the IOL and/or the technology device may send a wireless transmission, command instruction, computer-generated message, or the like to the external device to confirm that focus adjusted. Although the focus adjustment may be visible to a user, such feedback may aid in initial setup, calibration, troubleshooting, etc. In certain such implementations, the process may optionally further comprise receipt of a confirmation wireless transmission by the external device that the focus was adjusted.

The external device may optionally be configured to receive other wireless transmissions from the IOL and/or the technology device (e.g., low battery, error codes, limits reached, etc.). In certain such implementations, the emission of the wireless transmission by the external device 5504 may be based on confirmation that the IOL is able to focus in accordance with the wireless transmission. The external device may optionally be configured to receive other wireless transmissions from the IOL and/or the technology device other than regarding focus, for example as described in further detail herein.

The process ends at block 5508. The focus of the IOL may revert after some amount of time or in response to a second wireless transmission from the external device (e.g., upon receipt of a second user input). Some of the processes discussed above and other processes are described in more detail with respect to FIGS. 55B-55F.

FIG. 55B is a schematic of a system for controlling an electronic device (e.g., technology device and/or an IOL) using an external device. In the illustrated flowchart, a prosthetic capsular device 5510 includes a technology device. The prosthetic capsular device 5510 at least partially contains an IOL 5512. The technology device of the prosthetic capsular device 5510 and/or the IOL 5512 is in communication with a primary external device 5514. The primary external device 5514 may comprise, for example, a smartphone, a smartwatch, etc. The primary external device 5514 is optionally in communication with a secondary external device 5516. The secondary external device 5516 may comprise, for example, a smartwatch (e.g., in combination with the primary external device 5514 comprising a smartphone). The secondary external device 5516 is optionally in communication with a tertiary external device 5518. The tertiary external device 5518 may comprise, for example, a ring (e.g., in combination with the secondary external device 5516 comprising a smartwatch). The primary external device 5514, the secondary external device 5516, and the tertiary external device 5518 may act singly, in subcombination, or in full combination to, inter alia, receive input by a user and emit a wireless transmission to the technology device of the prosthetic capsular device 5510 and/or the IOL 5512. Additional external devices (e.g., quartenary, quinary, etc.) are also possible.

Figures 55C, 55D:
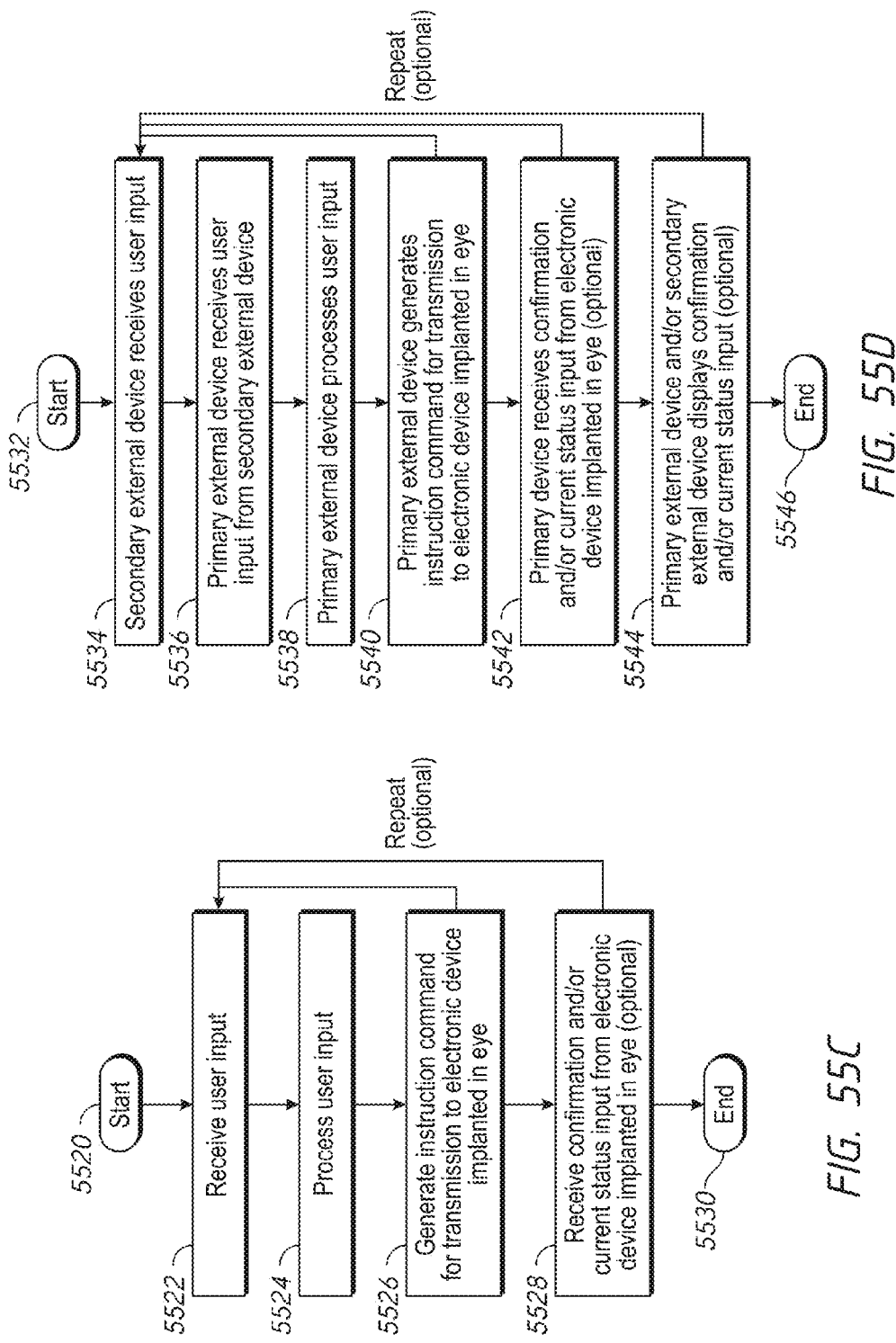
FIG. 55C is a flowchart of an example of controlling an electronic device using an external device.
FIG. 55D is a flowchart of another example of controlling an electronic device using an external device.

FIG. 55C is a flowchart of an example method of controlling an electronic device (e.g., technology device and/or an IOL) using an external device. Starting at block 5520, the external device receives input from a user at block 5522. Upon receipt of the user input at block 5522, the external device processes the user input at block 5524. The external device may include a processing module, a static memory module, a dynamic or temporary memory module, a power source, a user input receipt module, a wireless transmission emitting module, a wireless transmission receiving module, and the like. Upon processing of the user input at block 5524, the external device generates an instruction command for transmission to an electronic device (e.g., a technology device of a prosthetic capsular device, an IOL, etc.) implanted in the eye at block 5526. The generation of the instruction command may be automatic upon receipt and processing of the user input, or may include further interaction with the user or another device. The instructions may include, for example, to focus the IOL. Upon generation of the instruction command at block 5526, the external device may optionally receive confirmation and/or a current status input from the electronic device (e.g., a technology device of a prosthetic capsular device, an IOL, etc.) implanted in the eye at block 5528. Depending on generation of the instruction command and/or receipt of the confirmation and/or current status input from the electronic device, the process may repeat starting at block 5522 or end at block 5530.

FIG. 55D is a flowchart of another example method of controlling an electronic device (e.g., technology device and/or an IOL) using an external device. Referring to FIG. 55B, for example, the external device comprises a primary external device (e.g., a smartphone) and a secondary external device (e.g., a smartwatch). Starting at block 5532, the secondary external device receives input from a user at block 5534. Upon receipt of the user input at block 5534, the secondary external device can be configured to process the user input (for example, a button push or the like) and generate a signal based on the user input for transmitting to the primary external device. The primary external device can be configured to receive the transmitted signal based on the user input from the secondary external device at block 5536. The primary external device may be in wired or wireless communication with the secondary external device so as to receive the user input directly or as a result of a wireless transmission from the secondary external device. Upon receipt of the user input at block 5536, the primary external device processes the user input at block 5538. Upon processing of the user input at block 5538, the primary external device generates an instruction command for transmission to an electronic device (e.g., a technology device of a prosthetic capsular device, an IOL, etc.) implanted in the eye at block 5540. The generation of the instruction command may be automatic upon receipt and processing of the user input, or may include further interaction with the user, the secondary external device, another device, etc. The instructions may include, for example, to focus the IOL. Upon generation of the instruction command at block 5540, the primary external device may optionally receive confirmation and/or a current status input from the electronic device (e.g., a technology device of a prosthetic capsular device, an IOL, etc.) implanted in the eye at block 5542. The primary external device and/or the secondary external device may optionally display the confirmation and/or current status input at block 5544. Depending on generation of the instruction command, receipt of the confirmation and/or current status input from the electronic device, and/or display of the confirmation and/or current status input, the process may repeat starting at block 5534 or end at block 5546.

Figure 55E:
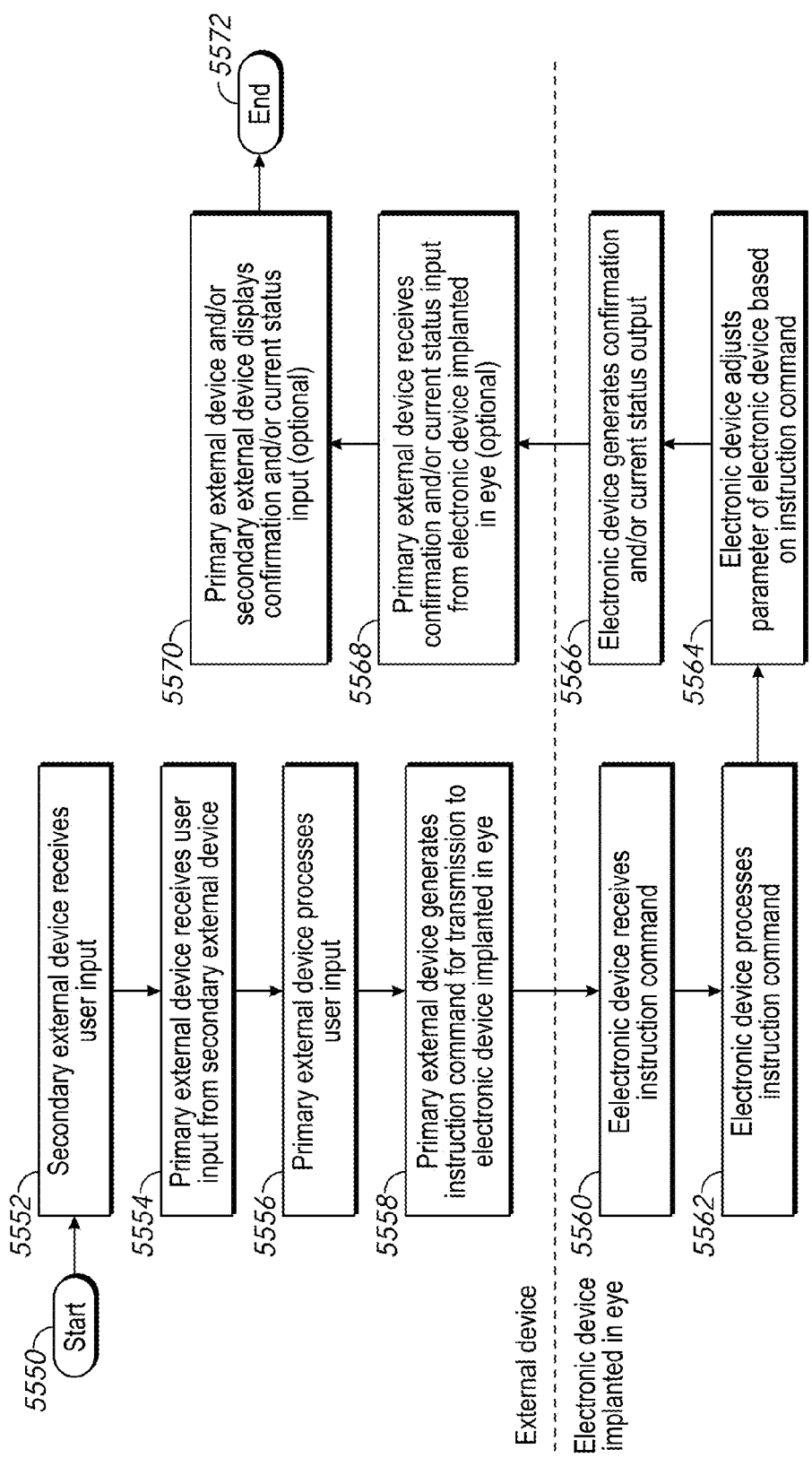
FIG. 55E is a flowchart of another example of controlling an electronic device using an external device.

FIG. 55E is a flowchart of another example method of controlling an electronic device (e.g., technology device and/or an IOL) using an external device. Referring to FIG. 55B, for example, the external device comprises a primary external device (e.g., a smartphone) and a secondary external device (e.g., a smartwatch). Starting at block 5550, the secondary external device receives input from a user at block 5552. Upon receipt of the user input at block 5552, the secondary external device can be configured to process the user input (for example, a button push or the like) and generate a signal based on the user input for transmitting to the primary external device. The primary external device can be configured to receive the transmitted signal generated based on the user input from the secondary external device at block 5554. The primary external device may be in wired or wireless communication with the secondary external device so as to receive the user input directly or as a result of a wireless transmission from the secondary external device. Upon receipt of the user input at block 5554, the primary external device processes the user input at block 5556. Upon processing of the user input at block 5556, the primary external device generates an instruction command for transmission to an electronic device (e.g., a technology device of a prosthetic capsular device, an IOL, etc.) implanted in the eye at block 5558. The generation of the instruction command may be automatic upon receipt and processing of the user input, or may include further interaction with the user, the secondary external device, another device, etc. The instructions may include, for example, to focus the IOL.

FIG. 55E includes a dashed horizontal line indicative of processes that may be performed by the electronic device (e.g., a technology device of a prosthetic capsular device, an IOL, etc.) implanted in the eye. It will be appreciated that the electronic device may be separate from the external device, and that the processes described with respect to FIG. 55E are examples for reference only. In some implementations, the external device and the electronic device form a system or kit.

The electronic device may receive the instruction command at block 5560. Upon receipt of the instruction command at block 5560, the electronic device may process the instruction command at block 5562. Upon processing of the instruction command at block 5562, the electronic device may adjust a parameter of the electronic device based on the instruction command at block 5564. The adjustment of the parameter may be automatic upon receipt and processing of the instruction command, or may include further interaction with the user, the primary external device, the secondary external device, and/or another device, analysis of the parameter and/or another parameter, etc. The parameter may include, for example, IOL focus (e.g., an amount of masking, an amount of movement, an amount of rotation, etc.). Upon adjustment of the parameter at block 5564, the electronic device may generate confirmation and/or a current status output at block 5566. The electronic device may perform more, fewer, different, differently ordered, etc. processes, may include interaction between multiple electronic devices (e.g., between a technology device of a prosthetic capsular device and an IOL), etc.

The primary external device may optionally receive confirmation and/or a current status input (generated as output) from the electronic device implanted in the eye at block 5568. The primary external device and/or the secondary external device may optionally display the confirmation and/or current status input at block 5570. The process ends at block 5572.

Figure 55F:
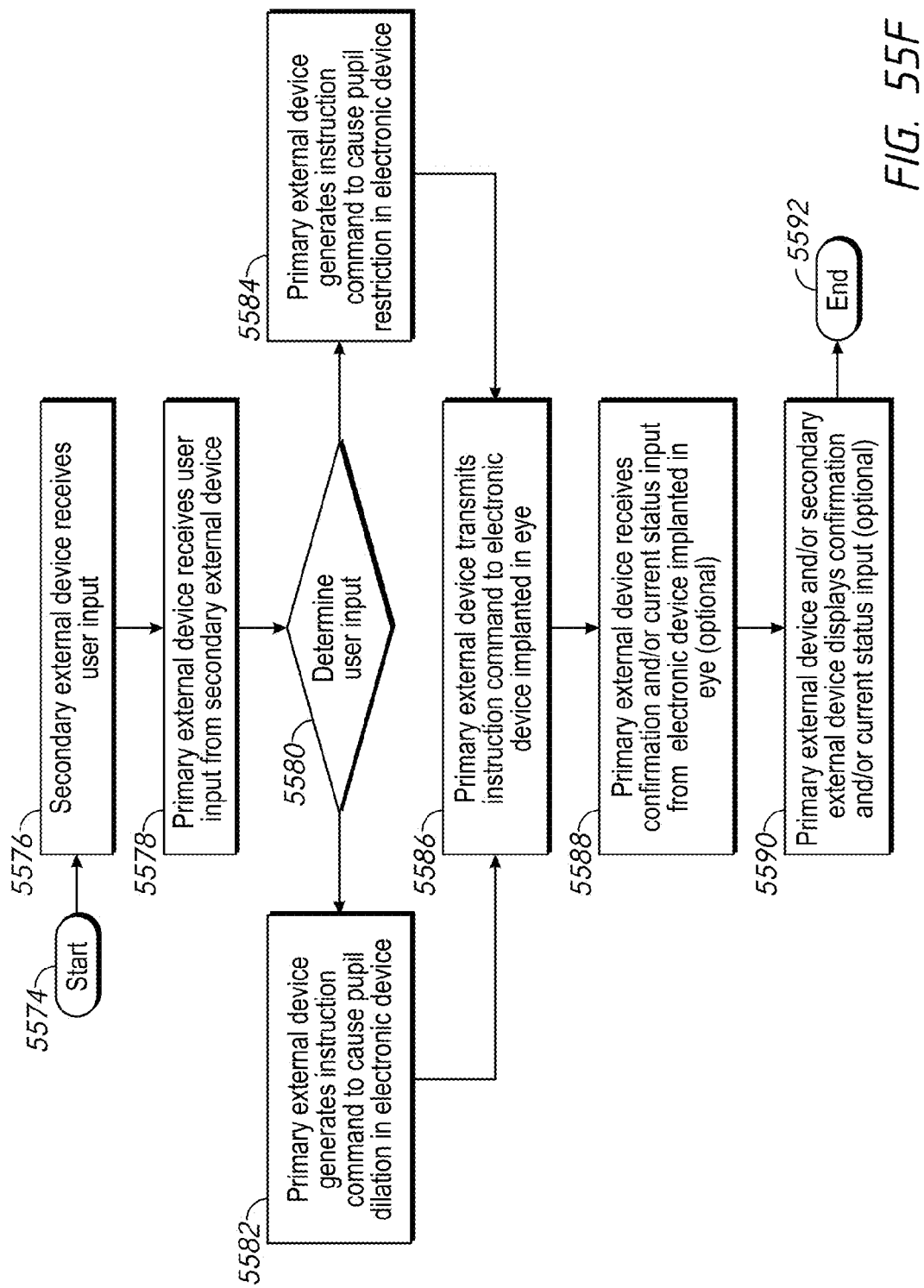
FIG. 55F is a flowchart of another example of controlling an electronic device using an external device.

FIG. 55F is a flowchart of another example method of controlling an electronic device (e.g., technology device and/or an IOL) using an external device. Referring to FIG. 55B, for example, the external device comprises a primary external device (e.g., a smartphone) and a secondary external device (e.g., a smartwatch). Starting at block 5574, the secondary external device receives input from a user at block 5576. Upon receipt of the user input at block 5576, the secondary external device can be configured to process the user input (for example, a button push or the like) and generate a signal based on the user input for transmitting to the primary external device. The primary external device can be configured to receive the transmitted signal generated based on the user input from the secondary external device at block 5578. The primary external device may be in wired or wireless communication with the secondary external device so as to receive the user input directly or as a result of a wireless transmission from the secondary external device.

The primary external device determines the user input at block 5580. In the event of a first user input, the primary external device generates an instruction command to change focus to near objects (e.g., myopic accommodation as described herein with respect to the Elenza IOL) at block 5582. In the event of a second user input different than the first user input, the primary external device generates an instruction command to change focus to intermediate and/or distant objects (e.g., emmetropia or a dis-accommodated state as described herein) at block 5584. For clarity, the Elenza IOL uses pupillary constriction as a sign that the eye is trying to accommodate (focus) and the lens changes focus based on the natural pupillary constriction. That is, the Elenza IOL does not cause the pupil to constrict and does not contain a prosthetic iris device. In some implementations, instruction commands described herein could, for example, cause the Elenza IOL to change focus regardless of constriction of the natural pupil.

In some implementations, for example using an IOL other than an Elenza IOL or by way of a technology device of a prosthetic capsular device, an instruction command could, for example, effect constriction or dilation of an artificial pupil.

Focus adjustment of an Elenza IOL and constriction/dilation of an artificial pupil and are provided as example parameter changes, and it will be appreciated that other parameter changes based on different inputs is also possible. The generation of the instruction commands may be automatic upon receipt and processing of the user input, or may include further interaction with the user (e.g., instruction command in combination with sensing of natural pupil dilation), the secondary external device, another device, etc. In some implementations, the secondary external device may determine the user input and the primary external device may receive an instruction command.

Upon generation of the instruction command at block 5582 or 5584, the primary external device transmits the instruction command to an electronic device (e.g., a technology device of a prosthetic capsular device, an IOL, etc.) implanted in the eye at block 5586. The instructions may include, for example, to focus the IOL. Upon transmission of the instruction command at block 5586, the primary external device may optionally receive confirmation and/or a current status input from the electronic device (e.g., a technology device of a prosthetic capsular device, an IOL, etc.) implanted in the eye at block 5588. The primary external device and/or the secondary external device may optionally display the confirmation and/or current status input at block 5590. The process ends at block 5592.

Figure 56:
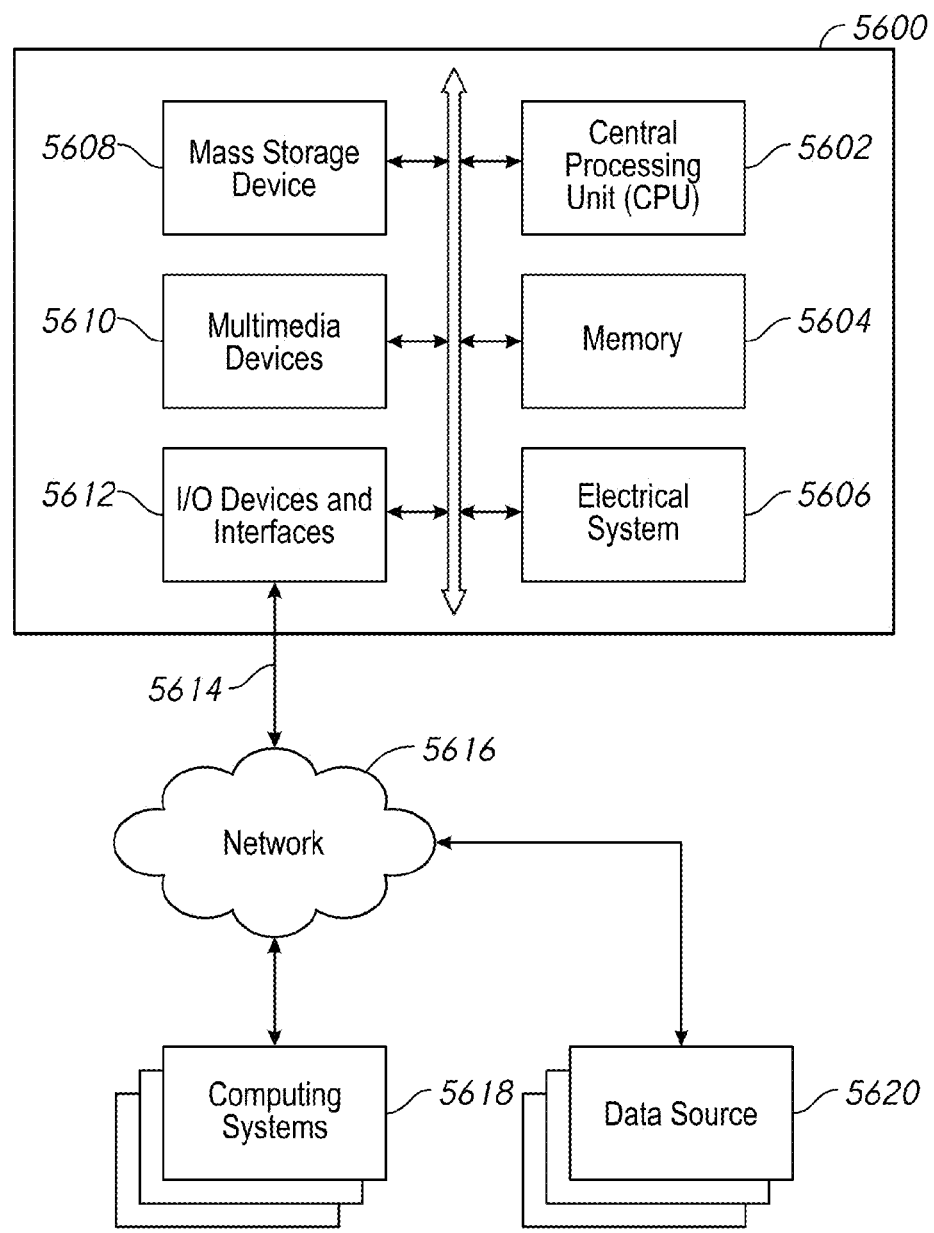
FIG. 56 is a block diagram depicting an example computer hardware system configured to execute software for implementing one or more embodiments of electronic device control disclosed herein.

FIG. 56 is a block diagram depicting an example computer hardware system configured to execute software for implementing one or more implementations of electronic device control disclosed herein In some implementations, the hardware systems and/or devices described above take the form of a computing system 5600, which is a block diagram of one implementation of a computing system that is in communication with one or more computing systems 5618 and/or one or more data sources 5620 via one or more networks 5616. The computing system 5600 may be used to implement one or more of the systems and methods described herein. In some implementations, the computing system 5600 is configured to manage access or administer a software application. While FIG. 56 illustrates an example computing system 5600, it is recognized that the functionality provided for in the components and modules of the computing system 5600 may be combined into fewer components and modules or further separated into additional components and modules.

Electrical System

In some implementations, the computing system 5600 comprises an electrical system 5606 configured to carry out one or more of the functions described herein with reference to control of an electronic device implanted in an eye, including any one of techniques described above. The electrical system 5606 and/or other modules may be executed on the computing system 5600 by a central processing unit 5602 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into submodules despite their physical organization or storage.

Computing System Components

The computing system 5600 can comprise a central processing unit (CPU) 5602, which may comprise a conventional microprocessor. The computing system 5600 further comprises a memory 5604, such as random access memory (RAM) for temporary storage of information and/or a read only memory (ROM) for permanent storage of information, and a mass storage device 5608, such as a hard drive, diskette, or optical media storage device. In some implementations, the modules of the computing system 5600 are connected to the computer using a standards based bus system. In some implementations, the standards-based bus system could include Peripheral Component Interconnect (PCI), Microchannel, SCSI, Industrial Standard Architecture (ISA) and Extended ISA (EISA) architectures, for example.

The computing system 5600 comprises one or more commonly available input/output (I/O) devices and interfaces 5612, such as a keyboard, mouse, touchpad, touchscreen, ring, printer, etc. In some implementations, the I/O devices and interfaces 5612 comprise one or more display devices, such as a monitor or touchscreen, that allows the visual presentation of data to a user. A display device can provide for the presentation of graphical user interfaces (GUI), application software data, and multimedia presentations, for example. In some implementations, the I/O devices and interfaces 5612 comprise a microphone, motion, and/or NFC sensor that allows a user to generate input to the computing system 5600 using sounds, voice, motion, gestures, or the like. In FIG. 56, the I/O devices and interfaces 5612 also provide a communications interface to various external devices via a link 5614 to the network 5616. The computing system 5600 may also comprise one or more multimedia devices 5610, such as speakers, video cards, graphics accelerators, and microphones, for example.

Computing System Device/Operating System

The computing system 5600 may run on a variety of computing devices, such as, for example, a specifically designed device, a server, a Windows server, a Structure Query Language server, a Unix server, a personal computer, a mainframe computer, a laptop computer, a tablet computer, a cellular phone, a smartphone, a smartwatch, a personal digital assistant, a kiosk, an audio player, an e-reader device, and so forth. The computing system 5600 is generally controlled and coordinated by operating system software, such z/OS, Windows 95, Windows 98, Windows NT, Windows 2000, Windows XP, Windows Vista, Windows 7, Windows 8, Linux, BSD, SunOS, Solaris, Android, iOS, BlackBerry OS, or other compatible operating systems. In Macintosh systems, the operating system may be any available operating system, such as MAC OS X. In some implementations, the computing system 5600 is controlled by a proprietary operating system. The operating system may, for example, control and schedule computer processes for execution, perform memory management, provide file system, networking, and I/O services, and provide a user interface, such as a GUI, among other things.

Network

FIG. 56 illustrates the computing system 5600 is coupled to an optional network 5616, such as a LAN, WAN, or the Internet, for example, via a wired, wireless, or combination of wired and wireless, communication link 5614. The network 5616 communicates with various computing devices and/or other electronic devices via wired or wireless communication links. In FIG. 56, the network 5616 is communicating with one or more computing systems 5618 and/or one or more data sources 5620.

Access to the electrical system 5606 of the computer system 5600 by computing systems 5618 and/or by data sources 5620 may be through a web-enabled user access point such as the computing systems' 5618 or data source's 5620 personal computer, mobile device, cellular phone, smartphone, smartwatch, laptop, tablet computer, e-reader device, audio player, or other device capable of connecting or configured to connect to the network 5616. Such a device may have a browser module or specific application that is implemented as a module that uses text, graphics, audio, video, and other media to present data and to allow interaction with data via the network 5616.

The browser module or specific application may be implemented as a combination of an all points addressable display such as a cathode-ray tube (CRT), a liquid crystal display (LCD), a plasma display, or other types and/or combinations of displays. The browser module or specific application may be implemented to communicate with input devices 5612 and may comprise software with the appropriate interfaces to allow a user to access data through the use of stylized screen elements such as, for example, menus, windows, dialog boxes, toolbars, and controls (for example, radio buttons, check boxes, sliding scales, and so forth). The browser module may communicate with a set of input and output devices to receive wireless transmissions from the user.

The input device(s) may comprise a keyboard, roller ball, pen and stylus, mouse, ring, smartwatch, knob, trackball, voice recognition system, or pre-designated switches or buttons. The output device(s) may comprise a speaker, a display screen, a printer, or a voice synthesizer. A touch screen may act as a hybrid input/output device. In some implementations, a user may interact with the system through a system terminal without communications over the Internet, a WAN, or LAN, or similar network.

In some implementations, the system 5600 comprises a physical or logical connection between a remote microprocessor and a mainframe host computer for the purpose of uploading, downloading, or viewing interactive data and databases on-line in real time. The remote microprocessor may be operated by an entity operating the computer system 5600, including the client server systems or the main server system, an/or may be operated by one or more of the data sources 5620 and/or one or more of the computing systems 5618. In some implementations, terminal emulation software may be used on the microprocessor for participating in the micro-mainframe link.

In some implementations, computing systems 5618 that are internal to an entity operating the computer system 5600 may access the electrical system 5606 internally as an application or process run by the CPU 5602.

User Access Point

In some implementations, a user access point or user interface comprises a personal computer, a laptop computer, a tablet computer, an e-reader device, a mobile device, a cellular phone, a smartphone, a smartwatch, a GPS system, a Blackberry® device, a portable computing device, a server, a computer workstation, a local area network of individual computers, an interactive kiosk, a personal digital assistant, an interactive wireless communications device, a handheld computer, an embedded computing device, an audio player, or the like.

Other Systems

In addition to the systems illustrated and described above, the network 5616 may communicate with other data sources and/or other computing devices. The computing system 5600 may comprise one or more internal and/or external data sources. In some implementations, one or more of the data repositories and the data sources may be implemented using a relational database, such as DB2, Sybase, Oracle, CodeBase, Microsoft® SQL Server, as well as other types of databases such as, for example, a flat file database, an entity-relationship database, and object-oriented database, and/or a record-based database.

FIG. 73A illustrates an anterior side perspective view of an example prosthetic capsular device 7300 in an unfolded state. FIG. 73B illustrates an anterior plan view of the example prosthetic capsular device 7300 of FIG. 73A in an unfolded state. FIG. 73C illustrates a side view of the example prosthetic capsular device 7300 of FIG. 73A in an unfolded state. The device 7300 comprises a plurality of segments or leaves or petals 7302 spaced by gaps 7304. The device 7300 optionally comprises an optic 7310. As best seen in FIGS. 73A and 73C, the devices 7300 is substantially flat or planar or two-dimensional in a first or unfolded state or configuration, which can increase ease of manufacturing versus a device that is three-dimensional in an unfolded state.

Referring again to FIGS. 73B and 73C, certain example dimensions of the device 7300 in the unfolded state are provided. In some implementations, the device 7300 has a diameter 7320, including the petals, between about 10 mm and about 20 mm (e.g., about 10 mm, about 11 mm, about 12 mm, about 13 mm, about 14 mm, about 15 mm, about 16 mm, about 17 mm, about 18 mm, about 19 mm, about 20 mm, ranges between such values, etc.). In some implementations, the device 7300 has a diameter 7322, excluding the petals, between about 5 mm and about 15 mm (e.g., about 5 mm, about 6 mm, about 7 mm, about 8 mm, about 9 mm, about 10 mm, about 11 mm, about 12 mm, about 13 mm, about 14 mm, about 15 mm, ranges between such values, etc.). In some implementations, the circumferential width 7324 of a petal 7302 is between about 20° and about 30° (e.g., about 20°, about 21°, about 22°, about 23°, about 24°, about 25°, about 26°, about 27°, about 28°, about 29°, about 30°, ranges between such values, etc.). In some implementations, the circumferential width 7326 of a gap 7304 is between about 20° and about 30° (e.g., about 20°, about 21°, about 22°, about 23°, about 24°, about 25°, about 26°, about 27°, about 28°, about 29°, about 30°, ranges between such values, etc.). In some implementations, a ratio of the circumferential width 7326 of a petal 7302 to a circumferential width 7328 of a gap 7304 is between about 1:2 and about 2:1 (e.g., about 1:2, about 5:8, about 2:3, about 7:8, about 15:16, about 25:26, about 1:1, about 8:7, about 16:15, about 26:25, about 3:2, about 8:5, about 2:1, ranges between such values, etc.). In some implementations, a diameter 7328 of the optic 7310 is between about 4 mm and about 10 mm (e.g., about 4 mm, about 5 mm, about 6 mm, about 7 mm, about 8 mm, about 9 mm, about 10 mm, ranges between such values, etc.). In some implementations, a thickness 7330 of the device 7300 except the optic 7310, or a petal 7302, is between about 0.1 mm and about 0.5 mm (e.g., about 0.1 mm, about 0.15 mm, about 0.2 mm, about 0.25 mm, about 0.3 mm, about 0.35 mm, about 0.4 mm, about 0.45 mm, about 0.5 mm, ranges between such values, etc.).

The unfolded device 7300 may be folded for insertion into a natural capsular bag. The two-dimensional nature of the unfolded device 7300 may allow further folding, for example compared to a three-dimensional structure, which can allow insertion through a smaller incision. In some implementations, the size of the incision is solely determined by the IOL to be placed in the capsular device, as the device can be inserted through an incision smaller than any known IOL.

FIG. 73D illustrates an anterior plan view of the example prosthetic capsular device 7300 of FIG. 73A in a folded state. FIG. 73E illustrates an anterior side perspective view of the example prosthetic capsular device 7300 of FIG. 73A in a folded state. As the device 7300 is inserted into a natural capsular bag, the device may unfold towards its unfolded state. The optic 7310 may contact the posterior side of the natural capsular bag. The petals 7302 may fold towards the anterior and then radially inwardly, eventually folding in upon themselves. The folded device 7300 comprises an anterior opening 7312 through which an IOL may be inserted. The device 7300 is configured to contain an IOL.

The folded device 7300 may include other features described herein, for example electronic devices, tabs, ring structures, etc. In some implementations, the two-dimensional nature of the unfolded device 7300 may allow easier manufacturing of such features. For example, a flex circuit may be patterned on a first side of the device 7300 that is configured to be an interior of the capsular device 7300. For another example, ring haptics or tabs may be patterned on a second side of the device 7300 that is configured to be an exterior of the capsular device 7300. For yet another example, openings and/or anchor points can be formed on one or both sides of the device 7300.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. For example, actions such as "inserting an intraocular lens into a prosthetic capsular device" include "instructing the insertion of an intraocular lens into a prosthetic capsular device." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

What is claimed is:

1. A prosthetic capsular device configured to be inserted in a natural capsular bag of an eye after removal of a lens, the device comprising:
 a housing structure capable of containing an intraocular lens (IOL), the housing structure including:
  a first flat lateral side, the first flat side including:
   a first end, and
   a second end;
  a second flat lateral side opposite the first flat lateral side, the second flat lateral side including:
   a first end, and
   a second end;
  a third arcuate lateral side extending between the first end of the first flat lateral side and the first end of the second flat lateral side, the third arcuate lateral side comprising a capsular bag-contacting surface;
  a fourth arcuate lateral side extending between the second end of the first flat lateral side and the second end of the second flat lateral side, the fourth arcuate lateral side opposite the third arcuate lateral side, the fourth arcuate lateral side comprising a capsular bag-contacting surface;
  a posterior side including a refractive surface;
 an anterior side opposite the posterior side, the anterior side including an opening configured to allow insertion of an intraocular lens and a lip formed around the opening; and
 a longitudinal axis,
 the first flat lateral side, the second flat lateral side, the third arcuate lateral side, the fourth arcuate lateral side, the posterior side, and the anterior side at least partially defining a cavity, the cavity of the housing structure capable of containing an intraocular lens; and
 a ring structure including:
 a first ring structure portion extending from proximate to the first end of the first flat lateral side radially outward and towards the second end of the first flat lateral side, the first ring structure portion comprising a capsular-bag contacting surface; and
 a second ring structure portion extending from proximate to the second end of the second flat lateral side radially outward and towards the first end of the second flat lateral side, the second ring structure portion comprising a capsular-bag contacting surface,
 wherein the first ring structure portion includes an anchor comprising a first anchor portion that extends a distance along the first flat lateral side and a second anchor portion that extends a distance along the third arcuate lateral side, the anchor of the first ring structure portion being embedded within the housing structure;
 wherein the second ring structure portion includes an anchor comprising a first anchor portion that extends a distance along the second flat lateral side and a second anchor portion that extends a distance along the fourth arcuate lateral side, the anchor of the second ring structure portion being embedded within the housing structure; and
 wherein each of the first ring structure portion and the second ring structure portion includes an anterior-posterior opening proximate to a terminal end.

2. The device of claim 1, wherein the housing structure comprises a first material and the ring structure comprises a second material different than the first material.

3. The device of claim 2, wherein the first material comprises silicone and the second material comprises polyimide.

4. The device of claim 2, wherein the first material comprises silicone.

5. The device of claim 2, wherein the second material comprises polyimide.

6. The device of claim 1, wherein the refractive surface has a refractive power between −35 D and +35 D.

7. The device of claim 1, wherein each of the first flat lateral side, the second flat lateral side, the third arcuate lateral side, and the fourth arcuate lateral side includes a first portion extending parallel to the longitudinal axis from the posterior side towards the anterior side.

8. The device of claim 7, wherein each of the first flat lateral side, the second flat lateral side, the third arcuate lateral side, and the fourth arcuate lateral side further includes a second portion extending radially inwardly from the first portion towards the opening of the anterior side.

9. The device of claim 1, wherein the ring structure further includes:
 a third ring structure portion extending from proximate to the first end of the second flat lateral side radially outward and towards the second end of the second flat lateral side, the third ring structure portion comprising a capsular-bag contacting surface; and
 a fourth ring structure portion extending from proximate to the second end of the first flat lateral side radially outward and towards the first end of the first flat lateral side, the fourth ring structure portion comprising a capsular-bag contacting surface.

10. The device of claim 1, wherein the opening is oblong.

11. The device of claim 1, wherein the posterior side comprises a first fin and a second fin, the first fin and the second fin circumferentially offset by about 180° and aligned along a major axis of the device.

12. The device of claim 1, wherein the housing structure is capable of containing a biometric measurement device comprising a sensor.

13. The device of claim 12, wherein the biometric measurement device comprises a wireless transmitter, the biometric data sensor device configured to measure biometric data using the sensor and to transmit the biometric data to an external device configured to receive the biometric data.

14. The device of claim 13, wherein the biometric data comprises intraocular pressure.

15. The device of claim 13, wherein the biometric data comprises glucose level.

16. The device of claim 1, wherein the posterior side comprises an opening.

17. The device of claim 16, wherein the opening of the posterior side is capable of allowing delivery of a medicament from an inserted drug delivery platform to a posterior segment of an eye.

* * * * *

UNITED STATES PATENT AND TRADEMARK OFFICE
CERTIFICATE OF CORRECTION

PATENT NO. : 9,517,127 B2
APPLICATION NO. : 15/138679
DATED : December 13, 2016
INVENTOR(S) : Wortz It is certified that error appears in the above-identified patent and that said Letters Patent is hereby corrected as shown below:

On the Title Page

Column 2 (page 1, item (56)) Line 12, change "Ophthalmologel," to --Ophthalmology,--.

Column 2 (page 3, item (56)) Line 18, change "Postive" to --Positive--.

In the Specification

Column 9 Line 36, After "59A" insert --;--.

Column 17 Line 8, Change "aberommetry" to --aberrometry--.

Column 20 Line 46, Change "pupiloplasty" to --pupilloplasty--.

Column 24 Line 19, Change "sequlae" to --sequelae--.

Column 25 Line 21, Change "diopteric" to --dioptric--.

Column 30 Line 54, Change "Crysalens" to --Crystalens--.

Column 35 Line 52, Change "chromaphores," to --chromophores,--.

Column 39 Lines 5-6, Change "Photochromatic" to --Photochromic--.

Column 39 Line 13, Change "Photochromatic" to --Photochromic--.

Column 40 Lines 25-26, Change "collarmer," to --Collamer,--.

Column 41 Line 58, Before "of the" delete "the".

Signed and Sealed this
Eighteenth Day of April, 2017

Michelle K. Lee
*Director of the United States Patent and Trademark Office*

Column 42 Line 1, Change "and or" to --and/or--.

Column 43 Line 54, Change "appose" to --oppose--.

Column 45 Lines 35-36, Change "frusto-pryamidal)," to --frusto-pyramidal),--.

Column 56 Line 35, Change "non-refractivity" to --non-refractively--.

Column 56 Line 36, Change "reflectively" to --refractively--.

Column 81 Lines 11-12, Change "ranibizuman" to --ranibizumab--.

Column 81 Line 13, Change "Regerneron Pharmacueticals)" to --Regeneron Pharmaceuticals)--.

Column 89 Line 67, Change "carabener" to --carabiner--.

Column 91 Line 47, Change "mirror image" to --mirror-image--.

Column 95 Line 58, Change "gortex" to --goretex--.

Column 97 Line 26, Change "(disaccomodation" to --(disaccommodation--.

Column 97 Line 27, Change "dis-accomodated" to --dis-accommodated--.

Column 107 Line 26, Change "quartenary" to --quaternary--.

Column 110 Line 33, After "herein" insert --.--.

Column 112 Line 55, Change "an/or" to --and/or--.